(12) United States Patent
Morse et al.

US010991893B2

(10) Patent No.: US 10,991,893 B2
(45) Date of Patent: Apr. 27, 2021

(54) ORGANIC SEMICONDUCTING COMPOUNDS

(71) Applicant: Raynergy Tek Incorporation, Hsinchu (TW)

(72) Inventors: Graham Morse, Southampton (GB); Lana Nanson, Southampton (GB); William Mitchell, Chandler's Ford (GB); Michal Krompiec, Southampton (GB); Mansoor D'Lavari, Bude (GB); Agnieszka Pron, Eastleigh (GB)

(73) Assignee: RAYNERGY TEK INCORPORATION, Hsinchu (TW)

( * ) Notice: Subject to any disclaimer, the term of this patent is extended or adjusted under 35 U.S.C. 154(b) by 0 days.

(21) Appl. No.: 16/339,433

(22) PCT Filed: Oct. 2, 2017

(86) PCT No.: PCT/EP2017/074951
§ 371 (c)(1),
(2) Date: Apr. 4, 2019

(87) PCT Pub. No.: WO2018/065350
PCT Pub. Date: Apr. 12, 2018

(65) Prior Publication Data
US 2020/0052227 A1 Feb. 13, 2020

(30) Foreign Application Priority Data

Oct. 5, 2016 (EP) .................................... 16192351
Nov. 23, 2016 (EP) .................................... 16200289
Jun. 12, 2017 (EP) .................................... 17175533

(51) Int. Cl.
*H01L 51/00* (2006.01)
*C07D 495/04* (2006.01)
*C07D 495/22* (2006.01)
*H01L 51/42* (2006.01)

(52) U.S. Cl.
CPC ........ *H01L 51/0074* (2013.01); *C07D 495/04* (2013.01); *C07D 495/22* (2013.01); *H01L 51/0036* (2013.01); *H01L 51/0046* (2013.01); *H01L 51/0047* (2013.01); *H01L 51/0058* (2013.01); *H01L 51/0068* (2013.01); *H01L 51/0069* (2013.01); *H01L 51/0071* (2013.01); *H01L 51/0073* (2013.01); *H01L 51/4253* (2013.01)

(58) Field of Classification Search
CPC ............. H01L 51/0046; H01L 51/0047; H01L 51/0058; H01L 51/0068; C07D 495/22
USPC ............................ 252/500, 510, 511; 257/40
See application file for complete search history.

(56) References Cited

U.S. PATENT DOCUMENTS

| 8,058,387 | B2 | 11/2011 | Chan et al. |
| 9,017,577 | B2 | 4/2015 | Tierney et al. |
| 2015/0255725 | A1 | 9/2015 | Mitchell et al. |
| 2017/0117477 | A1 | 4/2017 | Mansoor |

FOREIGN PATENT DOCUMENTS

| DE | 102013110693 A1 * | 4/2015 | ......... H01L 51/0071 |
| EP | 2075274 B1 | 6/2010 | |
| WO | 10020329 | 2/2010 | |
| WO | 14053206 A1 | 4/2014 | |
| WO | 15044377 A1 | 4/2015 | |
| WO | 15154845 A1 | 10/2015 | |

OTHER PUBLICATIONS

Li "Non-fullerene acceptor with low energy loss and high external quantum efficiency: towards high performance polymer solar cells." J. Mater. Chem. A, 2016, 4, 5890 (Year: 2016).*
K-T. Wong; T-C. Chao; L-C. Chi; Y-Y. Chu; A. Balaiah; S-F. Chiu; Y-H. Liu; Y. Wang: "OSC small molecules with an IDT core have been proposed for use as chromophores in OLEDs", Org. Lett., vol. 8, No. 22, 2006, pp. 5033.
H. Lin; S. Chen; Z. Li; J. Y. L. Lai; G. Yang; T. McAfee; K. Jiang; Y. Li; Y. Liu; H. Hu, Adv. Mater., vol. 27, 2015, pp. 7299-7304.
Y. Lin; J. Wang; Z.-G. Zhang; H. Bai; Y. Li; D. Zhu; X. Zhan, Adv. Mater., vol. 27, 2015, pp. 1170-1174.
Christoph Wetzel et al: "Development of strongly absorbing S,N-heterohexacene-based donor materials for efficient vacuum-processed organic solar cells", Journal of Materials Chemistry C: Materials for Optical and Electronic Devices, vol. 4, No. 17, Jan. 1, 2016 (Jan. 1, 2016), UK, pp. 3715-3725, XP055429774, ISSN: 2050-7526.
Chung Chin-Lung et al: "Novel organic dyes containing N-bridged oligothiophene coplanar cores for dye-sensitized solar cells", Organic Electronics, vol. 18, Jan. 9, 2015 (Jan. 9, 2015), pp. 8-16, XP029165065, ISSN: 1566-1199.
Azzam Charaf-Eddin et al: "Vibronic spectra of organic electronic chromophores", RSC Adv., vol. 4, No. 98, Jan. 1, 2014 (Jan. 1, 2014), pp. 55466-55472, XP055429777.
Xueliang Shi et al: "Solution-processable n-type and ambipolar semiconductors based on a fused cyclopentadithiophenebis(dicyanovinylene) core", Chemical Communications, vol. 49, No. 64, Jan. 1, 2013 (Jan. 1, 2013), pp. 7135-7137, XP055429783, ISSN: 1359-7345.
International Search report WO2017EP74951 dated Dec. 7, 2017 (pp. 1-3).

* cited by examiner

*Primary Examiner* — Tri V Nguyen
(74) *Attorney, Agent, or Firm* — WPAT, PC

(57) ABSTRACT

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

22 Claims, No Drawings

ORGANIC SEMICONDUCTING COMPOUNDS

TECHNICAL FIELD

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, perovskite-based solar cell (PSC) devices, sensors, memory elements and logic circuits to name just a few. The organic semiconducting materials are typically present in the electronic device in the form of a thin layer, for example of between 50 and 300 nm thickness.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 10%.

Another particular area of importance are OFETs. The performance of OFET devices is principally based upon the charge carrier mobility of the semiconducting material and the current on/off ratio, so the ideal semiconductor should have a low conductivity in the off state, combined with high charge carrier mobility ($>1\times10^{-3}$ cm$^2$ V$^{-1}$ s$^{-1}$). In addition, it is important that the semiconducting material is stable to oxidation i.e. it has a high ionisation potential, as oxidation leads to reduced device performance. Further requirements for the semiconducting material are good processability, especially for large-scale production of thin layers and desired patterns, and high stability, film uniformity and integrity of the organic semiconductor layer.

Organic photodetectors (OPDs) are a further particular area of importance, for which conjugated light-absorbing polymers offer the hope of allowing efficient devices to be produced by solution-processing technologies, such as spin casting, dip coating or ink jet printing, to name a few only.

The photosensitive layer in an OPV or OPD device is usually composed of at least two materials, a p-type semiconductor, which is typically a conjugated polymer, an oligomer or a defined molecular unit, and an n-type semiconductor, which is typically a fullerene or substituted fullerene, graphene, a metal oxide, or quantum dots.

However, the OSC materials disclosed in prior art for use in OE devices have several drawbacks. They are often difficult to synthesize or purify (fullerenes), and/or do not absorb light strongly in the near IR spectrum >700 nm. In addition, other OSC materials do not often form a favourable morphology and/or donor phase miscibility for use in organic photovoltaics or organic photodetectors.

Therefore there is still a need for OSC materials for use in OE devices like OPVs, PSCs, OPDs and OFETs, which have advantageous properties, in particular good processability, high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide new OSC compounds, especially n-type OSCs, which can overcome the drawbacks of the OSCs from prior art, and which provide one or more of the above-mentioned advantageous properties, especially easy synthesis by methods suitable for mass production, good processability, high stability, long lifetime in OE devices, good solubility in organic solvents, high charge carrier mobility, and a low bandgap. Another aim of the invention was to extend the pool of OSC materials and n-type OSCs available to the expert. Other aims of the present invention are immediately evident to the expert from the following detailed description.

The inventors of the present invention have found that one or more of the above aims can be achieved by providing compounds as disclosed and claimed hereinafter. These compounds comprise an indaceno-type polycyclic central unit as shown in formula I.

It has been found that compounds comprising such a central polycyclic unit, and further comprising two terminal electron withdrawing groups, can be used as n-type OSCs which show advantageous properties as described above.

Conjugated polymers based on linearly fused polycyclic aromatic units have been disclosed in prior art for use as p-type OSCs, such as indacenodithiophene (IDT) as disclosed for example in WO 2010/020329 A1 and EP 2075274 A1, or indacenodithienothiophene (IDTT) as disclosed for example in WO 2015/154845 A1.

OSC small molecules with an IDT core have been proposed for use as chromophores in OLEDs by K-T. Wong, T-C. Chao, L-C. Chi, Y-Y. Chu, A. Balaiah, S-F. Chiu, Y-H. Liu, and Y. Wang, *Org. Lett.*, 2006, 8, 5033.

More recently, OSC small molecules comprising an IDT or IDTT core that is end capped with 2-(3-oxo-2,3-dihydroinden-1-ylidene)malononitrile have been reported for use as non-fullerene n-type OSCs in OPV devices, for example by Y. Lin, J. Wang, Z.-G. Zhang, H. Bai, Y. Li, D. Zhu and X. Zhan, *Adv. Mater.*, 2015, 27, 1170, and by H. Lin, S. Chen, Z. Li, J. Y. L. Lai, G. Yang, T. McAfee, K. Jiang, Y. Li, Y. Liu, H. Hu, J. Zhao, W. Ma, H. Ade and H. Yan, Zhan, *Adv. Mater.*, 2015, 27, 7299, in CN104557968A and CN105315298 A.

However, the compounds as disclosed and claimed hereinafter have hitherto not been disclosed in prior art.

SUMMARY

The invention relates to a compound of formula I

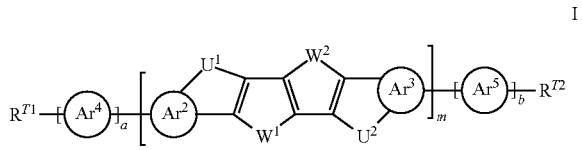

I wherein the individual radicals, independently of each other and on each occurrence identically or differently, have the following meanings $Ar^{2,3}$ arylene or heteroarylene that has from 5 to 20 ring atoms, is mono- or polycyclic, optionally contains fused rings, and is unsubstituted or substituted by one or more identical or different groups L, $Ar^{4,5}$ arylene or heteroarylene that has from 5 to 20 ring atoms, is mono- or polycyclic, optionally contains fused rings, and is unsubstituted or substituted by one or more identical or different groups L, or $CY^1=CY^2$ or —C≡C—, $Y^1$, $Y^2$ H, F, Cl or CN, $W^{1,2}$ S, O or Se, $U^1$ $CR^1R^2$, $SiR^1R^2$, $GeR^1R^2$, $NR^1$ or C=O, $U^2$ $CR^3R^4$, $SiR^3R^4$, $GeR^3R^4$, $NR^3$ or C=O, $R^{1-4}$ H, F, Cl or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^O$—, —$SiR^OR^{OO}$—, —$CF_2$—, —$CR^O=CR^{OO}$—, —$CY^1=CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and the pair of $R^1$ and $R^2$ and/or the pair of $R^3$ and $R^4$ together with the C, Si or Ge atom to which they are attached, may also form a spiro group with 5 to 20 ring atoms which is mono- or polycyclic, does optionally contain fused rings, and is unsubstituted or substituted by one or more identical or different groups L, $R^{T1}$, $R^{T2}$ a carbyl or hydrocarbyl group with 1 to 30 C atoms that is optionally substituted by one or more groups L and optionally comprises one or more hetero atoms, and wherein at least one of $R^{T1}$ and $R^{T2}$ is an electron withdrawing group, L F, Cl, —$NO_2$, —CN, —NC, —NCO, —NCS, —OCN, —SCN, $R^O$, $OR^O$, $SR^O$, —C(=O)$X^O$, —C(=O)$R^O$, —C(=O)—$OR^O$, —O—C(=O)—$R^O$, —$NH_2$, —$NHR^O$, —$NR^OR^{OO}$, —C(=O)$NHR^O$, —C(=O)$NR^OR^{OO}$, —$SO_3R^O$, —$SO_2R^O$, —OH, —$NO_2$, —$CF_3$, —$SF_5$, or optionally substituted silyl, or carbyl or hydrocarbyl with 1 to 30, preferably 1 to 20 C atoms that is optionally substituted and optionally comprises one or more hetero atoms, preferably F, —CN, $R^O$, —$OR^O$, —$SR^O$, —C(=O)—$R^O$, —C(=O)—$OR^O$, —O—C(=O)—$R^O$, —O—C(=O)—$OR^O$, —C(=O)—$NHR^O$, or —C(=O)—$NR^OR^{OO}$, $R^O$, $R^{OO}$ H or straight-chain or branched alkyl with 1 to 20, preferably 1 to 12, C atoms that is optionally fluorinated, $X^O$ halogen, preferably F or Cl, a, b 0, 1, 2 or 3, m 1, 2 or 3.

The invention further relates to novel synthesis methods for preparing compounds of formula I, and novel intermediates used therein.

The invention further relates to the use of compounds of formula I as semiconductor, preferably as electron acceptor or n-type semiconductor, preferably in a semiconducting material, an electronic or optoelectronic device, or a component of an electronic or optoelectronic device.

The invention further relates to the use of compounds of formula I as dyes or pigments.

The invention further relates to a composition comprising one or more compounds of formula I, and further comprising one or more compounds having one or more of a semiconducting, hole or electron transport, hole or electron blocking, insulating, binding, electrically conducting, photoconducting, photoactive or light emitting property.

The invention further relates to a composition comprising one or more compounds of formula I, and further comprising a binder, preferably an electrically inert binder, very preferably an electrically inert polymeric binder.

The invention further relates to a composition comprising a compound of formula I, and further comprising one or more electron donors or p-type semiconductors, preferably selected from conjugated polymers.

The invention further relates to a composition comprising one or more n-type semiconductors, at least one of which is a compound of formula I, and further comprising one or more p-type semiconductors.

The invention further relates to a composition comprising one or more n-type semiconductors, at least one of which is a compound of formula I, and at least one other of which is a fullerene or fullerene derivative, and further comprising one or more p-type semiconductors, preferably selected from conjugated polymers.

The invention further relates to a bulk heterojunction (BHJ) formed from a composition comprising a compound of formula I as electron acceptor or n-type semiconductor, and one or more compounds which are electron donor or p-type semiconductors, and are preferably selected from conjugated polymers.

The invention further relates to the use of a compound of formula I or a composition as described above and below, as semiconducting, charge transporting, electrically conducting, photoconducting, photoactive or light emitting material.

The invention further relates to the use of a compound of formula I or a composition as described above and below, in an electronic or optoelectronic device, or in a component of such a device or in an assembly comprising such a device.

The invention further relates to a semiconducting, charge transporting, electrically conducting, photoconducting, photoactive or light emitting material, comprising a compound of formula I or a composition as described above and below.

The invention further relates to an electronic or optoelectronic device, or a component thereof, or an assembly comprising it, which comprises a compound of formula I or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising one or more compounds of formula I, or comprising a composition or semiconducting material as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells (PSC), laser diodes, Schottky diodes, photoconductors, photodetectors and thermoelectric devices.

Preferred devices are OFETs, OTFTs, OPVs, PSCs, OPDs and OLEDs, in particular OPDs and BHJ OPVs or inverted BHJ OPVs.

The component of the electronic or optoelectronic device includes, without limitation, charge injection layers, charge transport layers, interlayers, planarising layers, antistatic films, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

In addition the compounds of formula I and compositions as described above and below can be used as electrode materials in batteries, or in components or devices for detecting and discriminating DNA sequences.

Terms and Definitions

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5, very preferably ≥10, repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, like for example a unit of formula I or a polymer of formula III or IV or their subformulae, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^{31}$ or $R^{32}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, Sn, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, P, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from F, Cl, —CN, —NC, —NCO, —NCS, —OCN, —SCN, —R$^0$, —OR$^0$, —SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O) NR$^0$R$^{00}$, —SO$_3$R$^0$, —SO$_2$R$^0$, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, wherein X$^0$ is halogen, preferably F or Cl, and R$^0$, R$^{00}$ denote H or straight-chain or branched alkyl with 1 to 20, preferably 1 to 12 C atoms that is optionally fluorinated.

Preferably L is selected from F, —CN, R$^0$, —OR$^0$, —SR$^0$, —C(=O)—R$^0$, —C(=O)—OR$^0$, —O—C(=O)—R$^0$, —O—C(=O)—OR$^0$, —C(=O)—NHR$^0$ and —C(=O)— NR$^0$R$^{00}$ Further preferably L is selected from F or alkyl, alkoxy, oxaalkyl, thioalkyl, fluoroalkyl, fluoroalkoxy, alkylcarbonyl, alkoxycarbonyl, with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

An arylalkyl or heteroarylalkyl group as referred to above and below preferably denotes —(CH$_2$)$_a$-aryl or —(CH$_2$)$_a$-heteroaryl, wherein a is an integer from 1 to 6, preferably 1, and "aryl" and "heteroaryl" have the meanings given above and below. A preferred arylalkyl group is benzyl which is optionally substituted by L.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred aryl and heteroaryl groups are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, 2,5-dithiophene-2',5'-diyl, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal CH$_2$ group is replaced by —O—, can be straight-chain or branched. Particularly preferred straight-chains have 2, 3, 4, 5, 6, 7, 8, 12 or 16 carbon atoms and accordingly denote preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more CH$_2$ groups are replaced by —CH═CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one CH$_2$ group is replaced by —O—, can be straight-chain. Particularly preferred straight-chains are 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-,6-,7-, 8- or 9-oxadecyl, for example.

In an alkyl group wherein one CH$_2$ group is replaced by —O— and one CH$_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more CH$_2$ groups are replaced by —O— and/or —C(O)O— can be straight-chain or branched. It is preferably straight-chain and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one CH$_2$ group is replaced by —S—, is preferably straight-chain thiomethyl (—SCH$_3$), 1-thioethyl (—SCH$_2$CH$_3$), 1-thiopropyl (═—SCH$_2$CH$_2$CH$_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the CH$_2$ group adjacent to the sp$^2$ hybridised vinyl carbon atom is replaced.

A fluoroalkyl group can either be perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 3,7-dimethyloctyl, 3,7,11-trimethyldodecyl, 2-propylpentyl, in particular 2-methylbutyl, 2-methylbutoxy, 2-methylpentoxy, 3-methyl-pentoxy, 2-ethyl-hexoxy, 2-butyloctoxyo, 2-hexyldecoxy, 2-octyldodecoxy, 3,7-dimethyloctoxy, 3,7,11-trimethyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloro-propionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-methylbutyl, 2-ethylhexyl, 2-butyloctyl, 2-hexyldecyl, 2-octyldodecyl, 3,7-dimethyloctyl, 3,7,11-trimethyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the substituents on an aryl or heteroaryl ring are independently of each other selected from primary, secondary or tertiary alkyl, alkoxy, oxaalkyl, thioalkyl, alkylcarbonyl or alkoxycarbonyl with 1 to 30 C atoms, wherein one or more H atoms are optionally replaced by F, or aryl, aryloxy, heteroaryl or heteroaryloxy that is optionally alkylated, alkoxylated, alkylthiolated or esterified and has 4 to 30 ring atoms. Further preferred substituents are selected from the group consisting of the following formulae

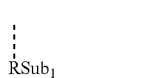
SUB1

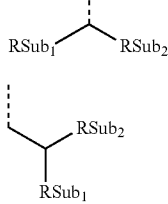
SUB2

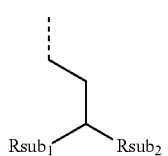
SUB3

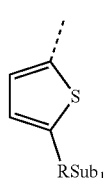
SUB4

-continued

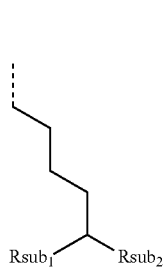
SUB5

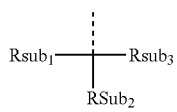
SUB6

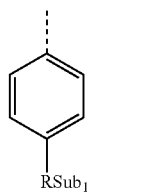
SUB7

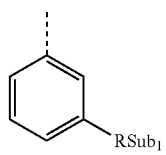
SUB8

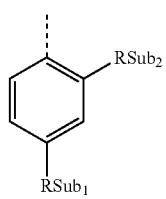
SUB9

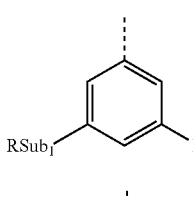
SUB10

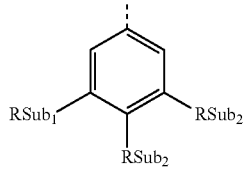
SUB11

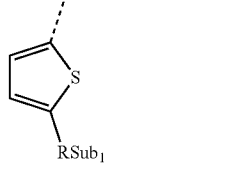
SUB12

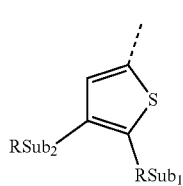
SUB13

-continued

SUB14

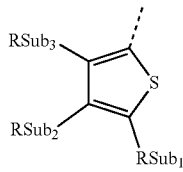

wherein $RSub_{1-3}$ denotes L as defined above and below and where at least, preferably all, of $RSub_{1-3}$ is alkyl, alkoxy, oxaalkyl, thioalkyl, alkylcarbonyl or alkoxycarbonyl with 1 to 24 C atoms, preferably 1 to 20 C atoms, that is optionally fluorinated, and wherein the dashed line denotes the link to the ring to which these groups are attached. Very preferred among these substituents are those wherein all $RSub_{1-3}$ subgroups are identical.

As used herein, if an aryl(oxy) or heteroaryl(oxy) group is "alkylated or alkoxylated", this means that it is substituted with one or more alkyl or alkoxy groups having from 1 to 24 C-atoms and being straight-chain or branched and wherein one or more H atoms are optionally substituted by an F atom.

Above and below, $Y^1$ and $Y^2$ are independently of each other H, F, Cl or CN.

As used herein, —CO—, —C(=O)— and —C(O)— will be understood to mean a carbonyl group, i.e. a group having the structure

As used herein, C=CR¹R² will be understood to mean a group having the structure

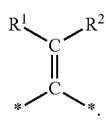

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer or an intermediate is preferably Br or I.

Above and below, the term "mirror image" means a moiety that can be obtained from another moiety by flipping it vertically or horizontally across an external symmetry plane or a symmetry plane extending through the moiety. For example the moiety

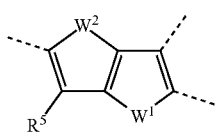

also includes the mirror images

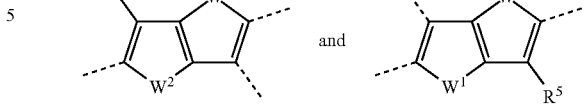

DETAILED DESCRIPTION

The compounds of the present invention are easy to synthesize and exhibit advantageous properties. They show good processibility for the device manufacture process, high solubility in organic solvents, and are especially suitable for large scale production using solution processing methods.

The compounds of formula I are especially suitable as (electron) acceptor or n-type semiconductor, and for the preparation of blends of n-type and p-type semiconductors which are suitable for use in OPD or BHJ OPV devices.

The compounds of formula I are further suitable to replace the fullerene compounds that have hitherto been used as n-type semiconductor in OPV or OPD devices.

Besides, the compounds of formula I show the following advantageous properties:

i) Substitution in positions $R^{1-4}$ and/or $Ar^{2-5}$ for example with solubilising groups enables greater light stability of the bulk heterojunction.

ii) Substitution in positions $R^{1-4}$ and/or $Ar^{2-5}$ for example with solubilising groups enables greater stability towards light illumination of the bulk heterojunction through mediation of the crystallisation and/or phase separation kinetic, thus stabilising the initial equilibrium thermodynamics in the BHJ.

iii) Substitution in positions $R^{1-4}$ and/or $Ar^{2-5}$ for example with solubilising groups enables greater thermal stability of the bulk heterojunction through mediation of the crystallisation and/or phase separation kinetic, thus stabilising the initial equilibrium thermodynamics in the BHJ.

iv) Compared to previously disclosed n-type OSCs for OPV/OPD application, the compounds of formula I provide the advantage that they enable further optimization of the HOMO and LUMO levels of the polycyclic unit through substitution, and careful selection of the $Ar^{2-5}$ units can give improved light absorption.

v) Further optimization of the HOMO and LUMO levels of the polycyclic unit in formula I through substitution and/or careful selection of the $Ar^{2-5}$ units can increase the open circuit potential ($V_{oc}$).

vi) When using the compounds as n-type OSC in a composition with a p-type OSC in the photoactive layer of an OPV or OPD, additional fine-tuning of the HOMO and LUMO levels of the polycyclic unit in formula I, for example through substitution and/or careful selection of the $Ar^{2-5}$ units, can reduce the energy loss in the electron transfer process between the n-type acceptor and the p-type donor material in the photoactive layer.

vii) Substitution in positions $R^{1-4}$ and/or $Ar^{2-5}$ can enable higher solubility in non-halogenated solvents due to the increased number of solubilising groups.

The synthesis of the compounds of formula I can be achieved based on methods that are known to the skilled person and described in the literature, as will be further illustrated herein.

Preferred compounds of formula I are those wherein $W^1$ and $W^2$ denote S or Se, very preferably S.

Further preferred compounds of formula I are those wherein $W^1$ and $W^2$ have the same meaning, and preferably both denote S or Se, very preferably S.

Further preferred compounds of formula I are those wherein $W^1$ and $W^2$ have different meaning, and preferably one denotes S and the other Se.

In the compounds of formula I $Ar^4$ and $Ar^5$ are preferably arylene or heteroarylene as defined above.

Preferred groups $Ar^{2-5}$ in formula I are selected from the following formulae and their mirror images:

$Ar^2$

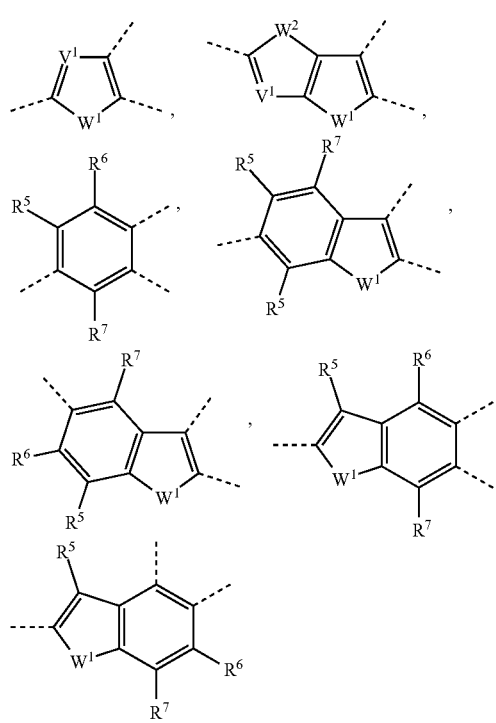

$Ar^3$

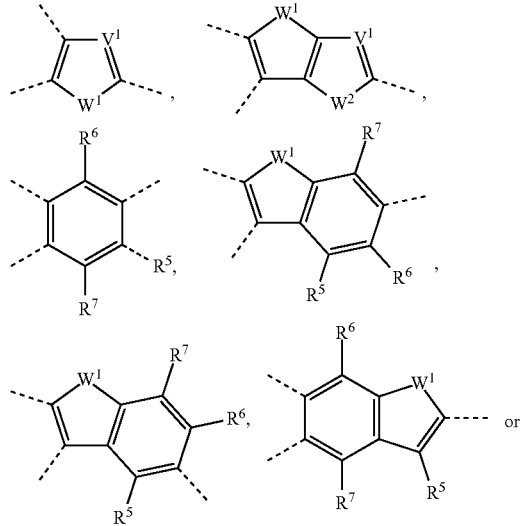

$Ar^4$,
$Ar^5$

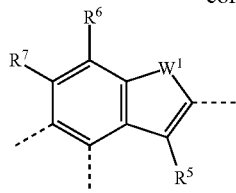

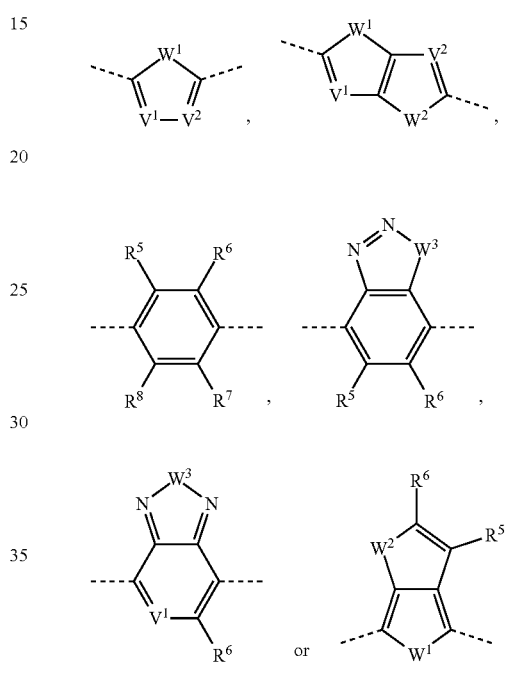

wherein the individual radicals, independently of each other and on each occurrence identically or differently, have the following meanings $W^{1,2}$ S, O or Se, $W^3$ $NR^0$, S, O or Se, $V^1$ $CR^5$ or N, $V^2$ $CR^6$ or N, $R^{5-10}$ H, F, Cl, CN or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0=CR^{00}$—, —$CY^1=CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L as defined above and below.

Very preferred groups Ar² and A³ in formula I are selected from the following formulae and their mirror images:
Ar²
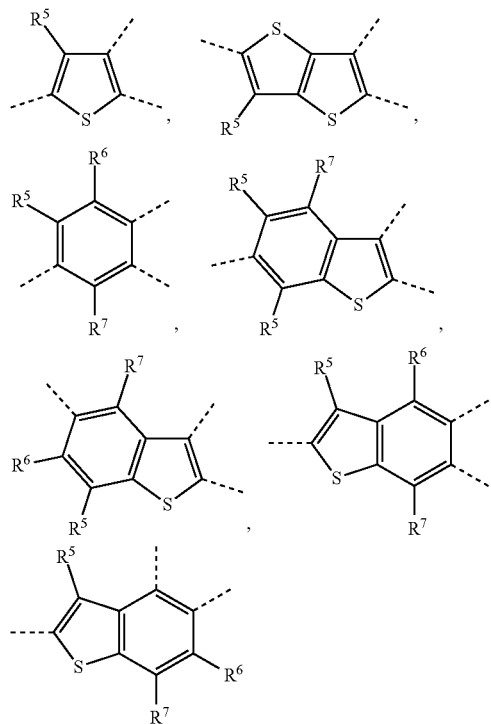
Ar³
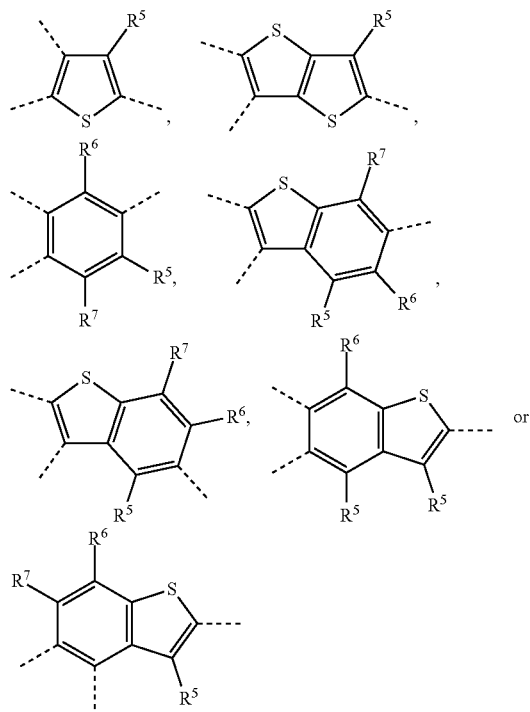
wherein $R^{5-10}$ have the meanings given above and below.
Very preferred groups Ar⁴ and Ar⁵ in formula I are selected from the following formulae and their mirror images.
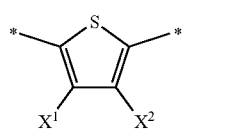 AR1
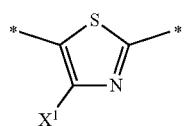 AR2
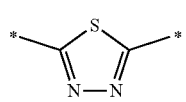 AR3
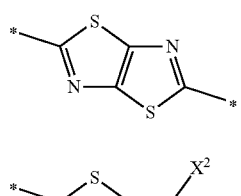 AR4
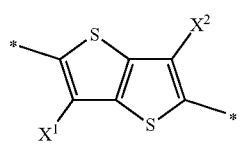 AR5
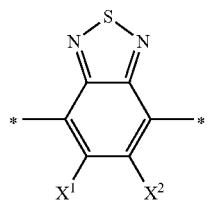 AR6
 AR7
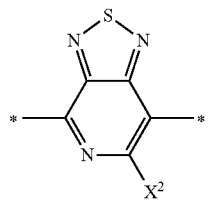 AR8
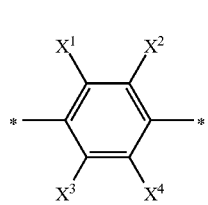 AR9
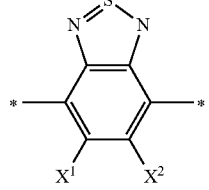

-continued

AR10

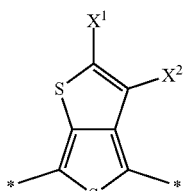

AR11

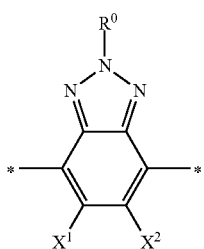

wherein $X^1$, $X^2$, $X^3$ and $X^4$ have one of the meanings given for $R^1$ above and below, and preferably denote H, F, Cl, —CN, $R^0$, $OR^0$ or $C(=O)OR^0$.

Preferred formulae AR1, AR2, AR5, AR6, AR7, AR8, AR9, AR10 and AR11 are those containing at least one, preferably one, two or four substituents $X^{1-4}$ selected from F and Cl, very preferably F.

Preferably the groups $R^{T1}$ and $R^{T2}$ in formula I are selected from H, F, Cl, Br, —$NO_2$, —CN, —$CF_3$, R*, —$CF_2$—R*, —O—R*, —S—R*, —$SO_2$—R*, —$SO_3$—R*, —C(=O)—H, —C(=O)—R*, —C(=S)—R*, —C(=O)—$CF_2$—R*, —C(=O)—OR*, —C(=S)—OR*, —O—C(=O)—R*, —O—C(=S)—R*, —C(=O)—SR*, —S—C(=O)—R*, —C(=O)NR*R**, —NR*—C(=O)—R*, —NHR*,—NR*R**, —CR*=CR*R**, —C=C—R*, —C≡C—SiR*RR*, —SiR*RR*, —CH=CH(CN), —CH=C$(CN)_2$, —C(CN)=C$(CN)_2$, —CH=C(CN)($R^a$), CH=C(CN)—C(=O)—OR*, —CH=C(CO—OR*$)_2$, —CH=C(CO—NR*R**$)_2$, and the group consisting of the following formulae

T1

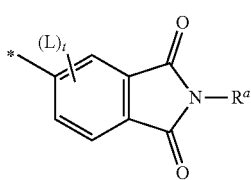

T2

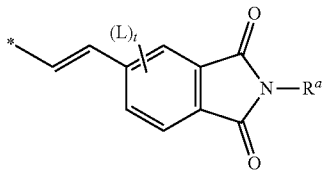

T3

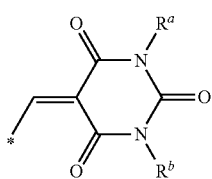

T4

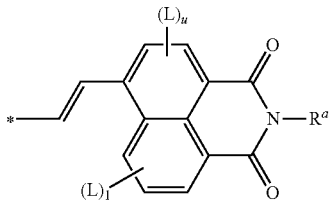

T5

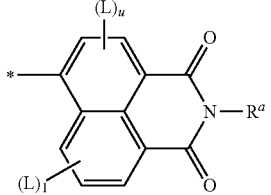

T6

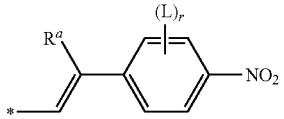

T7

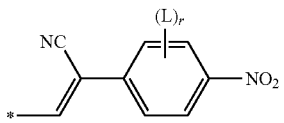

T8

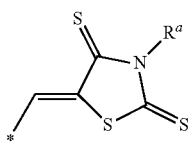

T9

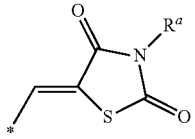

T10

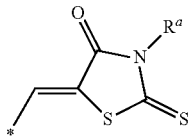

T11

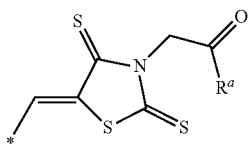

T12

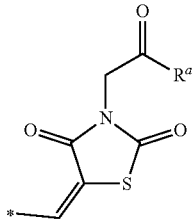

T13 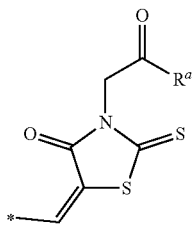
T14 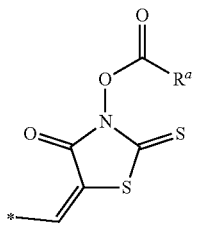
T15 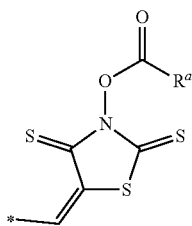
T16 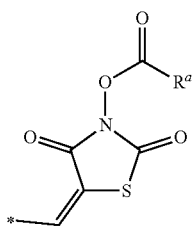
T17 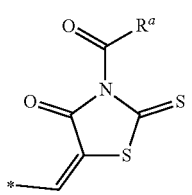
T18 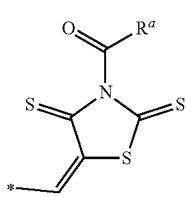
T19 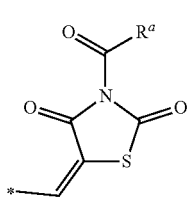
T20 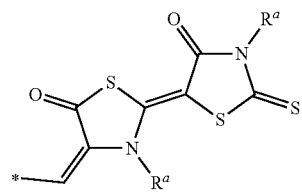
T21 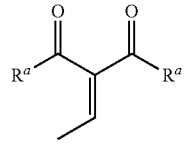
T22 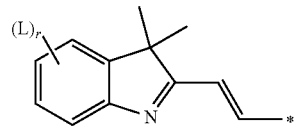
T23 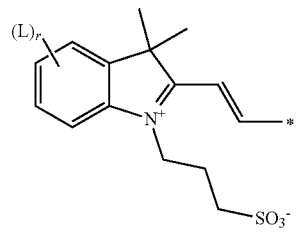
T24 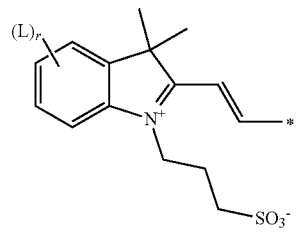
T25 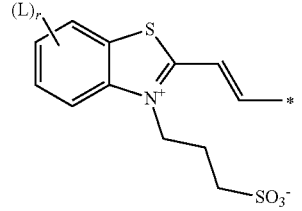
T26 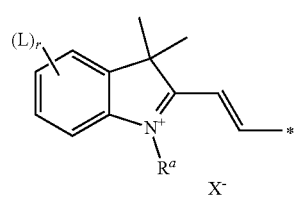
T27 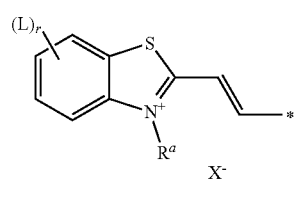
T28 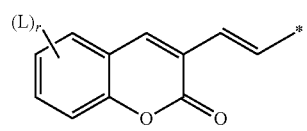

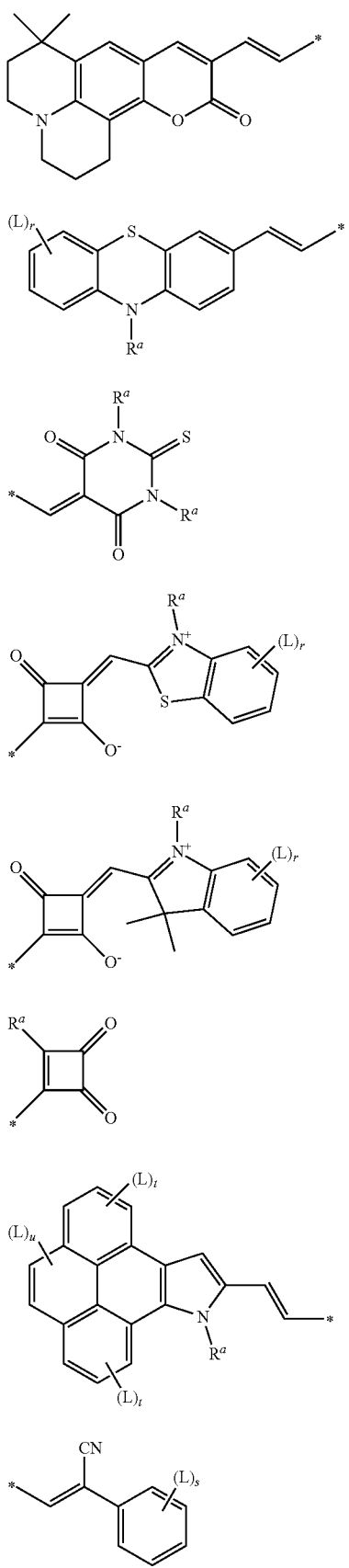
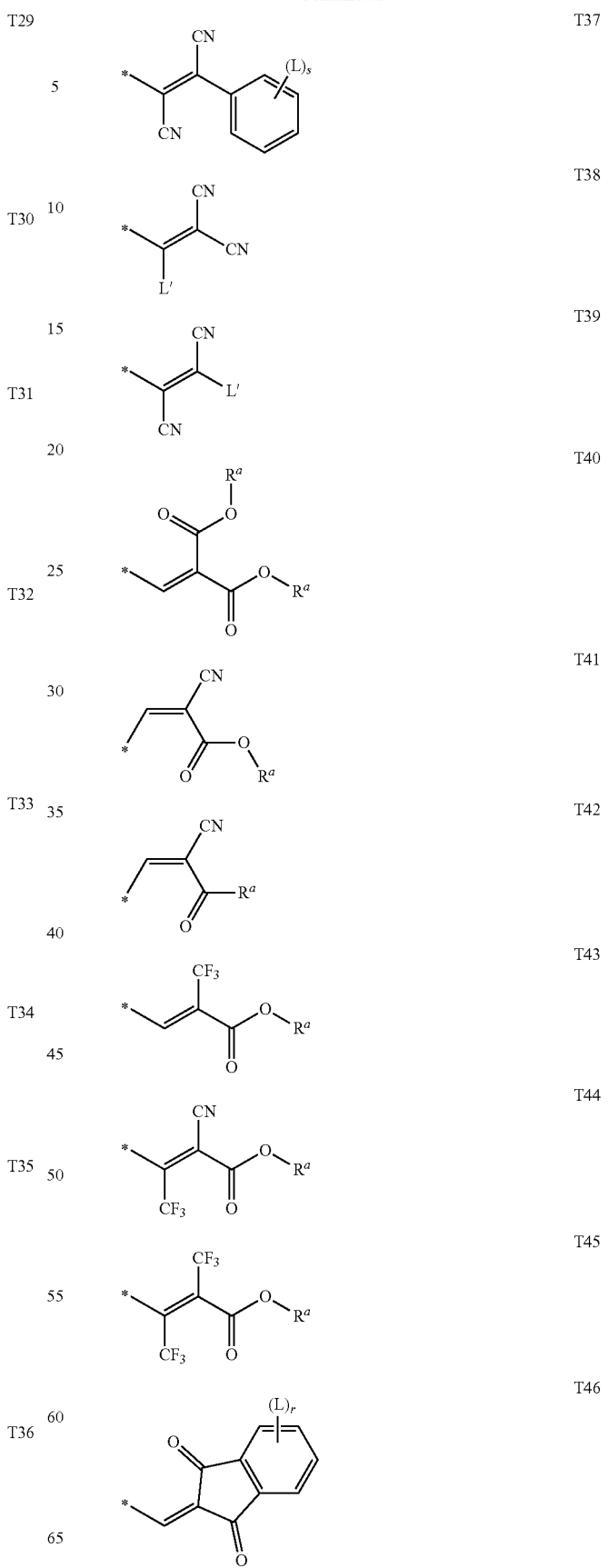

-continued

T47 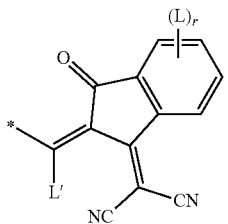

T48 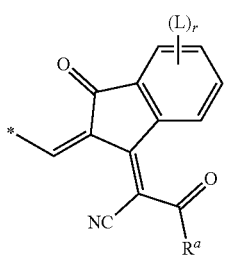

T49 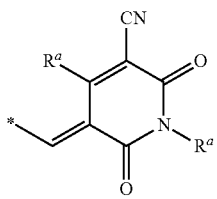

T50 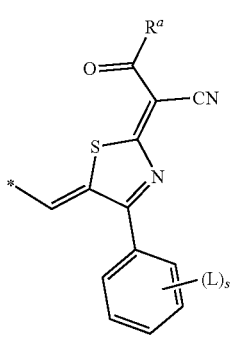

T51 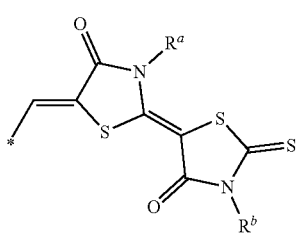

T52 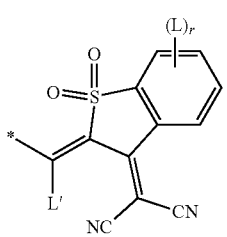

-continued

T53 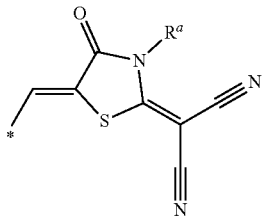

wherein the individual radicals, independently of each other and on each occurrence identically or differently, have the following meanings $R^a$, $R^b$ aryl or heteroaryl, each having from 4 to 30 ring atoms, optionally containing fused rings and being unsubstituted or substituted with one or more groups L, or one of the meanings given for L, R*, R, R* alkyl with 1 to 20 C atoms which is straight-chain, branched or cyclic, and is unsubstituted, or substituted with one or more F or Cl atoms or CN groups, or perfluorinated, and in which one or more C atoms are optionally replaced by —O—, —S—, —C(=O)—, —C(=S)—, —SiR°R°°—, —NR°R°°—, —CHR°=CR°°— or —C≡C-such that O- and/or S-atoms are not directly linked to each other, L F, Cl, —NO$_2$, —CN, —NC, —NCO, —NCS, —OCN, —SCN, R°, OR°, SR°, —C(=O)X°, —C(=O)R°, —C(=O)—OR°, —O—C(=O)—R°, —NH$_2$, —NHR°, —NR°R°°, —C(=O)NHR°, —C(=O)NR°R°°, —SO$_3$R°, —SO$_2$R°, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, preferably F, —CN, R°, —OR°, —SR°, —C(=O)—R°, —C(=O)—OR°, —O—C(=O)—R°, —O—C(=O)—OR°, —C(=O)—NHR°, —C(=O)—NR°R°°, L' H or one of the meanings of L, R°, R°° H or straight-chain or branched alkyl with 1 to 20, preferably 1 to 12 C atoms that is optionally fluorinated, $Y^1$, $Y^2$ H, F, Cl or CN, X° halogen, preferably F or Cl, r 0, 1, 2, 3 or 4, s 0, 1, 2, 3, 4 or 5, t 0, 1, 2 or 3, u 0, 1 or 2, and wherein at least one of $R^{T1}$ and $R^{T2}$ denotes an electron withdrawing group.

Preferred compounds of formula I are those wherein both of $R^{T1}$ and $R^{T2}$ denote an electron withdrawing group.

Preferred electron withdrawing groups $R^{T1}$ and $R^{T2}$ are selected from —CN, —C(=O)—OR*, —C(=S)—OR*, —CH=CH(CN), —CH=C(CN)$_2$, —C(CN)=C(CN)$_2$, —CH=C(CN)(R$^a$), CH=C(CN)—C(=O)—OR*, —CH=C(CO—OR*)$_2$, and formulae T1-T53.

Very preferred groups $R^{T1}$ and $R^{T2}$ are selected from the following formulae T10 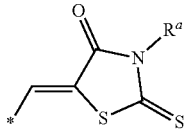

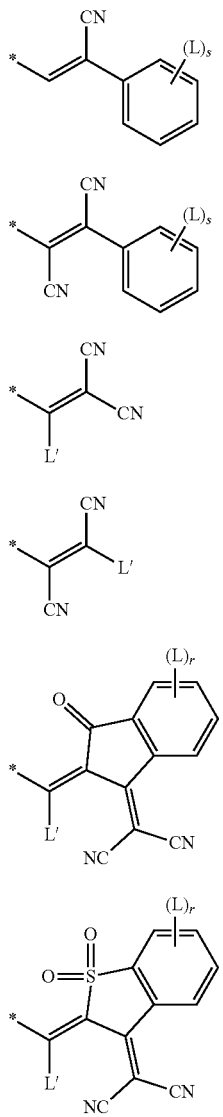

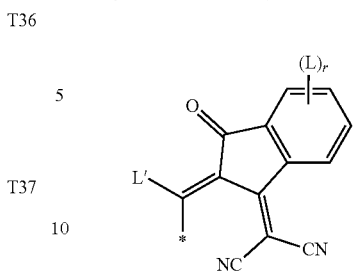

T36

T37

T38

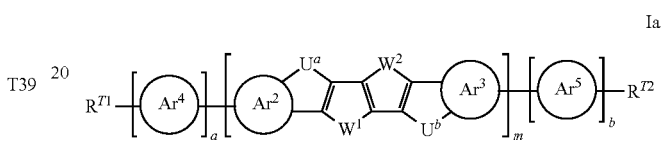

wherein $U^a$ denotes $CR^1R^2$, $SiR^1R^2$ or $GeR^1R^2$, preferably $CR^1R^2$ or $SiR^1R^2$, very preferably $CR^1R^2$, $U^b$ denotes $CR^3R^4$, $SiR^3R^4$ or $GeR^3R^4$, preferably $CR^3R^4$ or $SiR^3R^4$, very preferably $CR^3R^4$, and $R^{1-4}$, $Ar^{1-5}$, $R^{T1,T2}$, a, b and m have the meanings or preferred meanings given above and below.

In the compounds of formula I and Ia preferably $R^{1-4}$ are different from H.

In a preferred embodiment of the present invention, $R^{1-4}$ in formula I and Ia are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms.

In another preferred embodiment of the present invention, $R^{1-4}$ in formula I and Ia are selected from mono- or polycyclic aryl or heteroaryl, each of which is optionally substituted with one or more groups L as defined in formula I and has 4 to 30 ring atoms, and wherein two or more rings may be fused to each other or connected with each other by a covalent bond.

In a preferred embodiment of the present invention, $R^{5-10}$ in formula I and Ia are H.

In another preferred embodiment of the present invention, at least one of $R^{5-10}$ in formula I and Ia is different from H.

In a preferred embodiment of the present invention, $R^{5-10}$ in formula I and Ia, when being different from H, are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated.

In another preferred embodiment of the present invention, $R^{5-10}$ in formula I and Ia, when being different from H, are selected from aryl or heteroaryl, each of which is optionally substituted with one or more groups L as defined in formula I and has 4 to 30 ring atoms.

Preferred aryl and heteroaryl groups $R^{1-10}$ are selected from the following formulae

T39

T47

T52

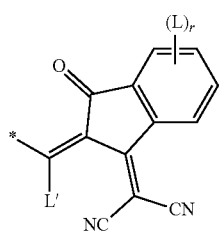

wherein L, L', $R^a$, r and s have the meanings given above and below, and L' is H or has one of the meanings given for L. Preferably in these formulae L' is H. Further preferably in these formulae r is 0.

The above formulae T1-T53 are meant to also include their respective E- or Z-stereoisomer with respect to the C=C bond in α-position to the adjacent group $Ar^4$ or $Ar^5$, thus for example the group -continued

[Structures C21, C22, C23, C24 shown with R₁₁–R₁₆ substituents on fused heterocyclic rings containing O, Se, N]

[Structure C25: bithiophene with R₁₁, R₁₂ substituents]

[Structure C26: bithiazole with R₁₁, R₁₂ substituents]

[Structure C27: bithiazole isomer with R₁₁, R₁₂ substituents]

wherein R$^{11-17}$, independently of each other, and on each occurrence identically or differently, denote H or have one of the meanings given for L in formula I or one of its preferred meanings as given above and below.

Very preferred aryl and heteroaryl groups R$^{1-10}$ are selected from the following formulae

[Structures C1-1, C4-1, C5-1, C7-1, C10-1 shown]

wherein R$^{11-15}$ are as defined above. Most preferred aryl groups R₁-R₁₀ are selected from formulae SUB7-SUB14 as defined above.

In another preferred embodiment one or more of R$^{1-10}$ denote a straight-chain, branched or cyclic alkyl group with 1 to 50, preferably 2 to 50, very preferably 2 to 30, more preferably 2 to 24, most preferably 2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms and very preferably is selected from formulae SUB1-6.

Further preferred cationic groups are selected from the group consisting of the following formulae

[Imidazolium and 1H-pyrazolium cation structures with R¹', R²', R⁴' substituents]

imidazolium        1H-pyrazolium

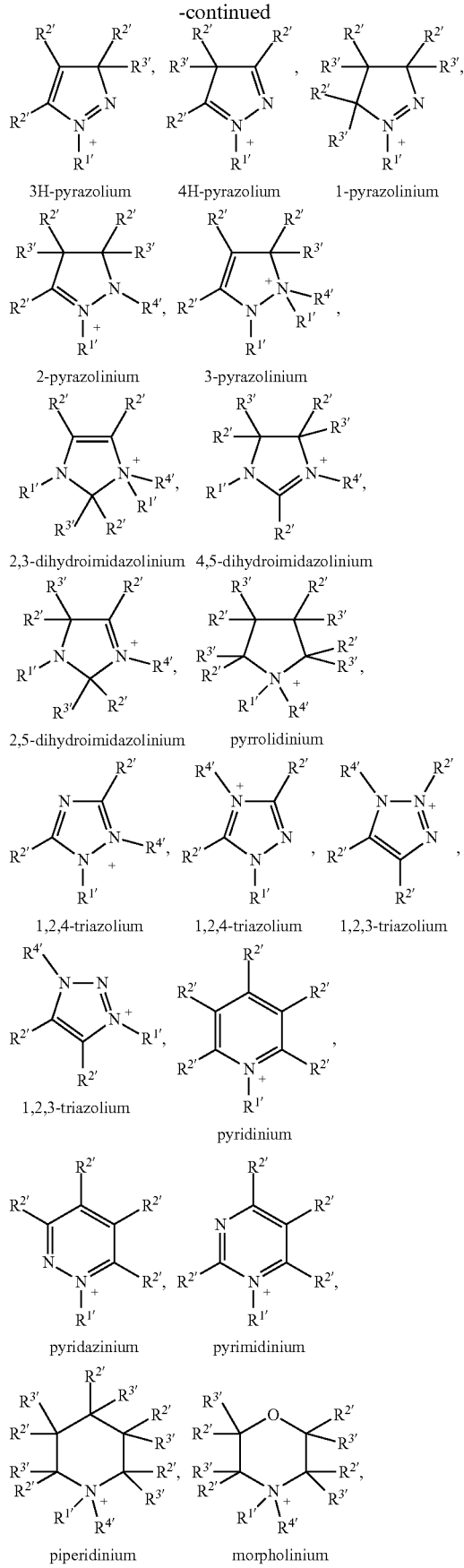
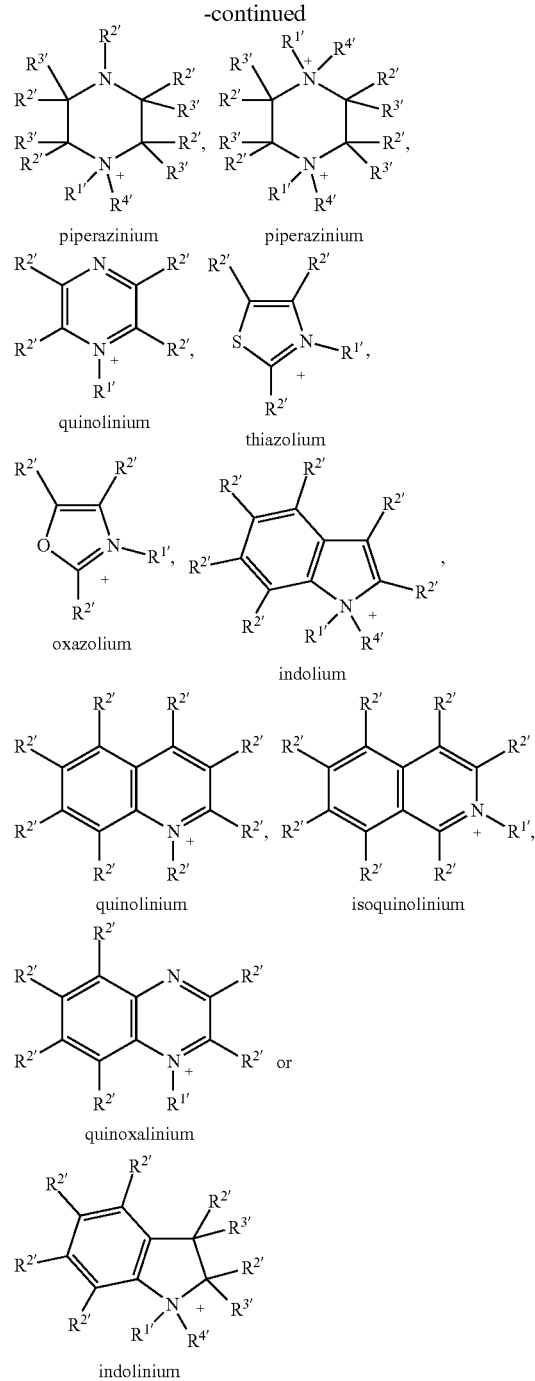

wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents L as defined above, or denote a link to the respective group $R^{1-10}$.

In the above cationic groups of the above-mentioned formulae any one of the groups $R^{1'}$, $R^{2'}$, $R^{3'}$ and $R^{4'}$ (if they replace a $CH_3$ group) can denote a link to the respective group $R^{1-10}$, or two neighbored groups $R^{1'}$, $R^{2'}$, $R^{3'}$ or $R^{4'}$ (if they replace a $CH_2$ group) can denote a link to the respective group $R^1$.

The anionic group is preferably selected from the group consisting of borate, imide, phosphate, sulfonate, sulfate, succinate, naphthenate or carboxylate, very preferably from phosphate, sulfonate or carboxylate.

In a preferred embodiment of the present invention the groups $R^{T1}$ and $R^{T2}$ in formula I are selected from alkyl with 1 to 16 C atoms which is straight-chain, branched or cyclic, and is unsubstituted, substituted with one or more F or Cl atoms or CN groups, or perfluorinated, and in which one or more C atoms are optionally replaced by —O—, —S—, —C(O)—, —C(S)—, —SiR°R°°—, —NR°R°°—, —CHR°=CR°°— or —C≡C— such that O- and/or S-atoms are not directly linked to each other.

Further preferred compounds of formula I are selected from the following preferred embodiments or any combination thereof:

$W^1$ and $W^2$ are S or Se, preferably S,
$U^1$ is $CR^1R^2$ or $SiR^1R^2$ and $U^2$ is $CR^3R^4$ or $SiR^3R^4$,
$U^1$ is $CR^1R^2$ and $U^2$ is $CR^3R^4$,
$V^1$ is $CR^5$ and $V^2$ is $CR^6$,
$V^1$ is $CR^5$ and $V^2$ is N,
$V^1$ and $V^2$ are N,
m=1,
a=b=1 or 2, preferably 1,
a=b=0,
in one or both of $Ar^2$ and $Ar^3$ all substituents $R^{5-7}$ are H,
in one or both of $Ar^2$ and $Ar^3$ at least one, preferably one or two of $R^{5-7}$ are different from H, and very preferably denote F,
in one or both of $Ar^4$ and $Ar^5$ all substituents $R^{5-8}$ are H,
in one or both of $Ar^4$ and $Ar^5$ at least one, preferably one or two of $R^{5-8}$ are different from H,
$Ar^4$ and $Ar^5$ denote thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene, benzotriazole or thiadiazole[3,4-c]pyridine, which are substituted by $X^1$, $X^2$, $X^3$ and $X^4$ as defined above,
$Ar^4$ and $Ar^5$ denote thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene, benzotriazole or thiadiazole[3,4-c]pyridine, wherein $X^1$, $X^2$, $X^3$ and $X^4$ are H,
$Ar^4$ and $Ar^5$ denote thiophene, thiazole, thieno[3,2-b]thiophene, thiazolothiazole, benzene, 2,1,3-benzothiadiazole, 1,2,3-benzothiadiazole, thieno[3,4-b]thiophene, benzotriazole or thiadiazole[3,4-c]pyridine, wherein one or more of $X^1$, $X^2$, $X^3$ and $X^4$ are different from H,
$R^1$, $R^2$, $R^3$ and $R^4$ are different from H,
$R^1$, $R^2$, $R^3$ and $R^4$ are selected from H, F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated, or alkyl or alkoxy having 1 to 12 C atoms that is optionally fluorinated,
$R^1$, $R^2$, $R^3$ and $R^4$ are selected from aryl or heteroaryl, each of which is optionally substituted with one or more groups L as defined in formula I and has 4 to 30 ring atoms, preferably from phenyl that is optionally substituted, preferably in 4-position or in 3,5-positions, with alkyl or alkoxy having 1 to 20 C atoms, preferably 1 to 16 C atoms, very preferably 4-alkylphenyl wherein alkyl is $C_1$-16 alkyl, most preferably 4-methylphenyl, 4-hexylphenyl, 4-octylphenyl or 4-dodecylphenyl, or 4-alkoxyphenyl wherein alkoxy is $C_1$-16 alkoxy, most preferably 4-hexyloxyphenyl, 4-octyloxyphenyl or 4-dodecyloxyphenyl or 3,5-dialkylphenyl wherein alkyl is $C_1$-16 alkyl, most preferably 3,5-dihexylphenyl or 3,5-dioctylphenyl or 3,5-dialkoxyphenyl wherein alkoxy is $C_1$-16 alkoxy, most preferably 3,5-dihexyloxyphenyl or 3,5-dioctyloxyphenyl, or 4-thioalkylphenyl wherein thioalkyl is $C_1$-16 thioalkyl, most preferably 4-thiohexylphenyl, 4-thiooctylphenyl or 4-thiododecylphenyl or 3,5-dithioalkylphenyl wherein thioalkyl is $C_1$-16 thioalkyl, most preferably 3,5-dithiohexylphenyl or 3,5-dithiooctylphenyl,
L' is H,
L, L' denote F, Cl, CN, $NO_2$, or alkyl or alkoxy with 1 to 16 C atoms that is optionally fluorinated,
r is 2 and L is F, Cl, CN, $NO_2$, or alkyl or alkoxy with 1 to 16 C atoms that is optionally fluorinated,
r is 1 and L is F, Cl, CN, $NO_2$, or alkyl or alkoxy with 1 to 16 C atoms that is optionally fluorinated,
r is 4 and L is F, Cl, CN, $NO_2$, or alkyl or alkoxy with 1 to 16 C atoms that is optionally fluorinated,
$R^{5-10}$, when being different from H, are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated, preferably from F, or alkyl or alkoxy having 1 to 16 C atoms that is optionally fluorinated.

Preferred compounds of formula I are selected from the following subformulae

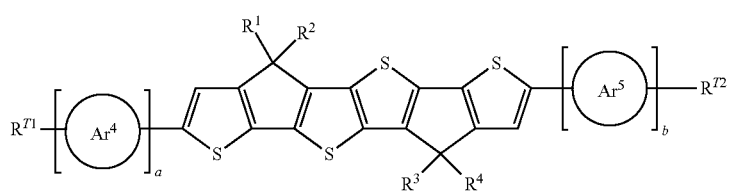

I1

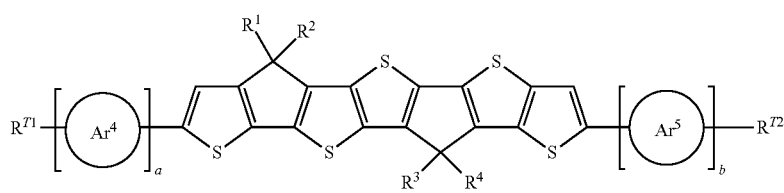

I2

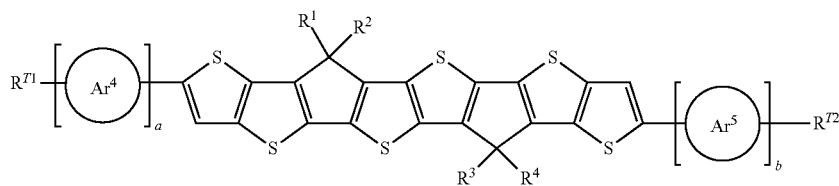

-continued
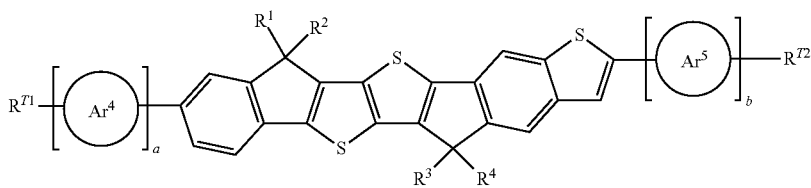
I11
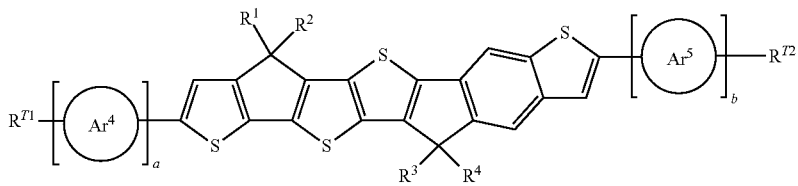
I12
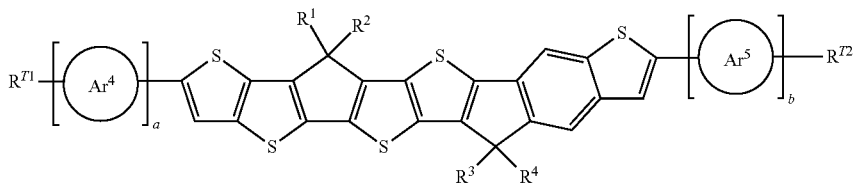
I13
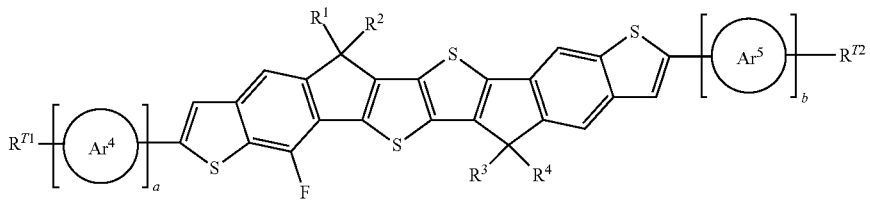
I14
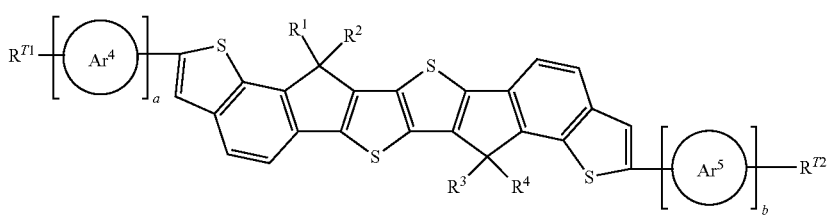
I15
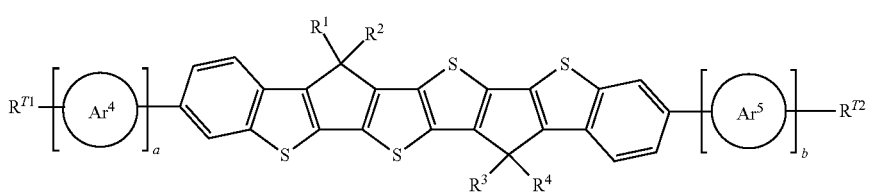
I16
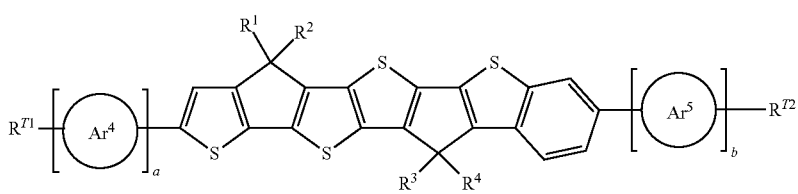
I17
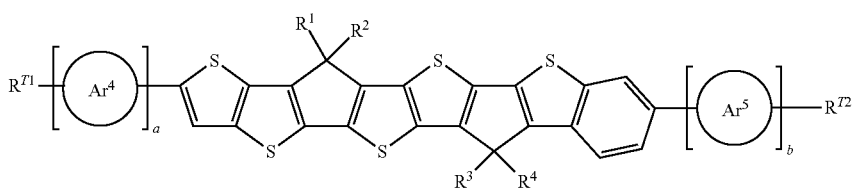
I18

-continued

I19

[Structure: R^{T1}—[Ar^4]_a—[fused ring system with R^1, R^2 at top carbon; S, S bridges; central S; R^3, R^4 at bottom carbon]—[Ar^5]_b—R^{T2}]

wherein $R^1$, $R^2$, $R^3$, $R^4$, $R^{T1}$, $R^{T2}$, $Ar^4$, $Ar^5$, a and b have the meanings given above.

Very preferred compounds of formula I are selected from the following groups:

1a) The group consisting of compounds of formula I1, wherein $Ar^4$ and $Ar^5$ are selected from formulae AR1-AR11, a and b are 0, 1 or 2, and $R^{T1}$ and $R^{T2}$ are selected from formula T10.
1b) The group consisting of compounds of formula I1, wherein $Ar^4$ and $Ar^5$ are selected from formulae AR1-AR11, a and b are 0, 1 or 2, and $R^{T1}$ and $R^{T2}$ are selected from formula T36.
1c) The group consisting of compounds of formula I1, wherein $Ar^4$ and $Ar^5$ are selected from formulae AR1-AR11, a and b are 0, 1 or 2, and $R^{T1}$ and $R^{T2}$ are selected from formula T37.
1d) The group consisting of compounds of formula I1, wherein $Ar^4$ and $Ar^5$ are selected from formulae AR1-AR11, a and b are 0, 1 or 2, and $R^{T1}$ and $R^{T2}$ are selected from formula T38.
1e) The group consisting of compounds of formula I1, wherein $Ar^4$ and $Ar^5$ are selected from formulae AR1-AR11, a and b are 0, 1 or 2, and $R^{T1}$ and $R^{T2}$ are selected from formula T39.
1f) The group consisting of compounds of formula I1, wherein $Ar^4$ and $Ar^5$ are selected from formulae AR1-AR11, a and b are 0, 1 or 2, and $R^{T1}$ and $R^{T2}$ are selected from formula T47.
2a) The group consisting of compounds of formula I2, wherein $Ar^4$ and $Ar^5$ are selected from formulae AR1-AR11, a and b are 0, 1 or 2, and $R^{T1}$ and $R^{T2}$ are selected from formula T10.
2b) The group consisting of compounds of formula I2, wherein $Ar^4$ and $Ar^5$ are selected from formulae AR1-AR11, a and b are 0, 1 or 2, and $R^{T1}$ and $R^{T2}$ are selected from formula T36.
2c) The group consisting of compounds of formula I2, wherein $Ar^4$ and $Ar^5$ are selected from formulae AR1-AR11, a and b are 0, 1 or 2, and $R^{T1}$ and $R^{T2}$ are selected from formula T37.
2d) The group consisting of compounds of formula I2, wherein $Ar^4$ and $Ar^5$ are selected from formulae AR1-AR11, a and b are 0, 1 or 2, and $R^{T1}$ and $R^{T2}$ are selected from formula T38.
2e) The group consisting of compounds of formula I2, wherein $Ar^4$ and $Ar^5$ are selected from formulae AR1-AR11, a and b are 0, 1 or 2, and $R^{T1}$ and $R^{T2}$ are selected from formula T39.
2f) The group consisting of compounds of formula I2, wherein $Ar^4$ and $Ar^5$ are selected from formulae AR1-AR11, a and b are 0, 1 or 2, and $R^{T1}$ and $R^{T2}$ are selected from formula T47.
3a) The group consisting of compounds of formula I3, wherein $Ar^4$ and $Ar^5$ are selected from formulae AR1-AR11, a and b are 0, 1 or 2, and $R^{T1}$ and $R^{T2}$ are selected from formula T10.
3b) The group consisting of compounds of formula I3, wherein $Ar^4$ and $Ar^5$ are selected from formulae AR1-AR11, a and b are 0, 1 or 2, and $R^{T1}$ and $R^{T2}$ are selected from formula T36.
3c) The group consisting of compounds of formula I3, wherein $Ar^4$ and $Ar^5$ are selected from formulae AR1-AR11, a and b are 0, 1 or 2, and $R^{T1}$ and $R^{T2}$ are selected from formula T37.
3d) The group consisting of compounds of formula I3, wherein $Ar^4$ and $Ar^5$ are selected from formulae AR1-AR11, a and b are 0, 1 or 2, and $R^{T1}$ and $R^{T2}$ are selected from formula T38.
3e) The group consisting of compounds of formula I3, wherein $Ar^4$ and $Ar^5$ are selected from formulae AR1-AR11, a and b are 0, 1 or 2, and $R^{T1}$ and $R^{T2}$ are selected from formula T39.
3f) The group consisting of compounds of formula I3, wherein $Ar^4$ and $Ar^5$ are selected from formulae AR1-AR11, a and b are 0, 1 or 2, and $R^{T1}$ and $R^{T2}$ are selected from formula T47.
4a) The group consisting of compounds of formula I4, wherein $Ar^4$ and $Ar^5$ are selected from formulae AR1-AR11, a and b are 0, 1 or 2, and $R^{T1}$ and $R^{T2}$ are selected from formula T10.
4b) The group consisting of compounds of formula I4, wherein $Ar^4$ and $Ar^5$ are selected from formulae AR1-AR11, a and b are 0, 1 or 2, and $R^{T1}$ and $R^{T2}$ are selected from formula T36.
4c) The group consisting of compounds of formula I4, wherein $Ar^4$ and $Ar^5$ are selected from formulae AR1-AR11, a and b are 0, 1 or 2, and $R^{T1}$ and $R^{T2}$ are selected from formula T37.
4d) The group consisting of compounds of formula I4, wherein $Ar^4$ and $Ar^5$ are selected from formulae AR1-AR11, a and b are 0, 1 or 2, and $R^{T1}$ and $R^{T2}$ are selected from formula T38.
4e) The group consisting of compounds of formula I4, wherein $Ar^4$ and $Ar^5$ are selected from formulae AR1-AR11, a and b are 0, 1 or 2, and $R^{T1}$ and $R^{T2}$ are selected from formula T39.
4f) The group consisting of compounds of formula I4, wherein $Ar^4$ and $Ar^5$ are selected from formulae AR1-AR11, a and b are 0, 1 or 2, and $R^{T1}$ and $R^{T2}$ are selected from formula T47.
5a) The group consisting of compounds of formula I5, wherein $Ar^4$ and $Ar^5$ are selected from formulae AR1-AR11, a and b are 0, 1 or 2, and $R^{T1}$ and $R^{T2}$ are selected from formula T10.
5b) The group consisting of compounds of formula I5, wherein $Ar^4$ and $Ar^5$ are selected from formulae AR1-AR11, a and b are 0, 1 or 2, and $R^{T1}$ and $R^{T2}$ are selected from formula T36.
5c) The group consisting of compounds of formula I5, wherein $Ar^4$ and $Ar^5$ are selected from formulae AR1-AR11, a and b are 0, 1 or 2, and $R^{T1}$ and $R^{T2}$ are selected from formula T37.

5d) The group consisting of compounds of formula I5, wherein $Ar^4$ and $Ar^5$ are selected from formulae AR1-AR11, a and b are 0, 1 or 2, and $R^{T1}$ and $R^{T2}$ are selected from formula T38.

5e) The group consisting of compounds of formula I5, wherein $Ar^4$ and $Ar^5$ are selected from formulae AR1-AR11, a and b are 0, 1 or 2, and $R^{T1}$ and $R^{T2}$ are selected from formula T39.

5f) The group consisting of compounds of formula I5, wherein $Ar^4$ and $Ar^5$ are selected from formulae AR1-AR11, a and b are 0, 1 or 2, and $R^{T1}$ and $R^{T2}$ are selected from formula T47.

6a) The group consisting of compounds of formula I6, wherein $Ar^4$ and $Ar^5$ are selected from formulae AR1-AR11, a and b are 0, 1 or 2, and $R^{T1}$ and $R^{T2}$ are selected from formula T10.

6b) The group consisting of compounds of formula I6, wherein $Ar^4$ and $Ar^5$ are selected from formulae AR1-AR11, a and b are 0, 1 or 2, and $R^{T1}$ and $R^{T2}$ are selected from formula T36.

6c) The group consisting of compounds of formula I6, wherein $Ar^4$ and $Ar^5$ are selected from formulae AR1-AR11, a and b are 0, 1 or 2, and $R^{T1}$ and $R^{T2}$ are selected from formula T37.

6d) The group consisting of compounds of formula I6, wherein $Ar^4$ and $Ar^5$ are selected from formulae AR1-AR11, a and b are 0, 1 or 2, and $R^{T1}$ and $R^{T2}$ are selected from formula T38.

6e) The group consisting of compounds of formula I6, wherein $Ar^4$ and $Ar^5$ are selected from formulae AR1-AR11, a and b are 0, 1 or 2, and $R^{T1}$ and $R^{T2}$ are selected from formula T39.

6f) The group consisting of compounds of formula I6, wherein $Ar^4$ and $Ar^5$ are selected from formulae AR1-AR11, a and b are 0, 1 or 2, and $R^{T1}$ and $R^{T2}$ are selected from formula T47.

7a) The group consisting of compounds of formula I7, wherein $Ar^4$ and $Ar^5$ are selected from formulae AR1-AR11, a and b are 0, 1 or 2, and $R^{T1}$ and $R^{T2}$ are selected from formula T10.

7b) The group consisting of compounds of formula I7, wherein $Ar^4$ and $Ar^5$ are selected from formulae AR1-AR11, a and b are 0, 1 or 2, and $R^{T1}$ and $R^{T2}$ are selected from formula T36.

7c) The group consisting of compounds of formula I7, wherein $Ar^4$ and $Ar^5$ are selected from formulae AR1-AR11, a and b are 0, 1 or 2, and $R^{T1}$ and $R^{T2}$ are selected from formula T37.

7d) The group consisting of compounds of formula I7, wherein $Ar^4$ and $Ar^5$ are selected from formulae AR1-AR11, a and b are 0, 1 or 2, and $R^{T1}$ and $R^{T2}$ are selected from formula T38.

7e) The group consisting of compounds of formula I7, wherein $Ar^4$ and $Ar^5$ are selected from formulae AR1-AR11, a and b are 0, 1 or 2, and $R^{T1}$ and $R^{T2}$ are selected from formula T39.

7f) The group consisting of compounds of formula I7, wherein $Ar^4$ and $Ar^5$ are selected from formulae AR1-AR11, a and b are 0, 1 or 2, and $R^{T1}$ and $R^{T2}$ are selected from formula T47.

8a) The group consisting of compounds of formula I8, wherein $Ar^4$ and $Ar^5$ are selected from formulae AR1-AR11, a and b are 0, 1 or 2, and $R^{T1}$ and $R^{T2}$ are selected from formula T10.

8b) The group consisting of compounds of formula I8, wherein $Ar^4$ and $Ar^5$ are selected from formulae AR1-AR11, a and b are 0, 1 or 2, and $R^{T1}$ and $R^{T2}$ are selected from formula T36.

8c) The group consisting of compounds of formula I8, wherein $Ar^4$ and $Ar^5$ are selected from formulae AR1-AR11, a and b are 0, 1 or 2, and $R^{T1}$ and $R^{T2}$ are selected from formula T37.

8d) The group consisting of compounds of formula I8, wherein $Ar^4$ and $Ar^5$ are selected from formulae AR1-AR11, a and b are 0, 1 or 2, and $R^{T1}$ and $R^{T2}$ are selected from formula T38.

8e) The group consisting of compounds of formula I8, wherein $Ar^4$ and $Ar^5$ are selected from formulae AR1-AR11, a and b are 0, 1 or 2, and $R^{T1}$ and $R^{T2}$ are selected from formula T39.

8f) The group consisting of compounds of formula I8, wherein $Ar^4$ and $Ar^5$ are selected from formulae AR1-AR11, a and b are 0, 1 or 2, and $R^{T1}$ and $R^{T2}$ are selected from formula T47.

9a) The group consisting of compounds of formula I9, wherein $Ar^4$ and $Ar^5$ are selected from formulae AR1-AR11, a and b are 0, 1 or 2, and $R^{T1}$ and $R^{T2}$ are selected from formula T10.

9b) The group consisting of compounds of formula I9, wherein $Ar^4$ and $Ar^5$ are selected from formulae AR1-AR11, a and b are 0, 1 or 2, and $R^{T1}$ and $R^{T2}$ are selected from formula T36.

9c) The group consisting of compounds of formula I9, wherein $Ar^4$ and $Ar^5$ are selected from formulae AR1-AR11, a and b are 0, 1 or 2, and $R^{T1}$ and $R^{T2}$ are selected from formula T37.

9d) The group consisting of compounds of formula I9, wherein $Ar^4$ and $Ar^5$ are selected from formulae AR1-AR11, a and b are 0, 1 or 2, and $R^{T1}$ and $R^{T2}$ are selected from formula T38.

9e) The group consisting of compounds of formula I9, wherein $Ar^4$ and $Ar^5$ are selected from formulae AR1-AR11, a and b are 0, 1 or 2, and $R^{T1}$ and $R^{T2}$ are selected from formula T39.

9f) The group consisting of compounds of formula I9, wherein $Ar^4$ and $Ar^5$ are selected from formulae AR1-AR11, a and b are 0, 1 or 2, and $R^{T1}$ and $R^{T2}$ are selected from formula T47.

10a) The group consisting of compounds of formula I10, wherein $Ar^4$ and $Ar^5$ are selected from formulae AR1-AR11, a and b are 0, 1 or 2, and $R^{T1}$ and $R^{T2}$ are selected from formula T10.

10b) The group consisting of compounds of formula I10, wherein $Ar^4$ and $Ar^5$ are selected from formulae AR1-AR11, a and b are 0, 1 or 2, and $R^{T1}$ and $R^{T2}$ are selected from formula T36.

10c) The group consisting of compounds of formula I10, wherein $Ar^4$ and $Ar^5$ are selected from formulae AR1-AR11, a and b are 0, 1 or 2, and $R^{T1}$ and $R^{T2}$ are selected from formula T37.

10d) The group consisting of compounds of formula I10, wherein $Ar^4$ and $Ar^5$ are selected from formulae AR1-AR11, a and b are 0, 1 or 2, and $R^{T1}$ and $R^{T2}$ are selected from formula T38.

10e) The group consisting of compounds of formula I10, wherein $Ar^4$ and $Ar^5$ are selected from formulae AR1-AR11, a and b are 0, 1 or 2, and $R^{T1}$ and $R^{T2}$ are selected from formula T39.

10f) The group consisting of compounds of formula I10, wherein $Ar^4$ and $Ar^5$ are selected from formulae AR1-AR11, a and b are 0, 1 or 2, and $R^{T1}$ and $R^{T2}$ are selected from formula T47.

11a) The group consisting of compounds of formula I11, wherein $Ar^4$ and $Ar^5$ are selected from formulae AR1-AR11, a and b are 0, 1 or 2, and $R^{T1}$ and $R^{T2}$ are selected from formula T11.

11b) The group consisting of compounds of formula I11, wherein $Ar^4$ and $Ar^5$ are selected from formulae AR1-AR11, a and b are 0, 1 or 2, and $R^{T1}$ and $R^{T2}$ are selected from formula T36.

11c) The group consisting of compounds of formula I11, wherein $Ar^4$ and $Ar^5$ are selected from formulae AR1-AR11, a and b are 0, 1 or 2, and $R^{T1}$ and $R^{T2}$ are selected from formula T37.

11d) The group consisting of compounds of formula I11, wherein $Ar^4$ and $Ar^5$ are selected from formulae AR1-AR11, a and b are 0, 1 or 2, and $R^{T1}$ and $R^{T2}$ are selected from formula T38.

11e) The group consisting of compounds of formula I11, wherein $Ar^4$ and $Ar^5$ are selected from formulae AR1-AR11, a and b are 0, 1 or 2, and $R^{T1}$ and $R^{T2}$ are selected from formula T39.

11f) The group consisting of compounds of formula I11, wherein $Ar^4$ and $Ar^5$ are selected from formulae AR1-AR11, a and b are 0, 1 or 2, and $R^{T1}$ and $R^{T2}$ are selected from formula T47.

12a) The group consisting of compounds of formula I12, wherein $Ar^4$ and $Ar^5$ are selected from formulae AR1-AR11, a and b are 0, 1 or 2, and $R^{T1}$ and $R^{T2}$ are selected from formula T12.

12b) The group consisting of compounds of formula I12, wherein $Ar^4$ and $Ar^5$ are selected from formulae AR1-AR11, a and b are 0, 1 or 2, and $R^{T1}$ and $R^{T2}$ are selected from formula T36.

12c) The group consisting of compounds of formula I12, wherein $Ar^4$ and $Ar^5$ are selected from formulae AR1-AR11, a and b are 0, 1 or 2, and $R^{T1}$ and $R^{T2}$ are selected from formula T37.

12d) The group consisting of compounds of formula I12, wherein $Ar^4$ and $Ar^5$ are selected from formulae AR1-AR11, a and b are 0, 1 or 2, and $R^{T1}$ and $R^{T2}$ are selected from formula T38.

12e) The group consisting of compounds of formula I12, wherein $Ar^4$ and $Ar^5$ are selected from formulae AR1-AR11, a and b are 0, 1 or 2, and $R^{T1}$ and $R^{T2}$ are selected from formula T39.

12f) The group consisting of compounds of formula I12, wherein $Ar^4$ and $Ar^5$ are selected from formulae AR1-AR11, a and b are 0, 1 or 2, and $R^{T1}$ and $R^{T2}$ are selected from formula T47.

13a) The group consisting of compounds of formula I13, wherein $Ar^4$ and $Ar^5$ are selected from formulae AR1-AR11, a and b are 0, 1 or 2, and $R^{T1}$ and $R^{T2}$ are selected from formula T13.

13b) The group consisting of compounds of formula I13, wherein $Ar^4$ and $Ar^5$ are selected from formulae AR1-AR11, a and b are 0, 1 or 2, and $R^{T1}$ and $R^{T2}$ are selected from formula T36.

13c) The group consisting of compounds of formula I13, wherein $Ar^4$ and $Ar^5$ are selected from formulae AR1-AR11, a and b are 0, 1 or 2, and $R^{T1}$ and $R^{T2}$ are selected from formula T37.

13d) The group consisting of compounds of formula I13, wherein $Ar^4$ and $Ar^5$ are selected from formulae AR1-AR11, a and b are 0, 1 or 2, and $R^{T1}$ and $R^{T2}$ are selected from formula T38.

13e) The group consisting of compounds of formula I13, wherein $Ar^4$ and $Ar^5$ are selected from formulae AR1-AR11, a and b are 0, 1 or 2, and $R^{T1}$ and $R^{T2}$ are selected from formula T39.

13f) The group consisting of compounds of formula I13, wherein $Ar^4$ and $Ar^5$ are selected from formulae AR1-AR11, a and b are 0, 1 or 2, and $R^{T1}$ and $R^{T2}$ are selected from formula T47.

14a) The group consisting of compounds of formula I14, wherein $Ar^4$ and $Ar^5$ are selected from formulae AR1-AR11, a and b are 0, 1 or 2, and $R^{T1}$ and $R^{T2}$ are selected from formula T14.

14b) The group consisting of compounds of formula I14, wherein $Ar^4$ and $Ar^5$ are selected from formulae AR1-AR11, a and b are 0, 1 or 2, and $R^{T1}$ and $R^{T2}$ are selected from formula T36.

14c) The group consisting of compounds of formula I14, wherein $Ar^4$ and $Ar^5$ are selected from formulae AR1-AR11, a and b are 0, 1 or 2, and $R^{T1}$ and $R^{T2}$ are selected from formula T37.

14d) The group consisting of compounds of formula I14, wherein $Ar^4$ and $Ar^5$ are selected from formulae AR1-AR11, a and b are 0, 1 or 2, and $R^{T1}$ and $R^{T2}$ are selected from formula T38.

14e) The group consisting of compounds of formula I14, wherein $Ar^4$ and $Ar^5$ are selected from formulae AR1-AR11, a and b are 0, 1 or 2, and $R^{T1}$ and $R^{T2}$ are selected from formula T39.

14f) The group consisting of compounds of formula I14, wherein $Ar^4$ and $Ar^5$ are selected from formulae AR1-AR11, a and b are 0, 1 or 2, and $R^{T1}$ and $R^{T2}$ are selected from formula T47.

15a) The group consisting of compounds of formula I15, wherein $Ar^4$ and $Ar^5$ are selected from formulae AR1-AR11, a and b are 0, 1 or 2, and $R^{T1}$ and $R^{T2}$ are selected from formula T14.

15b) The group consisting of compounds of formula I15, wherein $Ar^4$ and $Ar^5$ are selected from formulae AR1-AR11, a and b are 0, 1 or 2, and $R^{T1}$ and $R^{T2}$ are selected from formula T36.

15c) The group consisting of compounds of formula I15, wherein $Ar^4$ and $Ar^5$ are selected from formulae AR1-AR11, a and b are 0, 1 or 2, and $R^{T1}$ and $R^{T2}$ are selected from formula T37.

15d) The group consisting of compounds of formula I15, wherein $Ar^4$ and $Ar^5$ are selected from formulae AR1-AR11, a and b are 0, 1 or 2, and $R^{T1}$ and $R^{T2}$ are selected from formula T38.

15e) The group consisting of compounds of formula I15, wherein $Ar^4$ and $Ar^5$ are selected from formulae AR1-AR11, a and b are 0, 1 or 2, and $R^{T1}$ and $R^{T2}$ are selected from formula T39.

15f) The group consisting of compounds of formula I15, wherein $Ar^4$ and $Ar^5$ are selected from formulae AR1-AR11, a and b are 0, 1 or 2, and $R^{T1}$ and $R^{T2}$ are selected from formula T47.

16a) The group consisting of compounds of formula I16, wherein $Ar^4$ and $Ar^5$ are selected from formulae AR1-AR11, a and b are 0, 1 or 2, and $R^{T1}$ and $R^{T2}$ are selected from formula T14.

16b) The group consisting of compounds of formula I16, wherein $Ar^4$ and $Ar^5$ are selected from formulae AR1-AR11, a and b are 0, 1 or 2, and $R^{T1}$ and $R^{T2}$ are selected from formula T36.

16c) The group consisting of compounds of formula I16, wherein $Ar^4$ and $Ar^5$ are selected from formulae AR1-AR11, a and b are 0, 1 or 2, and $R^{T1}$ and $R^{T2}$ are selected from formula T37.

16d) The group consisting of compounds of formula I16, wherein $Ar^4$ and $Ar^5$ are selected from formulae AR1-AR11, a and b are 0, 1 or 2, and $R^{T1}$ and $R^{T2}$ are selected from formula T38.

16e) The group consisting of compounds of formula I16, wherein $Ar^4$ and $Ar^5$ are selected from formulae AR1-AR11, a and b are 0, 1 or 2, and $R^{T1}$ and $R^{T2}$ are selected from formula T39.

16f) The group consisting of compounds of formula I16, wherein $Ar^4$ and $Ar^5$ are selected from formulae AR1-AR11, a and b are 0, 1 or 2, and $R^{T1}$ and $R^{T2}$ are selected from formula T47.

17a) The group consisting of compounds of formula I17, wherein $Ar^4$ and $Ar^5$ are selected from formulae AR1-AR11, a and b are 0, 1 or 2, and $R^{T1}$ and $R^{T2}$ are selected from formula T14.

17b) The group consisting of compounds of formula I17, wherein $Ar^4$ and $Ar^5$ are selected from formulae AR1-AR11, a and b are 0, 1 or 2, and $R^{T1}$ and $R^{T2}$ are selected from formula T36.

17c) The group consisting of compounds of formula I17, wherein $Ar^4$ and $Ar^5$ are selected from formulae AR1-AR11, a and b are 0, 1 or 2, and $R^{T1}$ and $R^{T2}$ are selected from formula T37.

17d) The group consisting of compounds of formula I17, wherein $Ar^4$ and $Ar^5$ are selected from formulae AR1-AR11, a and b are 0, 1 or 2, and $R^{T1}$ and $R^{T2}$ are selected from formula T38.

17e) The group consisting of compounds of formula I17, wherein $Ar^4$ and $Ar^5$ are selected from formulae AR1-AR11, a and b are 0, 1 or 2, and $R^{T1}$ and $R^{T2}$ are selected from formula T39.

17f) The group consisting of compounds of formula I17, wherein $Ar^4$ and $Ar^5$ are selected from formulae AR1-AR11, a and b are 0, 1 or 2, and $R^{T1}$ and $R^{T2}$ are selected from formula T47.

18a) The group consisting of compounds of formula I18, wherein $Ar^4$ and $Ar^5$ are selected from formulae AR1-AR11, a and b are 0, 1 or 2, and $R^{T1}$ and $R^{T2}$ are selected from formula T14.

18b) The group consisting of compounds of formula I18, wherein $Ar^4$ and $Ar^5$ are selected from formulae AR1-AR11, a and b are 0, 1 or 2, and $R^{T1}$ and $R^{T2}$ are selected from formula T36.

18c) The group consisting of compounds of formula I18, wherein $Ar^4$ and $Ar^5$ are selected from formulae AR1-AR11, a and b are 0, 1 or 2, and $R^{T1}$ and $R^{T2}$ are selected from formula T37.

18d) The group consisting of compounds of formula I18, wherein $Ar^4$ and $Ar^5$ are selected from formulae AR1-AR11, a and b are 0, 1 or 2, and $R^{T1}$ and $R^{T2}$ are selected from formula T38.

18e) The group consisting of compounds of formula I18, wherein $Ar^4$ and $Ar^5$ are selected from formulae AR1-AR11, a and b are 0, 1 or 2, and $R^{T1}$ and $R^{T2}$ are selected from formula T39.

18f) The group consisting of compounds of formula I18, wherein $Ar^4$ and $Ar^5$ are selected from formulae AR1-AR11, a and b are 0, 1 or 2, and $R^{T1}$ and $R^{T2}$ are selected from formula T47.

19a) The group consisting of compounds of formula I19, wherein $Ar^4$ and $Ar^5$ are selected from formulae AR1-AR11, a and b are 0, 1 or 2, and $R^{T1}$ and $R^{T2}$ are selected from formula T14.

19b) The group consisting of compounds of formula I19, wherein $Ar^4$ and $Ar^5$ are selected from formulae AR1-AR11, a and b are 0, 1 or 2, and $R^{T1}$ and $R^{T2}$ are selected from formula T36.

19c) The group consisting of compounds of formula I19, wherein $Ar^4$ and $Ar^5$ are selected from formulae AR1-AR11, a and b are 0, 1 or 2, and $R^{T1}$ and $R^{T2}$ are selected from formula T37.

19d) The group consisting of compounds of formula I19, wherein $Ar^4$ and $Ar^5$ are selected from formulae AR1-AR11, a and b are 0, 1 or 2, and $R^{T1}$ and $R^{T2}$ are selected from formula T38.

19e) The group consisting of compounds of formula I19, wherein $Ar^4$ and $Ar^5$ are selected from formulae AR1-AR11, a and b are 0, 1 or 2, and $R^{T1}$ and $R^{T2}$ are selected from formula T39.

19f) The group consisting of compounds of formula I19, wherein $Ar^4$ and $Ar^5$ are selected from formulae AR1-AR11, a and b are 0, 1 or 2, and $R^{T1}$ and $R^{T2}$ are selected from formula T47.

Further preferred embodiments of the invention relate to
compounds selected from the above groups 1a-1f,
compounds selected from the above groups 2a-2f,
compounds selected from the above groups 3a-3f,
compounds selected from the above groups 4a-4f,
compounds selected from the above groups 5a-5f,
compounds selected from the above groups 6a-6f,
compounds selected from the above groups 7a-7f,
compounds selected from the above groups 8a-8f,
compounds selected from the above groups 9a-9f,
compounds selected from the above groups 10a-10f.
compounds selected from the above groups 11a-11f.
compounds selected from the above groups 12a-12f.
compounds selected from the above groups 13a-13f.
compounds selected from the above groups 14a-14f.
compounds selected from the above groups 15a-15f.
compounds selected from the above groups 16a-16f.
compounds selected from the above groups 17a-17f.
compounds selected from the above groups 18a-18f.
compounds selected from the above groups 19a-19f.

Further preferred embodiments of the invention relate to compounds selected from each of the individual groups 1a-19f as defined above.

In the above groups 1a-19f, $R^{1-4}$ are preferably selected from alkyl or alkoxy with 1 to 16 C atoms which is optionally fluorinated, or aryl or heteroaryl that is mono- or polycyclic, optionally contains fused rings, has 4 to 30 ring atoms, and is optionally substituted by one or more groups L as defined in formula I, and preferably denotes phenyl that is substituted with one or more optionally fluorinated alkyl or alkoxy group with 1 to 16 C atoms.

Very preferred compounds of formula I are selected from the following subformulae:

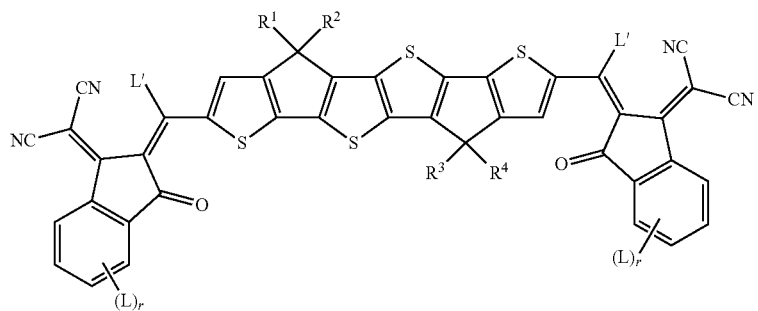
I1a
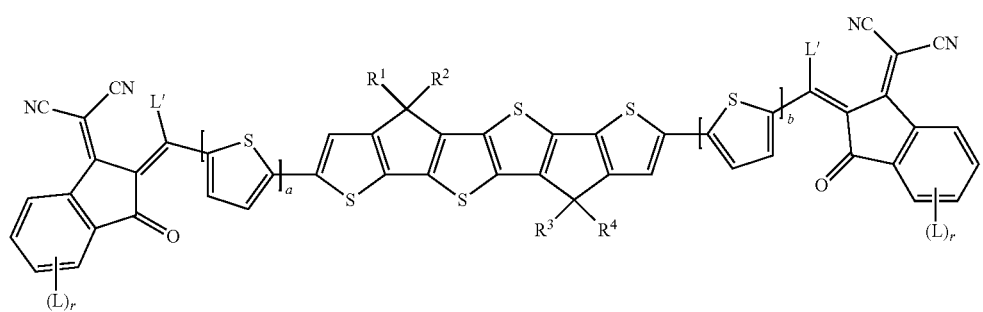
I1b
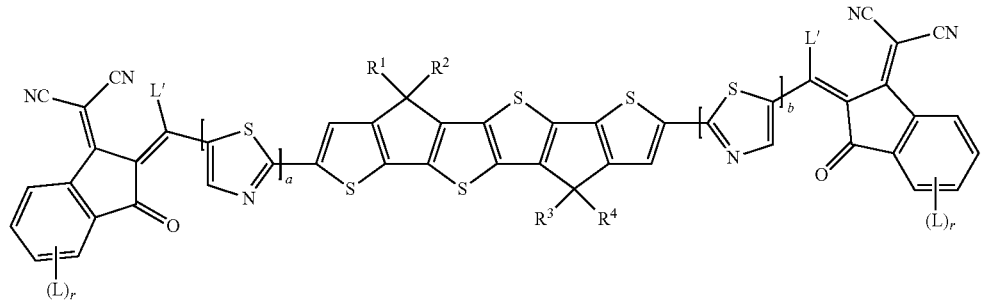
I1c
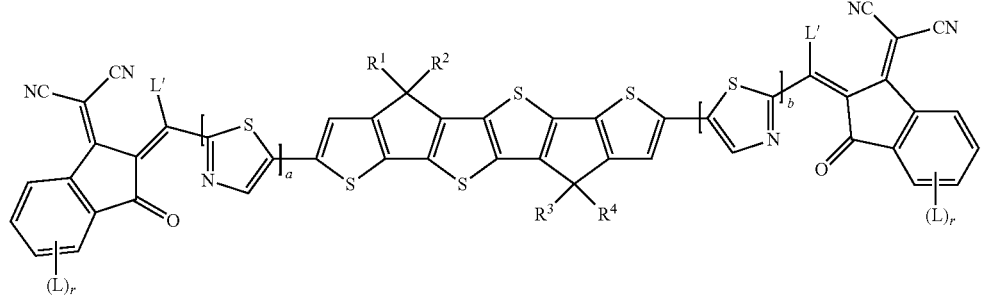
I1d
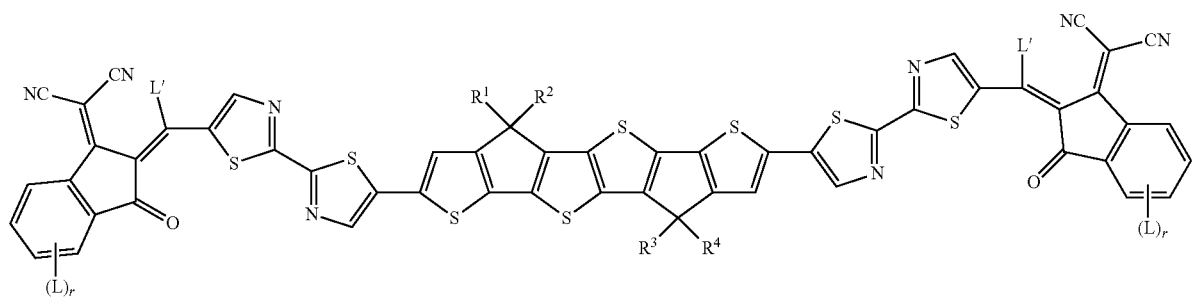
I1e

-continued
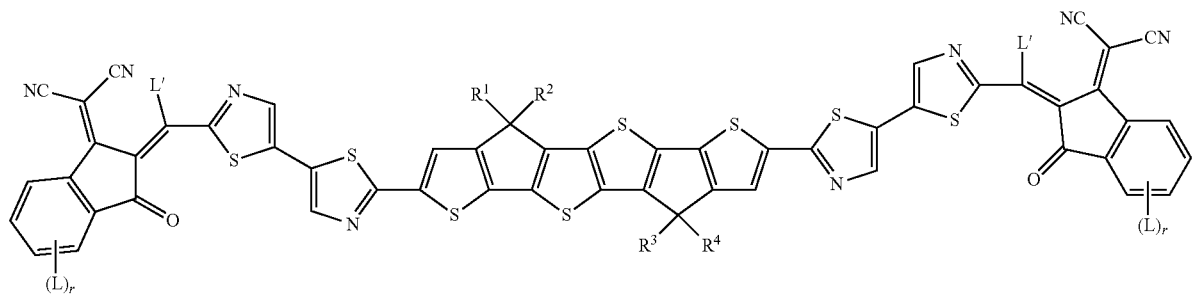
I1f
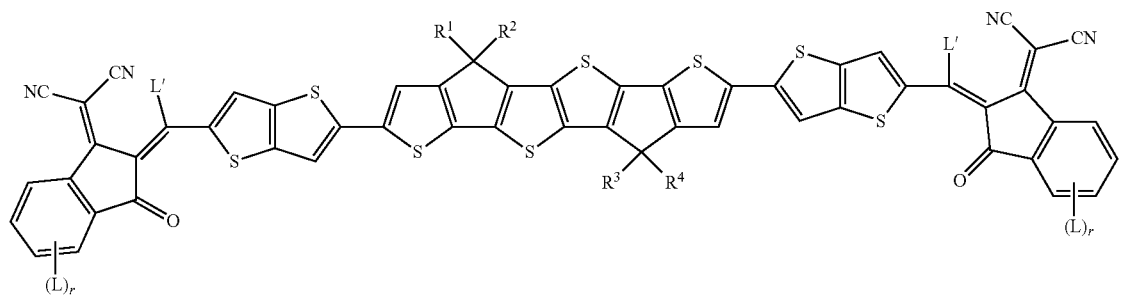
I1g
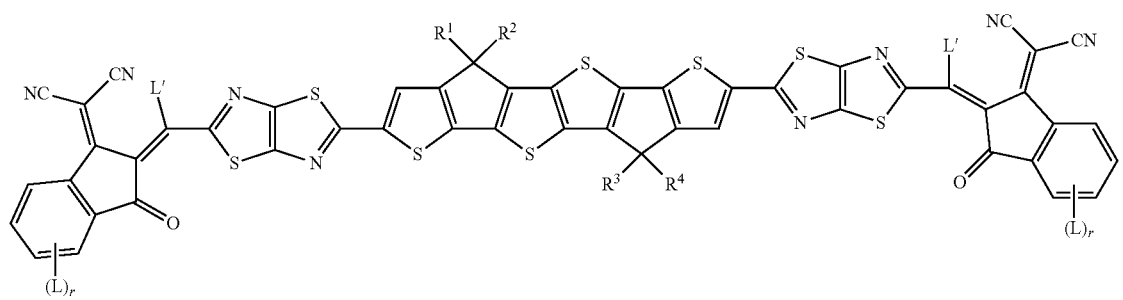
I1h
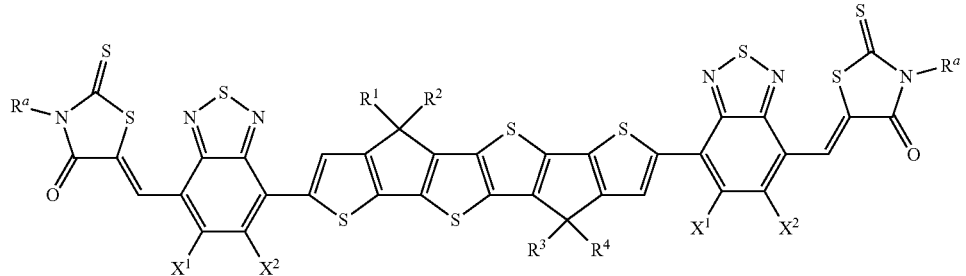
I1i
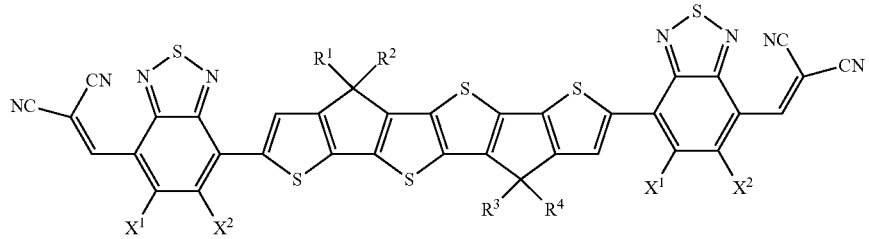
I1k -continued
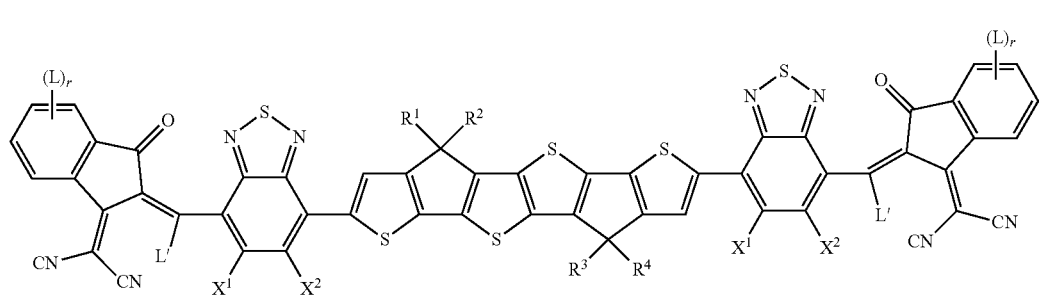
I1m
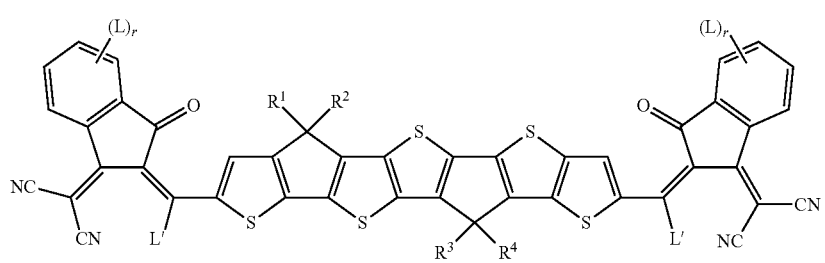
I2a
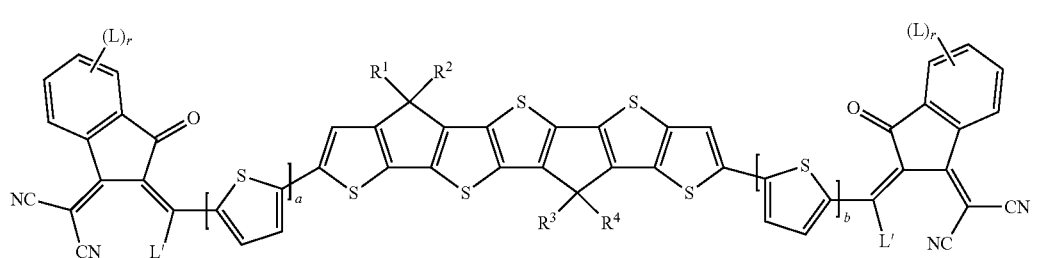
I2b
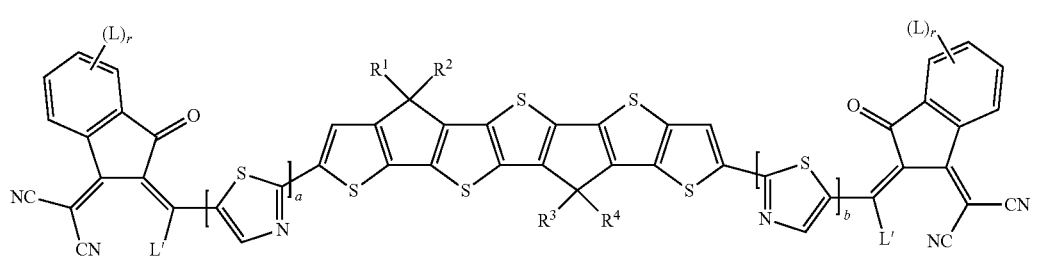
I2c
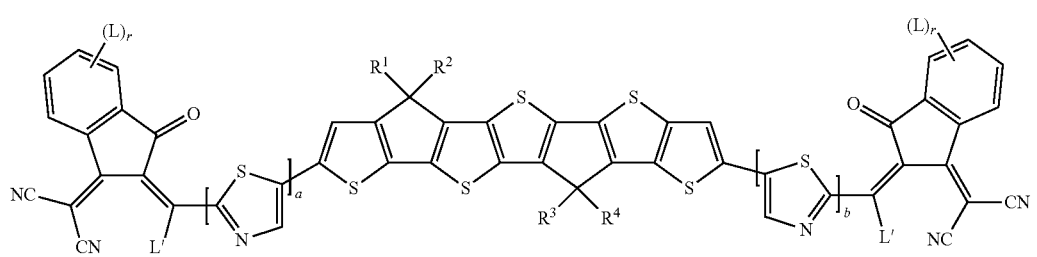
I2d
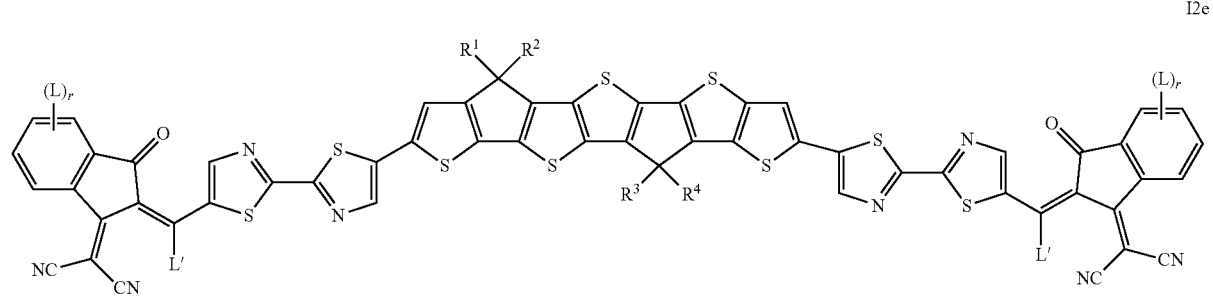
I2e -continued
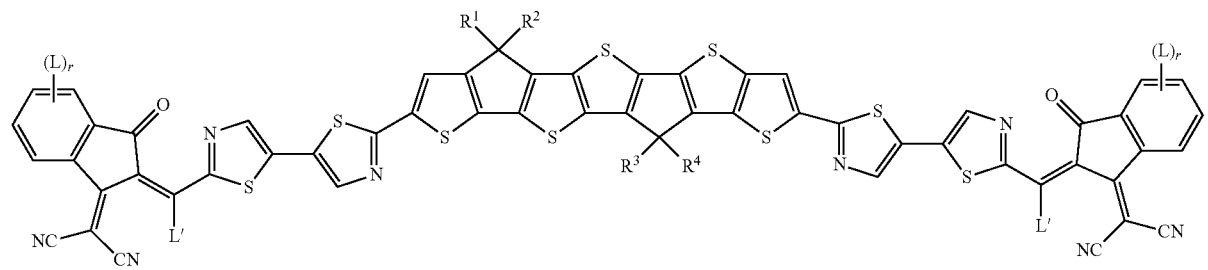
I2f
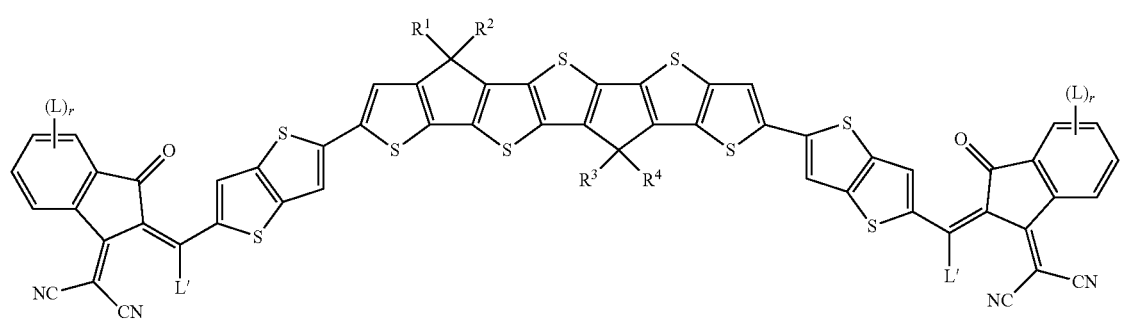
I2g
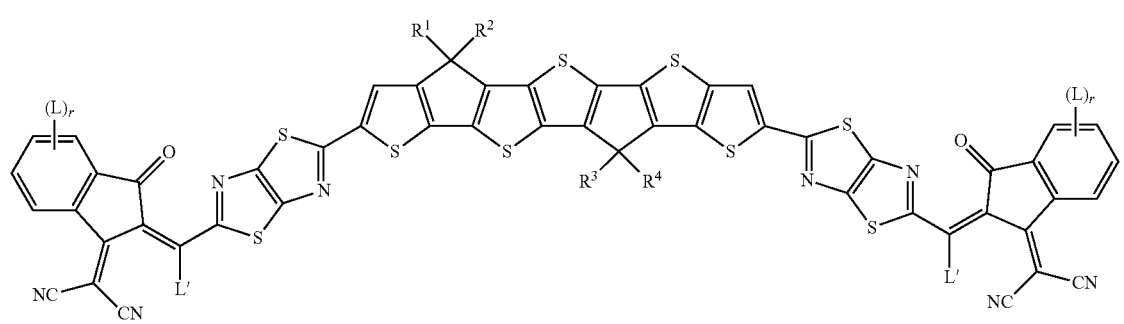
I2h
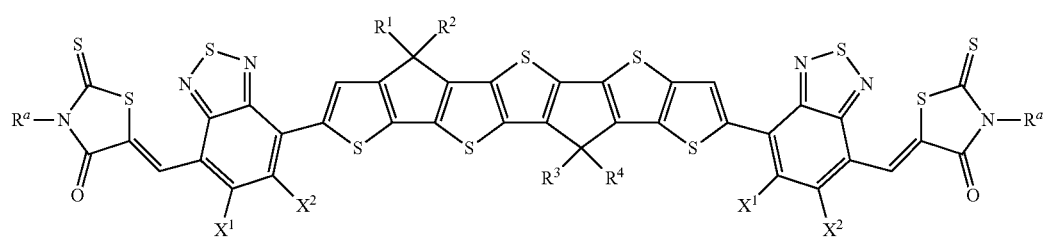
I2i
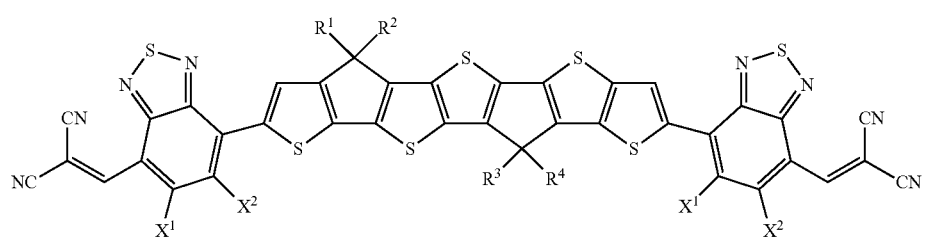
I2k -continued
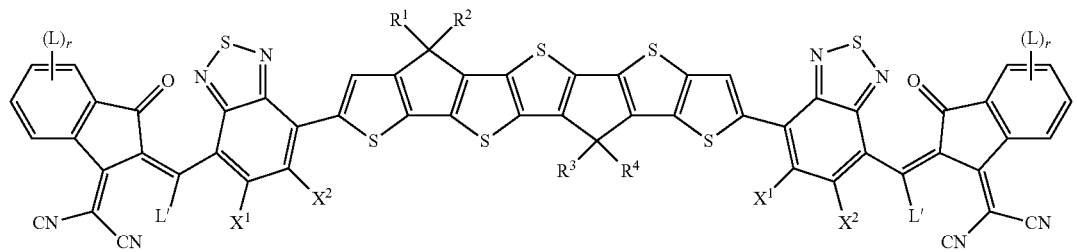
I2m
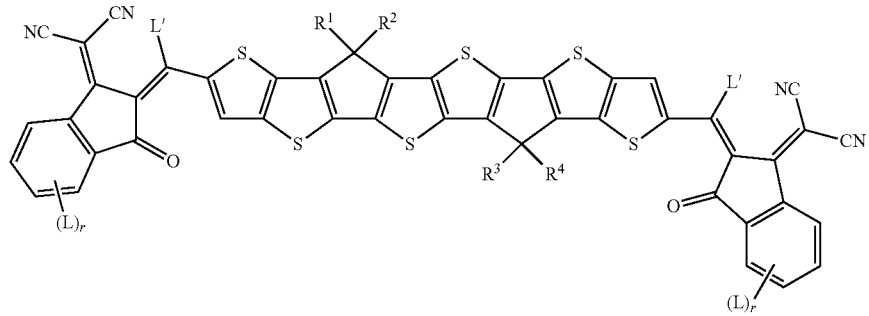
I3a
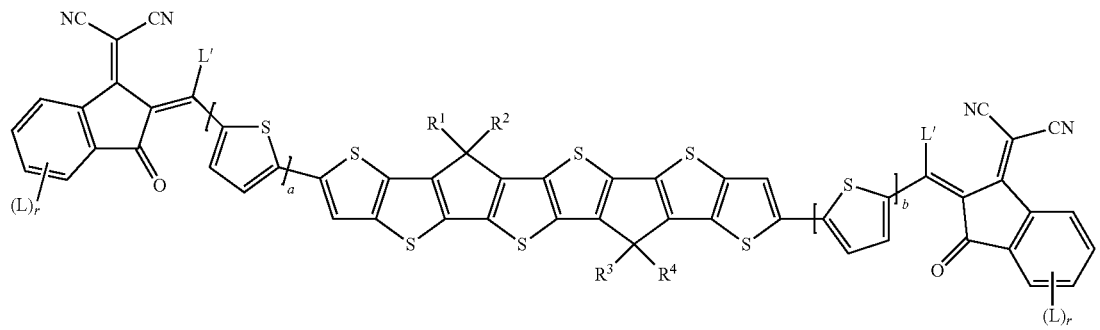
I3b
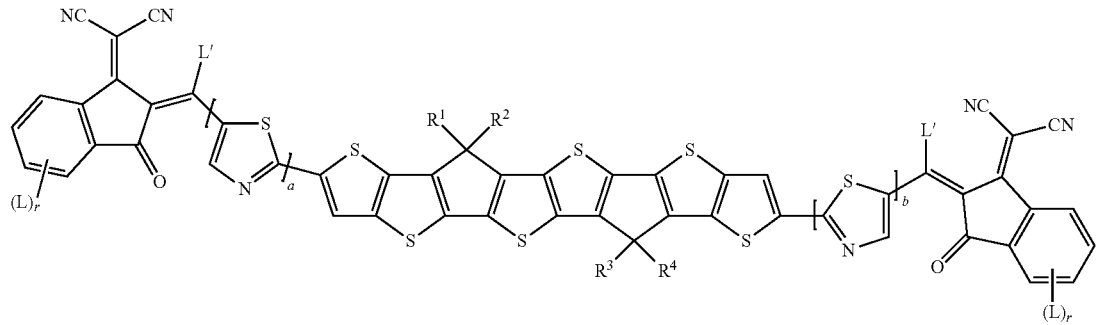
I3c
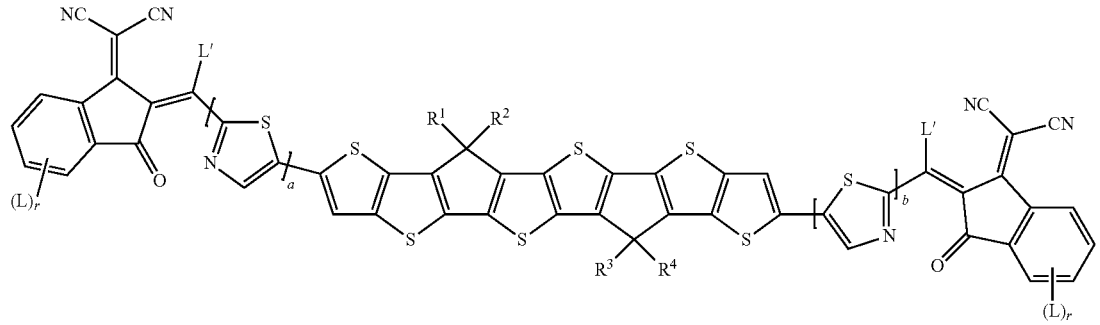
I3d -continued
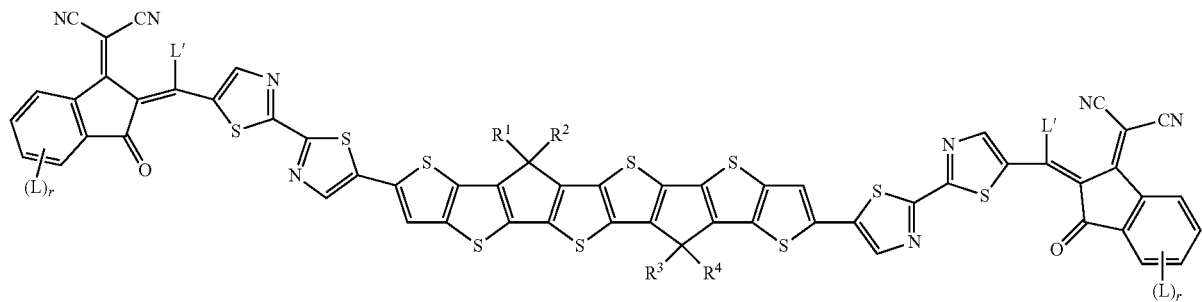
I3e
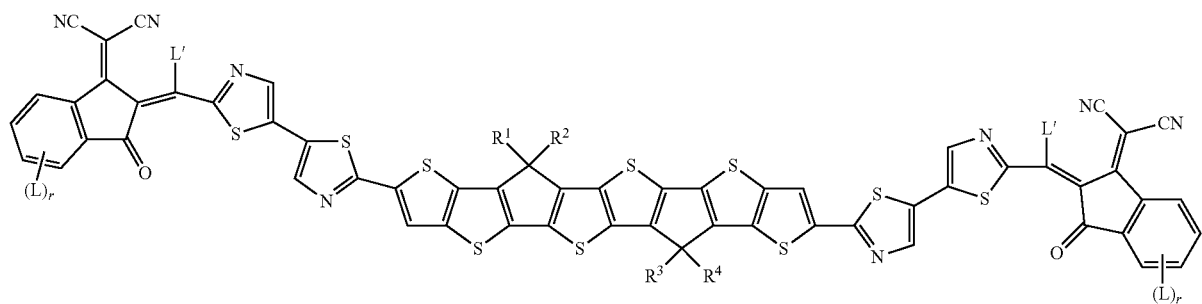
I3f
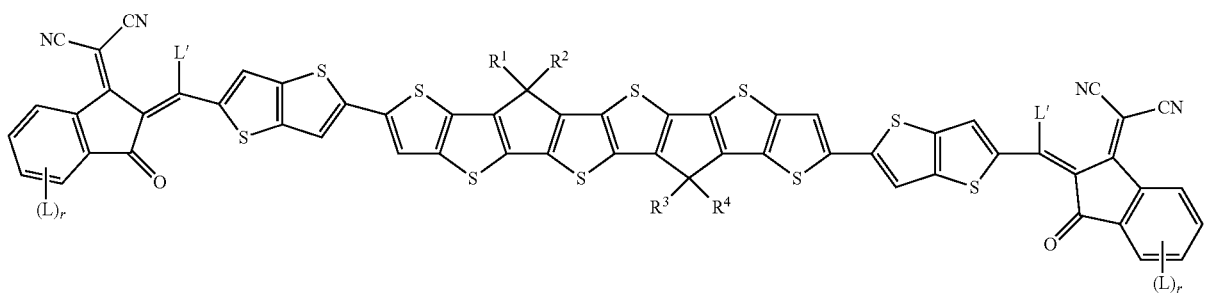
I3g
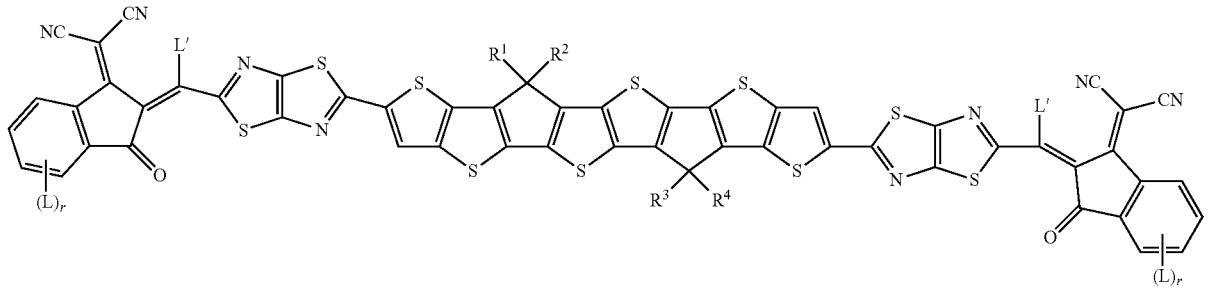
I3h
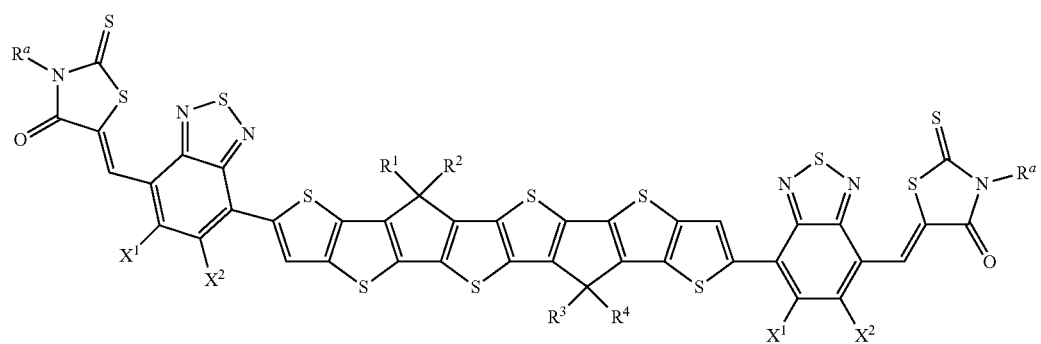
I3i I3k
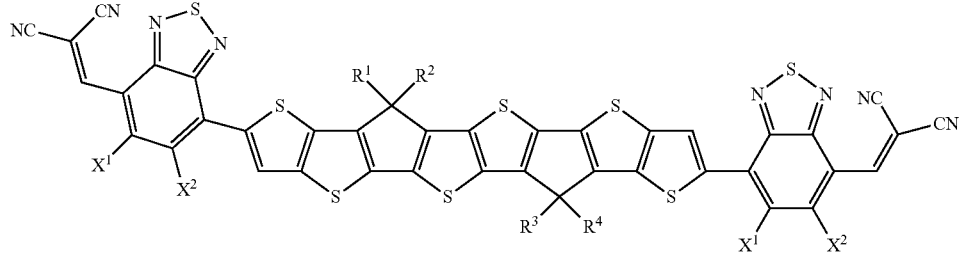
I3m
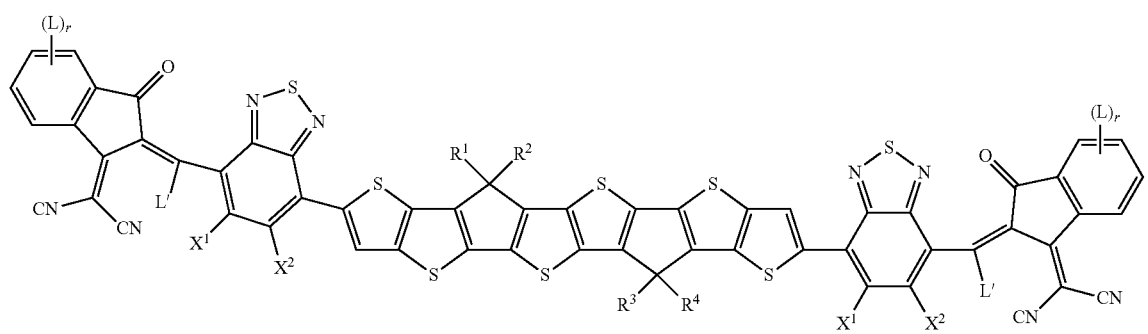
I4a
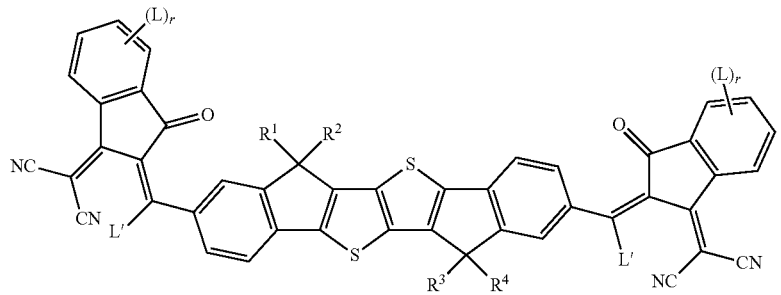
I4b
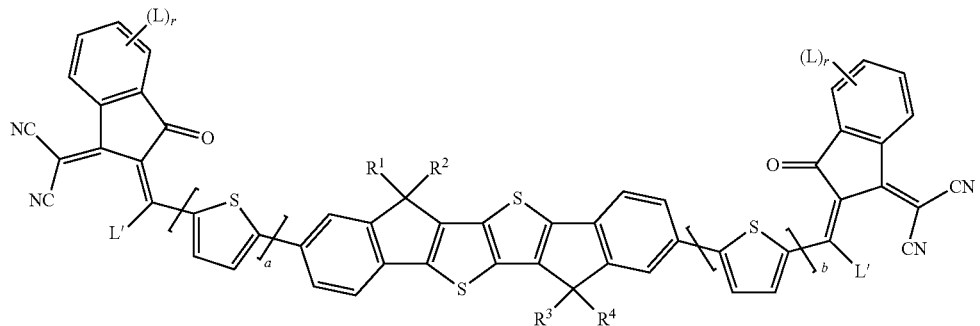
I4c
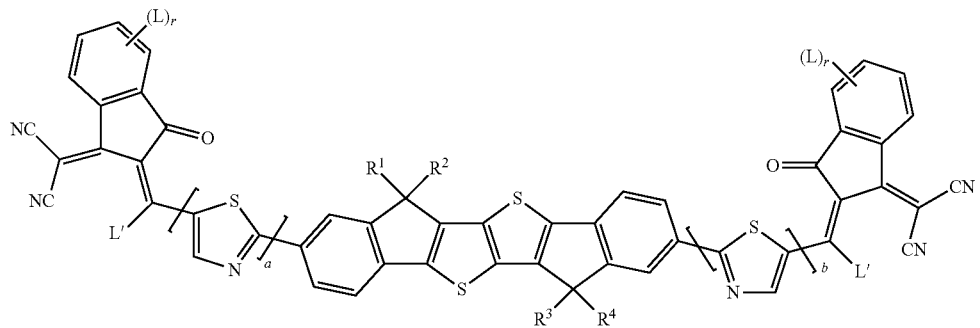

I4d
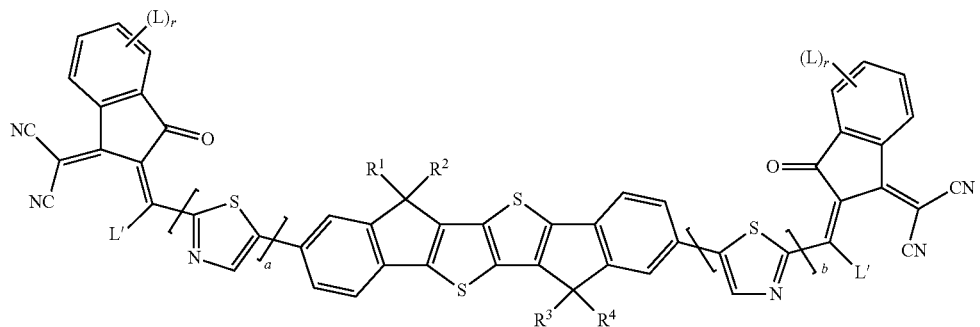
I4e
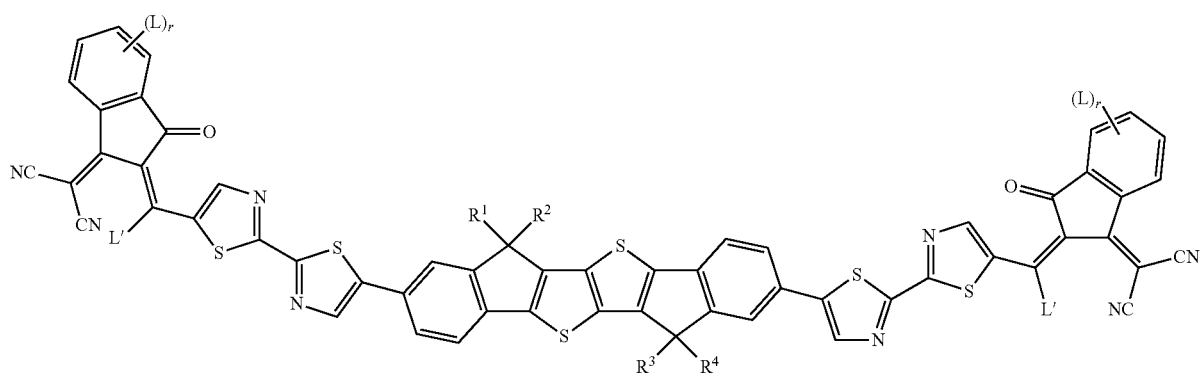
I4f
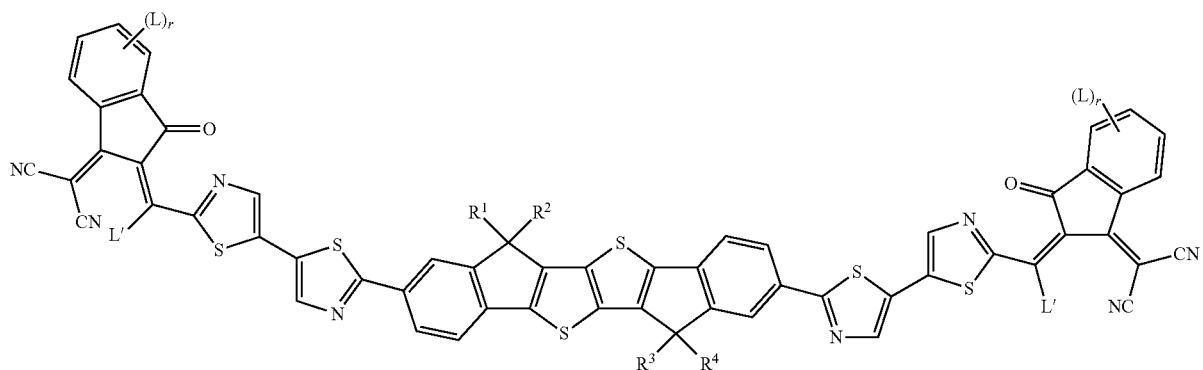
I4g
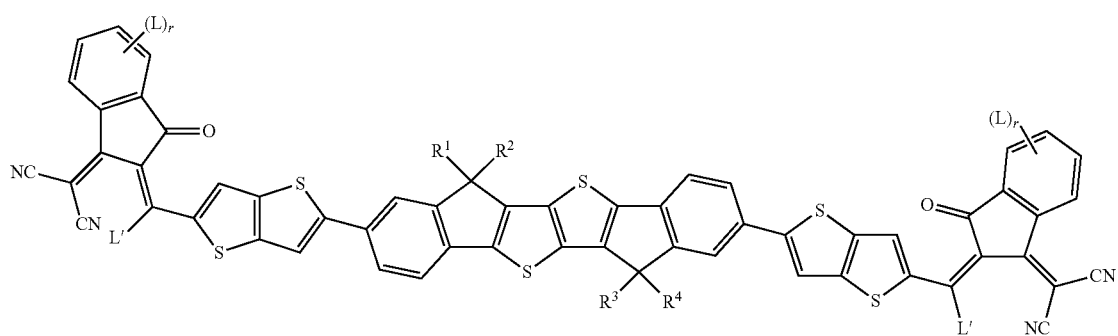

-continued
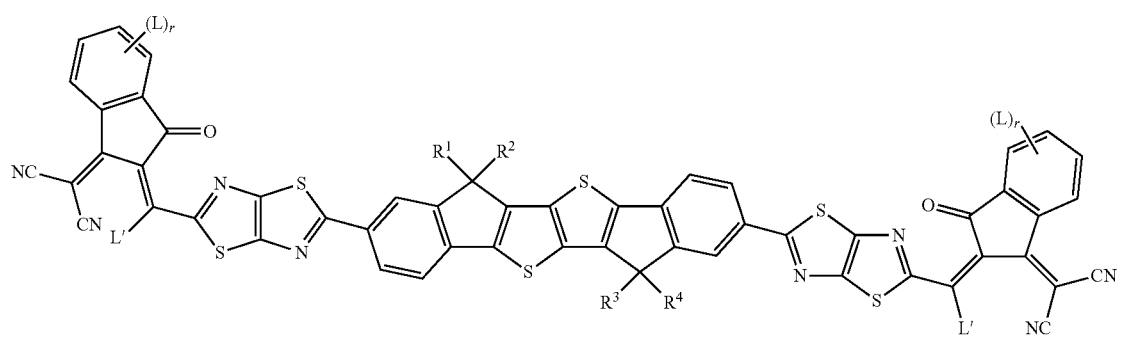
I4h
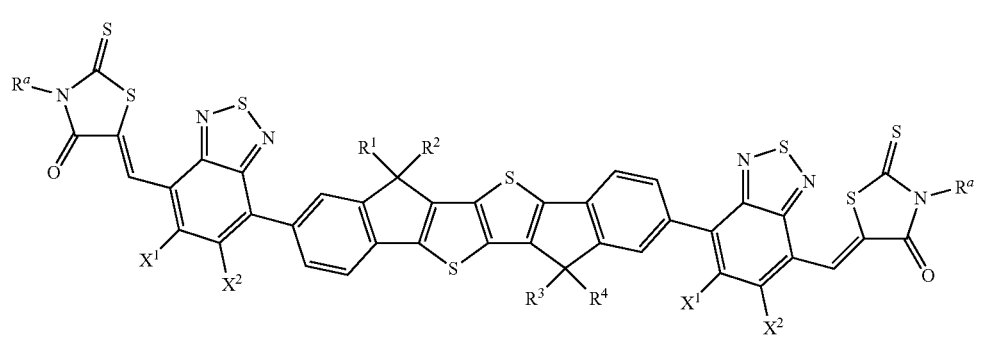
I4i
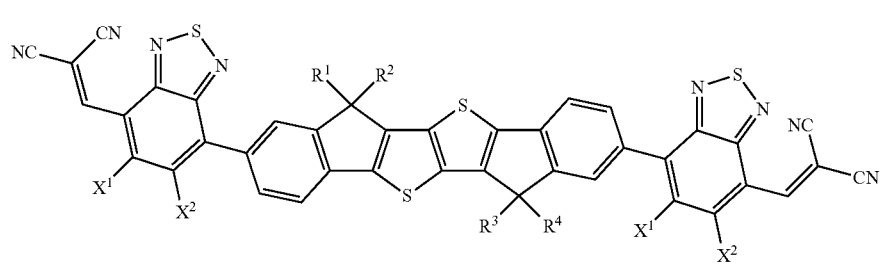
I4k
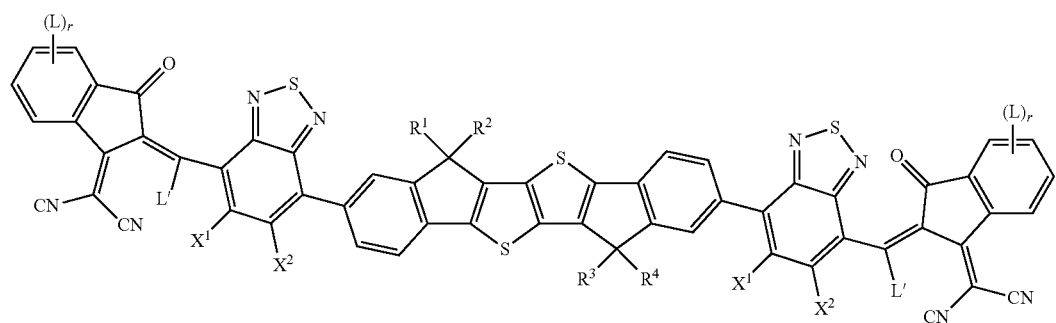
I4m
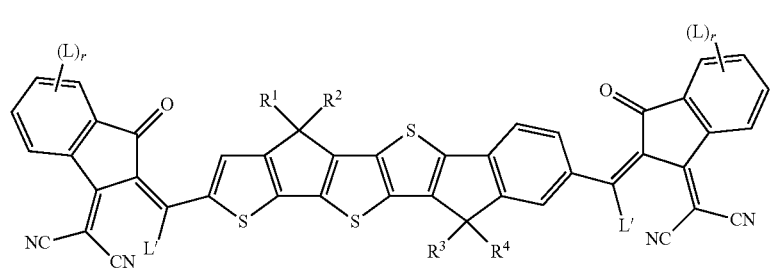
I5a -continued
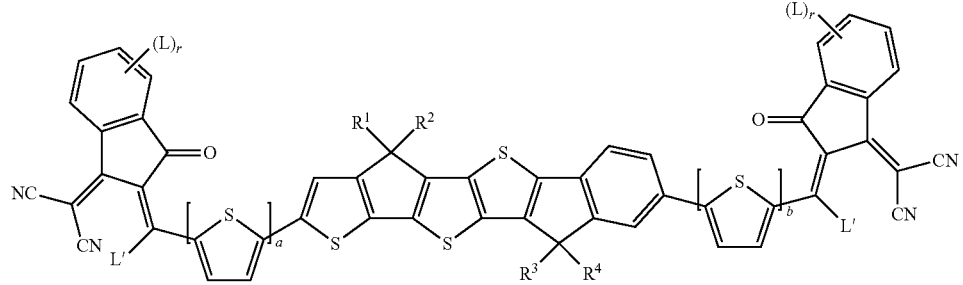
I5b
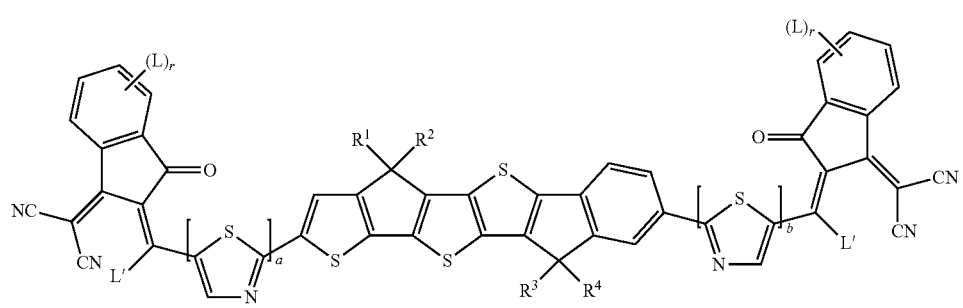
I5c
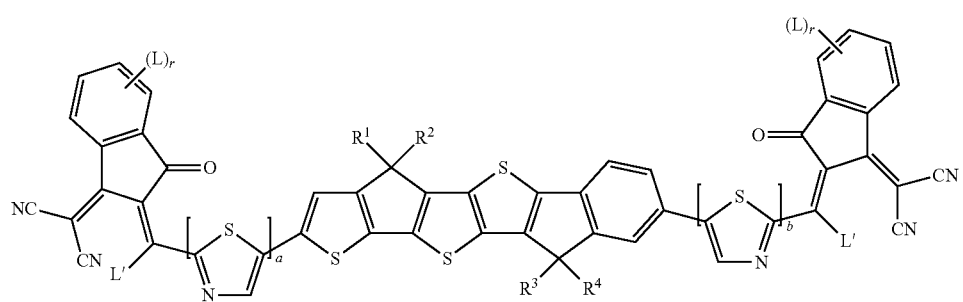
I5d
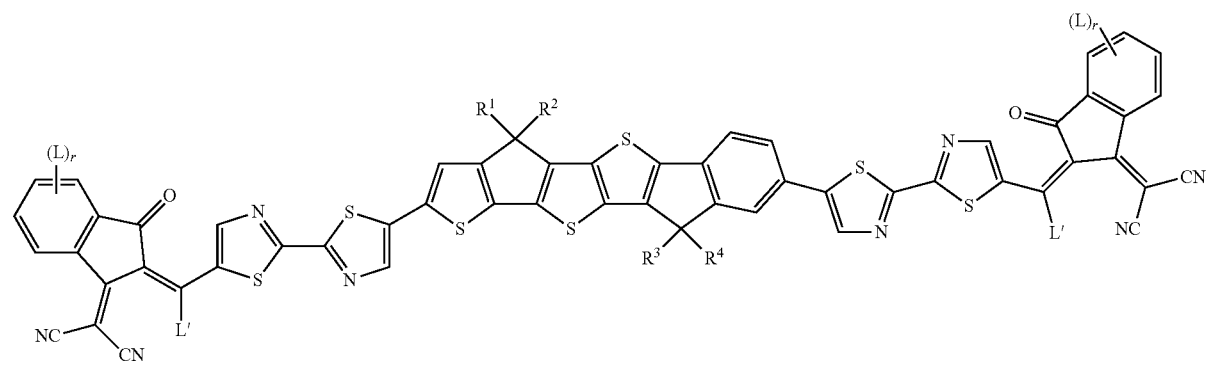
I5e -continued
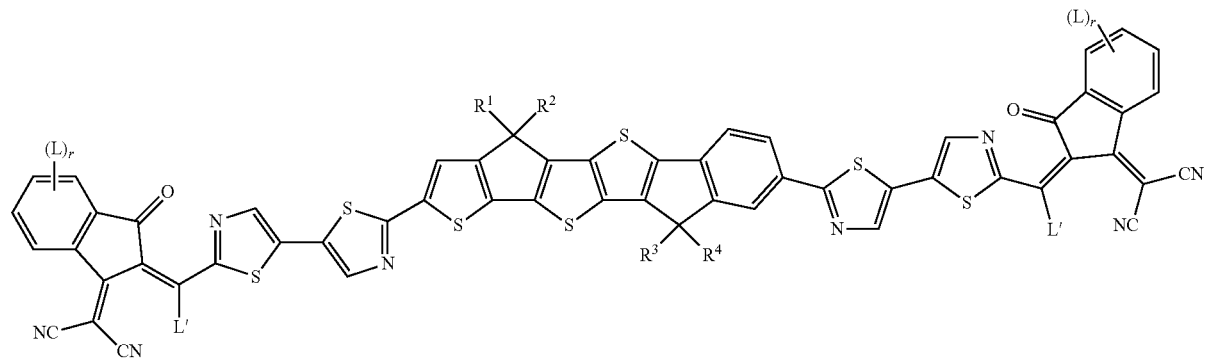
I5f
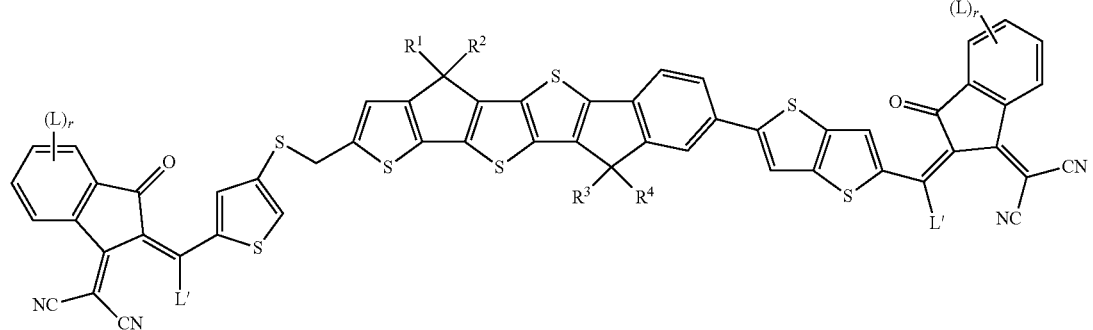
I5g
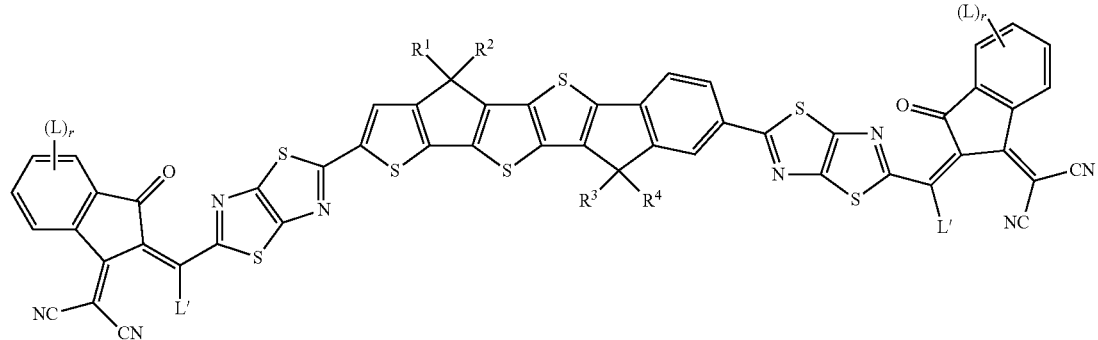
I5h
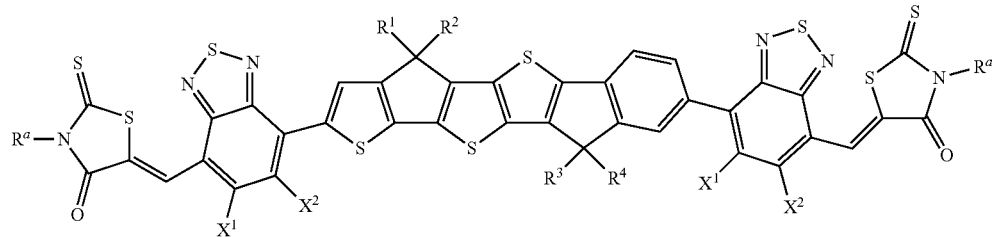
I5i
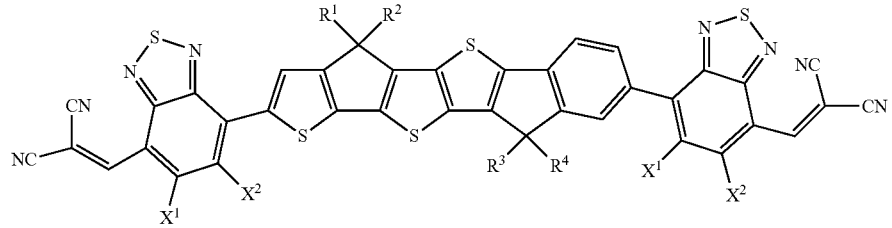
I5k

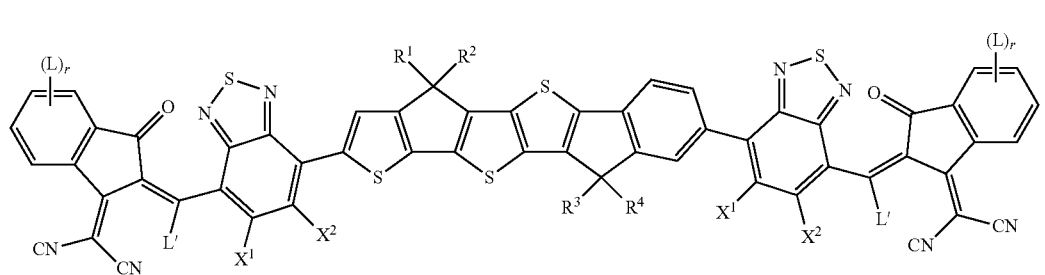
I5m
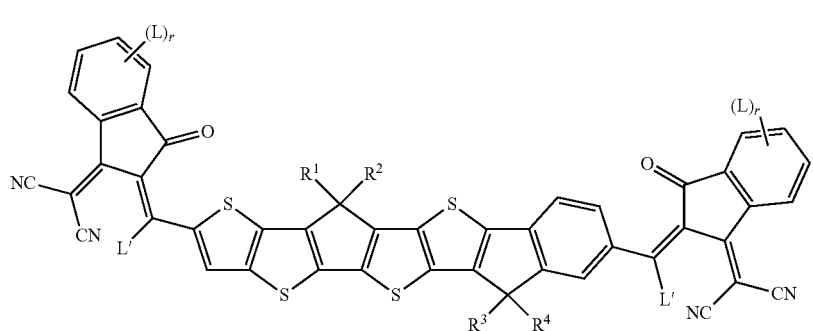
I6a
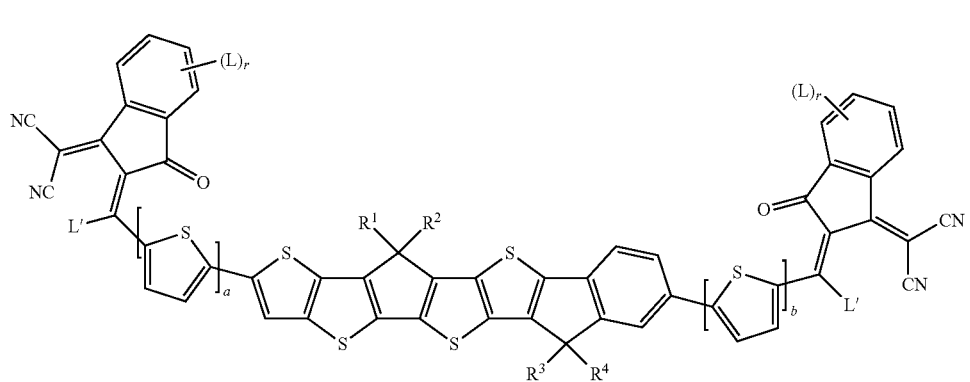
I6b
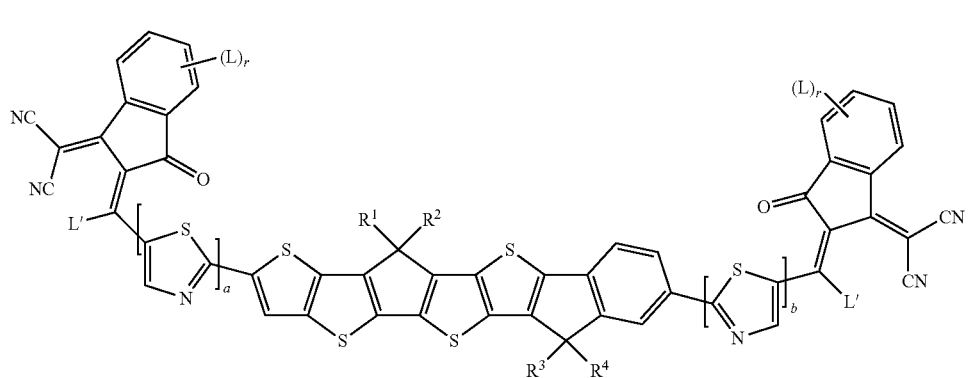
I6c

-continued
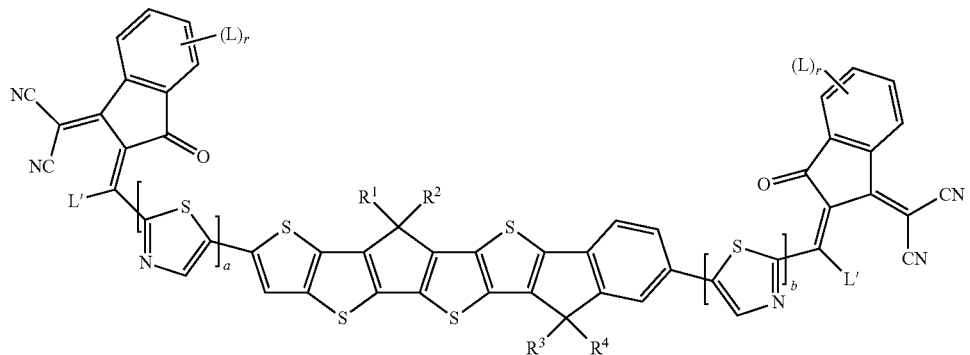
I6d
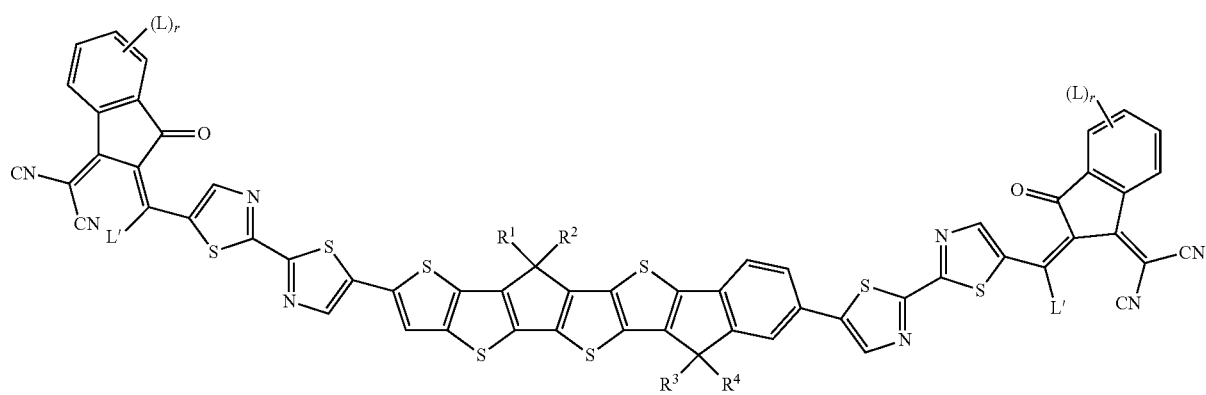
I6e
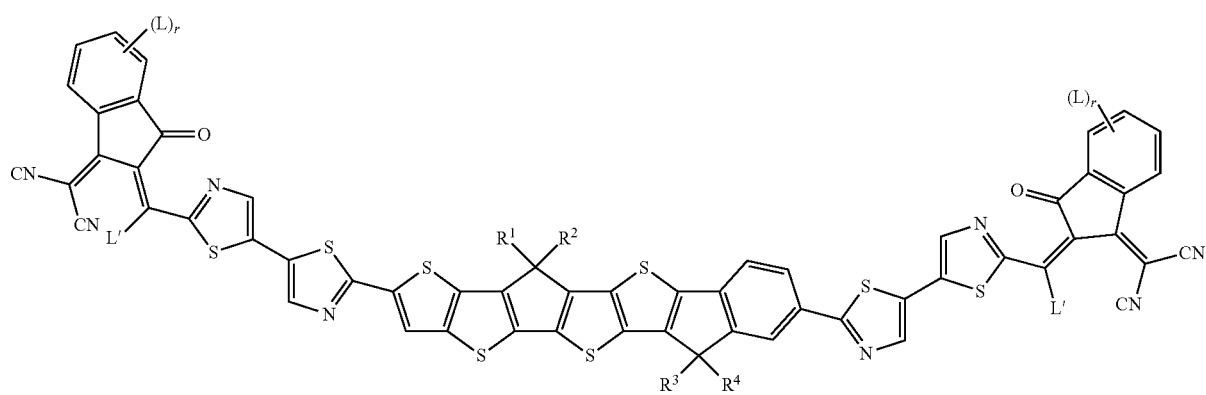
I6f
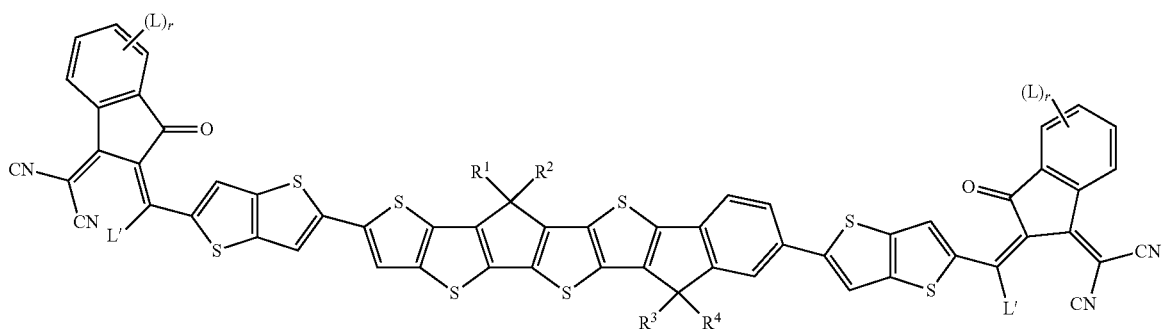
I6g

-continued
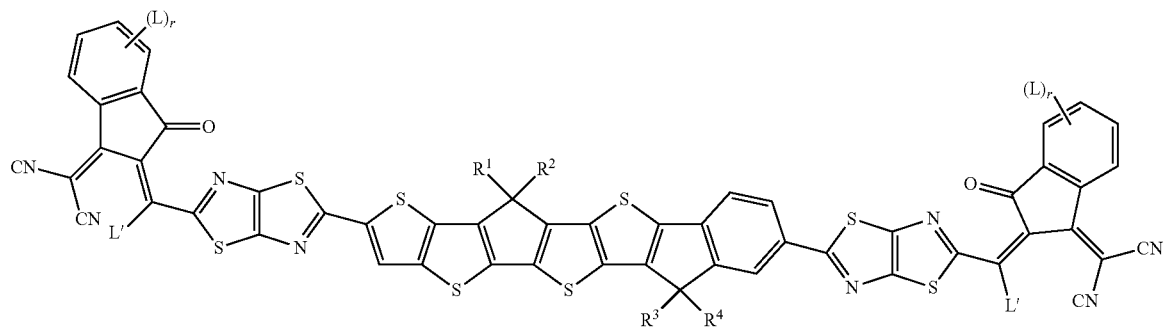
I6h
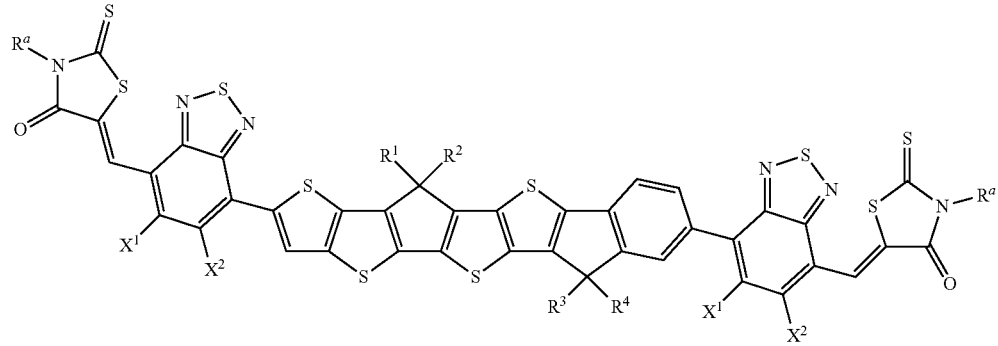
I6i
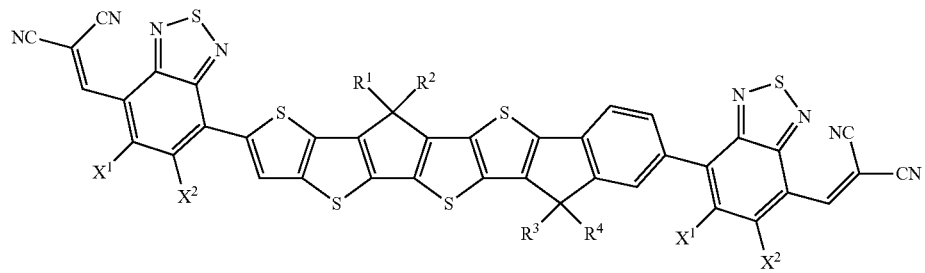
I6k
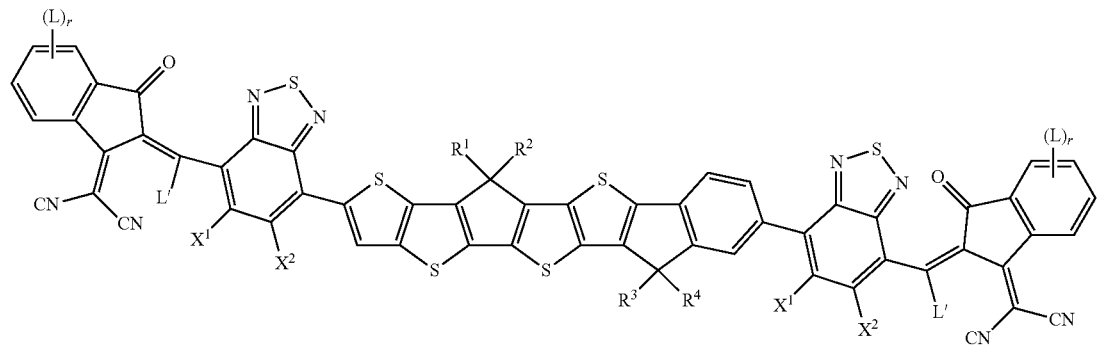
I6m
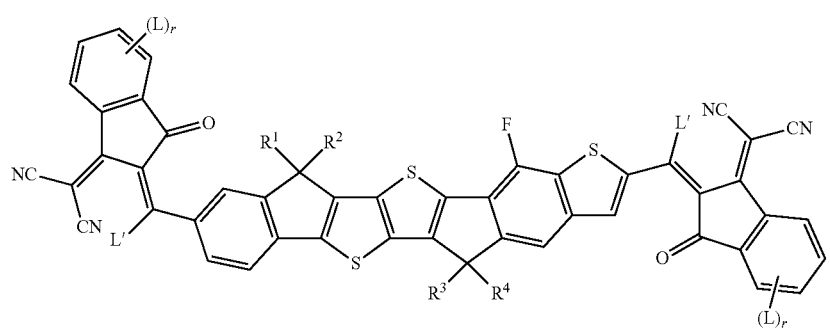
I7a

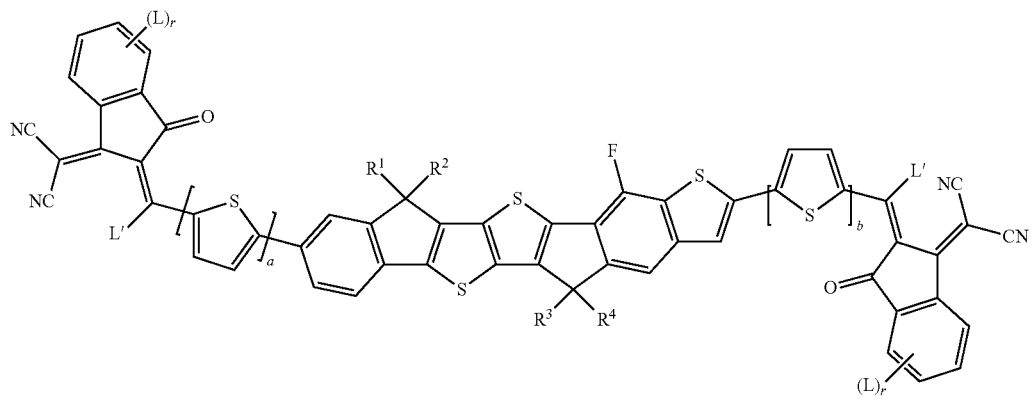
I7b
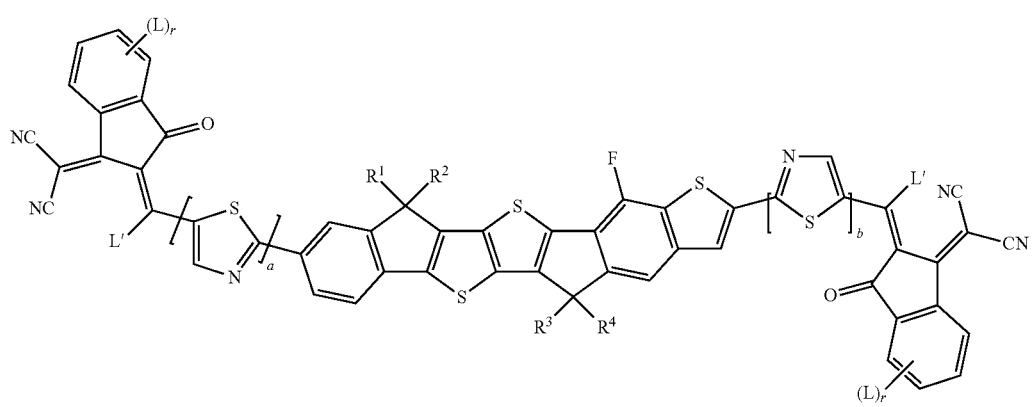
I7c
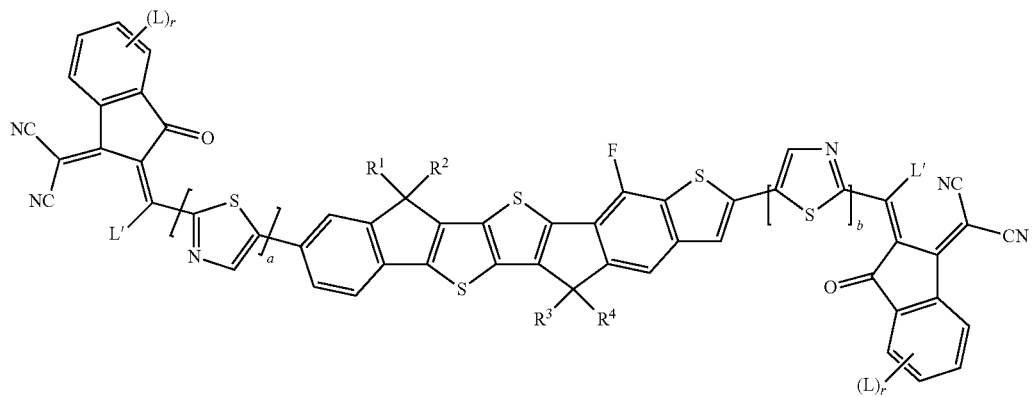
I7d
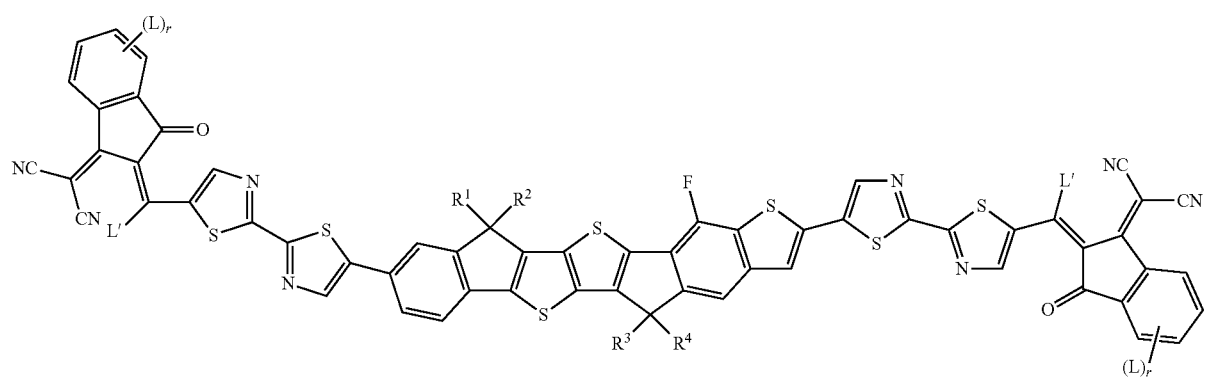
I7e

-continued
I7f
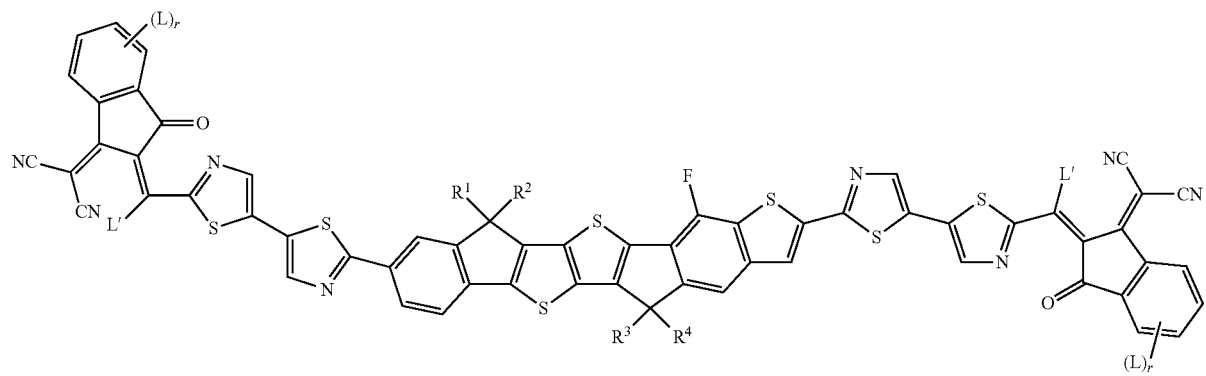
I7g
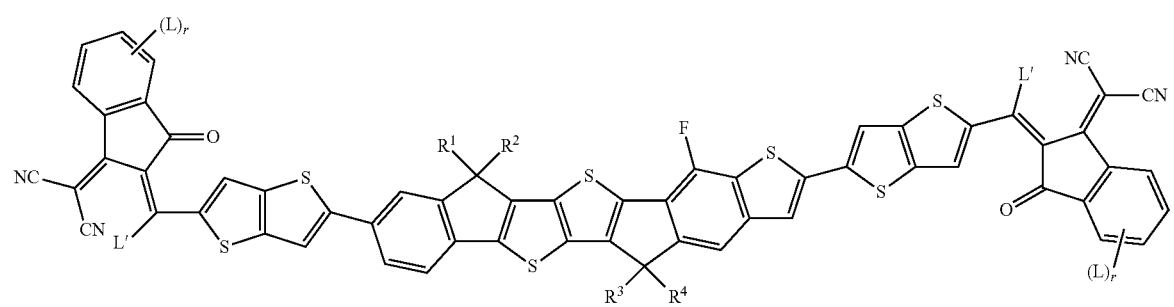
I7h
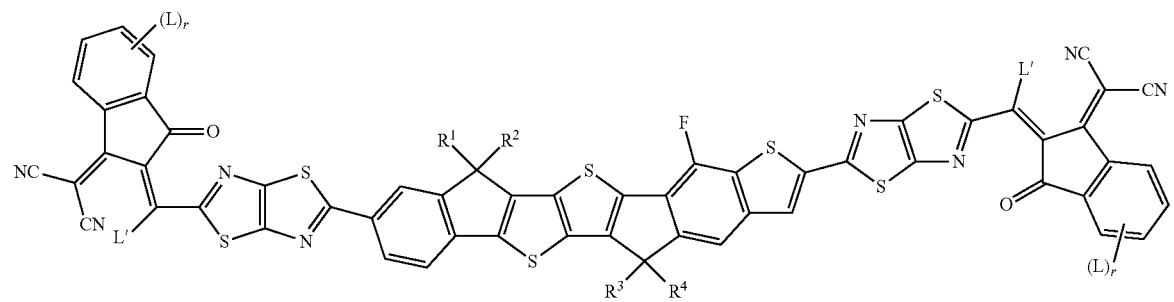
I7i
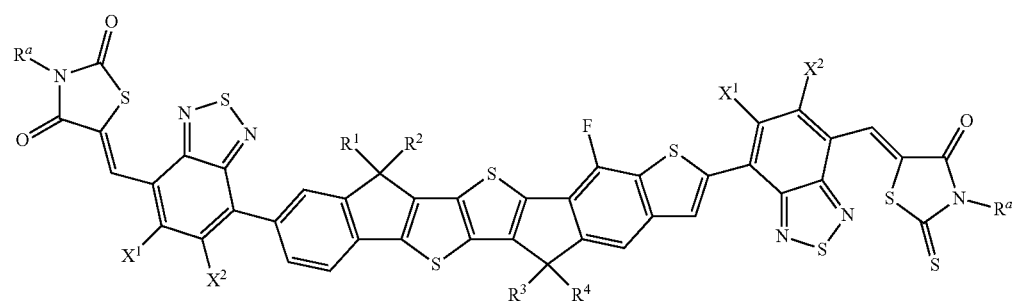
I7k
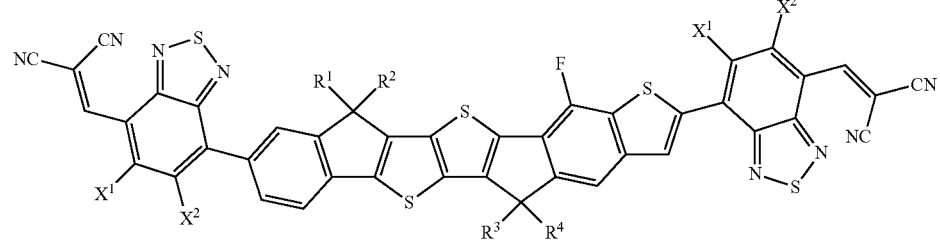

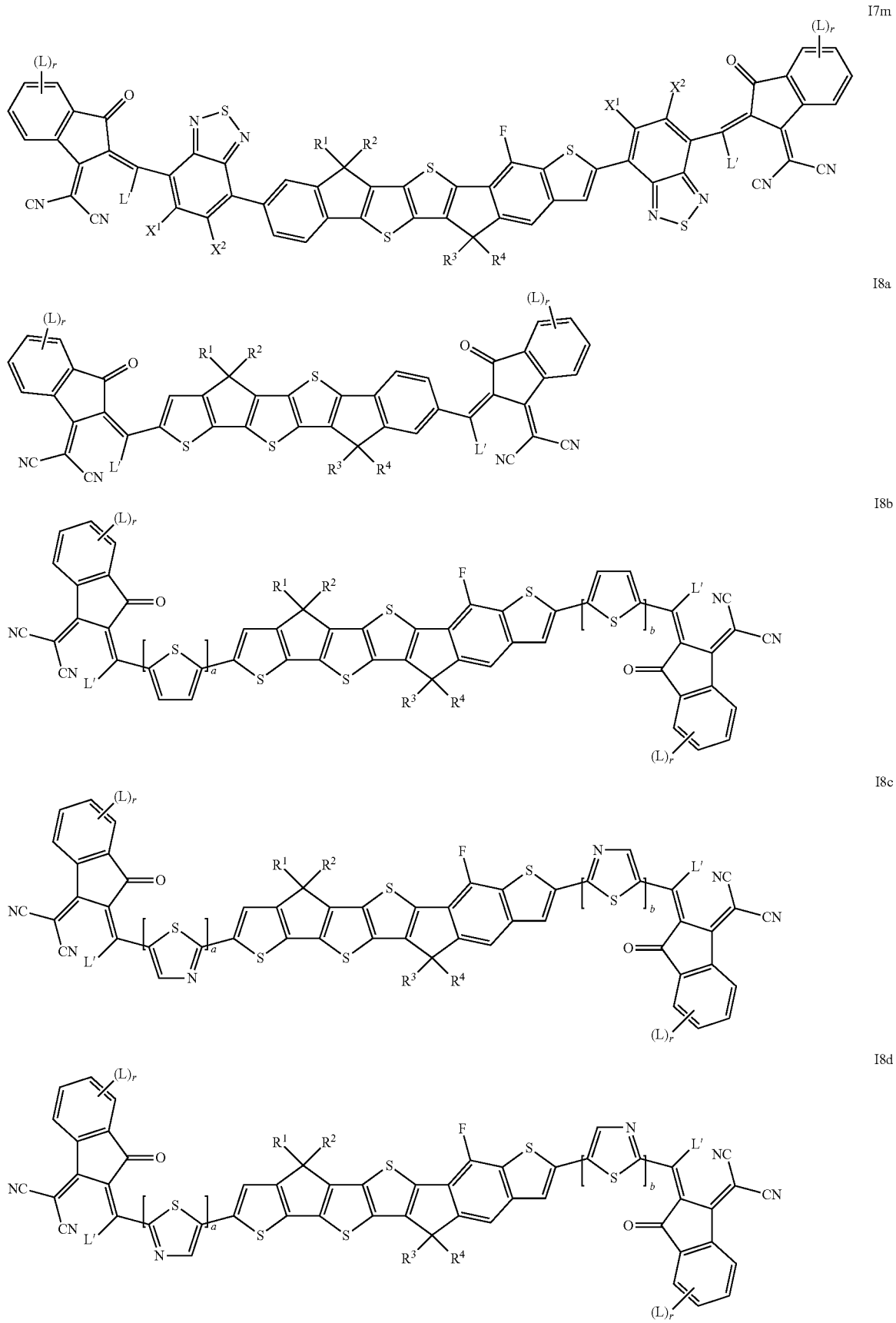

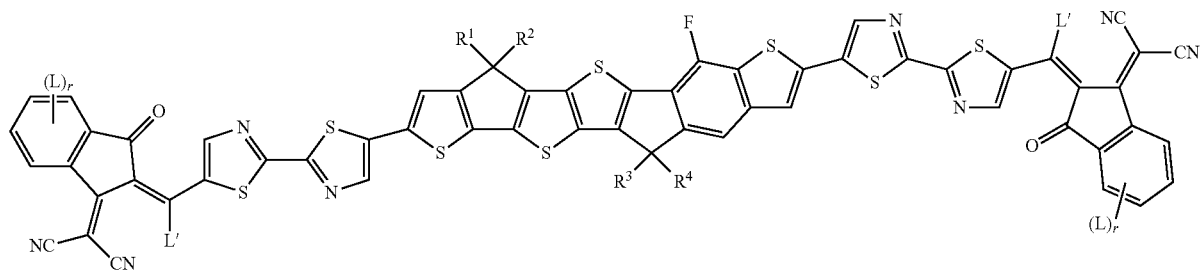
I8e
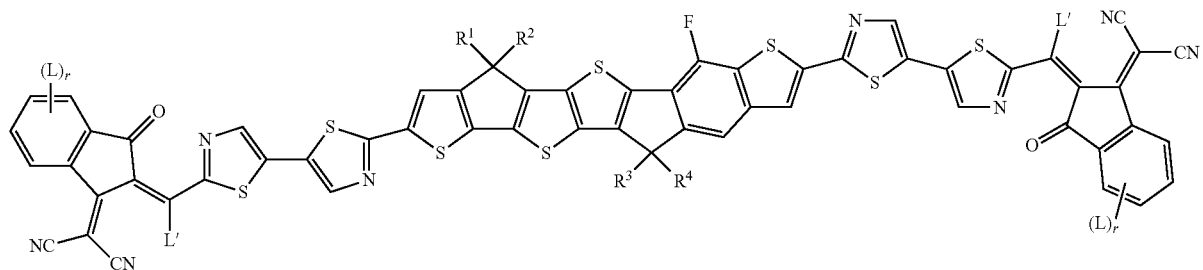
I8f
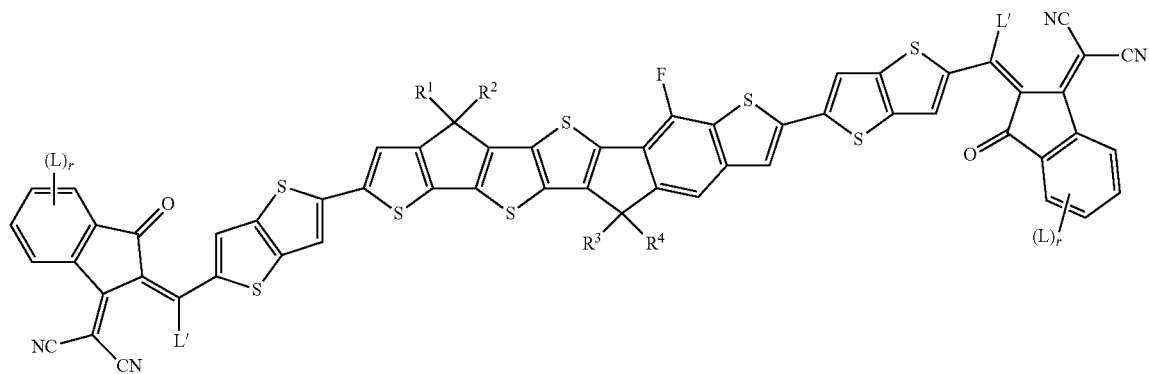
I8g
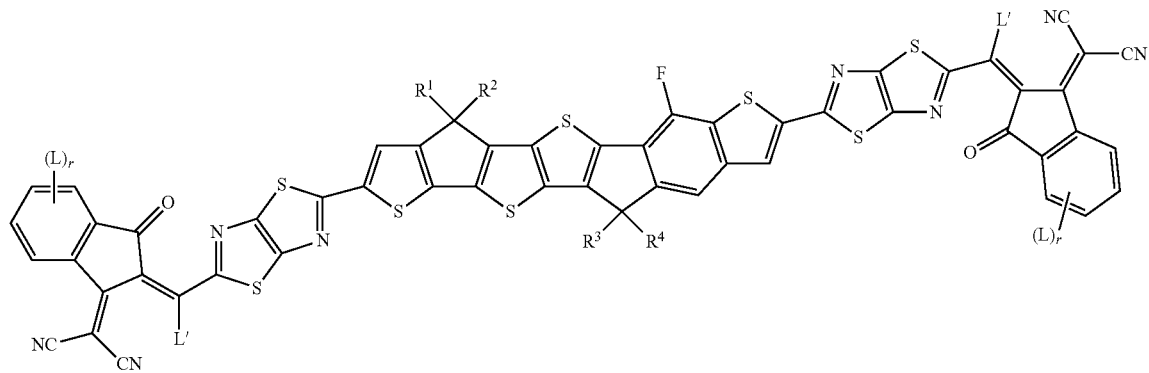
I8h

-continued
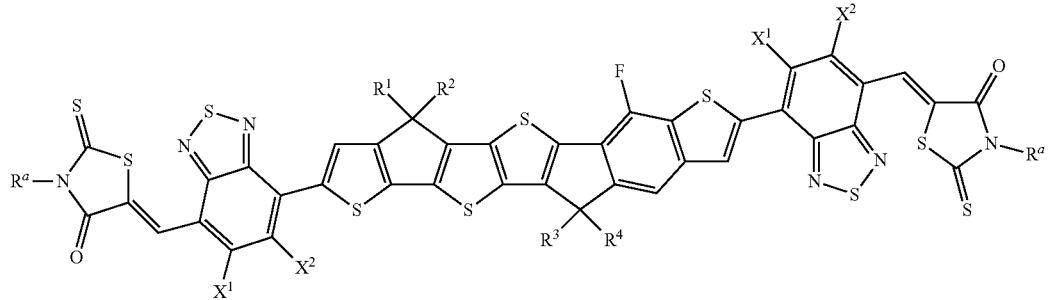
I8i
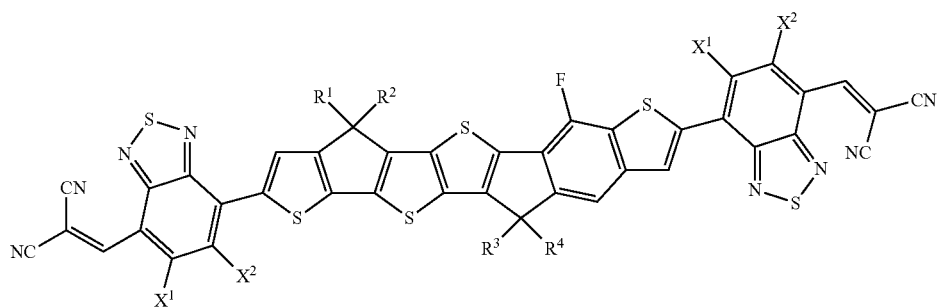
I8k
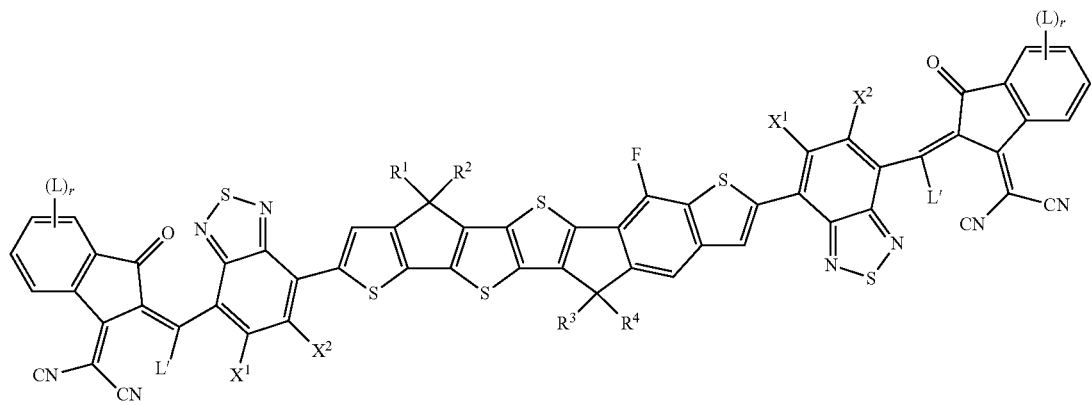
I8m
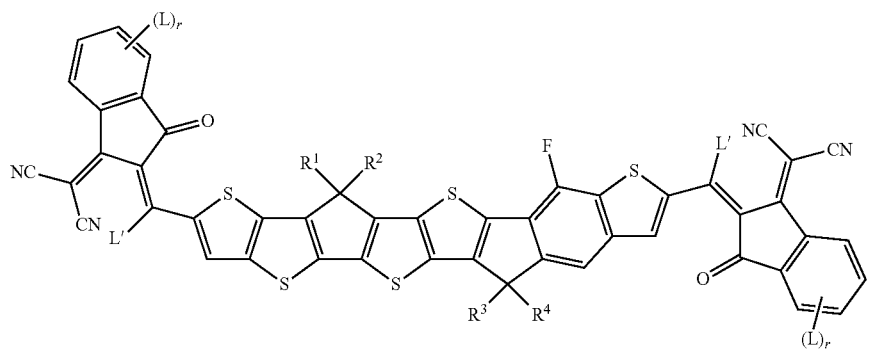
I9a

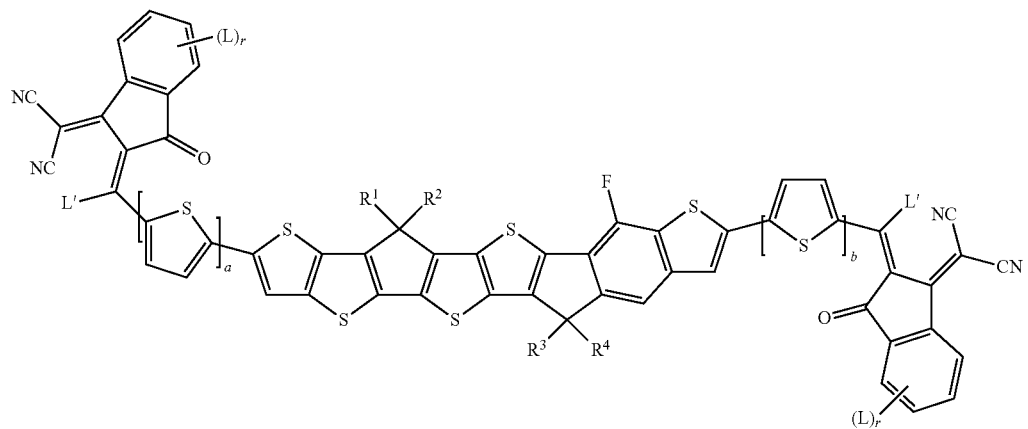
I9b
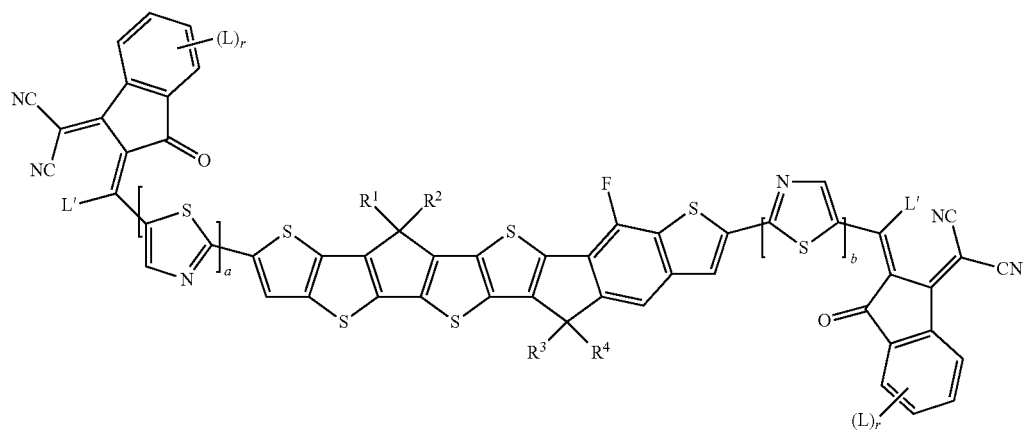
I9c
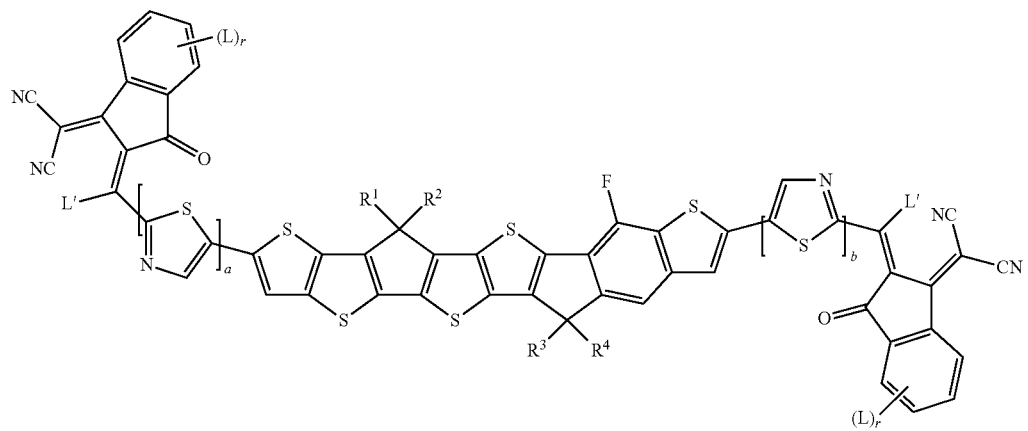
I9d

-continued
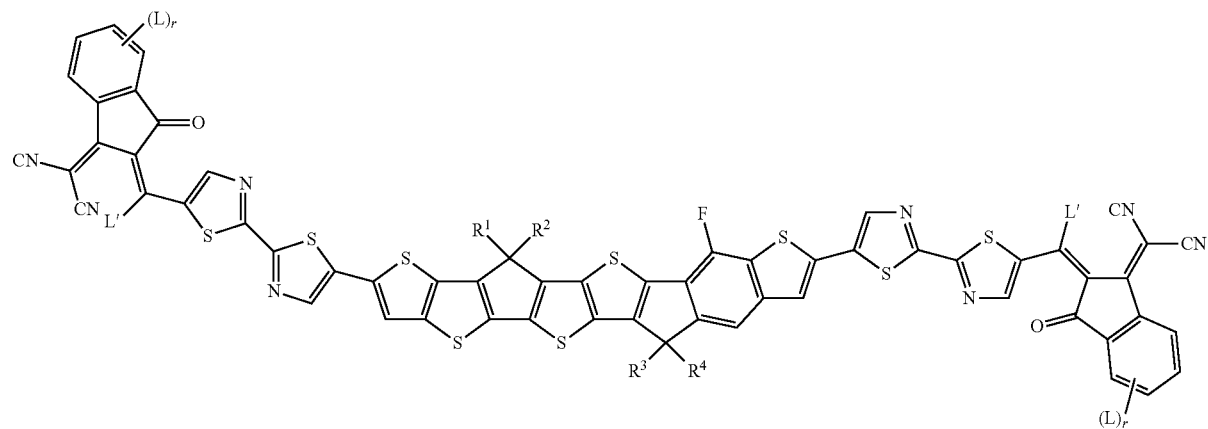
I9e
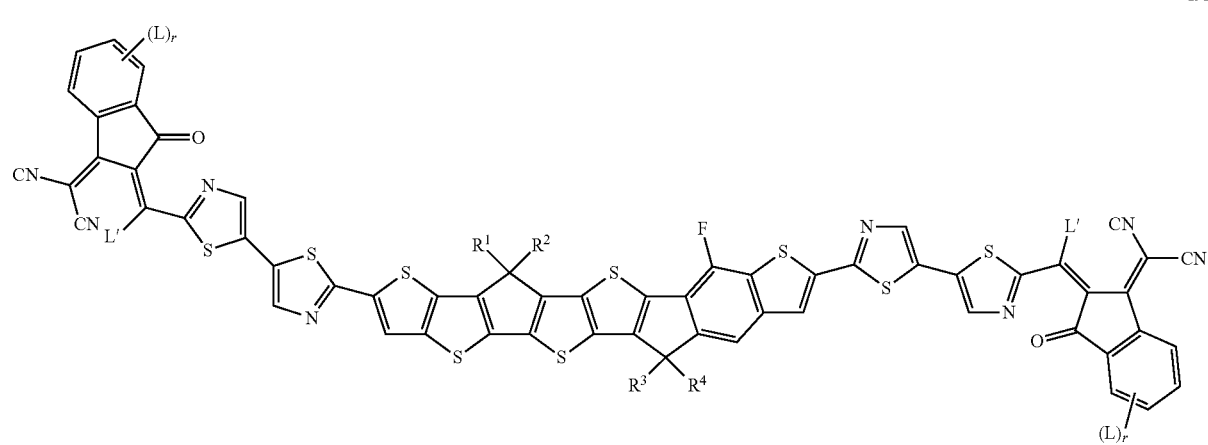
I9f
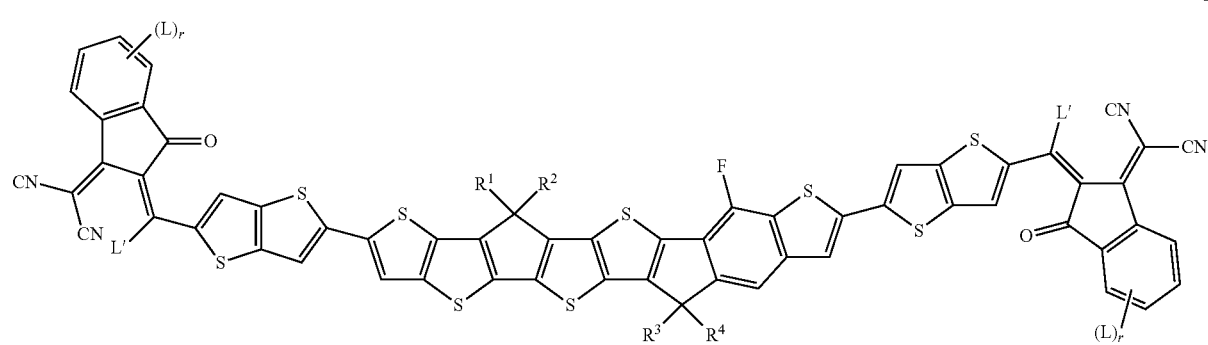
I9g
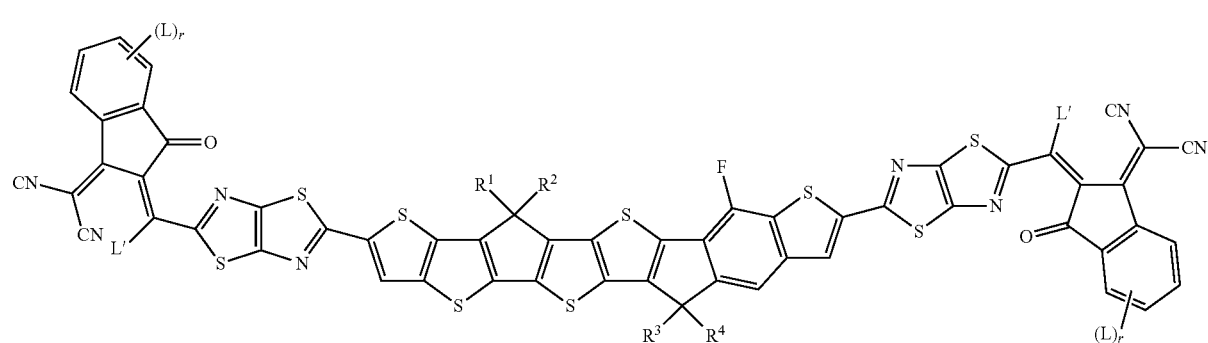
I9h

-continued
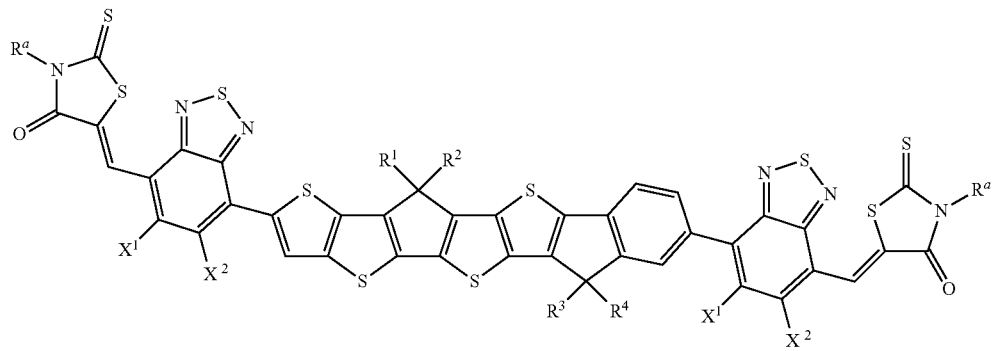
I9i
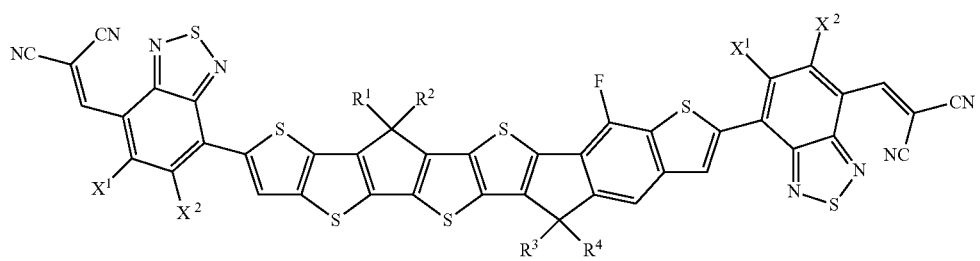
I9k
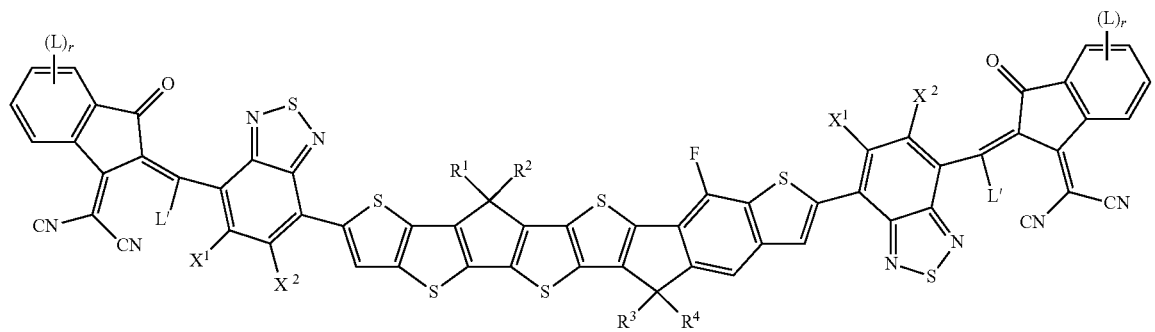
I9m
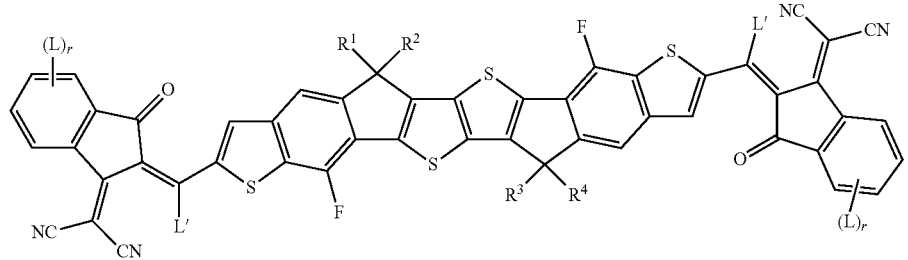
I10a
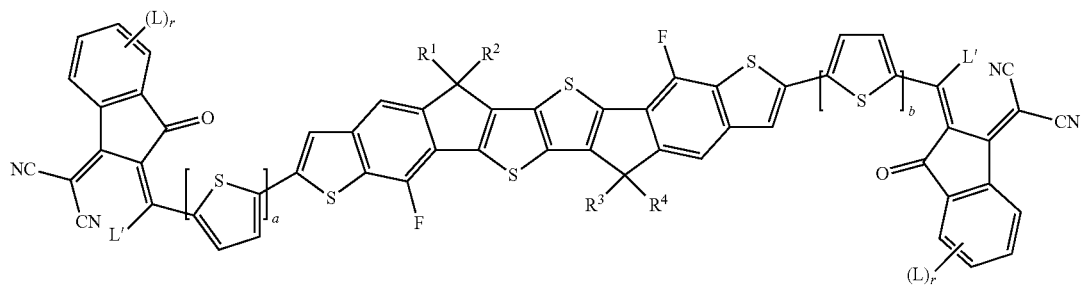
I10b I10c
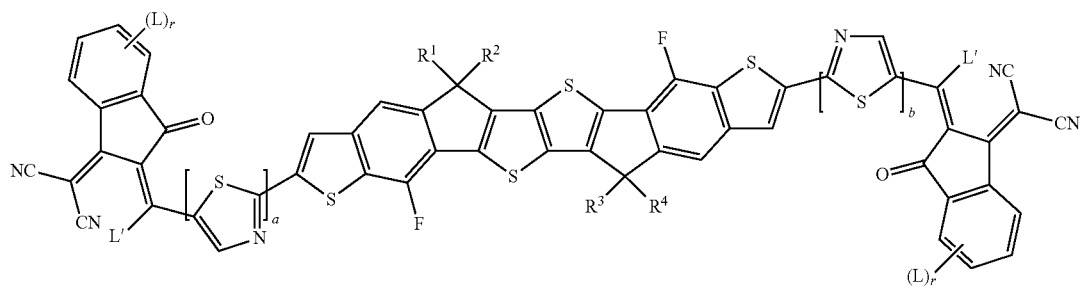
I10d
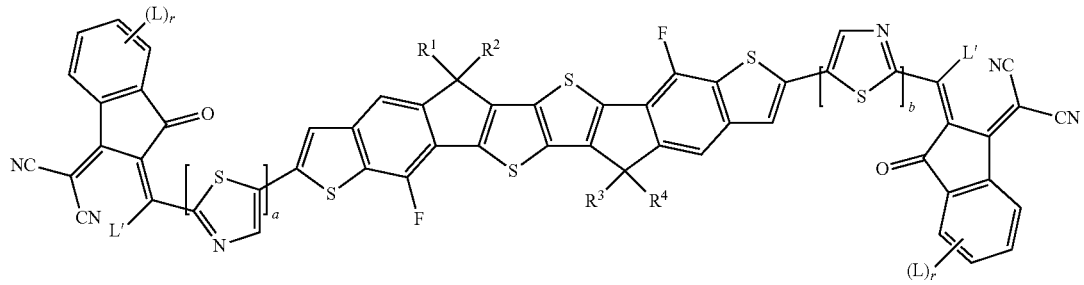
I10e
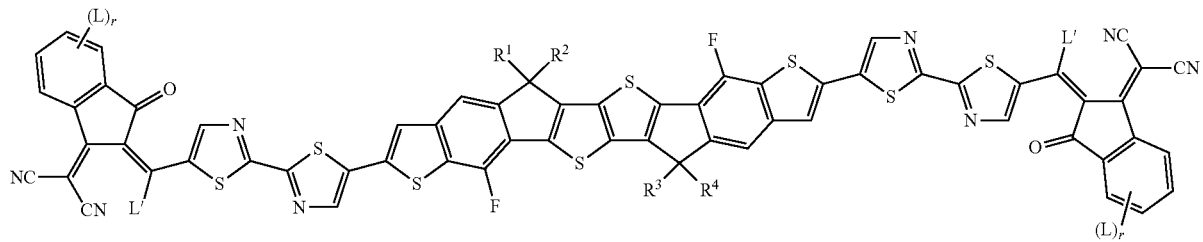
I10f
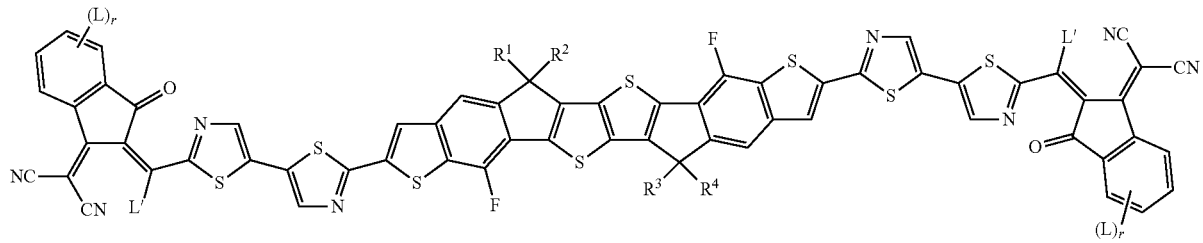
I10g
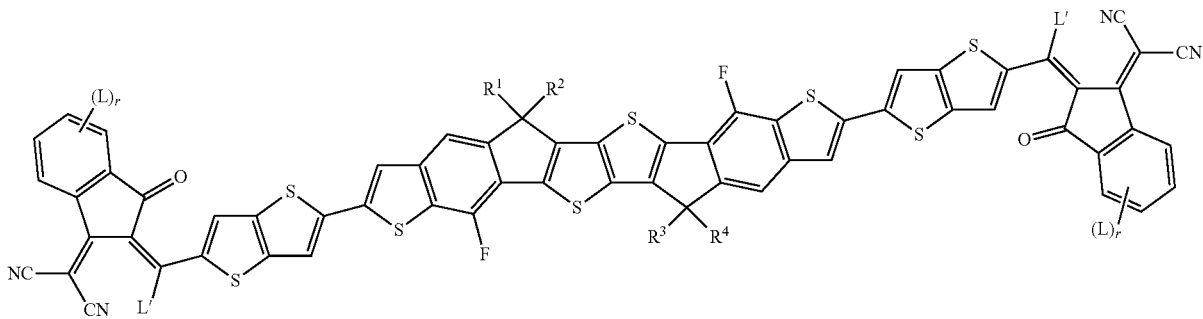

-continued
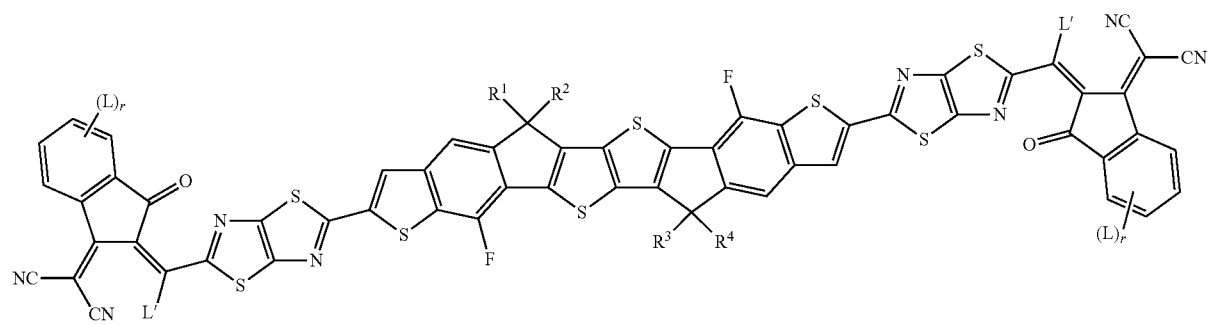
I10h
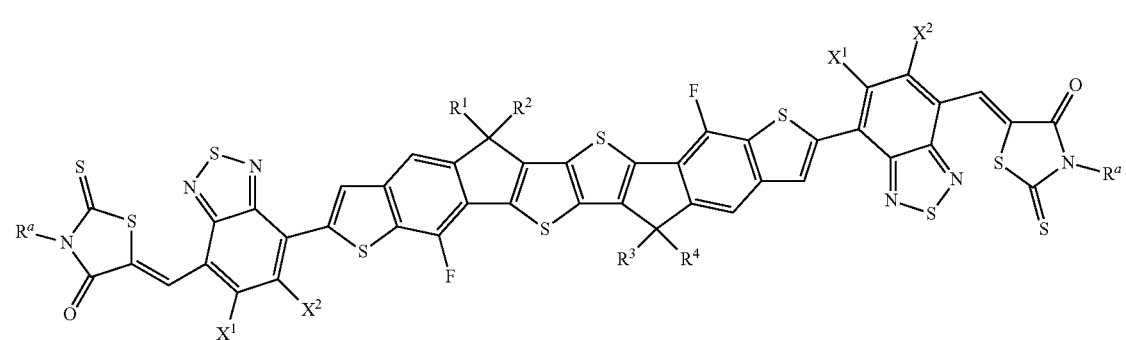
I10i
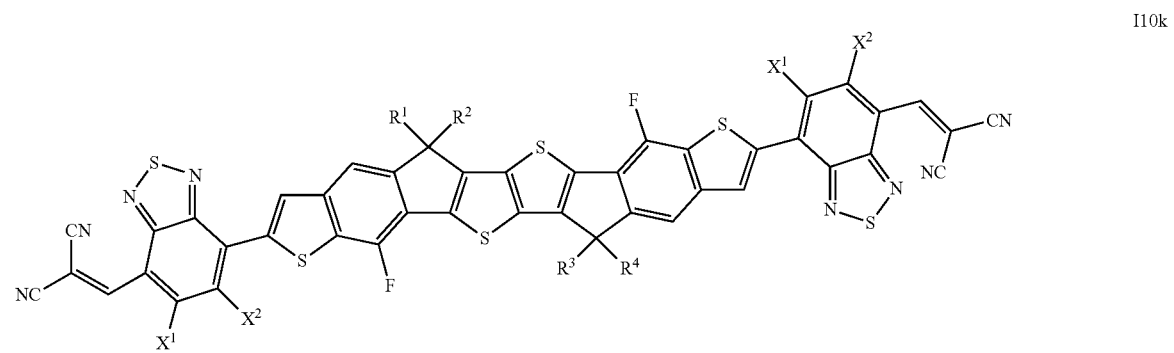
I10k
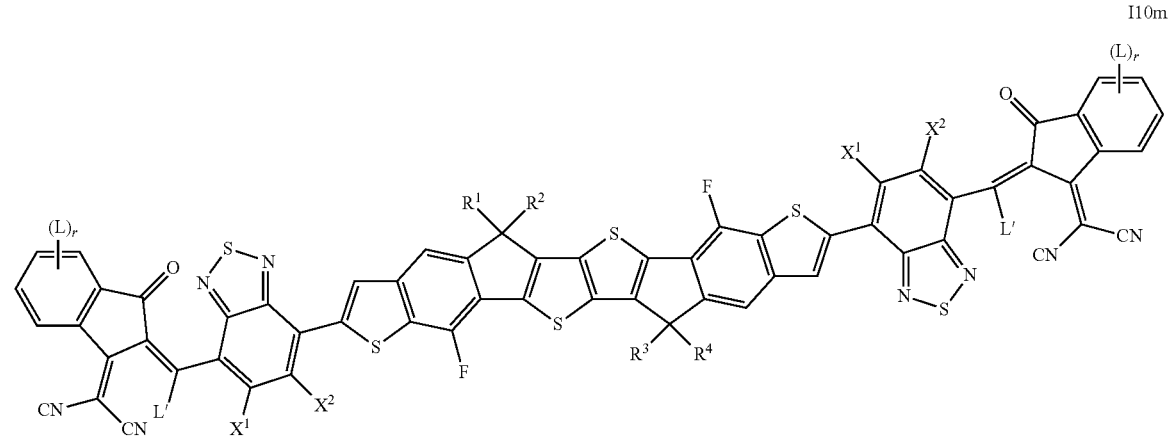
I10m

-continued
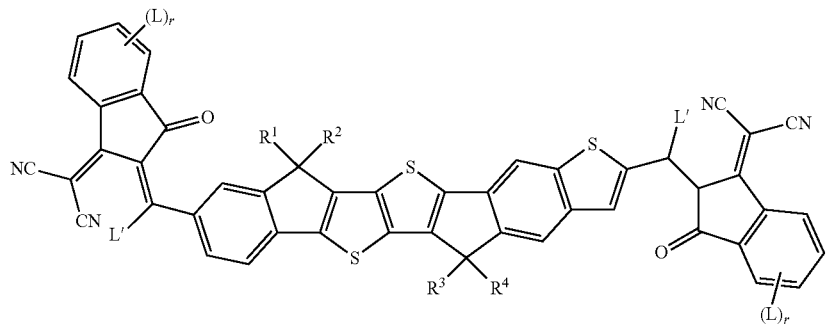
I11a
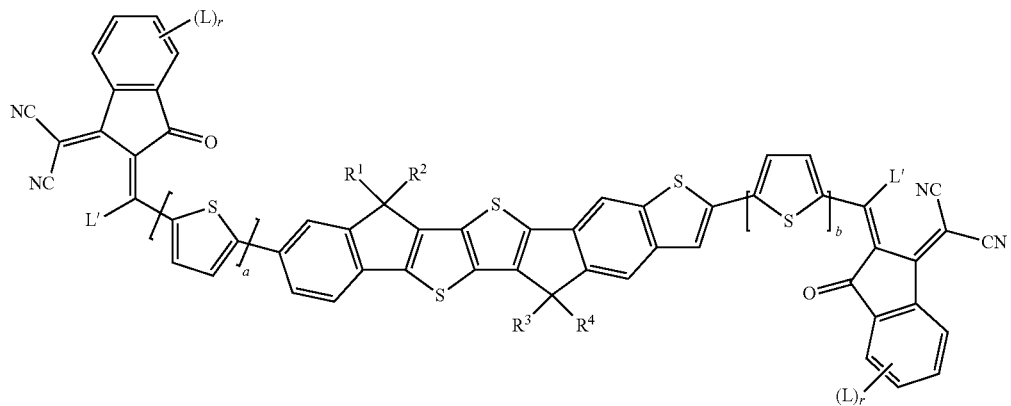
I11b
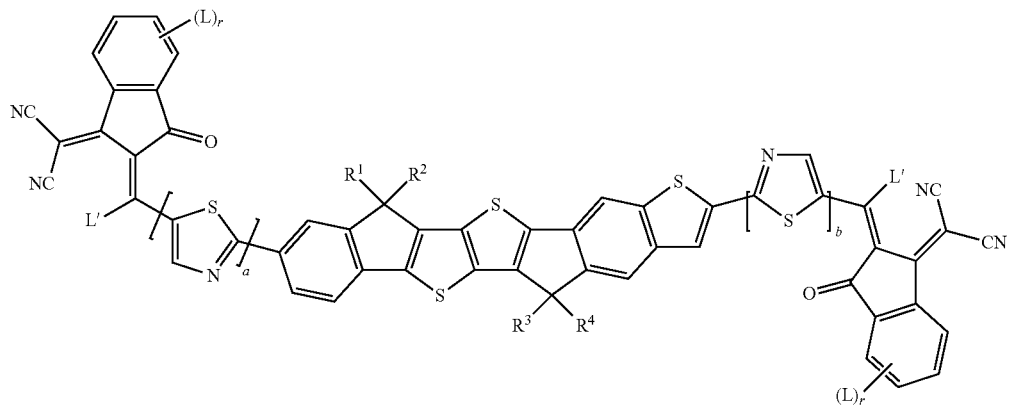
I11c
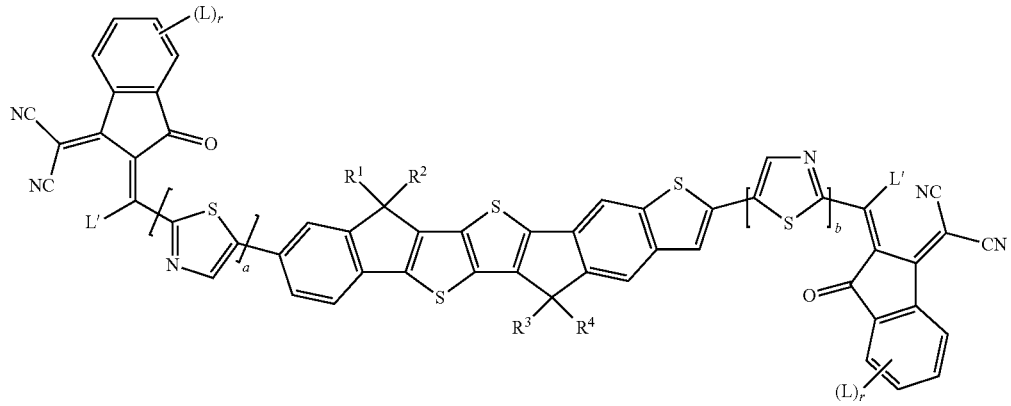
I11d

-continued
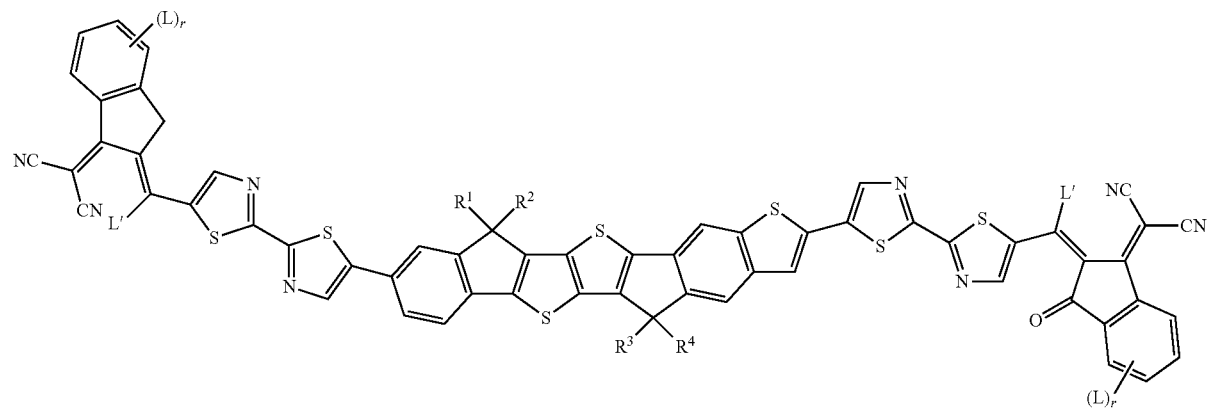
I11e
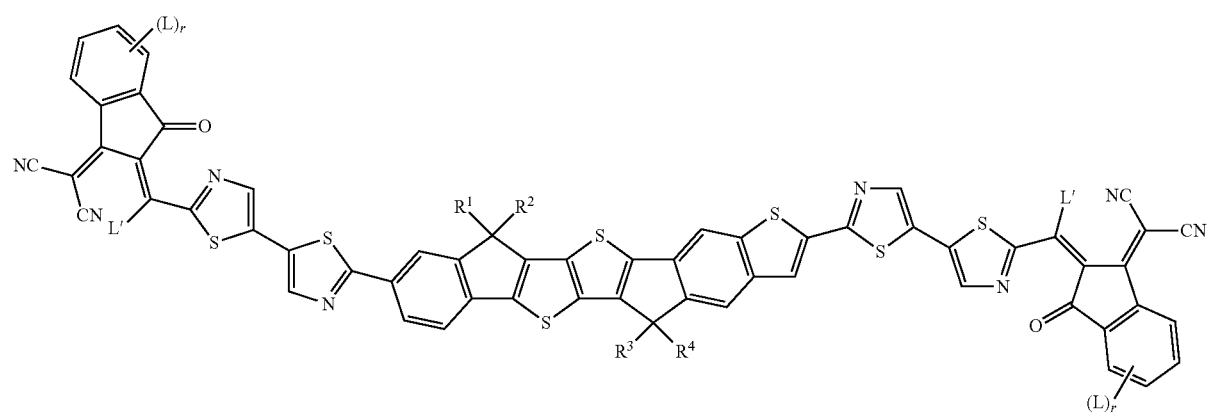
I11f
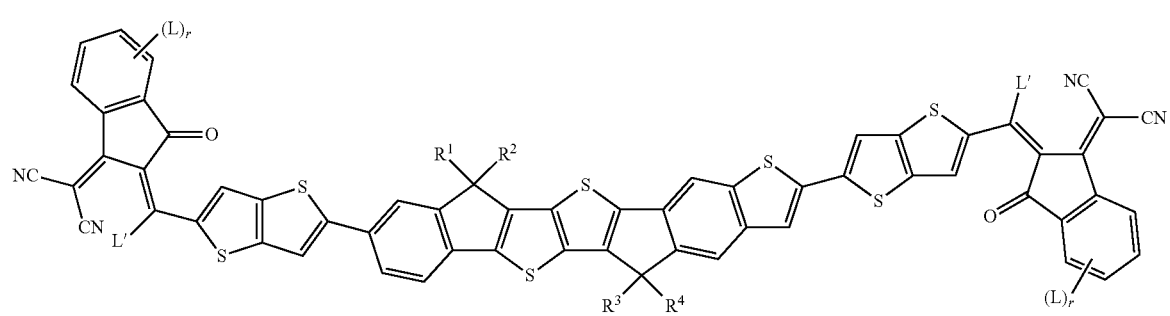
I11g
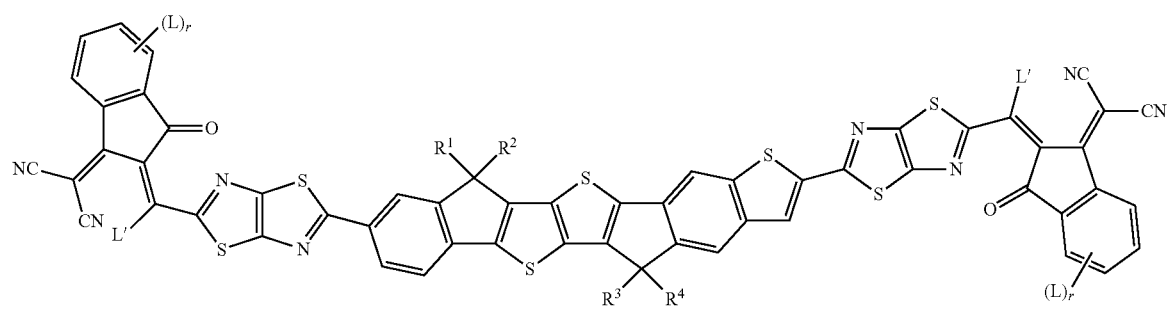
I11h

-continued
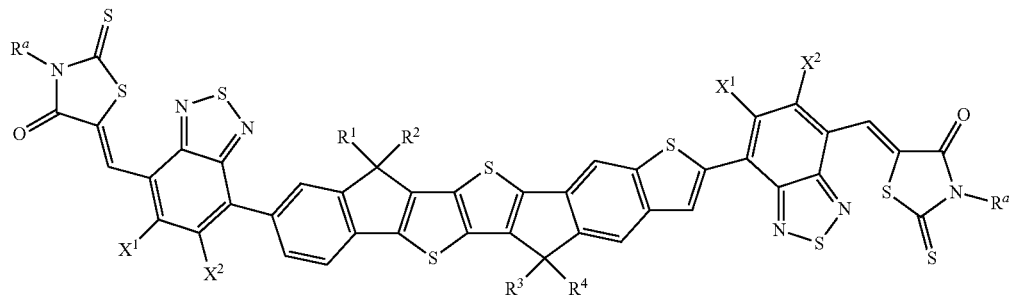
I11i
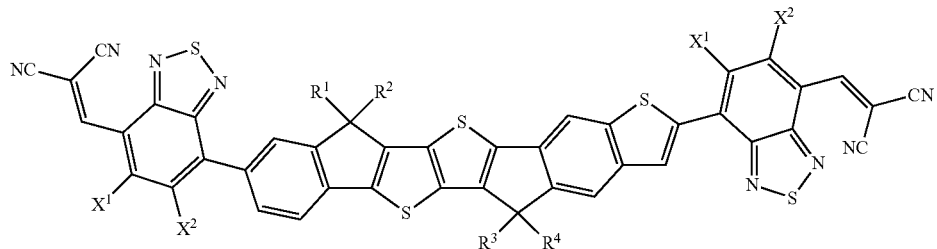
I11k
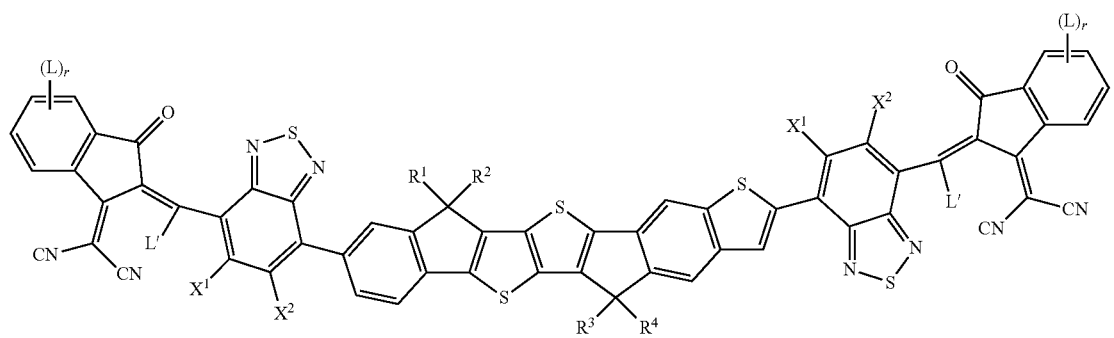
I11m
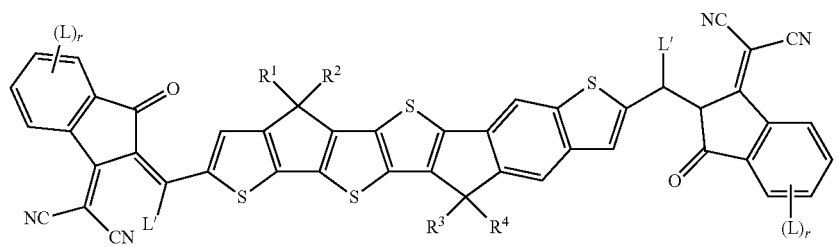
I12a
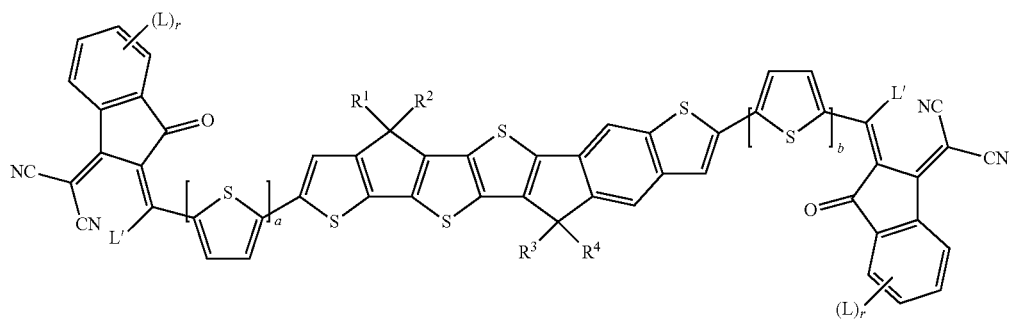
I12b -continued
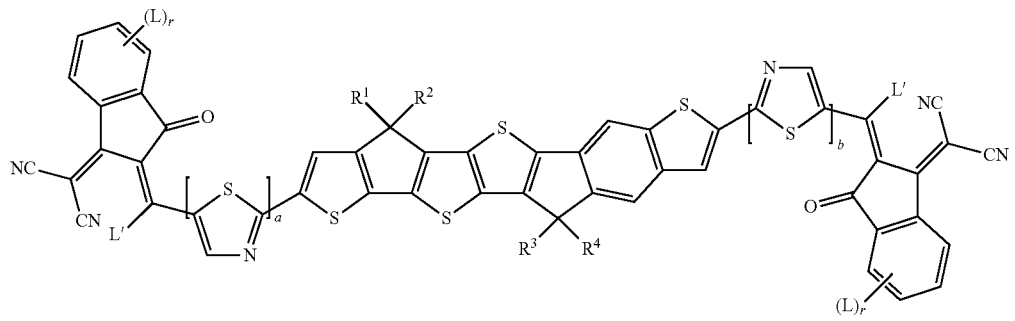
I12c
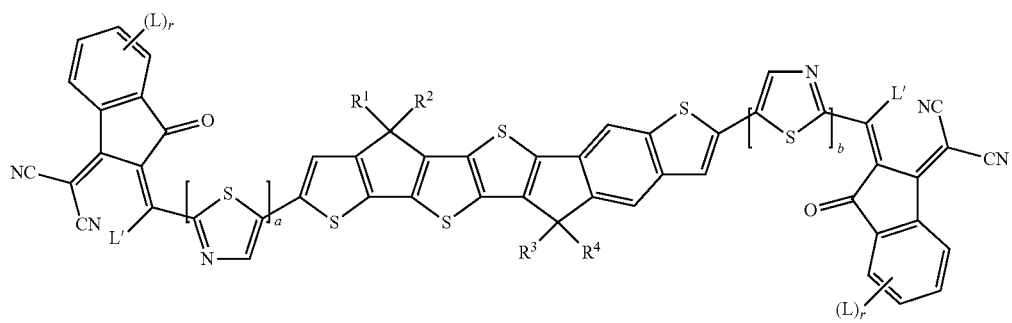
I12d
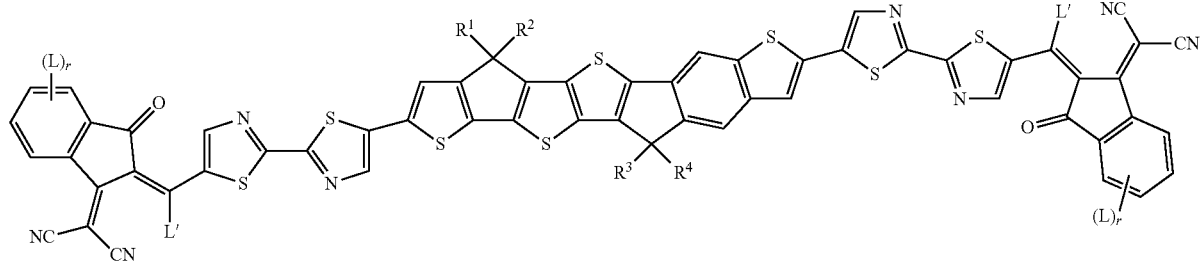
I12e
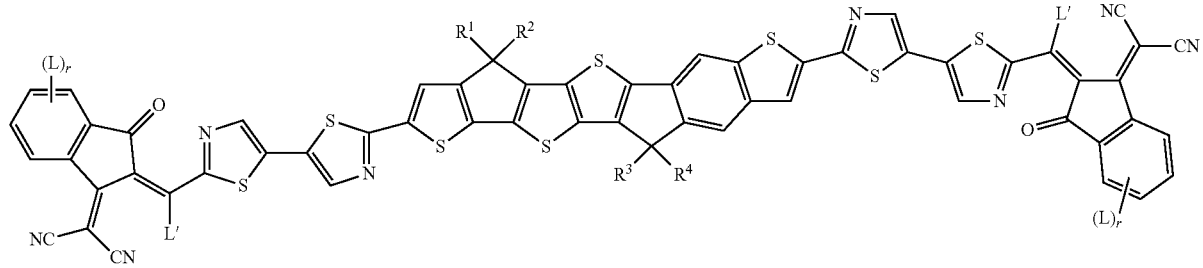
I12f
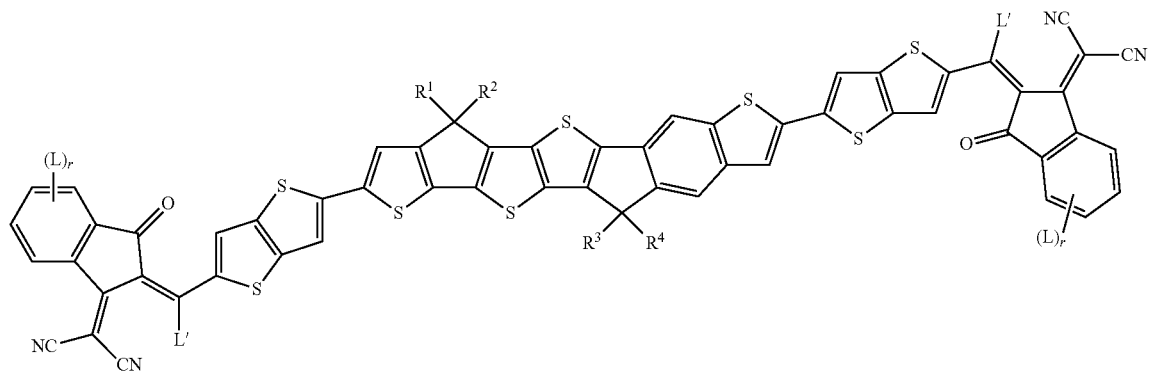
I12g

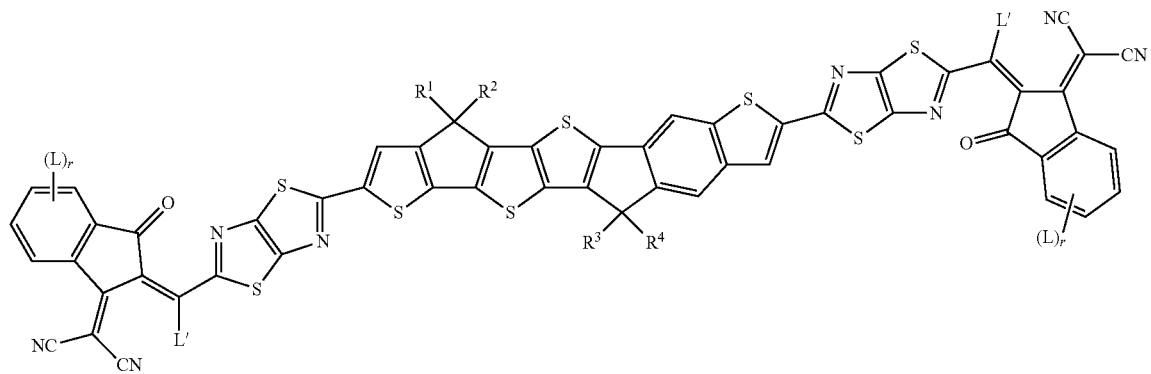
I12h
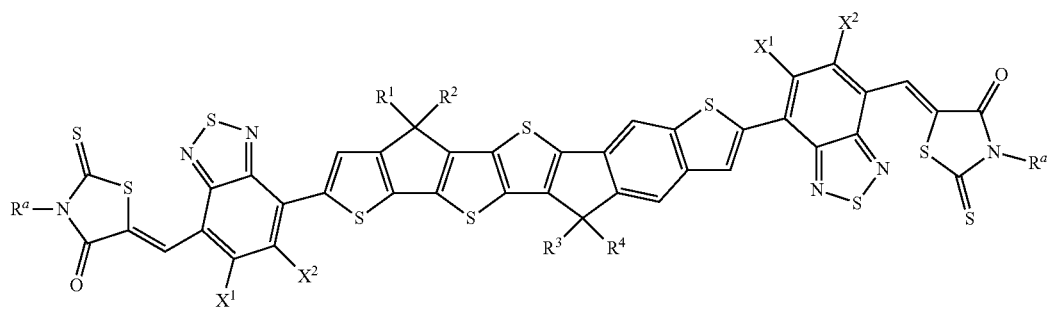
I12i
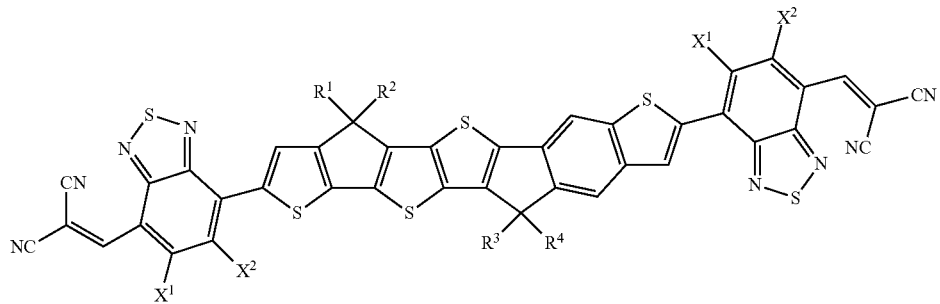
I12k
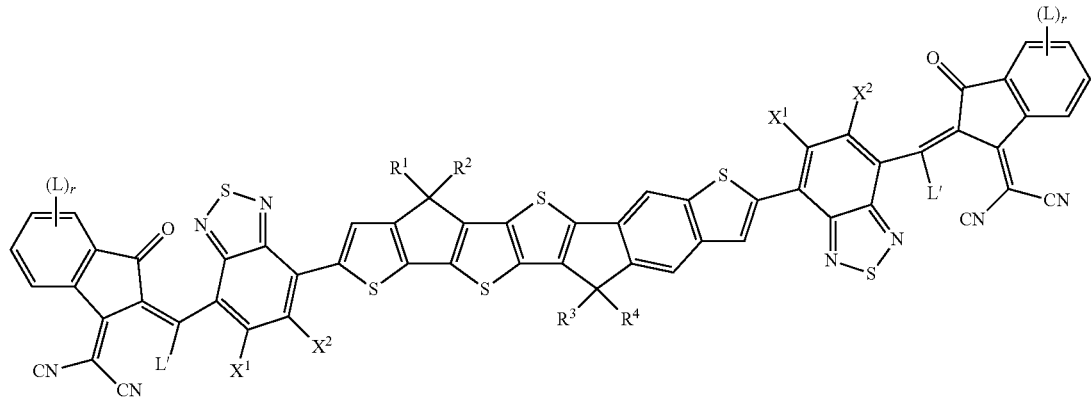
I12m

-continued
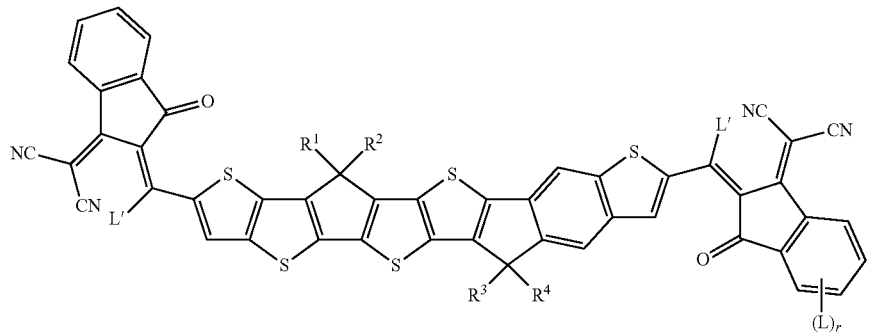
I13a
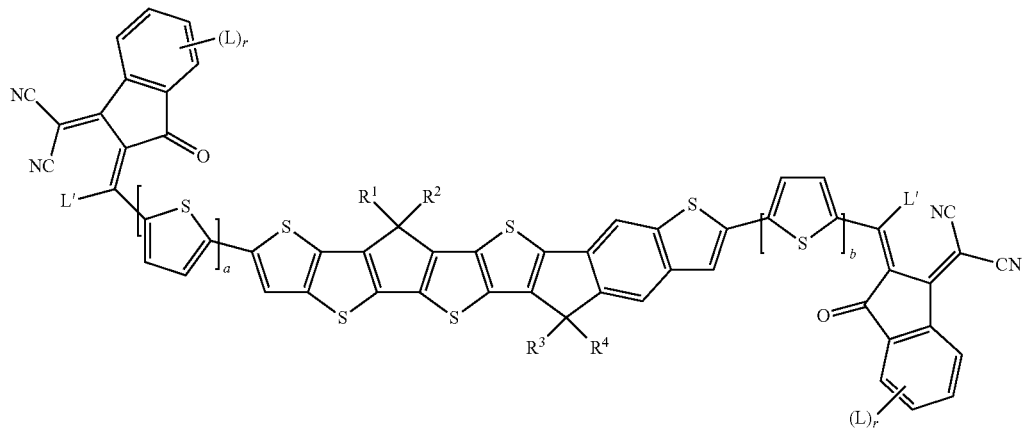
I13b
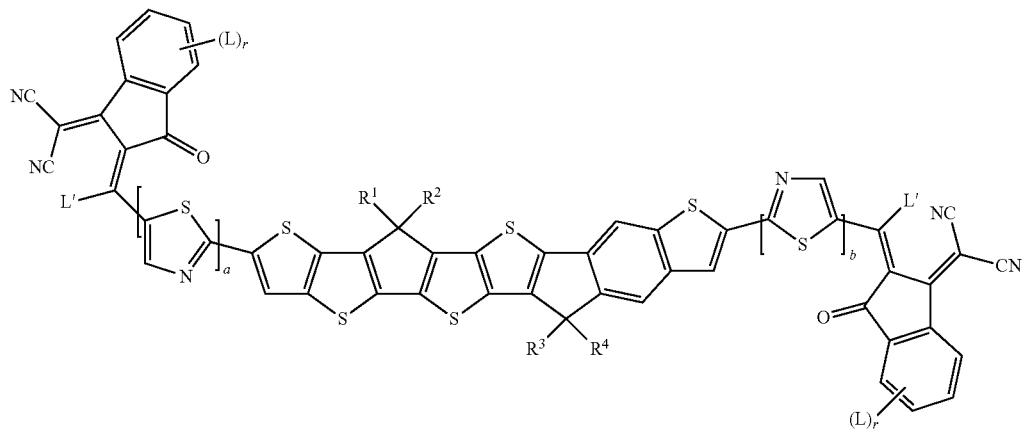
I13c
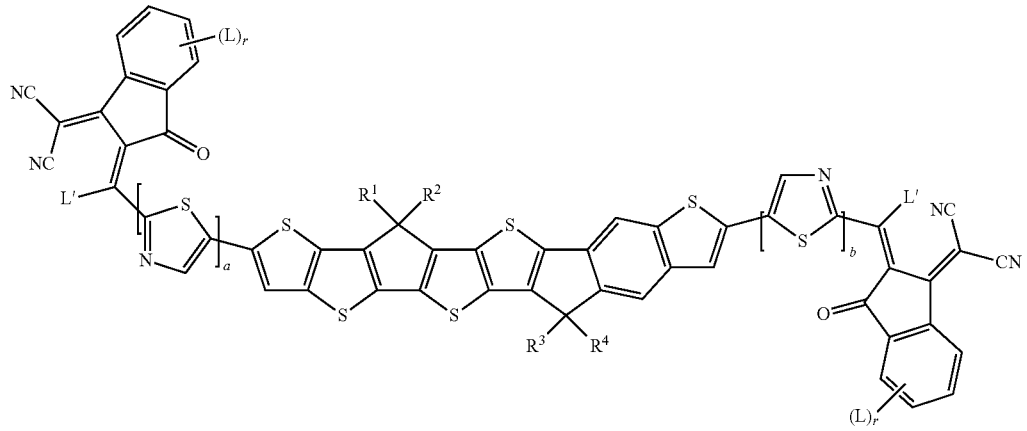
I13d

-continued
I13e
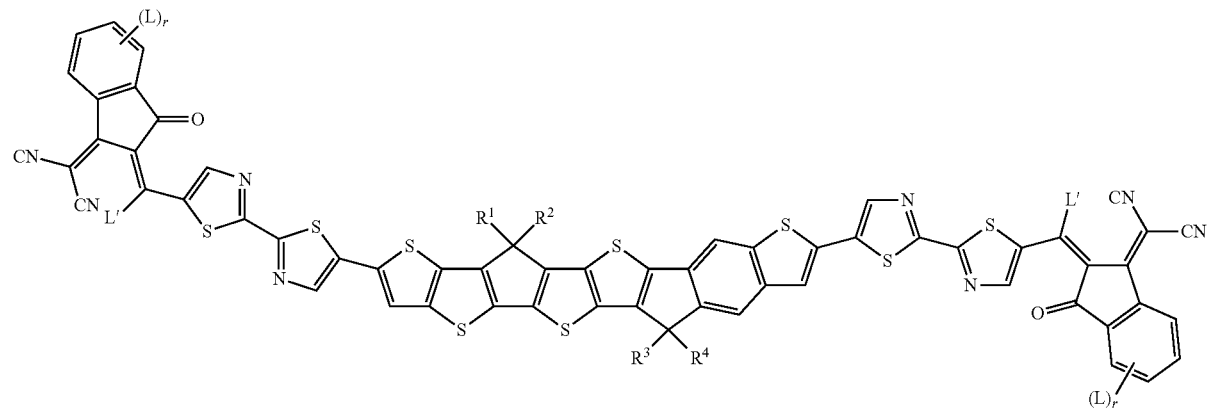
I13f
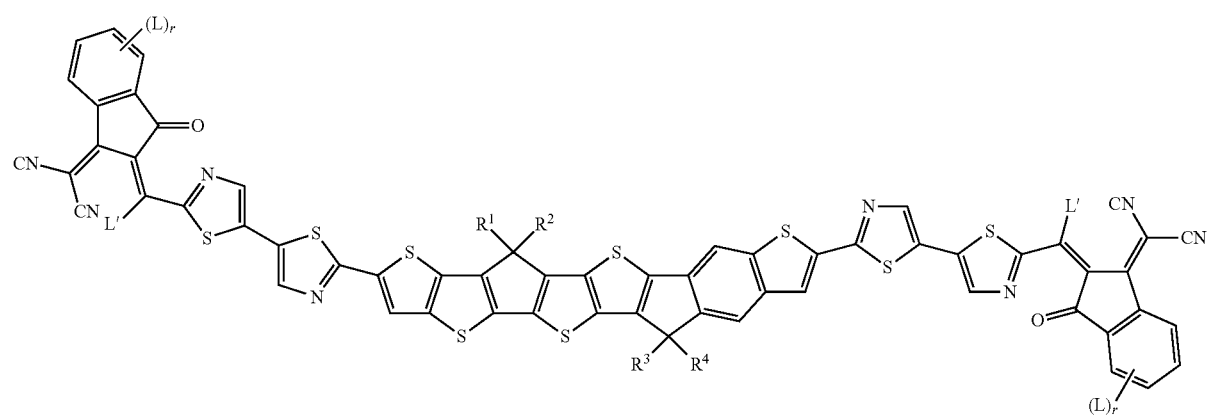
I13g
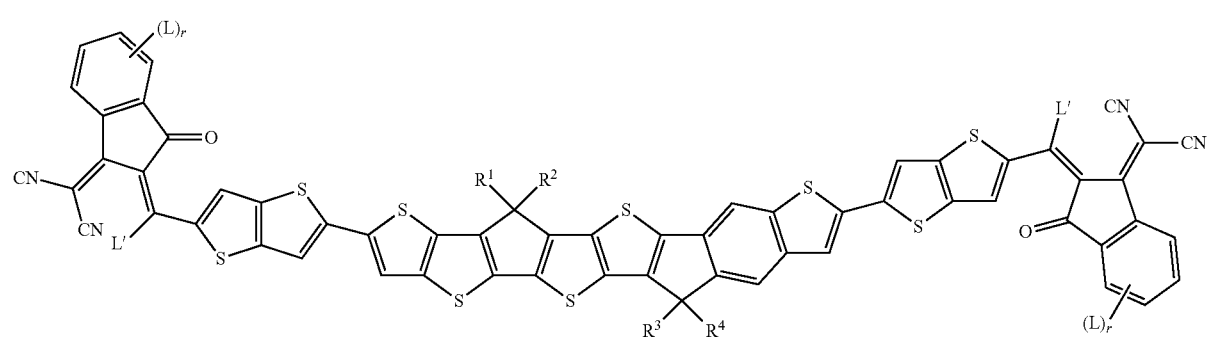
I13h
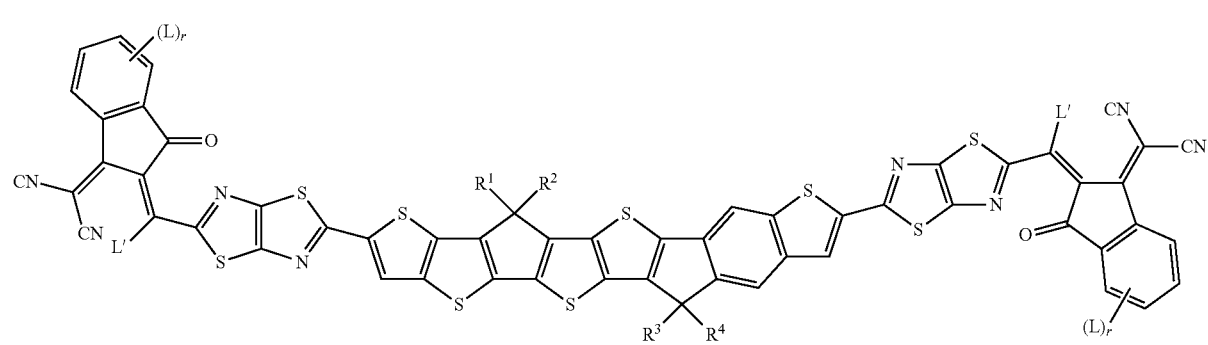

I13i
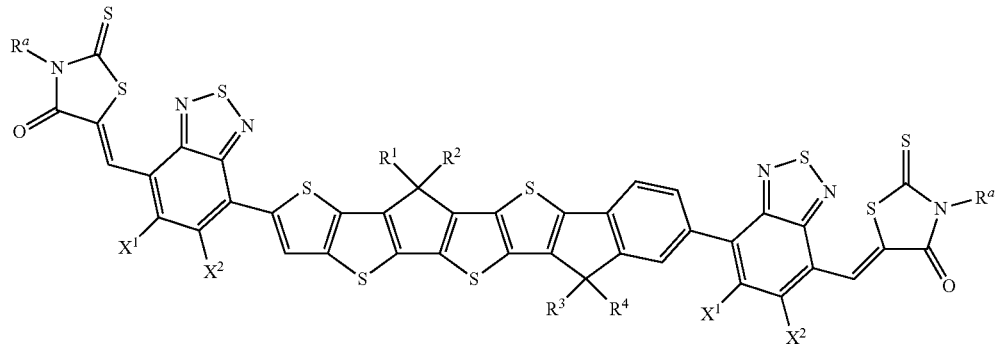
I13k
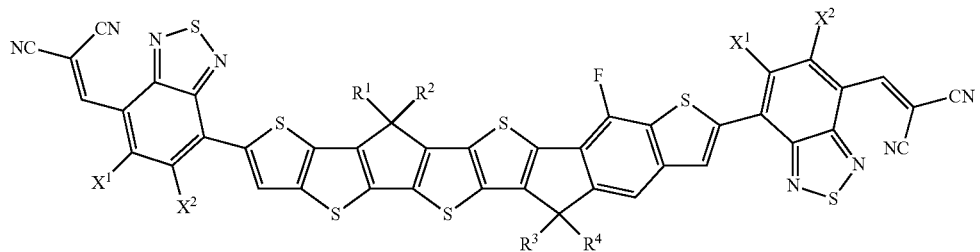
I13m
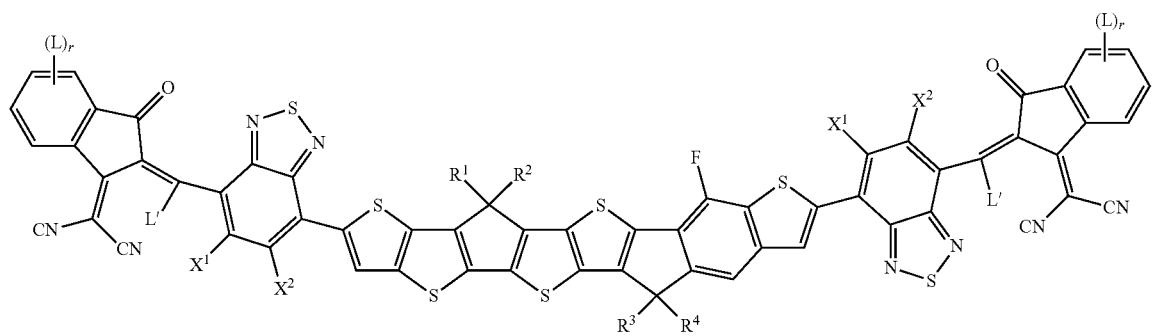
I14a
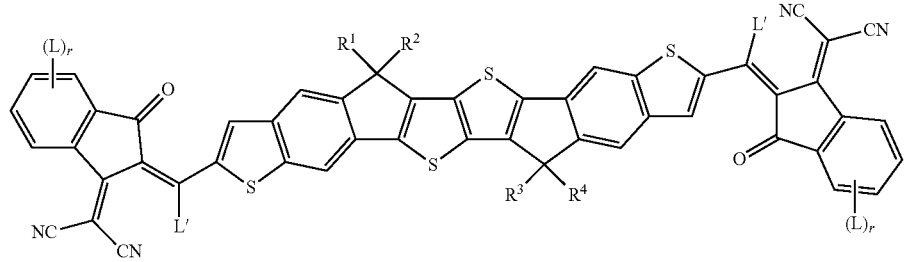
I14b
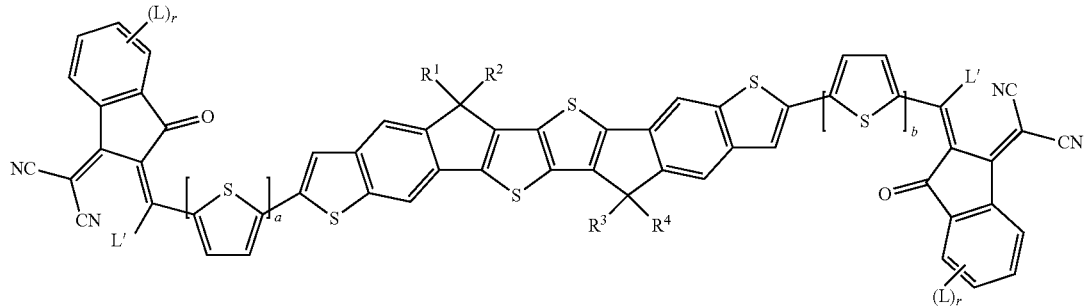

-continued
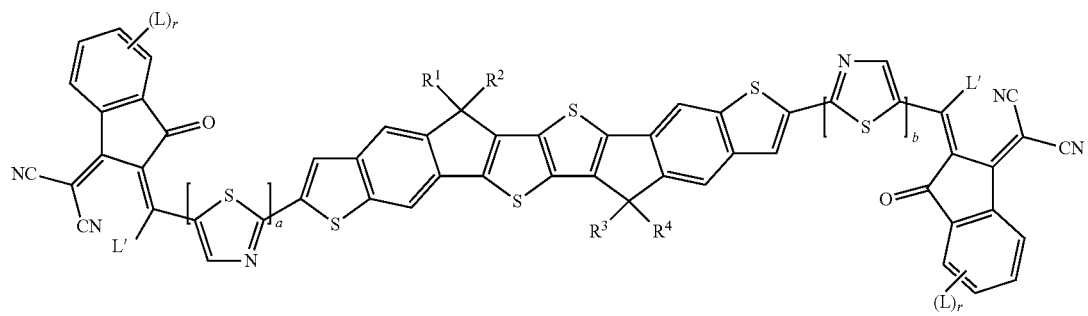
I14c
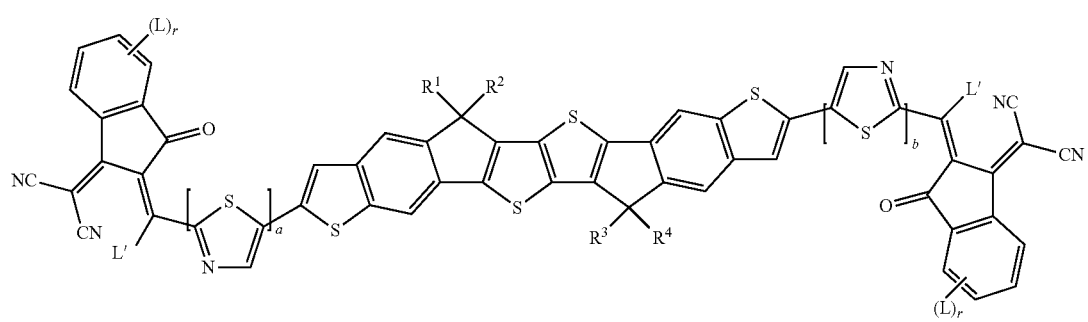
I14d
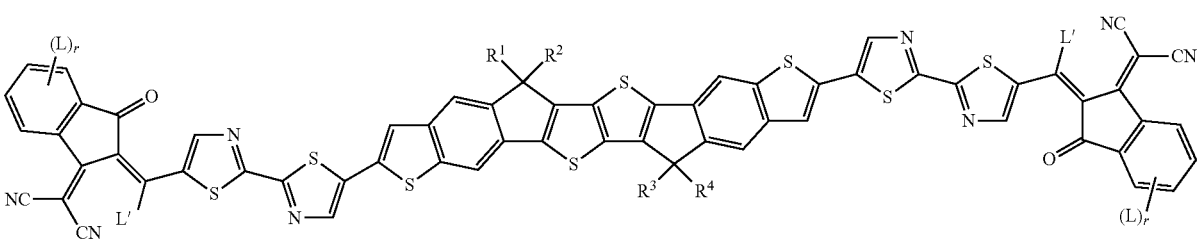
I14e
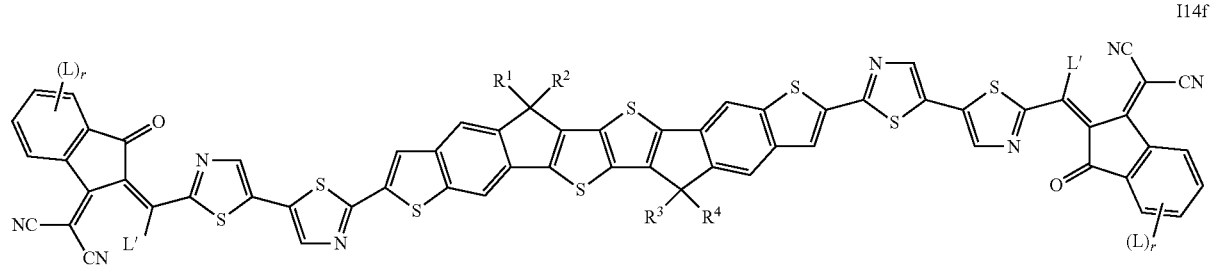
I14f
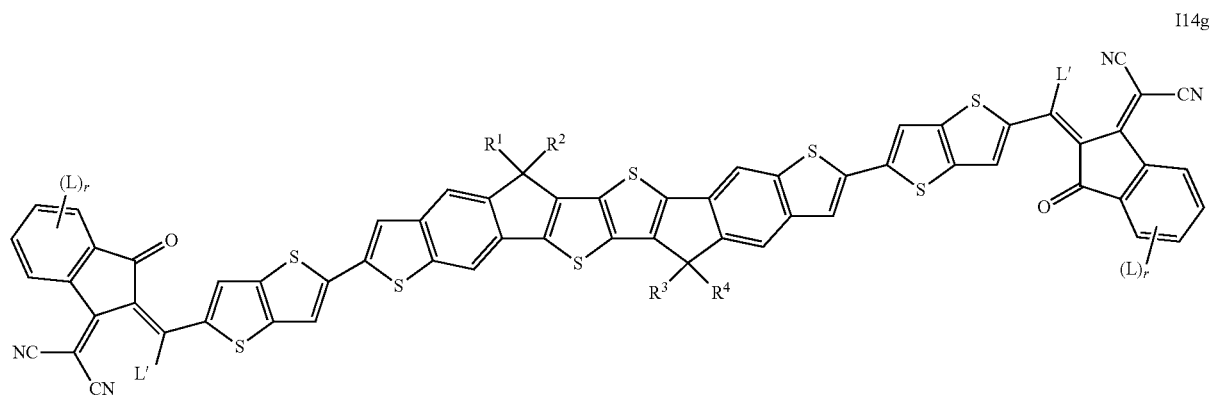
I14g -continued
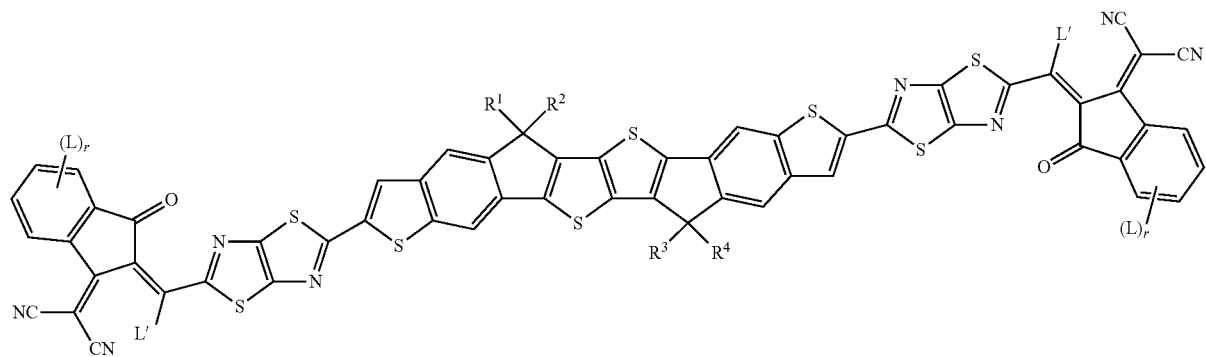
I14h
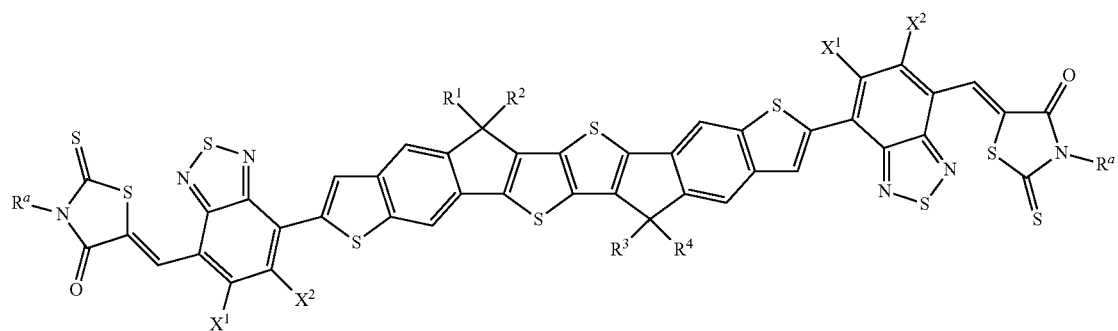
I14i
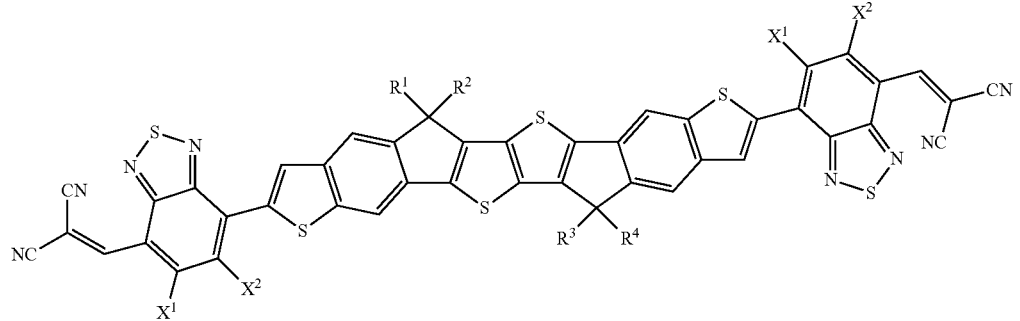
I14k
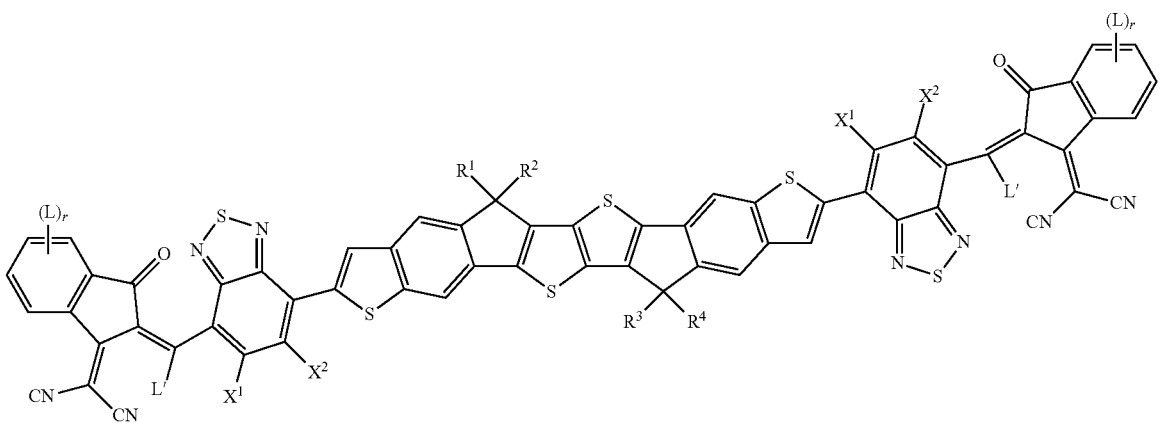
I14m

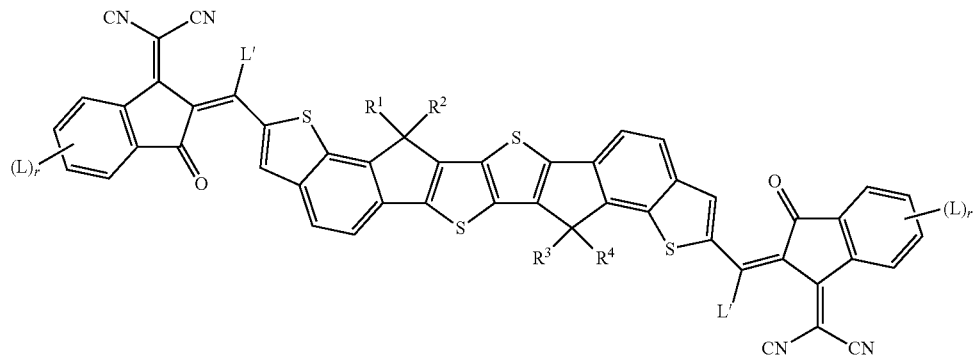
I15a
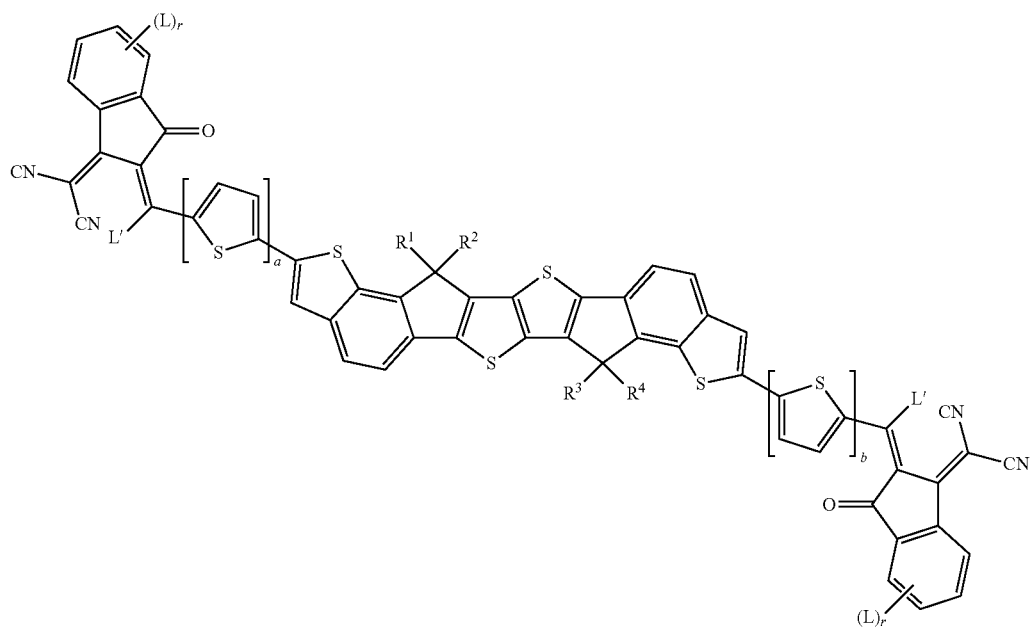
I15b
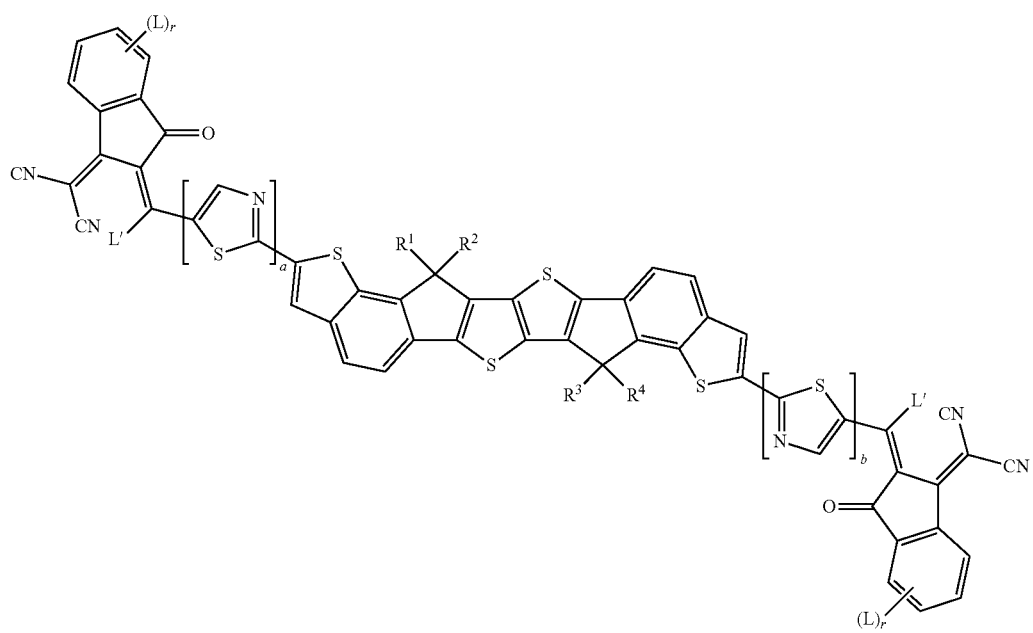
I15c

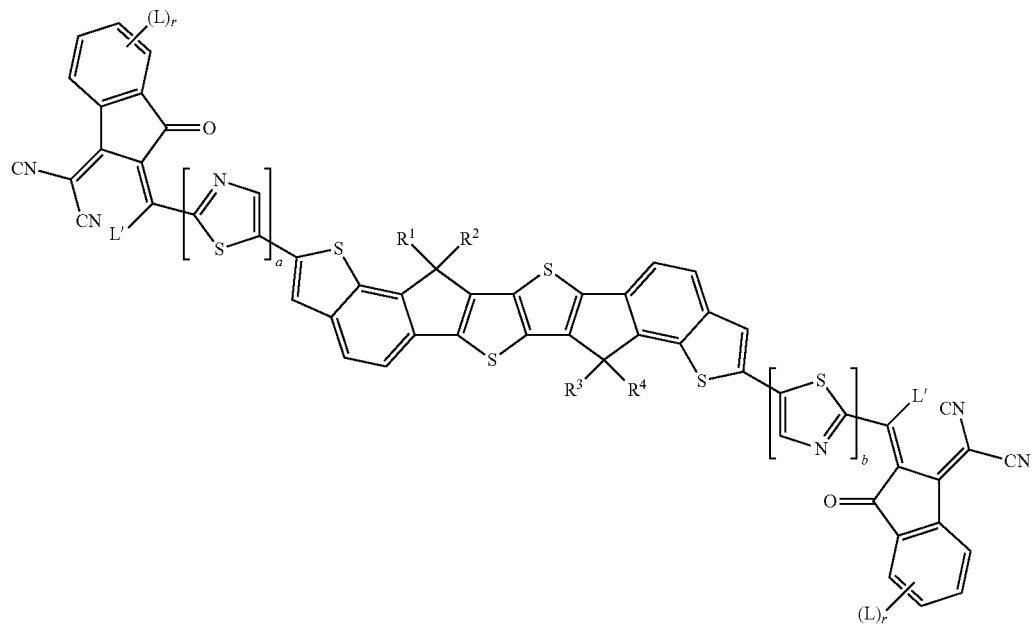
I15d
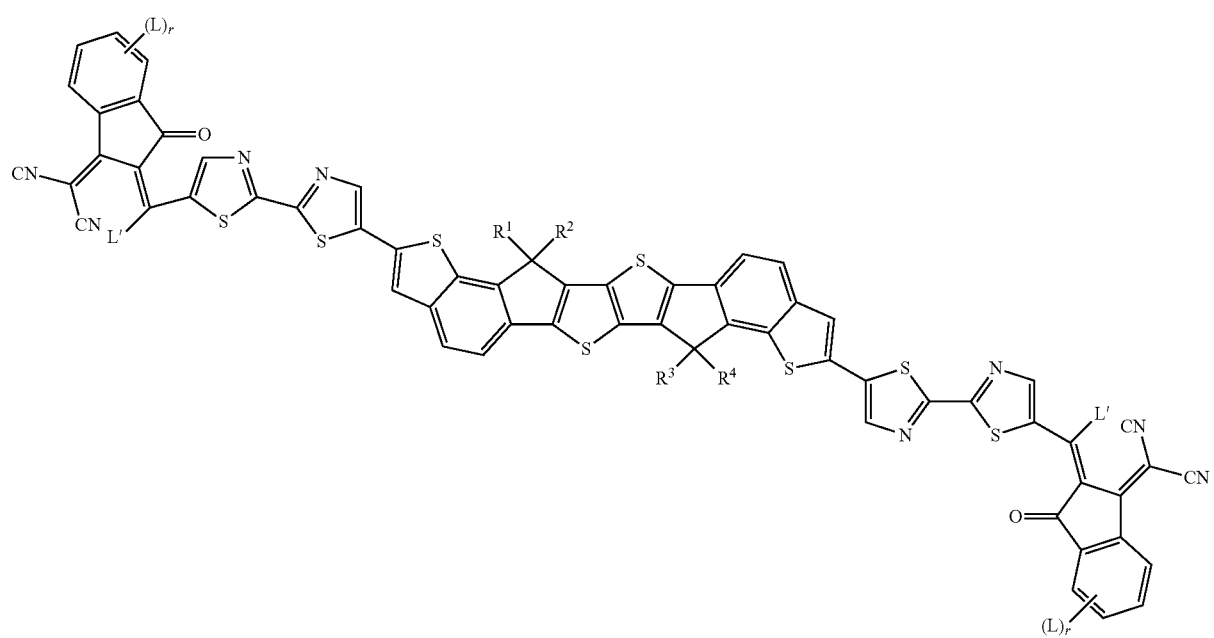
I15e

-continued
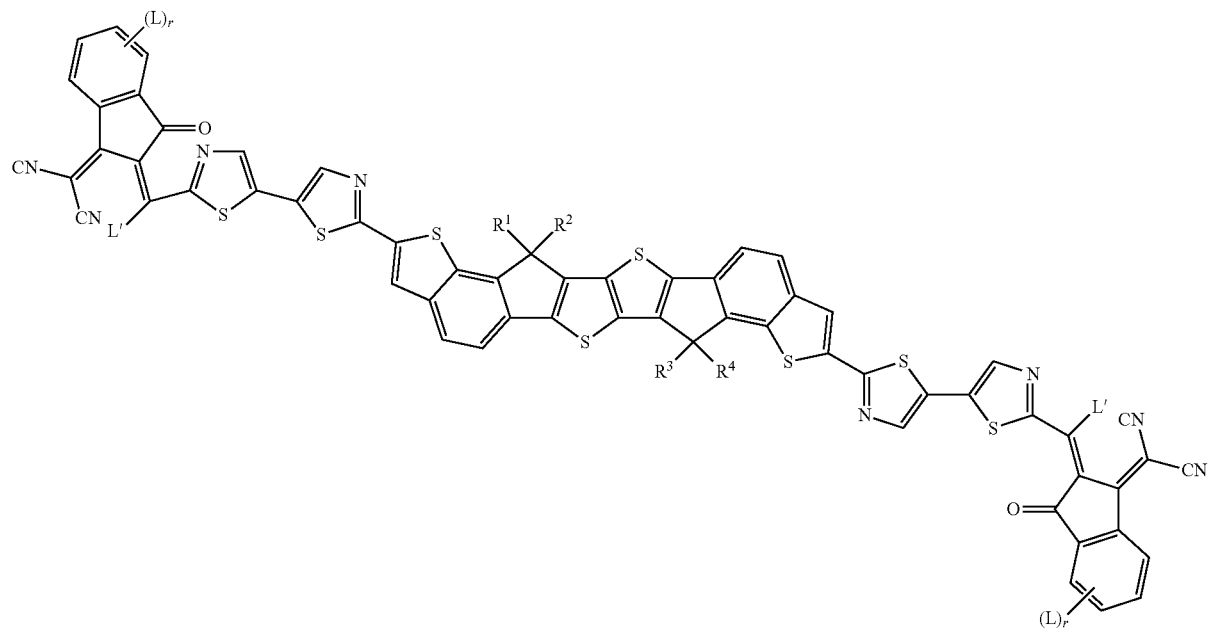
I15f
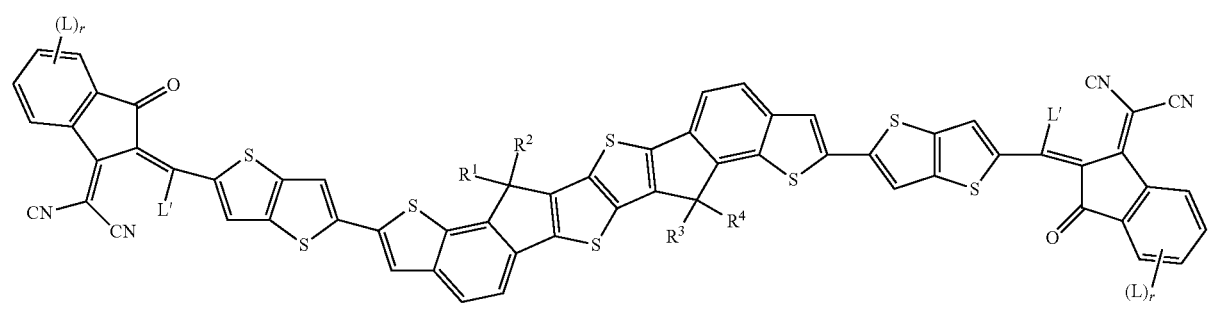
I15g
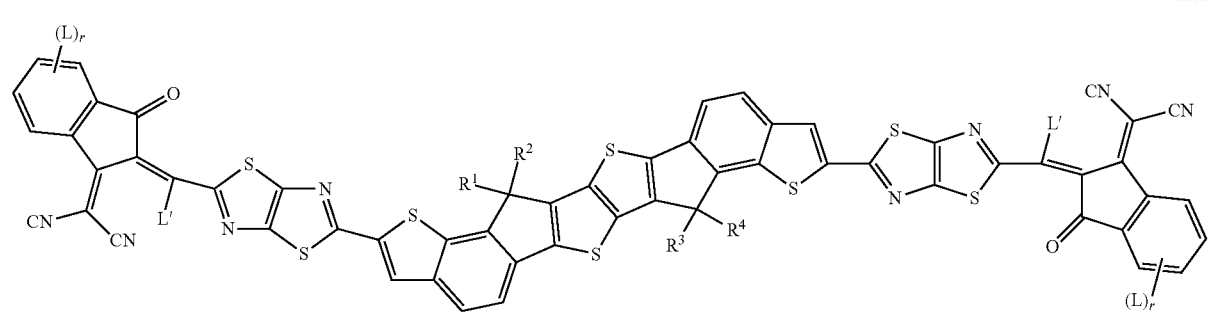
I15h
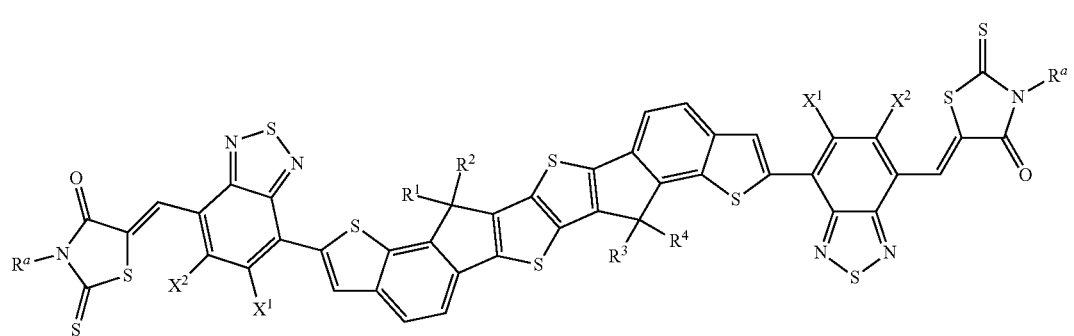
I15i

I15k
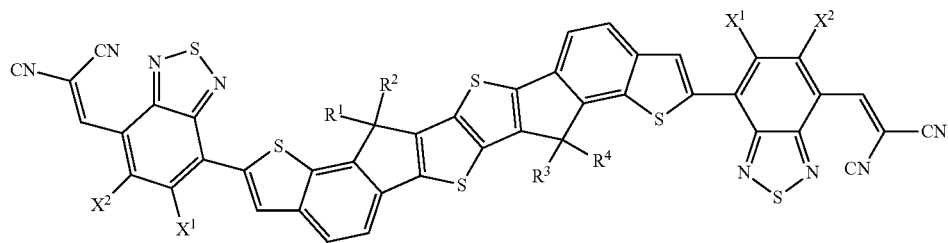
I15m
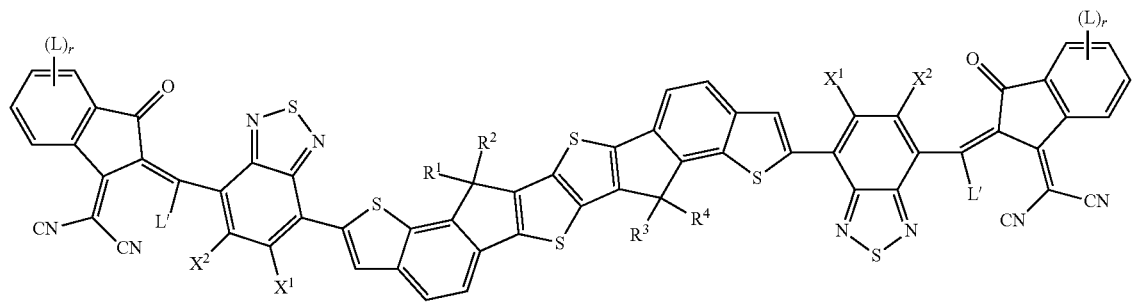
I16a
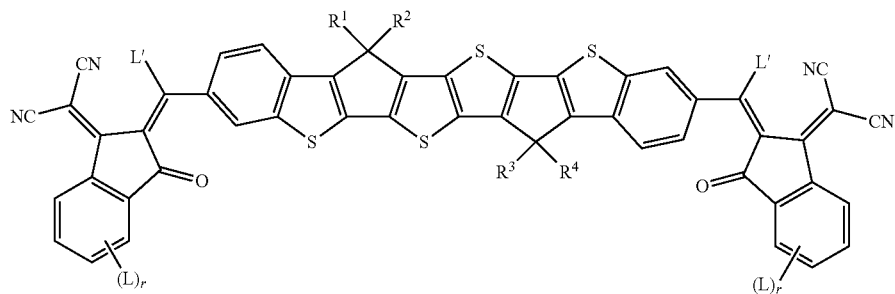
I16b
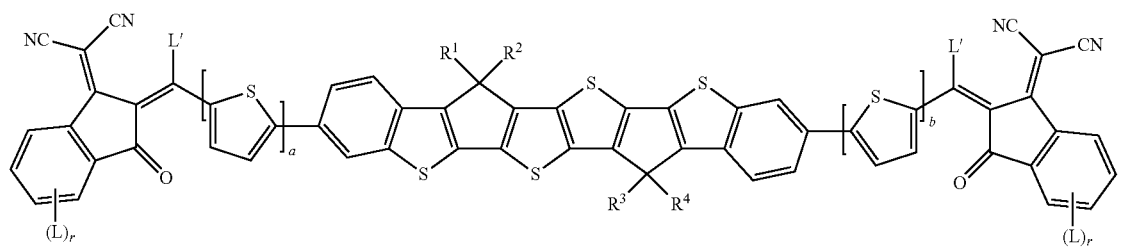
I16c
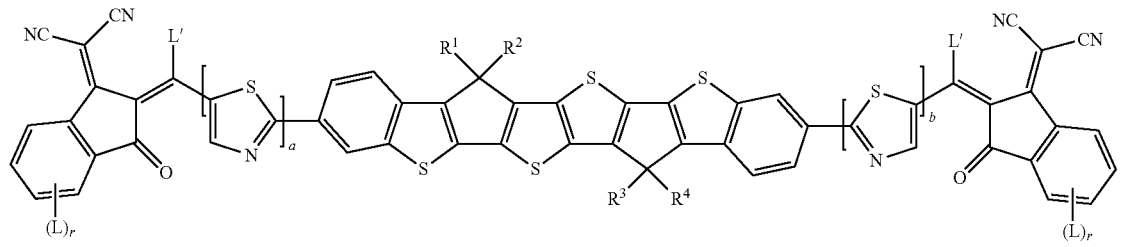

-continued
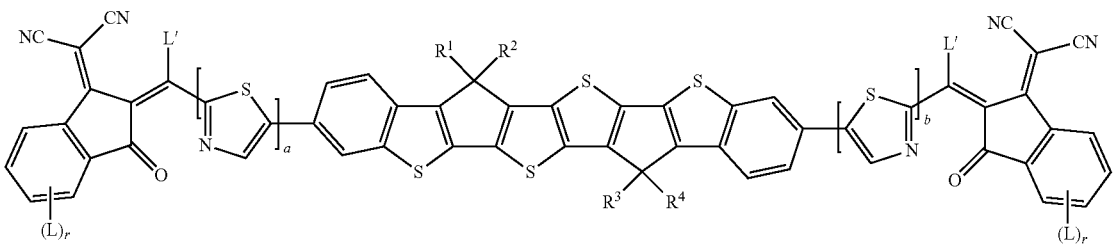
I16d
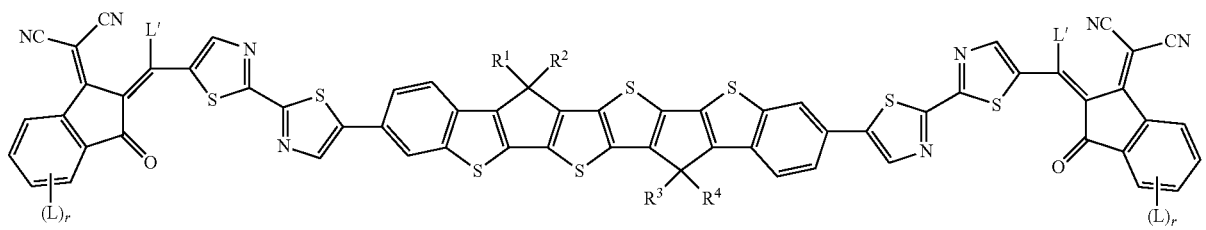
I16e
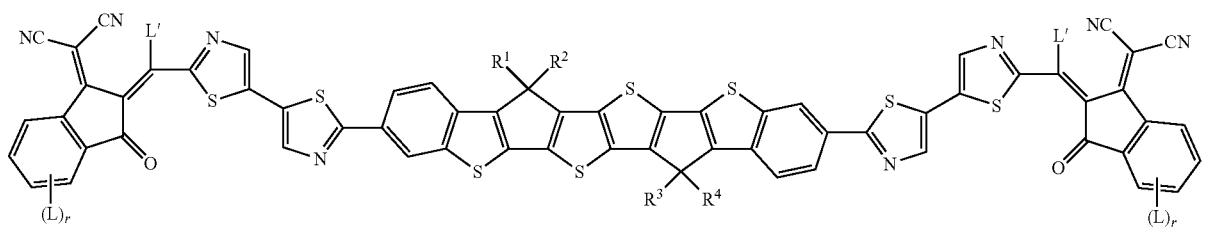
I16f
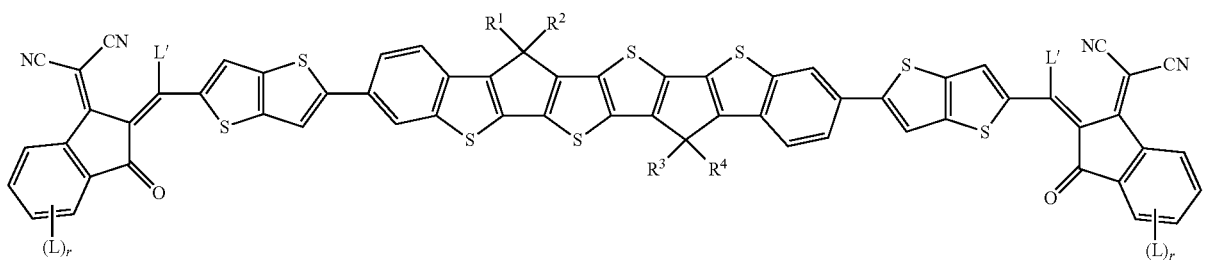
I16g
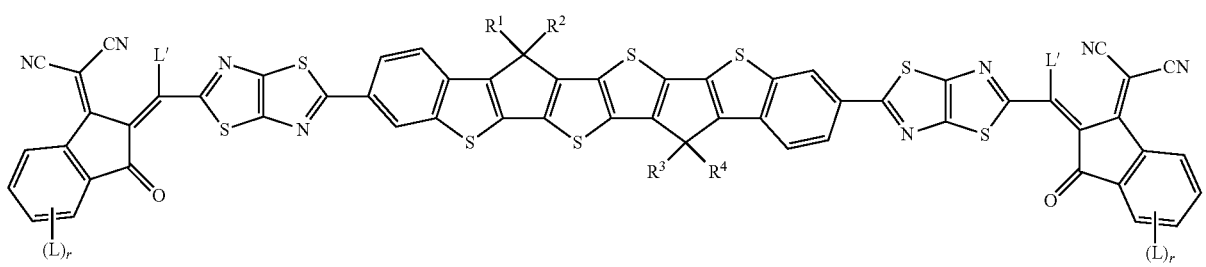
I16h
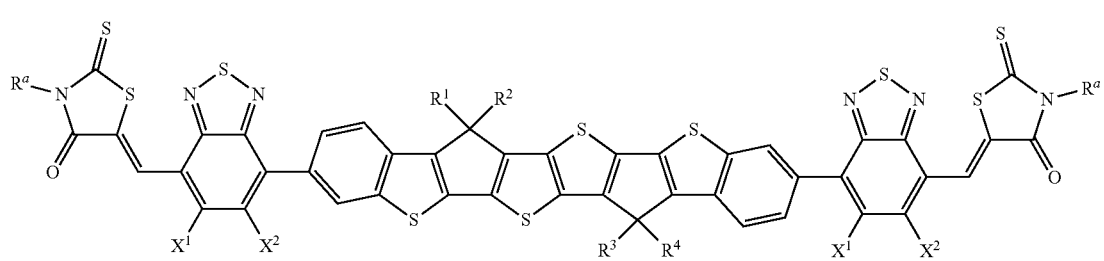
I16i -continued
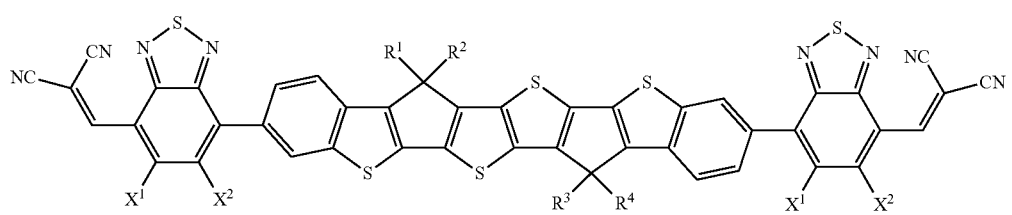
I16k
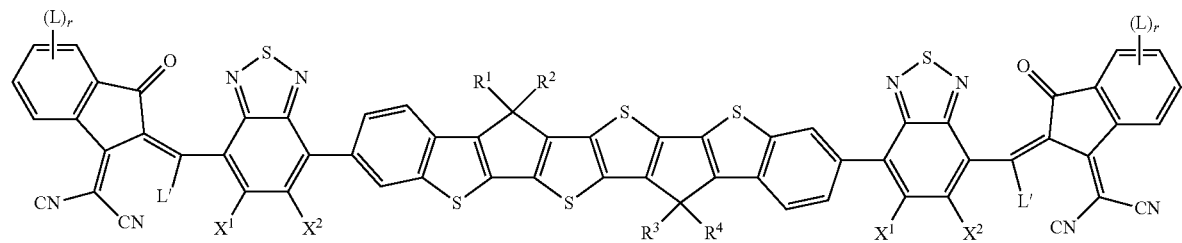
I16m
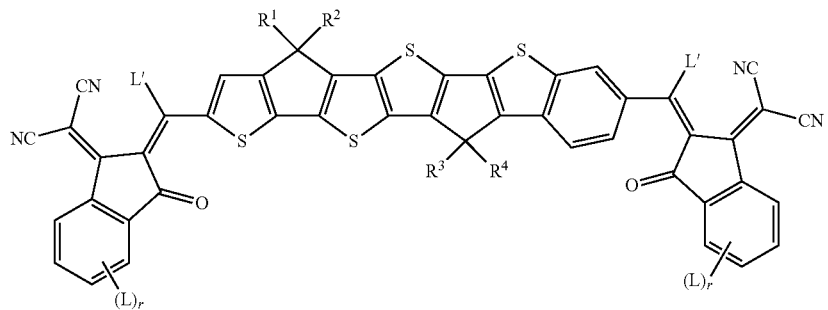
I17a
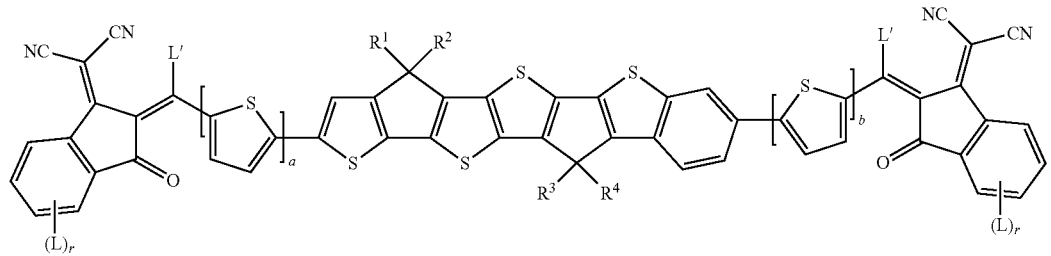
I17b
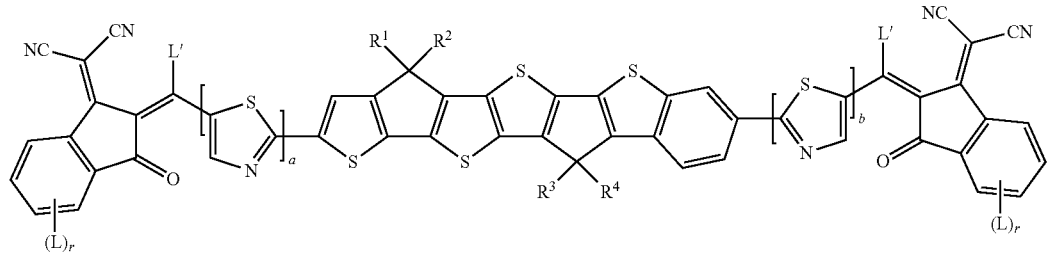
I17c
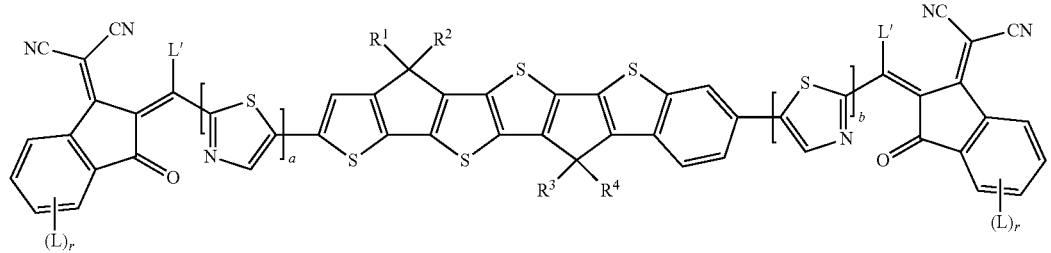
I17d -continued
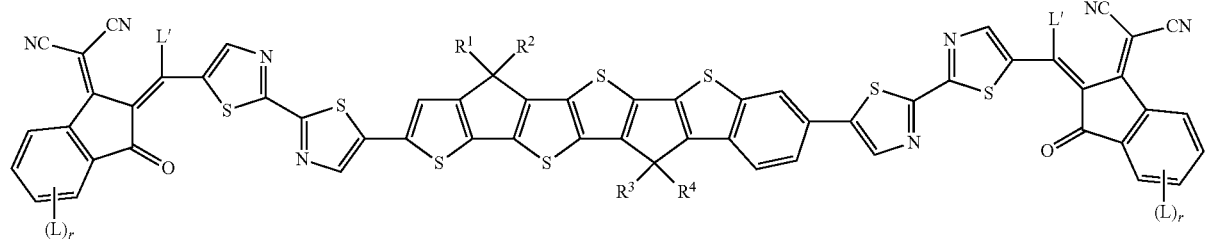
I17e
I17f
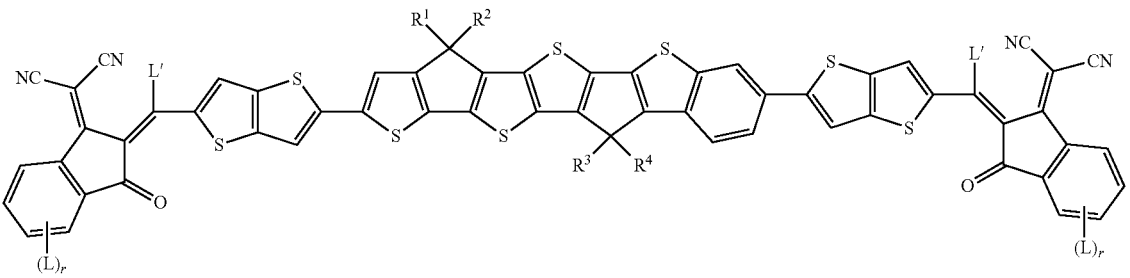
I17g
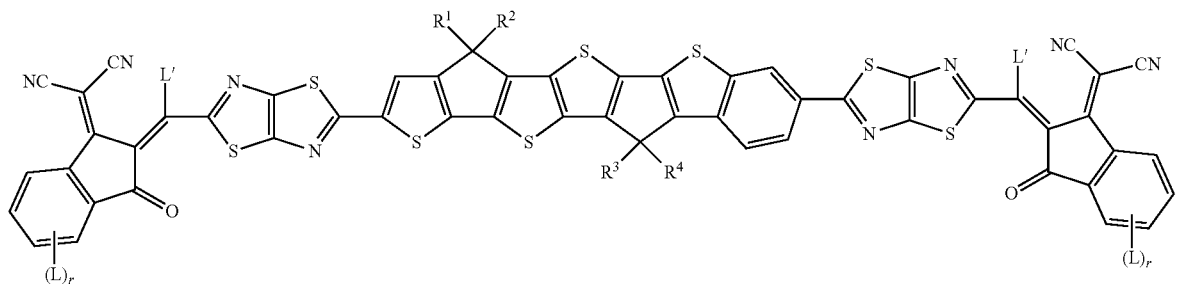
I17h
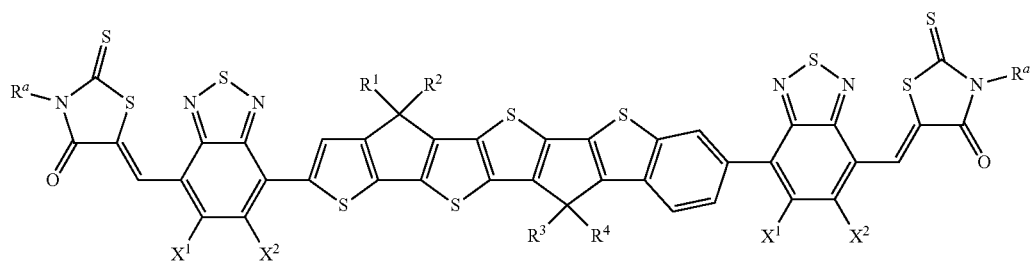
I17i
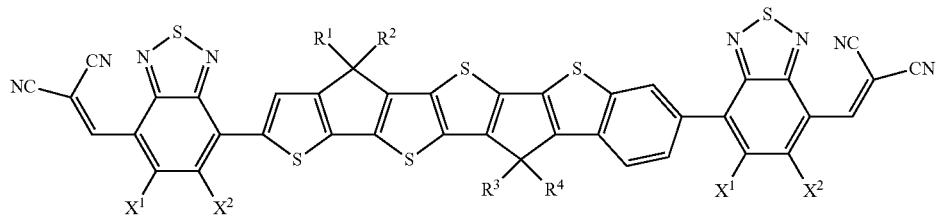
I17k -continued
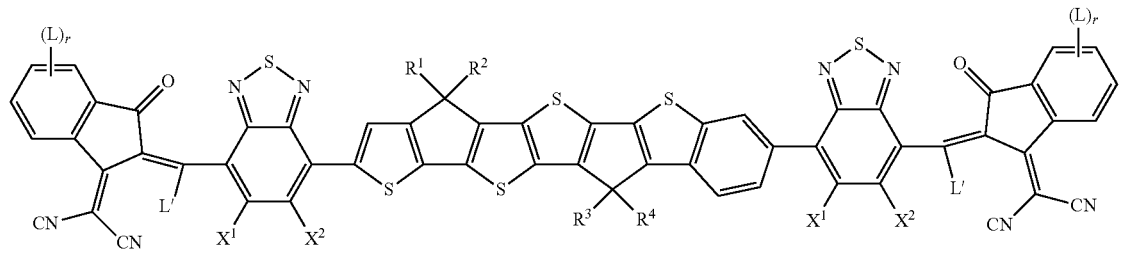
I17m
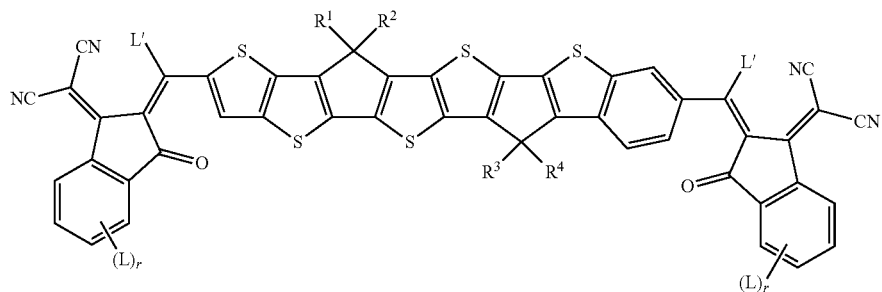
I18a
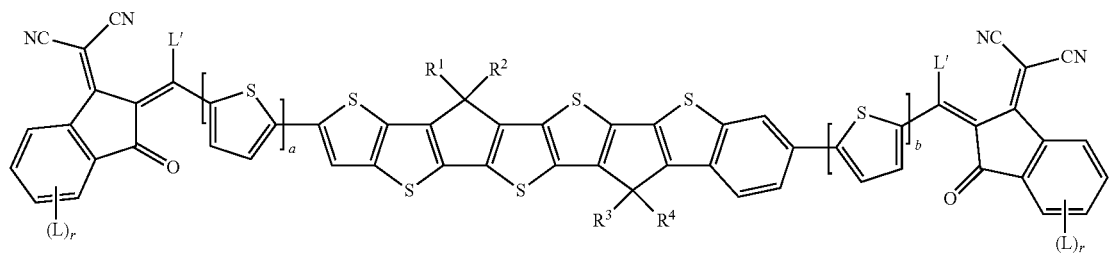
I18b
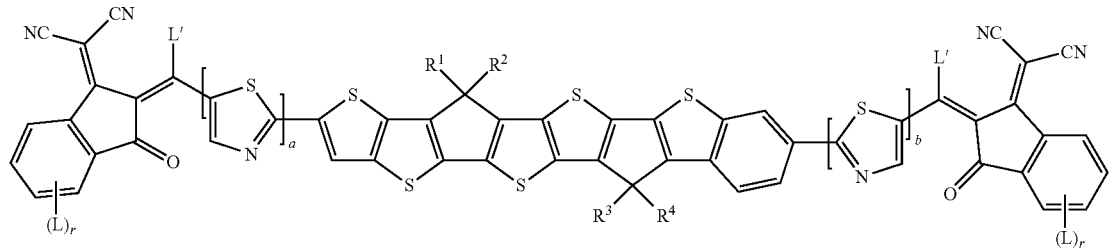
I18c
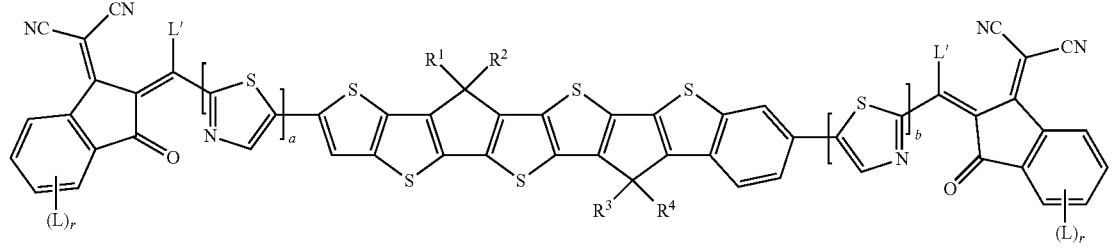
I18d
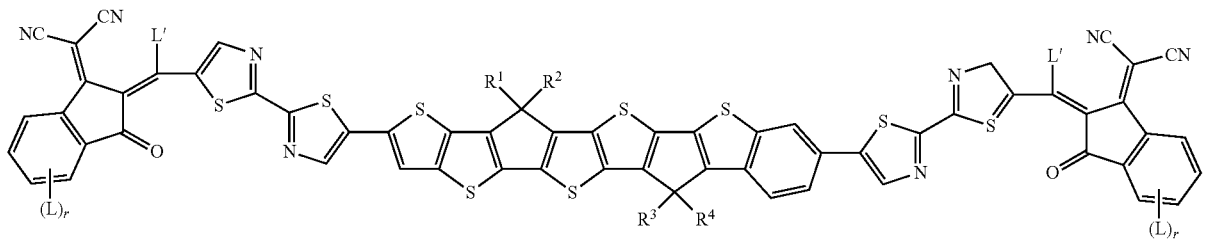
I18e -continued
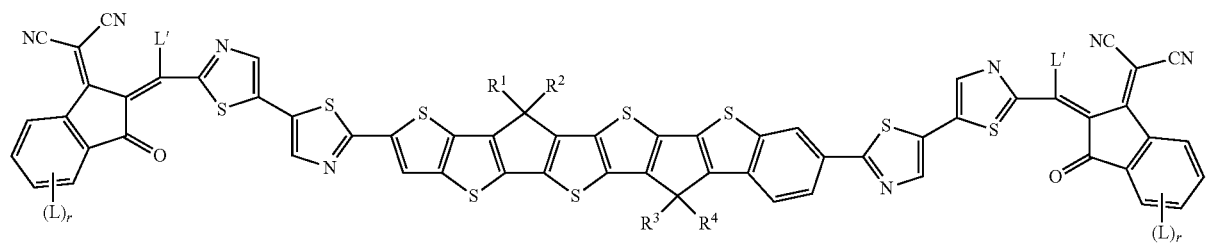
I18f
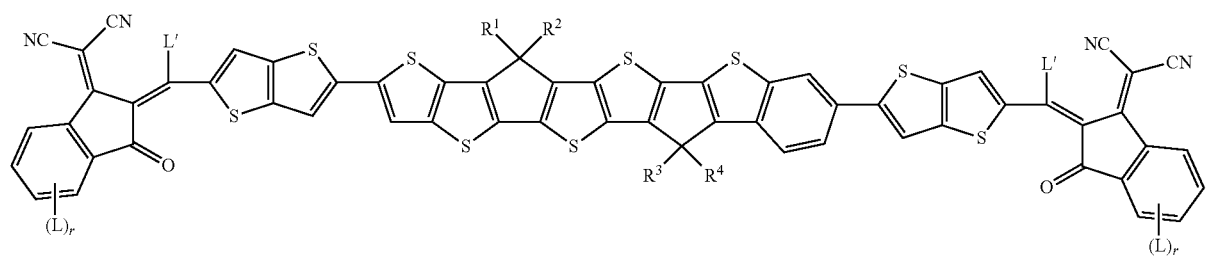
I18g
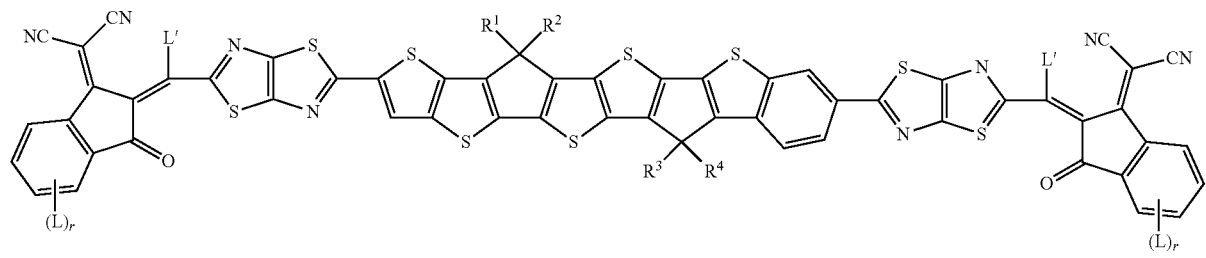
I18h
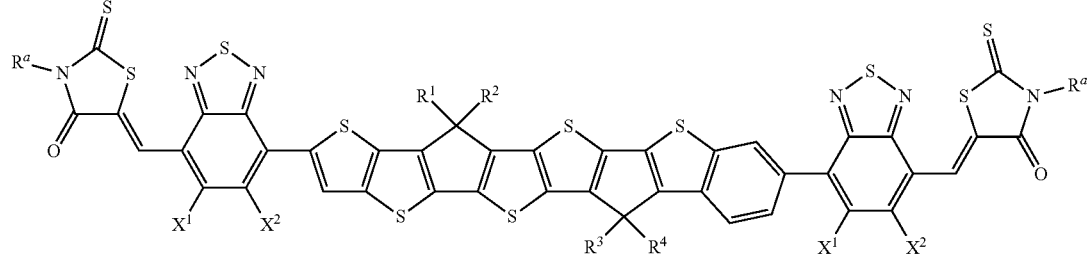
I18i
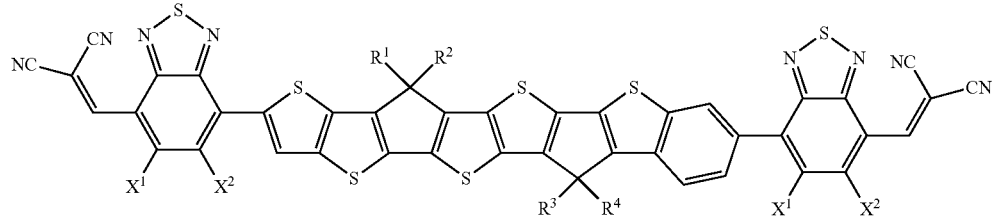
I18k
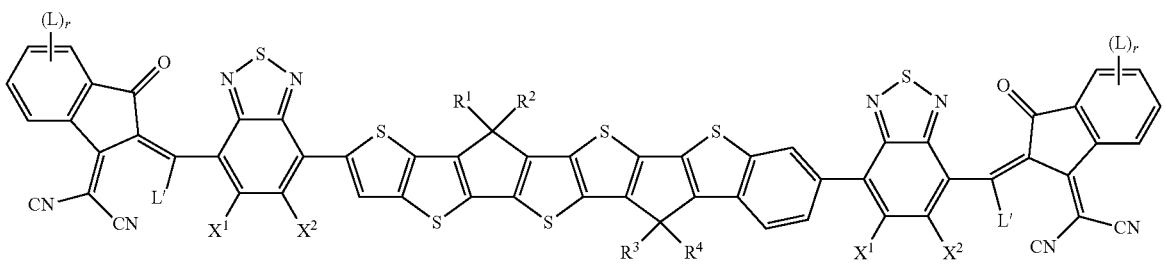
I18m -continued
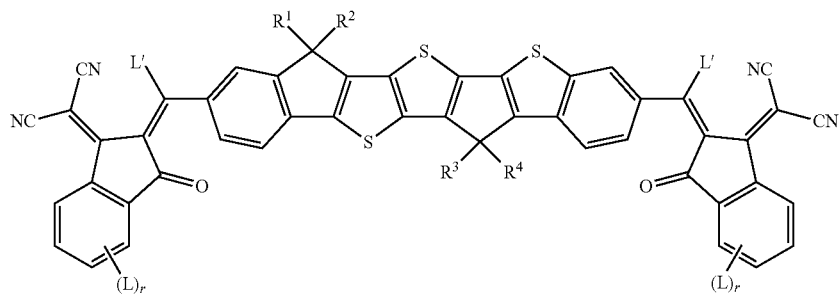
I19a
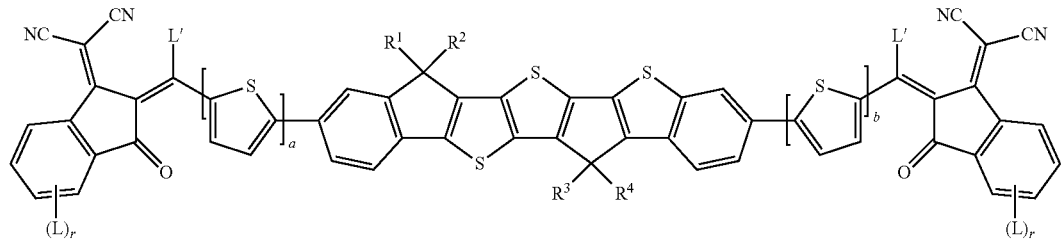
I19b
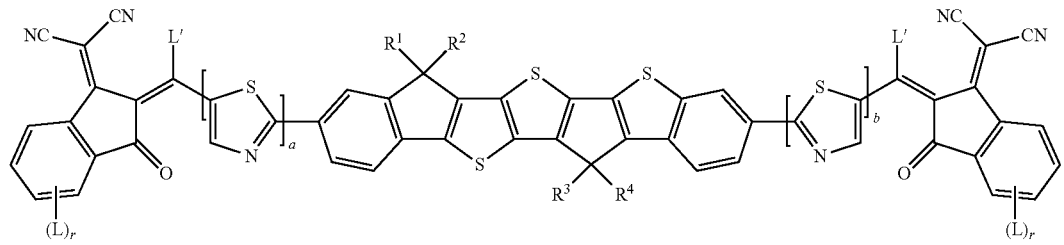
I19c
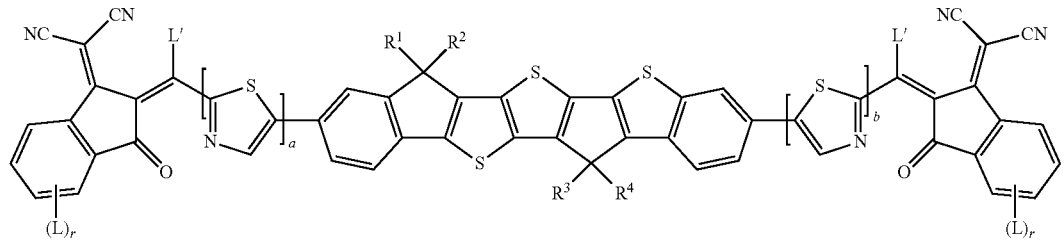
I19d
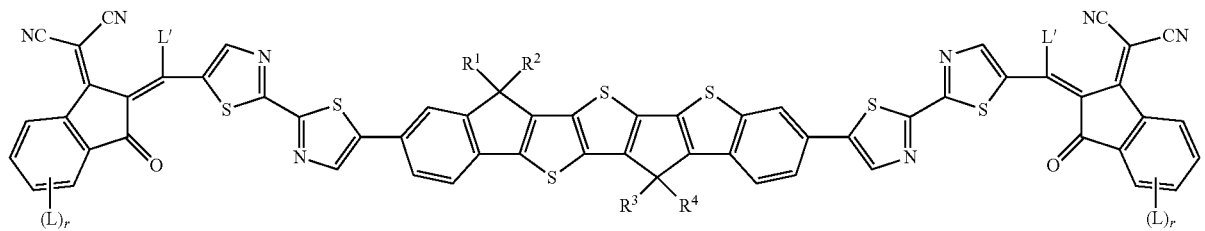
I19e
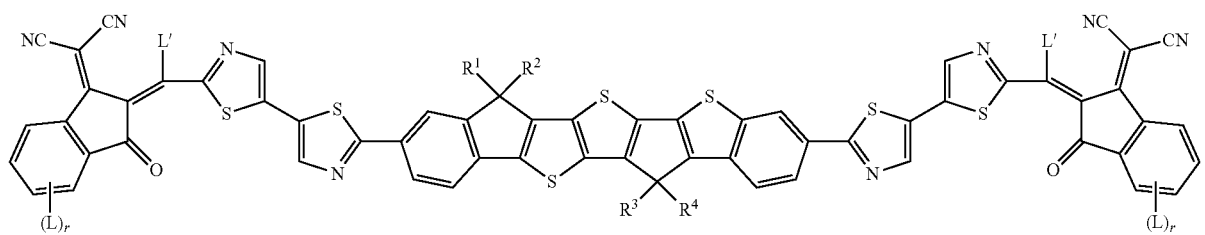
I19f -continued
I19g
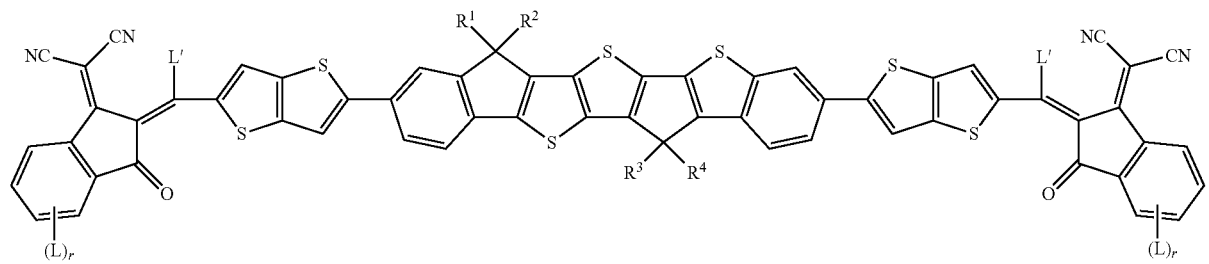
I19h
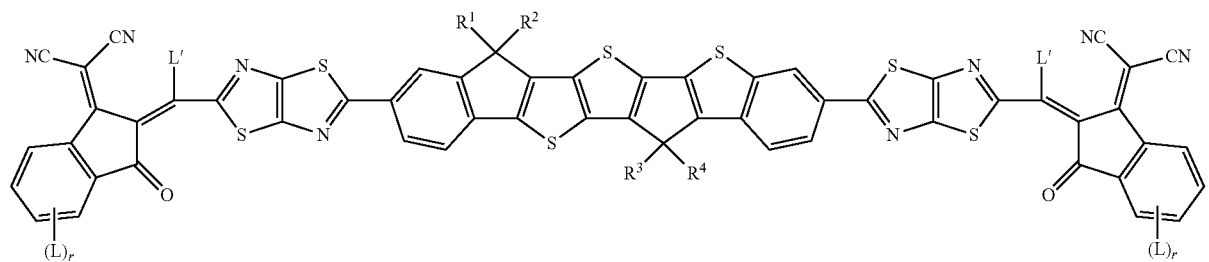
I19i
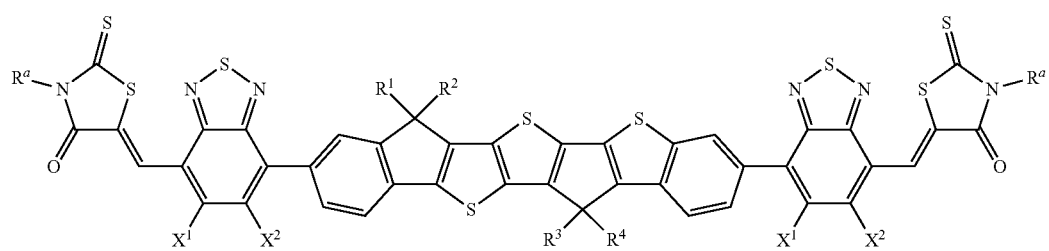
I19k
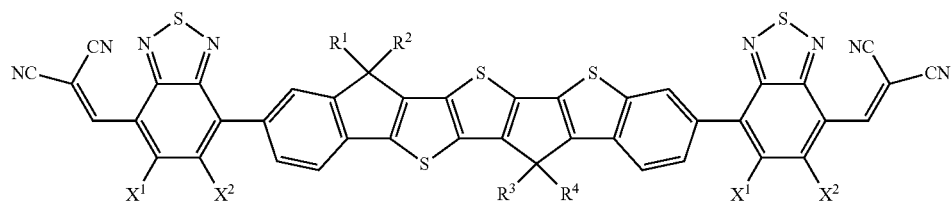
I19m
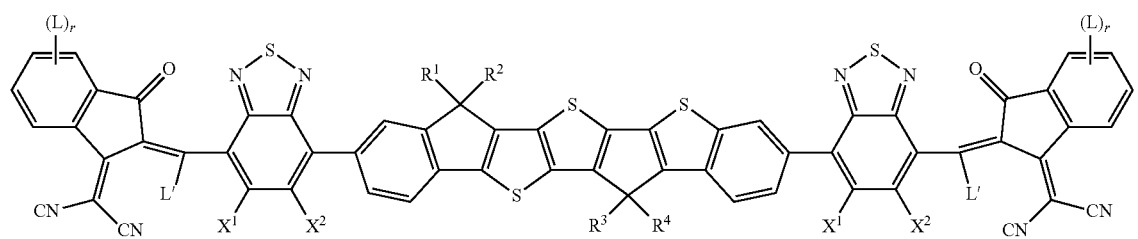

wherein $R^1$, $R^2$, $R^3$, $R^4$, $X^1$, $X^2$, $R^a$, $R^b$, L, L' and r have the meanings given above, and a and b are 1 or 2.

The above formulae I1a-I19m do also include their E- or Z-stereoisomers with respect to the C=C double bond of the terminal group in α-position to the adjacent group $Ar^{1-5}$, for example the following group

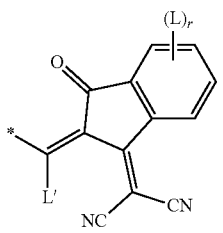

on each occurrence identically or differently may also denote

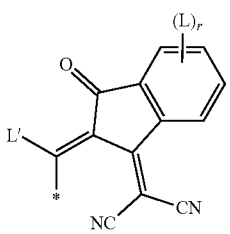

Preferably in formulae I1a-I19m L' is H. Further preferably in formulae I1a-I19m r is 0.

Preferably in formulae I1a-I19m $R^1$, $R^2$, $R^3$ and $R^4$ are selected from alkyl or alkoxy having 1 to 16 C atoms that is optionally fluorinated.

Further preferably in formulae I1a-I19m $R^1$, $R^2$, $R^3$ and $R^4$ are selected from phenyl that is optionally substituted, preferably in 4-position or 3,5-positions, with alkyl, alkoxy or thioalkyl having 1 to 16 C atoms.

Another embodiment of the invention relates to a composition comprising a compound of formula I, and further comprising one or more electron donors or p-type semiconductors, preferably selected from conjugated polymers. Preferably, the conjugated polymer used in the said composition comprises at least one electron donating unit ("donor unit") and at least one electron accepting unit ("acceptor unit"), and optionally at least one spacer unit separating a donor unit from an acceptor unit, wherein each donor and acceptor units is directly connected to another donor or acceptor unit or to a spacer unit, and wherein all of the donor, acceptor and spacer units are selected from arylene or heteroarylene that has from 5 to 20 ring atoms, is mono- or polycyclic, optionally contains fused rings, are is unsubstituted or substituted by one or more identical or different groups L as defined above.

Preferably the spacer units, if present, are located between the donor and acceptor units such that a donor unit and an acceptor unit are not directly connected to each other.

Preferred conjugated polymers comprise, very preferably consist of, one or more units selected from formula U1, U2 and U3, and/or one or more units selected from formula U3 and U4

-(D-Sp)-     U1

-(A-Sp)-     U2

-(A-D)-     U3

-(D)-     U4

-(Sp-A-Sp)-     U5 wherein D denotes a donor unit, A denotes an acceptor unit and Sp denotes a spacer unit, all of which are selected from arylene or heteroarylene that has from 5 to 20 ring atoms, is mono- or polycyclic, optionally contains fused rings, are is unsubstituted or substituted by one or more identical or different groups L as defined above.

Very preferred are polymers of formula Pi and Pii

-[(D-Sp)$_x$-(A-Sp)$_y$]$_n$-     Pi

-[(A-D)$_x$-(A-Sp)$_y$]$_n$-     Pii

-[(D)$_x$-(Sp-A-Sp)]$_n$-     Piii wherein A, D and Sp are as defined in formula U1-U5, x and y denote the molar fractions of the corresponding units, x and y are each, independently of one another >0 and <1, with x+y=1, and n is an integer >1.

Preferred donor units or units D are selected from the following formulae

(D1)

(D7)

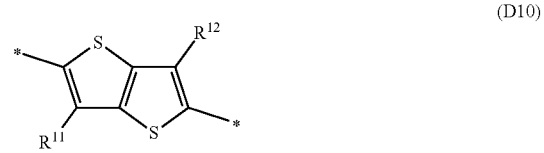
(D10)

(D11)

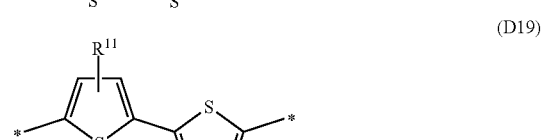
(D19)

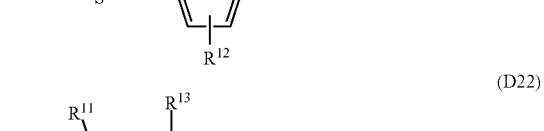
(D22)

(D29)
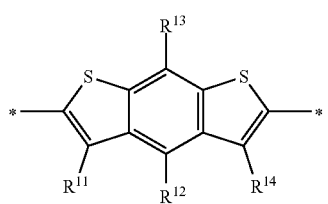
(D30)
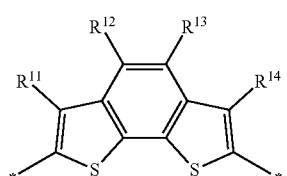
(D35)
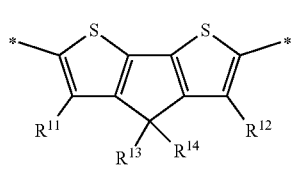
(D36)
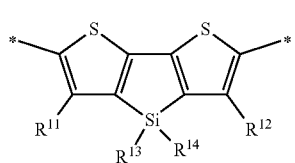
(D37)
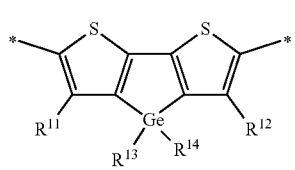
(D44)
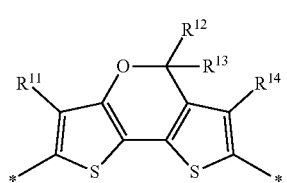
(D55)
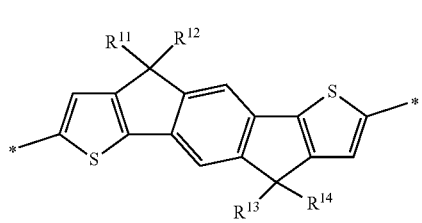
(D84)
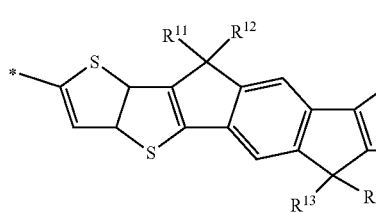
(D87)
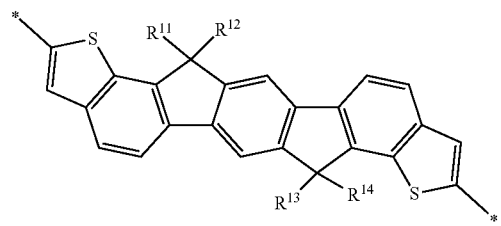
(D88)
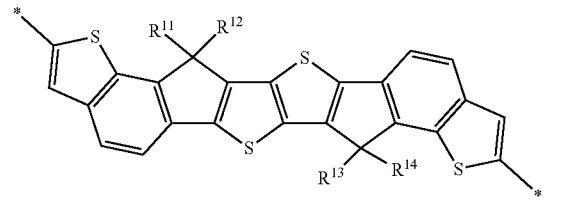
(D89)
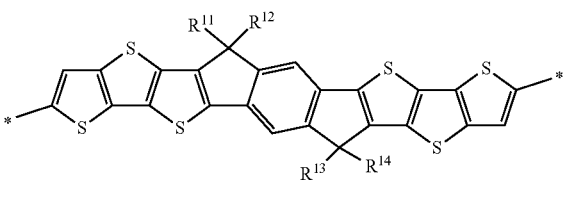
(D93)
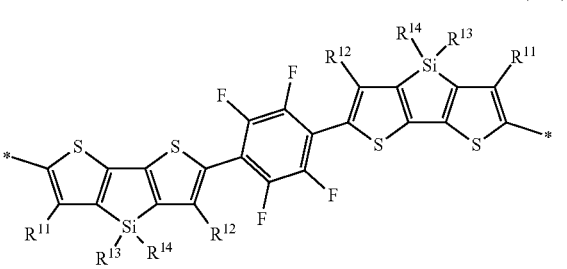
(D106)
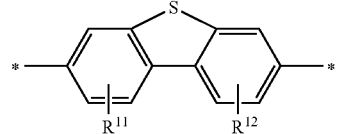
(D111)
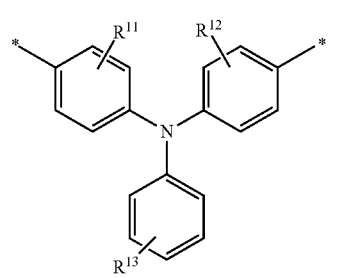

-continued
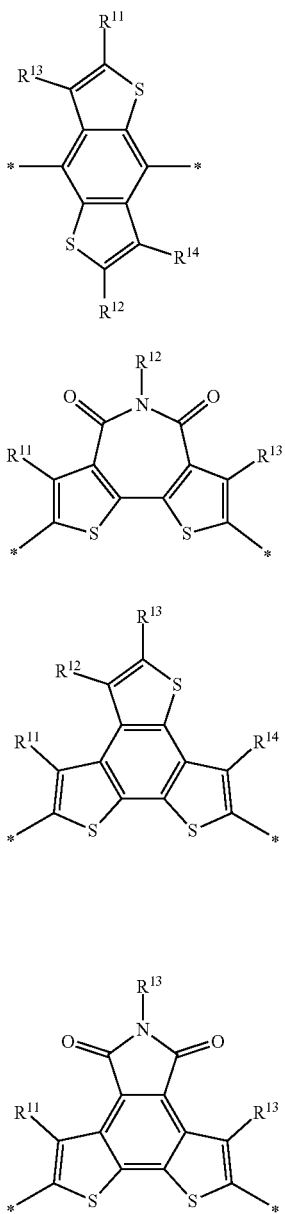
(D119)
(D140)
(D141)
(D146)
(D147)
wherein $R^{11}$, $R^{12}$, $R^{13}$, $R^{14}$ independently of each other denote H or have one of the meanings of L as defined above.
Preferred acceptor units or units A are selected from the following formulae
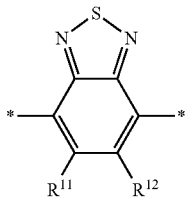
(A1)
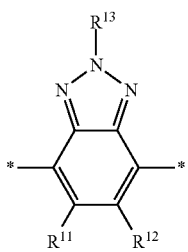
(A5)
(A7)
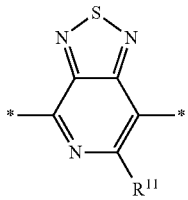
(A15)
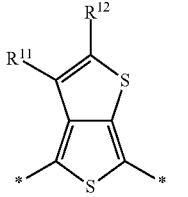
(A16)
(A20)
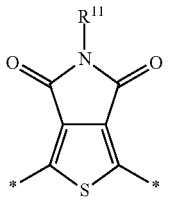
(A74)
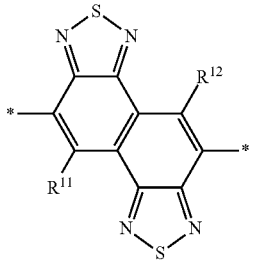

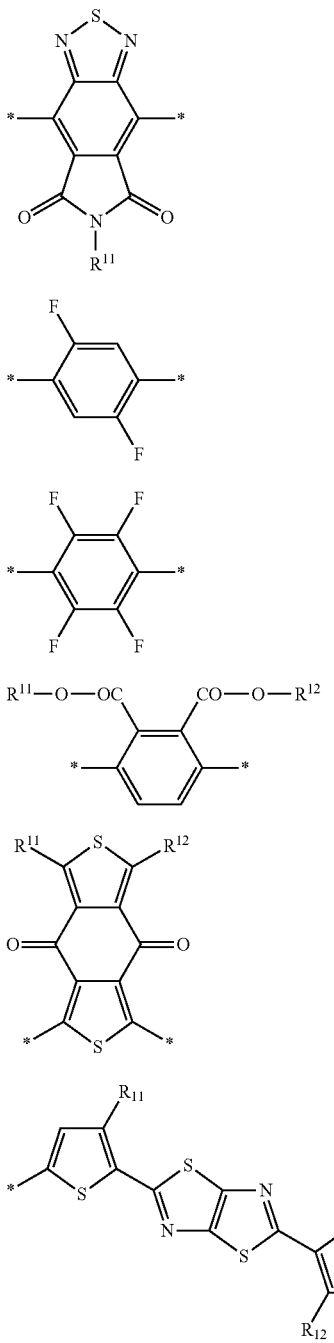
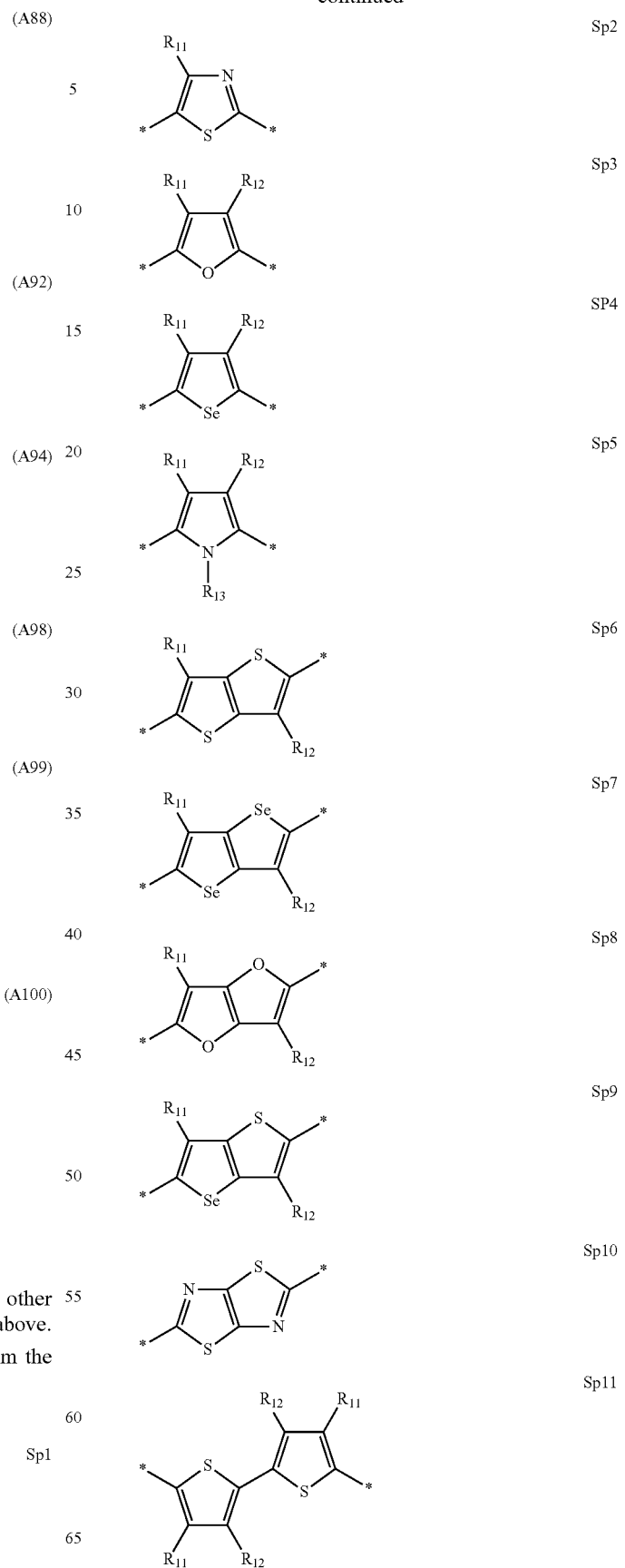
wherein $R^{11}$, $R^{12}$, $R^{13}$, $R^{14}$ independently of each other denote H or have one of the meanings of L as defined above.
Preferred spacer units or units Sp are selected from the following formulae
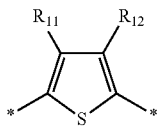

Sp12
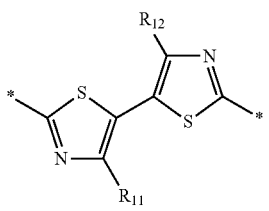

Sp13
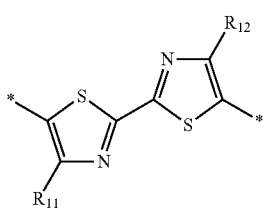

Sp14
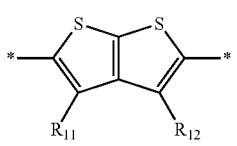

Sp15
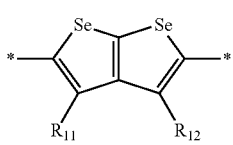

Sp16
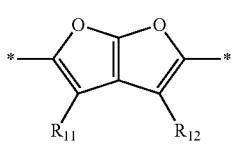

Sp17
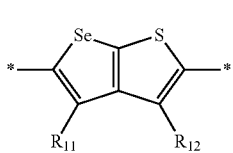

Sp18
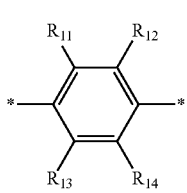

wherein $R^{11}$, $R^{12}$, $R^{13}$, $R^{14}$ independently of each other denote H or have one of the meanings of L as defined above.

In the formulae Sp1 to Sp17 preferably $R^{11}$ and $R^{12}$ are H. In formula Sp18 preferably $R^{11-14}$ are H or F.

Preferably the conjugated polymer contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or b) one or more acceptor units selected from the group consisting of the formulae A1, A5, A7, A15, A16, A20, A74, A88, A92, A94 and A98, A99, A100 and c) optionally one or more spacer units selected from the group consisting of the formulae Sp1-Sp18, very preferably of the formulae Sp1, Sp6, Sp11 and Sp14, wherein the spacer units, if present, are preferably located between the donor and acceptor units such that a donor unit and an acceptor unit are not directly connected to each other.

In a second preferred embodiment the compound of formula I is a conjugated polymer that comprises, preferably consists of one or more, preferably one, two, three or four, distinct repeating units D, and one or more, preferably one, two or three, distinct repeating units A.

Preferably the conjugated polymer according to this second preferred embodiment contains from one to six, very preferably one, two, three or four distinct units D and from one to six, very preferably one, two, three or four distinct units A, wherein d1, d2, d3, d4, d5 and d6 denote the molar ratio of each distinct unit D, and a1, a2, a3, a4, a5 and a6 denote the molar ratio of each distinct unit A, and each of d1, d2, d3, d4, d5 and d6 is from 0 to 0.6, and d1+d2+d3+d4+d5+d6 is from 0.2 to 0.8, preferably from 0.3 to 0.7, and each of a1, a2, a3, a4, a5 and a6 is from 0 to 0.6, and a1+a2+a3+a4+a5+d6 is from 0.2 to 0.8, preferably from 0.3 to 0.7, and d1+d2+d3+d4+d5+d6+a1+a2+a3+a4+a5+a6 is from 0.8 to 1, preferably 1.

Preferably the conjugated polymer according to this second preferred embodiment contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or b) one or more acceptor units selected from the group consisting of the formulae A1, A5, A7, A15, A16, A20, A74, A88, A92, A94, A98, A99 and A100.

In the above conjugated polymers, like those of formula P and its subformulae, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The conjugated polymers are preferably statistical or random copolymers.

Very preferred conjugated polymers are selected from the following formulae

P1
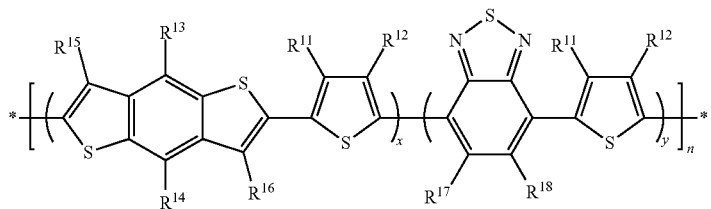
P2
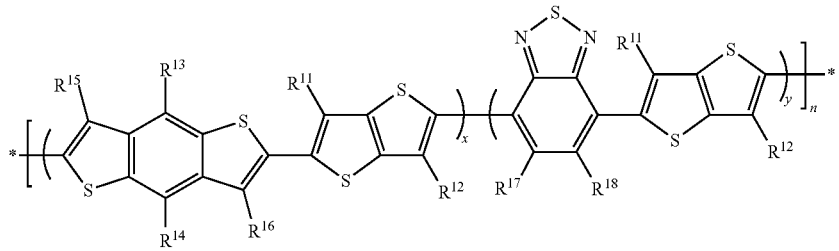
P3
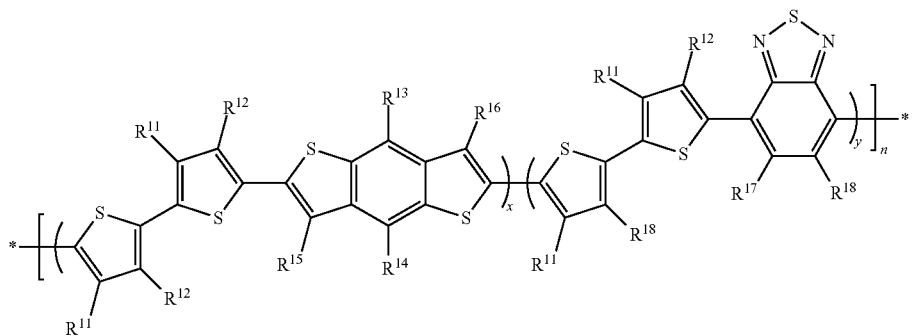
P4
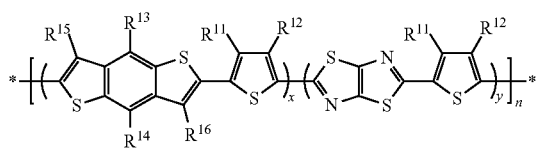
P5
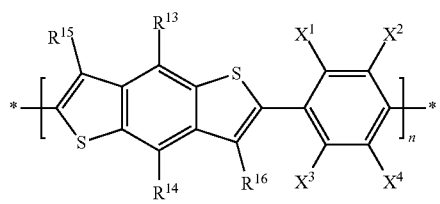
P6
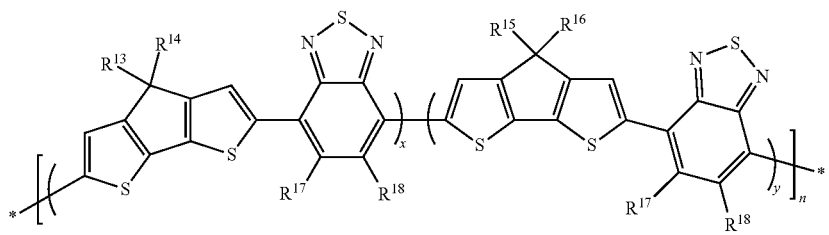
P7
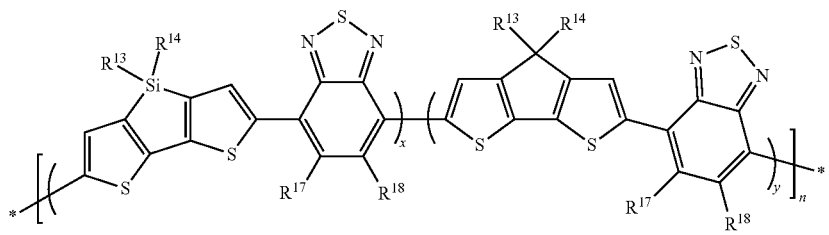

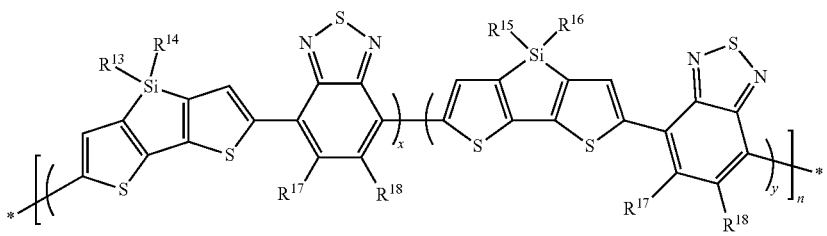
P8
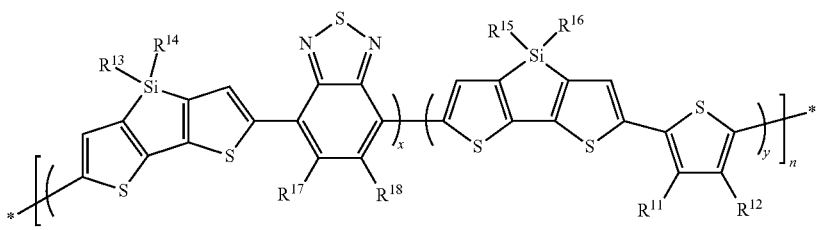
P9
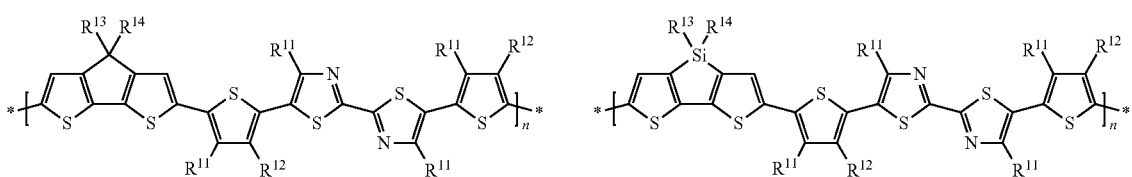
P10                             P11
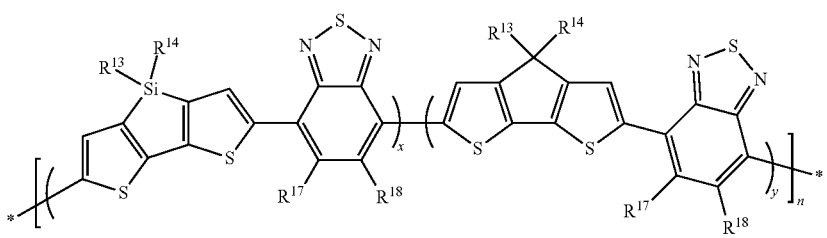
P12
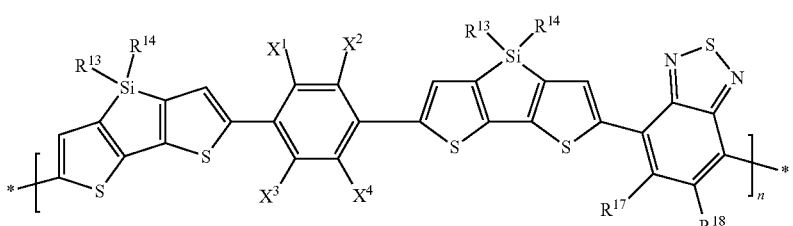
P13
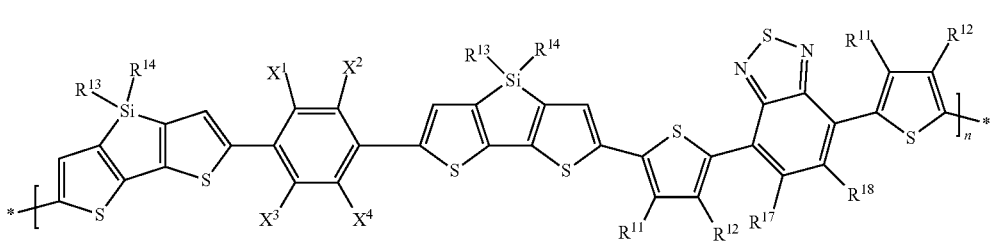
P14
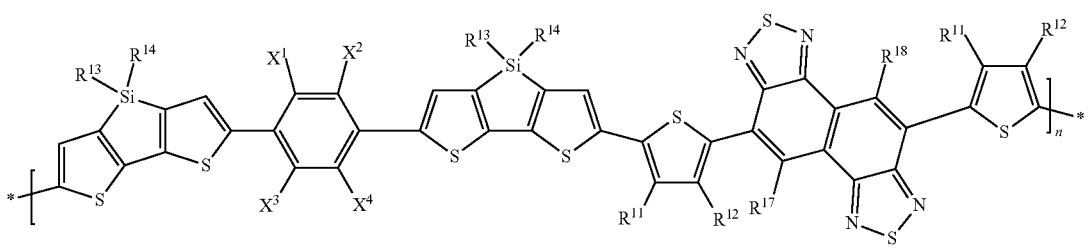
P15

-continued
P16
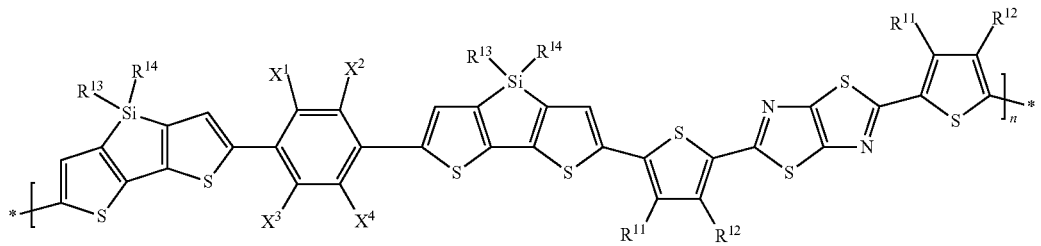
P17
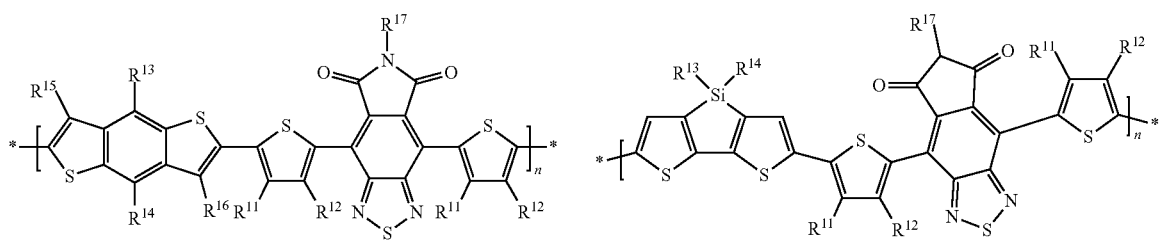
P18
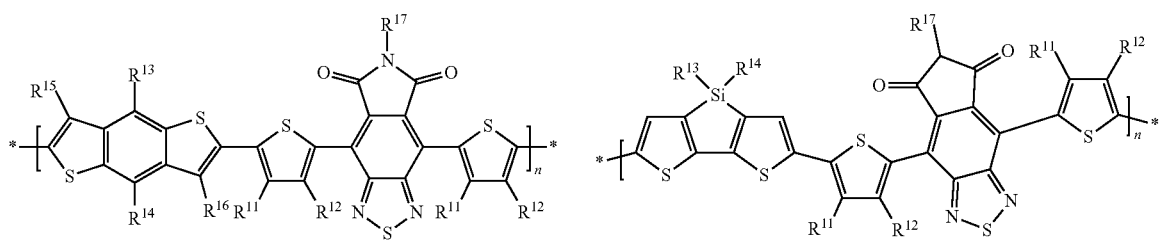
P19
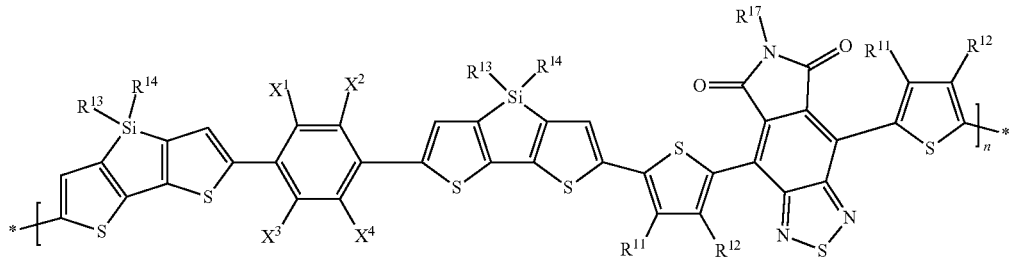
P20
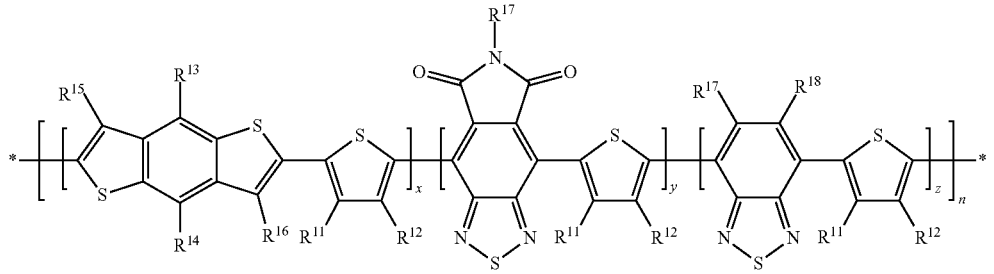
P21
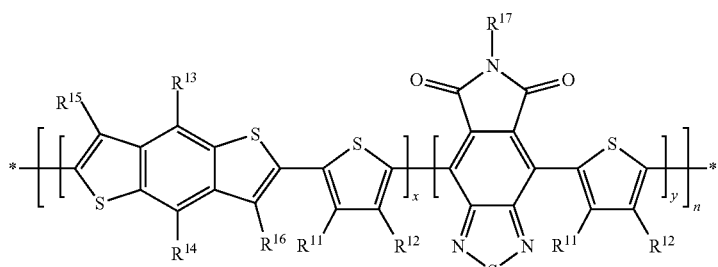
P22
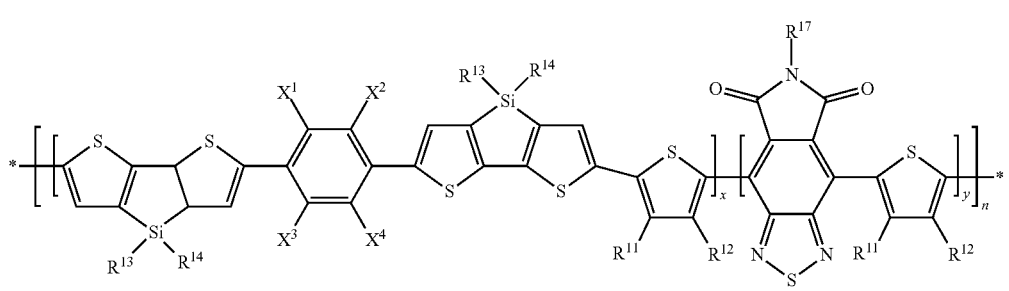

-continued
P23
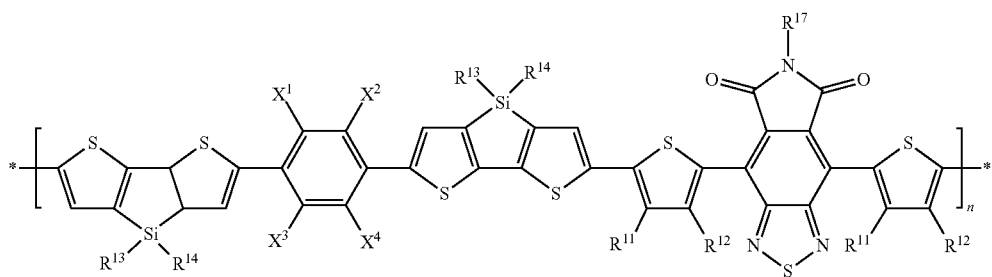
P24
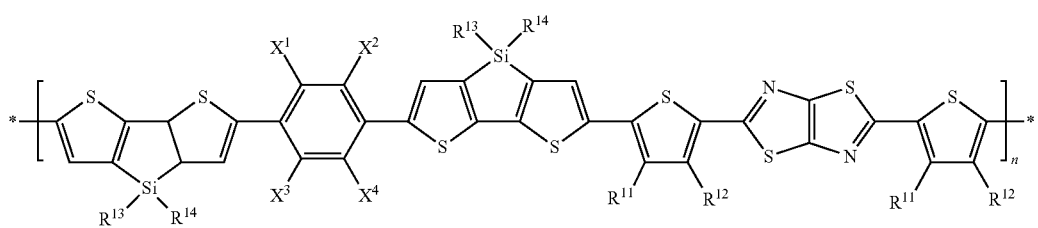
P25
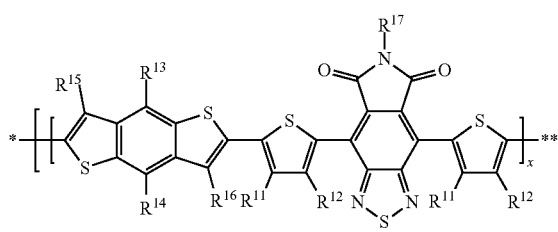 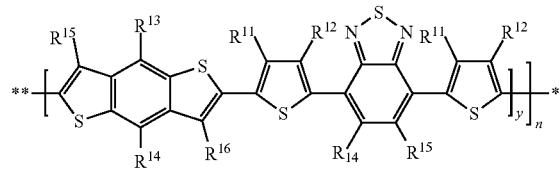
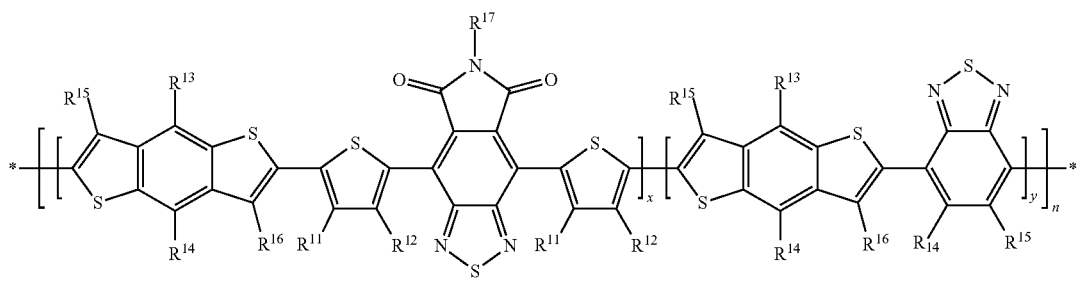
P26
P27
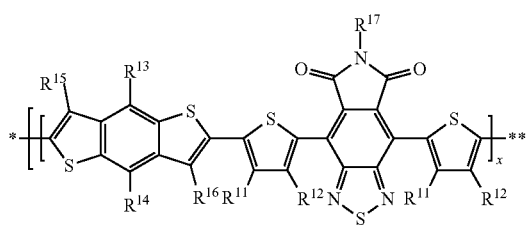 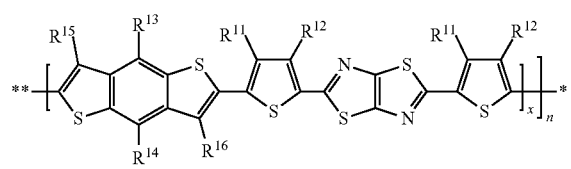
P28
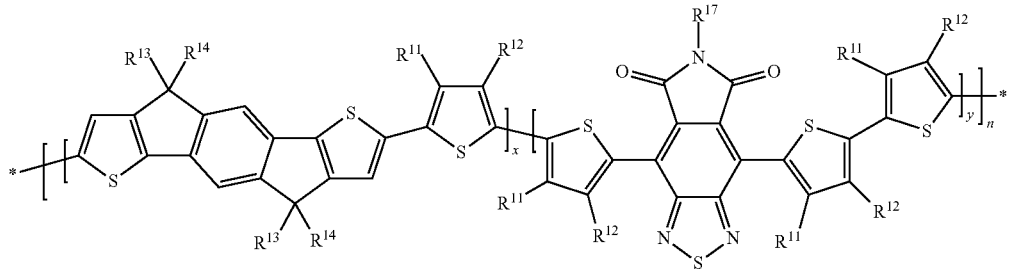

-continued
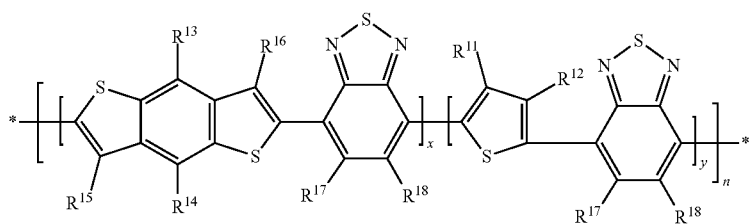
P29
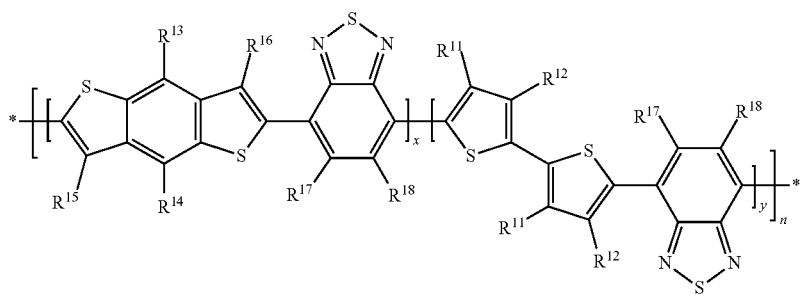
P30
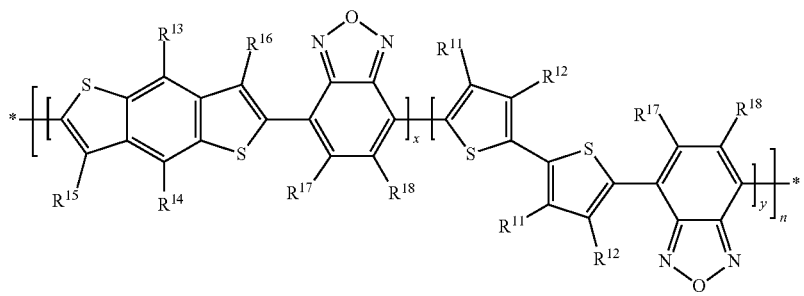
P31
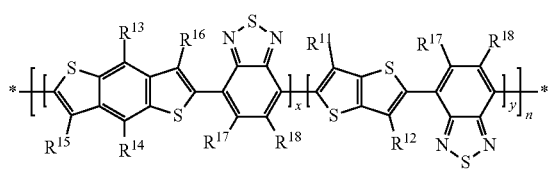
P32
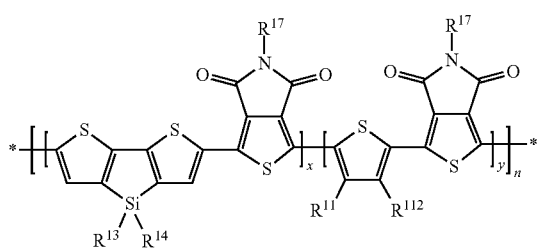
P34
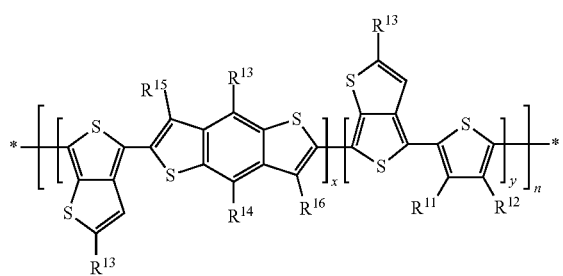
P35
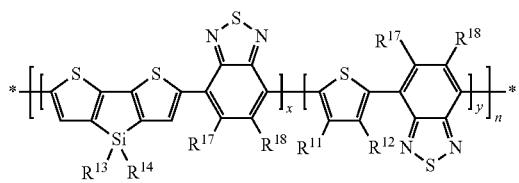
P36
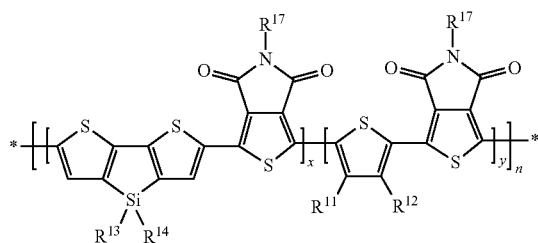
P37

-continued
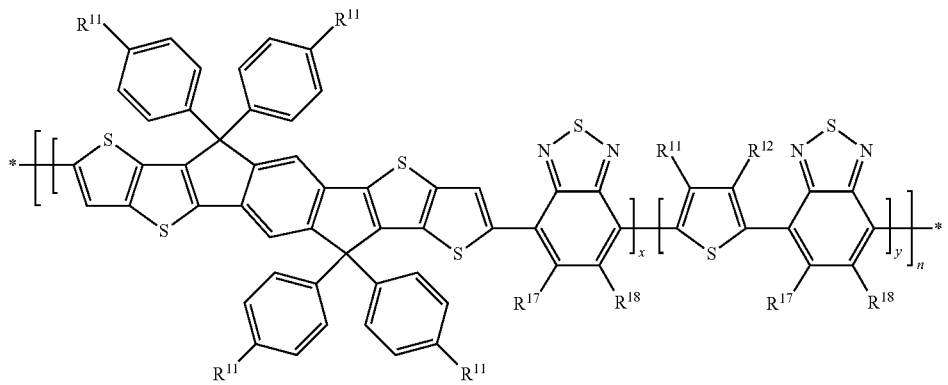
P38
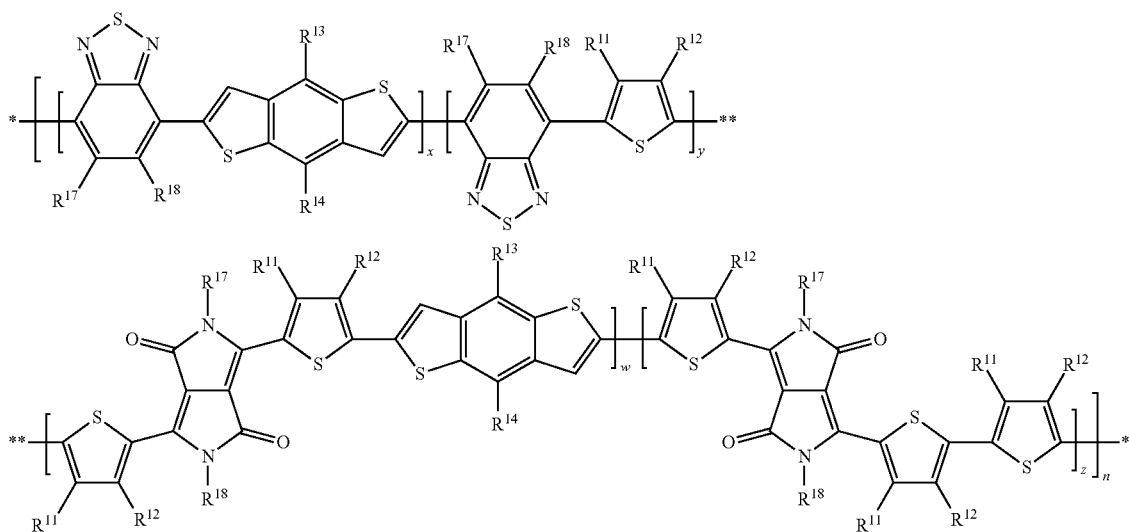
P39
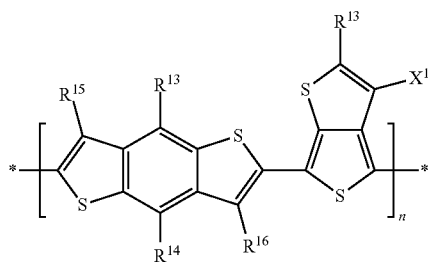
P40
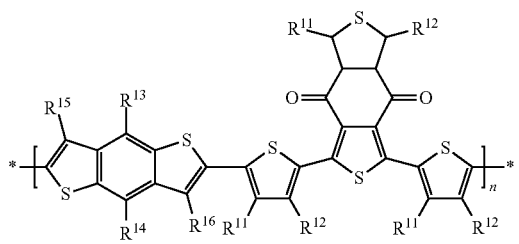
P41
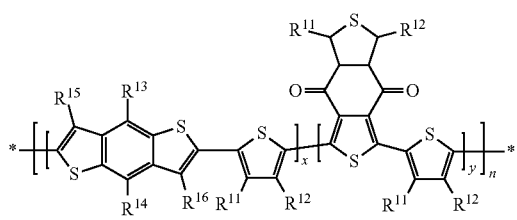
P42
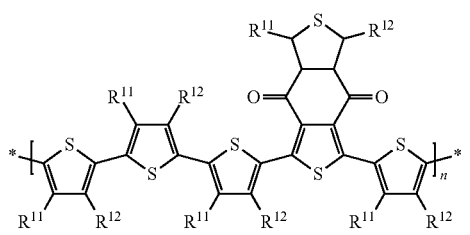
P43
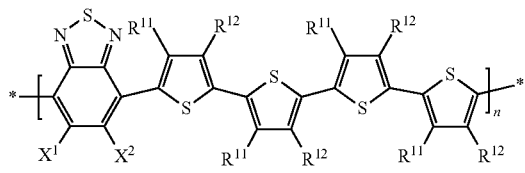
P44
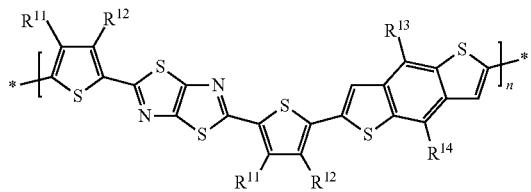
P45

-continued
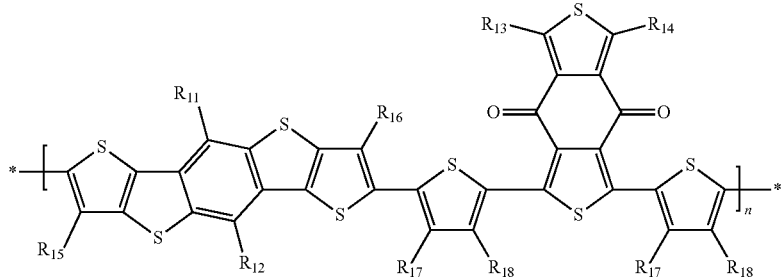
P46
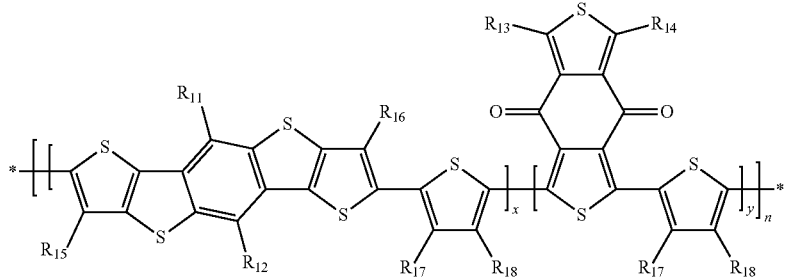
P47
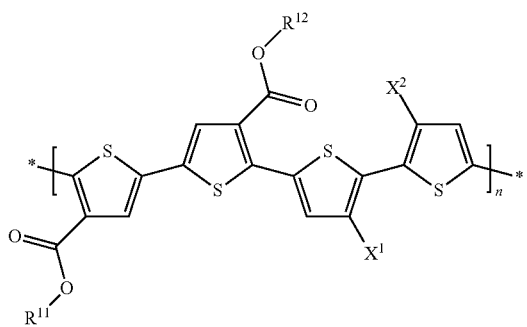
P48
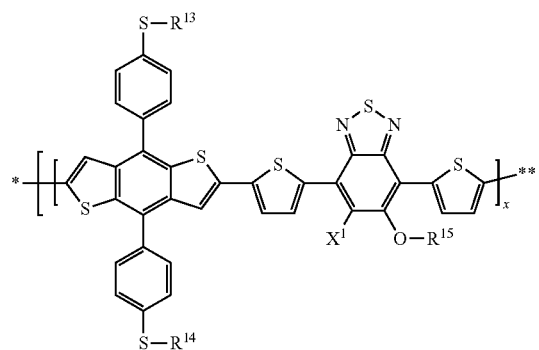
P49
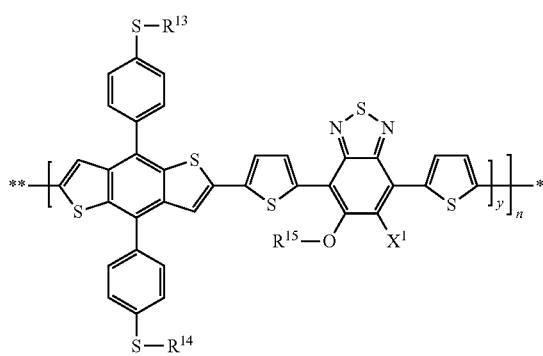
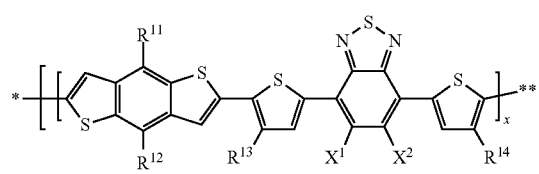
P50
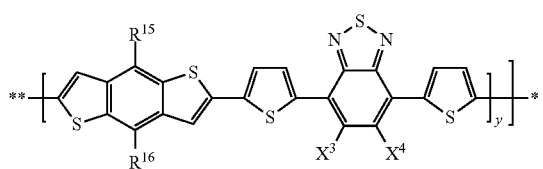
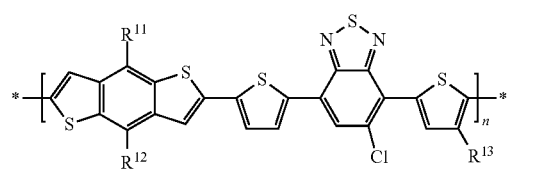
P51

P52 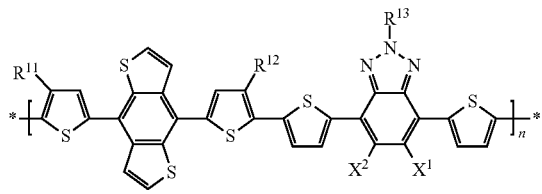

P53 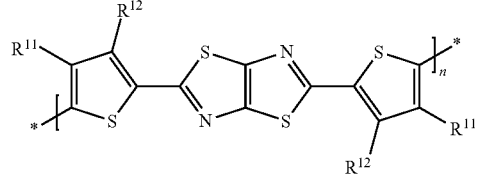

wherein $R^{11-17}$, x, y and n are as defined above, w and z have one of the meanings given for y, x+y+w+z=1, $R^{18}$ and $R^{19}$ have one of the meanings given for $R^{11}$, and $X^1$, $X^2$, $X^3$ and $X^4$ denote H, F or Cl.

Further preferred are polymers comprising one of the formulae P1-P53 as one or more repeating unit.

In the polymers of formula Pi, Pii, Piii and P1-P53 which are composed of two building blocks [ ]$_x$ and [ ]$_y$, x and y are preferably from 0.1 to 0.9, very preferably from 0.25 to 0.75, most preferably from 0.4 to 0.6.

In the polymers of formula Pi, Pii, Piii and P1-P53 which are composed of three building blocks [ ]$_x$, [ ]$_y$, and [ ]$_z$, x, y and z are preferably from 0.1 to 0.8, very preferably from 0.2 to 0.6, most preferably from 0.25 to 0.4.

In the formulae P1-P53 preferably one or more of $X^1$, $X^2$, $X^3$ and $X^4$ denote F, very preferably all of $X^1$, $X^2$, $X^3$ and $X^4$ denote F or $X^1$ and $X^2$ denote H and $X^3$ and $X^4$ denote F.

In the formulae P1-P53 preferably $R^{11}$ and $R^{12}$ are H. Further preferably $R^{11}$ and $R^{12}$, when being different from H, denote straight-chain or branched alkyl with 1 to 30, preferably 1 to 20, C atoms that is optionally fluorinated.

In the formulae P1-P53, preferably $R^{15}$ and $R^{16}$ are H, and $R^{13}$ and $R^{14}$ are different from H.

In the formulae P1-P53, preferably $R^{13}$, $R^{14}$, $R^{15}$ and $R^{16}$, when being different from H, are selected from the following groups:
the group consisting of straight-chain or branched alkyl, alkoxy or sulfanylalkyl with 1 to 30, preferably 1 to 20, C atoms that is optionally fluorinated,
the group consisting of straight-chain or branched alkylcarbonyl or alkylcarbonyloxy with 2 to 30, preferably 2 to 20, C atoms, that is optionally fluorinated.

In the formulae P1-P53, preferably $R^{17}$ and $R^{18}$, when being different from H, are selected from the following groups:
the group consisting of straight-chain or branched alkyl, alkoxy or sulfanylalkyl with 1 to 30, preferably 1 to 20, C atoms that is optionally fluorinated,
the group consisting of straight-chain or branched alkylcarbonyl or alkylcarbonyloxy with 2 to 30, preferably 2 to 20, C atoms, that is optionally fluorinated.
the group consisting of F and Cl.

Further preferred are conjugated polymers selected of formula PT $R^{31}$-chain-$R^{32}$    PT wherein "chain" denotes a polymer chain selected of formula Pi, Pii or P1-P53, and $R^{31}$ and $R^{32}$ have independently of each other one of the meanings of $R^{11}$ as defined above, or denote, independently of each other, H, F, Br, Cl, I, —CH$_2$Cl, —CHO, —CR'=CR"$_2$, —SiR'R"R"', —SiR'X'X", —SiR'R"X', —SnR'R"R'", —BR'R", —B(OR') (OR"), —B(OH)$_2$, —O—SO$_2$—R', —C≡CH, —C≡C—SiR'$_3$, —ZnX' or an endcap group, X' and X" denote halogen, R', R" and R'" have independently of each other one of the meanings of $R^0$ given in formula 1, and preferably denote alkyl with 1 to 12 C atoms, and two of R', R" and R'" may also form a cyclosilyl, cyclostannyl, cycloborane or cycloboronate group with 2 to 20 C atoms together with the respective hetero atom to which they are attached.

Preferred endcap groups $R^{31}$ and $R^{32}$ are H, $C_{1-20}$ alkyl, or optionally substituted $C_{6-12}$ aryl or $C_{2-10}$ heteroaryl, very preferably H, phenyl or thiophene.

The compounds of formula I and the conjugated polymers of formula Pi, Pii, Piii, P1-P53 and PT can be synthesized according to or in analogy to methods that are known to the skilled person and are described in the literature. Other methods of preparation can be taken from the examples.

For example, the compounds of the present invention can be suitably prepared by aryl-aryl coupling reactions, such as Yamamoto coupling, Suzuki coupling, Stille coupling, Sonogashira coupling, Heck coupling or Buchwald coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in J. Chem. Soc., Chem. Commun., 1977, 683-684. Yamamoto coupling is described in for example in T. Yamamoto et al., Prog. Polym. Sci., 1993, 17, 1153-1205, or WO 2004/022626 A1. Stille coupling is described for example in Z. Bao et al., J. Am. Chem. Soc., 1995, 117, 12426-12435 and C—H activation is described for example in M. Leclerc et al, Angew. Chem. Int. Ed., 2012, 51, 2068-2071. For example, when using Yamamoto coupling, educts having two reactive halide groups are preferably used. When using Suzuki coupling, educts having two reactive boronic acid or boronic acid ester groups or two reactive halide groups are preferably used. When using Stille coupling, edcuts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-idenacetone)dipalladium(0), bis (dibenzylideneacetone)palladium(0), or Pd(II) salts e.g. palladium acetate, with a phosphine ligand, for example triphenylphosphine, tris(ortho-tolyl)phosphine or tri(tert-butyl)

phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula $-O-SO_2Z^o$ can be used wherein $Z^o$ is an alkyl or aryl group, preferably $C_{1-10}$ alkyl or $C_{6-12}$ aryl. Particular examples of such leaving groups are tosylate, mesylate and triflate.

Especially suitable and preferred synthesis methods of the compounds of formula I and its subformulae are illustrated in the synthesis schemes shown hereinafter.

The synthesis of the polycyclic unit is exemplarily shown in Schemes 1-4.

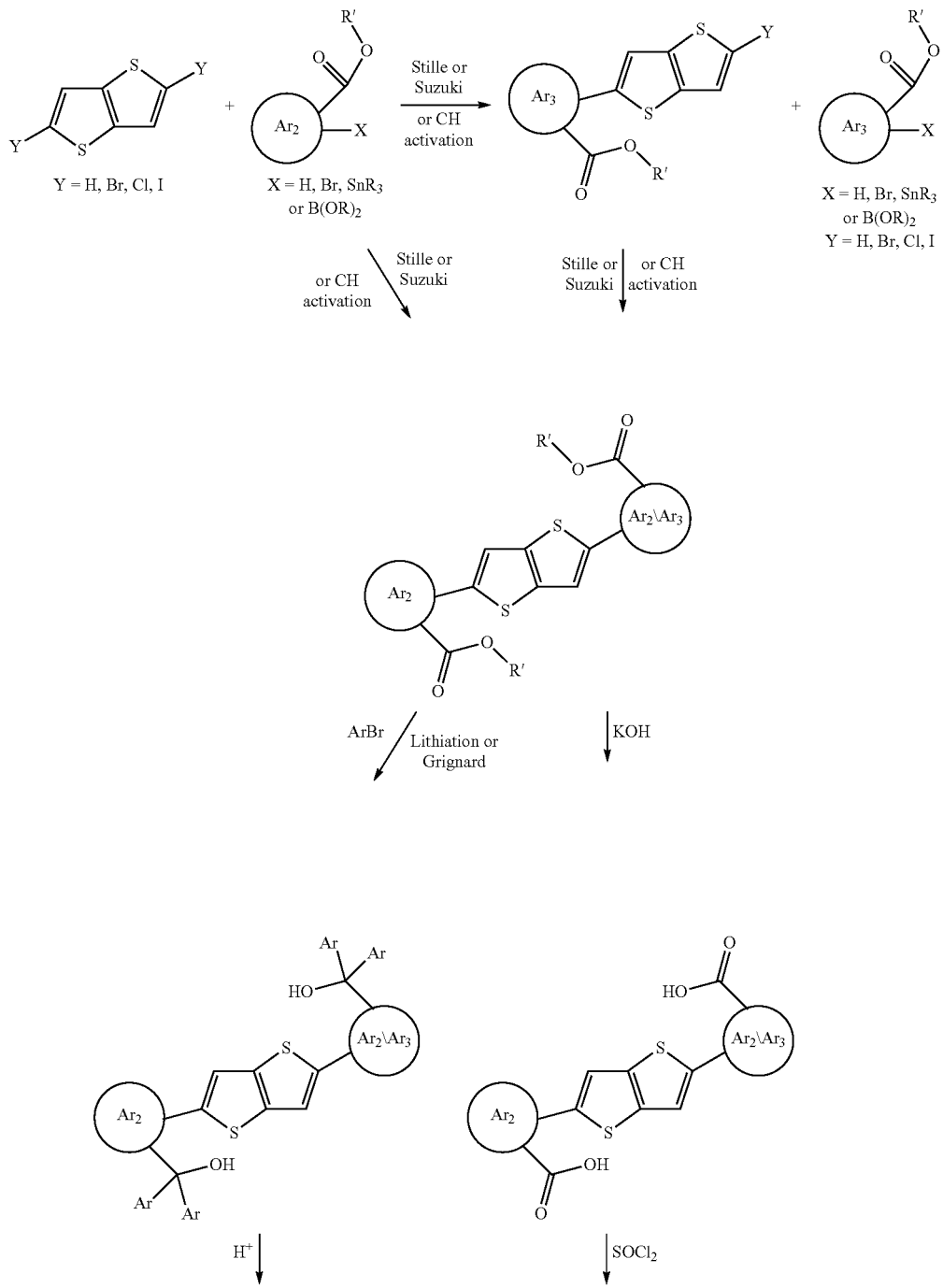

-continued
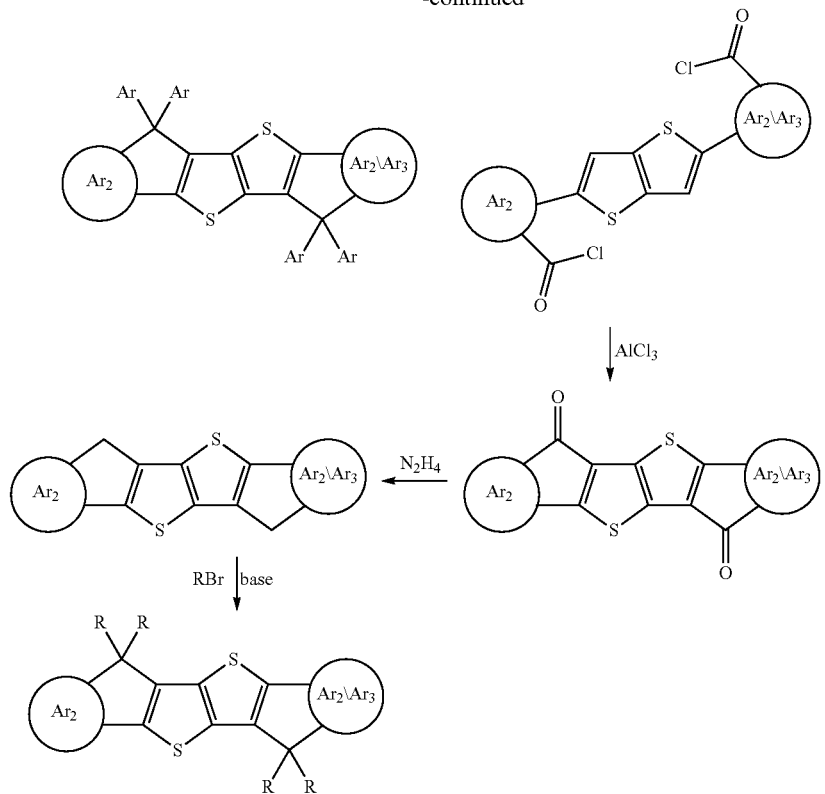
Scheme 1b
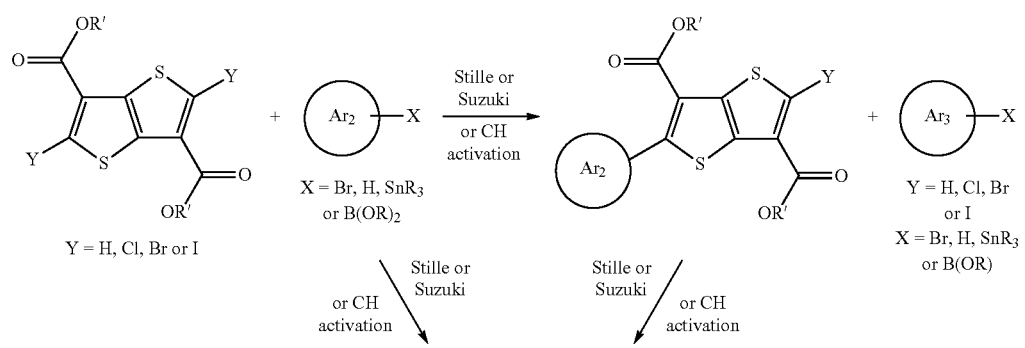
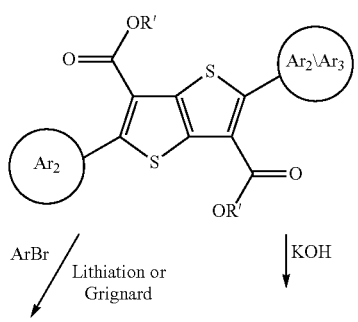

-continued
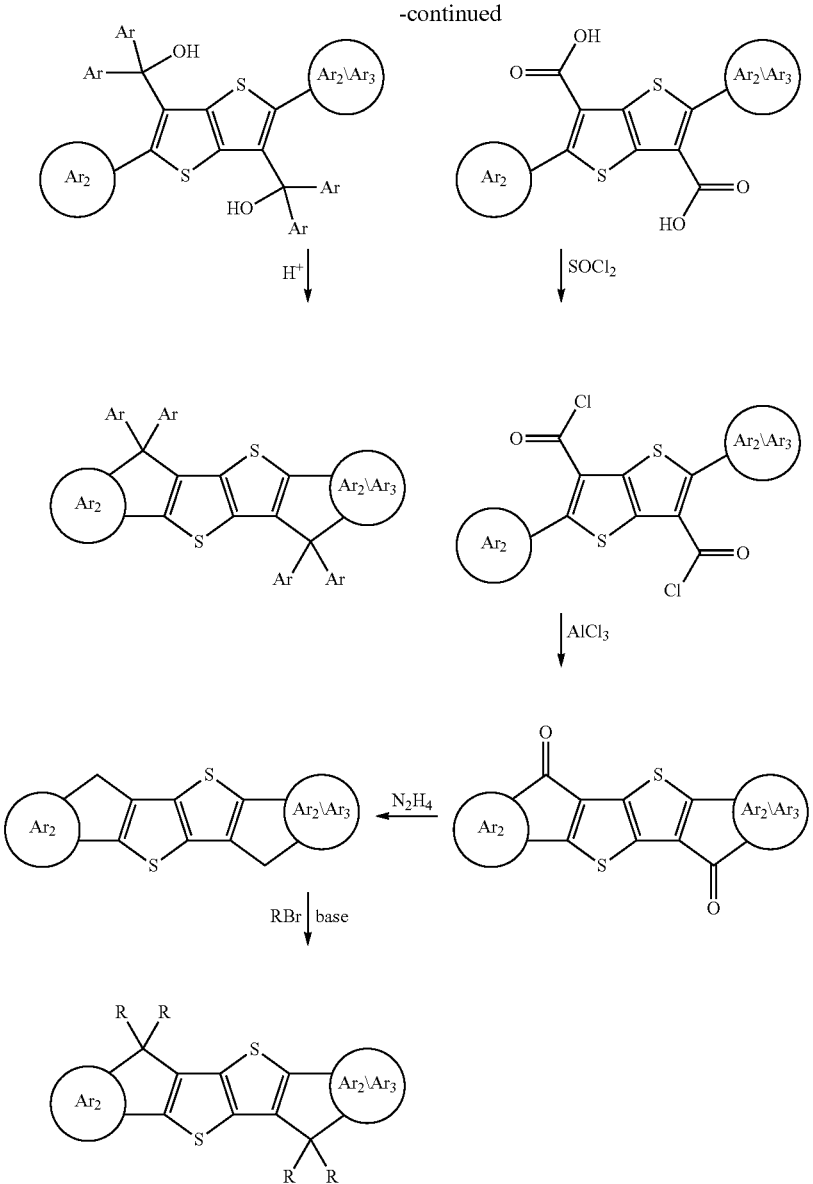
Scheme 2
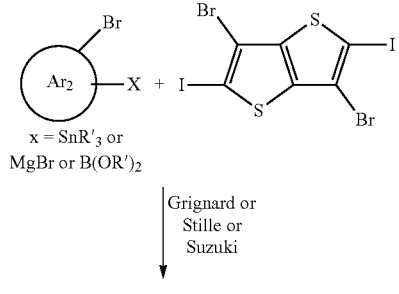
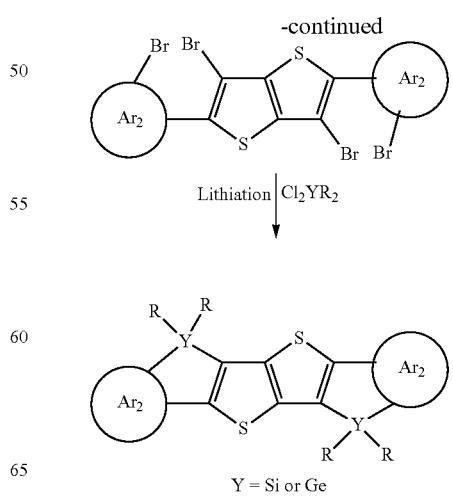

Scheme 3
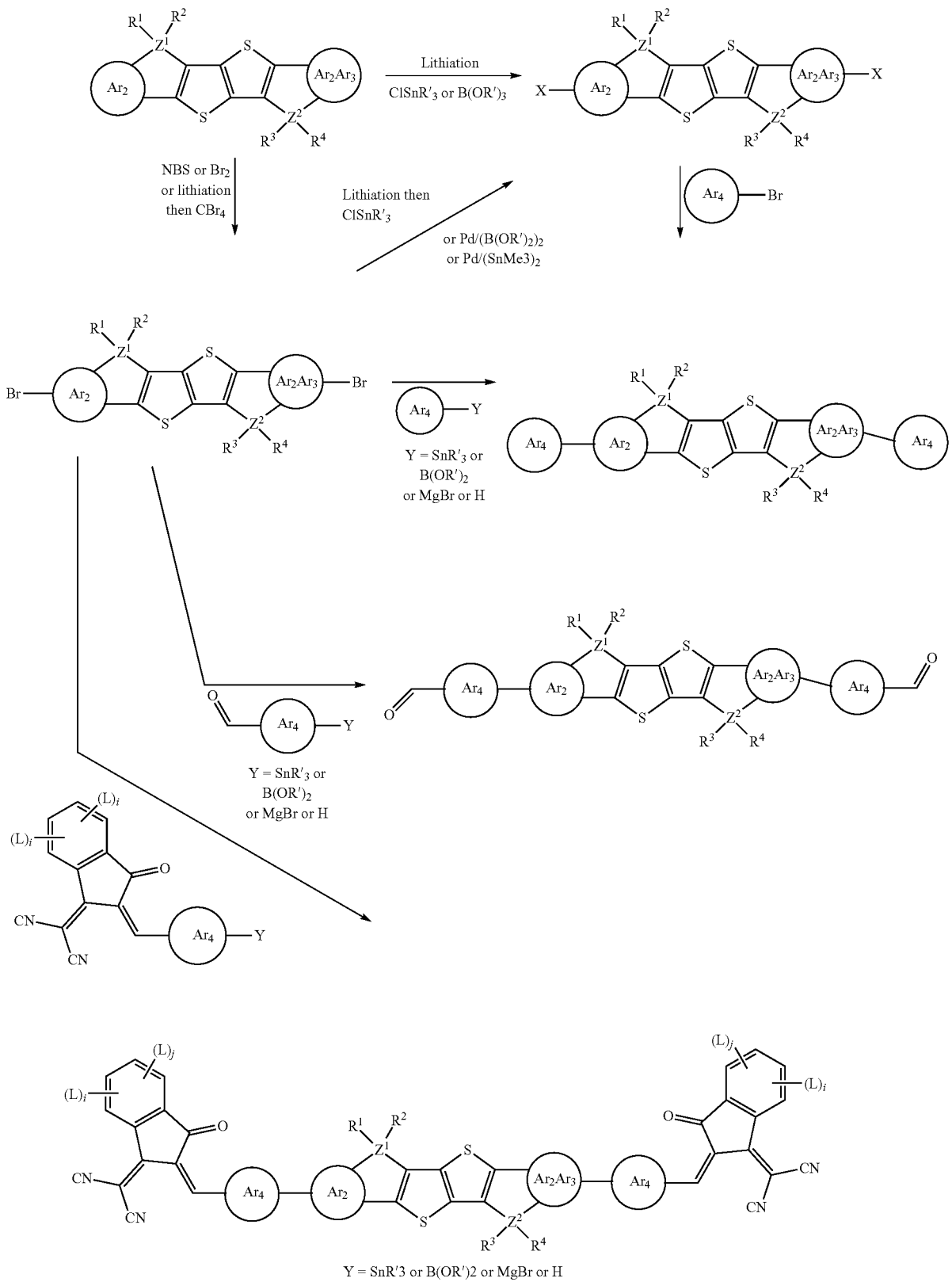

Scheme 4

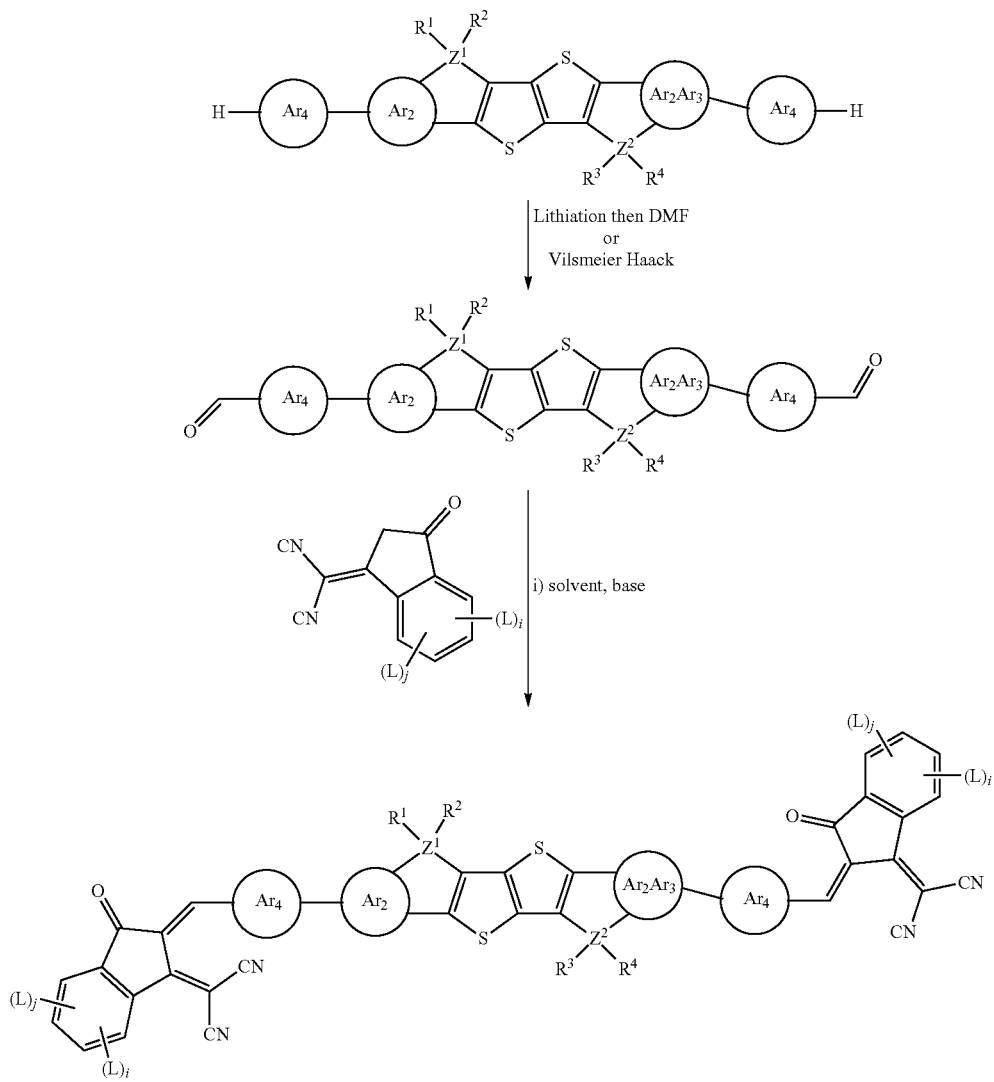

Novel methods of preparing compounds of formula I as described above and below are another aspect of the invention.

The compounds of formula I can also be used in compositions, for example together with monomeric or polymeric compounds having chargetransport, semiconducting, electrically conducting, photoconducting and/or light emitting semiconducting properties, or for example with compounds having hole blocking or electron blocking properties for use as interlayers or charge blocking layers in PSCs or OLEDs.

Thus, another aspect of the invention relates to a composition comprising one or more compounds of formula I and one or more small molecule compounds and/or polymers having one or more of a charge-transport, semiconducting, electrically conducting, photoconducting, hole blocking and electron blocking property.

These compositions blends can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more compounds of formula I or compositions as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology,* 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds of formula I can also be used in patterned OSC layers in the devices as described above and below. For applications in modern microelectronics it is generally desirable to generate small structures or patterns to reduce cost (more devices/unit area), and power consumption. Patterning of thin layers comprising a compound according to the present invention can be carried out for example by photolithography, electron beam lithography or laser patterning.

For use as thin layers in electronic or electrooptical devices the compounds, compositions or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound of formula I by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent (s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds according to the present invention are useful as charge transport, semiconducting, electrically conducting, photoconducting or light emitting materials in optical, electrooptical, electronic, electroluminescent or photoluminescent components or devices. In these devices, the compounds of the present invention are typically applied as thin layers or films.

Thus, the present invention also provides the use of the semiconducting compound or composition or layer in an electronic device. The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising compound or composition or organic semiconducting layer according to the present invention. Especially preferred devices are OFETs, TFTs, ICs, logic circuits, capacitors, RFID tags, OLEDs, OLETs, OPEDs, OPVs, PSCs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV, PSC and OPD devices, in particular OPD, PSC and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

For use in the photoactive layer of OPV or OPD devices the compounds according to the present invention are preferably used in a composition that comprises or contains, more preferably consists of, one or more p-type (electron donor) semiconductors and one or more n-type (electron acceptor) semiconductors.

The n-type semiconductor is for example constituted by a compound of formula I.

The p-type semiconductor is preferably a conjugated polymer as defined above.

The composition can also comprise a compound of formula I as n-type semiconductor, a p-type semiconductor like a conjugated polymer, and a second n-type semiconductor, which is preferably a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-C60" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.* 2004, 16, 4533).

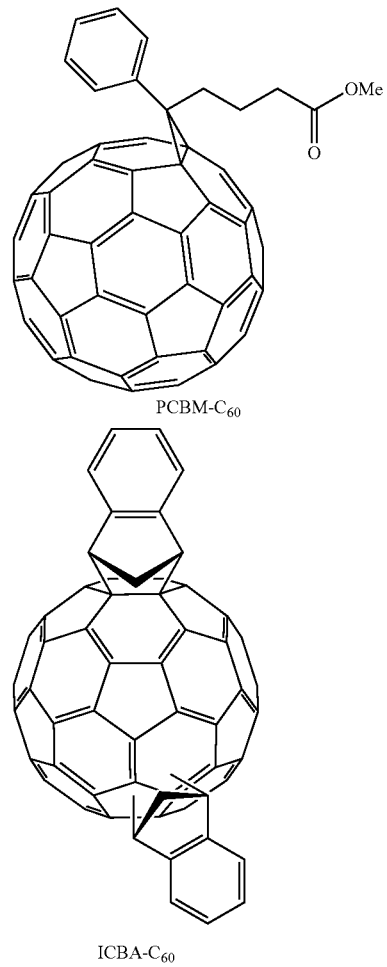

PCBM-$C_{60}$

ICBA-$C_{60}$

Preferably the polymer according to the present invention is blended with an n-type semiconductor such as a fullerene or substituted fullerene of formula Full-I to form the active layer in an OPV or OPD device wherein,

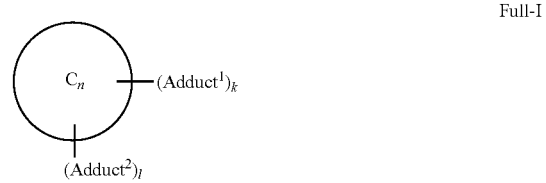

Full-I $C_n$ denotes a fullerene composed of n carbon atoms, optionally with one or more atoms trapped inside, Adduct$^1$ is a primary adduct appended to the fullerene $C_n$ with any connectivity, Adduct$^2$ is a secondary adduct, or a combination of secondary adducts, appended to the fullerene $C_n$ with any connectivity, k is an integer ≥1, and l is 0, an integer ≥1, or a non-integer >0.

In the formula Full-I and its subformulae, k preferably denotes 1, 2, 3 or, 4, very preferably 1 or 2.

The fullerene $C_n$ in formula Full-I and its subformulae may be composed of any number n of carbon atoms Preferably, in the compounds of formula XII and its subformulae the number of carbon atoms n of which the fullerene $C_n$ is composed is 60, 70, 76, 78, 82, 84, 90, 94 or 96, very preferably 60 or 70.

The fullerene $C_n$ in formula Full-I and its subformulae is preferably selected from carbon based fullerenes, endohedral fullerenes, or mixtures thereof, very preferably from carbon based fullerenes.

Suitable and preferred carbon based fullerenes include, without limitation, $(C_{60\text{-}Ih})[5,6]$fullerene, $(C_{70\text{-}D5h})[5,6]$fullerene, $(C_{76\text{-}D2}*)[5,6]$fullerene, $(C_{84\text{-}D2}*)[5,6]$fullerene, $(C_{84\text{-}D2d})[5,6]$fullerene, or a mixture of two or more of the aforementioned carbon based fullerenes.

The endohedral fullerenes are preferably metallofullerenes. Suitable and preferred metallofullerenes include, without limitation, $La@C_{60}$, $La@C_{82}$, $Y@C_{82}$, $Sc_3N@C_{80}$, $Y_3N@C_{80}$, $Sc_3C_2@C_{80}$ or a mixture of two or more of the aforementioned metallofullerenes.

Preferably the fullerene $C_n$ is substituted at a [6,6] and/or [5,6] bond, preferably substituted on at least one [6,6] bond.

Primary and secondary adduct, named "Adduct" in formula Full-I and its subformulae, is preferably selected from the following formulae

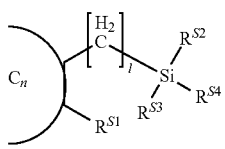

S-1

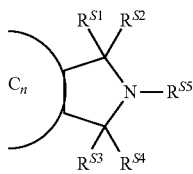

S-2

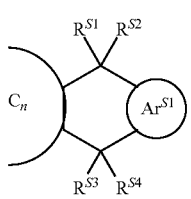

S-3

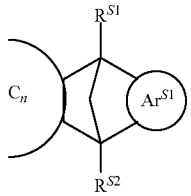

S-4

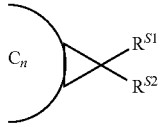

S-4

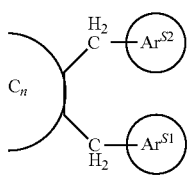

S-5

-continued

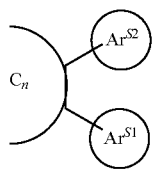

S-6

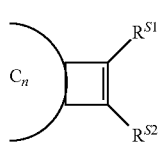

S-7

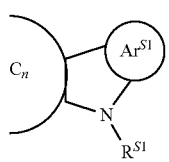

S-8

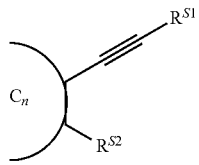

S-9

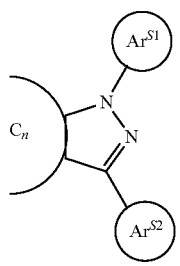

S-10

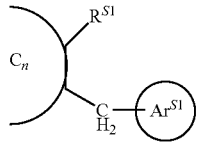

S-11

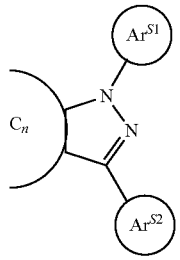

S-12

-continued

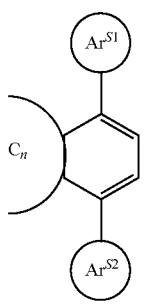
S-13

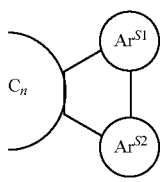
S-14 wherein $Ar^{S1}$, $Ar^{S2}$ denote, independently of each other, an aryl or heteroaryl group with 5 to 20, preferably 5 to 15, ring atoms, which is mono- or polycyclic, and which is optionally substituted by one or more identical or different substituents having one of the meanings of L as defined above and below, $R^{S1}$, $R^{S2}$, $R^{S3}$, $R^{S4}$ and $R^{S5}$ independently of each other denote H, CN or have one of the meanings of $R^S$ as defined above and below.

Preferred compounds of formula Full-I are selected from the following subformulae:

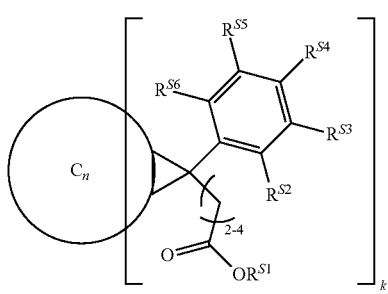
Full-Ia

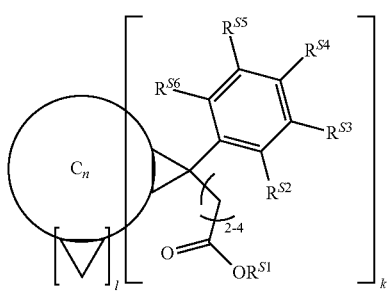
Full-Ib

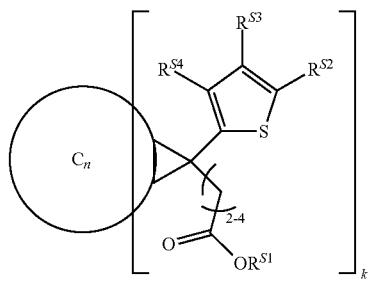
Full-Ic

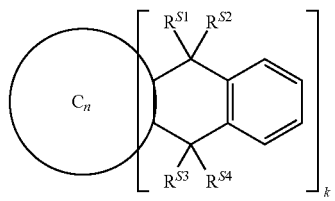
Full-Id

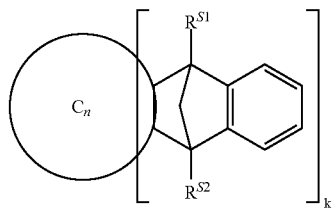
Full-Ie

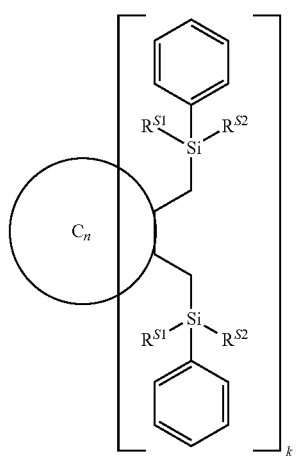
Full-If

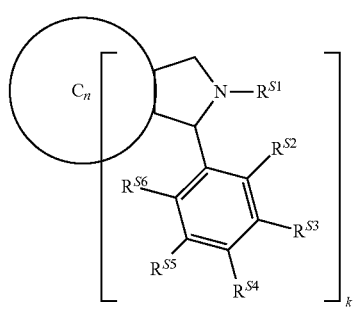
Full-Ig

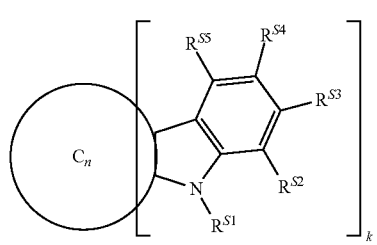

Full-Ih wherein
$R^{S1}$, $R^{S2}$, $R^{S3}$, $R^{S4}$ $R^{S5}$ and $R^{S6}$ independently of each other denote H or have one of the meanings of $R^S$ as defined above and below.

Most preferably the fullerene is PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-Ih), or bis-oQDM-C60.

The OPV or OPD device preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an insulating polymer, like for example nafion, polyethyleneimine or polystyrene-sulphonate, an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly [(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a composition according to the present invention comprising a compound of formula I and a conjugated polymer, the ratio polymer:compound of formula I is preferably from 5:1 to 1:5 by weight, more preferably from 3:1 to 1:3 by weight, most preferably 2:1 to 1:2 by weight.

The composition according to the present invention may also comprise a polymeric binder, preferably from 0.001 to 95% by weight. Examples of binder include polystyrene (PS), polydimethylsilane (PDMS), polypropylene (PP) and polymethylmethacrylate (PMMA).

A binder to be used in the formulation as described before, which is preferably a polymer, may comprise either an insulating binder or a semiconducting binder, or mixtures thereof, may be referred to herein as the organic binder, the polymeric binder or simply the binder.

Preferably, the polymeric binder comprises a weight average molecular weight in the range of 1000 to 5,000,000 g/mol, especially 1500 to 1,000,000 g/mol and more preferable 2000 to 500,000 g/mol. Surprising effects can be achieved with polymers having a weight average molecular weight of at least 10000 g/mol, more preferably at least 100000 g/mol.

In particular, the polymer can have a polydispersity index $M_w/M_n$ in the range of 1.0 to 10.0, more preferably in the range of 1.1 to 5.0 and most preferably in the range of 1.2 to 3.

Preferably, the inert binder is a polymer having a glass transition temperature in the range of −70 to 160° C., preferably 0 to 150° C., more preferably 50 to 140° C. and most preferably 70 to 130° C. The glass transition temperature can be determined by measuring the DSC of the polymer (DIN EN ISO 11357, heating rate 10° C. per minute).

The weight ratio of the polymeric binder to the OSC compound, like that of formula I, is preferably in the range of 30:1 to 1:30, particularly in the range of 5:1 to 1:20 and more preferably in the range of 1:2 to 1:10.

According to a preferred embodiment the binder preferably comprises repeating units derived from styrene monomers and/or olefin monomers. Preferred polymeric binders can comprise at least 80%, preferably 90% and more preferably 99% by weight of repeating units derived from styrene monomers and/or olefins.

Styrene monomers are well known in the art. These monomers include styrene, substituted styrenes with an alkyl substituent in the side chain, such as α-methylstyrene and α-ethylstyrene, substituted styrenes with an alkyl substituent on the ring such as vinyltoluene and p-methylstyrene, halogenated styrenes such as monochlorostyrenes, dichlorostyrenes, tribromostyrenes and tetrabromostyrenes.

Olefin monomers consist of hydrogen and carbon atoms. These monomers include ethylene, propylene, butylenes, isoprene and 1,3-butadiene.

According to a preferred embodiment of the present invention, the polymeric binder is polystyrene having a weight average molecular weight in the range of 50,000 to 2,000,000 g/mol, preferably 100,000 to 750,000 g/mol, more preferably in the range of 150,000 to 600,000 g/mol and most preferably in the range of 200,000 to 500,000 g/mol.

Further examples of suitable binders are disclosed for example in US 2007/0102696 A1. Especially suitable and preferred binders are described in the following.

The binder should preferably be capable of forming a film, more preferably a flexible film.

Suitable polymers as binders include poly(1,3-butadiene), polyphenylene, polystyrene, poly(α-methylstyrene), poly (α-vinylnaphtalene), poly(vinyltoluene), polyethylene, cis-polybutadiene, polypropylene, polyisoprene, poly(4-methyl-1-pentene), poly (4-methylstyrene), poly (chorotrifluoroethylene), poly(2-methyl-1,3-butadiene), poly(p-xylylene), poly(α-α-α'-α' tetrafluoro-p-xylylene), poly[1,1-(2-methyl propane)bis(4-phenyl)carbonate], poly (cyclohexyl methacrylate), poly(chlorostyrene), poly(2,6-dimethyl-1,4-phenylene ether), polyisobutylene, poly(vinyl cyclohexane), poly(vinylcinnamate), poly(4-vinylbiphenyl), 1,4-polyisoprene, polynorbornene, poly(styrene-block-butadiene); 31% wt styrene, poly(styrene-block-butadiene-block-styrene); 30% wt styrene, poly(styrene-co-maleic anhydride) (and ethylene/butylene) 1-1.7% maleic anhydride, poly(styrene-block-ethylene/butylene-block-styrene) triblock polymer 13% styrene, poly(styrene-block-ethylene-propylene-block-styrene) triblock polymer 37% wt styrene, poly(styrene-block-ethylene/butylene-block-styrene) triblock polymer 29% wt styrene, poly(1-vinylnaphthalene), poly(1-vinylpyrrolidone-co-styrene) 64% styrene, poly(1-vinylpyrrolidone-co-vinyl acetate) 1.3:1, poly(2-chlorostyrene), poly(2-vinylnaphthalene), poly(2-vinylpyridine-co-styrene) 1:1, poly(4,5-Difluoro-2,2-bis(CF3)-1,3-dioxole-co-tetrafluoroethylene) Teflon, poly(4-chlorostyrene), poly (4-methyl-1-pentene), poly(4-methylstyrene), poly(4-vinylpyridine-co-styrene) 1:1, poly(alpha-methylstyrene), poly(butadiene-graft-poly(methyl acrylate-co-acrylonitrile)) 1:1:1, poly(butyl methacrylate-co-isobutyl methacrylate) 1:1, poly(butyl methacrylate-co-methyl methacrylate) 1:1, poly(cyclohexylmethacrylate), poly(ethylene-co-1-butene-co-1-hexene) 1:1:1, poly(ethylene-co-ethylacrylate-co-maleic anhydride); 2% anhydride, 32% ethyl acrylate, poly (ethylene-co-glycidyl methacrylate) 8% glycidyl methacrylate, poly(ethylene-co-methyl acrylate-co-glycidyl meth-acrylate) 8% glycidyl metha-crylate 25% methyl acrylate, poly(ethylene-co-octene) 1:1, poly(ethylene-co-propylene-co-5-methylene-2-norbornene) 50% ethylene, poly(ethylene-co-tetrafluoroethylene) 1:1, poly(isobutyl methacrylate), poly(isobutylene), poly(methyl methacrylate)-co-(fluorescein O-methacrylate) 80% methyl methacrylate, poly(methyl methacrylate-co-butyl methacrylate) 85% methyl methacrylate, poly(methyl methacrylate-co-ethyl acrylate) 5% ethyl acrylate, poly(propylene-co-butene) 12% 1-butene, poly(styrene-co-allyl alcohol) 40% allyl alcohol, poly(styrene-co-maleic anhydride) 7% maleic anhydride, poly(styrene-co-maleic anhydride) cumene terminated (1.3:1), poly(styrene-co-methyl methacrylate) 40% styrene, poly(vinyltoluene-co-alpha-methylstyrene) 1:1, poly-2-vinylpyridine, poly-4-vinylpyridine, poly-alpha-pinene, polymethylmethacrylate, polybenzylmethacrylate, polyethylmethacrylate, polyethylene, polyethylene terephthalate, polyethylene-co-ethylacrylate 18% ethyl acrylate, polyethylene-co-vinylacetate 12% vinyl acetate, polyethylene-graft-maleic anhydride 0.5% maleic anhydride, polypropylene, polypropylene-graft-maleic anhydride 8-10% maleic anhydride, polystyrene poly(styrene-block-ethylene/butylene-block-styrene) graft maleic anhydride 2% maleic anhydride 1:1:1 others, poly(styrene-block-butadiene) branched 1:1, poly(styrene-block-butadiene-block-styrene), 30% styrene, poly(styrene-block-isoprene) 10% wt styrene, poly(styrene-block-isoprene-block-styrene) 17% wt styrene, poly(styrene-co-4-chloromethylstyrene-co-4-methoxymethylstyrene 2:1:1, polystyrene-co-acrylonitrile 25% acrylonitrile, polystyrene-co-alpha-methylstyrene 1:1, polystyrene-co-butadiene 4% butadiene, polystyrene-co-butadiene 45% styrene, polystyrene-co-chloromethylstyrene 1:1, polyvinylchloride, polyvinylcinnamate, polyvinylcyclohexane, polyvinylidenefluoride, polyvinylidenefluoride-co-hexafluoropropylene assume 1:1, poly(styrene-block-ethylene/propylene-block-styrene) 30% styrene, poly(styrene-block-ethylene/propylene-block-styrene) 18% styrene, poly (styrene-block-ethylene/propylene-block-styrene) 13% styrene, poly(styrene-block ethylene block-ethylene/propylene-block styrene) 32% styrene, poly(styrene-block ethylene block-ethylene/propylene-block styrene) 30% styrene, poly(styrene-block-ethylene/butylene-block-styrene) 31% styrene, poly(styrene-block-ethylene/butylene-block-styrene) 34% styrene, poly(styrene-block-ethylene/butylene-block-styrene) 30% styrene, poly(styrene-block-ethylene/butylene-block-styrene) 60%, styrene, branched or non-branched polystyrene-block-polybutadiene, polystyrene-block(polyethylene-ran-butylene)-block-polystyrene, polystyrene-block-polybutadiene-block-polystyrene, poly-styrene-(ethylene-propylene)-diblock-copolymers (e.g. KRATON®-G1701E, Shell), poly(propylene-co-ethylene) and poly(styrene-co-methylmethacrylate).

Preferred insulating binders to be used in the formulations as described before are polystryrene, poly(α-methylstyrene), polyvinylcinnamate, poly(4-vinylbiphenyl), poly(4-methylstyrene), and polymethyl methacrylate. Most preferred insulating binders are polystyrene and polymethyl methacrylate.

The binder can also be selected from crosslinkable binders, like e.g. acrylates, epoxies, vinylethers, thiolenes etc. The binder can also be mesogenic or liquid crystalline.

The organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility of at least $10^{-5}$ cm$^2$V$^{-1}$s$^{-1}$, more preferably at least $10^{-4}$ cm$^2$V$^{-1}$s$^{-1}$.

A preferred semiconducting binder comprises a homopolymer or copolymer (including block-copolymer) containing arylamine (preferably triarylamine).

To produce thin layers in BHJ OPV devices the compounds, compositions and formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the mixture of a compound of formula I and a polymer must be prepared. In the preparation of formulations, suitable solvent must be selected to ensure full dissolution of both component, p-type and n-type and take into account the boundary conditions (for example rheological properties) introduced by the chosen printing method.

Organic solvents are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
- optionally a substrate,
- a high work function electrode, preferably comprising a metal oxide, like for example ITO, serving as anode,
- an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
- a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
- optionally a layer having electron transport properties, for example comprising LiF or PFN,
- a low work function electrode, preferably comprising a metal like for example aluminium, serving as cathode,
- wherein at least one of the electrodes, preferably the anode, is transparent to visible light, and
- wherein the n-type semiconductor is a compound of formula I.

A second preferred OPV device according to the invention is an inverted OPV device and comprises the following layers (in the sequence from bottom to top):
- optionally a substrate,
- a high work function metal or metal oxide electrode, comprising for example ITO, serving as cathode,
- a layer having hole blocking properties, preferably comprising an organic polymer, polymer blend, metal or metal oxide like $TiO_x$, $ZnO_x$, Ca, Mg, poly(ethyleneimine), poly(ethyleneimine) ethoxylated or poly [(9,9-bis(3'-(N,N-dimethylamino)propyl)-2,7-fluorene)-alt-2,7-(9,9-dioctylfluorene)],
- a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
- an optional conducting polymer layer or hole transport layer, preferably comprising an organic polymer or polymer blend, metal or metal oxide, for example PEDOT:PSS, nafion, a substituted triaryl amine derivative like for example TBD or NBD, or $WO_N$, $MoO_x$, $NiO_x$, Pd or Au,
- an electrode comprising a high work function metal like for example silver, serving as anode,
- wherein at least one of the electrodes, preferably the cathode, is transparent to visible light, and
- wherein the n-type semiconductor is a compound of formula I.

In the OPV devices of the present invention the p-type and n-type semiconductor materials are preferably selected from the materials, like the compound/polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

Another preferred embodiment of the present invention relates to the use of a compound or composition according to the present invention as dye, hole transport layer, hole blocking layer, electron transport layer and/or electron blocking layer in a DSSC or a perovskite-based solar cell (PSC), and to a DSSC or PSC comprising a compound or composition according to the present invention.

DSSCs and PSCs can be manufactured as described in the literature, for example in Chem. Rev. 2010, 110, 6595-6663, Angew. Chem. Int. Ed. 2014, 53, 2-15 or in WO2013171520A1

A preferred OE device according to the invention is a solar cell, preferably a PSC, comprising a light absorber which is at least in part inorganic as described below.

In a solar cell comprising the light absorber according to the invention there are no restrictions per se with respect to the choice of the light absorber material which is at least in part inorganic.

The term "at least in part inorganic" means that the light absorber material may be selected from metalorganic complexes or materials which are substantially inorganic and possess preferably a crystalline structure where single positions in the crystalline structure may be allocated by organic ions.

Preferably, the light absorber comprised in the solar cell according to the invention has an optical band-gap $\leq 2.8$ eV and $\geq 0.8$ eV.

Very preferably, the light absorber in the solar cell according to the invention has an optical band-gap $\leq 2.2$ eV and $\geq 1.0$ eV.

The light absorber used in the solar cell according to the invention does preferably not contain a fullerene. The chemistry of fullerenes belongs to the field of organic chemistry. Therefore fullerenes do not fulfil the definition of being "at least in part inorganic" according to the invention.

Preferably, the light absorber which is at least in part inorganic is a material having perovskite structure or a material having 2D crystalline perovskite structure.

The term "perovskite" as used above and below denotes generally a material having a perovskite crystalline structure or a 2D crystalline perovskite structure.

The term perovskite solar cell (PSC) means a solar cell comprising a light absorber which is a material having perovskite structure or a material having 2D crystalline perovskite structure.

The light absorber which is at least in part inorganic is without limitation composed of a material having perovskite crystalline structure, a material having 2D crystalline perovskite structure (e.g. CrystEngComm, 2010, 12, 2646-2662), $Sb_2S_3$(stibnite), $Sb_2(S_xSe_{(x-1)})_3$, $PbS_xSe_{(x-1)}$, $CdS_xSe_{(x-1)}$, ZnTe, CdTe, $ZnS_xSe_{(x-1)}$, InP, FeS, $FeS_2$, $Fe_2S_3$, $Fe_2SiS_4$, $Fe_2GeS_4$, $Cu_2S$, CuInGa, $CuIn(Se_xS_{(1-x)})_2$, $Cu_3Sb_xBi_{(x-1)}$, $(S_ySe_{(y-1)})_3$, $Cu_2SnS_3$, $SnS_xSe_{(x-1)}$, $Ag_2S$, $AgBiS_2$, BiSI, BiSeI, $Bi_2(S_xSe_{(x-1)})_3$, $BiS_{(1-x)}Se_xI$, $WSe_2$, AlSb, metal halides (e.g. $BiI_3$, $Cs_2SnI_6$), chalcopyrite (e.g. $CuIn_xGa_{(1-x)}(S_ySe_{(1-y)})_2$), kesterite (e.g. $Cu_2ZnSnS_4$, $Cu_2ZnSn(Se_xS_{(1-x)})_4$, $Cu_2Zn(Sn_{1-x}Ge_x)S_4$) and metal oxide (e.g. CuO, $Cu_2O$) or a mixture thereof.

Preferably, the light absorber which is at least in part inorganic is a perovskite.

In the above definition for light absorber, x and y are each independently defined as follows: ($0 \leq x \leq 1$) and ($0 \leq y \leq 1$).

Very preferably, the light absorber is a special perovskite namely a metal halide perovskite as described in detail above and below. Most preferably, the light absorber is an organic-inorganic hybrid metal halide perovskite contained in the perovskite solar cell (PSC).

In one particularly preferred embodiment of the invention, the perovskite denotes a metal halide perovskite with the formula $ABX_3$,
where
A is a monovalent organic cation, a metal cation or a mixture of two or more of these cations
B is a divalent cation and
X is F, Cl, Br, I, $BF_4$ or a combination thereof.

Preferably, the monovalent organic cation of the perovskite is selected from alkylammonium, wherein the alkyl group is straight chain or branched having 1 to 6 C atoms, formamidinium or guanidinium or wherein the metal cation is selected from $K^+$, $Cs^+$ or $Rb^+$.

Suitable and preferred divalent cations B are $Ge^{2+}$, $Sn^{2+}$ or $Pb^{2+}$.

Suitable and preferred perovskite materials are $CsSnI_3$, $CH_3NH_3Pb(I_{1-x}Cl_x)_3$, $CH_3NH_3PbI_3$, $CH_3NH_3Pb(I_{1-x}Br_x)_3$, $CH_3NH_3Pb(I_{1-x}(BF_4)_x)_3$, $CH_3NH_3Sn(I_{1-x}Cl_x)_3$, $CH_3NH_3SnI_3$ or $CH_3NH_3Sn(I_{1-x}Br_x)_3$ wherein x is each independently defined as follows: ($0 < x \leq 1$).

Further suitable and preferred perovskites may comprise two halides corresponding to formula $Xa_{(3-x)}Xb_{(x)}$, wherein Xa and Xb are each independently selected from Cl, Br, or I, and x is greater than 0 and less than 3.

Suitable and preferred perovskites are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskites are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The invention further relates to a solar cell comprising the light absorber, preferably a PSC, as described above and below, wherein the compound of formula I is employed as a layer between one electrode and the light absorber layer.

The invention further relates to a solar cell comprising the light absorber, preferably a PSC, as described above and below, wherein the compound of formula I is comprised in an electron-selective layer.

The electron selective layer is defined as a layer providing a high electron conductivity and a low hole conductivity favoring electron-charge transport.

The invention further relates to a solar cell comprising the light absorber, preferably a PSC, as described above and below, wherein the compound of formula I is employed as electron transport material (ETM) or as hole blocking material as part of the electron selective layer.

Preferably, the compound of formula I is employed as electron transport material (ETM).

In an alternative preferred embodiment, the compound of formula I is employed as hole blocking material.

The device architecture of a PSC device according to the invention can be of any type known from the literature.

A first preferred device architecture of a PSC device according to the invention comprises the following layers (in the sequence from bottom to top):
  optionally a substrate which, in any combination, can be flexible or rigid and transparent, semi-transparent or non-transparent and electrically conductive or non-conductive;
  a high work function electrode, preferably comprising a doped metal oxide, for example fluorine-doped tin oxide (FTO), tin-doped indium oxide (ITO), or aluminium-doped zinc oxide;
  an electron-selective layer which comprises one or more electron-transporting materials, at least one of which is a compound of formula I, and which, in some cases, can also be a dense layer and/or be composed of nanoparticles, and which preferably comprises a metal oxide such as $TiO_2$, $ZnO_2$, $SnO_2$, $Y_2O_5$, $Ga_2O_3$, $SrTiO_3$, $BaTiO_3$ or combinations thereof;
  optionally a porous scaffold which can be conducting, semi-conducting or insulating, and which preferably comprises a metal oxide such as $TiO_2$, $ZnO_2$, $SnO_2$, $Y_2O_5$, $Ga_2O_3$, $SrTiO_3$, $BaTiO_3$, $Al_2O_3$, $ZrO_2$, $SiO_2$ or combinations thereof, and which is preferably composed of nanoparticles, nanorods, nanoflakes, nanotubes or nanocolumns;
  a layer comprising a light absorber which is at least in part inorganic, particularly preferably a metal halide perovskite as described above which, in some cases, can also be a dense or porous layer and which optionally partly or fully infiltrates into the underlying layer;
  optionally a hole selective layer, which comprises one or more hole-transporting materials, and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;
and a back electrode which can be metallic, for example made of Au, Ag, Al, Cu, Ca, Ni or combinations thereof, or non-metallic and transparent, semi-transparent or non-transparent.

A second preferred device architecture of a PSC device according to the invention comprises the following layers (in the sequence from bottom to top):
  optionally a substrate which, in any combination, can be flexible or rigid and transparent, semi-transparent or non-transparent and electrically conductive or non-conductive;
  a high work function electrode, preferably comprising a doped metal oxide, for example fluorine-doped tin oxide (FTO), tin-doped indium oxide (ITO), or aluminium-doped zinc oxide;
  optionally a hole injection layer which, for example, changes the work function of the underlying electrode, and/or modifies the surface of the underlying layer and/or helps to planarize the rough surface of the underlying layer and which, in some cases, can also be a monolayer;
  optionally a hole selective layer, which comprises one or more hole-transporting materials and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris (bis(trifluoromethylsulfonyl)imide)), which can enhance the properties of the hole selective layer, for example the electrical conductivity, and/or facilitate its processing;

a layer comprising a light absorber which is at least in part inorganic, particularly preferably a metal halide perovskite as described or preferably described above;

an electron-selective layer, which comprises one or more electron-transporting materials, at least one of which is a compound of formula I and which, in some cases, can also be a dense layer and/or be composed of nanoparticles, and which, for example, can comprise a metal oxide such as $TiO_2$, $ZnO_2$, $SnO_2$, $Y_2O_5$, $Ga_2O_3$, $SrTiO_3$, $BaTiO_3$ or combinations thereof, and/or which can comprise a substituted fullerene, for example [6,6]-phenyl C61-butyric acid methyl ester, and/or which can comprise a molecular, oligomeric or polymeric electron-transport material, for example 2,9-Dimethyl-4,7-diphenyl-1,10-phenanthroline, or a mixture thereof;

and a back electrode which can be metallic, for example made of Au, Ag, Al, Cu, Ca, Ni or combinations thereof, or non-metallic and transparent, semi-transparent or non-transparent.

To produce electron selective layers in PSC devices according to the invention, the compounds of formula I, optionally together with other compounds or additives in the form of blends or mixtures, may be deposited by any suitable method. Liquid coating of devices is more desirable than vacuum deposition techniques. Solution deposition methods are especially preferred. Formulations comprising the compounds of formula I enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot die coating or pad printing. For the fabrication of PSC devices and modules, deposition techniques for large area coating are preferred, for example slot die coating or spray coating.

Formulations that can be used to produce electron selective layers in optoelectronic devices according to the invention, preferably in PSC devices comprise one or more compounds of formula I or preferred embodiments as described above in the form of blends or mixtures optionally together with one or more further electron transport materials and/or hole blocking materials and/or binders and/or other additives as described above and below, and one or more solvents.

The formulation may include or comprise, essentially consist of or consist of the said necessary or optional constituents as described above or below. All compounds or components which can be used in the formulations are either known or commercially available, or can be synthesised by known processes.

The formulation as described before may be prepared by a process which comprises:
(i) first mixing a compound of formula I, optionally a binder or a precursor of a binder as described before, optionally a further electron transport material, optionally one or more further additives as described above and below and a solvent or solvent mixture as described above and below and
(ii) applying such mixture to a substrate; and optionally evaporating the solvent(s) to form an electron selective layer according to the present invention.

In step (i) the solvent may be a single solvent for the compound of formula I and the organic binder and/or further electron transport material may each be dissolved in a separate solvent followed by mixing the resultant solutions to mix the compounds.

Alternatively, the binder may be formed in situ by mixing or dissolving a compound of formula I in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound formula I in a suitable solvent as described before, and the solution deposited for example by dipping, spraying, painting or printing it on a substrate to form a liquid layer and then removing the solvent to leave a solid layer. It will be appreciated that solvents are chosen which are able to dissolve all ingredients of the formulation, and which upon evaporation from the solution blend give a coherent defect free layer.

Besides the said components, the formulation as described before may comprise further additives and processing assistants. These include, inter alia, surface-active substances (surfactants), lubricants and greases, additives which modify the viscosity, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

Additives can be used to enhance the properties of the electron selective layer and/or the properties of any of the neighbouring layers and/or the performance of the optoelectronic device according to the invention. Additives can also be used to facilitate the deposition, the processing or the formation of the electron selective layer and/or the deposition, the processing or the formation of any of the neighbouring layers. Preferably, one or more additives are used which enhance the electrical conductivity of the electron selective layer and/or passivate the surface of any of the neighbouring layers.

Suitable methods to incorporate one or more additives include, for example exposure to a vapor of the additive at atmospheric pressure or at reduced pressure, mixing a solution or solid containing one or more additives and a material or a formulation as described or preferably described before, bringing one or more additives into contact with a material or a formulation as described before, by thermal diffusion of one or more additives into a material or a formulation as described before, or by ion-implantantion of one or more additives into a material or a formulation as described before.

Additives used for this purpose can be organic, inorganic, metallic or hybrid materials. Additives can be molecular compounds, for example organic molecules, salts, ionic liquids, coordination complexes or organometallic compounds, polymers or mixtures thereof. Additives can also be particles, for example hybrid or inorganic particles, preferably nanoparticles, or carbon based materials such as fullerenes, carbon nanotubes or graphene flakes.

Examples for additives that can enhance the electrical conductivity are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl–$SO_3^-$), cations (e.g. $H^+$, $Li^+$, $Na^+$, $K^+$, $Rb^+$, $Cs^+$, $Co^{3+}$ and $Fe^{3+}$), $O_2$, redox active salts (e.g. $XeOF_4$, $(NO_2^+)(SbF_6^-)$, $(NO_2^+)(SbCl_6^-)$, $(NO_2^+)(BF_4^-)$, $NOBF_4$, $NOPF_6$, $AgClO_4$, $H_2IrCl_6$ and La $(NO_3)_3.6H_2O$), strongly electron-accepting organic molecules (e.g. 2,3,5,6-tetrafluoro-7,7,8,8-tetracyanoquinodimethane ($F_4$-TCNQ)), transition metal oxides (e.g. $WO_3$, $Re_2O_7$ and $MoO_3$), metalorganic complexes of cobalt, iron, bismuth and molybdenum, (p-$BrC_6H_4$)$_3NSbCl_6$, bismuth (III) tris(trifluoroacetate), $FSO_2OOSO_2F$, acetylcholine, $R_4N^+$, (R is an alkyl group), $R_4P^+$ (R is a straight-chain or branched alkyl group 1 to 20), $R_6As^+$ (R is an alkyl group), $R_3S^+$ (R is an alkyl group) and ionic liquids (e.g. 1-Ethyl-3-methylimidazolium bis(trifluoromethylsulfonyl)imide). Suitable cobalt complexes beside of tris(2-(1H-pyrazol-1-yl)-4-tert-butylpyridine)-cobalt(III) tris(bis(trifluoromethylsulfonyl)imide)) are cobalt complex salts as described in WO 2012/114315, WO 2012/114316, WO 2014/082706, WO 2014/082704, EP 2883881 or JP 2013-131477.

Suitable lithium salts are beside of lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluoroposphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl) imide.

Preferably, the formulation comprises from 0.1 mM to 50 mM, preferably from 5 to 20 mM of the lithium salt.

Suitable device structures for PSCs comprising a compound formula I and a mixed halide perovskite are described in WO 2013/171517, claims 52 to 71 and claims 72 to 79, which is entirely incorporated herein by reference.

Suitable device structures for PSCs comprising a compound formula and a dielectric scaffold together with a perovskite are described in WO 2013/171518, claims 1 to 90 or WO 2013/171520, claims 1 to 94 which are entirely incorporated herein by reference.

Suitable device structures for PSCs comprising a compound of formula I, a semiconductor and a perovskite are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures for PSCs comprising a compounds of formula and comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

The invention further relates to a method of preparing a PSC as described above or below, the method comprising the steps of:
providing a first and a second electrode;
providing an electron selective layer comprising a compound of formula I.

The invention relates furthermore to a tandem device comprising at least one device according to the invention as described above and below. Preferably, the tandem device is a tandem solar cell.

The tandem device or tandem solar cell according to the invention may have two semi-cells wherein one of the semi cells comprises the compounds, oligomers or polymers in the active layer as described or preferably described above. There exists no restriction for the choice of the other type of semi cell which may be any other type of device or solar cell known in the art.

There are two different types of tandem solar cells known in the art. The so called 2-terminal or monolithic tandem solar cells have only two connections. The two subcells (or synonymously semi cells) are connected in series. Therefore, the current generated in both subcells is identical (current matching). The gain in power conversion efficiency is due to an increase in voltage as the voltages of the two subcells add up. The other type of tandem solar cells is the so called 4-terminal or stacked tandem solar cell. In this case, both subcells are operated independently. Therefore, both subcells can be operated at different voltages and can also generate different currents. The power conversion efficiency of the tandem solar cell is the sum of the power conversion efficiencies of the two subcells.

The invention furthermore relates to a module comprising a device according to the invention as described before or preferably described before.

The compounds and compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound and compositions according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer preferably comprises a compound of formula I.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the materials according to the present invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the materials according to the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows.

The materials according to the present invention may also be combined with photoisomerisable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

EXAMPLES

Example 1

Molecular structures were optimized at B3LYP/6-31G* level using Firefly QC package (see Alex A. Granovsky, Firefly version 8, www http://classic.chem.msu.su/gran/firefly/index.html), which is partially based on the GAMESS (US) source code (see M. W. Schmidt, K. K. Baldridge, J. A. Boatz, S. T. Elbert, M. S. Gordon, J. H. Jensen, S. Koseki, N. Matsunaga, K. A. Nguyen, S. Su, T. L. Windus, M. Dupuis, J. A. Montgomery J. Comput. Chem. 14, 1347-1363 (1993)). In order to reduce the calculation time an alkyl chain is represented by a methyl group which does not dramatically alter the calculated energy levels and does not infer that a methyl group is preferred, $E_{HOMO}$ and $E_{LUMO}$ are defined as the eigenvalues of, respectively, the highest occupied and lowest unoccupied Kohn-Sham molecular orbitals, and are used as approximations of, respectively, ionisation potential (IP) and electron affinity (EA). $E_g$ is defined as $|E_{LUMO}-E_{HOMO}|$ and is the transport band gap of the material. $S_0$-$S_1$ is the vertical excitation energy from the ground state $S_0$ to the first singlet excited state $S_1$, and is used as the measure of the optical band gap $E_g$(opt).

An approximate relation between $E_{HOMO}$, $E_{LUMO}$ and $E_g$ of donor and acceptor materials in a bulk-heterojunction and device performance is known as the Scharber model [M. C. Scharber, D. Mühlbacher, M. Koppe, P. Denk, C. Waldauf, A. J. Heeger, C. J. Brabec, Adv. Mater. 2006, 18, 789-794]. It is widely accepted that when the donor material of the donor-acceptor blend absorbs light and forms an excited state, the excited electron must hop onto the neighbouring acceptor site in order for the free carriers to be formed. The driving force of this process is the energetic difference between the excited state of the donor material and the electron affinity (approximated by $E_{LUMO}$) of the acceptor material and has been empirically found to be at least ca. 0.35 eV for charge generation to be efficient [D. Veldman, S. C. J. Meskers, R. A. J. Janssen, Adv. Funct. Mater. 2009, 19, 1939-1948; M. C. Scharber, N. S. Sariciftci, Progr. Polym. Sci. 38 (2013) 1929-1940]. Therefore, tuning of acceptor's $E_{LUMO}$ is of paramount importance, lowering its value will increase the driving force for charge generation and may allow using lower-bandgap donor material, whilst increasing $E_{LUMO}$ may hinder charge generation. For the present OSC materials, owing to their small optical band gap, another mechanism is also possible: light absorption by the acceptor followed by hole injection to the donor material, driven by the energy difference between $E_{HOMO}$ of donor and acceptor, respectively [W. Zhao, D. Qian, S. Zhang, S. Li, O. Inganäs, F. Gao, J. Hou, Adv. Mater. 2016, DOI: 10.1002/adma.201600281]. This mechanism is responsible for non-negligible external quantum efficiency beyond the absorption edge of the donor material, and retaining of this advantage of the acceptor material requires careful tuning of HOMO energy.

Comparative Example C1

Compound C1 as shown below is calculated as a reference.

| No. | Structure | $E_{HOMO}$/eV | $E_{LUMO}$/eV | $E_g$/eV | $S_0$-$S_1$/eV |
|---|---|---|---|---|---|
| C1 | 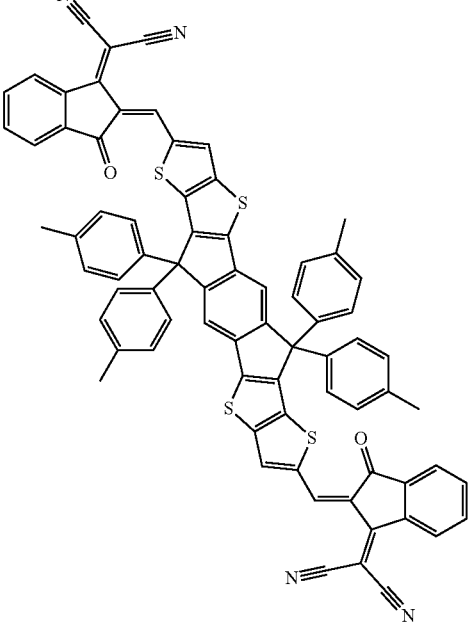 | −5.46 | −3.34 | 2.12 | 1.91 |
Examples 1-74
The computed values of $E_{HOMO}$, $E_{LUMO}$, $E_g$ and $S_0$-$S_1$ of compound C1 (whilst being different from experimentally determined IP, EA and $E_g$) are compared with the computed values of compounds 1-3 of formula I.

| No. | Structure | $E_{HOMO}$/ eV | $E_{LUMO}$/ eV | $E_g$/ eV | $S_0$-$S_1$/ eV |
|---|---|---|---|---|---|
| 1 | 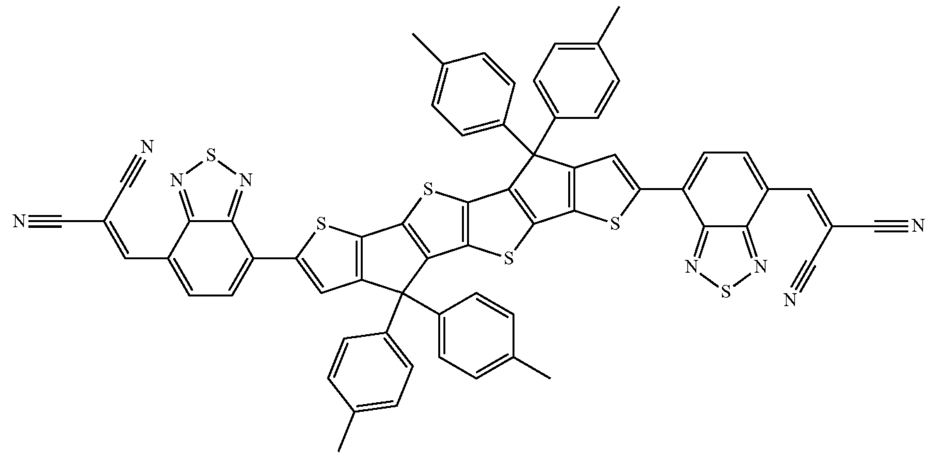 [SMILES: Cc1ccc(C2(c3ccc(C)cc3)c3cc(-c4ccc(C=C(C#N)C#N)c5nsnc45)sc3-c3sc4c5c(sc4c32)-c2sc(-c3ccc(C=C(C#N)C#N)c4nsnc34)cc2C5(c2ccc(C)cc2)c2ccc(C)cc2)cc1] | −5.27 | −3.54 | 1.73 | 1.61 |
| 2 | 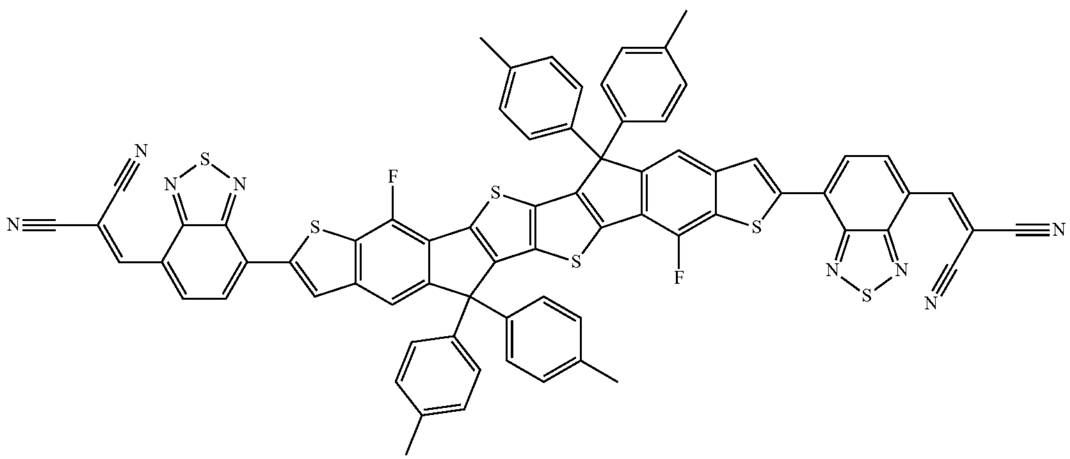 [SMILES: Cc1ccc(C2(c3ccc(C)cc3)c3cc4cc(-c5ccc(C=C(C#N)C#N)c6nsnc56)sc4c(F)c3-c3sc4c5c(sc4c32)-c2c(cc3cc(-c4ccc(C=C(C#N)C#N)c6nsnc46)sc3c2F)C5(c2ccc(C)cc2)c2ccc(C)cc2)cc1] | −5.35 | −3.54 | 1.81 | 1.55 |

-continued

| No. | Structure | $E_{HOMO}$/eV | $E_{LUMO}$/eV | $E_g$/eV | $S_0$-$S_1$/eV |
|---|---|---|---|---|---|
| 3 | 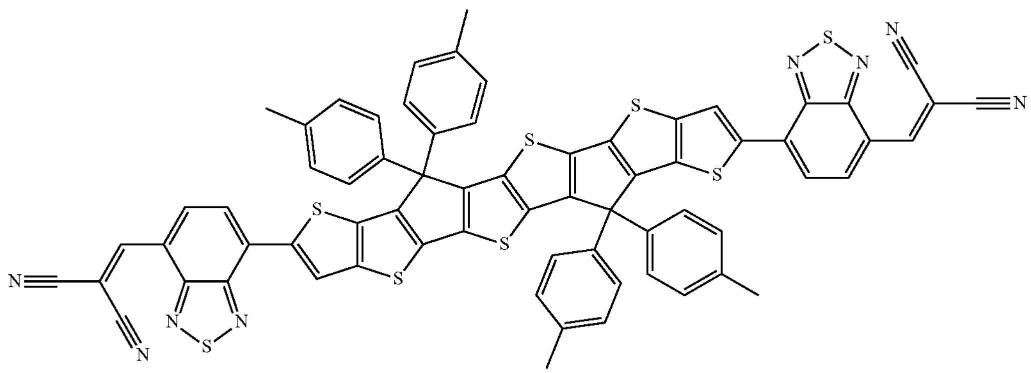 [SMILES: Cc1ccc(C2(c3ccc(C)cc3)c3c(sc4cc(-c5ccc(C=C(C#N)C#N)c6nsnc56)sc34)-c3sc4c5c(sc4c32)-c2sc3cc(-c4ccc(C=C(C#N)C#N)c6nsnc46)sc3c2C5(c2ccc(C)cc2)c2ccc(C)cc2)cc1] | −5.16 | −3.49 | 1.67 | 1.47 |
| 4 | 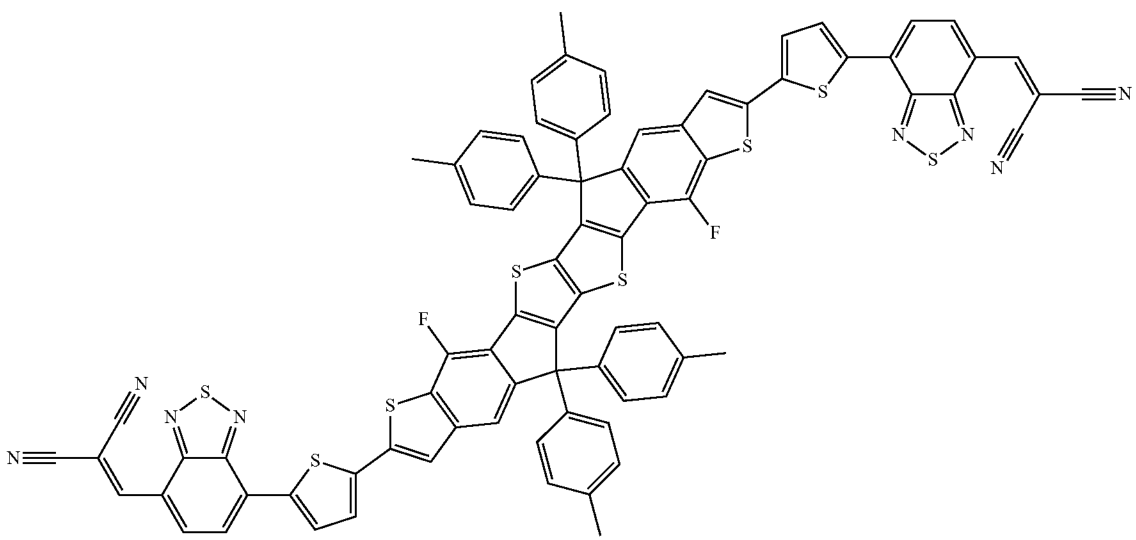 [SMILES: Cc1ccc(C2(c3ccc(C)cc3)c3cc4cc(-c5ccc(-c6ccc(C=C(C#N)C#N)c7nsnc67)s5)sc4c(F)c3-c3sc4c5c(sc4c32)-c2c(cc3cc(-c4ccc(-c6ccc(C=C(C#N)C#N)c7nsnc67)s4)sc3c2F)C5(c2ccc(C)cc2)c2ccc(C)cc2)cc1] | −5.20 | −3.49 | 1.71 | 1.46 |

-continued

| No. | Structure | $E_{HOMO}$/ eV | $E_{LUMO}$/ eV | $E_g$/ eV | $S_0$-$S_1$/ eV |
|---|---|---|---|---|---|
| 5 | 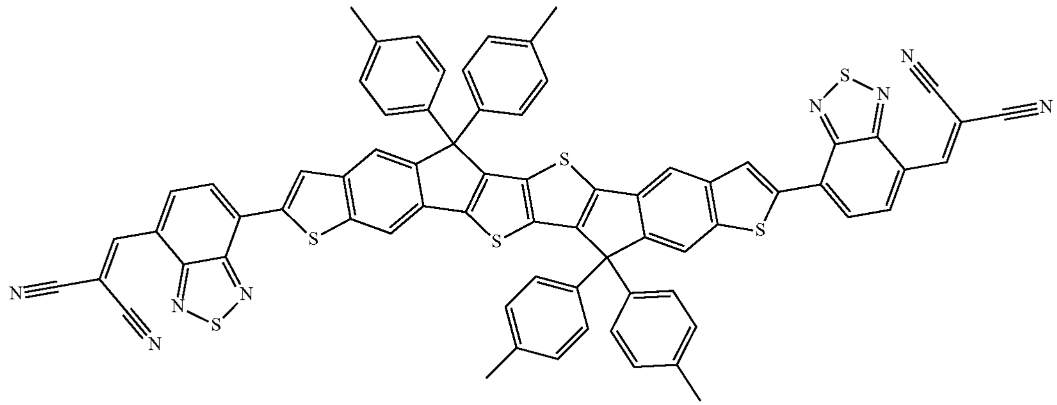 [SMILES: Cc1ccc(C2(c3ccc(C)cc3)c3cc4cc(-c5ccc(C=C(C#N)C#N)c6nsnc56)sc4cc3-c3sc4c5c(sc4c32)-c2cc3cc(-c4ccc(C=C(C#N)C#N)c6nsnc46)sc3cc2C5(c2ccc(C)cc2)c2ccc(C)cc2)cc1] | −5.32 | −3.48 | 1.84 | 1.50 |
| 6 | 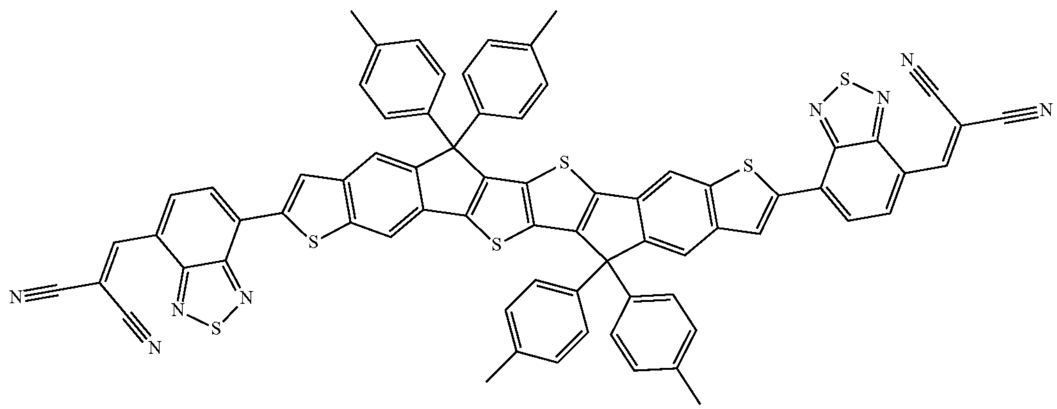 [SMILES: Cc1ccc(C2(c3ccc(C)cc3)c3cc4cc(-c5ccc(C=C(C#N)C#N)c6nsnc56)sc4cc3-c3sc4c5c(sc4c32)-c2cc3sc(-c4ccc(C=C(C#N)C#N)c6nsnc46)cc3cc2C5(c2ccc(C)cc2)c2ccc(C)cc2)cc1] | −5.33 | −3.48 | 1.85 | 1.60 |

| No. | Structure | $E_{HOMO}$/eV | $E_{LUMO}$/eV | $E_g$/eV | $S_0$-$S_1$/eV |
|---|---|---|---|---|---|
| 7 | 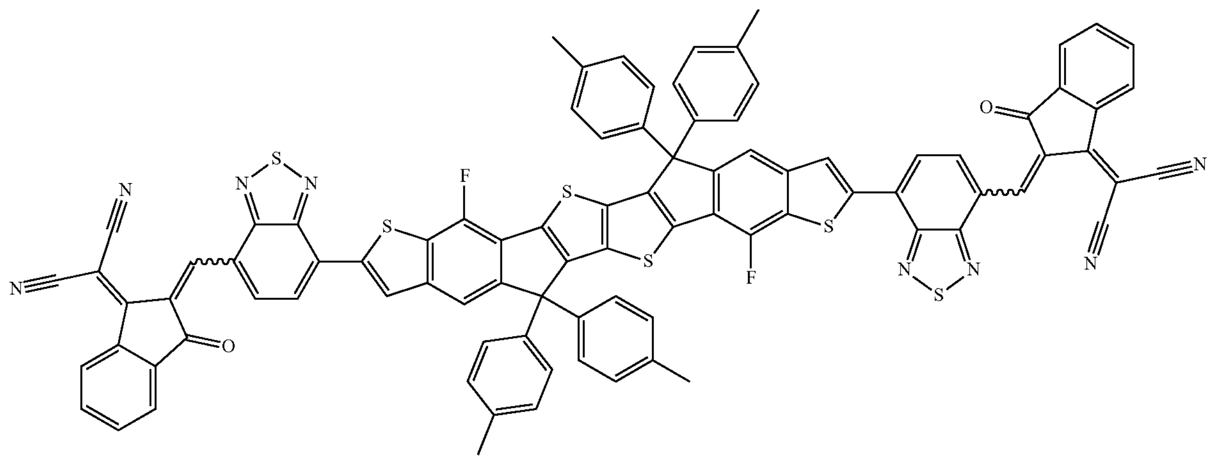 [SMILES: Cc1ccc(C2(c3ccc(C)cc3)c3cc4cc(-c5ccc(C=C6C(=O)c7ccccc7C6=C(C#N)C#N)c6nsnc56)sc4c(F)c3-c3sc4c5c(sc4c32)-c2c(cc3cc(-c4ccc(C=C6C(=O)c7ccccc7C6=C(C#N)C#N)c6nsnc46)sc3c2F)C5(c2ccc(C)cc2)c2ccc(C)cc2)cc1] | −5.17 | −3.47 | 1.70 | 1.47 |
| 8 | 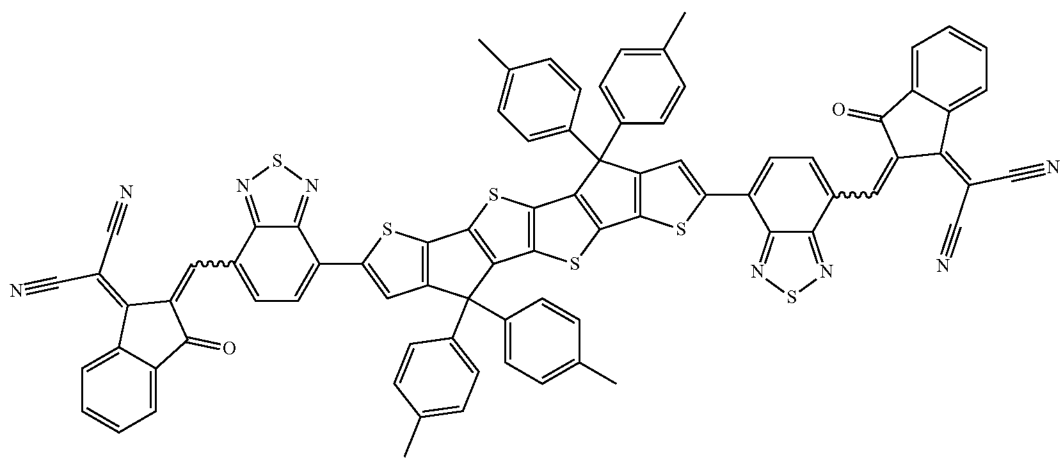 [SMILES: Cc1ccc(C2(c3ccc(C)cc3)c3cc(-c4ccc(C=C5C(=O)c6ccccc6C5=C(C#N)C#N)c5nsnc45)sc3-c3sc4c5c(sc4c32)-c2sc(-c3ccc(C=C4C(=O)c6ccccc6C4=C(C#N)C#N)c4nsnc34)cc2C5(c2ccc(C)cc2)c2ccc(C)cc2)cc1] | −5.08 | −3.47 | 1.61 | 1.49 |

| No. | Structure | $E_{HOMO}$/eV | $E_{LUMO}$/eV | $E_g$/eV | $S_0$-$S_1$/eV |
|---|---|---|---|---|---|
| 9 | 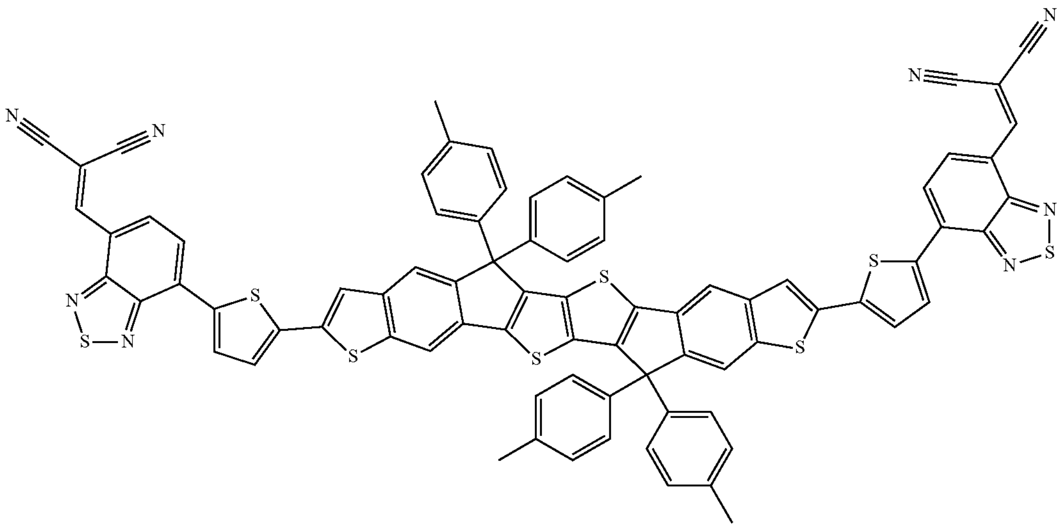 [SMILES: Cc1ccc(C2(c3ccc(C)cc3)c3cc4cc(-c5ccc(-c6ccc(C=C(C#N)C#N)c7nsnc67)s5)sc4cc3-c3sc4c5c(sc4c32)-c2cc3cc(-c4ccc(-c6ccc(C=C(C#N)C#N)c7nsnc67)s4)sc3cc2C5(c2ccc(C)cc2)c2ccc(C)cc2)cc1] | −5.20 | −3.46 | 1.74 | 1.46 |
| 10 | 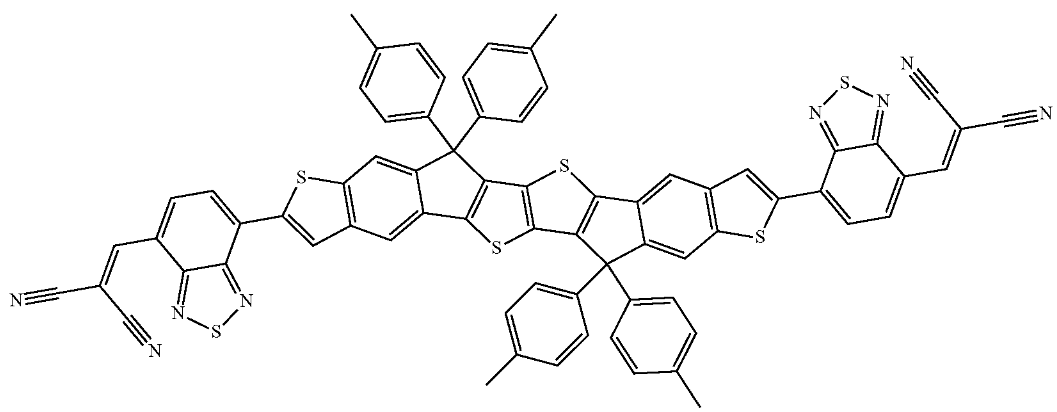 [SMILES: Cc1ccc(C2(c3ccc(C)cc3)c3cc4sc(-c5ccc(C=C(C#N)C#N)c6nsnc56)cc4cc3-c3sc4c5c(sc4c32)-c2cc3cc(-c4ccc(C=C(C#N)C#N)c6nsnc46)sc3cc2C5(c2ccc(C)cc2)c2ccc(C)cc2)cc1] | −5.32 | −3.45 | 1.87 | 1.48 |

-continued

| No. | Structure | $E_{HOMO}$/eV | $E_{LUMO}$/eV | $E_g$/eV | $S_0$-$S_1$/eV |
|---|---|---|---|---|---|
| 11 | 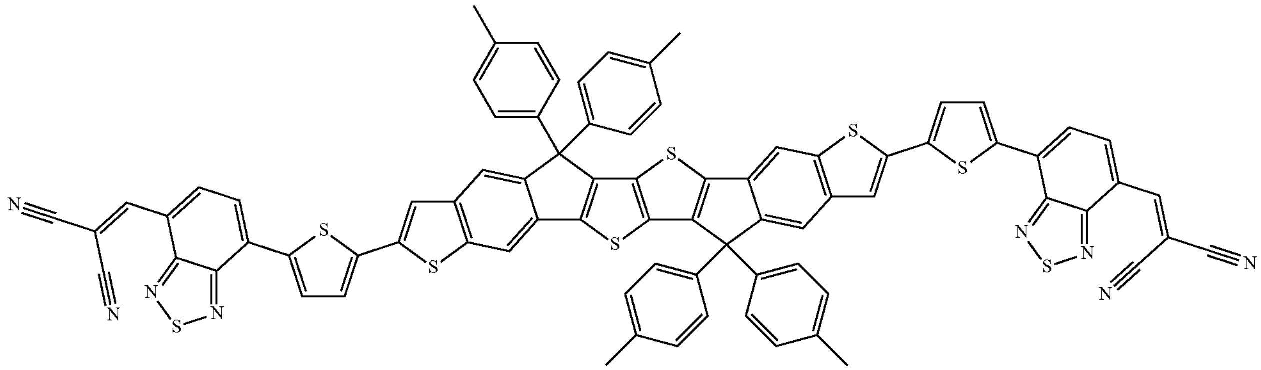 [SMILES: Cc1ccc(C2(c3ccc(C)cc3)c3cc4cc(-c5ccc(-c6ccc(C=C(C#N)C#N)c7nsnc67)s5)sc4cc3-c3sc4c5c(sc4c32)-c2cc3sc(-c4ccc(-c6ccc(C=C(C#N)C#N)c7nsnc67)s4)cc3cc2C5(c2ccc(C)cc2)c2ccc(C)cc2)cc1] | −5.17 | −3.45 | 1.72 | 1.48 |
| 12 | 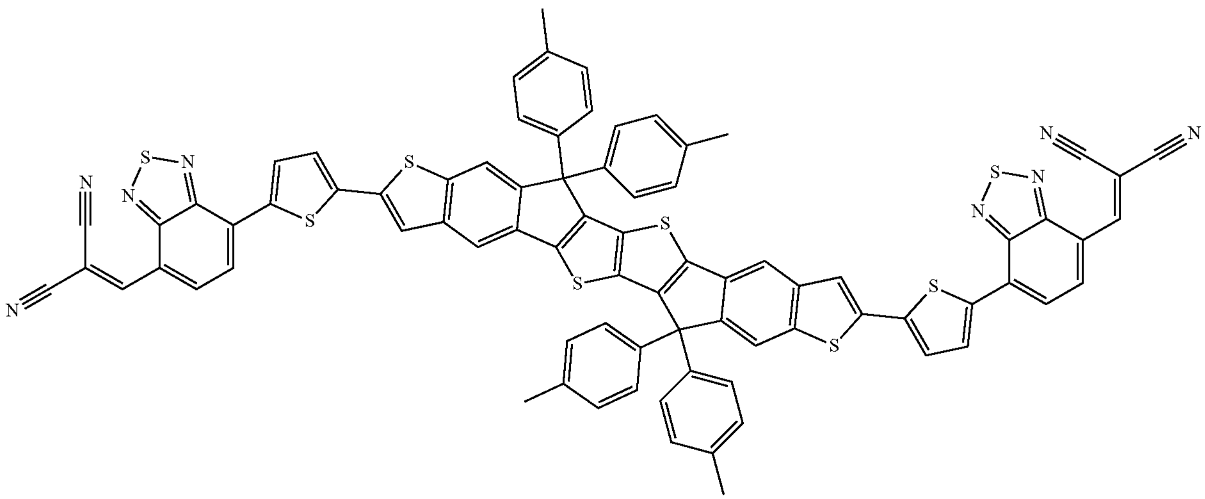 [SMILES: Cc1ccc(C2(c3ccc(C)cc3)c3cc4sc(-c5ccc(-c6ccc(C=C(C#N)C#N)c7nsnc67)s5)cc4cc3-c3sc4c5c(sc4c32)-c2cc3cc(-c4ccc(-c6ccc(C=C(C#N)C#N)c7nsnc67)s4)sc3cc2C5(c2ccc(C)cc2)c2ccc(C)cc2)cc1] | −5.25 | −3.44 | 1.81 | 1.48 |

| No. | Structure | $E_{HOMO}$/ eV | $E_{LUMO}$/ eV | $E_g$/ eV | $S_0$-$S_1$/ eV |
|---|---|---|---|---|---|
| 13 | 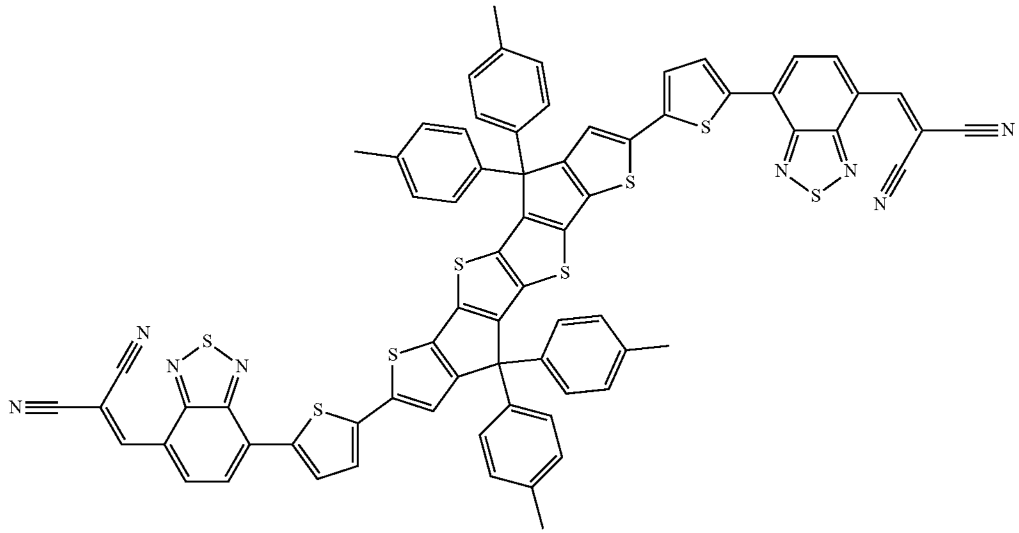 [SMILES: Cc1ccc(C2(c3ccc(C)cc3)c3cc(-c4ccc(-c5ccc(C=C(C#N)C#N)c6nsnc56)s4)sc3-c3sc4c5c(sc4c32)-c2sc(-c3ccc(-c4ccc(C=C(C#N)C#N)c6nsnc46)s3)cc2C5(c2ccc(C)cc2)c2ccc(C)cc2)cc1] | −5.04 | −3.44 | 1.60 | 1.40 |
| 14 | 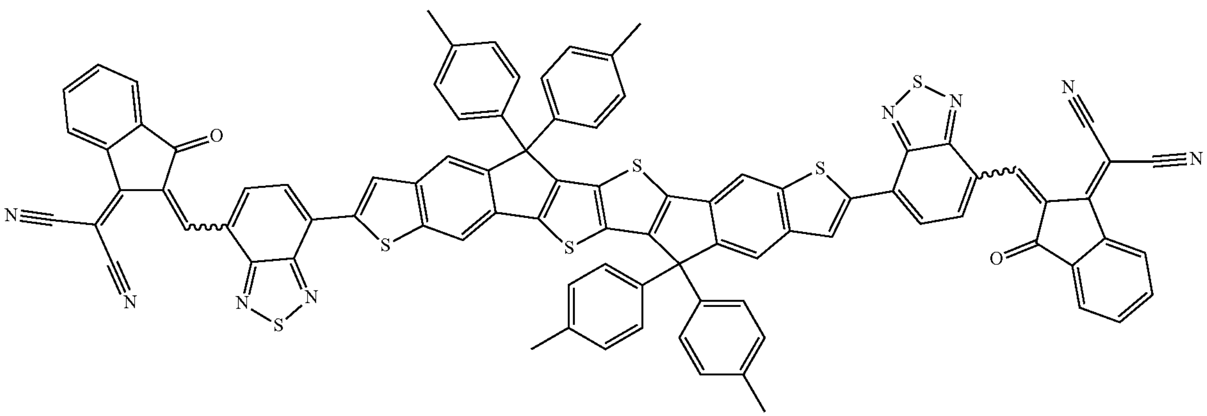 [SMILES: Cc1ccc(C2(c3ccc(C)cc3)c3cc4cc(-c5ccc(C=C6C(=O)c7ccccc7C6=C(C#N)C#N)c6nsnc56)sc4cc3-c3sc4c5c(sc4c32)-c2cc3sc(-c4ccc(C=C6C(=O)c7ccccc7C6=C(C#N)C#N)c6nsnc46)cc3cc2C5(c2ccc(C)cc2)c2ccc(C)cc2)cc1] | −5.15 | −3.43 | 1.72 | 1.52 |

-continued

| No. | Structure | $E_{HOMO}$/ eV | $E_{LUMO}$/ eV | $E_g$/ eV | $S_0$-$S_1$/ eV |
|---|---|---|---|---|---|
| 15 | 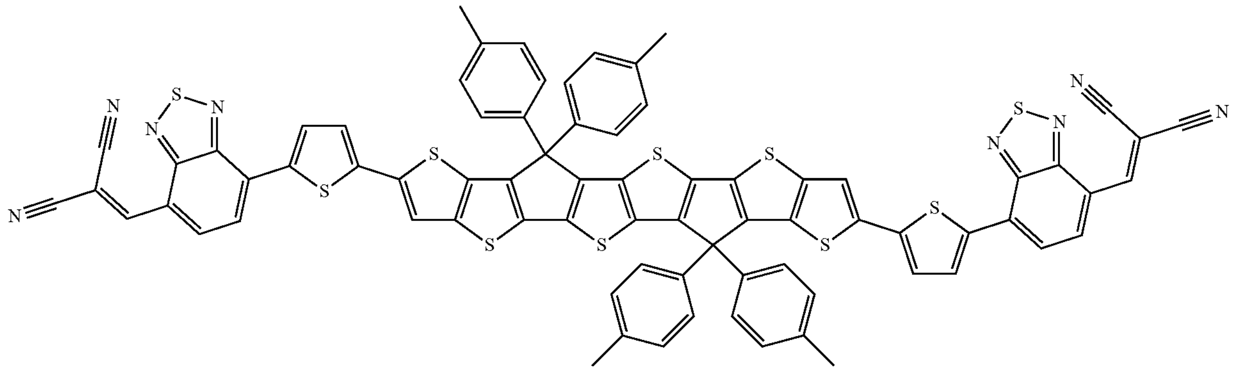 [SMILES: Cc1ccc(C2(c3ccc(C)cc3)c3c(sc4cc(-c5ccc(-c6ccc(C=C(C#N)C#N)c7nsnc67)s5)sc34)-c3sc4c5c(sc4c32)-c2sc3cc(-c4ccc(-c6ccc(C=C(C#N)C#N)c7nsnc67)s4)sc3c2C5(c2ccc(C)cc2)c2ccc(C)cc2)cc1] | −4.97 | −3.43 | 1.54 | 1.30 |
| 16 | 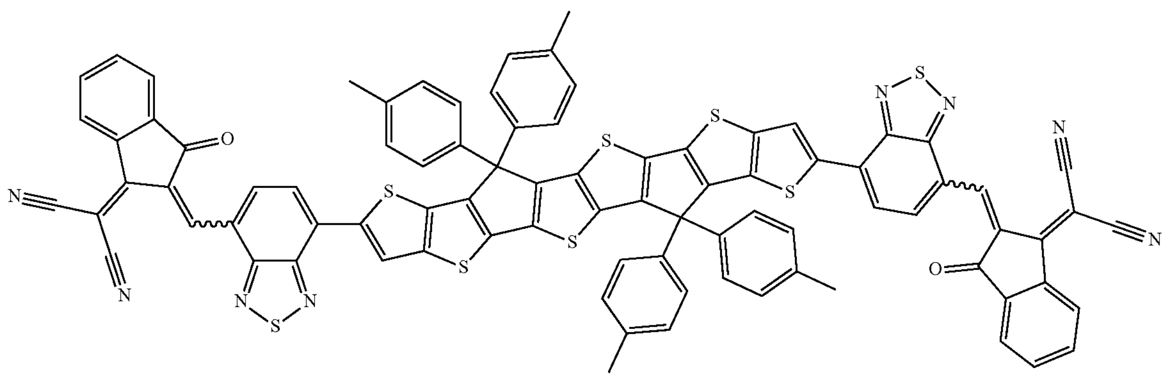 [SMILES: Cc1ccc(C2(c3ccc(C)cc3)c3c(sc4cc(-c5ccc(C=C6C(=O)c7ccccc7C6=C(C#N)C#N)c6nsnc56)sc34)-c3sc4c5c(sc4c32)-c2sc3cc(-c4ccc(C=C6C(=O)c7ccccc7C6=C(C#N)C#N)c6nsnc46)sc3c2C5(c2ccc(C)cc2)c2ccc(C)cc2)cc1] | −4.99 | −3.43 | 1.56 | 1.36 |

-continued
| No. | Structure | $E_{HOMO}/$ eV | $E_{LUMO}/$ eV | $E_g/$ eV | $S_0\text{-}S_1/$ eV |
|---|---|---|---|---|---|
| 17 | 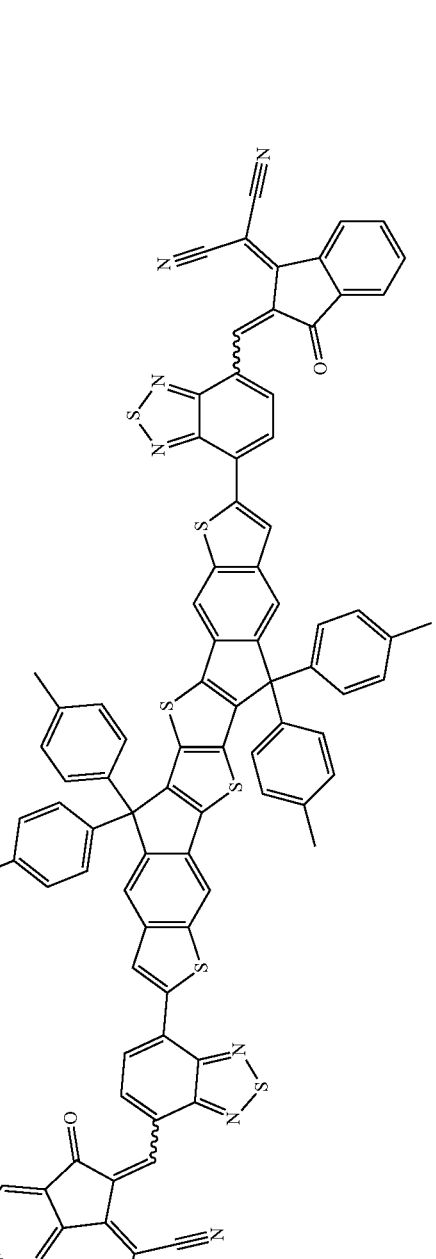 | −5.15 | −3.43 | 1.72 | 1.38 |
| 18 | 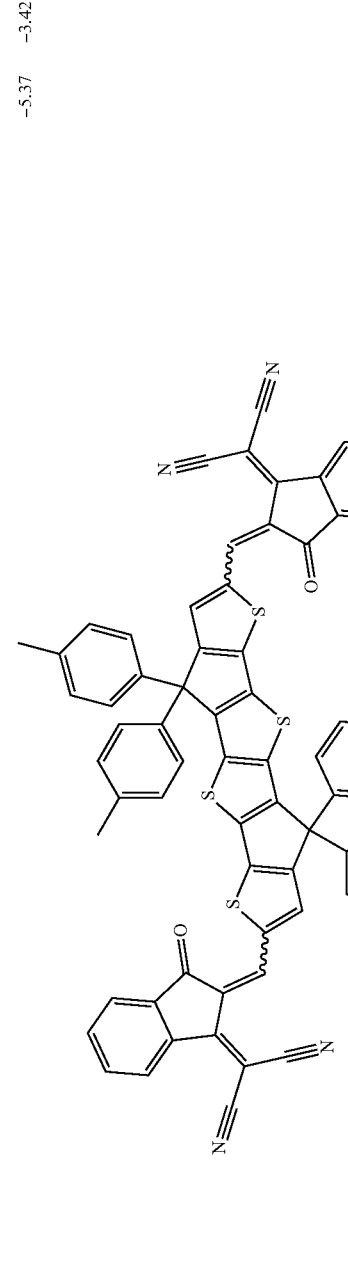 | −5.37 | −3.42 | 1.95 | 1.92 |

-continued

| No. | Structure | $E_{HOMO}$/ eV | $E_{LUMO}$/ eV | $E_g$/ eV | $S_0$-$S_1$/ eV |
|---|---|---|---|---|---|
| 19 | 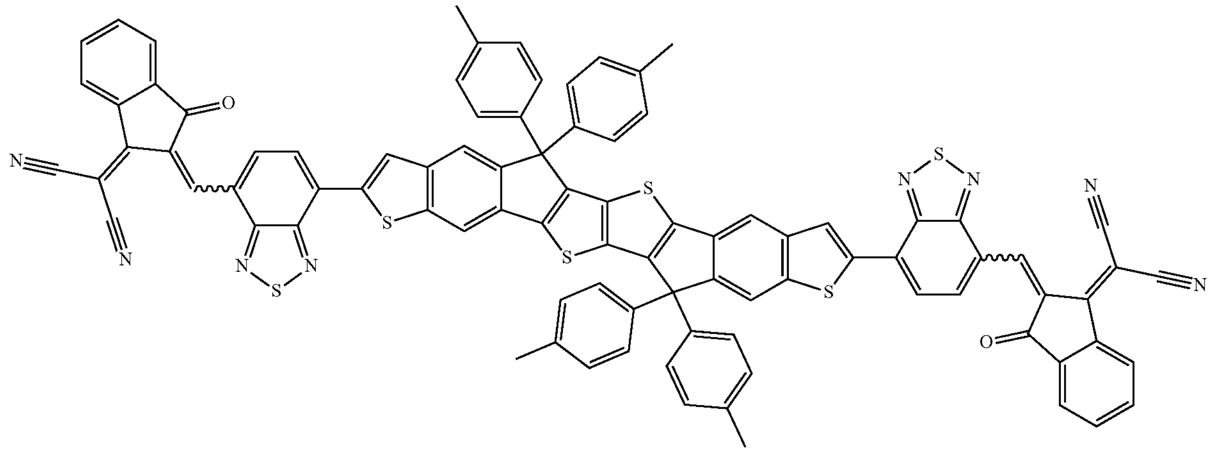 [SMILES: Cc1ccc(C2(c3ccc(C)cc3)c3cc4cc(-c5ccc(C=C6C(=O)c7ccccc7C6=C(C#N)C#N)c6nsnc56)sc4cc3-c3sc4c5c(sc4c32)-c2cc3cc(-c4ccc(C=C6C(=O)c7ccccc7C6=C(C#N)C#N)c6nsnc46)sc3cc2C5(c2ccc(C)cc2)c2ccc(C)cc2)cc1] | −5.16 | −3.41 | 1.75 | 1.46 |
| 20 | 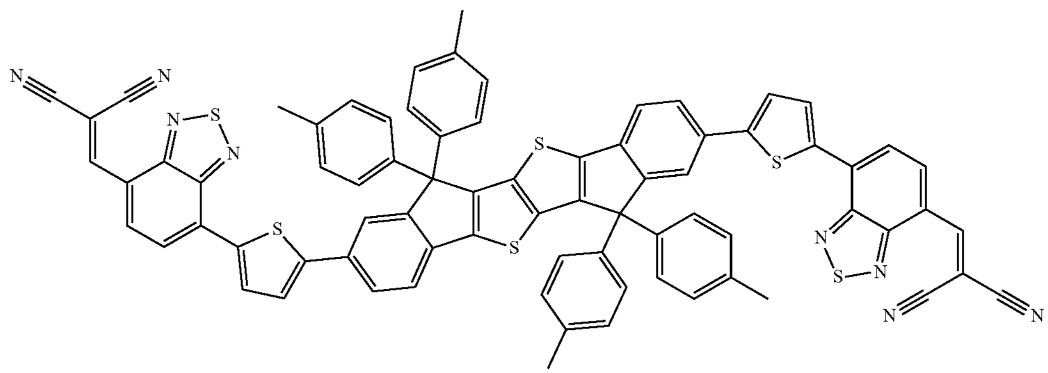 [SMILES: Cc1ccc(C2(c3ccc(C)cc3)c3cc(-c4ccc(-c5ccc(C=C(C#N)C#N)c6nsnc56)s4)ccc3-c3sc4c5c(sc4c32)-c2ccc(-c3ccc(-c4ccc(C=C(C#N)C#N)c6nsnc46)s3)cc2C5(c2ccc(C)cc2)c2ccc(C)cc2)cc1] | −5.27 | −3.40 | 1.87 | 1.57 |

-continued

| No. | Structure | $E_{HOMO}$/eV | $E_{LUMO}$/eV | $E_g$/eV | $S_0\text{-}S_1$/eV |
|---|---|---|---|---|---|
| 21 | 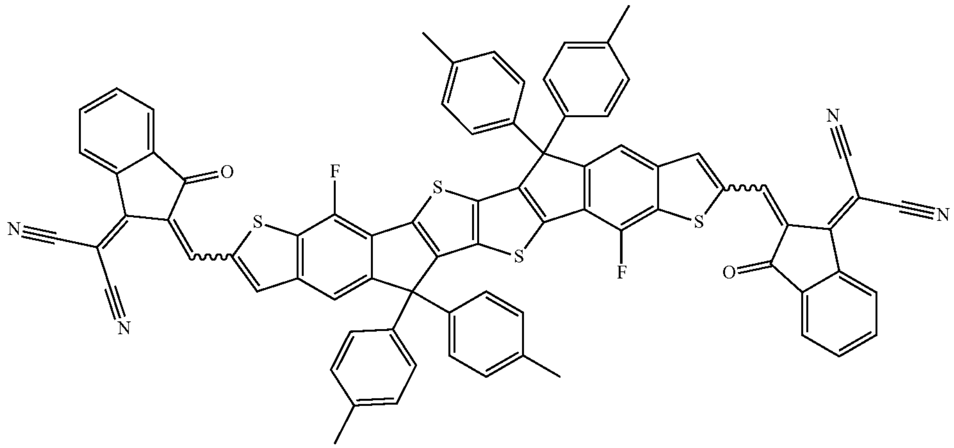 [SMILES: Cc1ccc(C2(c3ccc(C)cc3)c3cc4cc(C=C5C(=O)c6ccccc6C5=C(C#N)C#N)sc4c(F)c3-c3sc4c5c(sc4c32)-c2c(cc3cc(C=C4C(=O)c6ccccc6C4=C(C#N)C#N)sc3c2F)C5(c2ccc(C)cc2)c2ccc(C)cc2)cc1] | −5.37 | −3.39 | 1.98 | 1.64 |
| 22 | 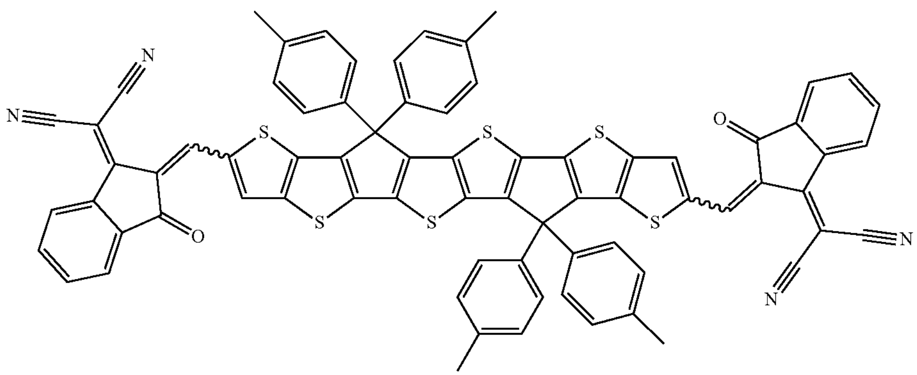 [SMILES: Cc1ccc(C2(c3ccc(C)cc3)c3c(sc4cc(C=C5C(=O)c6ccccc6C5=C(C#N)C#N)sc34)-c3sc4c5c(sc4c32)-c2sc3cc(C=C4C(=O)c6ccccc6C4=C(C#N)C#N)sc3c2C5(c2ccc(C)cc2)c2ccc(C)cc2)cc1] | −5.22 | −3.36 | 1.86 | 1.75 |

-continued
| No. | Structure | $E_{HOMO}$/eV | $E_{LUMO}$/eV | $E_g$/eV | $S_0$-$S_1$/eV |
|---|---|---|---|---|---|
| 23 | 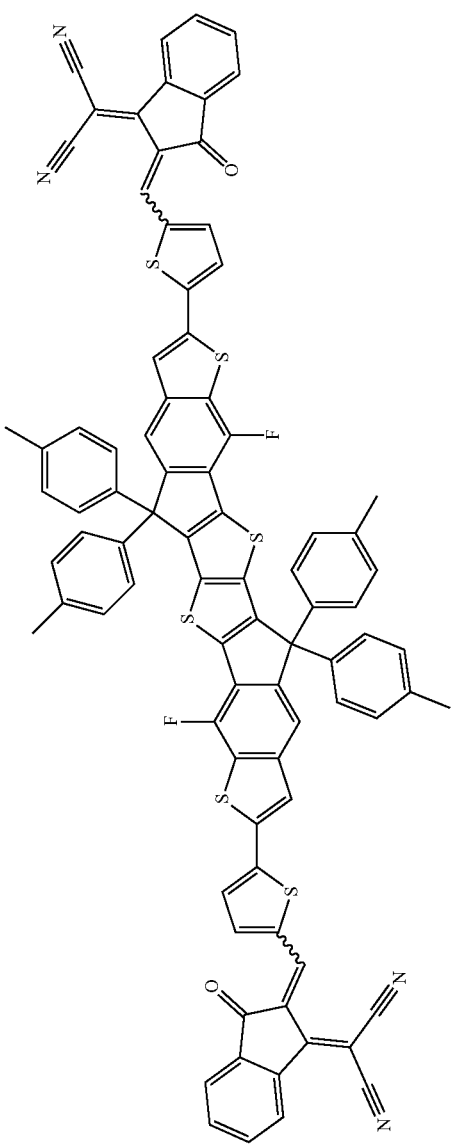 | −5.21 | −3.32 | 1.89 | 1.69 |
| 24 | 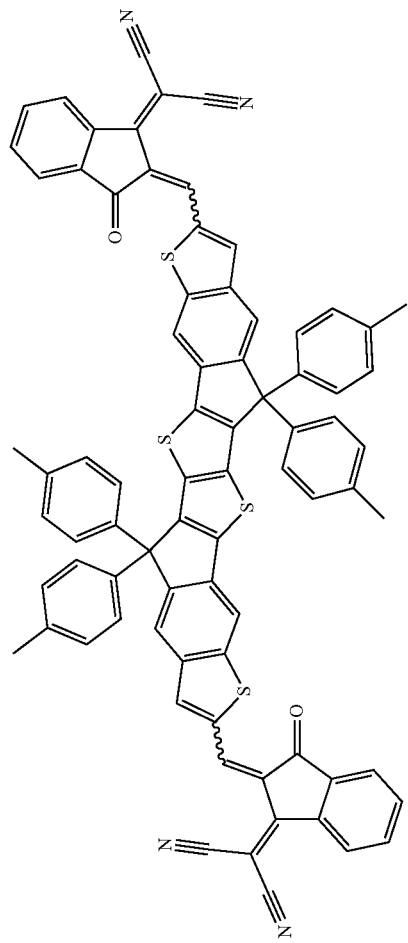 | −5.36 | −3.32 | 2.04 | 1.63 |

-continued

| No. | Structure | $E_{HOMO}$/ eV | $E_{LUMO}$/ eV | $E_g$/ eV | $S_0$-$S_1$/ eV |
|---|---|---|---|---|---|
| 25 | 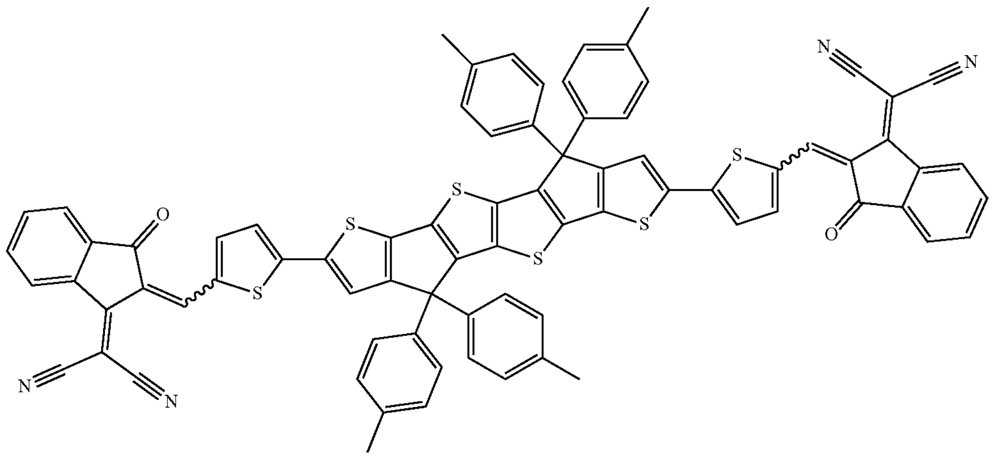 [SMILES: Cc1ccc(C2(c3ccc(C)cc3)c3cc(-c4ccc(C=C5C(=O)c6ccccc6C5=C(C#N)C#N)s4)sc3-c3sc4c5c(sc4c32)-c2sc(-c3ccc(C=C4C(=O)c6ccccc6C4=C(C#N)C#N)s3)cc2C5(c2ccc(C)cc2)c2ccc(C)cc2)cc1] | −5.07 | −3.30 | 1.77 | 1.67 |
| 26 | 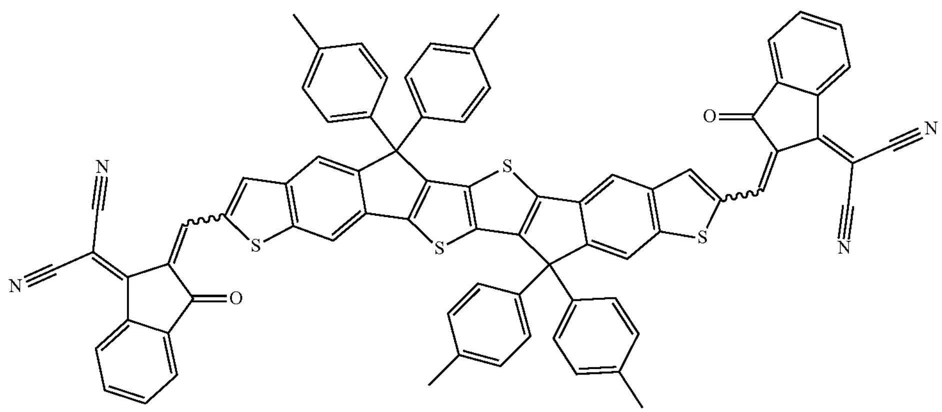 [SMILES: Cc1ccc(C2(c3ccc(C)cc3)c3cc4cc(C=C5C(=O)c6ccccc6C5=C(C#N)C#N)sc4cc3-c3sc4c5c(sc4c32)-c2cc3cc(C=C4C(=O)c6ccccc6C4=C(C#N)C#N)sc3cc2C5(c2ccc(C)cc2)c2ccc(C)cc2)cc1] | −5.34 | −3.29 | 2.05 | 1.81 |

-continued

| No. | Structure | $E_{HOMO}$/ eV | $E_{LUMO}$/ eV | $E_g$/ eV | $S_0$-$S_1$/ eV |
|---|---|---|---|---|---|
| 27 | 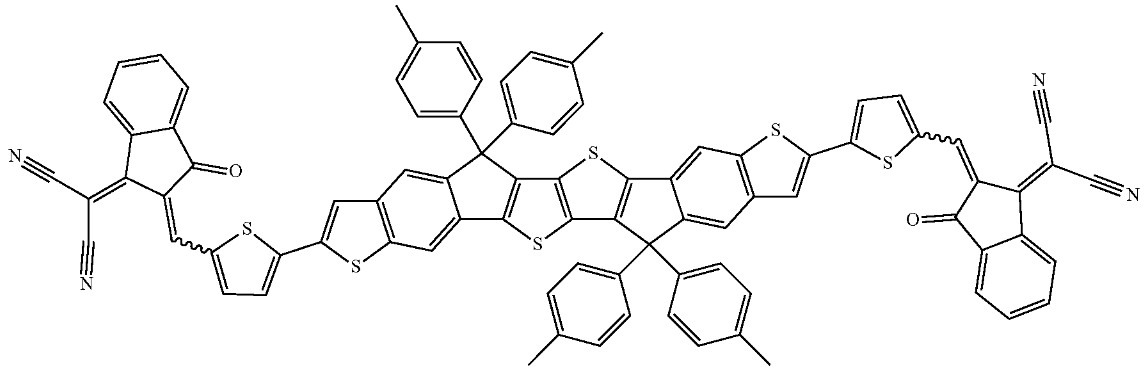 [SMILES: Cc1ccc(C2(c3ccc(C)cc3)c3cc4cc(-c5ccc(C=C6C(=O)c7ccccc7C6=C(C#N)C#N)s5)sc4cc3-c3sc4c5c(sc4c32)-c2cc3sc(-c4ccc(C=C6C(=O)c7ccccc7C6=C(C#N)C#N)s4)cc3cc2C5(c2ccc(C)cc2)c2ccc(C)cc2)cc1] | −5.18 | −3.27 | 1.91 | 1.73 |
| 28 | 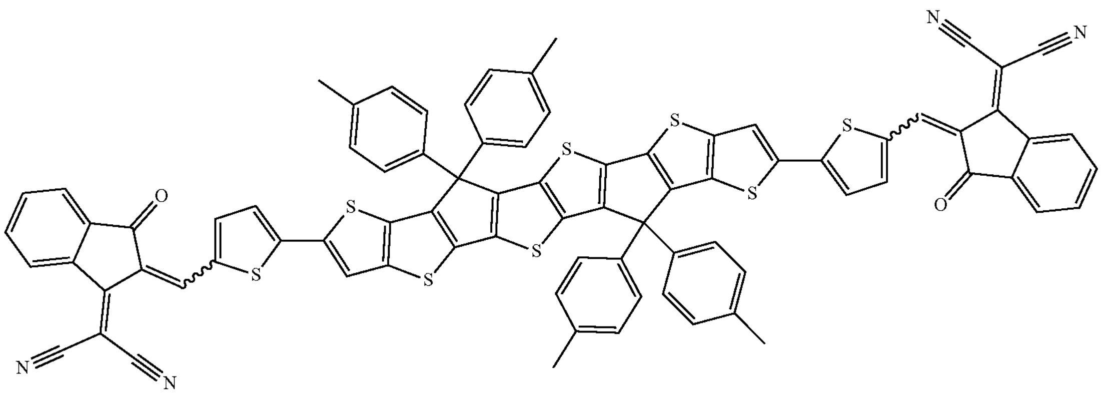 [SMILES: Cc1ccc(C2(c3ccc(C)cc3)c3c(sc4cc(-c5ccc(C=C6C(=O)c7ccccc7C6=C(C#N)C#N)s5)sc34)-c3sc4c5c(sc4c32)-c2sc3cc(-c4ccc(C=C6C(=O)c7ccccc7C6=C(C#N)C#N)s4)sc3c2C5(c2ccc(C)cc2)c2ccc(C)cc2)cc1] | −4.99 | −3.27 | 1.72 | 1.57 |

-continued

| No. | Structure | $E_{HOMO}$/ eV | $E_{LUMO}$/ eV | $E_g$/ eV | $S_0$-$S_1$/ eV |
|---|---|---|---|---|---|
| 29 | 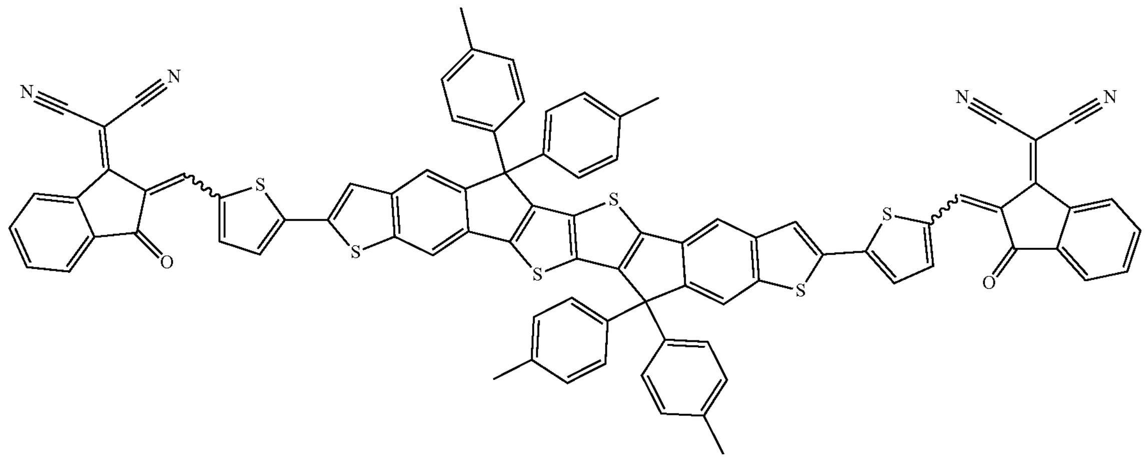 [SMILES: Cc1ccc(C2(c3ccc(C)cc3)c3cc4cc(-c5ccc(C=C6C(=O)c7ccccc7C6=C(C#N)C#N)s5)sc4cc3-c3sc4c5c(sc4c32)-c2cc3cc(-c4ccc(C=C6C(=O)c7ccccc7C6=C(C#N)C#N)s4)sc3cc2C5(c2ccc(C)cc2)c2ccc(C)cc2)cc1] | −5.20 | −3.27 | 1.93 | 1.75 |
| 30 | 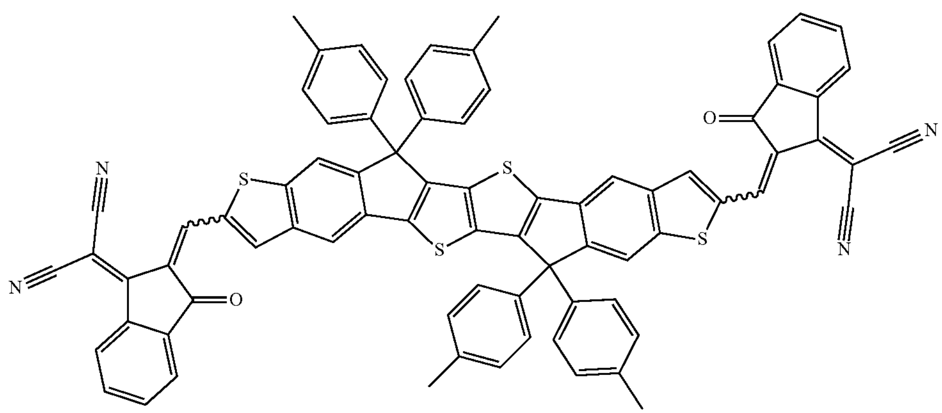 [SMILES: Cc1ccc(C2(c3ccc(C)cc3)c3cc4sc(C=C5C(=O)c6ccccc6C5=C(C#N)C#N)cc4cc3-c3sc4c5c(sc4c32)-c2cc3cc(C=C4C(=O)c6ccccc6C4=C(C#N)C#N)sc3cc2C5(c2ccc(C)cc2)c2ccc(C)cc2)cc1] | −5.31 | −3.25 | 2.06 | 1.5 |

-continued

| No. | Structure | $E_{HOMO}$/eV | $E_{LUMO}$/eV | $E_g$/eV | $S_0$-$S_1$/eV |
|---|---|---|---|---|---|
| 31 | 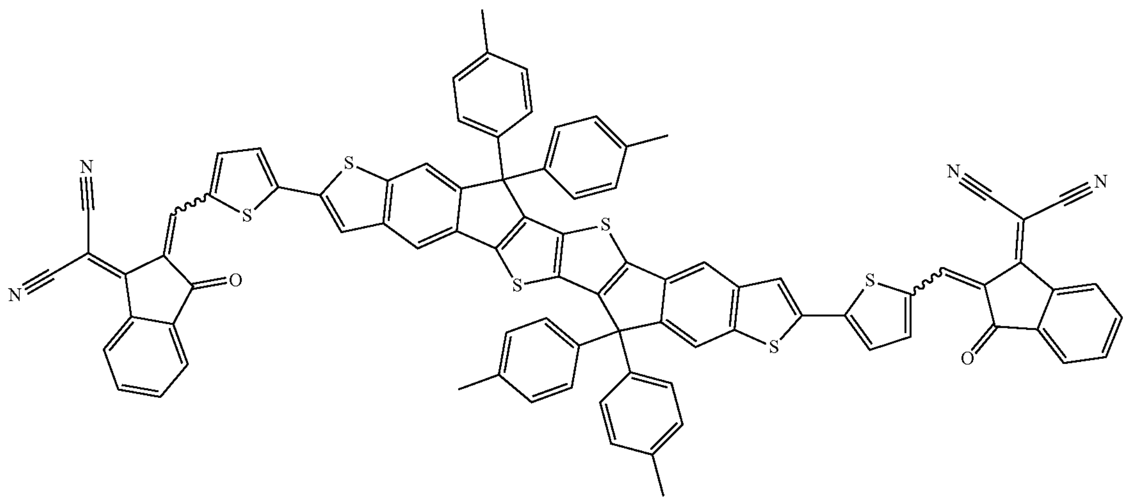 [SMILES: Cc1ccc(C2(c3ccc(C)cc3)c3cc4sc(-c5ccc(C=C6C(=O)c7ccccc7C6=C(C#N)C#N)s5)cc4cc3-c3sc4c5c(sc4c32)-c2cc3cc(-c4ccc(C=C6C(=O)c7ccccc7C6=C(C#N)C#N)s4)sc3cc2C5(c2ccc(C)cc2)c2ccc(C)cc2)cc1] | −5.24 | −3.25 | 1.99 | 1.77 |
| 32 | 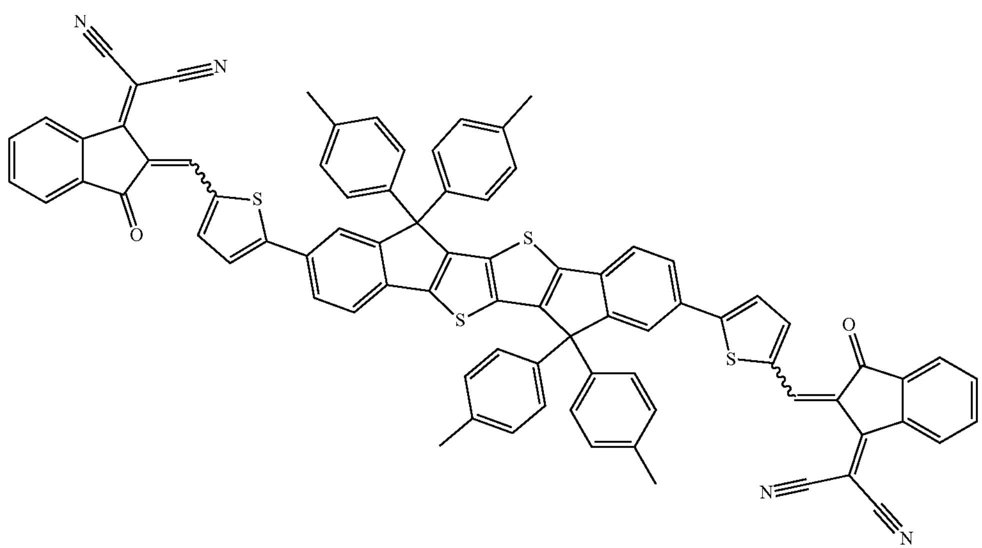 [SMILES: Cc1ccc(C2(c3ccc(C)cc3)c3cc(-c4ccc(C=C5C(=O)c6ccccc6C5=C(C#N)C#N)s4)ccc3-c3sc4c5c(sc4c32)-c2ccc(-c3ccc(C=C4C(=O)c6ccccc6C4=C(C#N)C#N)s3)cc2C5(c2ccc(C)cc2)c2ccc(C)cc2)cc1] | −5.27 | −3.20 | 2.07 | 1.85 |

-continued

| No. | Structure | $E_{HOMO}$/eV | $E_{LUMO}$/eV | $E_g$/eV | $S_0$-$S_1$/eV |
|---|---|---|---|---|---|
| 33 | 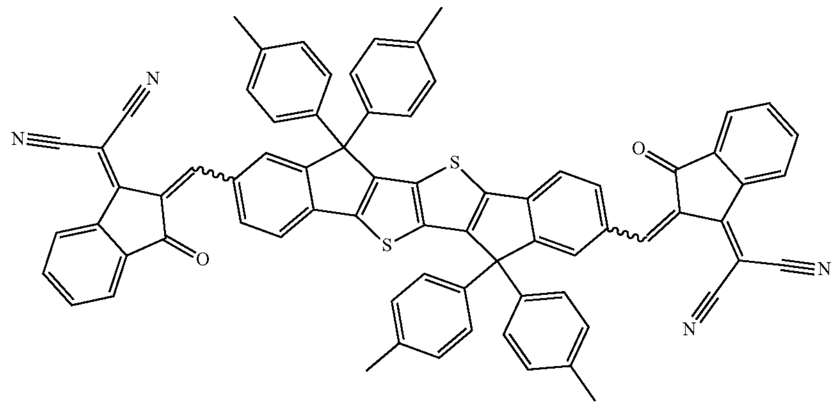 [SMILES: Cc1ccc(C2(c3ccc(C)cc3)c3cc(C=C4C(=O)c5ccccc5C4=C(C#N)C#N)ccc3-c3sc4c5c(sc4c32)-c2ccc(C=C3C(=O)c4ccccc4C3=C(C#N)C#N)cc2C5(c2ccc(C)cc2)c2ccc(C)cc2)cc1] | −5.39 | −3.20 | 2.19 | 1.95 |
| 34 | 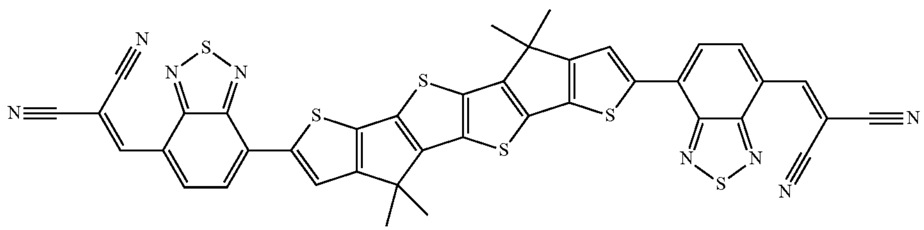 [SMILES: CC1(C)c2cc(-c3ccc(C=C(C#N)C#N)c4nsnc34)sc2-c2sc3c4c(sc3c21)-c1sc(-c2ccc(C=C(C#N)C#N)c3nsnc23)cc1C4(C)C] | −5.36 | −3.60 | 1.76 | 1.65 |
| 35 | 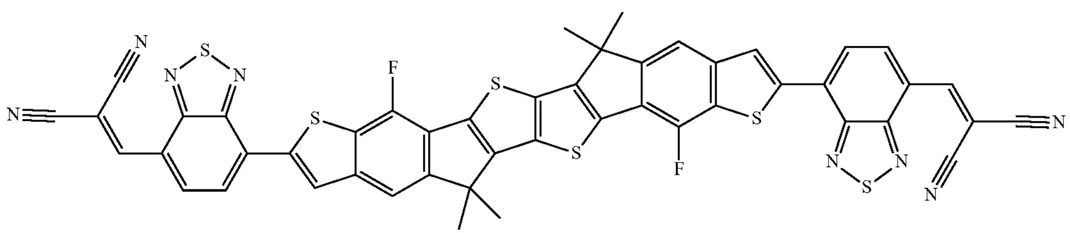 [SMILES: CC1(C)c2cc3cc(-c4ccc(C=C(C#N)C#N)c5nsnc45)sc3c(F)c2-c2sc3c4c(sc3c21)-c1c(cc2cc(-c3ccc(C=C(C#N)C#N)c5nsnc35)sc2c1F)C4(C)C] | −5.43 | −3.58 | 1.85 | 1.61 |

-continued

| No. | Structure | $E_{HOMO}$/eV | $E_{LUMO}$/eV | $E_g$/eV | $S_0$-$S_1$/eV |
|---|---|---|---|---|---|
| 36 | 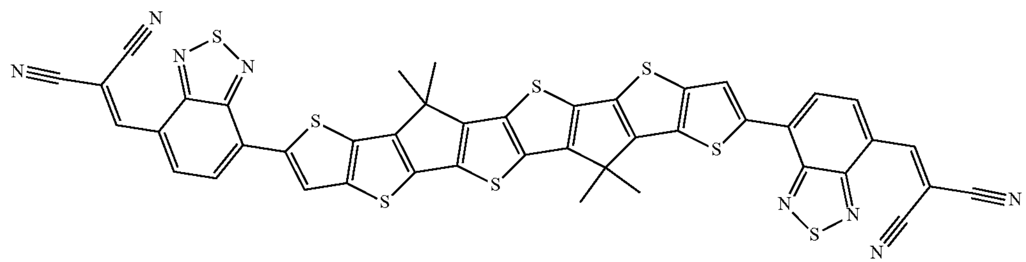 [SMILES: CC1(C)c2c(sc3cc(-c4ccc(C=C(C#N)C#N)c5nsnc45)sc23)-c2sc3c4c(sc3c21)-c1sc2cc(-c3ccc(C=C(C#N)C#N)c5nsnc35)sc2c1C4(C)C] | −5.25 | −3.55 | 1.70 | 1.52 |
| 37 | 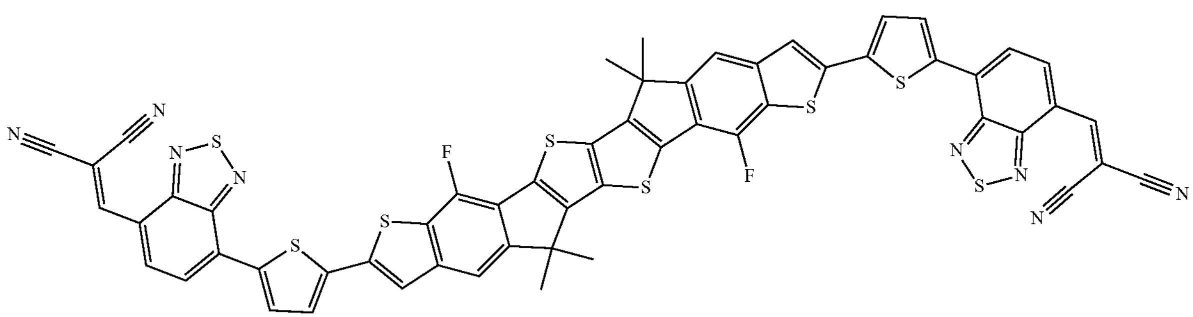 [SMILES: CC1(C)c2cc3cc(-c4ccc(-c5ccc(C=C(C#N)C#N)c6nsnc56)s4)sc3c(F)c2-c2sc3c4c(sc3c21)-c1c(cc2cc(-c3ccc(-c5ccc(C=C(C#N)C#N)c6nsnc56)s3)sc2c1F)C4(C)C] | −5.26 | −3.52 | 1.74 | 1.51 |
| 38 | 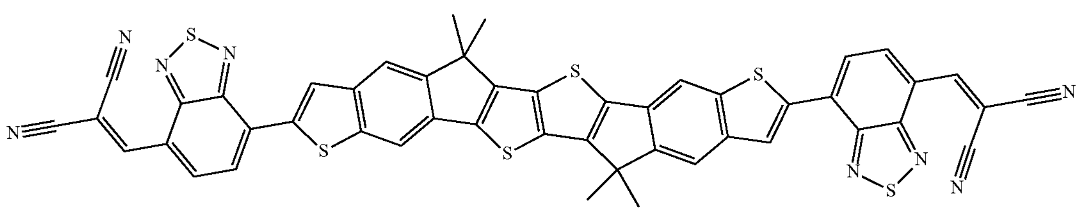 [SMILES: CC1(C)c2cc3cc(-c4ccc(C=C(C#N)C#N)c5nsnc45)sc3cc2-c2sc3c4c(sc3c21)-c1cc2sc(-c3ccc(C=C(C#N)C#N)c5nsnc35)cc2cc1C4(C)C] | −5.40 | −3.52 | 1.88 | 1.65 |

-continued

| No. | Structure | $E_{HOMO}$/eV | $E_{LUMO}$/eV | $E_g$/eV | $S_0$-$S_1$/eV |
|---|---|---|---|---|---|
| 39 | 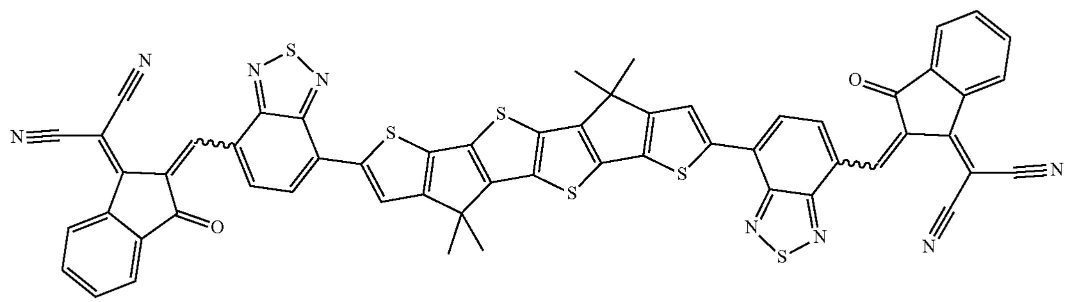 [SMILES: CC1(C)c2cc(-c3ccc(C=C4C(=O)c5ccccc5C4=C(C#N)C#N)c4nsnc34)sc2-c2sc3c4c(sc3c21)-c1sc(-c2ccc(C=C3C(=O)c5ccccc5C3=C(C#N)C#N)c3nsnc23)cc1C4(C)C] | −5.15 | −3.51 | 1.64 | 1.51 |
| 40 | 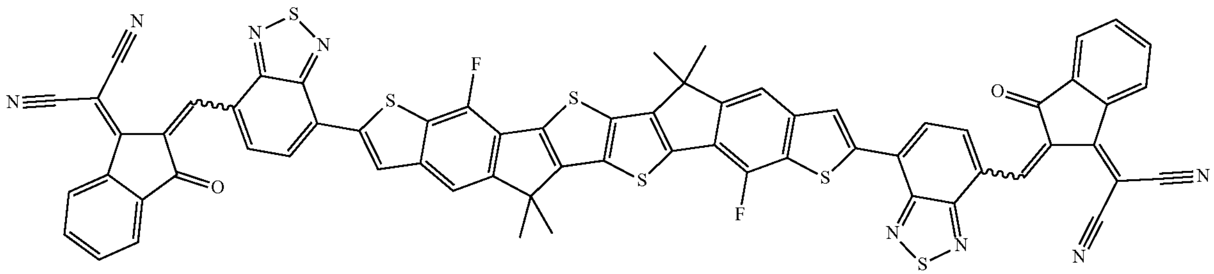 [SMILES: CC1(C)c2cc3cc(-c4ccc(C=C5C(=O)c6ccccc6C5=C(C#N)C#N)c5nsnc45)sc3c(F)c2-c2sc3c4c(sc3c21)-c1c(cc2cc(-c3ccc(C=C5C(=O)c6ccccc6C5=C(C#N)C#N)c5nsnc35)sc2c1F)C4(C)C] | −5.24 | −3.50 | 1.74 | 1.53 |
| 41 | 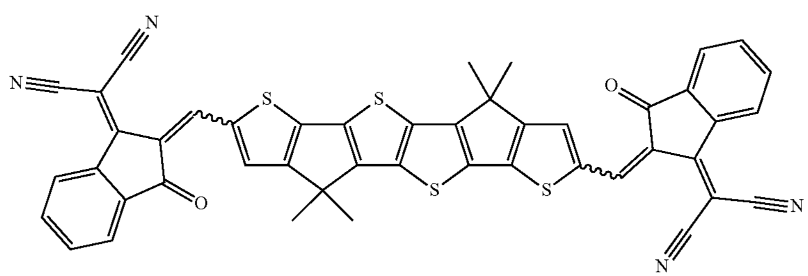 [SMILES: CC1(C)c2cc(C=C3C(=O)c4ccccc4C3=C(C#N)C#N)sc2-c2sc3c4c(sc3c21)-c1sc(C=C2C(=O)c3ccccc3C2=C(C#N)C#N)cc1C4(C)C] | −5.48 | −3.50 | 1.98 | 1.97 |

-continued

| No. | Structure | $E_{HOMO}$/ eV | $E_{LUMO}$/ eV | $E_g$/ eV | $S_0$-$S_1$/ eV |
|---|---|---|---|---|---|
| 42 | 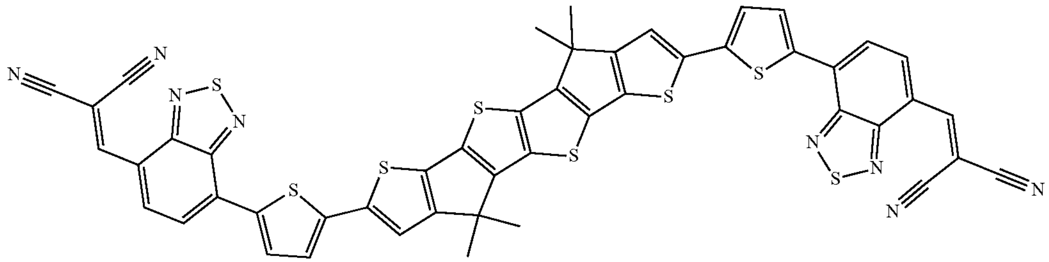 [SMILES: CC1(C)c2cc(-c3ccc(-c4ccc(C=C(C#N)C#N)c5nsnc45)s3)sc2-c2sc3c4c(sc3c21)-c1sc(-c2ccc(-c3ccc(C=C(C#N)C#N)c5nsnc35)s2)cc1C4(C)C] | -5.11 | -3.49 | 1.62 | 1.44 |
| 43 | 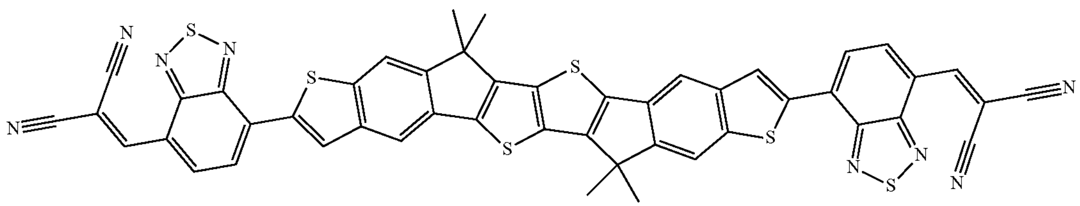 [SMILES: CC1(C)c2cc3sc(-c4ccc(C=C(C#N)C#N)c5nsnc45)cc3cc2-c2sc3c4c(sc3c21)-c1cc2cc(-c3ccc(C=C(C#N)C#N)c5nsnc35)sc2cc1C4(C)C] | -5.40 | -3.49 | 1.91 | 1.55 |
| 44 | 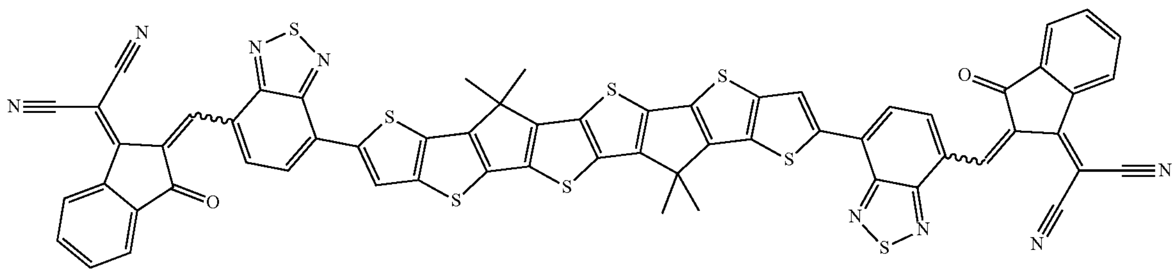 [SMILES: CC1(C)c2c(sc3cc(-c4ccc(C=C5C(=O)c6ccccc6C5=C(C#N)C#N)c5nsnc45)sc23)-c2sc3c4c(sc3c21)-c1sc2cc(-c3ccc(C=C5C(=O)c6ccccc6C5=C(C#N)C#N)c5nsnc35)sc2c1C4(C)C] | -5.06 | -3.48 | 1.58 | 1.39 |
| 45 | 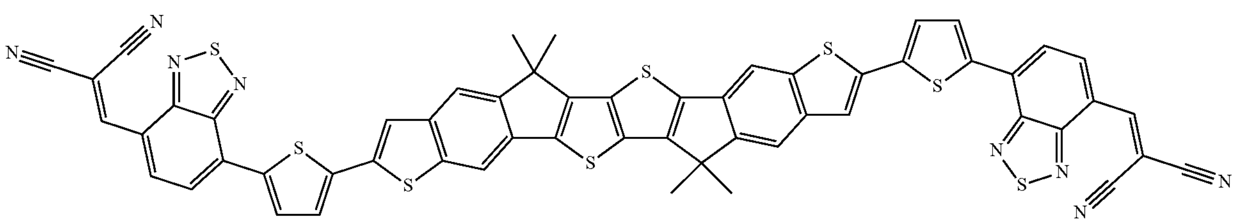 [SMILES: CC1(C)c2cc3cc(-c4ccc(-c5ccc(C=C(C#N)C#N)c6nsnc56)s4)sc3cc2-c2sc3c4c(sc3c21)-c1cc2sc(-c3ccc(-c5ccc(C=C(C#N)C#N)c6nsnc56)s3)cc2cc1C4(C)C] | -5.22 | -3.47 | 1.75 | 1.53 |

-continued

| No. | Structure | $E_{HOMO}/$ eV | $E_{LUMO}/$ eV | $E_g/$ eV | $S_0$-$S_1/$ eV |
|---|---|---|---|---|---|
| 46 | 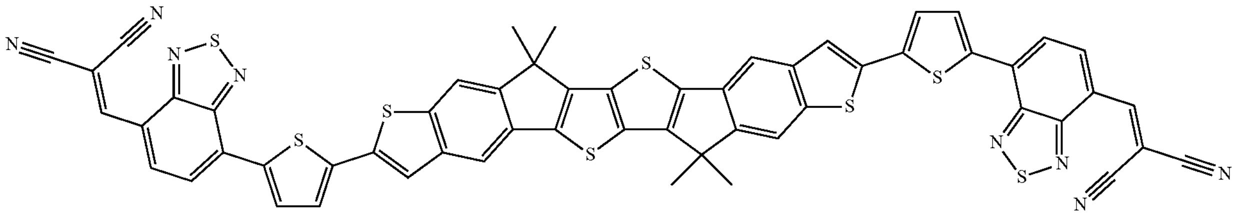 | −5.33 | −3.47 | 1.86 | 1.56 |
| 47 | 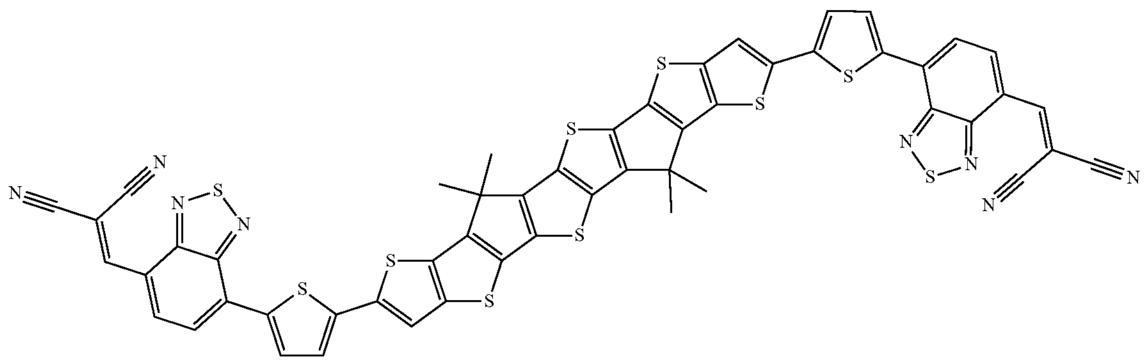 [SMILES: CC1(C)c2c(sc3cc(-c4ccc(-c5ccc(C=C(C#N)C#N)c6nsnc56)s4)sc23)-c2sc3c4c(sc3c21)-c1sc2cc(-c3ccc(-c5ccc(C=C(C#N)C#N)c6nsnc56)s3)sc2c1C4(C)C] | −5.04 | −3.47 | 1.57 | 1.19 |
| 48 | 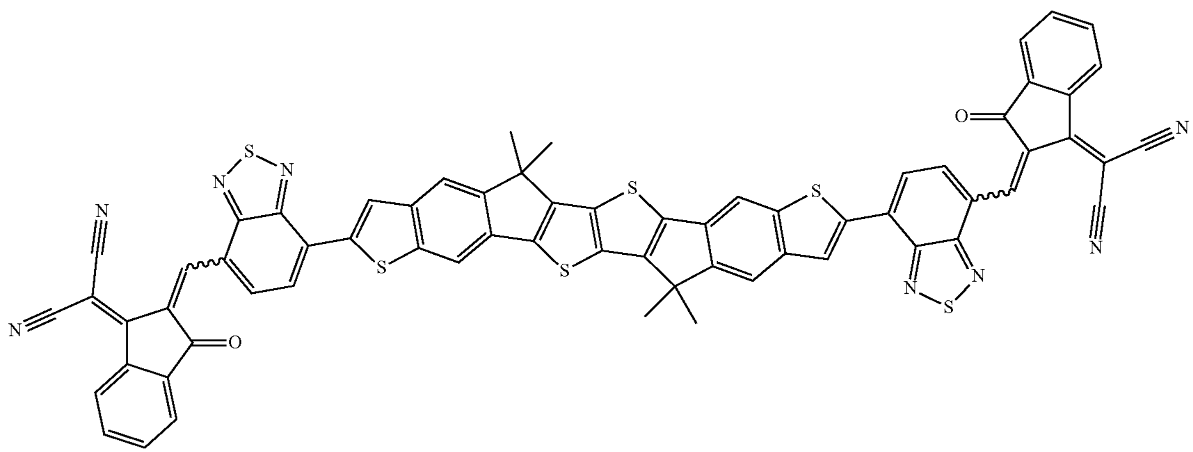 [SMILES: CC1(C)c2cc3cc(-c4ccc(C=C5C(=O)c6ccccc6C5=C(C#N)C#N)c5nsnc45)sc3cc2-c2sc3c4c(sc3c21)-c1cc2sc(-c3ccc(C=C5C(=O)c6ccccc6C5=C(C#N)C#N)c5nsnc35)cc2cc1C4(C)C] | −5.21 | −3.46 | 1.75 | 1.54 |

-continued

| No. | Structure | $E_{HOMO}$/eV | $E_{LUMO}$/eV | $E_g$/eV | $S_0$-$S_1$/eV |
|---|---|---|---|---|---|
| 49 | 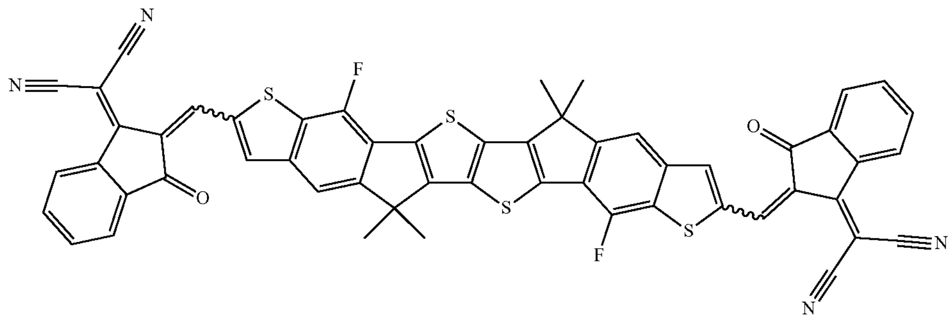 [SMILES: CC1(C)c2cc3cc(C=C4C(=O)c5ccccc5C4=C(C#N)C#N)sc3c(F)c2-c2sc3c4c(sc3c21)-c1c(cc2cc(C=C3C(=O)c5ccccc5C3=C(C#N)C#N)sc2c1F)C4(C)C] | −5.45 | −3.44 | 2.01 | 1.73 |
| 50 | 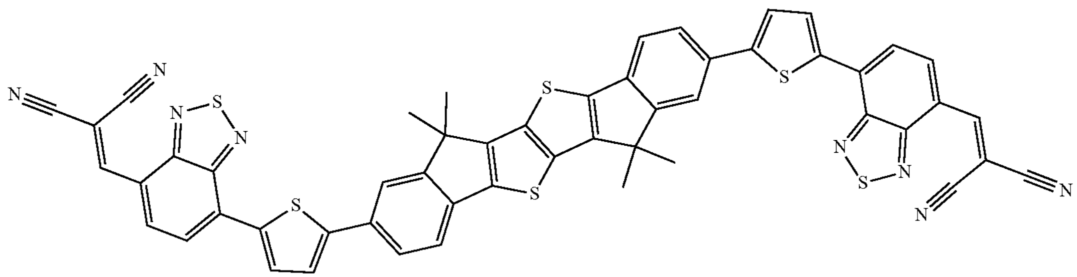 [SMILES: CC1(C)c2cc(-c3ccc(-c4ccc(C=C(C#N)C#N)c5nsnc45)s3)ccc2-c2sc3c4c(sc3c21)-c1ccc(-c2ccc(-c3ccc(C=C(C#N)C#N)c5nsnc35)s2)cc1C4(C)C] | −5.34 | −3.43 | 1.91 | 1.62 |
| 51 | 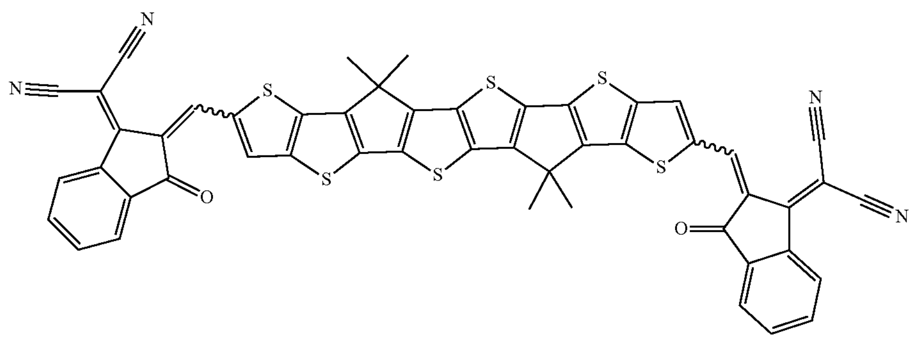 [SMILES: CC1(C)c2c(sc3cc(C=C4C(=O)c5ccccc5C4=C(C#N)C#N)sc23)-c2sc3c4c(sc3c21)-c1sc2cc(C=C3C(=O)c5ccccc5C3=C(C#N)C#N)sc2c1C4(C)C] | −5.33 | −3.43 | 1.90 | 1.80 |

-continued

| No. | Structure | $E_{HOMO}$/eV | $E_{LUMO}$/eV | $E_g$/eV | $S_0$-$S_1$/eV |
|---|---|---|---|---|---|
| 52 | 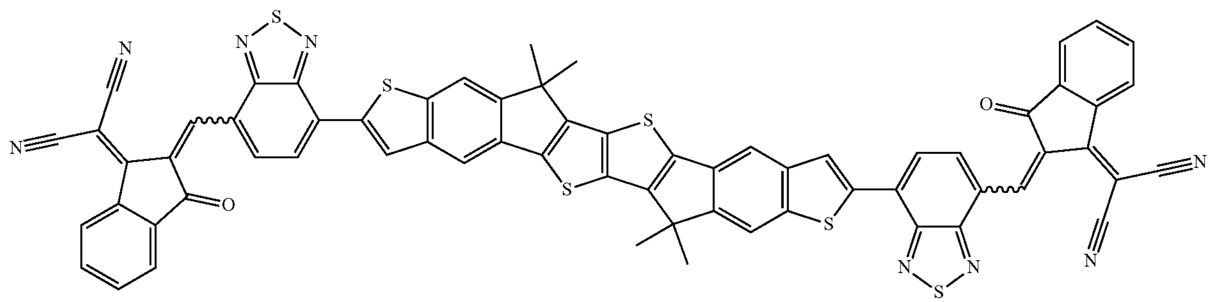 [SMILES: CC1(C)c2cc3sc(-c4ccc(C=C5C(=O)c6ccccc6C5=C(C#N)C#N)c5nsnc45)cc3cc2-c2sc3c4c(sc3c21)-c1cc2cc(-c3ccc(C=C5C(=O)c6ccccc6C5=C(C#N)C#N)c5nsnc35)sc2cc1C4(C)C] | −5.23 | −3.43 | 1.80 | 1.50 |
| 53 | 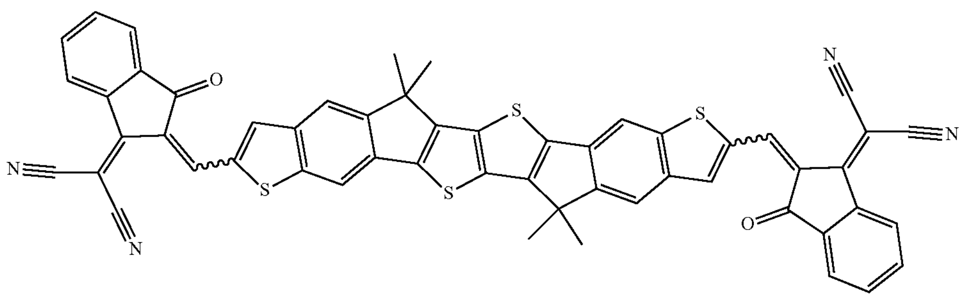 [SMILES: CC1(C)c2cc3cc(C=C4C(=O)c5ccccc5C4=C(C#N)C#N)sc3cc2-c2sc3c4c(sc3c21)-c1cc2sc(C=C3C(=O)c5ccccc5C3=C(C#N)C#N)cc2cc1C4(C)C] | −5.44 | −3.37 | 2.07 | 1.83 |
| 54 | 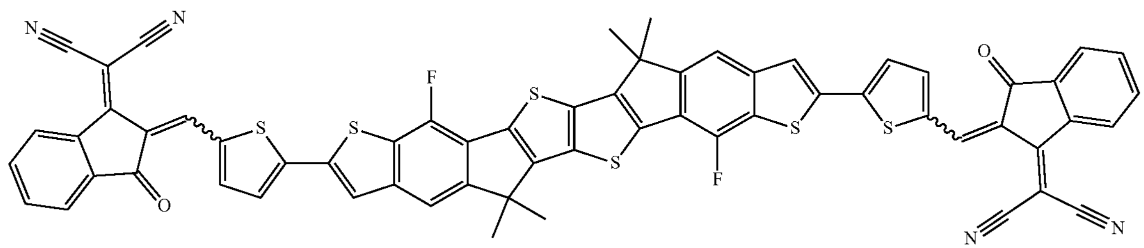 [SMILES: CC1(C)c2cc3cc(-c4ccc(C=C5C(=O)c6ccccc6C5=C(C#N)C#N)s4)sc3c(F)c2-c2sc3c4c(sc3c21)-c1c(cc2cc(-c3ccc(C=C5C(=O)c6ccccc6C5=C(C#N)C#N)s3)sc2c1F)C4(C)C] | −5.27 | −3.35 | 1.92 | 1.79 |

-continued

| No. | Structure | $E_{HOMO}$/eV | $E_{LUMO}$/eV | $E_g$/eV | $S_0$-$S_1$/eV |
|---|---|---|---|---|---|
| 55 | 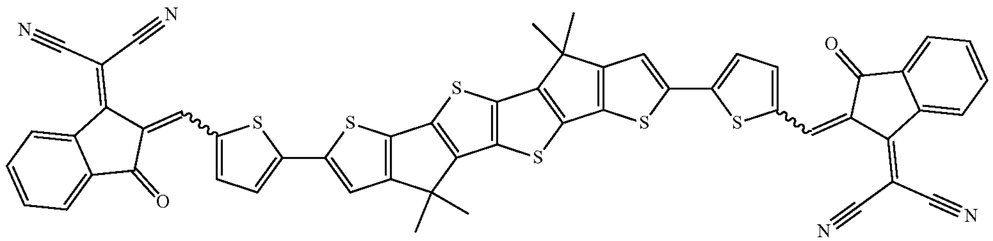 [SMILES: CC1(C)c2cc(-c3ccc(C=C4C(=O)c5ccccc5C4=C(C#N)C#N)s3)sc2-c2sc3c4c(sc3c21)-c1sc(-c2ccc(C=C3C(=O)c5ccccc5C3=C(C#N)C#N)s2)cc1C4(C)C] | −5.15 | −3.35 | 1.80 | 1.70 |
| 56 | 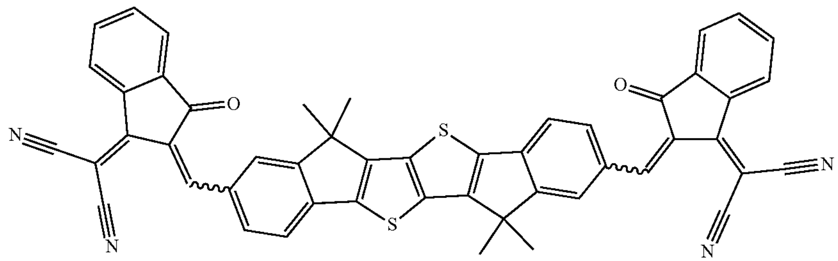 [SMILES: CC1(C)c2cc(C=C3C(=O)c4ccccc4C3=C(C#N)C#N)ccc2-c2sc3c4c(sc3c21)-c1ccc(C=C2C(=O)c3ccccc3C2=C(C#N)C#N)cc1C4(C)C] | −5.56 | −3.34 | 2.22 | 2.02 |
| 57 | 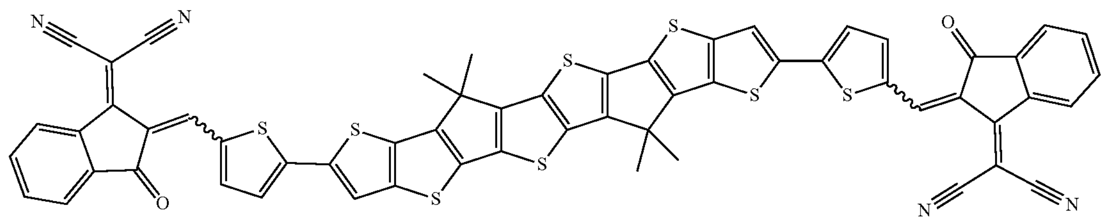 [SMILES: CC1(C)c2c(sc3cc(-c4ccc(C=C5C(=O)c6ccccc6C5=C(C#N)C#N)s4)sc23)-c2sc3c4c(sc3c21)-c1sc2cc(-c3ccc(C=C5C(=O)c6ccccc6C5=C(C#N)C#N)s3)sc2c1C4(C)C] | −5.07 | −3.32 | 1.75 | 1.61 |
| 58 | 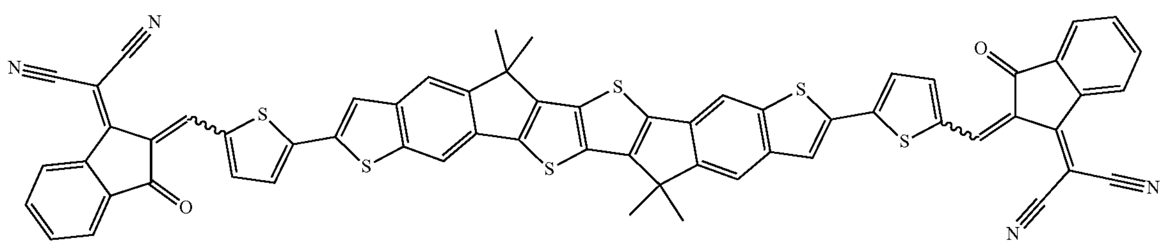 [SMILES: CC1(C)c2cc3cc(-c4ccc(C=C5C(=O)c6ccccc6C5=C(C#N)C#N)s4)sc3cc2-c2sc3c4c(sc3c21)-c1cc2sc(-c3ccc(C=C5C(=O)c6ccccc6C5=C(C#N)C#N)s3)cc2cc1C4(C)C] | −5.24 | −3.30 | 1.94 | 1.81 |

-continued

| No. | Structure | $E_{HOMO}$/eV | $E_{LUMO}$/eV | $E_g$/eV | $S_0$-$S_1$/eV |
|---|---|---|---|---|---|
| 59 | 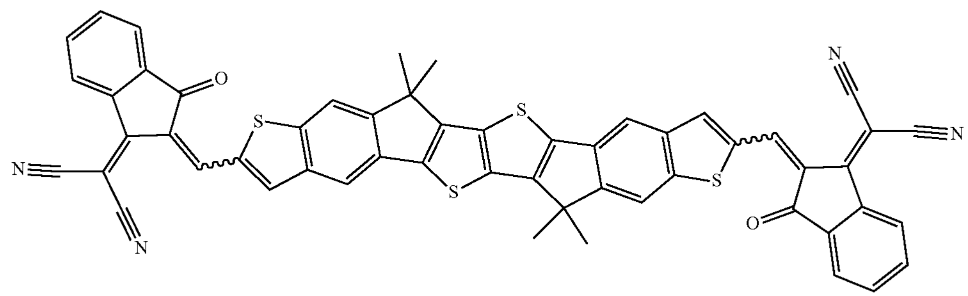 [SMILES: CC1(C)c2cc3sc(C=C4C(=O)c5ccccc5C4=C(C#N)C#N)cc3cc2-c2sc3c4c(sc3c21)-c1cc2cc(C=C3C(=O)c5ccccc5C3=C(C#N)C#N)sc2cc1C4(C)C] | −5.39 | −3.29 | 2.10 | 1.85 |
| 60 | 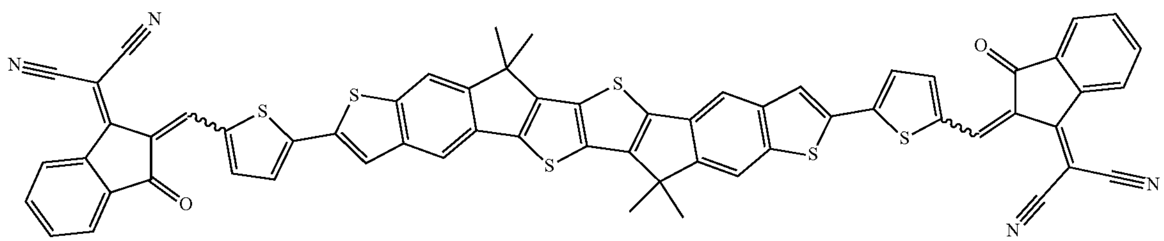 [SMILES: CC1(C)c2cc3sc(-c4ccc(C=C5C(=O)c6ccccc6C5=C(C#N)C#N)s4)cc3cc2-c2sc3c4c(sc3c21)-c1cc2cc(-c3ccc(C=C5C(=O)c6ccccc6C5=C(C#N)C#N)s3)sc2cc1C4(C)C] | −5.31 | −3.27 | 2.04 | 1.85 |
| 61 | 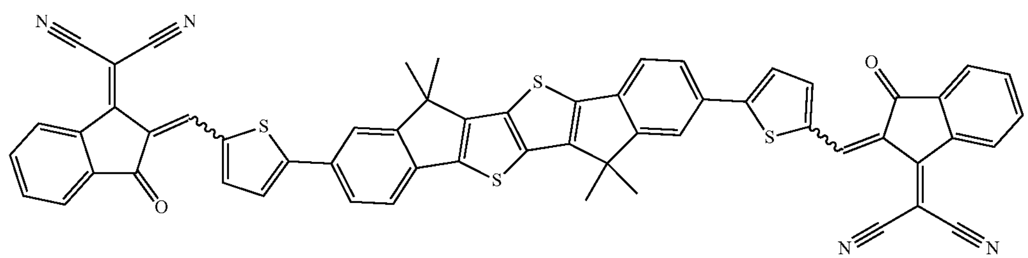 [SMILES: CC1(C)c2cc(-c3ccc(C=C4C(=O)c5ccccc5C4=C(C#N)C#N)s3)ccc2-c2sc3c4c(sc3c21)-c1ccc(-c2ccc(C=C3C(=O)c5ccccc5C3=C(C#N)C#N)s2)cc1C4(C)C] | −5.34 | −3.24 | 2.10 | 1.89 |

-continued

| No. | Structure | $E_{HOMO}$/ eV | $E_{LUMO}$/ eV | $E_g$/ eV | $S_0$-$S_1$/ eV |
|---|---|---|---|---|---|
| 62 | 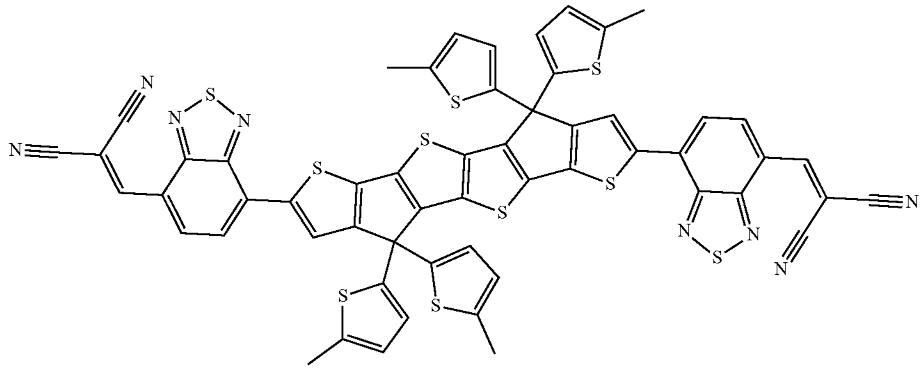 [SMILES: Cc1ccc(C2(c3ccc(C)s3)c3cc(-c4ccc(C=C(C#N)C#N)c5nsnc45)sc3-c3sc4c5c(sc4c32)-c2sc(-c3ccc(C=C(C#N)C#N)c4nsnc34)cc2C5(c2ccc(C)s2)c2ccc(C)s2)s1] | −5.31 | −3.55 | 1.76 | 1.63 |
| 63 | 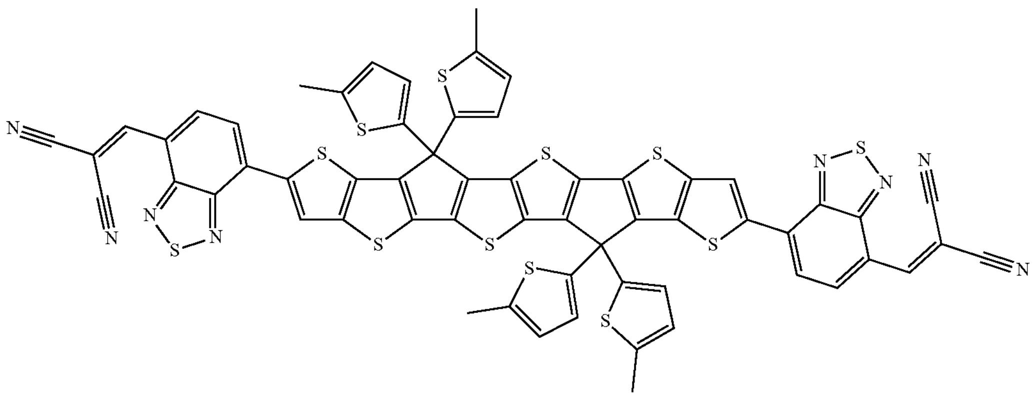 [SMILES: Cc1ccc(C2(c3ccc(C)s3)c3c(sc4cc(-c5ccc(C=C(C#N)C#N)c6nsnc56)sc34)-c3sc4c5c(sc4c32)-c2sc3cc(-c4ccc(C=C(C#N)C#N)c6nsnc46)sc3c2C5(c2ccc(C)s2)c2ccc(C)s2)s1] | −5.18 | −3.50 | 1.68 | 1.48 |

-continued

| No. | Structure | $E_{HOMO}$/ eV | $E_{LUMO}$/ eV | $E_g$/ eV | $S_0$-$S_1$/ eV |
|---|---|---|---|---|---|
| 64 | 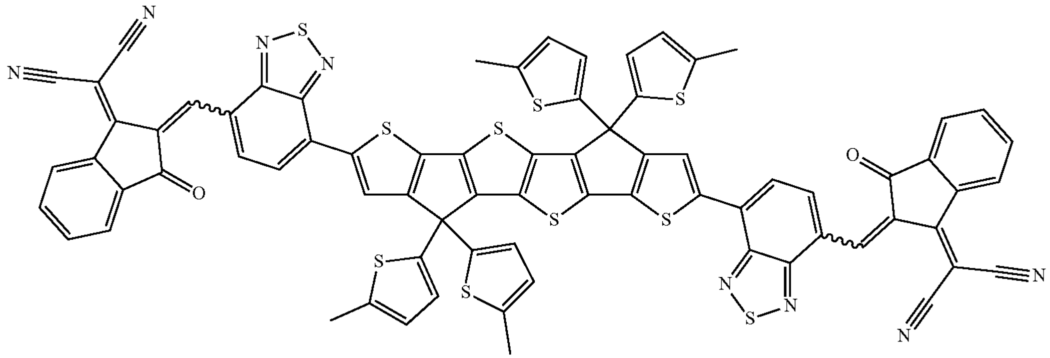 [SMILES: Cc1ccc(C2(c3ccc(C)s3)c3cc(-c4ccc(C=C5C(=O)c6ccccc6C5=C(C#N)C#N)c5nsnc45)sc3-c3sc4c5c(sc4c32)-c2sc(-c3ccc(C=C4C(=O)c6ccccc6C4=C(C#N)C#N)c4nsnc34)cc2C5(c2ccc(C)s2)c2ccc(C)s2)s1] | −5.10 | −3.48 | 1.62 | 1.48 |
| 65 | 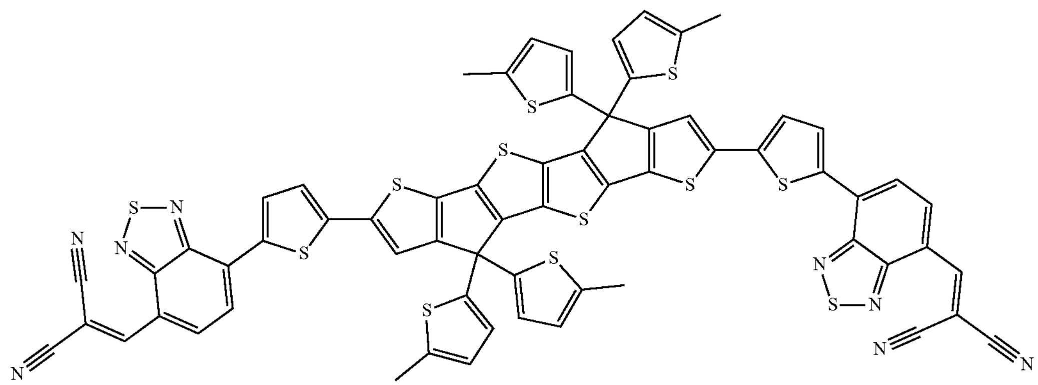 [SMILES: Cc1ccc(C2(c3ccc(C)s3)c3cc(-c4ccc(-c5ccc(C=C(C#N)C#N)c6nsnc56)s4)sc3-c3sc4c5c(sc4c32)-c2sc(-c3ccc(-c4ccc(C=C(C#N)C#N)c6nsnc46)s3)cc2C5(c2ccc(C)s2)c2ccc(C)s2)s1] | −5.07 | −3.46 | 1.61 | 1.42 |

| No. | Structure | $E_{HOMO}$/eV | $E_{LUMO}$/eV | $E_g$/eV | $S_0$-$S_1$/eV |
|---|---|---|---|---|---|
| 66 | 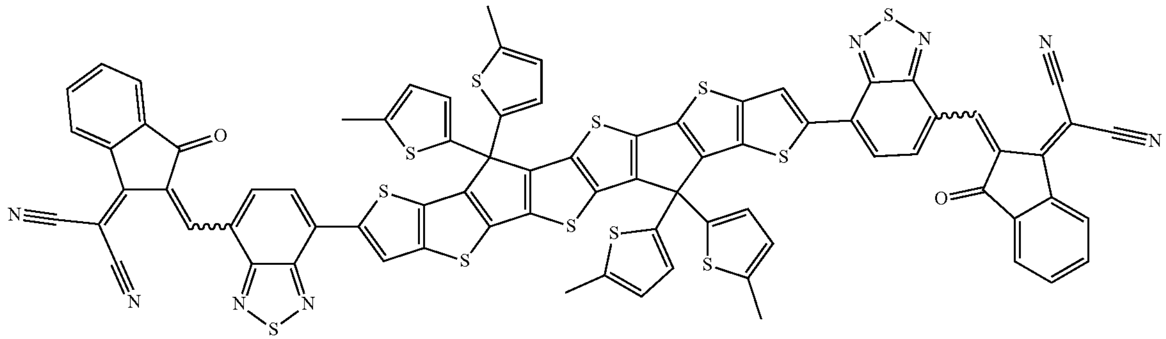 [SMILES: Cc1ccc(C2(c3ccc(C)s3)c3c(sc4cc(-c5ccc(C=C6C(=O)c7ccccc7C6=C(C#N)C#N)c6nsnc56)sc34)-c3sc4c5c(sc4c32)-c2sc3cc(-c4ccc(C=C6C(=O)c7ccccc7C6=C(C#N)C#N)c6nsnc46)sc3c2C5(c2ccc(C)s2)c2ccc(C)s2)s1] | −5.00 | −3.43 | 1.57 | 1.39 |
| 67 | 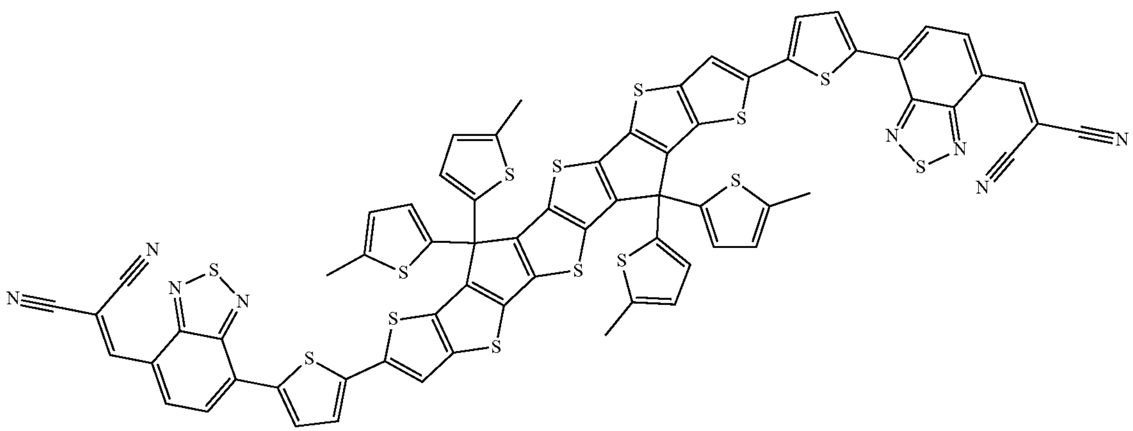 [SMILES: Cc1ccc(C2(c3ccc(C)s3)c3c(sc4cc(-c5ccc(-c6ccc(C=C(C#N)C#N)c7nsnc67)s5)sc34)-c3sc4c5c(sc4c32)-c2sc3cc(-c4ccc(-c6ccc(C=C(C#N)C#N)c7nsnc67)s4)sc3c2C5(c2ccc(C)s2)c2ccc(C)s2)s1] | −4.99 | −3.43 | 1.56 | 1.32 |

-continued

| No. | Structure | $E_{HOMO}$/ eV | $E_{LUMO}$/ eV | $E_g$/ eV | $S_0$-$S_1$/ eV |
|---|---|---|---|---|---|
| 68 | 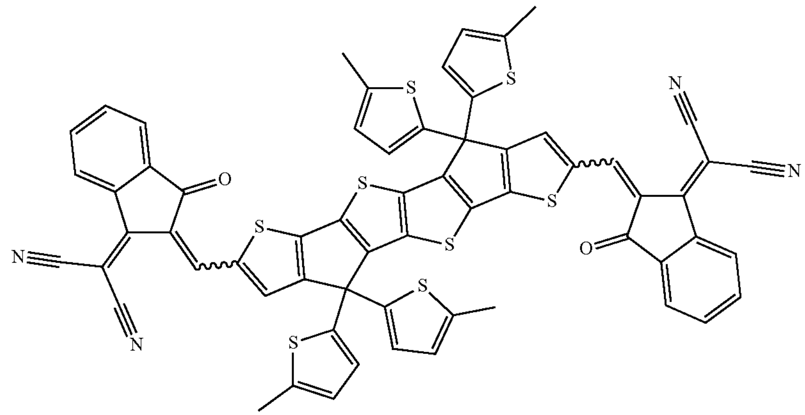 [SMILES: Cc1ccc(C2(c3ccc(C)s3)c3cc(C=C4C(=O)c5ccccc5C4=C(C#N)C#N)sc3-c3sc4c5c(sc4c32)-c2sc(C=C3C(=O)c4ccccc4C3=C(C#N)C#N)cc2C5(c2ccc(C)s2)c2ccc(C)s2)s1] | −5.39 | −3.42 | 1.97 | 1.84 |
| 69 | 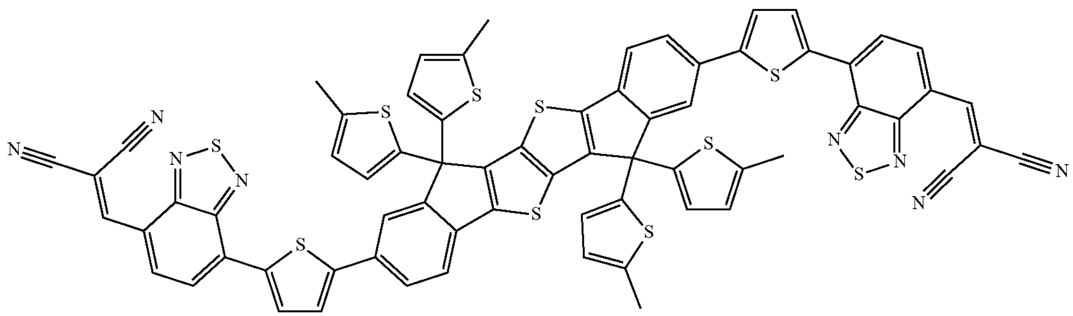 [SMILES: Cc1ccc(C2(c3ccc(C)s3)c3cc(-c4ccc(-c5ccc(C=C(C#N)C#N)c6nsnc56)s4)ccc3-c3sc4c5c(sc4c32)-c2ccc(-c3ccc(-c4ccc(C=C(C#N)C#N)c6nsnc46)s3)cc2C5(c2ccc(C)s2)c2ccc(C)s2)s1] | −5.29 | −3.40 | 1.89 | 1.59 |

-continued

| No. | Structure | $E_{HOMO}$/eV | $E_{LUMO}$/eV | $E_g$/eV | $S_0$-$S_1$/eV |
|---|---|---|---|---|---|
| 70 | 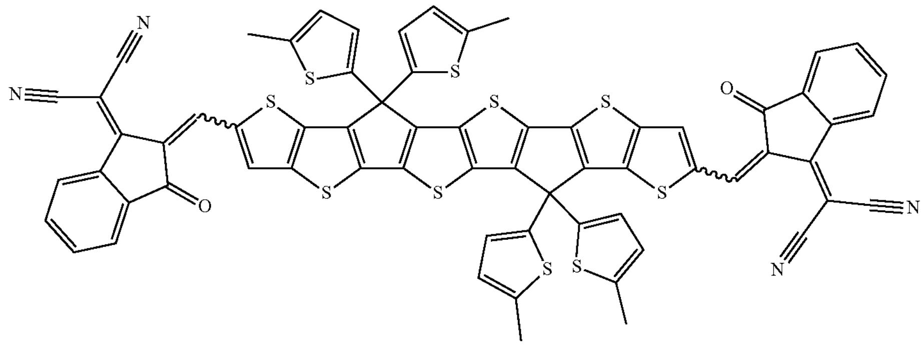 [SMILES: Cc1ccc(C2(c3ccc(C)s3)c3c(sc4cc(C=C5C(=O)c6ccccc6C5=C(C#N)C#N)sc34)-c3sc4c5c(sc4c32)-c2sc3cc(C=C4C(=O)c6ccccc6C4=C(C#N)C#N)sc3c2C5(c2ccc(C)s2)c2ccc(C)s2)s1] | −5.24 | −3.36 | 1.88 | 1.77 |
| 71 | 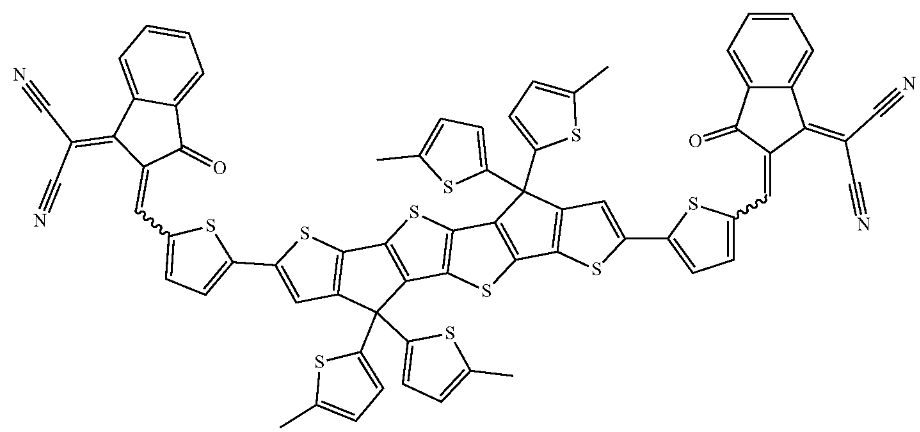 [SMILES: Cc1ccc(C2(c3ccc(C)s3)c3cc(-c4ccc(C=C5C(=O)c6ccccc6C5=C(C#N)C#N)s4)sc3-c3sc4c5c(sc4c32)-c2sc(-c3ccc(C=C4C(=O)c6ccccc6C4=C(C#N)C#N)s3)cc2C5(c2ccc(C)s2)c2ccc(C)s2)s1] | −5.09 | −3.30 | 1.79 | 1.68 |
| 72 | 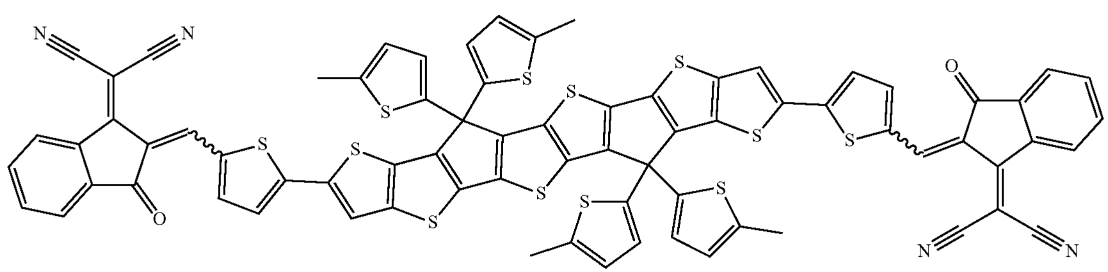 [SMILES: Cc1ccc(C2(c3ccc(C)s3)c3c(sc4cc(-c5ccc(C=C6C(=O)c7ccccc7C6=C(C#N)C#N)s5)sc34)-c3sc4c5c(sc4c32)-c2sc3cc(-c4ccc(C=C6C(=O)c7ccccc7C6=C(C#N)C#N)s4)sc3c2C5(c2ccc(C)s2)c2ccc(C)s2)s1] | −5.02 | −3.27 | 1.75 | 1.60 |

-continued

| No. | Structure | $E_{HOMO}/$ eV | $E_{LUMO}/$ eV | $E_g/$ eV | $S_0$-$S_1/$ eV |
|---|---|---|---|---|---|
| 73 | 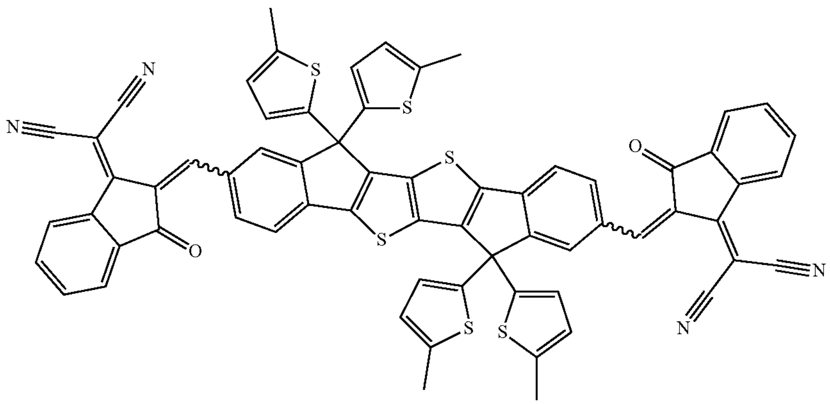 [SMILES: Cc1ccc(C2(c3ccc(C)s3)c3cc(C=C4C(=O)c5ccccc5C4=C(C#N)C#N)ccc3-c3sc4c5c(sc4c32)-c2ccc(C=C3C(=O)c4ccccc4C3=C(C#N)C#N)cc2C5(c2ccc(C)s2)c2ccc(C)s2)s1] | −5.39 | −3.22 | 2.17 | 1.89 |
| 74 | 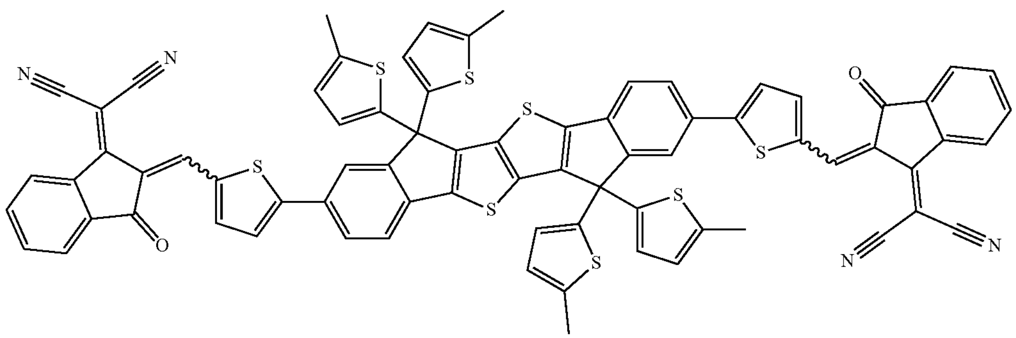 [SMILES: Cc1ccc(C2(c3ccc(C)s3)c3cc(-c4ccc(C=C5C(=O)c6ccccc6C5=C(C#N)C#N)s4)ccc3-c3sc4c5c(sc4c32)-c2ccc(-c3ccc(C=C4C(=O)c6ccccc6C4=C(C#N)C#N)s3)cc2C5(c2ccc(C)s2)c2ccc(C)s2)s1] | −5.29 | −3.21 | 2.08 | 1.85 |

Example 75

Intermediate 1

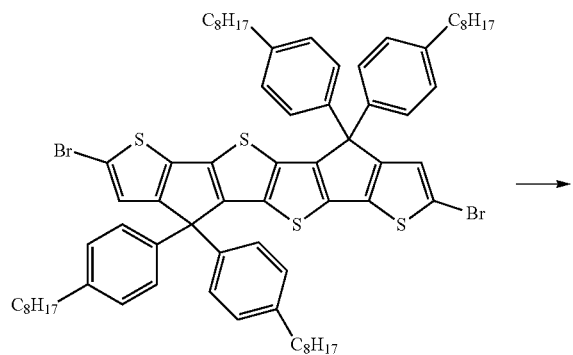

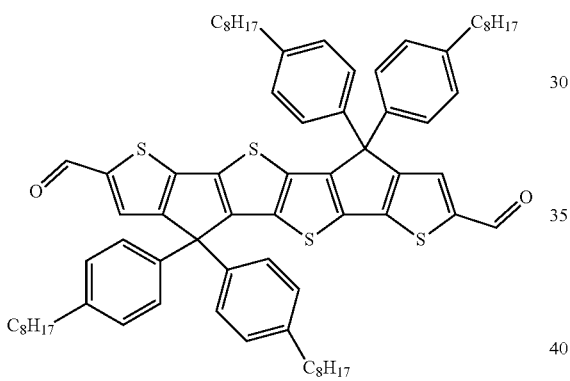

To a solution of 2,7-dibromo-4,4,9,9-tetrakis(4-octylphenyl)-4,9-dihydro-thieno[3',2':4,5]cyclopenta[1,2-b]thieno[2",3":3',4']cyclopenta[1',2':4,5]thieno[2,3-d]thiophene (0.5 g, 0.40 mmol) in anhydrous tetrahydrofuran (20 cm$^3$) at −78° C. is added dropwise n-butyllithium (0.50 cm$^3$, 1.3 mmol, 2.5 M in hexane) over 15 minutes. After addition, the reaction mixture is stirred at −78° C. for 60 minutes before a solution of N,N-dimethylformamide (0.8 cm$^3$, 10 mmol) in anhydrous diethyl ether (20 cm$^3$) is added in one go. The mixture is then allowed to warm to 23° C. over 17 hours. Dichloromethane (60 cm$^3$) and water (250 cm$^3$) is added and the mixture stirred at 23° C. for 30 minutes. The product is extracted with dichloromethane (3×60 cm$^3$). The combined organics are washed with brine (30 cm$^3$) and dried over anhydrous magnesium sulfate, filtered and the solvent removed in vacuo. The crude is purified by column chromatography (40-60 petrol:diethyl ether; 9.5:0.5) to give intermediate 1 (0.13 g, 27%) as an orange/yellow crystalline solid. $^1$H NMR (400 MHz, CDCl$_3$) 9.81 (2H, s), 7.69 (2H, s), 7.12 (16H, m), 2.52-2.61 (8H, m), 1.30 (48H, bs), 0.79-0.92 (12H, m).

Compound 75

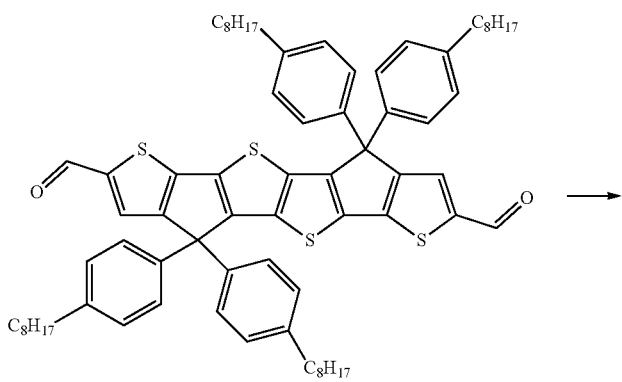

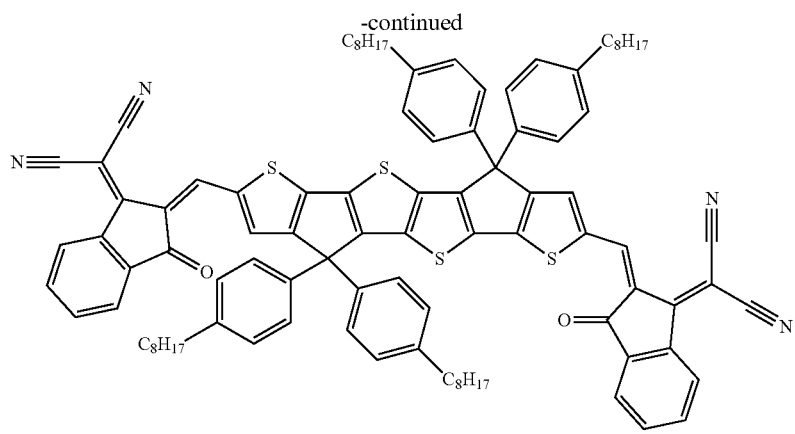

To a degassed solution of intermediate 1 (0.13 g, 0.11 mmol) and 3-(dicyanomethylidene)indan-1-one (1.5 g, 0.77 mmol) in chloroform (12 cm$^3$) is added pyridine (0.6 cm$^3$, 8 mmol). The mixture is then degassed with nitrogen for 30 minutes and then heated at 70° C. for 15 hours. The reaction mixture allowed to cool to 23° C. and the solvent removed in vacuo. The crude is purified by column chromatography (40-60 petrol:chloroform; 1:1) to give compound 75 (1.1 g, 65%) as a dark blue crystalline solid. $^1$H NMR (400 MHz, CDCl$_3$) 8.87 (2H, s), 8.69 (2H, d, J 7.6), 7.91 (2H, d, J 7.1), 7.68-7.79 (6H, m), 7.08-7.18 (16H, m), 2.60 (8H, t, J 7.7), 1.62 (8H, q, J 7.1 Hz), 1.21-1.39 (40H, m), 0.88 (12H, t, J 6.5).

Example 76

Intermediate 2

To a solution of 2,7-dibromo-4,4,9,9-tetrakis(4-octylphenyl)-4,9-dihydro-thieno[3',2':4,5]cyclopenta[1,2-b]thieno[2",3":3',4']cyclopenta[1',2':4,5]thieno[2,3-d]thiophene (2.00 g, 1.61 mmol) in anhydrous tetrahydrofuran (100 cm$^3$) at −78° C. is added n-butyllithium (2.6 cm$^3$, 6.5 mmol, 2.5 M in hexanes) over 10 minutes. The mixture is stirred at −78° C. for 1 hour before tributyltin chloride (2.0 cm$^3$, 7.4 mmol) is added and the mixture stirred to 23° C. overnight. Methanol (10 cm$^3$) is added and the material concentrated in vacuo. The crude product is then taken up in pentane (20 cm$^3$), anhydrous magnesium sulfate added, filtered and the solid washed with additional pentane (3×10 cm$^3$). The filtrate is then concentrated in vacuo and the solid triturated with methanol (3×20 cm$^3$) and the product collected by filtration to give intermediate 2 (2.57 g, 96%) as a yellow waxy solid. $^1$H NMR (400 MHz, CDCl$_3$, 45° C.) 7.16 (8H, d, J 8.2), 7.06 (10H, d, J 7.8), 2.55 (8H, t, J 7.8), 1.53-1.67 (20H, m), 1.22-1.41 (56H, m), 1.07-1.14 (8H, m), 0.84-0.97 (30H, m).

Intermediate 3

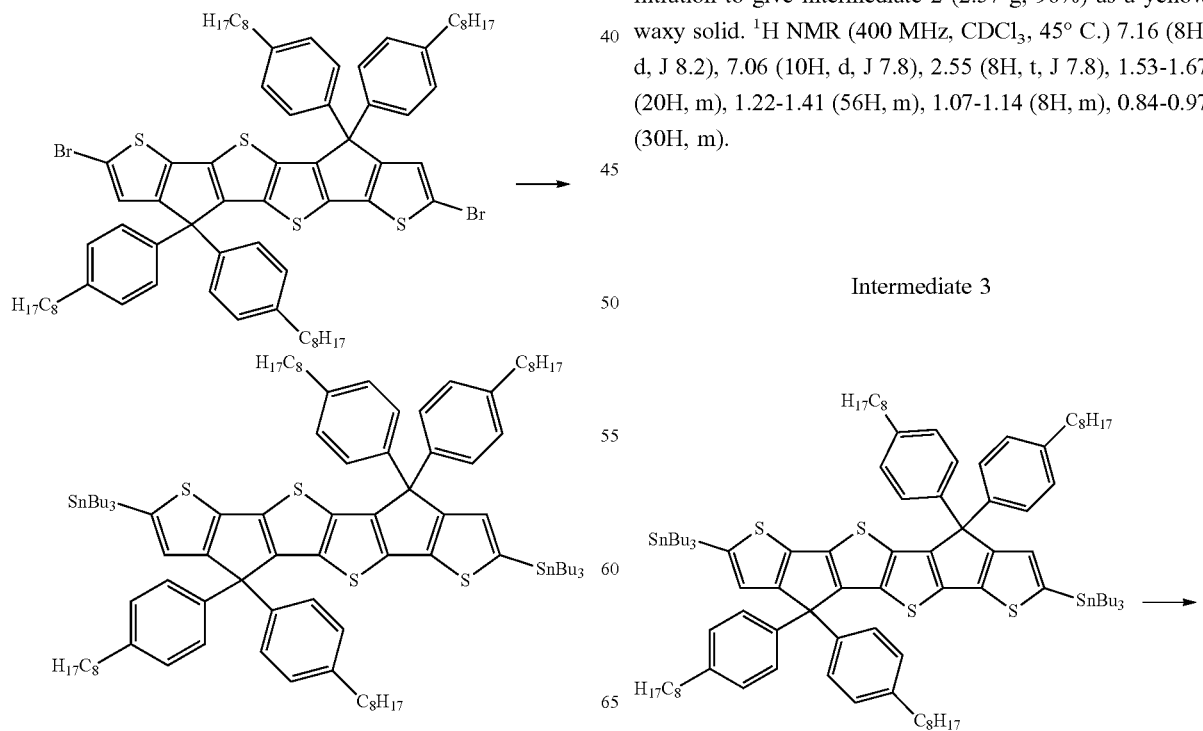

-continued

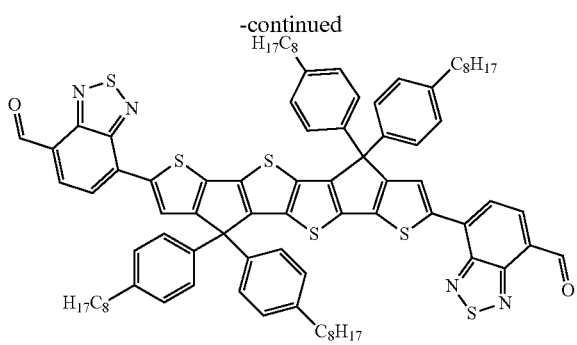

To a degassed solution of intermediate 2 (500 mg, 0.30 mmol) and 7-bromo-benzo[1,2,5]thiadiazole-4-carbaldehyde (161 mg, 0.66 mmol) in anhydrous toluene (36 cm$^3$), tris(dibenzylideneacetone)dipalladium(0) (22 mg, 0.02 mmol) and tris(o-tolyl)phosphine (28 mg, 0.09 mmol) is added. After degassing the reaction mixture for 30 minutes it is heated at 80° C. for 1.5 hours. After cooling to 23° C., the mixture is concentrated in vacuo. The crude is then triturated with methanol (3×25 cm$^3$) and the solid filtered to give intermediate 3 (357 mg, 84%) as a blue crystalline solid. $^1$H NMR (400 MHz, CDCl$_3$) 10.69 (2H, s), 8.33 (2H, s), 8.19 (2H, d, J 7.8), 7.95 (2H, d, J 7.6), 7.25 (8H, d, J 8.3), 7.14 (8H, d, J 8.3), 2.58 (8H, t, J 7.8), 1.58-1.64 (8H, m), 1.20-1.38 (40H, m), 0.86 (12H, t, J 6.8).

Compound 76

To a solution of intermediate 3 (357 mg, 0.25 mmol) in anhydrous chloroform (27 cm$^3$) is added pyridine (1.4 cm$^3$, 17 mmol). The mixture is degassed with nitrogen before 3-ethyl-2-thioxo-thiazolidin-4-one (286 mg, 1.77 mmol) is added. After further degassing, the reaction mixture is heated at reflux for 2 days. Additional degassed anhydrous chloroform (20 cm$^3$) is added and the reaction heated at reflux for a further 24 hours. Additional 3-ethyl-2-thioxo-thiazolidin-4-one (286 mg, 1.77 mmol) is added and the reaction heated at reflux for 24 hours before the reaction is cooled to 23° C., concentrated in vacuo and triturated with methanol (4×20 cm$^3$) followed by diethyl ether (3×20 cm$^3$). The triturated material is then heated at 90° C. in 2-butanone/water (4:1) (70 cm$^3$) for 30 minutes, cooled to 0° C. and the solid collected by filtration and washed with additional cold 2-butanone (4×10 cm$^3$) to give compound 76 (233 mg, 54%) as a green/black powder. $^1$H NMR (400 MHz, CDCl$_3$) 8.50 (2H, s), 8.27 (2H, s), 7.89 (2H, d, J 7.8), 7.66 (2H, d, J 7.8), 7.24 (8H, d, J 8.1), 7.13 (8H, d, J 8.3), 4.25 (4H, q, J 6.9), 2.57 (8H, t, J 7.7), 1.58-1.63 (8H, m), 1.20-1.37 (46H, m), 0.86 (12H, t, J 6.7).

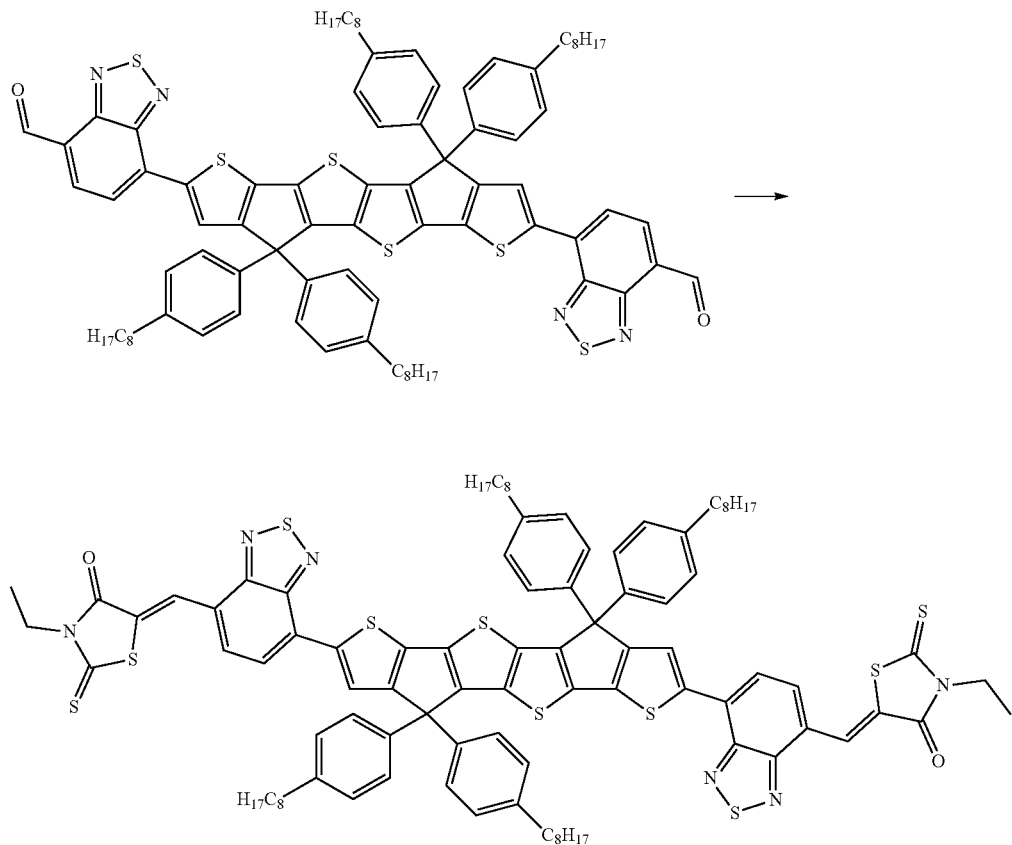

Example 77

Compound 77

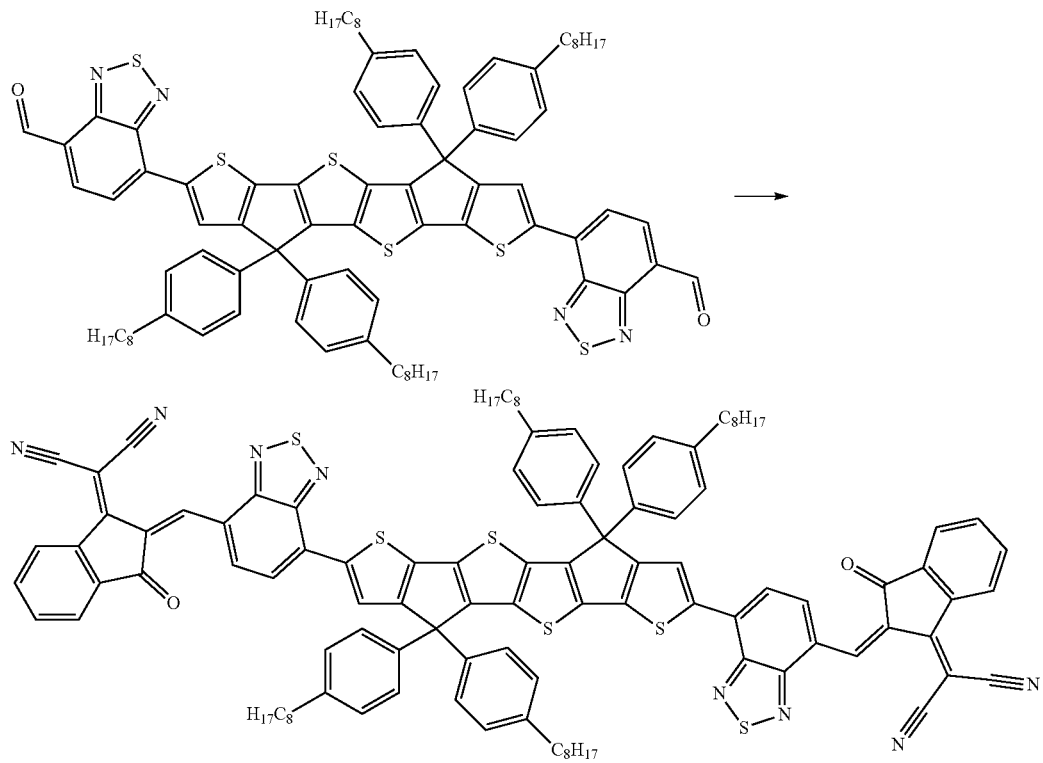

To a solution of intermediate 3 (170 mg, 0.12 mmol) in anhydrous chloroform (13 cm$^3$) is added pyridine (0.7 cm$^3$, 8.7 mmol). The mixture is then degassed with nitrogen before 3-(dicyanomethylidene)indan-1-one (164 mg, 0.84 mmol) is added. The solution is then degassed further before heating at reflux for 40 minutes. The reaction is then added to methanol (150 cm$^3$) and the precipitated product collected by filtration and washed with methanol (5 cm$^3$). The solid is then passed through a silica plug (dichloromethane) to give compound 77 (36 mg, 17%) as a black solid. $^1$H NMR (400 MHz, CDCl$_3$) 9.56 (2H, s), 9.26 (2H, d, J 8.1), 8.72 (2H, d, J 7.8), 8.36 (2H, s), 7.93 (4H, d, J 7.8), 7.73-7.84 (4H, m), 7.22-7.25 (8H, m), 7.14 (8H, d, J 8.1), 2.57 (8H, t, J 7.7), 1.57-1.64 (8H, m), 1.24 (40H, m), 0.85 (12H, t, J 6.5).

Example 78

Intermediate 4

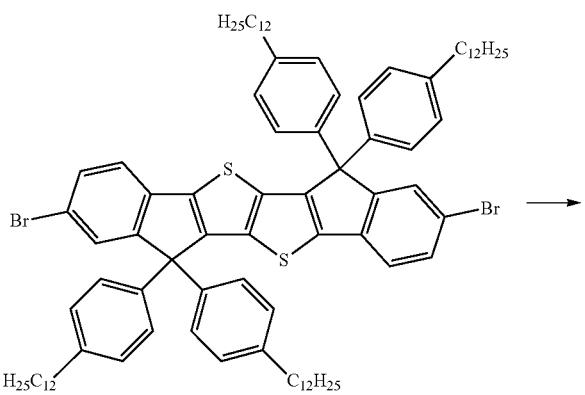

-continued

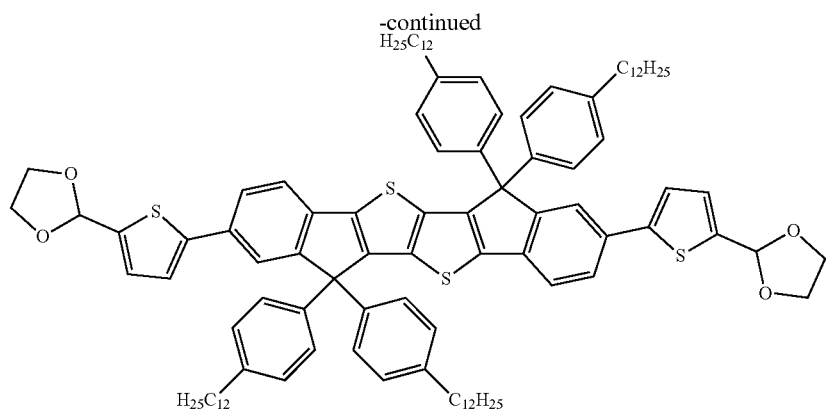

To a solution of 2,8-dibromo-6,12-dihydro-6,6,12,12-tetrakis(4-dodecylphenyl)indeno[1,2-b]indeno[2',1':4,5]thieno[2,3-d]thiophene (500 mg, 0.34 mmol) in anhydrous toluene (41 cm³) is added tributyl-(5-[1,3]dioxolan-2-yl-thiophen-2-yl)-stannane (0.4 cm³, 0.9 mmol) before the solution is degassed with nitrogen.

Tris(dibenzylideneacetone)dipalladium(0) (25 mg, 0.03 mmol) and tris(o-tolyl)phosphine (31 mg, 0.10 mmol) are then added and after additional degassing the reaction mixture is heated at 80° C. for 24 hours. The reaction mixture is then concentrated in vacuo and triturated with methanol (3×50 cm³). The solid is then eluted though a silica plug (40-60 petrol:dichloromethane; 4:1 to 0:1) and triturated with 2-propanol (100 cm³) at 80° C., which with cooling to 0° C. and collection by filtration gives intermediate 4 (454 mg, 82%) as a sticky yellow solid. $^1$H NMR (400 MHz, CHCl$_3$) 7.61 (2H, s), 7.52 (2H, d, J 8.1), 7.35 (2H, d, J 8.1), 7.18 (8H, d, J 7.9), 7.14 (2H, d, J 3.7), 7.09 (10H, d, J 8.1), 6.09 (2H, s), 4.10-4.19 (4H, m), 4.00-4.09 (4H, m), 2.55 (8H, t, J 7.8), 1.57-1.63 (8H, m), 1.21-1.36 (72H, m), 0.87 (12H, t, J 6.7).

Intermediate 5

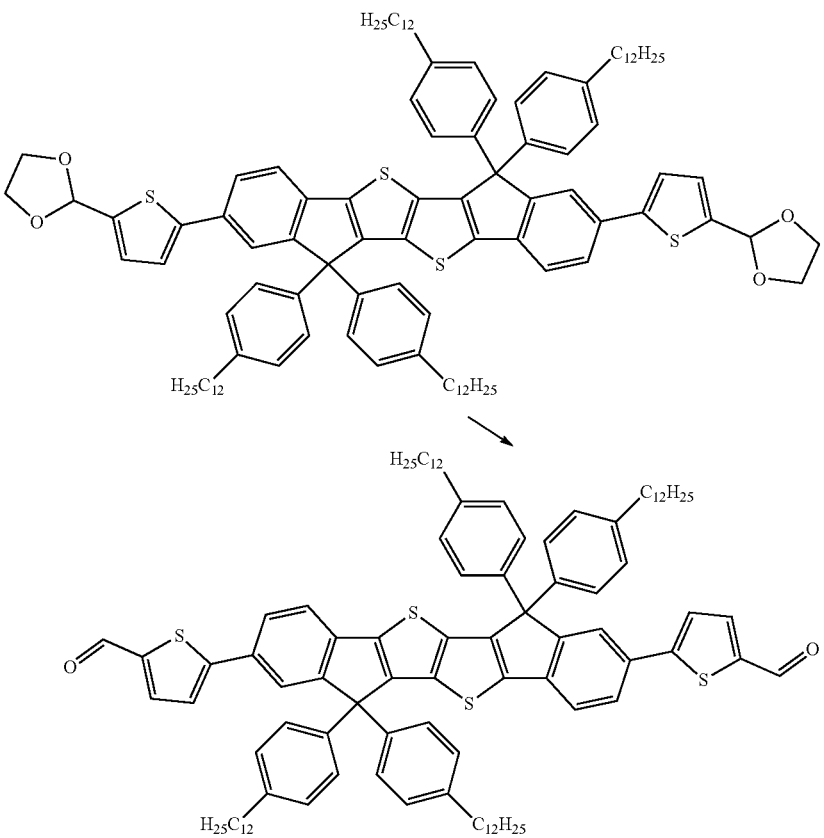

Concentrated hydrochloric acid (0.2 cm³, 1.8 mmol, 32%) is added dropwise to a solution of intermediate 4 (454 mg, 0.28 mmol) in tetrahydrofuran (20 cm³) at 23° C. and the reaction mixture stirred for 2 hours. Water (0.5 cm) is then added and the reaction mixture stirred for a further hour. Additional water (50 cm³) is then added and the solution extracted with ethyl acetate (50.2 cm³ then 25 cm³). The combined organic extracts are then washed with water (50 cm³) and brine (50 cm³), extracting the aqueous layer each time with additional ethyl acetate (25 cm³). The combined organic extracts are then dried over anhydrous magnesium sulfate, filtered and concentrated in vacuo. The crude product is then stirred in a mixture of 40-60 petrol (125 cm³) and acetone (10 cm³) at 70° C. The mixture is then cooled to 0° C., filtered and the solid washed with 40-60 petrol (3×10 cm³) to give intermediate 5 (191 mg, 45%) as a yellow solid. $^1$H NMR (400 MHz, CDCl$_3$) 9.86 (2H, s), 7.68-7.72 (4H, m), 7.63 (2H, d, J 8.1), 7.41 (2H, d, J 7.8), 7.36 (2H, d, J 3.9), 7.18 (8H, d, J 8.1), 7.11 (8H, d, J 8.1), 2.56 (8H, t, J 7.8), 1.58-1.64 (8H, m), 1.19-1.37 (72H, m), 0.87 (12H, t, J 6.6).

To a solution of intermediate 5 (191 mg, 0.13 mmol) in anhydrous chloroform (13 cm³) is added pyridine (0.7 cm³, 8.7 mmol). The mixture is then degassed with nitrogen before 3-(dicyanomethylidene)indan-1-one (172 mg, 0.89 mmol) is added. The solution is then further degassed and stirred at 23° C. for 200 minutes. The reaction mixture is then added to methanol (200 cm³), the resulting precipitate collected by filtration and washed with methanol (3×10 cm³). The solid is then triturated with diethyl ether (4×10 cm³) and the solid collected by filtration to give compound 78 (158 mg, 67%) as a black solid. $^1$H NMR (400 MHz, CDCl$_3$) 8.86 (2H, s), 8.67-8.72 (2H, m), 7.92-7.97 (2H, m), 7.83 (2H, d, J 4.4), 7.71-7.81 (8H, m), 7.42-7.47 (4H, m), 7.22 (8H, d, J 8.2), 7.13 (8H, d, J 8.3), 2.58 (8H, t, J 7.7), 1.59-1.65 (8H, m), 1.18-1.39 (72H, m), 0.87 (12H, t, J 6.9).

Compound 78

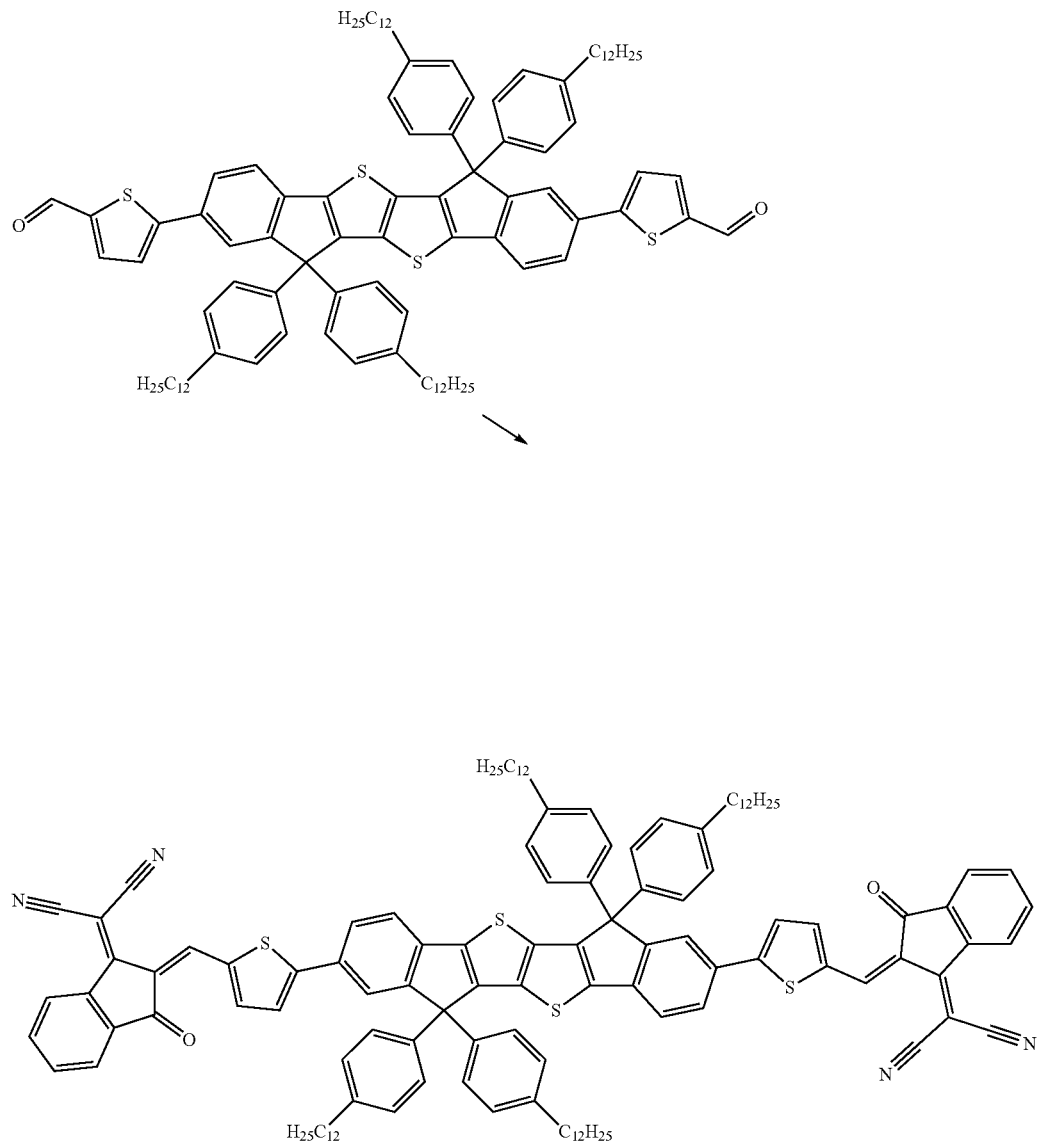

Example 79

Intermediate 6

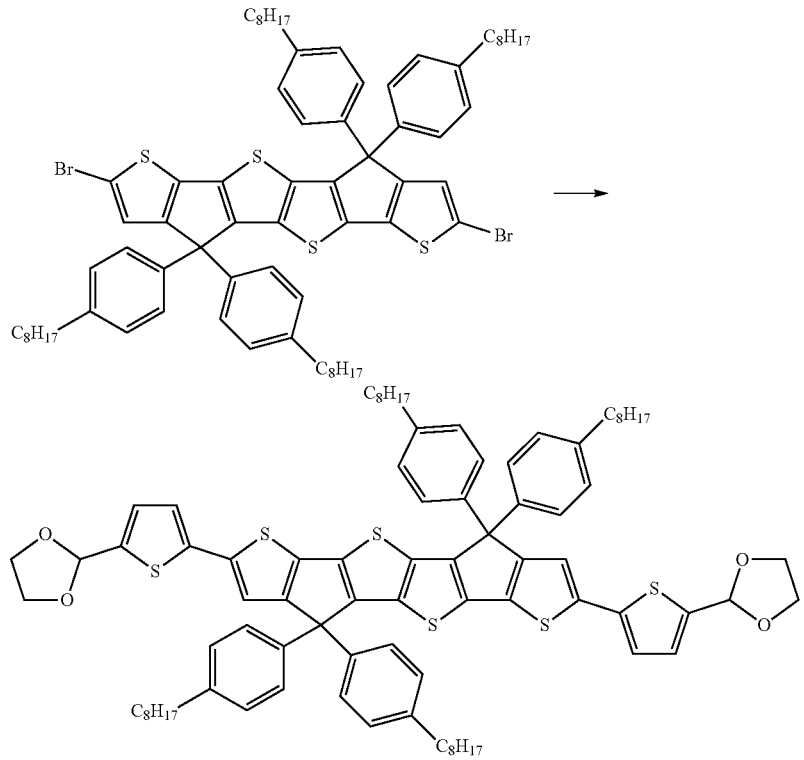

To a solution of 2,7-dibromo-4,4,9,9-tetrakis(4-octylphenyl)-4,9-dihydro-thieno[3',2':4,5]cyclopenta[1,2-b]thieno[2'',3'':3',4']cyclopenta[1',2':4,5]thieno[2,3-d]thiophene (500 mg, 0.34 mmol) in anhydrous toluene (150 cm³) is added tributyl-(5-[1,3]dioxolan-2-yl-thiophen-2-yl)-stannane (0.88 cm³, 1.94 mmol) before the solution is degassed with nitrogen. Tris(dibenzylideneacetone)dipalladium (59 mg, 0.03 mmol) and tris(o-tolyl)phosphine (74 mg, 0.24 mmol) are then added and after additional degassing, the reaction mixture is heated at 80° C. for 17 hours. The reaction mixture is then concentrated in vacuo and triturated with methanol (5×20 cm³) collecting the solid by filtration to give intermediate 6 (1.1 g, 99%) as an orange solid. ¹H NMR (400 MHz, CDCl₃) 7.12-7.19 (10H, m), 7.09 (8H, d, J 7.8), 7.00-7.05 (4H, m), 6.08 (2H, s), 4.08-4.17 (4H, m), 3.99-4.08 (4H, m), 2.56 (8H, t, J 7.8), 1.52-1.63 (8H, m), 1.22-1.35 (40H, m), 0.87 (12H, t, J 6.5).

Intermediate 7

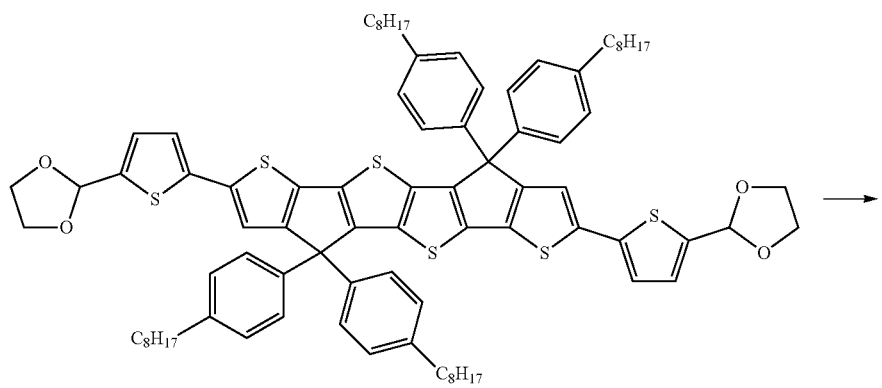

-continued

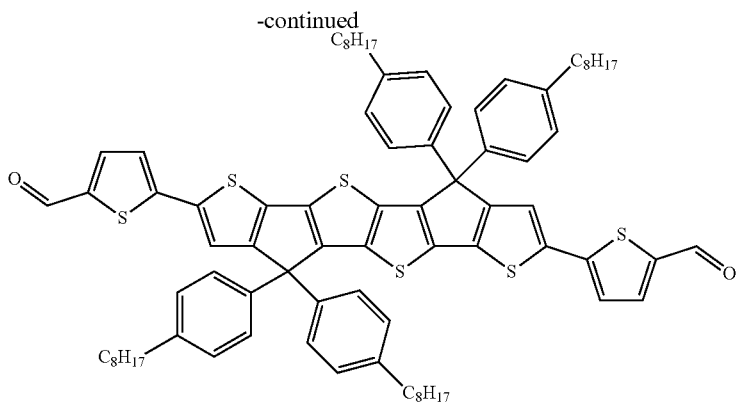

Concentrated hydrochloric acid (0.5 cm³, 4.07 mmol, 32%) is added dropwise to a solution of intermediate 6 (1.1 g, 0.81 mmol) in tetrahydrofuran (57 cm³) at 23° C. and the reaction mixture stirred for 1 hour. Water (0.5 cm³) is then added and the reaction mixture stirred for a further 17 hours. Additional water (100 cm³) is then added and the solution extracted with ethyl acetate (50 cm³ then 25 cm³). The combined organic extracts are then washed with water (50 cm³) and brine (50 cm³), extracting the aqueous layer each time with additional ethyl acetate (20 cm³). The combined organic extracts are then dried over anhydrous magnesium sulfate, filtered and concentrated in vacuo. The crude product is then triturated with methanol (3×15 cm³) with collection by filtration and the solid washed with 40-60 petrol (3×15 cm³) to give intermediate 7 (291 mg, 28%) as an orange solid. ¹H NMR (400 MHz, CDCl₃) 9.83 (2H, s), 7.64 (2H, d, J 3.9), 7.32 (2H, s), 7.20 (2H, d, J 3.9), 7.16 (8H, d, J 8.1), 7.11 (8H, d, J 8.0), 2.57 (8H, t, J 7.6), 1.54-1.64 (8H, m), 1.20-1.38 (40H, m), 0.82-0.92 (12H, m).

Compound 79

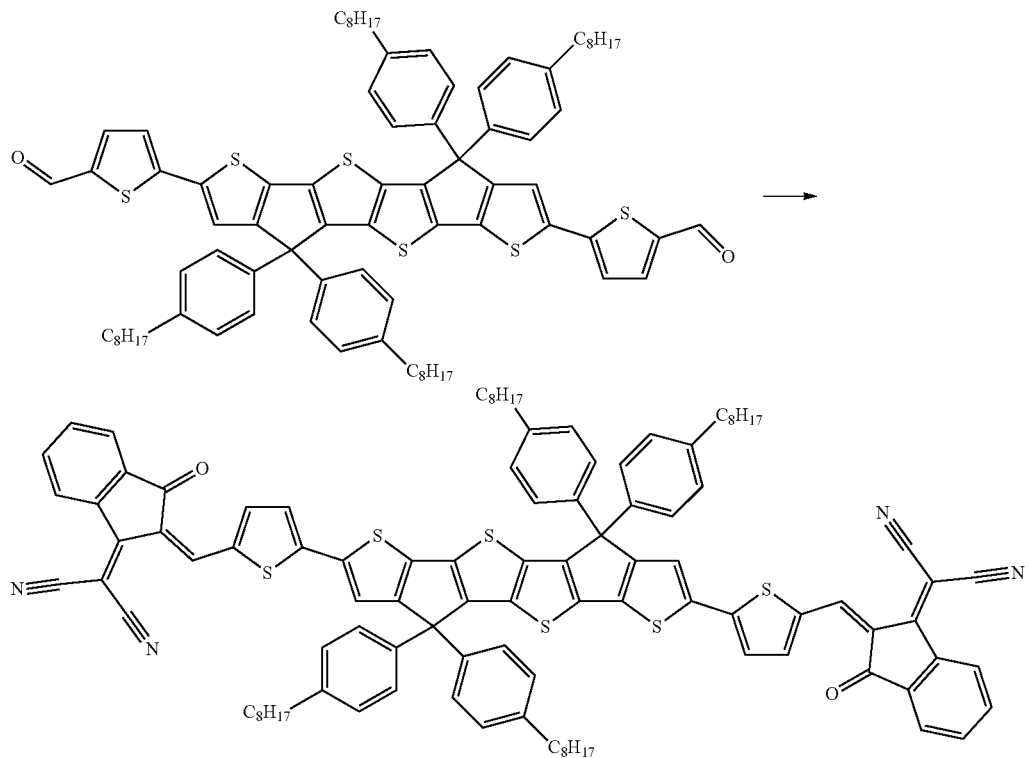

To a solution of intermediate 7 (287 mg, 0.22 mmol) in anhydrous chloroform (23 cm³) is added pyridine (1.3 cm³, 16 mmol). The mixture is then degassed with nitrogen before 3-(dicyanomethylidene)indan-1-one (300 mg, 1.54 mmol) is added. The solution is then further degassed and stirred at 23° C. for 3.25 hours. The reaction mixture is then added to methanol (300 cm³), the mixture concentrated in vacuo and the resulting solid triturated with methanol (3×25 cm³) with collection by filtration. The filtered solid is then washed with diethyl ether (2×10 cm³) and acetone (3×10 cm³). The partially purified product is then subjected to column chromatography, eluting with a graded solvent system (40-60 petrol:dichloromethane; 9.5:0.5 to 2:3) to give compound 79 (86 mg, 24%) as a green/black solid. $^1$H NMR (400 MHz, CDCl$_3$) 8.83 (2H, s), 8.69 (2H, d, J 7.6), 7.92 (2H, d, J 6.6), 7.69-7.79 (6H, m), 7.54 (2H, s), 7.29 (2H, d, J 4.4), 7.11-7.20 (16H, m), 2.59 (8H, t, J 7.7), 1.58-1.64 (8H, m), 1.21-1.38 (40H, m), 0.87 (12H, t, J 6.5).

Example 80

Intermediate 8

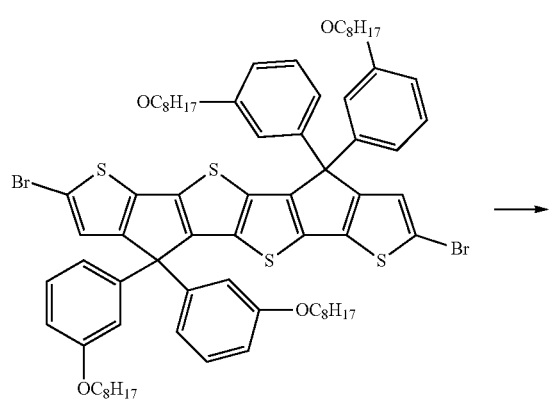

To a solution of 2,7-dibromo-4,4,9,9-tetrakis(3-octylphenyl)-4,9-dihydro-thieno[3',2':4,5]cyclopenta[1,2-b]thieno[2'',3'':3',4']cyclopenta[1',2':4,5]thieno[2,3-d]thiophene (1.00 g, 0.77 mmol) in tetrahydrofuran (25 cm$^3$) cooled to −78° C. is added dropwise n-butyllithium (0.92 cm$^3$, 2.30 mmol, 2.5 M in hexanes). The reaction is stirred for one hour and quenched with N,N-dimethylformamide (1.13 cm$^3$, 23.0 mmol) in a single portion. The reaction is warmed to 23° C. and stirred for 18 hours. The mixture is quenched with water (50 cm$^3$) and extracted with dichloromethane (3×30 cm$^3$). The resulting combined organic phase is washed with water (2×20 cm$^3$), dried over anhydrous magnesium sulfate, filtered and concentrated in vacuo. The crude is purified by flash chromatography eluting with a graded solvent system (40-60 petrol:dichloromethane; 6:4 to 4:6) to give intermediate 8 (330 mg, 36%) as an orange oil. $^1$H NMR (400 MHz, CDCl$_3$) 9.73 (2H, s), 7.62 (2H, s), 7.14 (4H, t, J 8.0), 6.65-6.77 (m, 12H), 3.80 (8H, t, J 6.6), 1.58-1.69 (8H, m), 1.27-1.38 (8H, m), 1.01-1.30 (32H, m), 0.71-0.87 (12H, m).

Compound 80

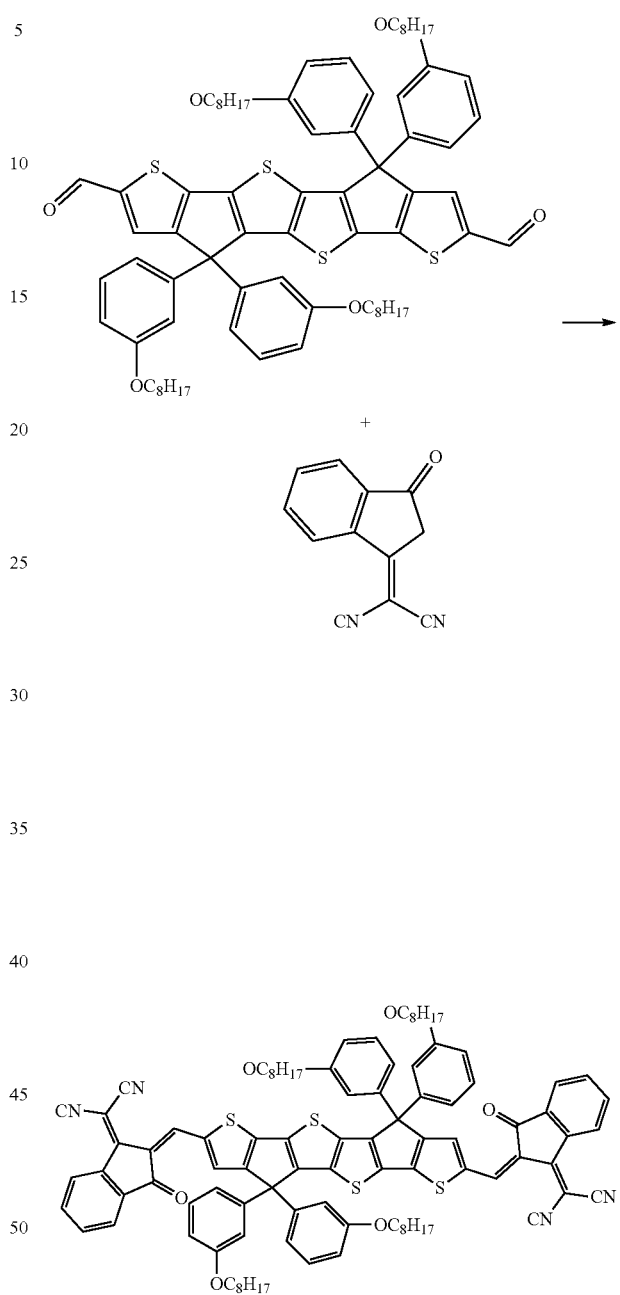

To a degassed solution of intermediate 8 (330 mg, 0.27 mmol) and 3-(dicyanomethylidene)indan-1-one (373 mg, 1.92 mmol) in chloroform (8.25 cm$^3$) is added pyridine (0.55 cm$^3$, 6.86 mmol) and the mixture stirred at 23° C. for 2 hours. Methanol (50 cm$^3$) is added and the resulting suspension filtered and washed with methanol (3×20 cm$^3$). The resulting solid is purified by column chromatography eluting with a graded solvent system (40-60 petrol:dichloromethane; 1:1 to 3:7) to give compound 80 (321 mg, 75%) as a blue solid. $^1$H NMR (400 MHz, CDCl$_3$) 8.79 (2H, s), 8.53-8.67 (2H, m), 7.83 (2H, m), 7.61-7.73 (6H, m), 7.18 (4H, m), 6.67-6.81 (12H, m), 3.83 (8H, t, J 6.7), 1.68 (8H, m), 1.33 (8H, m), 1.12-1.29 (32H, m), 0.78 (12H, t, J 6.7).

Example 81

Intermediate 9

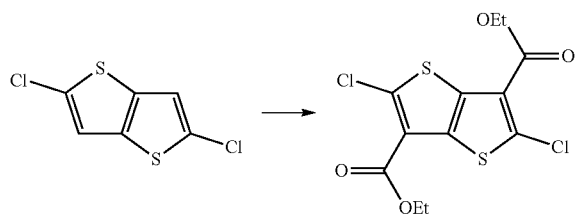 [SMILES: Clc1cc2sc(Cl)cc2s1 ; CCOC(=O)c1c(Cl)sc2c(C(=O)OCC)c(Cl)sc12]

To a solution of 2,5-dichloro-thieno[3,2-b]thiophene (17.3 g, 82.7 mmol) in anhydrous tetrahydrofuran (173 cm$^3$) at 5° C. is added ethyl chloroformate (23.7 cm$^3$, 248 mmol). A solution of 2,2,6,6-tetramethylpiperidinylmagnesium chloride lithium chloride complex (207 cm$^3$; 207 mmol, 1.0 M in tetrahydrofuran) is then added dropwise over 1 hour. The reaction is slowly warmed to 23° C. and stirred for 42 hours. Water (200 cm$^3$) is added, the mixture stirred for 10 minutes and the solid collected by filtration and washed with water (2×100 cm$^3$). The solid is triturated in acetone (200 cm$^3$), the solid collected by filtration and washed with acetone (2×100 cm$^3$) to give intermediate (26.6 g, 91%) as a white solid. $^1$H NMR (400 MHz, CDCl$_3$) 4.46 (4H, q, J 7.1), 1.47 (6H, t, J 7.1).

Intermediate 10

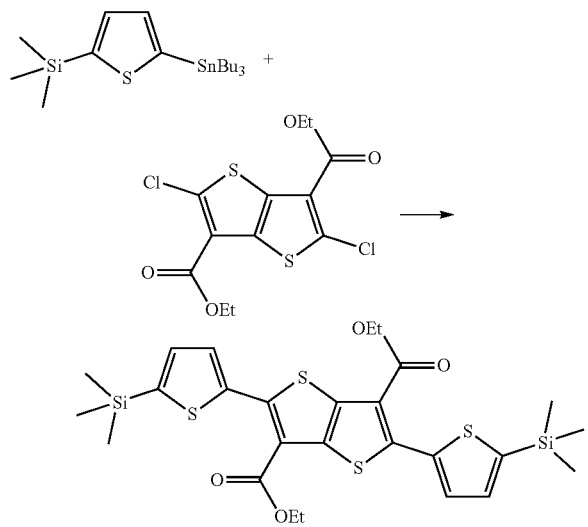

Trimethyl-(5-tributylstannanyl-thiophen-2-yl)-silane (30.5 g, 61.7 mmol), intermediate 9 (10.0 g, 28.3 mmol) and tetrakis(triphenylphosphine)palladium(0) (657 mg, 0.57 mmol) are suspended in anhydrous toluene (100 cm$^3$) and heated at 100° C. for 18 hours. The reaction is cooled to 23° C. and methanol (250 cm$^3$) added. The suspension is cooled in an ice-bath, the solid collected by filtration and washed with methanol (200 cm$^3$). The crude was purified by silica pad (dichloromethane) followed by flash chromatography eluting with 40-60 petrol:dichloromethane; 60:40 to give intermediate 10 (7.68 g, 46%) as a yellow solid. $^1$H NMR (400 MHz, CDCl$_3$) 7.42 (2H, d, J 3.5), 7.02 (2H, d, J 3.5), 4.19 (4H, q, J 7.1), 1.19 (6H, t, J 7.1), 0.15 (18H, s).

Intermediate 11

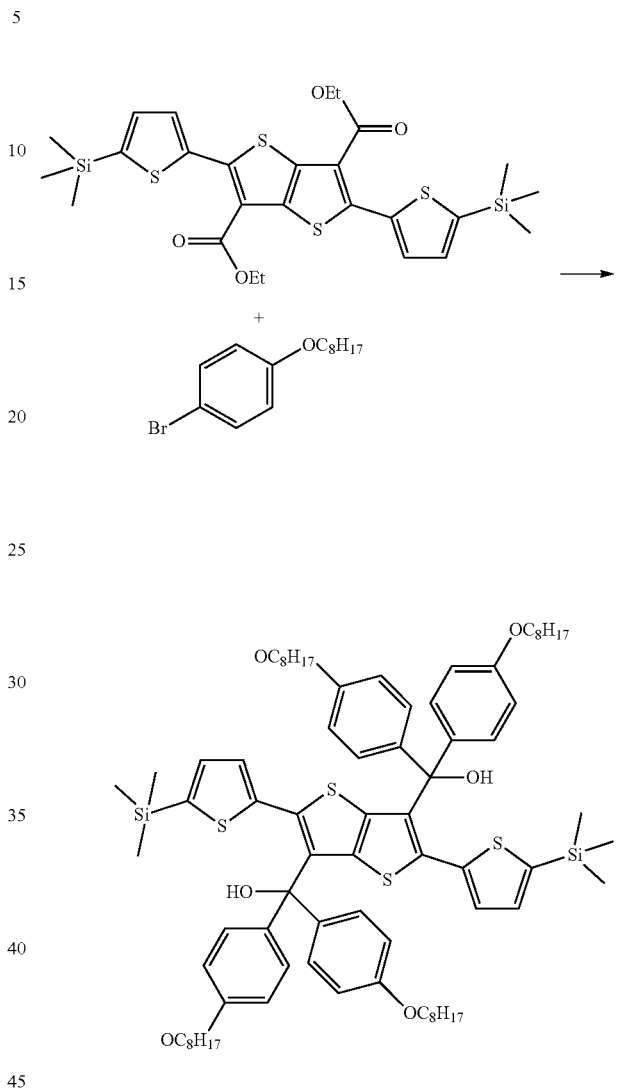

To a solution of 1-bromo-4-octyloxy-benzene (14.1 g, 49.5 mmol) in anhydrous tetrahydro-furan (73 cm$^3$) at −78° C. is added dropwise t-butyllithium (58.2 cm$^3$, 99.0 mmol, 1.7 M in pentane) over 20 minutes. The reaction is warmed to between −28° C. and −35° C. for 30 minutes. A second portion of 1-bromo-4-octyloxy-benzene (3.0 g, 11 mmol) is added and the reaction mixture stirred for 30 minutes. The reaction is cooled to −78° C. and a solution of intermediate 10 (4.89 g, 8.25 mmol) in anhydrous tetrahydrofuran (30 cm$^3$) is rapidly added. The reaction is warmed to 23° C. and stirred for 60 hours. Water (50 cm$^3$) is added and the organics extracted with ether (300 cm$^3$). The organic phase is washed with water (3×100 cm$^3$), dried over anhydrous magnesium sulfate, filtered and the solvent removed in vacuo. The crude purified by column chromatography using a gradient solvent system (40-60 petrol:dichloromethane; 9:1 to 8:2) to give intermediate 11 (3.17 g, 29%) as a pale brown solid. $^1$H NMR (400 MHz, CDCl$_3$) 7.16-7.23 (8H, m), 6.88 (2H, d, J 3.4), 6.78-6.85 (8H, m), 6.51 (2H, d, J 3.4), 3.97 (8H, t, J 6.6), 3.37 (2H, s), 1.75-1.84 (8H, m), 1.27-1.52 (40H, m), 0.82-0.95 (12H, m), 0.25 (18H, s).

Intermediate 12—Route A

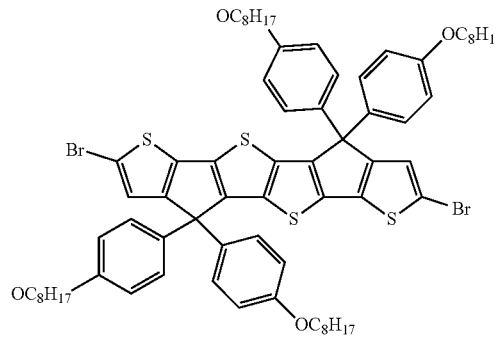

To a solution of 2,7-dibromo-4,4,9,9-tetrakis(4-(octyloxy)phenyl)-4,9-dihydro-thieno[3',2':4,5]cyclopenta[1,2-b]thieno[2",3"":3',4']cyclopenta[1', 2':4,5]thieno[2,3-d]thiophene (1.00 g, 0.77 mmol) in tetrahydrofuran (25 cm³) cooled to −78° C. is added dropwise n-butyllithium (0.92 cm³, 2.30 mmol, 2.5 M in hexanes). The reaction is stirred for a further 1 hour and quenched with N,N-dimethylformamide (1.13 cm³, 23.0 mmol) as a single portion. The reaction is warmed to 23° C. and stirred for 18 hours. The reaction is quenched with water (50 cm³), extracted with dichloromethane (3×30 cm³). The resulting organic phase is washed with water (2×20 cm³), dried over anhydrous magnesium sulfate, filtered and concentrated in vacuo. The crude is purified by flash chromatography eluting with a graded solvent system (40-60 petrol:dichloromethane; 6:4 to 4:6) to give intermediate 12 (330 mg, 36%) as an orange oil. ¹H NMR (400 MHz, CDCl₃) 9.72 (2H, s), 7.58 (2H, s), 7.00-7.08 (8H, m), 6.69-6.82 (8H, m), 3.83 (8H, t, J 6.5), 1.61-1.71 (8H, m), 1.34 (8H, m), 1.11-1.33 (32H, m), 0.72-0.90 (12H, m).

Intermediate 12—Route B

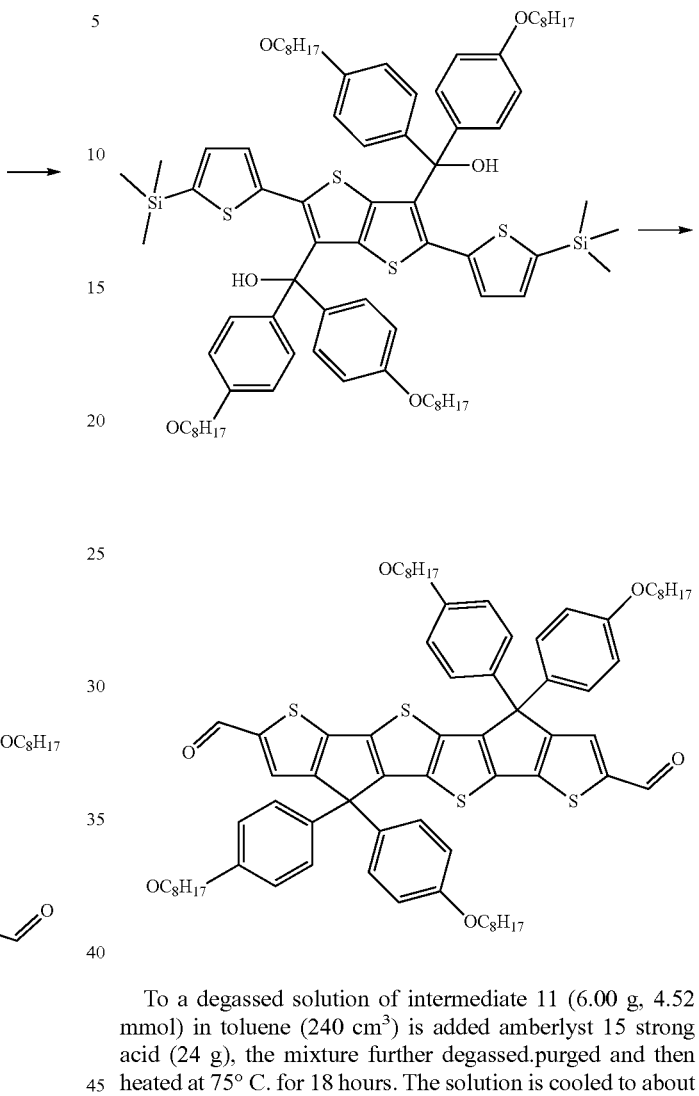

To a degassed solution of intermediate 11 (6.00 g, 4.52 mmol) in toluene (240 cm³) is added amberlyst 15 strong acid (24 g), the mixture further degassed.purged and then heated at 75° C. for 18 hours. The solution is cooled to about 50° C., filtered and the solid washed with toluene (200 cm³). The filtrate is concentrated and triturated with 80-100 petrol (3×30 cm³) with the solid collected by filtration. The solid is dissolved in chloroform (120 cm³), N,N-dimethylformamide (5.3 g, 72 mmol) added and the solution cooled to 0° C. Phosphorus(V) oxychloride (10.4 g, 67.9 mmol) is added over 10 minutes. The reaction mixture is then heated at 65° C. for 18 hours. Aqueous sodium acetate solution (150 cm³, 2 M) is added at 65° C. and the reaction mixture stirred for 1 hour. Saturated aqueous sodium acetate solution is added until the mixture is pH 6 and the reaction stirred for a further 30 minutes. The aqueous phase is extracted with chloroform (2×25 cm³) and the combined organic layers washed with water (50 cm³), dried over anhydrous magnesium sulfate, filtered and the solvent removed in vacuo. The solid was triturated in 80-100 petrol and the solid collected by filtration to give intermediate 12 (3.06 g, 56%) as an orange oil. ¹H NMR (400 MHz, CDCl₃) 9.72 (2H, s), 7.58 (2H, s), 7.00-7.08 (8H, m), 6.69-6.82 (8H, m), 3.83 (8H, t, J 6.5), 1.61-1.71 (8H, m), 1.34 (8H, m), 1.11-1.33 (32H, m), 0.72-0.90 (12H, m).

Compound 81

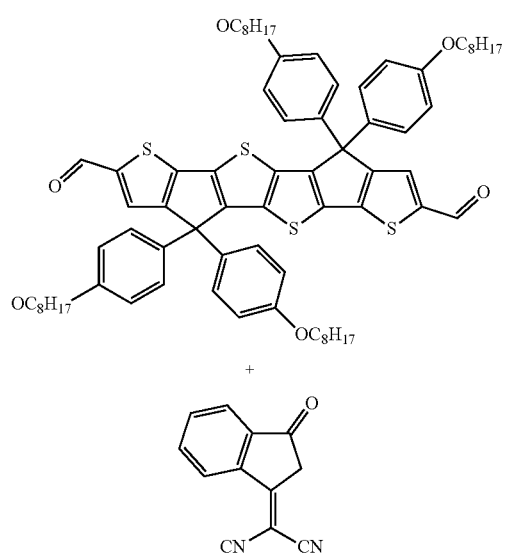

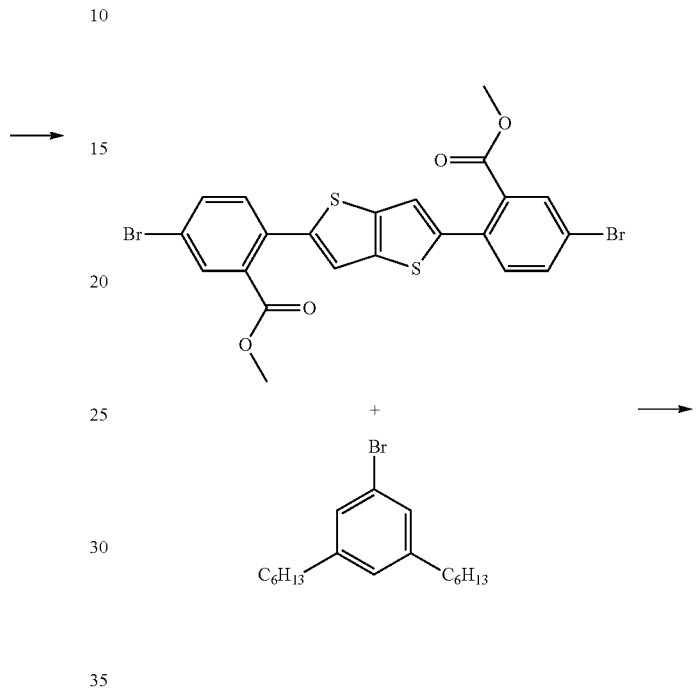

To a degassed solution of intermediate 12 (330 mg, 0.27 mmol) and 3-(dicyanomethylidene)indan-1-one (373 mg, 1.92 mmol) in chloroform (8.25 cm³) is added pyridine (0.55 cm³, 6.86 mmol) and the mixture stirred at 23° C. for 4 hours. Methanol (50 cm³) is added and the resulting suspension is filtered and washed with methanol (3×20 cm³). The crude is purified by column chromatography (40-60 petrol:dichloromethane; 1:1) to give compound 81 (141 mg, 33%) as a blue solid. ¹H NMR (400 MHz, CDCl₃) 8.79 (2H, s), 8.60 (2H, m), 7.75-7.91 (2H, m), 7.67 (4H, m), 7.61 (s, 2H), 7.04-7.12 (8H, m), 6.74-6.81 (8H, m), 3.85 (8H, t, J 6.5), 1.68 (8H, m), 1.11-1.43 (40H, m), 0.72-0.84 (12H, m).

Example 82

Intermediate 13

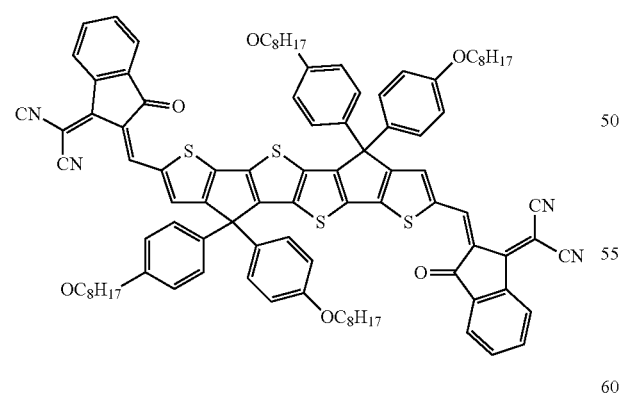

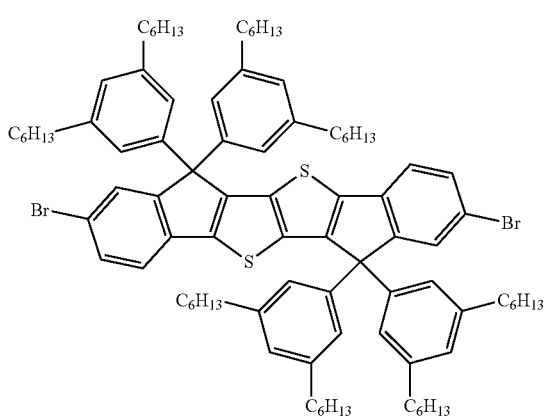

To a solution of 1-bromo-3,5-dihexyl-benzene (9.00 g, 27.7 mmol) in anhydrous tetrahydrofuran (135 cm³) cooled to −78° C. is added dropwise a solution of n-butyllithium (11.1 cm³, 27.7 mmol, 2.5 M in hexanes) over 10 minutes. The reaction is stirred for one hour and methyl 5-bromo-2-[5-(4-bromo-2-methoxycarbonyl-phenyl)thieno[3,2-b]thiophen-2-yl]benzoate (3.13 g, 5.53 mmol) is added as a single portion. The reaction is warmed to 23° C. and stirred for 18 hours. The reaction is partitioned between diethyl ether (50 cm³) and water (100 cm³). The organic phase is washed with water (30 cm³), brine (30 cm³), dried over anhydrous magnesium sulfate, filtered and concentrated in vacuo. The crude is triturated with 40-60 petrol, and the solid suspended in toluene (50 cm³). p-Toluene sulphonic acid (2.5 g) is added and the reaction mixture and stirred for 17 hours. The suspension is filtered, concentrated in vacuo and purified via flash chromatography eluting with a mixture of DCM petroleum ether 40:60. The resulting material is triturated in acetone and the solid collected to give intermediate 13 (2.71 g, 34%) as a yellow solid. ¹H NMR (400 MHz, CDCl₃) 7.42 (2H, d, J 1.7), 7.32 (2H, dd, J 8.1, 1.8), 7.11 (2H, d, J 8.1), 6.80 (4H, t, J 1.5), 6.71 (8H, d, J 1.5), 2.40 (16H, t, J 7.7), 1.38-1.48 (16H, m), 1.11-1.24 (48H, m), 0.70-0.79 (24H, m).

Intermediate 14

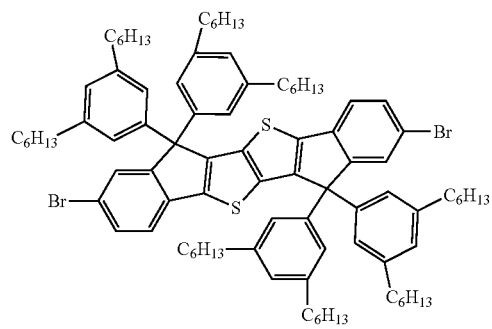

+

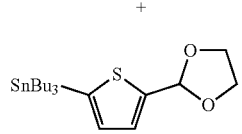 →

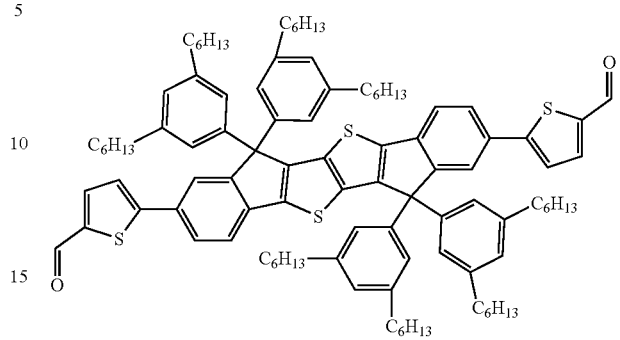

To a degassed solution of intermediate 13 (250 mg, 0.17 mmol), tributyl-(5-[1,3]dioxolan-2-yl-thiophen-2-yl)-stannane (0.18 cm³, 0.40 mmol) and tris(o-tolyl)phospine (16 mg, 0.05 mmol) in toluene (12.5 cm³) is added bis(dibenzylideneacetone)palladium(0) (16 mg, 0.02 mmol) and the mixture further degassed. The reaction is then heated to an external temperature of 140° C. for 6 hours. The reaction mixture is allowed to cool and concentrated in vacuo. The crude is purified by flash chromatography eluting with a graded solvent system (40-60 petrol:dichloromethane; 1:9 to 3:10). The resulting oil is dissolved in chloroform (30 cm³) and stirred with 2.5 N hydrochloric acid solution (10 cm³) for 18 hours. The organic phase is concentrated in vacuo and the residue purified by flash chromatography eluting with a graded solvent system (40-60 petrol:dichloromethane; 1:4 to 1:4). The resulting solid is triturated in acetone and the solid collected by filtration to give intermediate 14 (170 mg, 65%) as a yellow solid. ¹H NMR (400 MHz, CDCl₃) 9.78 (2H, s), 7.59-7.65 (4H, m), 7.55 (2H, dd, J 8.0, 1.6), 7.31 (2H, d, J 8.0), 7.24 (2H, d, J 3.9), 6.82 (4H, s), 6.78 (8H, s), 2.41 (16H, t, J 7.6), 1.39-1.49 (16H, m), 1.17 (48H, m), 0.69-0.85 (24H, m).

Compound 82

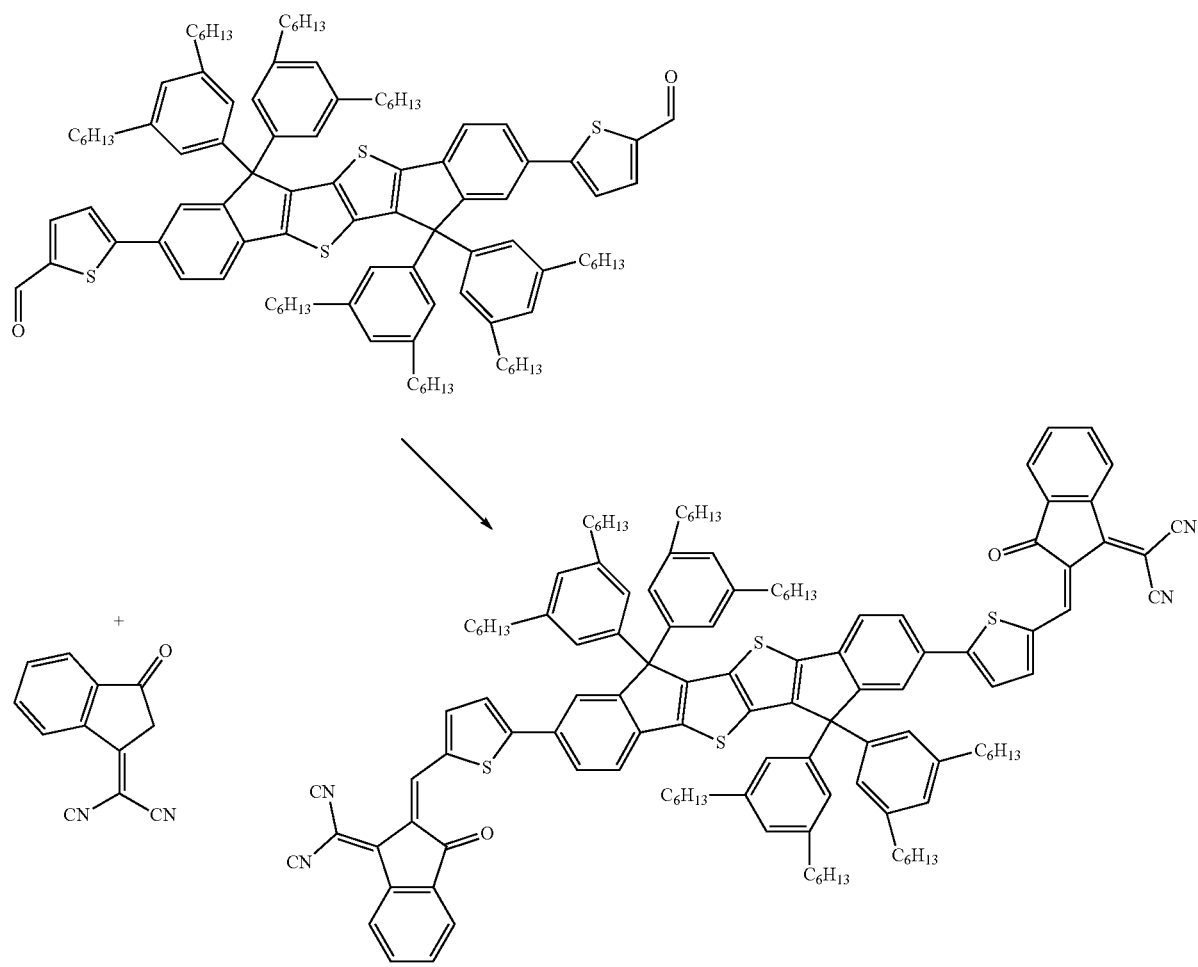

To a degassed solution of intermediate 14 (170 mg, 0.11 mmol) and 3-(dicyanomethylidene)indan-1-one (153 mg, 0.79 mmol) in chloroform (4.25 cm$^3$) is added pyridine (0.63 cm$^3$, 7.86 mmol) and the mixture stirred at 23° C. for 18 hours. Methanol (75 cm$^3$) is added and the resulting suspension filtered and washed with methanol (3×10 cm$^3$). The resulting solid is purified by column chromatography eluting with a graded solvent system (40-60 petrol:dichloromethane; 1:1 to 2:3) to give compound 82 (32 mg, 15%) as a blue solid. $^1$H NMR (400 MHz, CD$_2$Cl$_2$) 8.75 (2H, s), 8.55-8.64 (2H, m), 7.82-7.87 (2H, m), 7.64-7.80 (10H, m), 7.25-7.49 (4H, m), 6.80-6.87 (12H, m), 2.42 (16H, t, J 7.6), 1.47 (16H, m), 1.11-1.23 (48H, m), 0.67-0.75 (m, 24H).

Example 83

Intermediate 15

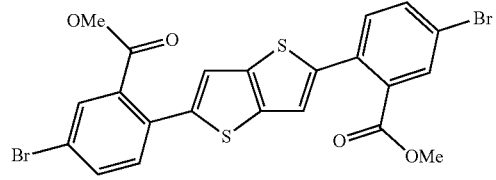

+

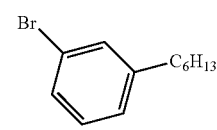

↓

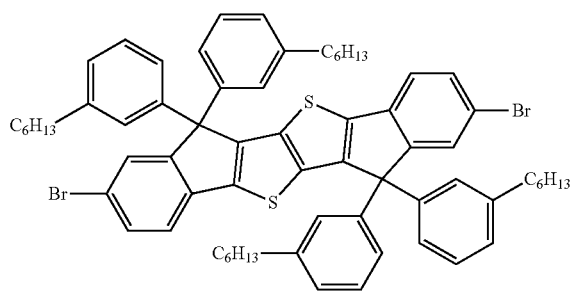

To a solution of 1-bromo-3-hexyl-benzene (6.39 g, 26.5 mmol) and anhydrous tetrahydrofuran (45 cm³) at −78° C. is added dropwise a solution of n-butyllithium (10.6 cm³, 26.5 mmol, 2.5 M in hexanes) over 10 minutes. The reaction mixture is stirred for 1 hour and methyl 5-bromo-2-[5-(4-bromo-2-methoxycarbonyl-phenyl)thieno[3,2-b]thiophen-2-yl]benzoate (3.00 g, 5.3 mmol) added as a single portion. The reaction is warmed to 23° C. and stirred for 17 hours. The reaction is partitioned between diethyl ether (100 cm³) and water (100 cm³). The organic phase is washed with water (2×50 cm³), brine (20 cm³), dried over anhydrous magnesium sulfate, filtered and concentrated in vacuo. The resulting oil is triturated with 40-60 petrol and the solid suspended in toluene (40 cm³). p-Toluene sulphonic acid (2.0 g) is added and the reaction mixture stirred for 17 hours. The suspension is filtered and concentrated in vacuo. The resulting material is triturated in acetone at 50° C. and then filtered at 0° C. to give intermediate 15 (1.28 g, 22%) as a yellow solid. $^1$H NMR (400 MHz, CDCl$_3$) 7.51 (2H, d, J 1.7), 7.41 (2H, dd, J 8.1, 1.8), 7.13-7.25 (6H, m), 7.04-7.12 (8H, m), 6.92-6.98 (4H, m), 2.50-2.59 (m, 8H), 1.54 (8H, m), 1.18-1.24 (m, 24H), 0.79-0.88 (m, 12H).

Intermediate 16

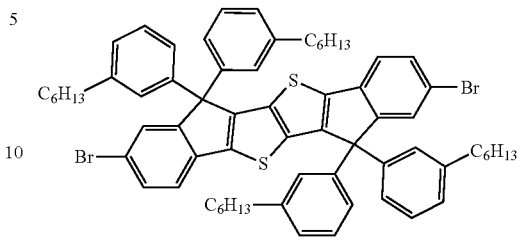

+

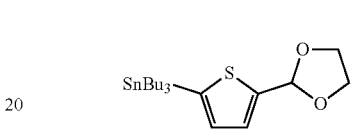

↓

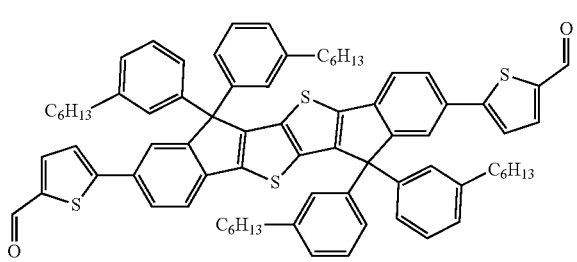

To a degassed solution of intermediate 15 (250 mg, 0.22 mmol), tributyl-(5-[1,3]dioxolan-2-yl-thiophen-2-yl)-stannane (277 mg, 0.52 mmol) and tris(o-tolyl)phosphine (21 mg, 0.07 mmol) in toluene (12.5 cm³) is added bis(dibenzylideneacetone)palladium(0) (21 mg, 0.02 mmol). The solution is further degassed and then heated to an external temperature of 140° C. for 6 hours. The reaction mixture is concentrated in vacuo and purified by flash chromatography eluting with a graded solvent system (40-60 petrol:dichloromethane; 1:1 to 1:3). The resulting oil is dissolved in chloroform (10 cm³) and stirred with 2.5 N hydrochloric acid (10 cm³) for 18 hours. The organic phase is washed with water (10 cm³) and brine (20 cm³) before being concentrated in vacuo. The resulting solid is triturated in acetone to give intermediate 16 (75 mg, 28%) as a yellow solid. $^1$H NMR (400 MHz, CDCl$_3$) 9.86 (2H, s), 7.67-7.74 (4H, m), 7.63 (2H, m), 7.41 (2H, d, J 8.0), 7.34 (2H, d, J 3.9), 7.06-7.23 (12H, m), 6.98-7.06 (4H, m), 2.56 (8H, t, J 7.6), 1.55 (8H, m), 1.19-1.33 (m, 24H), 0.82 (12H, m).

Compound 83

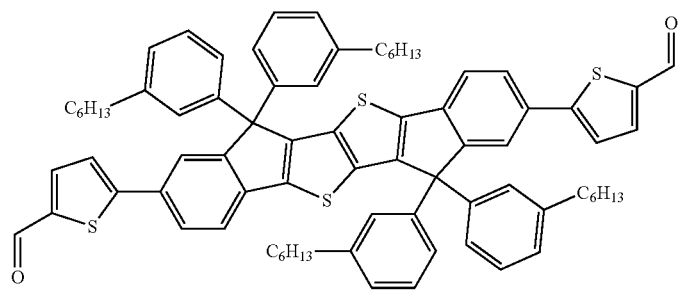

+

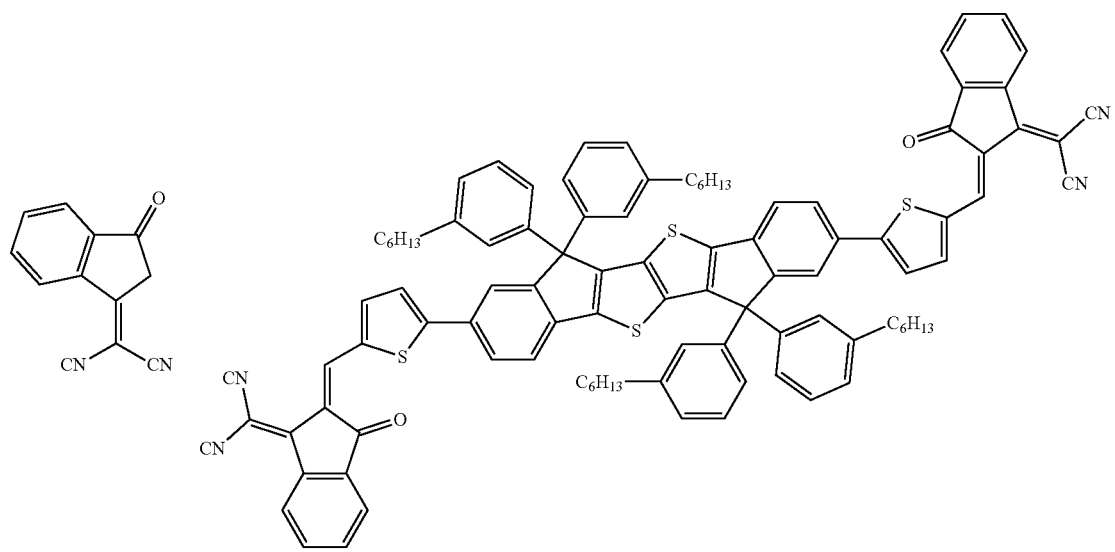

To a degassed solution of intermediate 16 (75 mg, 0.06 mmol) and 3-(dicyanomethylidene)indan-1-one (87 mg, 0.45 mmol) in chloroform (1.9 cm$^3$) is added pyridine (0.36 cm$^3$, 4.46 mmol) and the reaction mixture stirred at 23° C. for 18 hours. Methanol (40 cm$^3$) is added and the resulting suspension filtered and washed with methanol (3×10 cm$^3$). The resulting solid is purified by column chromatography eluting with a graded solvent system (40-60 petrol:dichloromethane; 1:1 to 2:3) to give compound 83 (63 mg, 65%) as a blue solid. $^1$H NMR (400 MHz CD$_2$Cl$_2$) 8.75 (2H, s), 8.60 (2H, dd, J 7.1, 11.4), 7.84 (2H, dd, J 6.9, 1.8), 7.63-7.80 (8H, m), 7.44 (2H, d, J 8.4), 7.39 (2H, d, J 4.2), 7.08-7.15 (8H, m), 7.04 (4H, d, J 7.6), 6.96 (4H, m), 2.49 (8H, t, J 7.6), 1.49 (8H, t, J 4.2), 1.09-1.26 (24H, m), 0.68-0.76 (12H, m).

Example 84

Compound 84

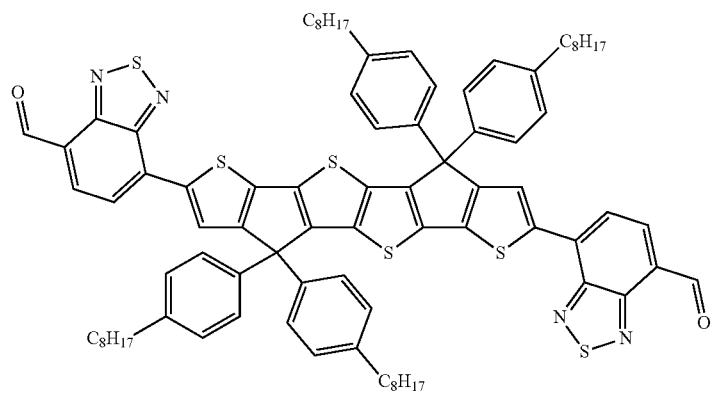

↓

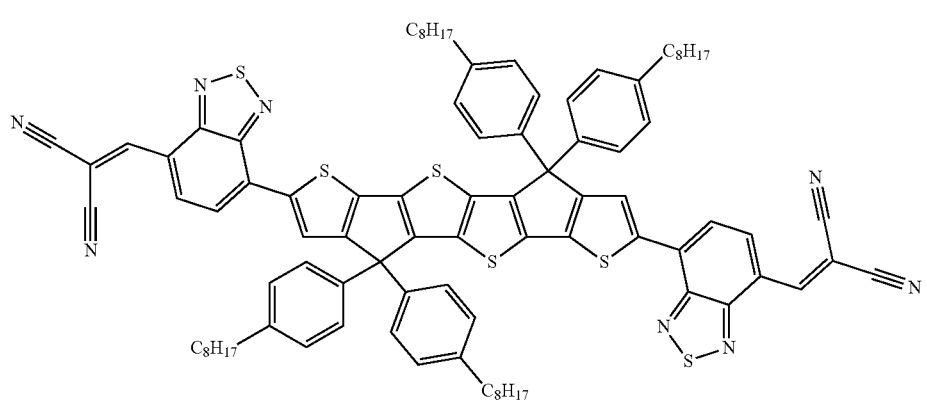

To a solution of intermediate 3 (450 mg, 0.32 mmol) in anhydrous chloroform (34 cm$^3$) is added pyridine (1.8 cm$^3$, 22 mmol). The mixture is then degassed with nitrogen before malononitrile (148 mg, 2.24 mmol) is added. The solution is then further degassed and stirred at 23° C. for 41 hours. The reaction mixture is then added to methanol (350 cm$^3$), washing in with additional methanol (2×10 cm$^3$) and dichloromethane (2×5 cm$^3$). Additional methanol (35 cm$^3$) is then added and the mixture stirred at 23° C. for 50 minutes before filtration, washing the solid with methanol (3×20 cm$^3$), 40-60 petrol (3×20 cm$^3$), 80-100 petrol (3×20 cm$^3$), cyclohexane (3×20 cm$^3$), diethyl ether (4×20 cm$^3$) and acetone (4×20 cm$^3$) to give compound 84 (429 mg, 89%) as a black solid. $^1$H NMR (400 MHz, CDCl$_3$) 8.75 (2H, s), 8.68 (2H, d, J 8.1), 8.29 (2H, s), 7.78 (2H, d, J 7.8), 7.24 (8H, d, J 8.4), 7.14 (8H, d, J 8.3), 2.58 (8H, t, J 7.7), 1.56-1.65 (8H, m), 1.20-1.37 (40H, m), 0.85 (12H, t, J 6.9).

Example 85

Compound 85

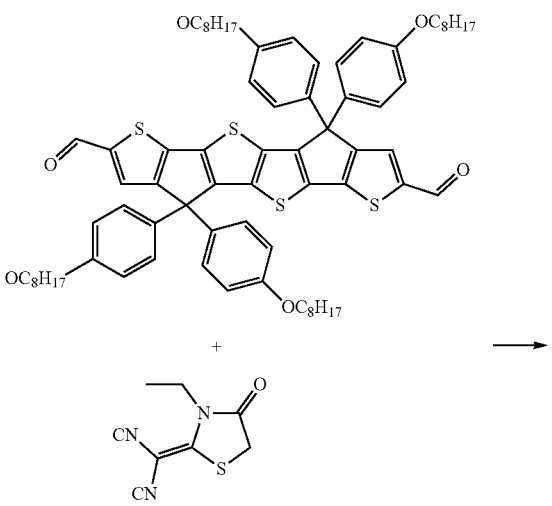

→

-continued

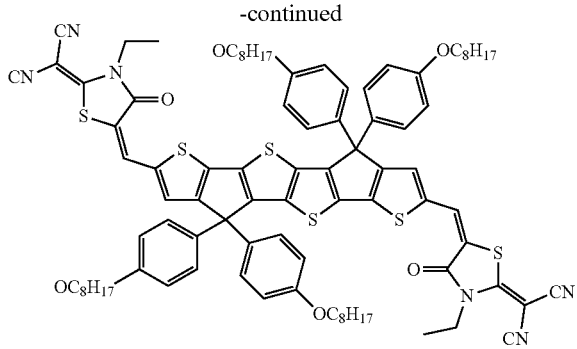

To a degassed solution of intermediate 12 (200 mg, 0.17 mmol) and 2-(3-ethyl-4-oxo-thiazolidin-2-ylidene)-malononitrile (225 mg, 1.16 mmol) in chloroform (5 cm³) is added pyridine (0.94 cm³, 12 mmol) followed by piperidine (992 mg, 11.7 mmol). The reaction is stirred at 23° C. for 18 hours and then precipitated with methanol (50 cm³), filtered and purified by flash chromatography eluting with a graded solvent system (40-60 petrol:dichloromethane; 3:2 to 2:3). The isolated material is then triturated in acetone (10 cm³) and the solid collected by filtration to give compound 85 (48 mg, 19%) as a blue solid. $^1$H NMR (400 MHz, CDCl$_3$) 7.97 (2H, s), 7.30 (2H, s), 7.01-7.08 (8H, m), 6.72-6.79 (8H, m), 4.24 (4H, q, J 7.1), 3.84 (8H, t, J 6.5), 1.67 (8H, q, J 6.8), 1.30-1.40 (14H, m), 1.11-1.28 (32H, m), 0.76-0.84 (12H, m).

Example 86

Intermediate 17

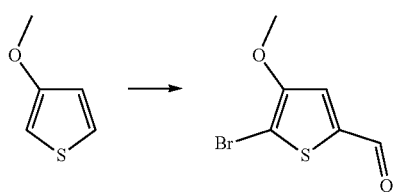

To a solution of 3-methoxy-thiophene (25.0 g, 219 mmol) in anhydrous N,N-dimethylformamide (100 cm³) at 0° C. is added dropwise, over 20 minutes, a solution of 1-bromopyrrolidine-2,5-dione (39.0 g, 219 mmol) in anhydrous N,N-dimethylformamide (150 cm³) and the reaction stirred to 23° C. for 65 hours. The reaction mixture is then diluted with diethyl ether (100 cm³), washed with brine (250 cm³) diluted with water (250 cm³) and the organic layer separated. The aqueous layer is then extracted with diethyl ether (2×100 cm³ then 50 cm³) and the combined organic extracts washed with brine (3×100 cm³) extracting the aqueous layer each time with diethyl ether (50 cm³). The combined organic extracts are then dried over anhydrous magnesium sulfate, filtered and concentrated in vacuo. The crude is purified by silica plug, eluting with a graded solvent system (40-60 petrol:dichloromethane; 1:0-4:1). The fractions containing product are concentrated in vacuo at 23° C. and rapidly placed on an ice water bath. Anhydrous tetrahydrofuran (150 cm³) is then added and the flask placed under nitrogen atmosphere. At 0° C. with stirring, additional anhydrous tetrahydrofuran (150 cm³) is added before the solution is cooled to −78° C. and lithium diisopropylamide (120 cm³, 240 mmol, 2.0 M in tetrahydrofuran/heptane/ethylbenzene) is added dropwise over 40 minutes. The reaction mixture is stirred at −78° C. for 2 hours before the reaction is quenched by the dropwise addition of anhydrous N,N-dimethylformamide (202 cm³, 2630 mmol), maintaining the reaction temperature at −78° C. The reaction is then allowed to warm to 23° C. with stirring over 17 hours before addition to ice (600 cm³), followed by the addition of pentane (400 cm³) and stirring for 17 hours. The pentane layer is isolated and the aqueous layer extracted with pentane (2×100 cm³). The combined pentane extracts are then washed with 20 wt % citric acid solution (2×150 cm³), water (150 cm³) and brine (150 cm³), extracting the aqueous layer each time with pentane (50 cm³). The combined pentane extracts are then dried over anhydrous magnesium sulfate, filtered and concentrated in vacuo. The crude is then purified by column chromatography eluting with a graded solvent system (40-60 petrol:dichloromethane; 1:0-3:2) to give intermediate 17 (1.96 g, 4%) as a yellow solid. $^1$H NMR (400 MHz, CDCl$_3$) 9.84 (1H, s), 6.90 (1H, s), 3.96 (3H, s).

Intermediate 18

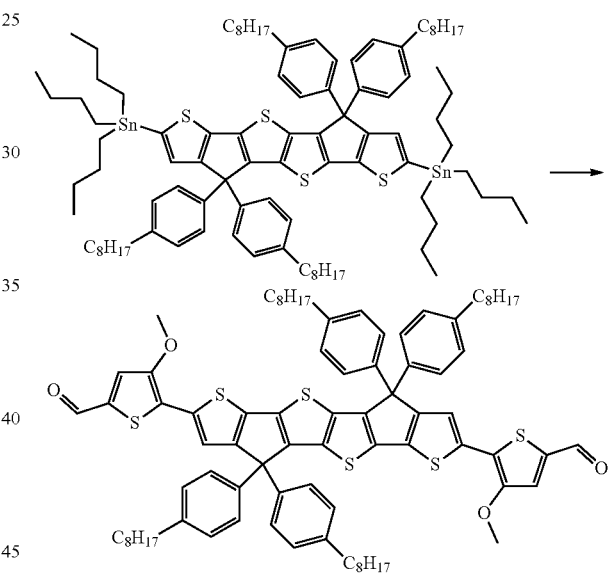

To a degassed solution of intermediate 2 (700 mg, 0.42 mmol) and 2-bromo-3-methoxythiophene-5-carboxaldehyde (205 mg, 0.93 mmol) in anhydrous toluene (45 cm³), tris(dibenzylideneacetone)dipalladium (31 mg, 0.03 mmol) and tris(o-tolyl)phosphine (39 mg, 0.13 mmol) are added. The reaction is then further degassed for 20 minutes before heating to 80° C. for 17 hours. The reaction mixture is then concentrated in vacuo, triturated with methanol (5×20 cm³) and the solid filtered. The crude product is then purified by silica plug eluting with a graded solvent system (40-60 petrol:dichloromethane; 1:1-1:4 then dichloromethane:methanol; 1:0-9.5:0.5). Final purification is achieved by column chromatography eluting with a graded solvent system (40-60 petrol:dichloromethane; 2:3-1:4 then dichloromethane:methanol; 1:0-9:1) to give intermediate 18 (134 mg, 23%) as a dark brown solid. $^1$H NMR (400 MHz, CDCl$_3$) 9.92 (2H, s), 7.31 (2H, s), 7.12-7.17 (8H, m), 7.08-7.12 (8H, m), 6.84 (2H, s), 4.01 (6H, s), 2.53-2.60 (8H, m), 1.54-1.64 (8H, m), 1.20-1.37 (40H, m), 0.87 (12H, t, J 6.9).

Compound 86

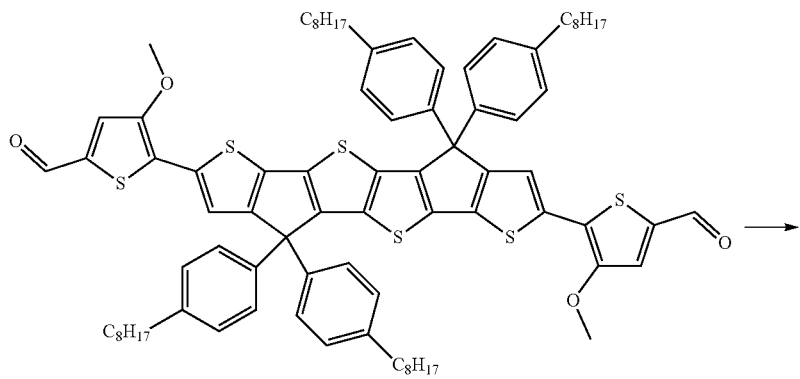

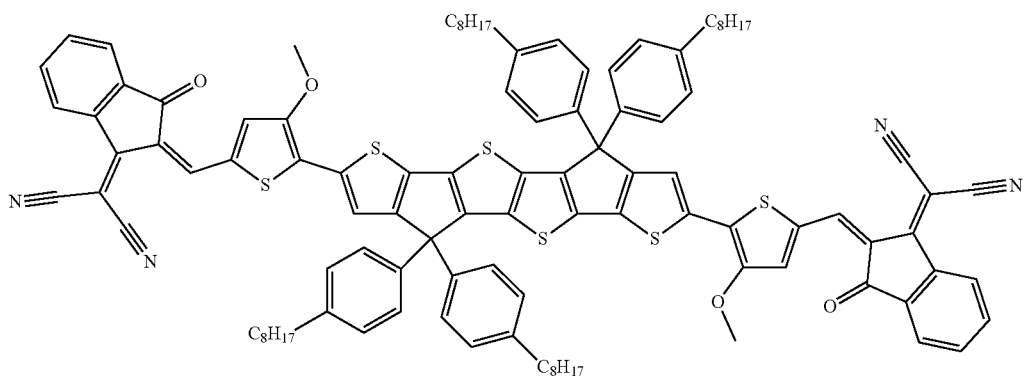

To a solution of intermediate 18 (134 mg, 0.10 mmol) in anhydrous chloroform (10 cm$^3$) is added pyridine (0.6 cm$^3$, 6.9 mmol). The mixture is then degassed with nitrogen before 3-(dicyanomethylidene)indan-1-one (134 mg, 0.69 mmol) is added. The solution is then further degassed and stirred at 23° C. for 20 minutes before additional anhydrous degassed chloroform (5 cm$^3$) is added and the reaction stirred for a further 3 hours 20 minutes. The reaction mixture is then added to methanol (250 cm$^3$), washing in with methanol (2×10 cm$^3$) and dichloromethane (2×5 cm$^3$). Additional methanol (50 cm$^3$) is then added before the solid is filtered and then washed with additional methanol (10×10 cm$^3$). The crude product is then partially purified by column chromatography using a graded solvent system (chloroform then dichloromethane:methanol; 9.5:0.5) with final purification achieved by trituration with methanol (3×10 cm$^3$) washing the filtered solid with 40-60 petrol (3×10 cm$^3$), cyclohexane (3×10 cm$^3$) and diethyl ether (3×10 cm$^3$) to give compound 86 (58 mg, 34%) as a black solid. $^1$H NMR (400 MHz, CDCl$_3$) 9.16 (2H, s), 8.62-8.67 (2H, m), 7.82-7.87 (2H, m), 7.63-7.72 (4H, m), 7.58 (2H, s), 7.12-7.19 (16H, m), 6.89 (2H, s), 4.13 (6H, s), 2.59 (8H, t, J 7.7), 1.57-1.65 (8H, m), 1.22-1.36 (40H, m), 0.87 (12H, t, J 6.8).

Example 87

Intermediate 19

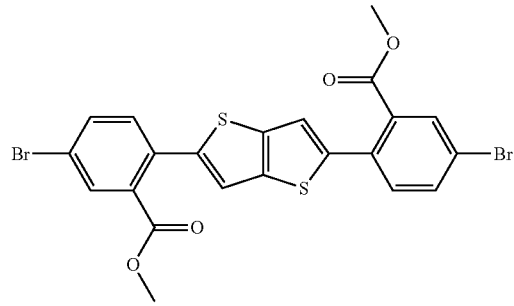

+

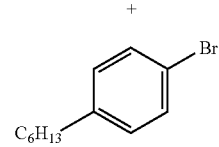

→

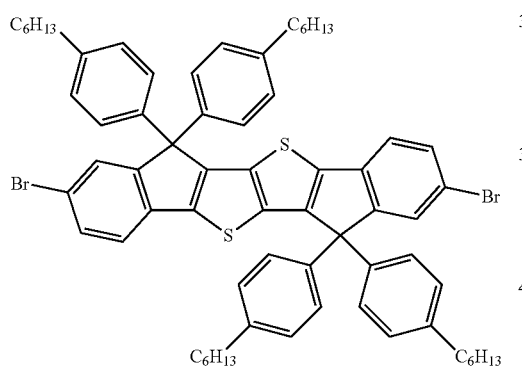

To a solution of 1-bromo-4-hexyl-benzene (10.0 g, 41.5 mmol) in anhydrous tetrahydrofuran (70 cm$^3$) at −78° C. is added n-butyllithium (16.6 cm$^3$, 41.5 mmol, 2.5 M in hexane) portion-wise over 10 minutes. The reaction is stirred for one hour and methyl 5-bromo-2-[5-(4-bromo-2-methoxycarbonyl-phenyl)thieno[3,2-b]thiophen-2-yl]benzoate (4.70 g, 8.29 mmol) added in a single portion. The reaction is warmed to 23° C. and stirred for 17 hours. The reaction is partitioned between diethyl ether (100 cm$^3$) and water (100 cm$^3$). The organic phase is washed with water (2×50 cm$^3$), brine (20 cm$^3$), dried over anhydrous magnesium sulfate, filtered and concentrated in vacuo. The resulting oil is triturated with 40-60 petrol, and the solid suspended in toluene (40 cm$^3$), p-toluene sulphonic acid (2.0 g) added and the reaction mixture stirred at 23° C. for 17 hours. The suspension is filtered and concentrated in vacuo. The resulting material is triturated in acetone at 50° C. then filtered at 0° C. to give intermediate 19 (3.4 g, 37%) as a yellow solid. $^1$H NMR (400 MHz, CDCl$_3$) 7.52 (2H, d, J 1.7), 7.40 (2H, dd, J 8.1, 1.8), 7.21 (2H, d, J 8.1), 7.06-7.15 (m, 16H), 2.52-2.61 (m, 8H), 1.58 (8H, m), 1.22-1.40 (24H, m), 0.83-0.92 (12H, m).

Intermediate 20

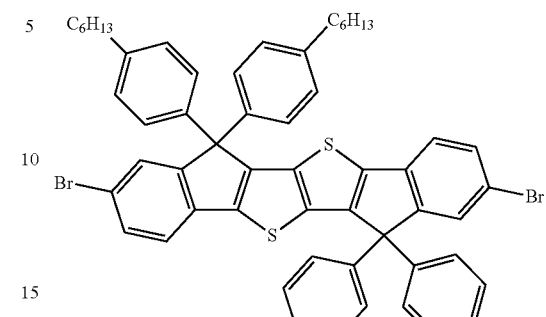

+

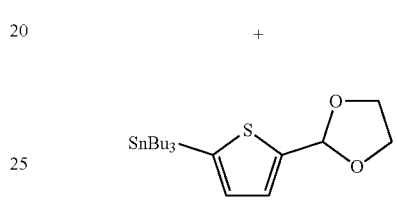

→

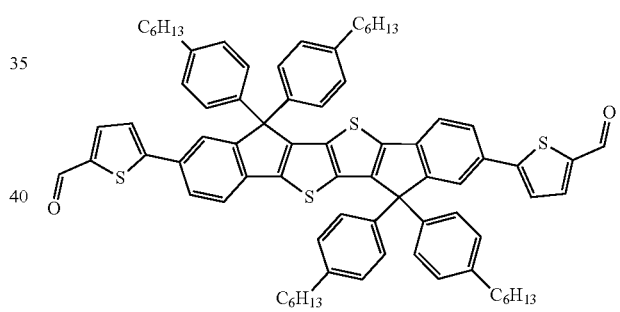

To a degassed solution of intermediate 19 (250 mg, 0.22 mmol), tributyl-(5-[1,3]dioxolan-2-yl-thiophen-2-yl)-stannane (273 mg, 0.51 mmol) and tris(o-tolyl)phosphine (2 mg, 0.01 mmol) in toluene (12.5 cm$^3$) is added bis(dibenzylideneacetone)palladium(0) (20 mg, 0.02 mmol). The solution is further degassed and heated to an external temperature of 140° C. for 18 hours. Methanol (20 cm$^3$) is added, the suspension is stirred for 30 minutes, filtered and the solid washed with methanol (20 cm$^3$). The resulting solid is purified by flash chromatography eluting with 40:60 petrol followed by dichloromethane. The resulting solid is dissolved in chloroform (30 cm$^3$) and stirred with hydrochloric acid (10 cm$^3$, 3 N) for 4 hours. The organic phase is washed with water (10 cm$^3$), dried over anhydrous magnesium sulfate, filtered before being concentrated in vacuo then triturated in acetone to give intermediate 20 (160 mg, 61%) as a yellow solid. $^1$H NMR (400 MHz, CDCl$_3$) 9.78 (2H, s), 7.59-7.66 (4H, m), 7.55 (2H, dd, J 8.0, 1.5), 7.33 (2H, d, J 7.9), 7.28 (2H, d, J 3.9), 7.11 (8H, d, J 8.0), 7.03 (8H, d, J 8.0), 2.49 (8H, t, J 7.9), 1.51 (8H, m), 1.23 (24H, m), 0.71-0.83 (12H, m).

Compound 87

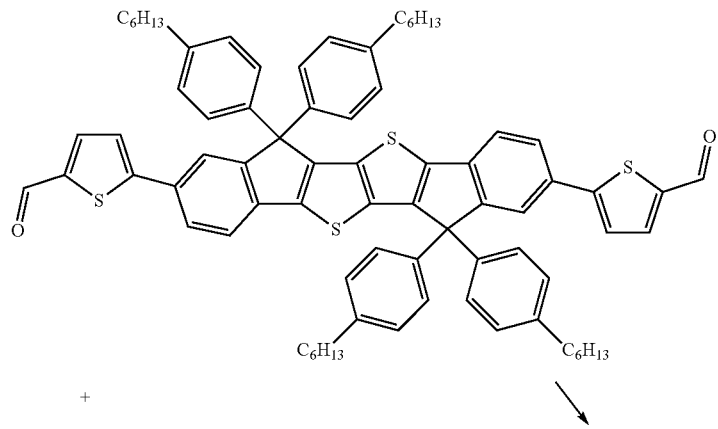

+

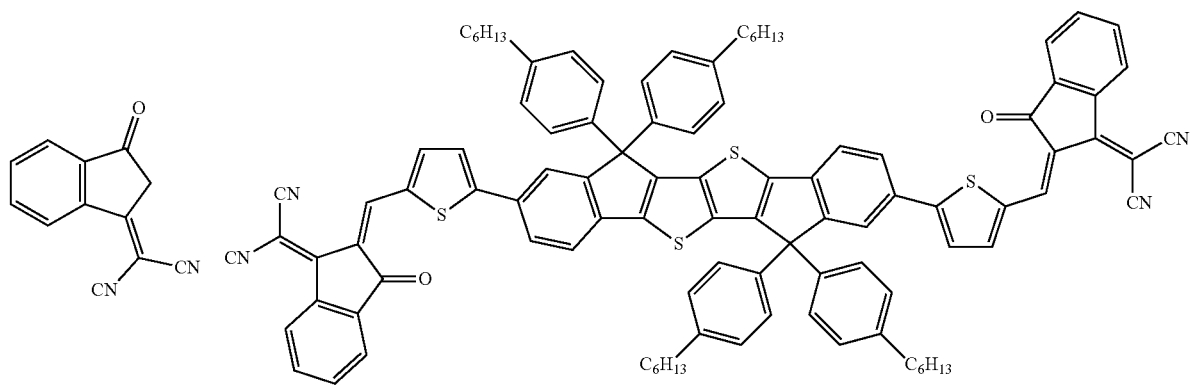

To a degassed solution of intermediate 20 (170 mg, 0.14 mmol) and 3-(dicyanomethylidene)indan-1-one (196 mg, 01.01 mmol) in chloroform (12.3 cm³) is added pyridine (799 mg, 10 mmol) and stirred at 23° C. for 18 hours. Methanol (30 cm³) is added and the resulting suspension filtered and the solid washed with methanol (30 cm³). The solid is triturated in acetone (10 cm³), filtered and washed with acetone (30 cm³) to give compound 87 (214 mg, 97%) as a blue solid. $^1$H NMR (400 MHz, CDCl$_3$) 8.87 (2H, s), 8.69-8.74 (2H, m), 7.92-8.00 (2H, m), 7.85 (2H, d, J 4.3), 7.72-7.82 (8H, m), 7.41-7.50 (m, 4H), 7.22 (8H, d, J 8.2), 7.14 (8H, d, J 8.1), 2.58 (8H, t, J 7.9), 1.57 (8H, m), 1.24-1.40 (24H, m), 0.82-0.91 (12H, m).

Example 88

Compound 88

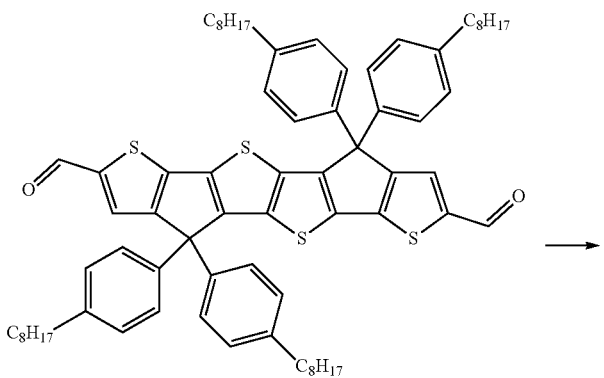

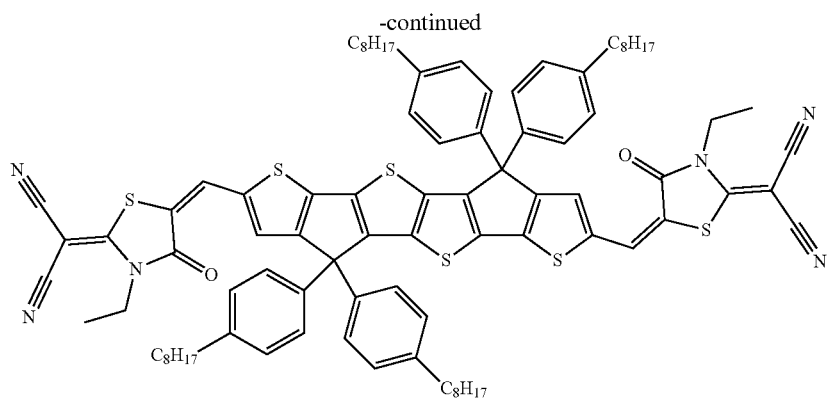

To a solution of intermediate 1 (303 mg, 0.27 mmol) in anhydrous chloroform (28 cm³) is added piperidine (0.1 cm³, 1.0 mmol). The mixture is then degassed with nitrogen before 2-(3-ethyl-4-oxothiazolidin-2-ylidene)malononitrile (134 mg, 0.69 mmol) is added. The solution is then further degassed and stirred at 23° C. for 17 hours. The reaction mixture is then added to methanol (300 cm³) washing in with methanol (3×5 cm³) and dichloromethane (5 cm³), before filtering the precipitate, washing in with methanol (2×10 cm³). The filtered solid is washed with additional methanol (3×10 cm³) and the crude product purified by column chromatography eluting with a graded solvent system (40-60 petrol:dichloromethane; 1:1-2:3). Final purification is achieved by trituration with methanol (3×10 cm³) washing the filtered solid with 40-60 petrol (3×10 cm³), diethyl ether (10 cm³) and acetone (10 cm³) to give compound 88 (144 mg, 36%) as a dark blue/black solid. ¹H NMR (400 MHz, CDCl₃) 8.05 (2H, s), 7.41 (2H, s), 7.10-7.16 (16H, m), 4.32 (4H, q, J 7.1), 2.58 (8H, t, J 7.8), 1.56-1.64 (8H, m), 1.40 (6H, t, J 7.1), 1.22-1.36 (40H, m), 0.87 (12H, t, J 6.9).

Example 89

Intermediate 21

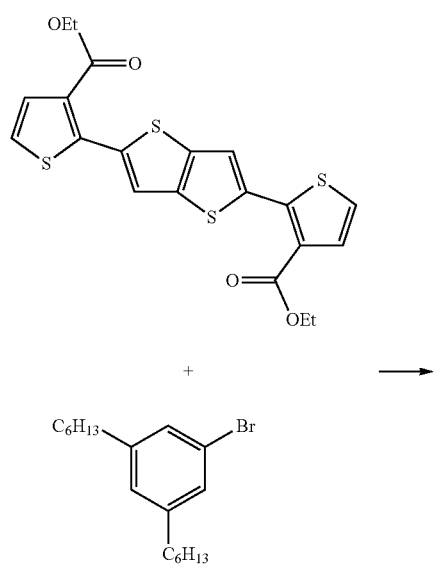

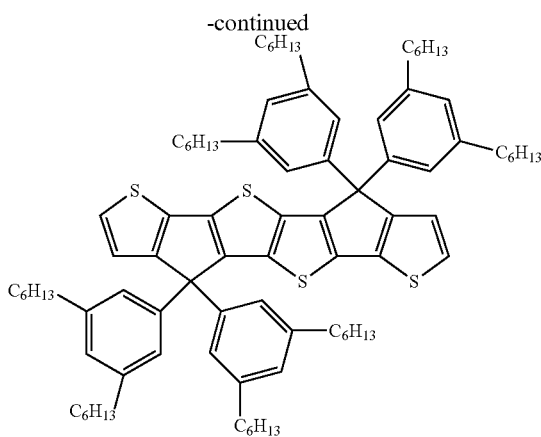

To a solution of 1-bromo-3,5-dihexyl-benzene (14.5 g, 44.6 mmol) in anhydrous tetrahydrofuran (60 cm³) at −78° C. is added dropwise n-butyllithium (17.8 cm³, 44.6 mmol, 2.5 M in hexane) over 10 minutes. The reaction is stirred for 2 hours and ethyl 2-[5-(3-ethoxycarbonyl-2-thienyl)thieno[3,2-b]thiophen-2-yl]thiophene-3-carboxylate (4.00 g, 8.92 mmol) added. The reaction is warmed to 23° C. and stirred for 17 hours. Water (100 cm³) added and the product extracted with ether (100 cm³). The organic phase is washed with water (2×50 cm³), dried over anhydrous magnesium sulfate, filtered and the solvent removed in vacuo. The crude is purified by flash chromatography eluting with 40-60 petrol then dichloromethane. The solid is suspended in toluene (40 cm³), p-toluene sulphonic acid (2.0 g) added and the reaction mixture heated at 60° C. for 4 hours. The solid is collected by filtration, washed with toluene (50 cm³) and purified by flash chromatography using a graded solvent system (40-60 petrol:dichloromethane; 1:0 to 95:5) to give intermediate 21 (2.5 g, 21%) as a pale brown oil. ¹H NMR (400 MHz, CDCl₃) 7.07 (2H, d, J 4.9), 6.96 (2H, d, J 4.9), 6.78 (4H, d, J 1.6), 6.74 (8H, d, J 1.5), 2.40 (16H, t, J 8.0), 1.40-1.48 (16H, m), 1.10-1.26 (48H, m), 0.69-0.82 (24H, m).

307
Intermediate 22

308
Compound 89

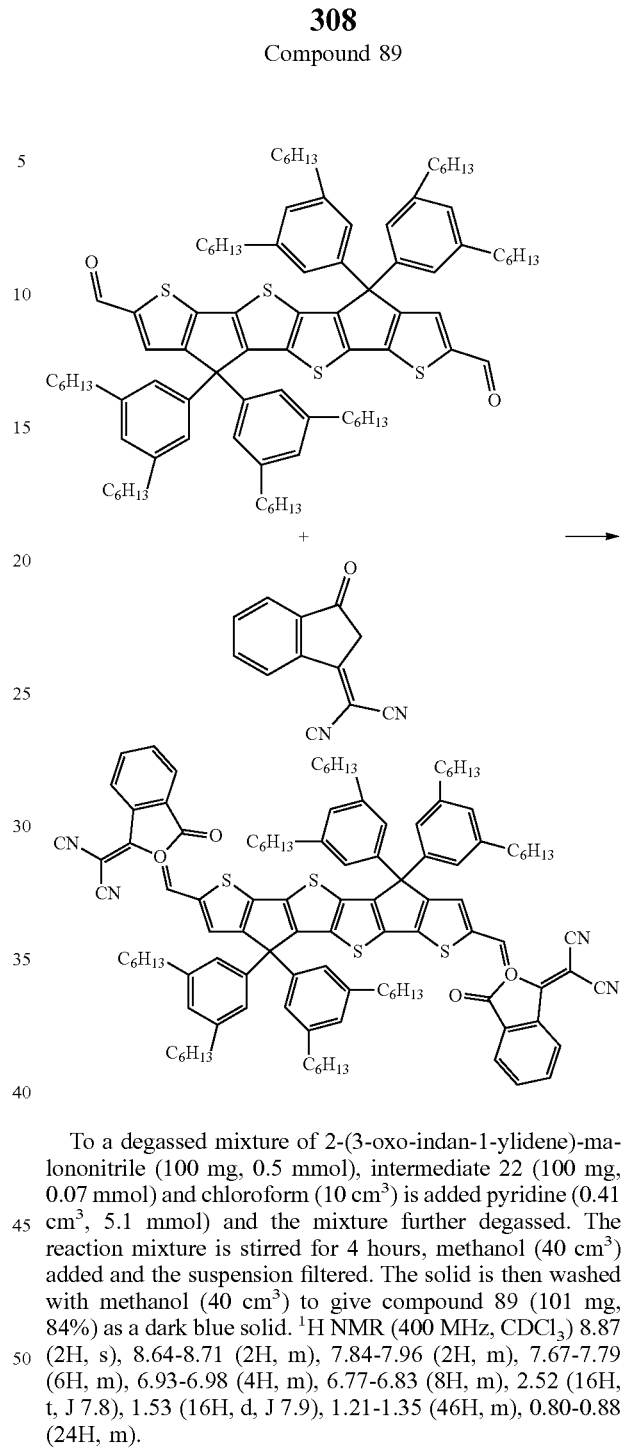

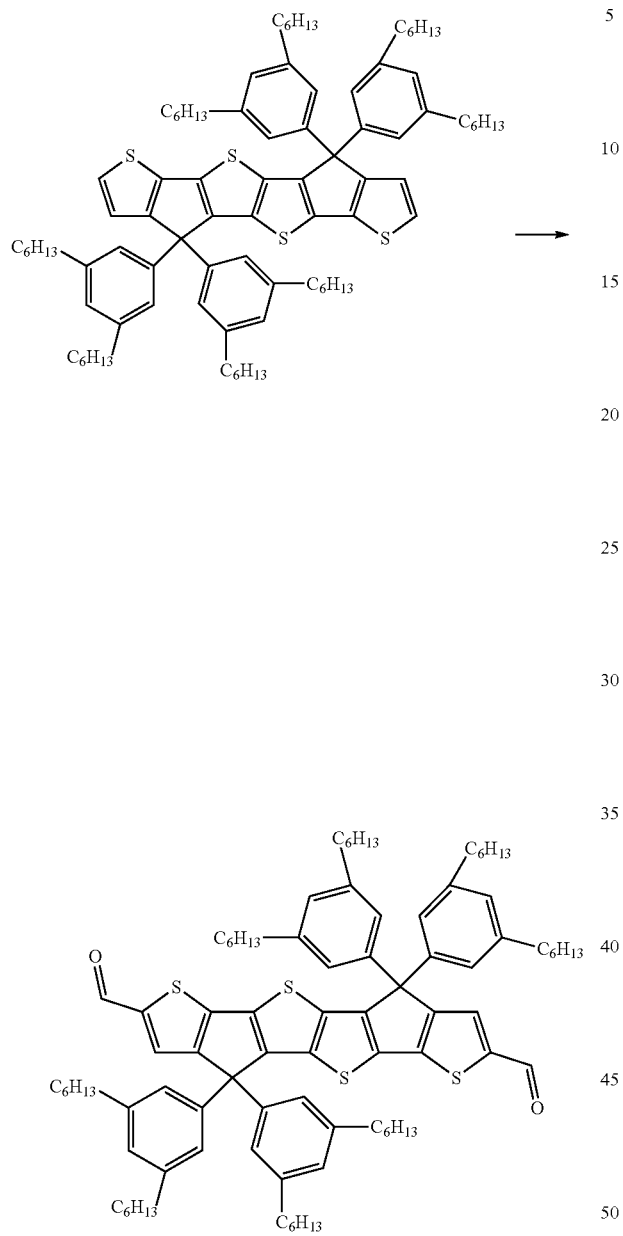

To intermediate 21 (0.50 g, 0.38 mmol), anhydrous N,N-dimethylformamide (0.40 cm³, 5.2 mmol) chloroform (20 cm³) at 0° C. is added dropwise phosphorus oxychloride (0.47 cm³, 5.0 mmol). The reaction is heated at 70° C. for 18 hours before cooling to 60° C., saturated aqueous sodium acetate solution (7 cm³) is added and the mixture stirred for 1 hour. The organic phase is separated and washed with water (20 cm³) dried with anhydrous sodium sulphate, filtered and the solvent removed in vacuo. The solid is triturated in acetone (3×5 cm³) to give intermediate 22 (400 mg, 76%) as a bright orange solid. $^1$H NMR (400 MHz, CD$_2$Cl$_2$) 9.78 (2H, s), 7.64 (2H, s), 6.90 (4H, d, J 1.6), 6.78 (8H, d, J 1.6), 2.46 (16H, d, J 7.9), 1.42-1.51 (16H, m), 1.17-1.28 (48H, m), 0.76-0.85 (24H, m).

To a degassed mixture of 2-(3-oxo-indan-1-ylidene)-malononitrile (100 mg, 0.5 mmol), intermediate 22 (100 mg, 0.07 mmol) and chloroform (10 cm³) is added pyridine (0.41 cm³, 5.1 mmol) and the mixture further degassed. The reaction mixture is stirred for 4 hours, methanol (40 cm³) added and the suspension filtered. The solid is then washed with methanol (40 cm³) to give compound 89 (101 mg, 84%) as a dark blue solid. $^1$H NMR (400 MHz, CDCl$_3$) 8.87 (2H, s), 8.64-8.71 (2H, m), 7.84-7.96 (2H, m), 7.67-7.79 (6H, m), 6.93-6.98 (4H, m), 6.77-6.83 (8H, m), 2.52 (16H, t, J 7.8), 1.53 (16H, d, J 7.9), 1.21-1.35 (46H, m), 0.80-0.88 (24H, m).

Example 90

Intermediate 23

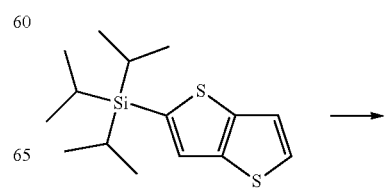

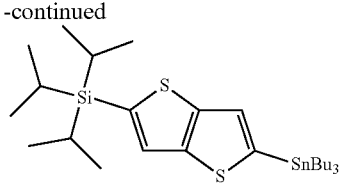

To a solution of triisopropyl-thieno[3,2-b]thiophen-2-yl-silane (11.86 g, 40.0 mmol) in anhydrous tetrahydrofuran (100 cm$^3$) at −78° C. is added dropwise n-butyllithium (20.8 cm$^3$, 52.0 mmol, 2.5 M in hexane) over 20 minutes. After addition, the reaction mixture is stirred at −78° C. for 120 minutes and then tributyltin chloride (15.8 cm$^3$, 56.0 mmol) is added in one go. The mixture is then allowed to warm to 23° C. over 17 hours and the solvent removed in vacuo. The crude is diluted in 40-60 petrol (250 cm$^3$) and filtered through a zeolite plug (50 g). The plug is washed with additional 40-60 petrol (250 cm$^3$). The solvent is removed in vacuo to give intermediate 23 (23.1 g, 99%) as a clear oil. $^1$H-NMR (400 MHz, CD$_2$Cl$_2$) 7.27 (1H, d J 0.7), 7.1 (1H, s), 1.35-1.63 (9H, m), 1.17-1.34 (12H, m), 0.98-1.13 (18H, m), 0.65-0.91 (12H, m).

Intermediate 24

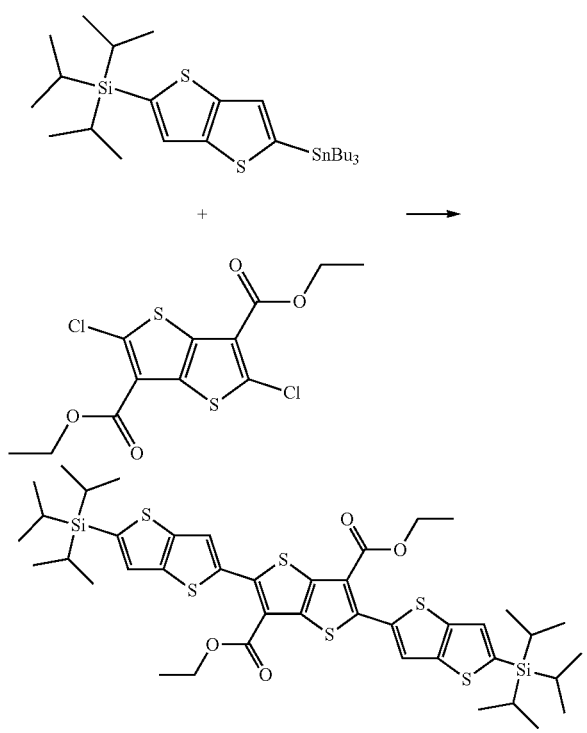

A mixture of intermediate 9 (7.5 g, 21 mmol), intermediate 23 (17.8 g, 30.4 mm) and anhydrous toluene (300 cm$^3$) is degassed by nitrogen for 25 minutes. To the mixture is added tetrakis(triphenylphosphine)palladium(0) (500 mg, 0.43 mmol) and the mixture further degassed for 15 minutes. The mixture is stirred at 85° C. for 17 hours. The reaction mixture is filtered hot through a celite plug (50 g) and washed through with hot toluene (100 cm$^3$). The solvent reduced in vacuo to 100 cm$^3$ and cooled in an ice bath to form a suspension. The product is filtered, washed with water (100 cm$^3$) and methanol (100 cm$^3$), collected and dried under vacuum to give intermediate 24 (9.5 g, 71%) as a yellow crystalline solid. $^1$H-NMR (400 MHz, CDCl$_3$) 7.75 (2H, d, J 0.7), 7.30 (2H, d, J 0.7), 4.36 (4H, q, J 7.2), 1.23-1.43 (12H, m), 1.07 (36H, d, J 7.3).

Intermediate 25

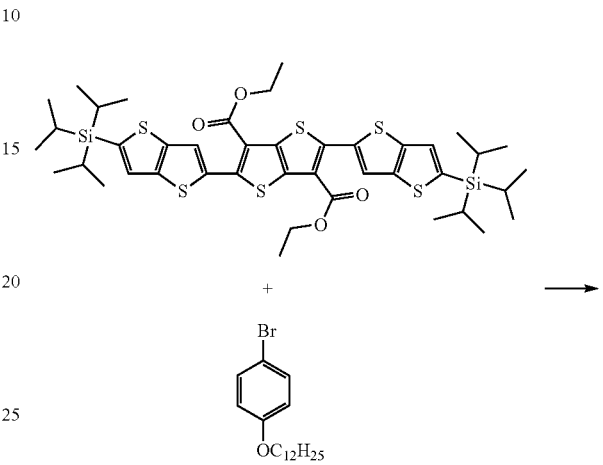

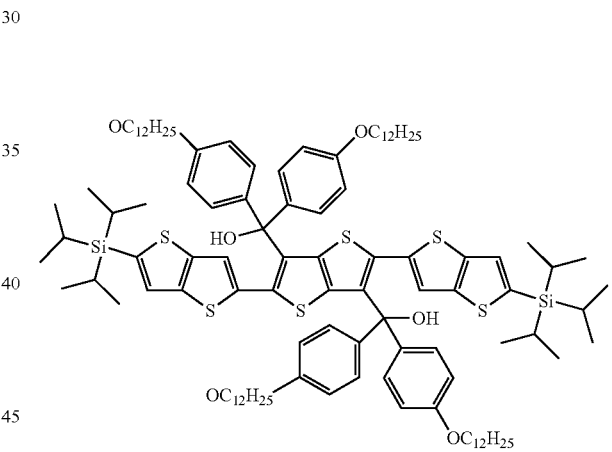

To a suspension of 1-bromo-4-dodecyloxy-benzene (10.6 g, 30.9 mmol) in anhydrous tetrahydrofuran (167 cm$^3$) at −78° C. is added dropwise tert-butyllithium (36.4 cm$^3$, 61.8 mmol, 1.7 M in pentane) over 60 minutes. After addition, the reaction mixture is stirred at −78° C. for 120 minutes. Intermediate 24 (6.0 g, 6.9 mmol) is added in one go. The mixture is then allowed to warm to 23° C. over 17 hours. Diethyl ether (200 cm$^3$) and water (200 cm$^3$) are added and the mixture stirred at 23° C. for 30 minutes. The product is extracted with diethyl ether (3×200 cm$^3$). The combined organics is dried over anhydrous magnesium sulfate, filtered and the solvent removed in vacuo. The crude is purified using silica gel column chromatography (40-60 petrol:diethyl ether; 7:3). The solid triturated with methanol (200 cm$^3$) and collected by filtration to give intermediate 25 (10.3 g, 82%) as a cream solid. $^1$H NMR (400 MHz, CDCl$_3$) 7.15-7.23 (10H, m), 6.77-6.85 (8H, m), 6.65 (2H, d, J 0.7), 3.45 (2H, s), 3.95 (8H, s), 1.71-1.85 (8H, m), 1.20-1.52 (72H, m), 1.11 (36H, d, J 7.3), 0.82-0.95 (12H, m).

Intermediate 26

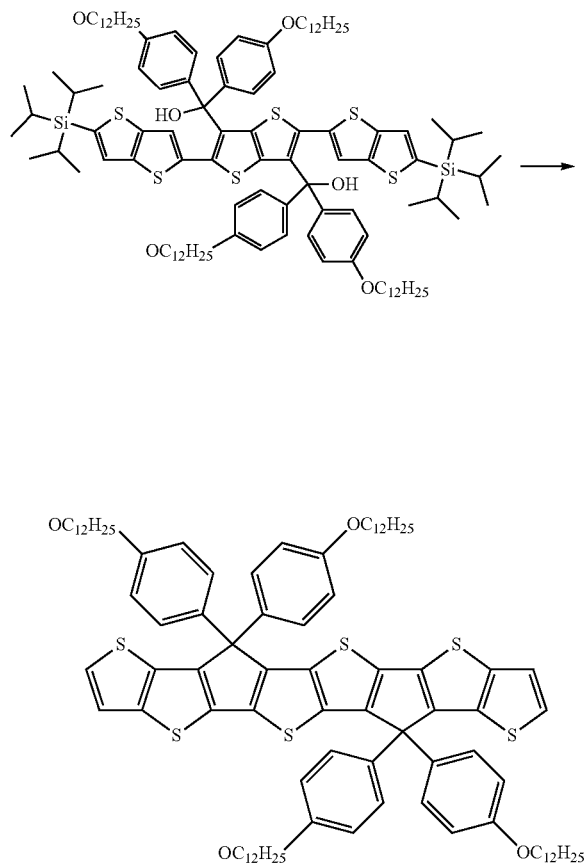

Nitrogen gas is bubbled through a solution of intermediate 25 in anhydrous toluene (250 cm³) at 0° C. for 60 minutes. Amberlyst 15 strong acid (50 g) is added and the mixture degassed for a further 30 minutes. The resulting suspension is stirred at 70° C. for 2 hours. The reaction mixture allowed to cool to 23° C., filtered and the solvent removed in vacuo. The crude is triturated with acetone (200 cm³). The solid is filtered to give intermediate 26 (4.2 g, 89%) as a dark orange solid. ¹H NMR (400 MHz, CDCl₃) 7.28 (4H, m), 7.16-7.24 (8H, m), 6.75-6.93 (8H, m), 3.91 (8H, t, J 6.5), 1.67-1.82 (8H, m), 1.37-1.48 (8H, m), 1.19-1.37 (64H, m), 0.80-1.00 (12H, m).

Intermediate 27

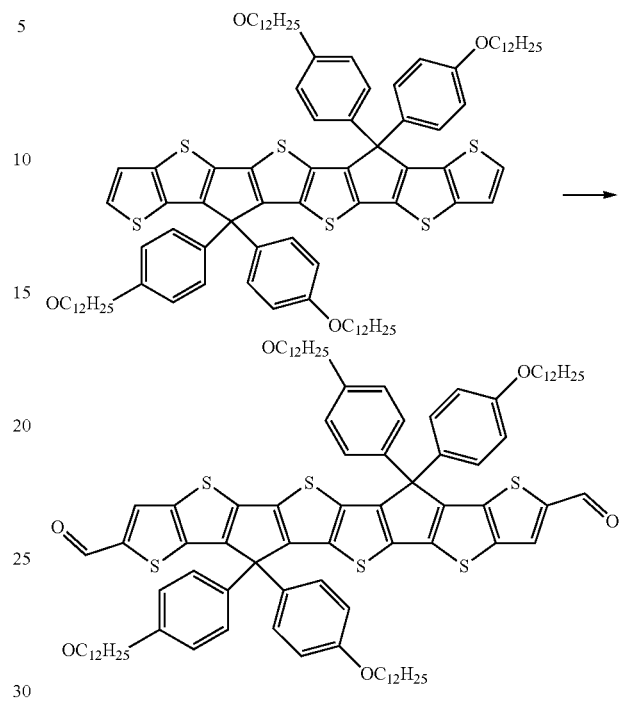

To a solution of intermediate 26 (0.6 g, 0.41 mmol) in anhydrous tetrahydrofuran (24 cm³) at −78° C. is added dropwise n-butyllithium (0.7 cm³, 1.6 mmol, 2.5 M in hexane) over 10 minutes. After addition, the reaction mixture is stirred at −78° C. for 60 minutes. N,N-dimethylformamide (0.16 cm³, 2.4 mmol) is added in one go and the mixture is allowed to warm to 23° C. over 2 hours. Diethyl ether (50 cm³) and water (50 cm³) are added and the mixture stirred at 23° C. for 30 minutes. The product is extracted with diethyl ether (3×100 cm³). The combined organics are dried over anhydrous magnesium sulfate, filtered and the solvent removed in vacuo. The crude is purified using silica gel column chromatography (40-60 petrol:dichloromethane; 8:2) to give intermediate 27 (380 mg, 61%) as a dark red oil. ¹H NMR (400 MHz, CDCl₃) 9.90 (2H, s), 7.94 (2H, s), 7.08-7.23 (8H, m), 6.78-6.93 (8H, m), 3.91 (8H, t, J 6.5), 1.65-1.85 (8H, m), 1.17-1.51 (72H, m), 0.82-0.96 (12H, m).

Compound 90

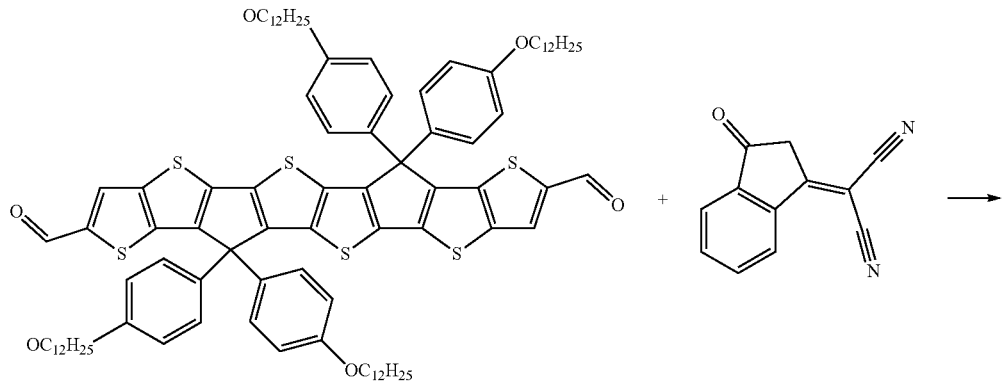

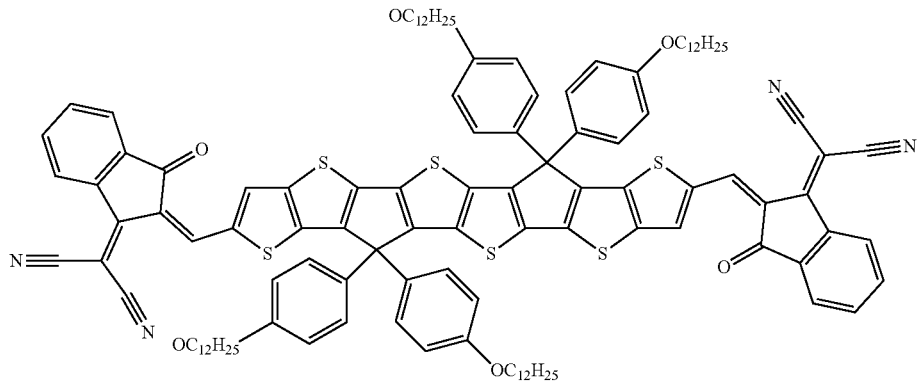

To a solution of intermediate 27 (370 mg, 0.24 mmol) in anhydrous chloroform (26 cm$^3$) is added pyridine (1.4 cm$^3$, 17 mmol). The mixture is then degassed with nitrogen before 3-(dicyanomethylidene) indan-1-one (280 mg, 1.4 mmol) is added. The solution is then further degassed and stirred at 23° C. for 20 minutes. The mixture is stirred at 40° C. for 2 hours and then the solvent is removed in vacuo. The crude is triturated with ethanol (200 cm$^3$) to produce a heavy suspension which is collected by filtration and the solid washed with acetone (50 cm$^3$). The crude is dissolved in dichloromethane (20 cm$^3$) added precipitated into acetone (250 cm$^3$) to form a suspension. The solid collected by filtration to give compound 90 (437 mg, 96%) as a gray solid. $^1$H NMR (400 MHz, CDCl$_3$) 8.87 (2H, s), 8.63-8.74 (2H, m), 8.13 (2H, s), 7.87-7.97 (2H, m), 7.68-7.82 (4H, m), 7.23 (8H, d, J 8.8), 6.90 (8H, d, J 9.0), 3.92 (8H, t, J 6.5), 1.69-1.84 (8H, m), 1.16-1.52 (72H, m), 0.80-0.97 (12H, m).

Example 91

Intermediate 28

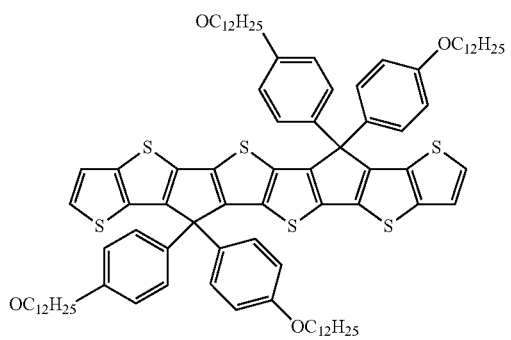

→

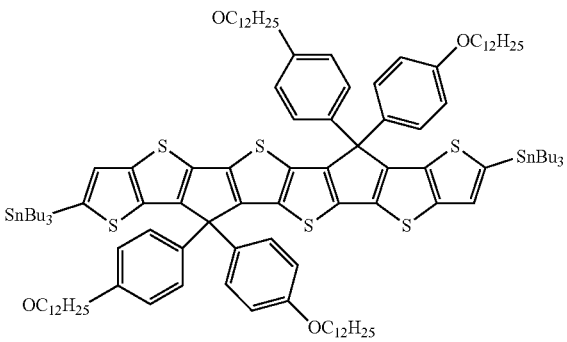

To a solution of intermediate 26 (1.6 g, 1.1 mmol) in anhydrous tetrahydrofuran (47 cm$^3$) at −78° C. is added dropwise n-butyllithium (1.7 cm$^3$, 4.3 mmol, 2.5 M in hexane) over 20 minutes. After addition, the reaction mixture is stirred at −78° C. for 60 minutes. Tributyltin chloride (1.3 cm$^3$, 4.9 mmol) is added in one go and then the mixture is allowed to warm to 23° C. over 72 hours. The solvent removed in vacuo. The crude is purified by passing through a zeolite plug (40-60 petrol) followed by triturating in ethanol (2×100 cm$^3$) to give intermediate 28 (2.0 g, 88%) as a dark red oil. $^1$H NMR (400 MHz, CDCl$_3$) 7.28 (2H, s), 7.18-7.24 (8H, m), 6.79-6.87 (8H, m), 3.91 (8H, t, J 6.6), 1.51-1.83 (32H, m), 1.20-1.48 (114H, m), 1.07-1.18 (15H, m), 0.76-1.03 (69H, m).

Compound 91

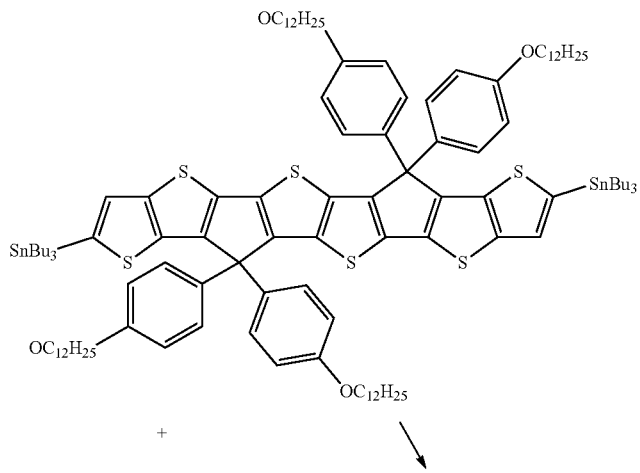

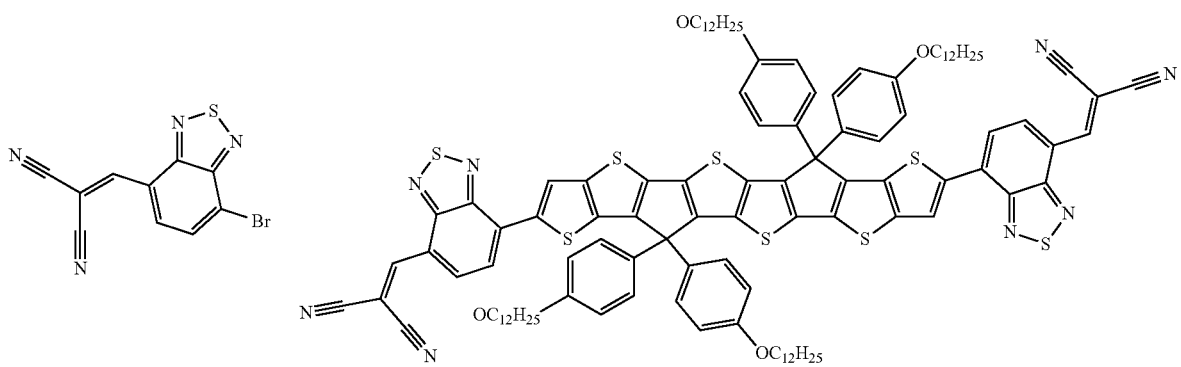

A mixture of intermediate 28 (700 mg, 0.34 mmol), 2-(7-bromo-benzo[1,2,5]thiadiazol-4-ylmethylene)-malononitrile (218 mg, 0.75 mmol), tri-o-tolyl-phosphine (31 mg, 0.75 mmol) and anhydrous toluene (41 cm$^3$) is degassed by nitrogen for 10 minutes. To the mixture is added tris(dibenzylideneacetone) dipalladium(0) (25 mg, 0.03 mmol) and the mixture further degassed for 15 minutes. The mixture is stirred at 80° C. for 17 hours and the solvent removed in vacuo. Dichloromethane (200 cm$^3$) and water (200 cm$^3$) are added and the mixture stirred at 23° C. for 30 minutes. The product is extracted with dichloromethane (3×100 cm$^3$). The combined organics are dried over anhydrous magnesium sulfate, filtered and the solvent removed in vacuo. The crude is dissolved in dichloromethane and precipitated into acetone. The solid collected by filtration to give compound 91 (451 mg, 70%) as a grey solid. $^1$H-NMR (400 MHz, CD$_2$Cl$_2$) 8.55-8.74 (6H, m), 7.83 (2H, d, J 7.8), 7.14 (8H, d, J 8.8), 6.77 (8H, d, J 8.8), 3.82 (8H, t, J 6.6), 1.58-1.69 (8H, m), 1.07-1.40 (72H, m), 0.68-0.85 (12H, m).

Example 92

Intermediate 29

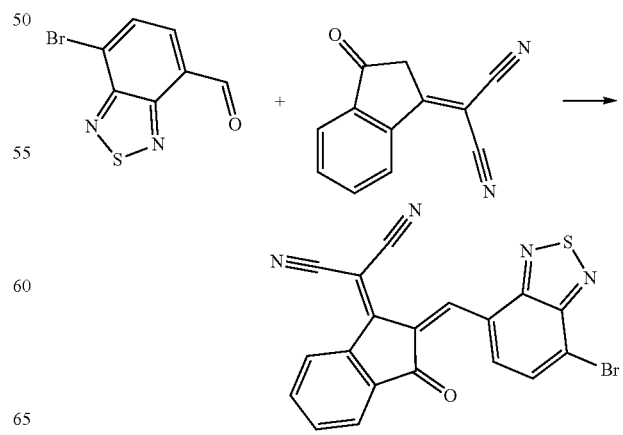

To a solution of 7-bromo-benzo[1,2,5]thiadiazole-4-carbaldehyde (2.0 g, 8.2 mmol) in anhydrous chloroform (875 cm³) is added pyridine (46.5 cm³, 576 mmol). The mixture is then degassed with nitrogen before 3-(dicyanomethylidene) indan-1-one (4.0 g, 21 mmol) is added. The solution is then further degassed and stirred for 20 minutes. The mixture is stirred at 40° C. for 17 hours. The solid collected by filtration and washed with acetone (200 cm³), water (200 cm³), diethyl ether (200 cm³) and dichloromethane (200 cm³) to give intermediate 29 (3.0 g, 86%) as a pale yellow solid with very limited solubility.

Compounds 92 and 93

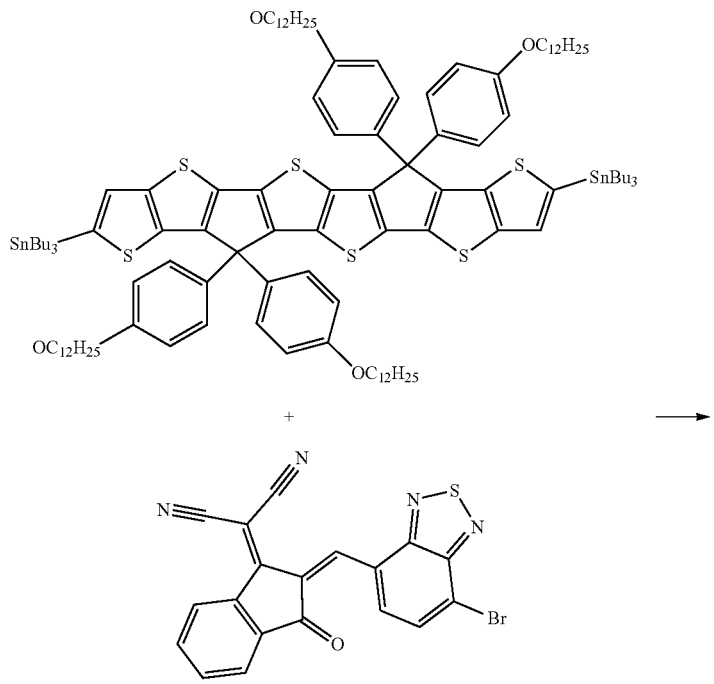

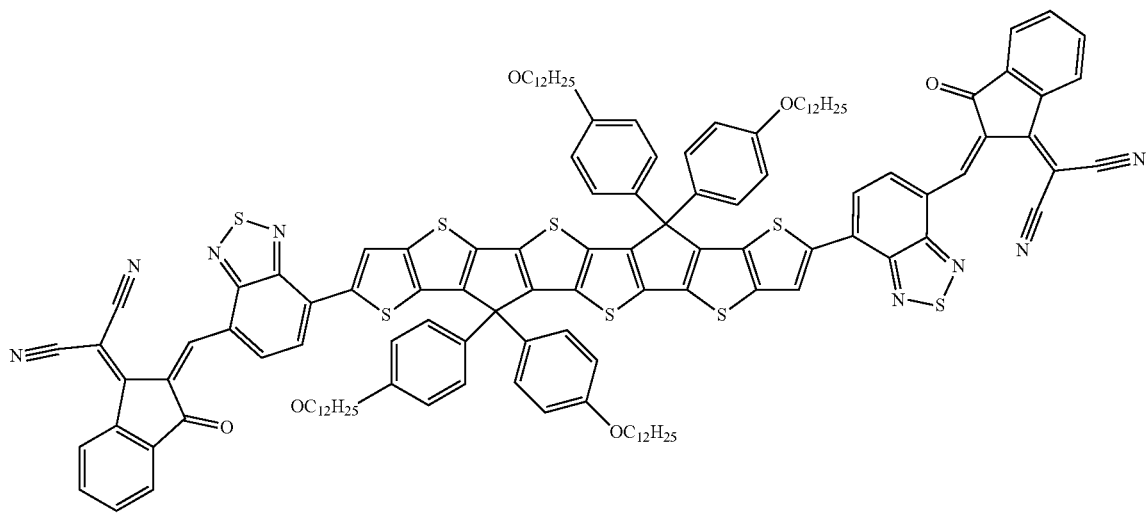

Compound 92

+

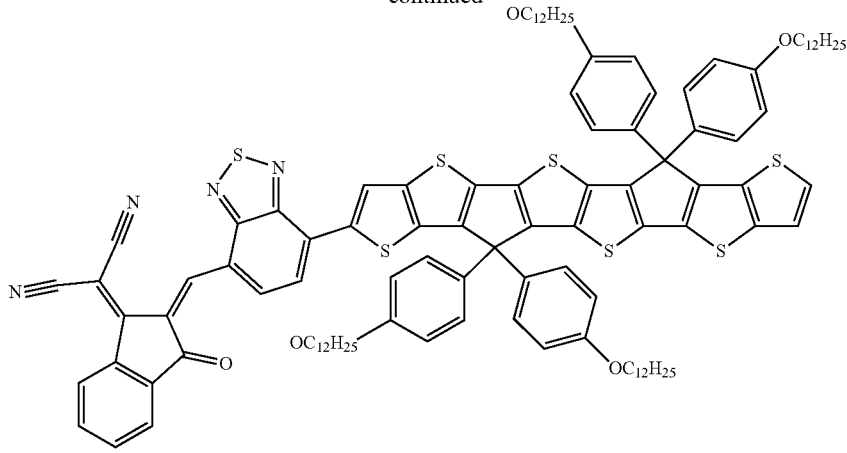

Compound 93

A mixture of intermediate 28 (700 mg, 0.34 mmol), intermediate 29 (356 mg, 0.85 mmol), tri-o-tolyl-phosphine (31 mg, 0.10 mmol) and anhydrous toluene (36 cm$^3$) is degassed by nitrogen for 10 minutes. To the mixture is added tris(dibenzylideneacetone) dipalladium(0) (25 mg, 0.03 mmol) and the mixture further degassed for 15 minutes. The mixture is stirred at 80° C. for 17 hours and the solvent removed in vacuo. The crude is stirred in acetone (200 cm$^3$) to form a suspension and the solid collected by filtration. The crude is purified using silica gel column chromatography eluting with 40-60 petrol:dichloromethane; 8:2 to give compound 92 (217 mg, 30%) and compound 93 (136 mg, 22%) as a dark grey solids. Compound 92: $^1$H-NMR (400 MHz, CD$_2$Cl$_2$) 9.32-9.52 (2H, m), 9.15 (2H, d, J 8.1), 8.52-8.75 (4H, m), 7.61-7.98 (8H, m), 7.16 (8H, d, J 8.8), 6.79 (8H, d, J 8.8), 3.83 (8H, t, J 6.5), 1.56-1.73 (8H, m), 0.94-1.38 (72H, m), 0.77 (12H, t, J 6.6). Compound 93: $^1$H-NMR (400 MHz, CD$_2$Cl$_2$) 9.41 (1H, s), 9.14 (1H, d, J 8.0), 8.56-8.71 (2H, m), 7.57-7.97 (4H, m), 7.02-7.30 (10H, m), 6.74 (8H, dd, J 9.0 18.1), 3.70-3.91 (8H, m), 1.54-1.72 (8H, m), 1.06-1.72 (72H, m), 0.70-0.84 (12H, m).

Example 94

Intermediate 30

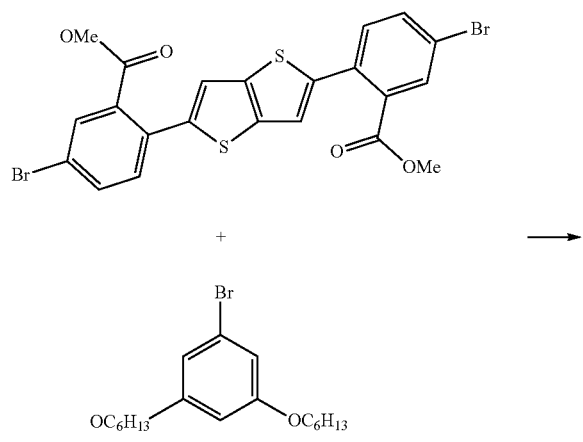

To a solution of 1-bromo-3,5-bis-hexyloxy-benzene (8.96 g, 25.1 mmol) in anhydrous tetrahydrofuran (50 cm$^3$) at −78° C. is added dropwise n-butyllithium (10.0 cm$^3$, 25.1 mmol). The mixture is stirred at −78° C. for 2 hours before methyl 5-bromo-2-[5-(4-bromo-2-methoxycarbonyl-phenyl)-3a,6a-dihydrothieno[3,2-b]thiophen-2-yl]benzoate (2.85 g, 5.0 mmol) is added in one portion. The mixture is allowed to warm to 23° C. and stirred for 17 hours. The reaction is carefully poured onto water (100 cm$^3$) and the organics extracted with dichloromethane (2×100 cm$^3$) is added. The combined organic layer is dried over anhydrous magnesium sulfate, filtered and the solvent removed in vacuo. The residue is purified by column chromatography (40-60 petol:dichloromethane; 6:4). The intermediate diol (3.42 g, 3.65 mmol) is taken up in toluene (200 cm$^3$) and p-toluenesulfonic acid monohydrate (1.39 g, 7.30 mmol) added. The mixture is stirred at 50° C. for 90 minutes and the mixture allowed to cool to 23° C. Water (100 cm$^3$) is added and the organic layer washed with water (100 cm$^3$) and brine (100 cm$^3$). The organic layer is dried over anhydrous magnesium sulfate, filtered and the solvent removed in vacuo. The crude product is triturated in ice-cooled acetone and the solid collected by filtration to give intermediate 30 (3.08 g, 87%) as a yellow solid. $^1$H NMR (400 MHz, CDCl$_3$) 7.54 (2H, d, J 1.8), 7.39 (2H, dd, J 8.1, 1.8), 7.17 (2H, d, J 8.1), 6.32 (12H, bs), 3.83 (16H, td, J 6.6, 1.6), 1.69 (16H, p, J 6.8), 1.37 (16H, tq, J 9.2, 4.9, 2.9), 1.29 (32H, dp, J 7.4, 4.6, 3.8), 0.80-0.91 (24H, m).

321
Intermediate 31

322
Intermediate 32

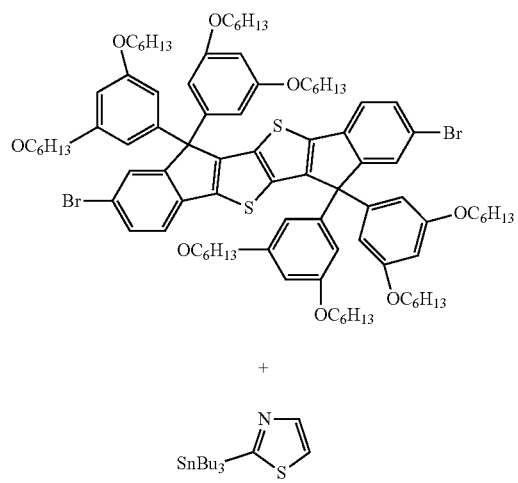

+

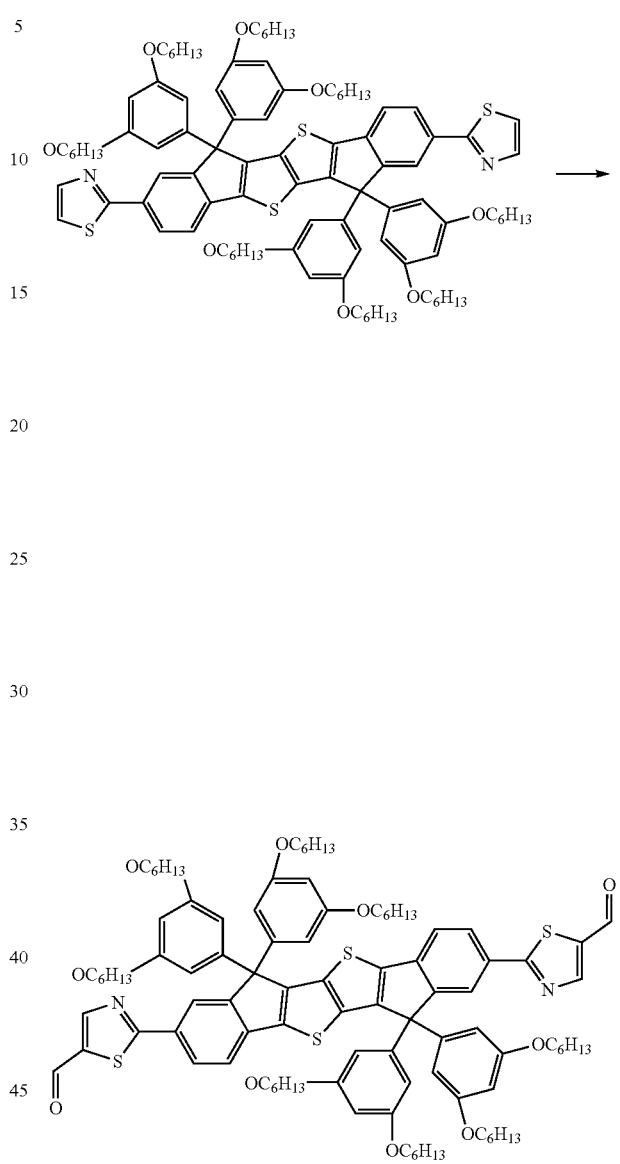

To a degassed solution of intermediate 30 (1.04 g, 0.66 mmol), 2-tributylstannanyl-thiazole (0.62 cm$^3$, 1.97 mmol) in toluene (50 cm$^3$) and N,N-dimethylformamide (10 cm$^3$) is added (tetrakis(triphenylphosphine))palladium(0) (76.1 mg, 0.07 mmol) and the mixture stirred at 110° C. for 5 days. The mixture is allowed to cool to 23° C. and the solvents removed in vacuo. The crude product is purified by column chromatography using a graded solvent system (40-60 petrol:dichloromethane: 6.5:4.5 to 3:7) to give intermediate 31 (973 mg, 93%) as a yellow oil. $^1$H NMR (400 MHz, CDCl$_3$) 8.07 (2H, d, J 1.5), 7.94 (2H, dd, J 8.0, 1.5), 7.82 (2H, J 3.3), 7.40 (2H, d, J 7.9), 7.27 (2H, d, J 3.2), 6.43 (8H, d, J 2.2), 6.34 (4H, t, J 2.2), 3.86 (16H, td, J 6.6, 1.8), 1.65-1.73 (16H, m), 1.25-1.42 (48H, m), 0.81-0.89 (24H, m).

To a stirred solution of intermediate 31 (973 mg, 0.61 mmol) in anhydrous tetrahydrofuran (100 cm$^3$) at −78° C. is added dropwise n-butyllithium (0.98 cm$^3$, 2.5 mmol, 2.5 M in hexane). The reaction mixture is stirred for 2 hours before anhydrous N,N-dimethylformamide (0.21 cm$^3$, 2.8 mmol) is added. The mixture is allowed to warm to 23° C., stirred for 4 hours and methanol (3 cm$^3$) added. The mixture is diluted with Et$_2$O (100 cm$^3$) and washed with water (2×100 cm$^3$). The organic layer is dried over anhydrous magnesium sulfate, filtered and the solvent removed in vacuo. The crude is purified by column chromatography using a graded solvent system (40-60 petrol:dichloromethane: 4:6 to 1:9) to give intermediate 32 (680 mg, 67%) as a red oil. $^1$H NMR (400 MHz, CDCl$_3$) 10.01 (2H, s), 8.37 (2H, s), 8.12 (2H, d, J 1.5), 7.99 (2H, dd, J 8.0, 1.6), 7.42 (2H, d, J 8.0), 6.40 (8H, d, J 2.2), 6.34 (4H, t, J 2.2), 3.85 (16H, td, J 6.6, 1.7), 1.64-1.73 (16H, m), 1.22-1.47 (48H, m), 0.80-0.89 (24H, m).

Compound 94

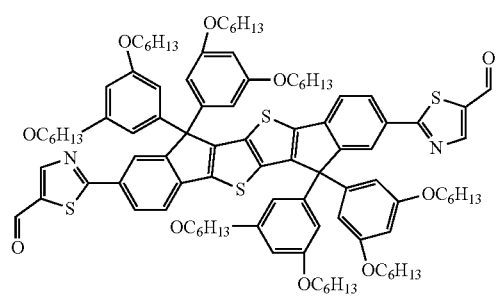

+

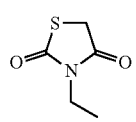

→

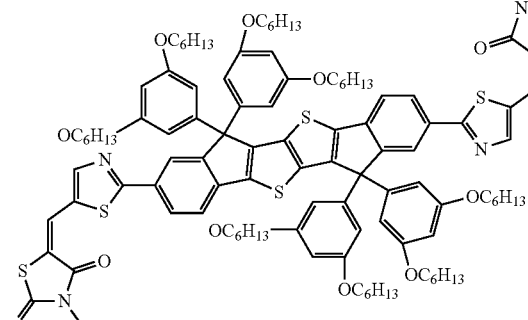

To a degassed solution of intermediate 32 (200 mg, 0.12 mmol), 3-ethyl-2-thioxo-thiazolidin-4-one (59 mg, 0.36 mmol) anhydrous N,N-dimethylformamide (10 cm$^3$) is added potassium carbonate (50 mg, 0.36 mmol) and the mixture is stirred for 16 hours. Dichloromethane is added and the organic layer washed with water (2×100 cm$^3$), brine (100 cm$^3$), dried over anhydrous magnesium sulfate, filtered and the solvent removed in vacuo. The residue is triturated in acetone and the solid collected by filtration to give compound 94 (69 mg, 29%) as a shiny red solid. $^1$H NMR (400 MHz, CDCl$_3$) 8.11 (2H, d, J 1.7), 8.05 (2H, s), 7.96 (2H, dd, J 8.0, 1.7), 7.89 (2H, s), 7.42 (2H, d, J 8.0), 6.41 (8H, d, J 2.2), 6.35 (4H, t, J 2.2), 4.19 (4H, q, J 7.1), 3.82-3.90 (16H, m), 1.33-1.42 (16H, m), 1.38 (16H, dq, J 14.2, 6.6), 1.20-1.32 (38H, m), 0.85 (24H, t, J 6.8).

Example 95

Compound 95

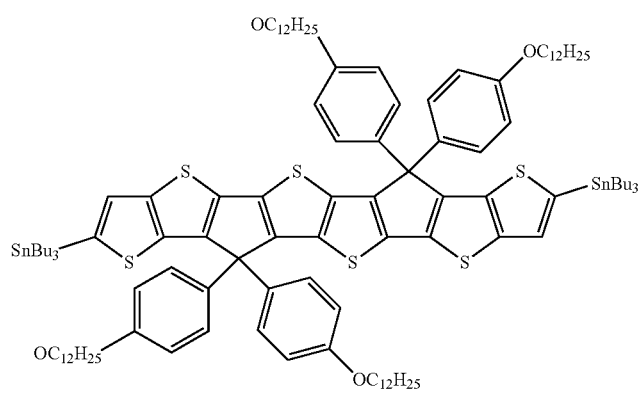

+

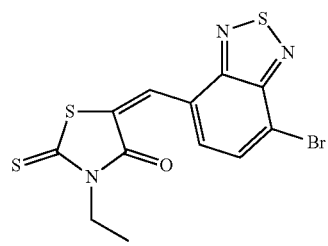

→

-continued

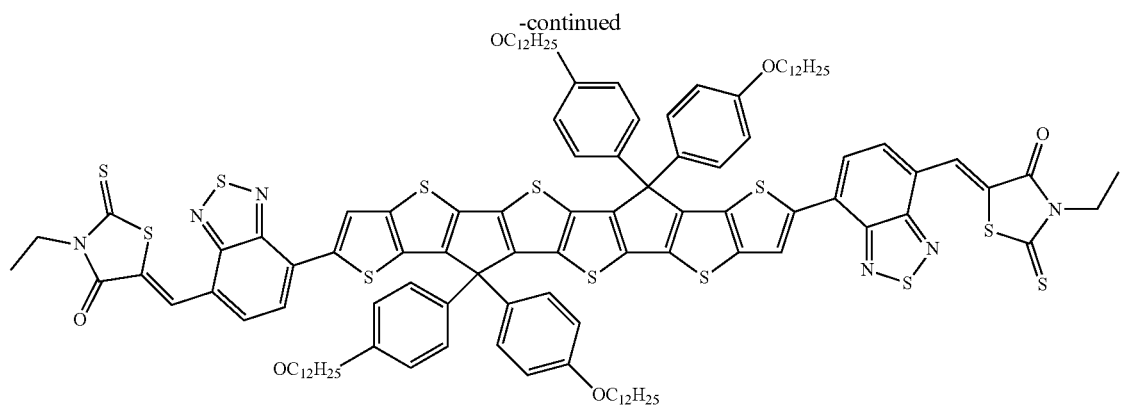

A mixture of intermediate 28 (500 mg, 0.24 mmol), 5-[1-(7-bromo-benzo[1,2,5]thiadiazol-4-yl)-meth-(E)-ylidene]-3-ethyl-2-thioxo-thiazolidin-4-one (197 mg, 0.51 mmol), tri-o-tolyl-phosphine (22 mg, 0.07 mmol) and anhydrous toluene (26 cm$^3$) is degassed by nitrogen for 10 minutes. To the mixture is added tris(dibenzylideneacetone)dipalladium(0) (18 mg, 0.02 mmol) and the mixture further degassed for 15 minutes. The mixture is stirred at 90° C. for 17 hours and the solvent removed in vacuo. The crude is stirred in acetone (200 cm$^3$) to form a suspension and the solid collected by filtration. The crude is purified using silica gel column chromatography eluted with 40-60 petrol:dichloromethane; 1:1 to give compound 95 (193 mg, 38%) as a dark green solid. $^1$H-NMR (400 MHz, CD$_2$Cl$_2$) 8.57 (2H, s), 8.34 (2H, s), 7.79 (2H, d, J 7.8), 7.58 (2H, d, J 7.8), 7.15 (8H, d, J 8.8), 6.77 (8H, d, J 8.6), 4.13 (4H, q, J 7.3), 3.81 (8H, t, J 6.5), 1.63 (8H, quin, J 6.9), 0.96-1.38 (78H, m), 0.77 (12H, t, J 6.6).

Example 96

Compound 96

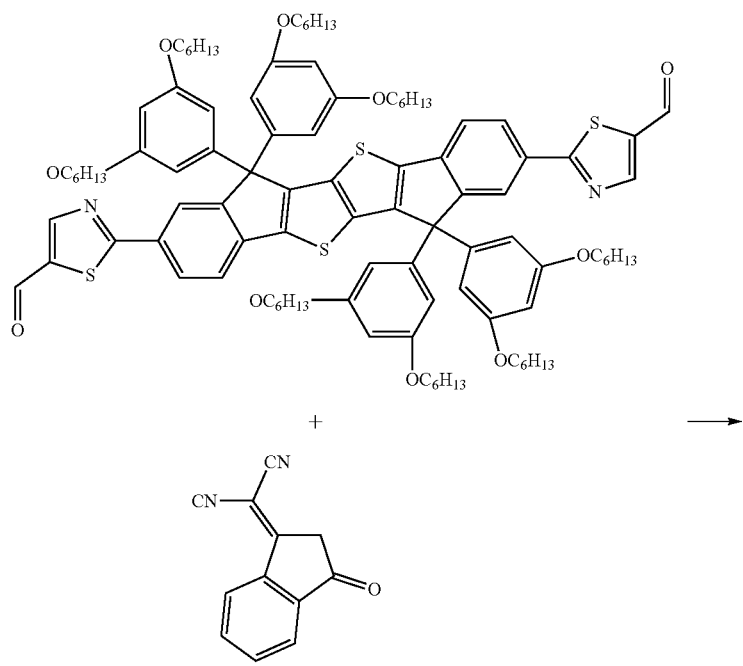

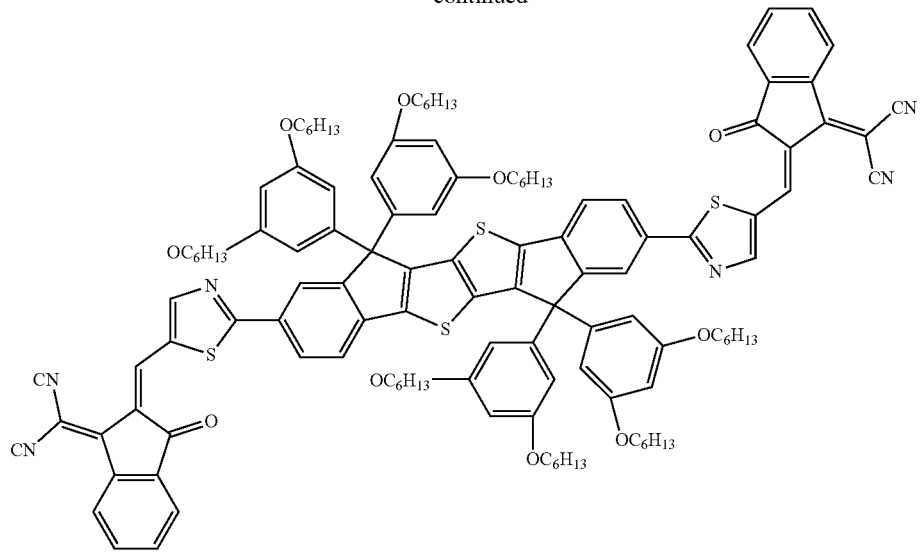

To a degassed solution of intermediate 32 (192 mg, 0.12 mmol) in chloroform (19 cm³) and pyridine (1 cm³) is added 2-(3-oxo-indan-1-ylidene)-malononitrile (68 mg, 0.35 mmol) and the mixture stirred for 2 hours. Aqueous hydrochloric acid (10 cm³, 2 M) is added and the mixture diluted with dichloromethane (50 cm³). The organic layer is washed with water (50 cm³) and brine (50 cm³), dried over anhydrous magnesium sulfate, filtered and the solvent removed in vacuo. The residue is triturated in acetone and the solid collected by filtration to give compound 96 (182 mg, 78%) as a blue powder. $^1$H NMR (400 MHz, CDCl$_3$) 8.90 (2H, s), 8.74 (2H, d, J 7.2), 8.41 (2H, s), 8.28 (2H, d, J 1.6), 8.14 (2H, dd, J 8.0, 1.6), 7.95 (2H, d, J 7.2), 7.76-7.86 (4H, m), 7.45 (2H, d, J 8.1), 6.43 (8H, d, J 2.2), 6.36 (4H, t, J 2.2), 3.88 (16H, td, J 6.6, 1.7), 1.67-1.74 (16H, m), 1.35-1.42 (16H, m), 1.23-1.31 (32H, m), 0.84 (24H, t, J 7.0).

Example 97

Intermediate 33

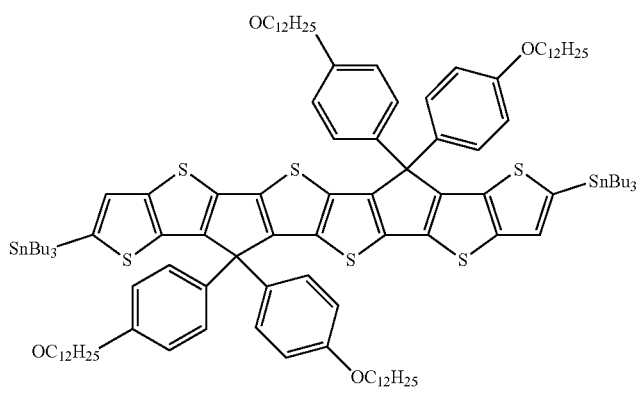

+

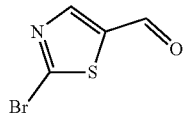

→

-continued

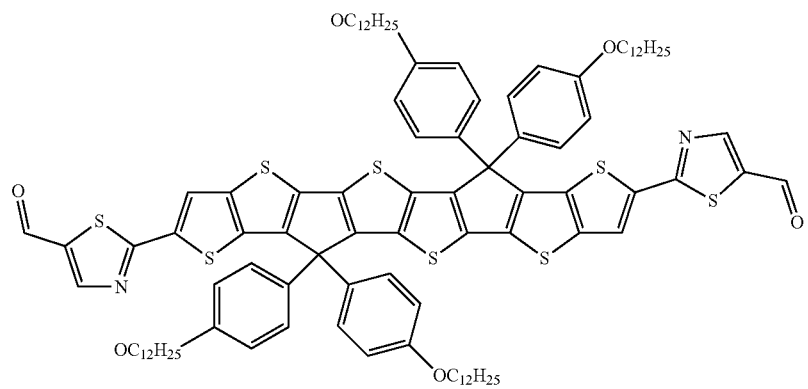

A mixture of intermediate 28 (400 mg, 0.19 mmol), 2-bromo-thiazole-5-carbaldehyde (112 mg, 0.58 mmol), tri-o-tolyl-phosphine (18 mg, 0.06 mmol) and anhydrous toluene (40 cm³) is degassed by nitrogen for 10 minutes. To the mixture is added tris(dibenzylideneacetone) dipalladium(0) (14 mg, 0.02 mmol) and the mixture further degassed for 15 minutes. The mixture is stirred at 90° C. for 17 hours and the solvent removed in vacuo. The crude is stirred in acetone (200 cm³) and the solid collected by filtration to give intermediate 33 (158 mg, 48%) as a dark purple solid. $^1$H-NMR (400 MHz, CD$_2$Cl$_2$) 9.89 (2H, s), 8.21 (2H, s), 7.82 (2H, s), 7.08 (8H, d, J 8.6), 6.68-6.81 (8H, m), 3.81 (8H, t, J 6.4), 1.64 (8H, brs), 1.10-1.36 (72H, m), 0.78 (12H, t, J 6.5).

Compound 97

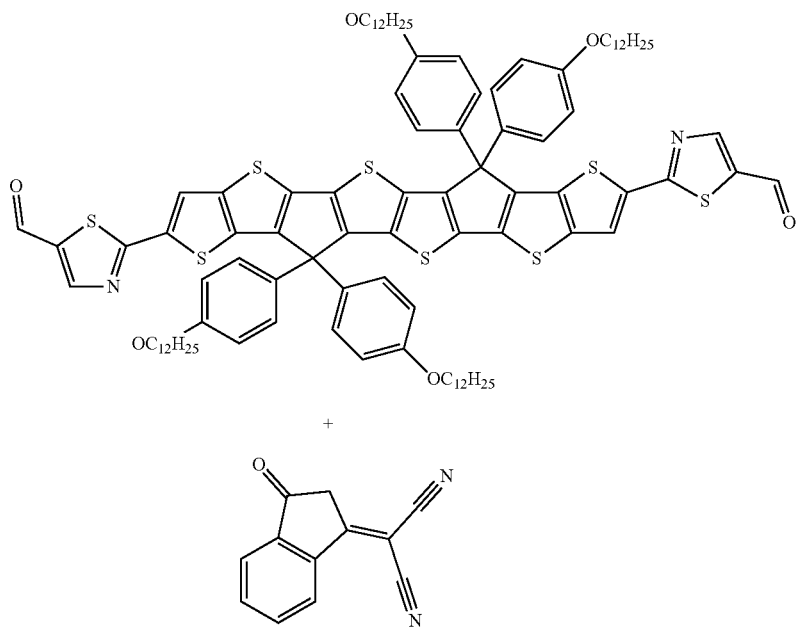

-continued

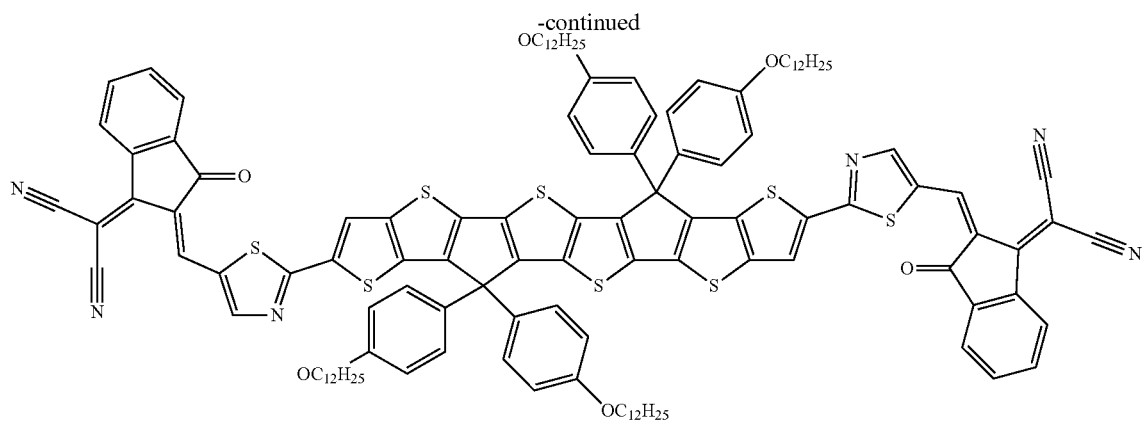

To a solution of intermediate 32 (150 mg, 0.09 mmol) in anhydrous chloroform (9 cm³) is added pyridine (0.5 cm³, 6.2 mmol). The mixture is then degassed with nitrogen before 3-(dicyanomethylidene) indan-1-one (120 mg, 0.62 mmol) is added. The solution is then further degassed and stirred at 23° C. for 20 minutes before the solvent is removed in vacuo. The crude is triturated with ethanol (200 cm³) and the solid collected by filtration. The crude is purified using silica gel column chromatography eluted with 40-60 petrol: dichloromethane; 6:4 to give compound 97 (17 mg, 9%) as a green solid. $^1$H NMR (400 MHz, CD$_2$Cl$_2$) 8.75 (2H, s), 8.61 (2H, d, J 7.3), 8.25 (2H, s), 7.94 (2H, s), 7.85 (2H, d, J 7.3), 7.70 (4H, quin, J 7.5), 7.02-7.16 (8H, d, J 8.8), 6.77 (8H, d, J 9.0), 3.82 (8H, t, J 6.4), 1.58-1.66 (8H, m), 1.07-1.39 (72H, m), 0.70-0.84 (12H, m).

Example 98

Compound 98

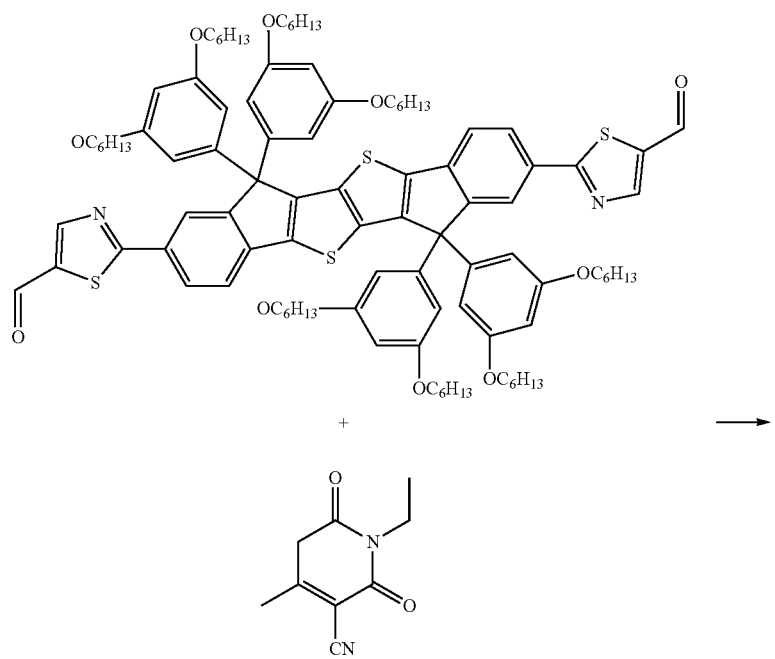

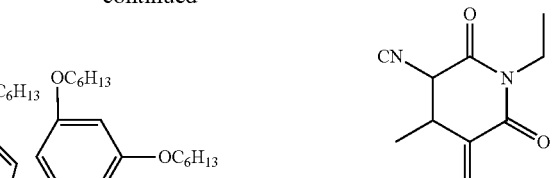
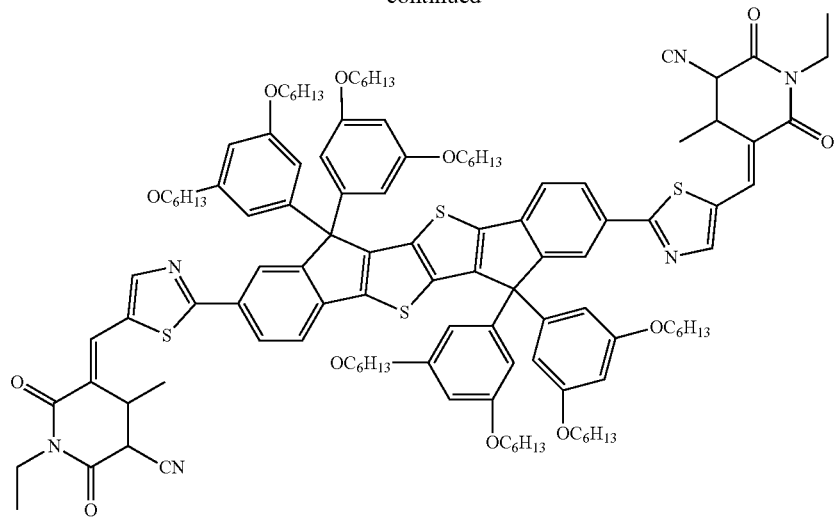

To a degassed solution of intermediate 32 (169 mg, 0.10 mmol), pyridine (2 cm³) and chloroform (10 cm³) is added 1-ethyl-4-methyl-2,6-dioxo-1,2,5,6-tetrahydro-pyridine-3-carbonitrile (55 mg, 0.31 mmol) and the mixture stirred for 20 hours. Aqueous hydrochloric acid (10 cm³, 2 M) is added and the mixture diluted with dichloromethane (50 cm³). The organic layer is washed with water (50 cm³) and brine (50 cm³), dried over anhydrous magnesium sulfate, filtered and the solvent removed in vacuo. The crude is purified by column chromatography using a graded solvent system (40-60 petrol:dichloromethane: 2:8 to 0:1) followed by recrystallization (ethanol/dichloromethane) to give compound 98 (69 mg, 34%) as a shiny blue solid. ¹H NMR (400 MHz, CDCl₃) 8.39 (2H, s), 8.24 (2H, d, J 1.5), 8.14 (2H, dd, J 8.1, 1.5), 7.90 (2H, s), 7.43 (2H, d, J 8.0), 6.42 (8H, d, J 2.1), 6.35 (4H, t, J 2.1), 4.07 (4H, q, J 7.1), 3.87 (16H, t, J 6.8), 2.65 (6H, s), 1.66-1.73 (16H, m), 1.32-1.43 (16H, m), 1.23-1.30 (38H, m), 0.85 (24H, t, J 6.9).

Example 99

Intermediate 34

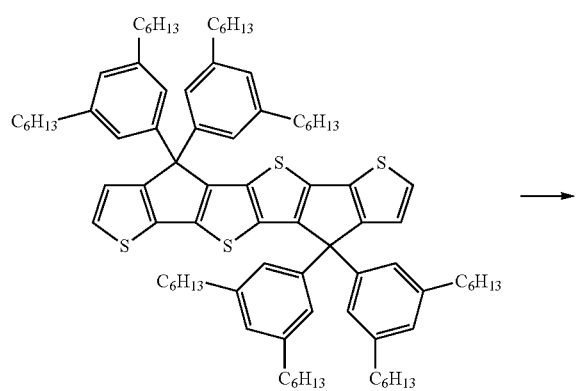

→

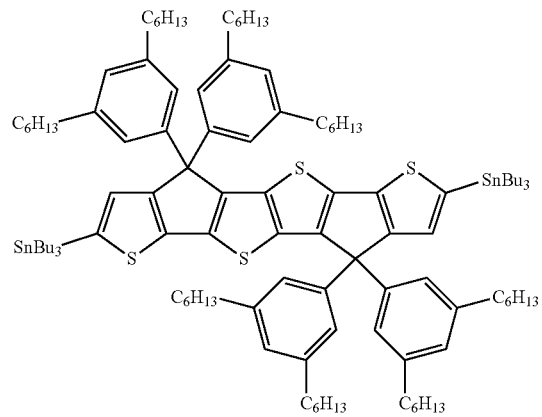

To a solution of intermediate 21 (1.60 g, 1.2 mmol) in anhydrous tetrahydrofuran (47 cm³) at −78° C. is added dropwise n-butyllithium (1.96 cm³, 4.9 mmol, 2.5 M in hexane) over 20 minutes. After addition, the reaction mixture is stirred at −78° C. for 60 minutes and then tributyltin chloride (1.5 cm³, 5.5 mmol) is added in one go. The mixture is then allowed to warm to 23° C. over 72 hours and the solvent removed in vacuo. The crude is purified by passing through a zeolite plug (40-60 petrol) followed by trituration in ethanol (2×100 cm³) to give a mixture of intermediate 34 and tributyltin chloride (2.7 g) as a dark brown oil. ¹H NMR (400 MHz, CD₂Cl₂) 6.99 (2H, s), 6.64-6.85 (12H, m), 2.38 (16H, t, J 7.7), 0.57-1.69 (98H, m).

Intermediate 35

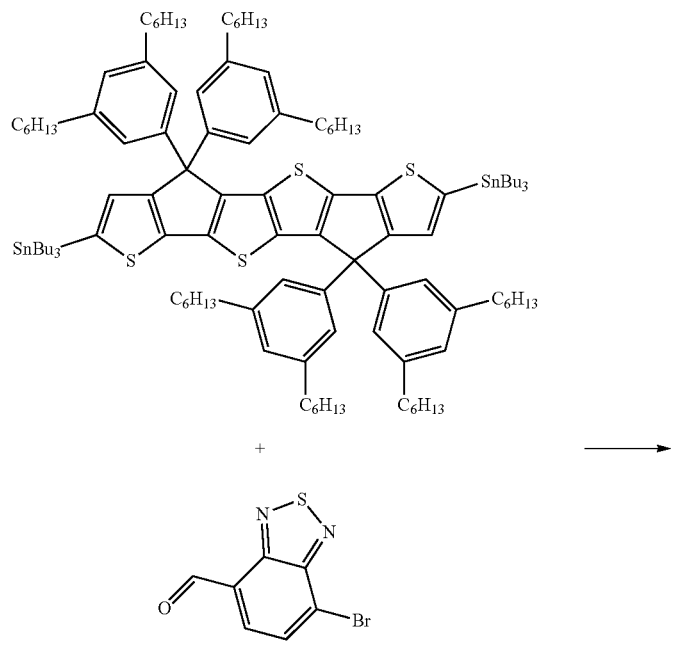

A mixture of intermediate 34 (1.5 g, 0.48 mmol), 7-bromo-benzo[1,2,5]thiadiazole-4-carbaldehyde (232 mg, 0.96 mmol), tri-o-tolyl-phosphine (44 mg, 0.14 mmol) and anhydrous toluene (51 cm$^3$) is degassed by nitrogen for 10 minutes. To the mixture is added tris(dibenzylideneacetone) dipalladium(0) (35 mg, 0.04 mmol) and the mixture further degassed for 15 minutes. The mixture is stirred at 100° C. for 17 hours and the solvent removed in vacuo. The crude is purified using silica gel column chromatography eluting with 40-60 petrol:dichloromethane; 7:3 to give intermediate 35 (650 mg, 84%) as a dark blue solid. $^1$H NMR (400 MHz, CDCl$_3$) 10.67-10.73 (2H, m), 8.34 (2H, s), 8.20 (2H, d, J 7.6), 7.93 (2H, d, J 7.6), 6.94 (12H, s), 2.54 (16H, t, J 7.7), 1.51-1.64 (16H, m), 1.20-1.36 (48H, m), 0.77-0.88 (24H, m).

Compound 99

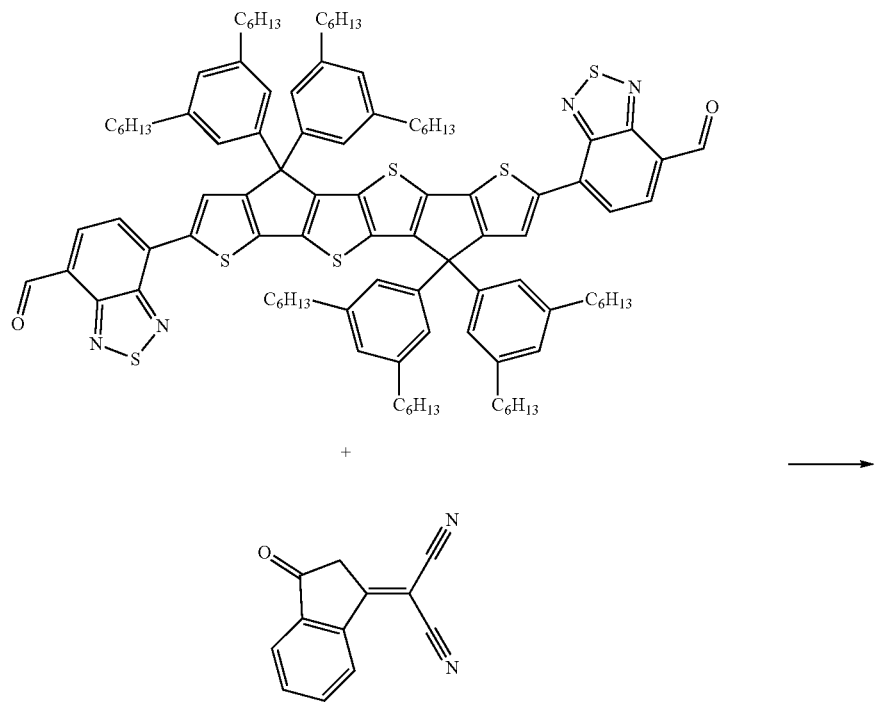

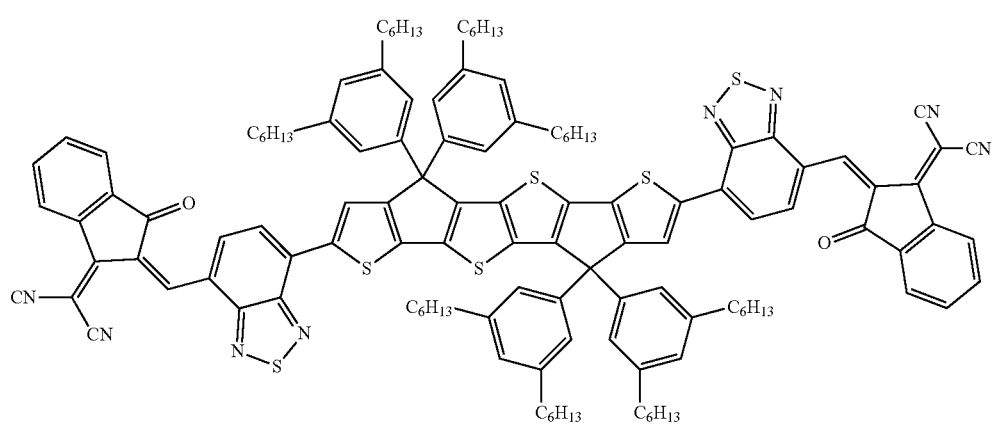

To a solution of intermediate 35 (500 mg, 0.31 mmol) in anhydrous chloroform (33 cm³) at −30° C. is added pyridine (1.7 cm³, 22 mmol). The mixture is then degassed with nitrogen before 3-(dicyanomethylidene) indan-1-one (417 mg, 2.15 mmol) is added. The solution is then further degassed and stirred at −30° C. for 30 minutes. The ice bath is removed, the reaction is allowed to warm to 20° C. over 60 minutes and the solvent removed in vacuo. The crude is triturated with ethanol and the solid collected by filtration. The crude is purified using silica gel column chromatography eluted with 40-60 petrol:dichloromethane; 1:1 to give compound 99 (205 mg, 34%) as a green solid. $^1$H NMR (400 MHz, CDCl$_3$) 9.61 (2H, s), 9.32 (2H, d, J 8.1), 8.75 (2H, d, J 7.8), 8.39 (2H, s), 7.94-8.03 (4H, m), 7.76-7.91 (4H, m), 6.95 (12H, s), 2.56 (16H, t, J 7.7), 1.48-1.68 (m, 16H), 1.20-1.40 (48H, m), 0.76-0.95 (24H, m).

Example 100

Intermediate 36

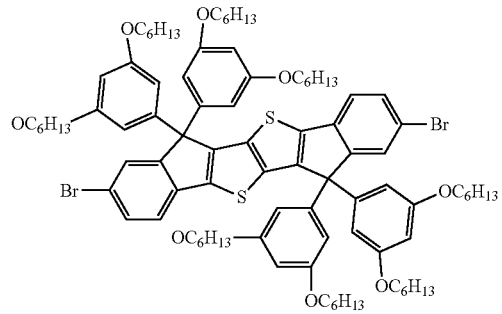

+

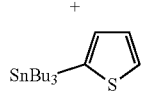

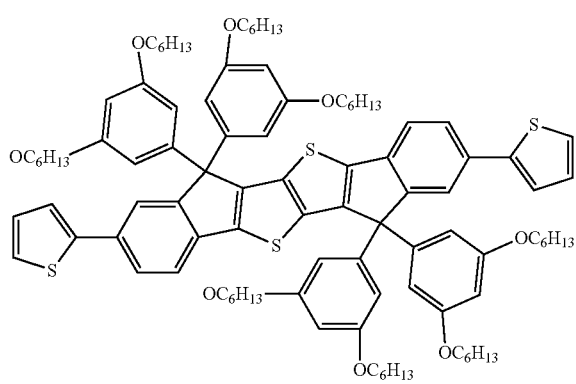

To a degassed solution of intermediate 13 (350 mg; 0.22 mmol), tributyl-thiophen-2-yl-stannane (248 mg, 0.66 mmol) and anhydrous toluene (20 cm³) are added tris(dibenzylideneacetone)dipalladium(0) (10 mg, 0.01 mmol) and 2-dicyclohexylphosphino-2',4',6'-triisopropylbiphenyl (42 mg, 0.09 mmol) and the mixture stirred at 80° C. for 17 hours. The mixture is allowed to cool to 23° C. and the solvent removed in vacuo. The crude is purified by column chromatography using a graded solvent system (40-60 petrol:dichloromethane: 9:1 to 1:1) followed by trituration in ice-cold acetone. The solid is collected by filtration to give intermediate 36 (216 mg, 61%) as a yellow powder. $^1$H NMR (400 MHz, CDCl$_3$) 7.68 (2H, d, J 1.6), 7.53 (2H, dd, J 7.9, 1.6), 7.32 (2H, d, J 7.9), 7.20-7.26 (4H, m), 7.04 (2H, dd, J 5.1, 3.6), 6.41 (8H, d, J 2.2), 6.32 (4H, t, J 2.2), 3.84 (16H, td, J 6.6, 2.2), 1.62-1.73 (16H, m), 1.32-1.42 (16H, m), 1.27 (32H, dq, J 7.3, 3.7, 3.0), 0.82-0.88 (24H, m).

Intermediate 37

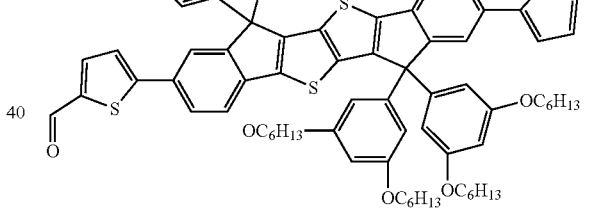

→

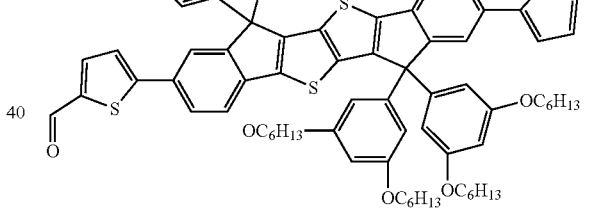

To a mixture of anhydrous N,N-dimethylformamide (1 cm³) and anhydrous chloroform (10 cm³) at 0° C. is added phosphoroxychloride (0.04 cm³, 0.41 mmol). The mixture is allowed to warm up at 23° C. and stirred for 1 hour before cooling to 0° C. where intermediate 36 (216 mg, 0.14 mmol) is added. The mixture is then stirred at 60° C. for 17 hours. The mixture is allowed to cool to 23° C. and poured on saturated aqueous sodium bicarbonate solution (50 cm³) and stirred at 23° C. for 30 minutes. The aqueous layer is extracted with dichloromethane (100 cm³). The organic layer is washed with brine (50 cm³), dried over anhydrous magnesium sulfate, filtered and the solvent removed in vacuo. The crude is purified by column chromatography using a graded solvent system (40-60 petrol:dichloromethane: 1:1 to 0:1) to give intermediate 37 (49 mg, 22%) as a red solid. $^1$H NMR (400 MHz, CDCl$_3$) 9.86 (2H, s), 7.73 (2H, d, J 1.7), 7.70 (2H, d, J 4.0), 7.61 (2H, dd, J 8.0, 1.7), 7.37 (2H, d, J 8.0), 7.34 (2H, d, J 4.0), 6.39 (8H d, J 2.2), 6.34 (4H, t, J 2.2), 3.85 (16H, m), 1.69 (16H, p, J 6.8), 1.23-1.45 (48H, m), 0.76-0.92 (24H, m).

Compound 100

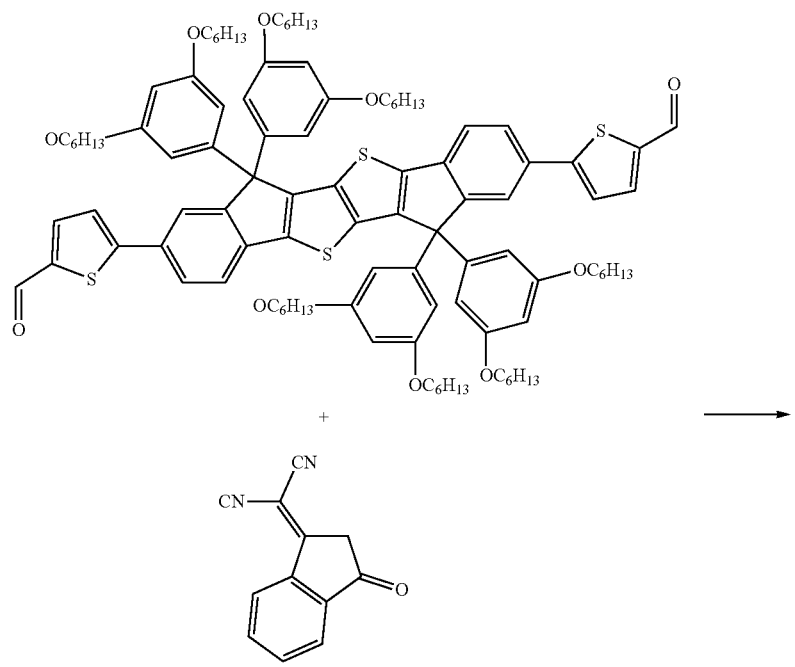

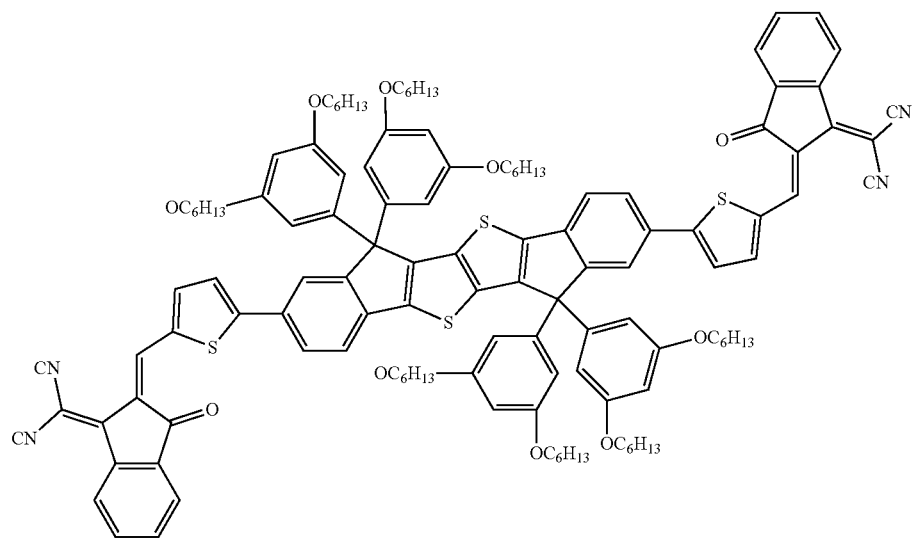

To a degassed solution of intermediate 37 (59 mg, 0.04 mmol), anhydrous chloroform (10 cm$^3$) and anhydrous pyridine (2 cm$^3$) at 0° C. is added 2-(3-oxo-indan-1-ylidene)-malononitrile (21 mg, 0.11 mmol) and the reaction mixture is stirred at 0° C. for 2 hours. The reaction is quenched by addition of aqueous hydrochloric acid (5 cm$^3$, 2 M). Dichloromethane (50 cm$^3$) is added and the organic layer is washed with water (2×50 cm$^3$) and brine (50 cm$^3$), dried over anhydrous magnesium sulfate, filtered and the solvent removed in vacuo. The residue is triturated in acetone and the solid collected by filtration to give compound 100 (18 mg, 25%) as a black powder. $^1$H NMR (400 MHz, CDCl$_3$) 8.86 (2H, s), 8.69-8.73 (2H, m), 7.91-7.94 (2H, m), 7.88 (2H, d, J 1.6), 7.84 (2H, d, J 4.3), 7.73-7.81 (6H, m), 7.46 (2H, d, J 4.2), 7.40 (2H, d, J 8.0), 6.42 (8H, d, J 2.2), 6.36 (4H, t, J 2.2), 3.88 (16H, td, J 6.5, 1.8), 1.71 (16H, p, J 6.7), 1.31-1.47 (16H, m), 1.22-1.32 (32H, m), 0.79-0.88 (24H, m).

Example 101

Intermediate 38

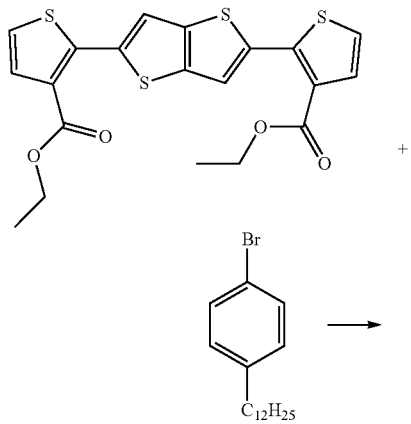

To a suspension of 1-bromo-4-dodecylbenzene (3.626 g, 11.15 mmol) in anhydrous tetrahydrofuran (48 cm³) at −78° C., tert-butyllithium (13 cm³, 22 mmol, 1.7 M in pentane) is added dropwise over 30 minutes. After 40 minutes the reaction is allowed to warm to −30° C. before the reaction mixture is then re-cooled to −78° C. Additional 1-bromo-4-dodecylbenzene (362 mg, 1.11 mmol) is added and after 15 minutes ethyl 2-[5-(3-ethoxycarbonyl-2-thienyl)thieno[3,2-b]thiophen-2-yl]thiophene-3-carboxylate (1.00 g, 2.23 mmol) is added in one portion to the reaction mixture. This mixture is then allowed to stir at −78° C. for 20 minutes before removing allowing the mixture to warm to 23° C. Water (100 cm³) is added and the mixture stirred for 5 minutes. Diethyl ether (50 cm³) is then added and the organic layer extracted. The organic extract is then washed with saturated ammonium chloride solution (100 cm³), water (100 cm³) and brine (100 cm³), dried over anhydrous magnesium sulfate, filtered and concentrated in vacuo. The crude is purified by column chromatography eluting with a graded solvent system (40-60 petrol:dichloromethane; 1:0 to 3:2) with final purification achieved by trituration with methanol (3×10 cm³), washing the filtered solid with 40-60 petrol (2×10 cm³), diethyl ether (10 cm³) and acetone (10 cm³) to give intermediate 38 (2.09 g, 70%) as a yellow solid. $^1$H NMR (400 MHz, CDCl$_3$) 7.12-7.17 (10H, m), 7.07-7.12 (8H, m), 6.64 (2H, s), 6.45 (2H, d, J 5.2), 3.24 (2H, s), 2.60 (8H, t, J 7.7), 1.57-1.65 (8H, m), 1.25-1.35 (72H, m), 0.89 (12H, t, J 6.8).

Intermediate 39

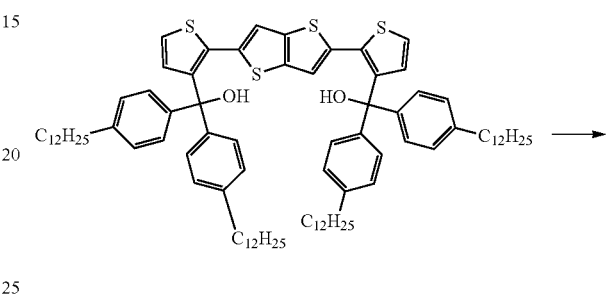

A degassed solution of intermediate 381 (1.00 g, 0.75 mmol) in anhydrous toluene (17 cm³) is added to a degassed suspension of Amberlist 15 strong acid (4.00 g) in toluene (18 cm³) and the reaction stirred at 50° C. for 80 minutes. After cooling the mixture to 23° C., the solid is removed by filtration and washed with toluene (3×50 cm³) and diethyl ether (3×50 cm³) and the filtrate concentrated in vacuo. Purification is achieved by column chromatography eluting with a graded solvent system (40-60 petrol:dichloromethane; 1:0 to 4:1) to give intermediate 39 (582 mg, 60%) as a brown oil. $^1$H NMR (400 MHz, CD$_2$Cl$_2$) 7.23 (2H, d, J 4.9), 7.11-7.16 (8H, m), 7.05-7.10 (10H, m), 2.54 (8H, t, J 7.8), 1.53-1.61 (8H, m), 1.22-1.33 (72H, m), 0.87 (12H, t, J 6.9).

Intermediate 40

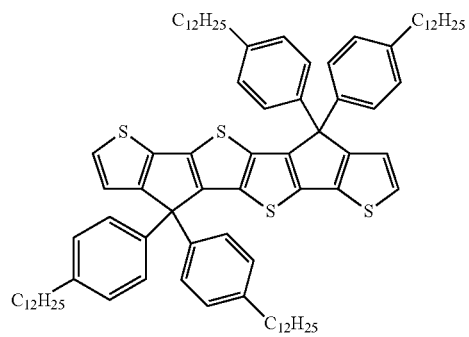

To a solution of intermediate 39 (582 mg, 0.45 mmol) in anhydrous tetrahydrofuran (27 cm³) at −78° C. is added n-butyllithium (0.43 cm³, 1.1 mmol, 2.5 M in hexanes) over 5 minutes. The mixture is stirred at −78° C. for 45 minutes before additional n-butyllithium (0.10 cm³, 0.25 mmol) is added. The mixture is stirred for an additional 5 minutes before tributyltin chloride (0.42 cm³, 1.56 mmol) is added and the mixture stirred to 23° C. over 17 hours. Methanol (15 cm³) is added and the material concentrated in vacuo. The crude product is then taken up in pentane and the suspension filtered through celite washing though with additional pentane. The filtrate is then concentrated in vacuo, the solid triturated with methanol (3×10 cm³) and the product collected by filtration to give intermediate 40 (790 mg, 94%) as a brown sticky solid. $^1$H NMR (400 MHz, CDCl$_3$) 7.13-7.18 (8H, m), 7.03-7.09 (10H, m), 2.54 (8H, t, J 7.8), 1.51-1.60 (20H, m), 1.21-1.38 (84H, m), 1.06-1.13 (12H, m), 0.85-0.91 (30H, m).

Intermediate 41

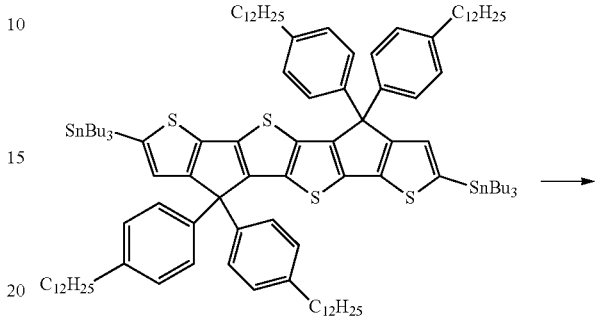

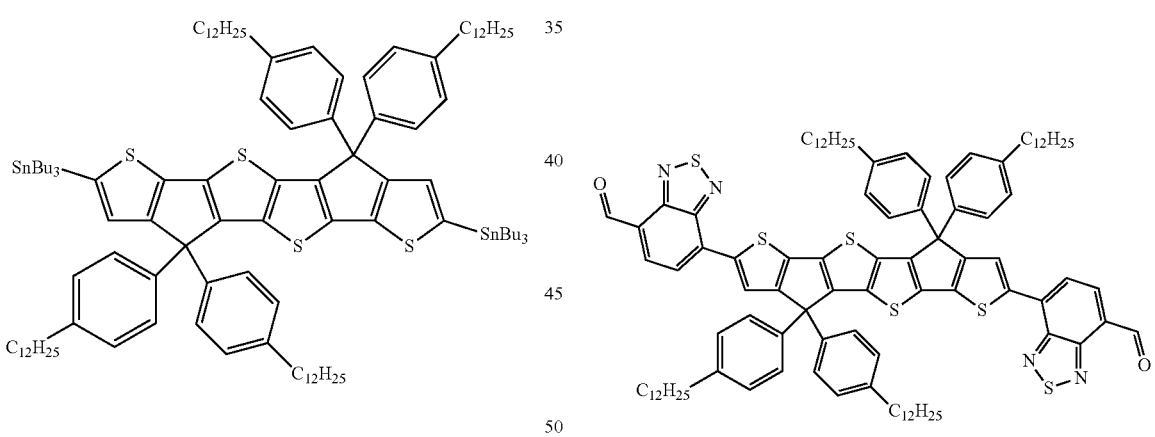

To a degassed solution of intermediate 40 (438 mg, 0.23 mmol) and 7-bromo-benzo[1,2,5]thiadiazole-4-carbaldehyde (124 mg, 0.51 mmol) in anhydrous toluene (28 cm³), tris(dibenzylideneacetone)dipalladium (17 mg, 0.02 mmol) and tris(o-tolyl)phosphine (21 mg, 0.07 mmol) are added. After degassing the reaction mixture for a further 20 minutes it is heated at 80° C. for 17 hours. After cooling to 23° C., the mixture is concentrated in vacuo. The crude is then triturated with methanol (3×10 cm³) and the solid filtered, washing with acetone (3×10 cm³) to give intermediate 41 (320 mg, 84%) as a blue/black solid. $^1$H NMR (400 MHz, CDCl$_3$) 10.69 (2H, s), 8.33 (2H, s), 8.19 (2H, d, J 7.6), 7.94 (2H, d, J 7.8), 7.22-7.27 (8H, m), 7.11-7.17 (8H, m), 2.58 (8H, t, J 7.9), 1.51-1.65 (8H, m), 1.18-1.38 (72H, m), 0.86 (12H, t, J 6.9).

Compound 101

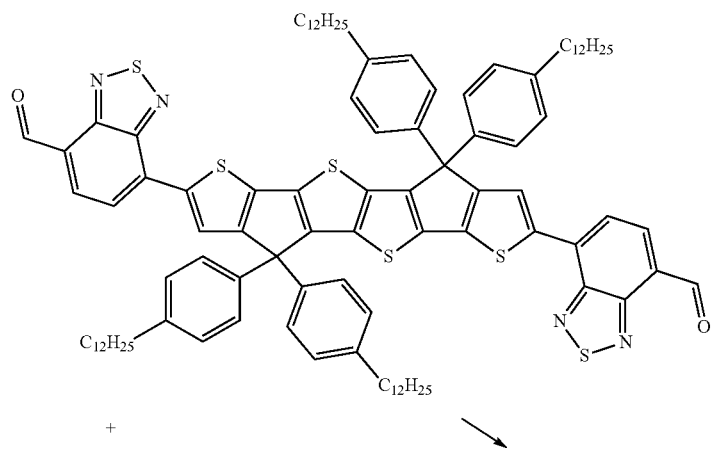

+

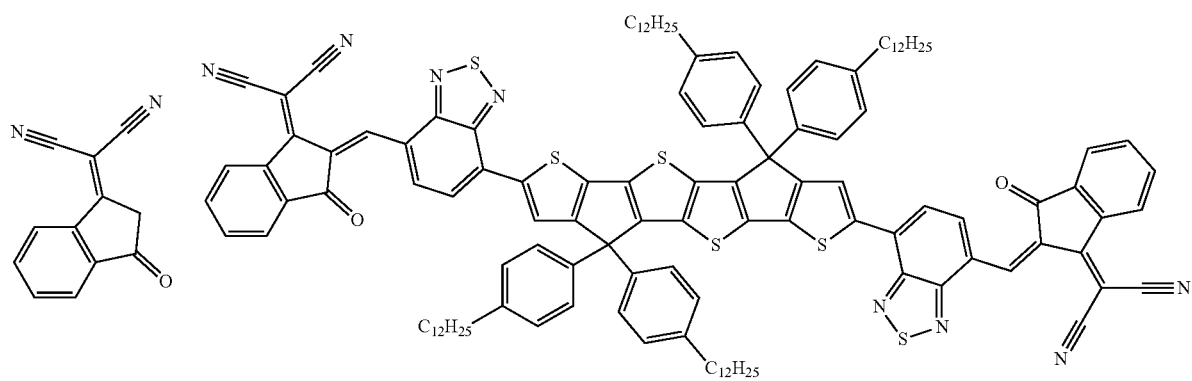

To a solution of intermediate 41 (319 mg, 0.20 mmol) in anhydrous chloroform (21 cm$^3$) is added anhydrous pyridine (1.1 cm$^3$, 14 mmol). The mixture is then degassed with nitrogen before 3-(dicyanomethylidene)indan-1-one (266 mg, 1.37 mmol) is added and the reaction cooled to −40° C. The solution is further degassed for 10 minutes and with stirring, is allowed to warm before being held at −15 to −20° C. After 5 hours the reaction mixture is then added to methanol (100 cm$^3$) washing in with dichloromethane (10 cm$^3$) and methanol (2×10 cm$^3$). Additional methanol (50 cm$^3$) is added before the suspension is filtered. The crude product is purified by column chromatography, eluting with a graded solvent system (40-60 petrol:dichloromethane; 1:0 to 1:1) to give compound 101 (24 mg, 6%) as a black solid. $^1$H NMR (400 MHz, CDCl$_3$) 9.58 (2H, s), 9.28 (2H, d, J 8.1), 8.73 (2H, d, J 7.8), 8.37 (2H, s), 7.94 (4H, d, J 7.6), 7.74-7.85 (4H, m), 7.23-7.27 (8H, m), 7.15 (8H, d, J 8.3), 2.58 (8H, t, J 7.8), 1.53-1.65 (8H, m), 1.18-1.38 (72H, m), 0.83-0.90 (12H, m).

Example 102

Compound 102

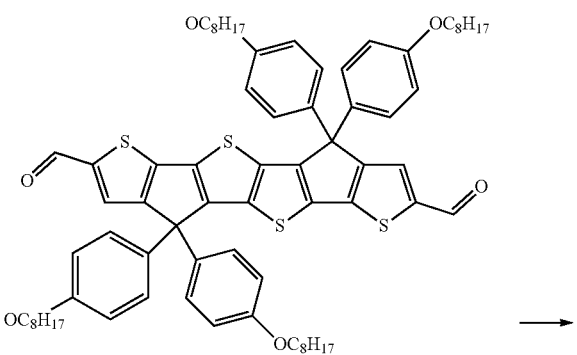

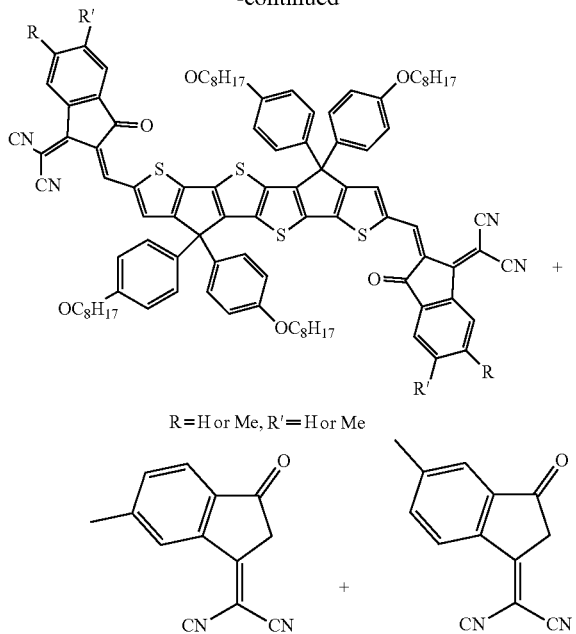

R=H or Me, R'=H or Me

To a degassed mixture of intermediate 12 (100 mg, 0.08 mmol) and 2:3 regiomeric mix of 2-(5-methyl-3-oxo-indan-1-ylidene)-malononitrile and 2-(6-methyl-3-oxo-indan-1-ylidene)-malononitrile (121 mg, 0.58 mmol) and chloroform (2.5 cm$^3$) is added pyridine (0.47 cm$^3$, 5.8 mmol). The solution is bubbled with nitrogen for 10 minutes and then stirred for 3 hours at 23° C. Methanol (20 cm$^3$) is added and the suspension filtered and washed with methanol (20 cm$^3$). The resulting solid is stirred in methyl ethyl ketone (5 cm$^3$) at 95° C. for 2 hours, cooled to 23° C. and the solid collected by filtration. The solid is washed with methyl ethyl ketone (5 cm$^3$) to give compound 102 (107 mg, 81%) as a dark blue solid. $^1$H NMR (400 MHz, CD$_2$Cl$_2$) 8.85 (2H, m), 8.40-8.66 (2H, m), 7.49-7.93 (6H, m), 7.20 (8H, d, J 8.6), 6.87 (8H, d, J 8.5), 3.95 (8H, t, J 6.5), 2.54-2.61 (6H, m), 1.73-1.82 (8H, m), 1.41-1.52 (8H, m), 1.24-1.40 (32H, m), 0.90 (12H, t, J 6.6).

Example 103

Intermediate 42

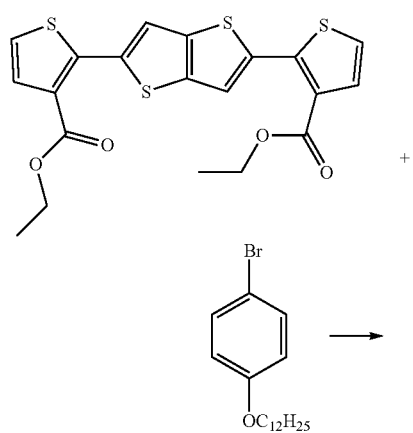

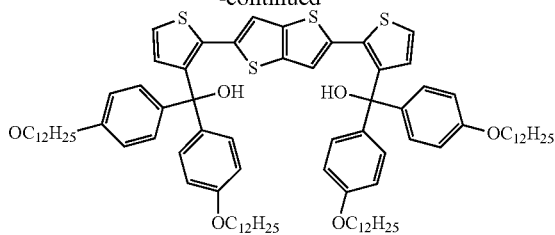

To a suspension of 1-bromo-4-dodecyloxybenzene (7.25 g, 21.2 mmol) in anhydrous tetrahydrofuran (91 cm$^3$) at −78° C., tert-butyllithium (25 cm$^3$, 42 mmol, 1.7 M in pentane) is added dropwise over 30 minutes. After 2 hours the reaction mixture is allowed to warm to −30° C. before re-cooling to −78° C. Additional 1-bromo-4-dodecyloxybenzene (720 mg, 2.11 mmol) and after 10 minutes ethyl 2-[5-(3-ethoxycarbonyl-2-thienyl)thieno[3,2-b]thiophen-2-yl]thiophene-3-carboxylate (1.91 g, 4.25 mmol) is added in one portion to the reaction mixture. This mixture is then allowed to stir to 23° C. over 17 hours. Water (50 cm$^3$) and diethyl ether (25 cm$^3$) are then added and the organic layer extracted. The residual aqueous layer is then additionally extracted with diethyl ether (50 cm$^3$) and the combined organic extracts washed with brine (75 cm$^3$), dried over anhydrous magnesium sulfate, filtered and concentrated in vacuo. The crude is purified by column chromatography eluting with a graded solvent system (40-60 petrol:dichloromethane; 1:0 to 3:7) to give intermediate 42 (4.10 g, 69%) as a brown oil which solidifies on standing to a yellow/brown solid. $^1$H NMR (400 MHz, CDCl$_3$) 7.09-7.17 (10H, m), 6.79-6.85 (8H, m), 6.76 (2H, s), 6.43 (2H, d, J 5.1), 3.95 (8H, t, J 6.6), 3.25 (2H, s), 1.73-1.83 (8H, m), 1.41-1.50 (8H, m), 1.24-1.39 (64H, m), 0.89 (12H, t, J 6.9).

Intermediate 43

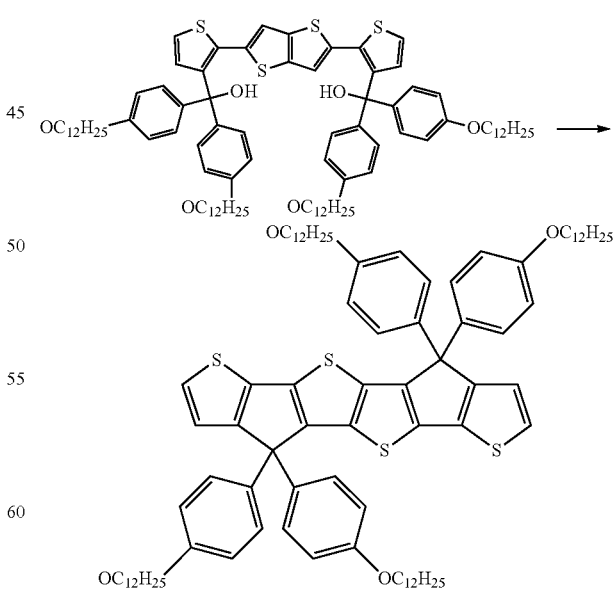

To a degassed solution of intermediate 42 (1.20 g, 0.85 mmol) in anhydrous toluene (20 cm$^3$) is added a degassed suspension of Amberlist 15 strong acid (5.00 g) in toluene (20 cm³) and the reaction mixture stirred at 100° C. for 3 hours. The solid is removed through filtration and washed with toluene (3×50 cm³) and diethyl ether (3×50 cm³) before the filtrate is concentrated in vacuo. Purification is achieved by column chromatography eluting with a graded solvent system (40-60 petrol:dichloromethane; 1:0 to 3:7) to give intermediate 43 (221 mg, 19%) as a brown oil. ¹H NMR (400 MHz, CDCl₃) 7.12-7.19 (10H, m), 7.04 (2H, d, J 4.9), 6.75-6.82 (8H, m), 3.89 (8H, t, J 6.48), 1.74 (8H, quin, J 7.1), 1.37-1.46 (8H, m), 1.19-1.36 (64H, m), 0.88 (12H, t, J 6.9).

Intermediate 44

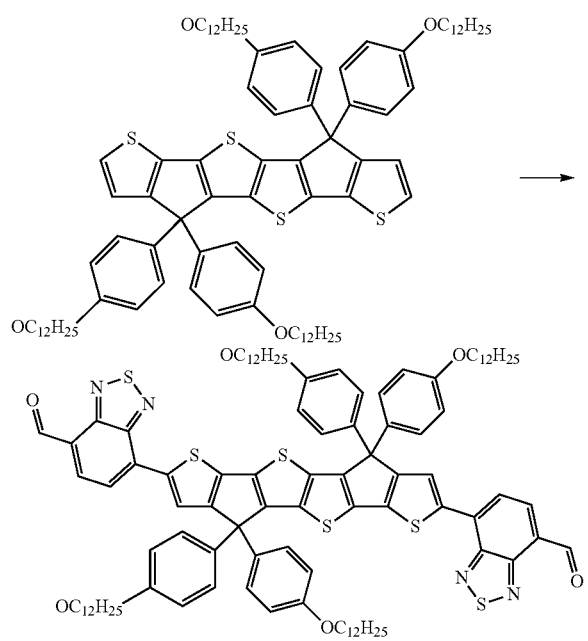

To a solution of intermediate 43 (493 mg, 0.36 mmol) in anhydrous tetrahydrofuran (22 cm³) at −78° C. is added n-butyllithium (0.43 cm³, 1.1 mmol, 2.5 M in hexanes) over 5 minutes. The mixture is stirred at −78° C. for 1 hour. Tributyltin chloride (0.34 cm³, 1.3 mmol) is added and the mixture stirred to 23° C. over 17 hours. Methanol (15 cm³) is added and the material concentrated in vacuo. The crude product is then taken up in pentane and the suspension filtered through celite washing through with additional pentane. The filtrate is then concentrated in vacuo, to give the crude product 2,7-bis(tributylstannyl)-4,4,9,9-tetrakis(4-dodecyloxyphenyl)-4,9-dihydro-thieno[3',2':4,5]cyclopenta[1,2-b]thieno[2",3":3',4']cyclopenta[1',2':4,5]thieno[2,3-d]thiophene (948 mg, 0.49 mmol) as a dark brown oil, used without further purification. To a degassed solution of 2,7-bis(tributylstannyl)-4,4,9,9-tetrakis(4-dodecyloxyphenyl)-4,9-dihydro-thieno[3',2':4,5]cyclopenta[1,2-b]thieno[2",3":3',4']cyclopenta[1',2':4,5]thieno[2,3-d]thiophene (701 mg, 0.36 mmol) and 7-bromo-benzo[1,2,5]thiadiazole-4-carbaldehyde (192 mg, 0.79 mmol) in anhydrous toluene (43 cm³), tris(dibenzylideneacetone)dipalladium (26 mg, 0.03 mmol) and tris(o-tolyl)phosphine (33 mg, 0.11 mmol) is added. After degassing the reaction mixture for a further 20 minutes it is heated at 80° C. for 17 hours. After cooling to 23° C., the mixture is concentrated in vacuo. The crude is triturated with methanol (4×10 cm³) and the solid filtered. The crude product is then twice partially purified by column chromatography, eluting with two graded solvent systems (40-60 petrol:dichloromethane; 1:0 to 1:4) (40-60 petrol:diethyl ether; 1:0 to 9:1) isolating partially pure fractions. Final purification is then achieved by trituration with warm acetone and warm diethyl ether to give intermediate 44 (255 mg, 42%) as a blue/black solid. ¹H NMR (400 MHz, CDCl₃) 10.69 (2H, s), 8.31 (2H, s), 8.19 (2H, d, J 7.8), 7.94 (2H, d, J 7.6), 7.22-7.27 (8H, m), 6.82-6.88 (8H, m), 3.91 (8H, t, J 6.5), 1.75 (8H, quin, J 7.2), 1.37-1.46 (8H, m), 1.20-1.35 (64H, m), 0.87 (12H, t, J 6.9).

Compound 103

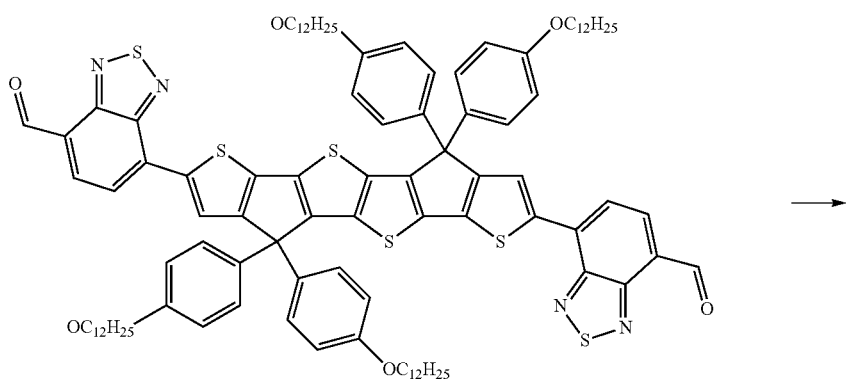

-continued

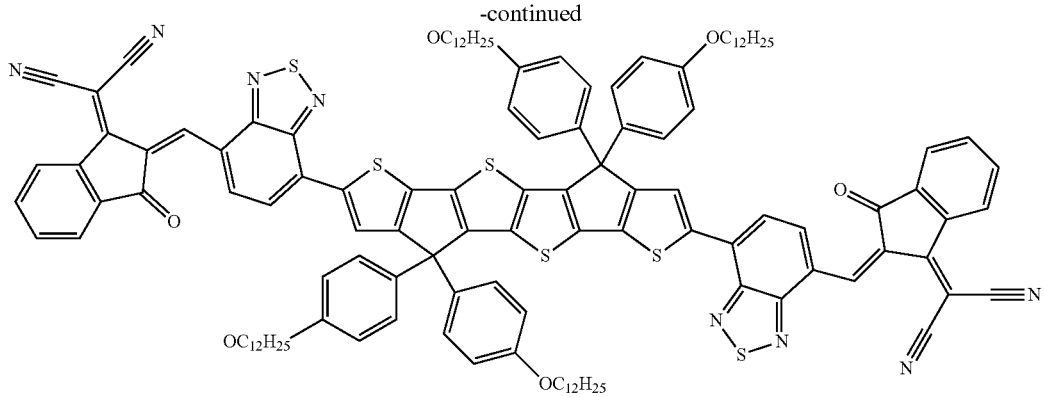

To a solution of intermediate 44 (255 mg, 0.15 mmol) in anhydrous chloroform (16 cm³) is added pyridine (0.85 cm³, 11 mmol). The mixture is then degassed with nitrogen before cooling to −40° C. 3-(Dicyanomethylidene)indan-1-one (205 mg, 1.05 mmol) is added and the solution is further degassed for 10 minutes and with stirring, is allowed to warm before being held at −15 to −20° C. After 4 hours the reaction mixture is then added to methanol (100 cm³) washing in with methanol (2×10 cm³) and dichloromethane (10 cm³). Additional methanol (50 cm³) is added and the suspension stirred for 10 minutes before the solid is collected by vacuum filtration, washing the solid with additional methanol (3×10 cm³). The crude product is purified by silica plug (40-60 petrol:dichloromethane; 1:4), concentrating the product in vacuo. The solid is then triturated with methanol (3×10 cm³) and collected by filtration, before being additionally washed with cyclohexane (3×10 cm³), diethyl ether (3×10 cm³), acetone (3×10 cm³), methyl ethyl ketone (10 cm³) and ethyl acetate (3×10 cm³) to give compound 103 (203 mg, 66%) as a partially pure black solid. $^1$H NMR (400 MHz, CDCl$_3$) 9.58 (2H, s), 9.28 (2H, d, J 8.6), 8.74 (2H, d, J 7.8), 8.36 (2H, s), 7.93-8.00 (4H, m), 7.75-7.86 (4H, m), 7.23-7.27 (8H, m), 6.83-6.89 (8H, m), 3.92 (8H, t, J 6.5), 1.70-1.80 (8H, m), 1.38-1.46 (8H, m), 1.18-1.37 (64H, m), 0.87 (12H, t, J 6.9).

Example 104

Intermediate 45

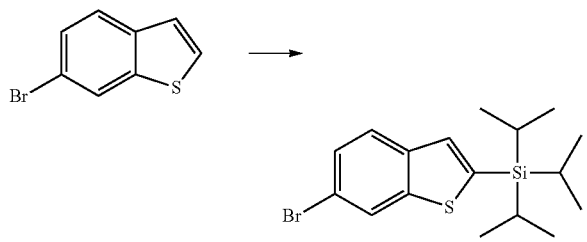

To a solution of 6-bromo-benzo[b]thiophene (9.09 g, 42.6 mmol) in anhydrous tetrahydrofuran (150 cm³) at −30° C. is added dropwise lithium diisopropylamide (23.5 cm³, 46.9 mmol, 2.0 M in tetrahydrofuran/heptane/ethylbenzene). The mixture is stirred at −30° C. for 1 hour before triisopropylsilyltrifluoromethanesulfonate (14.4 g, 46.9 mmol) is added in one portion. The mixture is allowed to warm to 23° C. and stirred for 15 hours. Water (150 cm³) is added and the mixture diluted with diethyl ether (100 cm³). The aqueous layer is extracted with diethyl ether (2×50 cm³). The combined organic layer is washed with brine (50 cm³), dried over anhydrous magnesium sulphate, filtered and the solvent removed in vacuo. The residue slowly crystallises which is triturated in ethanol (150 cm³) to give intermediate 45 (11.5 g, 72%) as an off-white solid. $^1$H NMR (400 MHz, CDCl$_3$) 8.04 (1H, d, J 1.8), 7.69 (1H, d, J 8.5), 7.46 (1H, s), 7.46 (1H, dd, J 8.6, 1.9), 1.37-1.47 (3H, m), 1.16 (18H, d, J 7.5).

Intermediate 46

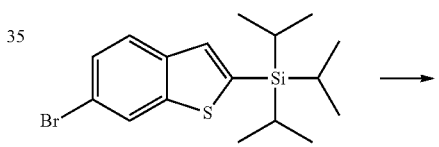

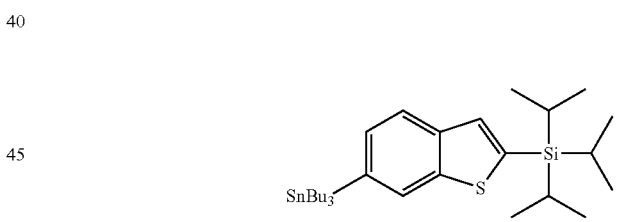

To a solution of intermediate 45 (5.00 g, 13.5 mmol) in anhydrous tetrahydrofuran (100 cm³) at −78° C. is added dropwise n-butyllithium (6.0 cm³, 14.9 mmol; 2.5 M in hexane). The mixture is stirred at −78° C. for 2 hours before tributyl(chloro)stannane (4.0 cm³, 15 mmol) is added. The mixture is stirred at −78° C. for 30 minutes before it is allowed to warm to 23° C. and stirred for 20 hours. Water (100 cm³) is added and the mixture diluted with diethyl ether (100 cm³). The aqueous layer is extracted with diethylether (2×50 cm³). The combined organic layer is washed with brine (50 cm³), dried over anhydrous magnesium sulphate, filtered and the solvent removed in vacuo to give 8.90 g of crude intermediate 46 as a yellow oil. The residue is used for the next step without any further purification. $^1$H NMR (400 MHz, CDCl$_3$) 8.01 (1H, d, J 0.9), 7.82 (1H, d, J 7.7, 0.7), 7.49 (1H, d, J 0.9), 7.43 (1H, dd, J 7.7, 0.7), 1.54-1.67 (9H, m), 1.33-1.44 (12H, m), 1.17 (18H, d, J 7.3), 0.92 (12H, t, J 7.3).

Intermediate 47

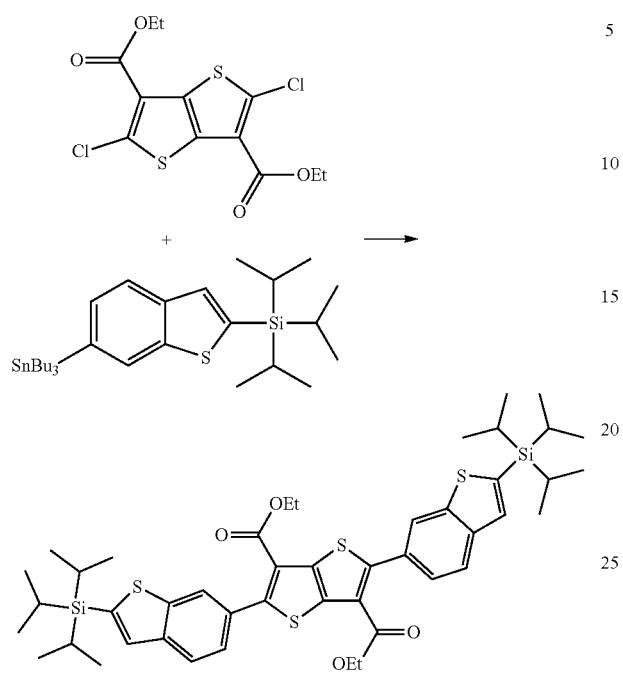

To a degassed solution of intermediate 9 (1.80 g, 5.10 mmol) and intermediate 46 (7.8 g, 12 mmol, 90% purity) in anhydrous toluene (60 cm³) and anhydrous N,N-dimethylformamide (10 cm³) is added 2-dicyclohexylphosphino-2',4',6'-triisopropylbiphenyl (850 mg, 1.78 mmol) and tris(dibenzylideneacetone)dipalladium(0) (187 mg, 0.20 mmol) and the mixture stirred at 80° C. for 20 hours. The reaction mixture is allowed to cool to 23° C. and the solvents removed in vacuo. The residue is triturated in ice-cooled diethyl ether (50 cm³), filtered off and the solid washed with 40-60 petrol (2×20 cm³) to give intermediate 47 (3.01 g, 68%) as a yellow solid. ¹H NMR (400 MHz, CDCl₃) 8.15 (2H, d, J 1.6), 7.90 (2H, d, J 8.2), 7.62 (2H, dd, J 8.2, 1.6), 7.57 (2H, s), 4.34 (4H, q, J 7.1), 1.40-1.49 (6H, m), 1.32 (6H, t, J 7.1), 1.19 (36H, d, J 7.5).

Intermediate 48

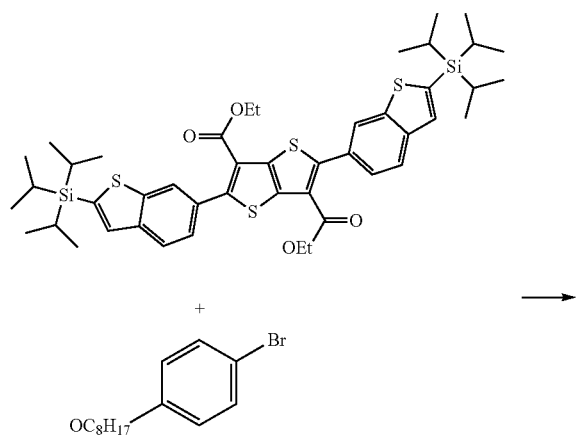

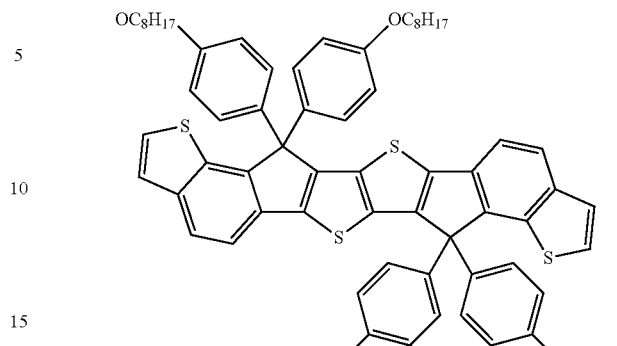

To a solution of 1-bromo-4-octyloxy-benzene (2.48 g, 8.71 mmol) in anhydrous tetrahydrofuran (60 cm³) at −78° C. is added dropwise n-butyllithium (3.48 cm³, 8.71 mmol, 2.5 M in hexanes). The mixture is stirred for 2 hours before intermediate 47 (1.50 g, 1.74 mmol) is added. The cooling bath is removed and the mixture is allowed to warm up at 23° C. over 17 hours. The reaction mixture is poured onto water (100 cm³) and diluted with dichloromethane (150 cm³). The aqueous layer is extracted twice with dichloromethane (2×50 cm³). The combined organic layer is washed with brine (50 cm³), dried over anhydrous magnesium sulphate, filtered and the solvent removed in vacuo. The residue is taken up in anhydrous toluene (300 cm³) and 4-methylbenzenesulfonic acid hydrate (662 mg, 3.48 mmol) is added. The mixture is stirred at 80° C. for 4 hours. After cooling to 23° C., the reaction is quenched by addition of saturated aqueous sodium hydrogenocarbonate solution (50 cm³), and diluted with water (50 cm³) and dichloromethane (150 cm³). The aqueous layer is extracted with dichloromethane (50 cm³). The combined organic layer is washed with brine (50 cm³), dried over anhydrous magnesium sulphate, filtered and the solvent removed in vacuo. The residue is taken up in anhydrous tetrahydrofuran (40 cm³) and tetrabutylammonium fluoride (2.73 g, 10.4 mmol) added. The mixture is stirred for 2 hours and then diluted with water (50 cm³) and dichloromethane (100 cm³). The aqueous layer is extracted with dichloromethane (50 cm³). The combined organic layer is washed with brine (50 cm³), dried over anhydrous magnesium sulphate, filtered and the solvent removed in vacuo. The residue is purified by column chromatography using a graded solvent system (40-60 petrol:dichloromethane; 19:1 to 7:3) to give intermediate 48 (990 mg, 45%) as a yellow gummy solid. ¹H NMR (400 MHz, CDCl₃) 7.80 (2H, d, J 8.1), 7.47 (2H, d, J 8.0), 7.36 (2H, d, J 5.5), 7.28 (2H, d, J 7.27), 7.16-7.23 (8H, m), 6.77-6.84 (8H, m), 3.90 (8H, t, J 6.5), 1.69-1.78 (8H, m), 1.37-1.46 (8H, m), 1.22-1.36 (32H, m), 0.88 (12H, t, J 7.0).

Intermediate 49

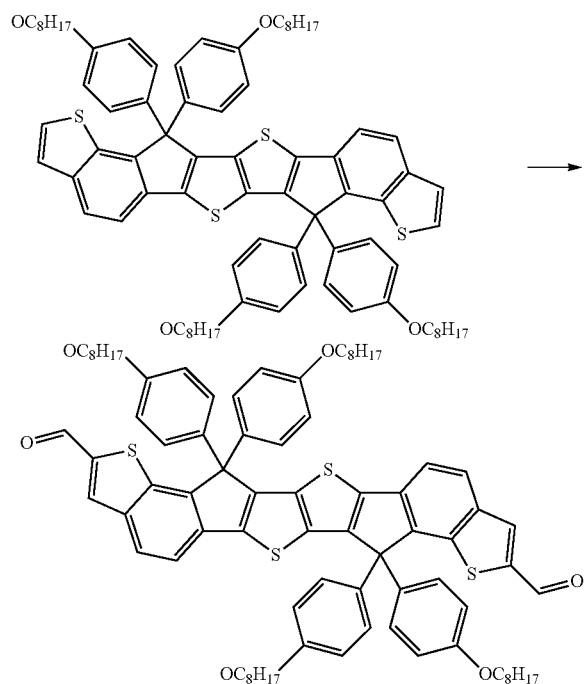

To a stirred solution of intermediate 48 (574 mg, 0.46 mmol) in anhydrous tetrahydrofuran (20 cm$^3$) at −78° C. is added dropwise n-butyllithium (0.74 cm$^3$, 1.8 mmol, 2.5 M in hexane). The mixture is stirred for 1 hour before anhydrous N,N-dimethylformamide (0.14 cm$^3$, 1.8 mmol) is added. The mixture is allowed to warm up at 23;C and is stirred for 3 hours. The reaction mixture is poured onto saturated aqueous ammonium chloride solution (20 cm$^3$) and diluted with dichloromethane (100 cm$^3$). The aqueous layer is extracted with dichloromethane (20 cm$^3$). The combined organic layer is washed with brine (50 cm$^3$), dried over anhydrous magnesium sulphate, filtered and the solvent removed in vacuo. The residue is purified by column chromatography using a graded solvent system (cyclohexane: dichloromethane; 3:7 to 2:3) to give intermediate 49 (280 mg; 46%) as an orange solid. $^1$H NMR (400 MHz, CDCl$_3$) 10.02 (2H, s), 8.03 (2H, s), 7.94 (2H, d, J 8.2), 7.54 (2H, d, J 8.1), 7.14-7.24 (8H, m), 6.79-6.85 (8H, m), 3.90 (8H, t, J 6.5), 1.67-1.79 (8H, m), 1.39-1.44 (8H, m), 1.20-1.36 (32H, m), 0.88 (12H, t, J 7.1).

Compound 104

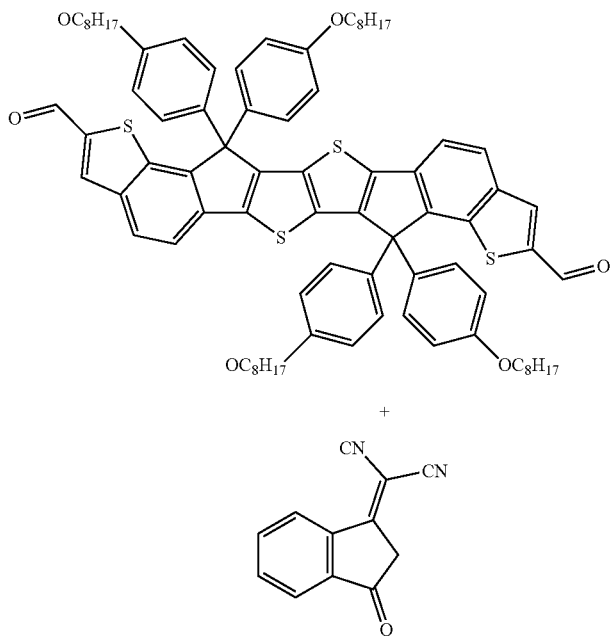

-continued

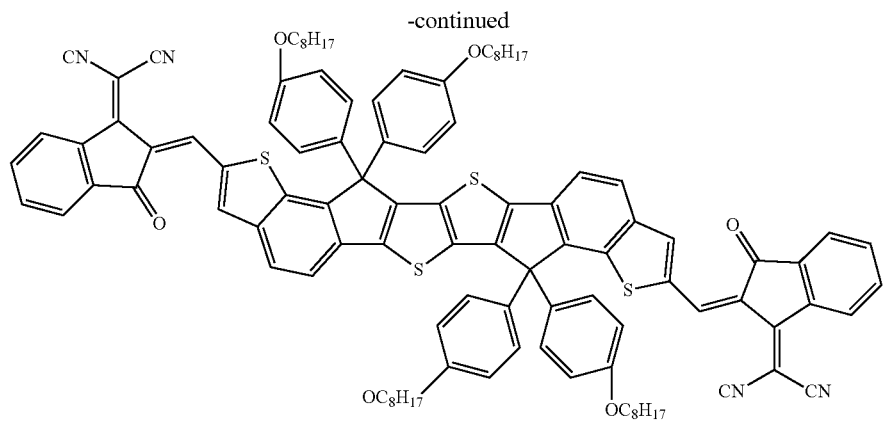

To a degassed solution of intermediate 49 (250 mg, 0.19 mmol) in a mixture of pyridine (2 cm$^3$) and chloroform (18 cm$^3$) at 0° C. is added 2-(3-oxo-indan-1-ylidene)-malononitrile (112 mg, 0.58 mmol) is added and the mixture stirred at 0° C. for 3 hours. The reaction is quenched by addition of aqueous hydrochloric acid solution (10 cm$^3$, 2 M) and the aqueous layer extracted with dichloromethane (20 cm$^3$). The combined organic layer is washed with brine (50 cm$^3$), dried over anhydrous magnesium sulphate, filtered and the solvent removed in vacuo. This residue is purified by column chromatography using a graded solvent system (40-60 petrol:dichloromethane; 3:2 to 3:7). The solid is triturated in ice-cooled acetone (30 cm$^3$) and with diethylether (20 cm$^3$) to give compound 104 (135 mg, 42%) as a blue solid. $^1$H NMR (400 MHz, CD$_2$Cl$_2$) 8.85 (2H, s), 8.67 (2H, d, J 7.5), 8.24 (2H, s), 7.95 (4H, t, J 9.2), 7.75-7.83 (4H, m), 7.59 (2H, d, J 8.3), 7.23 (8H, d, J 8.4), 6.83 (8H, d, J 8.4), 3.87 (8H, t, J 6.6), 1.63-1.74 (8H, m), 1.31-1.39 (8H, m), 1.18-1.31 (32H, m), 0.82 (12H, t, J 7.0).

Example 105

Intermediate 50

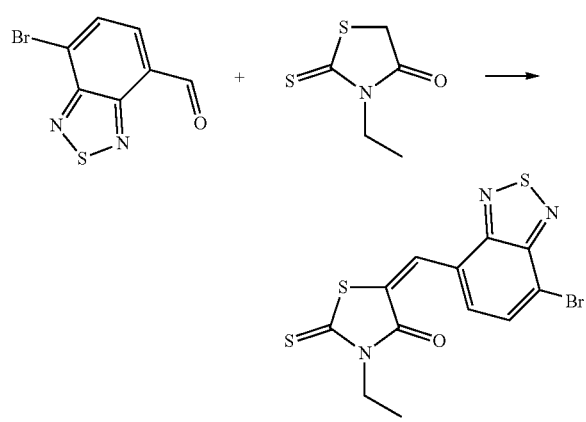

To a degassed mixture of 7-bromo-benzo[1,2,5]thiadiazole-4-carbaldehyde (500 mg, 2.0 mmol) and 3-ethyl-2-thioxo-thiazolidin-4-one (2.32 g, 14.4 mmol) and chloroform (220 cm$^3$) is added pyridine (5.8 cm$^3$, 72 mmol) and the reaction mixture further degassed for a 30 minutes. The reaction is then heated at 60° C. for 7 hours. The reaction is cooled to 23° C., filtered and the solid washed with dichloromethane (100 cm$^3$) to give intermediate 50 (534 mg, 67%) as a green/brown solid. $^1$H NMR (400 MHz, CDCl$_3$) 8.44 (1H, s), 7.98 (1H, d, J 7.7), 7.55 (1H, d, J 7.7), 4.25 (2H, q, J 7.2), 1.33 (3H, t, J 7.1).

Intermediate 51

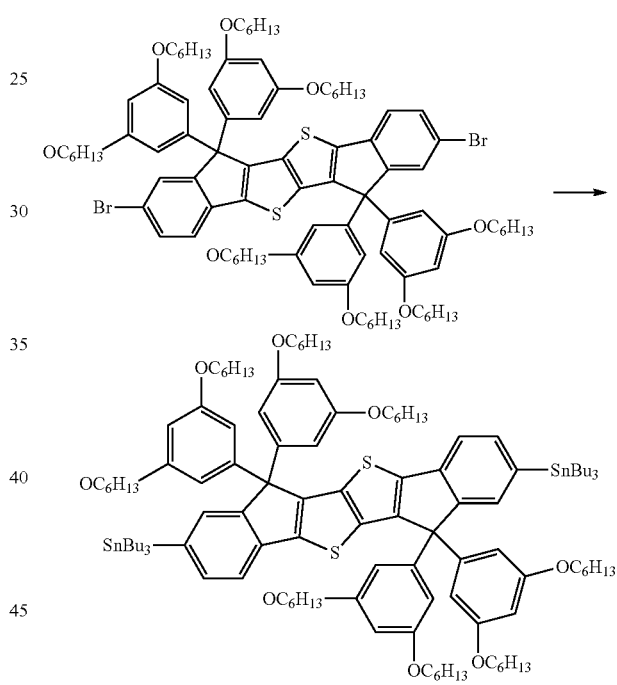

To a solution of intermediate 13 (3.09 g, 1.96 mmol) in anhydrous tetrahydrofuran (200 cm$^3$) at −78° C. is added dropwise n-butyllithium (3.1 cm$^3$, 7.8 mmol, 2.5 M in hexane) and the mixture stirred for 90 minutes. Tributyltin chloride (2.4 cm$^3$, 8.8 mmol) is added and the reaction mixture is allowed to warm to 23° C. and stirred for 15 hours. Methanol (2 cm$^3$) is added followed by water (50 cm$^3$) and diethyl ether (100 cm$^3$). The aqueous layer is extracted with diethyl ether (2×20 cm$^3$) and the combined organic layer is dried over anhydrous magnesium sulphate, filtered and the solvent removed in vacuo. The solid is washed with 40-60 petrol (2×10 cm$^3$) and taken up in dichloromethane. Evaporation of the solvents under vacuum gives a yellow oil that slowly crystallises at 23° C. Trituration in ice cooled acetone (20 cm$^3$) gives intermediate 51 (2.95 g, 75%) as a yellow solid. $^1$H NMR (400 MHz, CDCl$_3$) 7.57 (s, 2H), 7.36 (2H, d, J 7.4), 7.32 (2H, d, J 7.4), 6.39 (8H, d, J 2.2), 6.32 (4H, d, J 2.2), 3.73-3.91 (16H, m), 1.60-1.74 (16H, m), 1.43-1.55 (12H, m), 1.34-1.42 (16H, m), 1.20-1.34 (44H, m), 0.92-1.12 (12H, m), 0.84-0.89 (30H, m).

Compound 105

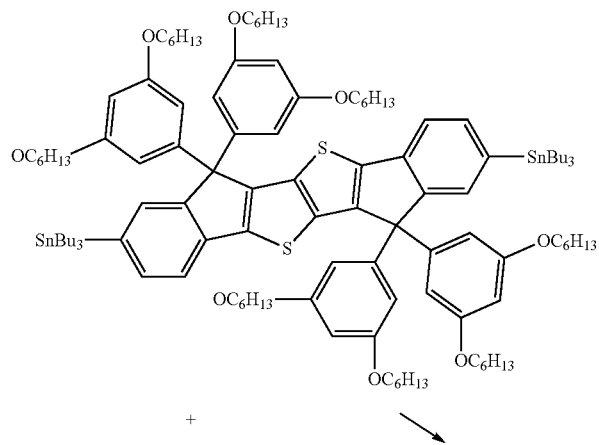

+

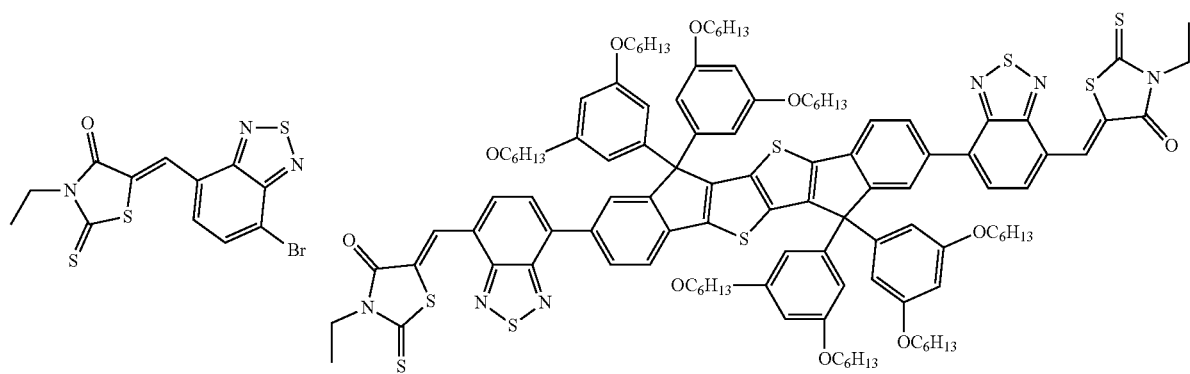

To a degassed solution of intermediate 51 (300 mg, 0.15 mmol) and intermediate 50 (174 mg, 0.45 mmol) in a mixture of anhydrous toluene (18 cm$^3$) and anhydrous N,N-dimethylformamide (2 cm$^3$) is added 2-dicyclohexylphosphino-2',4',6'-triisopropylbiphenyl (57 mg, 0.12 mmol) and tris(dibenzylideneacetone)dipalladium(0) (13 mg, 0.01 mmol) and the reaction mixture heated at 80° C. for 5 days. The reaction mixture cooled to 23° C. and the solvents removed in vacuo. The residue is purified by column chromatography using a graded solvent system (40-60 petrol:dichloromethane; 7:3 to 1:4). This solid is recrystallized (ethanol/dichloromethane) to give compound 105 (20 mg, 6%) as a deep red solid. $^1$H NMR (400 MHz, CDCl$_3$) 8.55 (2H, s), 8.20 (2H, d, J 1.6), 8.02 (2H, dd, J 8.0, 1.6), 7.83 (2H, d, J 7.6), 7.76 (2H, d, J 7.6), 7.54 (2H, d, J 7.9), 6.50 (8H, d, J 2.2), 6.37 (4H, t, J 2.2), 4.27 (4H, q, J 7.1), 3.78-3.97 (16H, m), 1.64-1.77 (16H, m), 1.33-1.43 (22H, m), 1.26-1.31 (32H, m), 0.83-0.89 (24H, m).

Example 106

Compound 106

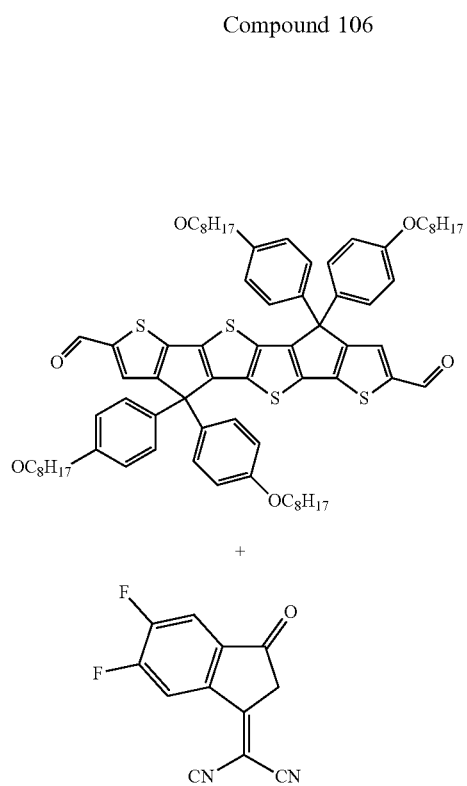

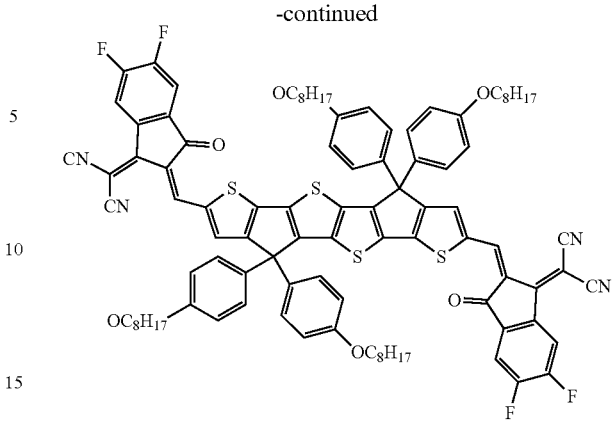

To a degassed mixture of intermediate 12 (100 mg, 0.08 mmol) and 2-(5,6-difluoro-3-oxo-indan-1-ylidene)-malononitrile (96 mg, 0.42 mmol) are dissolved in chloroform (2.5 cm³) is added pyridine (0.47 cm³, 5.8 mmol). The solution is stirred at 23° C. for 6 hours. Methanol (35 cm³) is added, the solid collected by filtration and washed with methanol (20 cm³). The solid is triturated in acetone (2 cm³), filtered and washed with acetone (2×1 cm³) to give compound 106 (133 mg, 98%) as a dark blue solid. $^1$H NMR (400 MHz, CDCl$_3$) 8.77 (2H, s), 8.46 (2H, dd, J 9.5, 6.5), 7.55-7.65 (4H, m), 7.02-7.11 (8H, m), 6.71-6.81 (8H, m), 3.85 (8H, t, J 6.5), 1.62-1.74 (8H, m), 1.35 (8H, p, J 7.3, 6.8), 1.13-1.31 (32H, m), 0.73-0.84 (12H, m).

Example 107

Compound 107

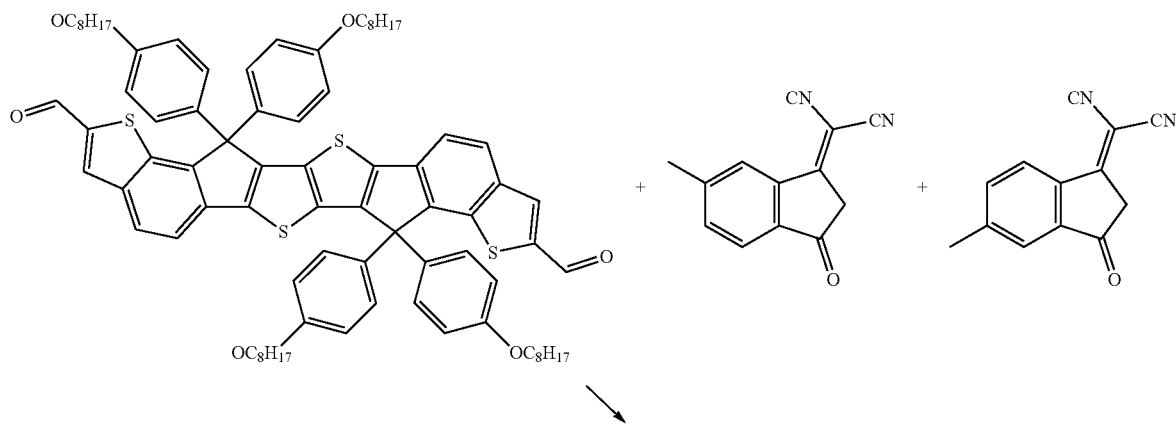

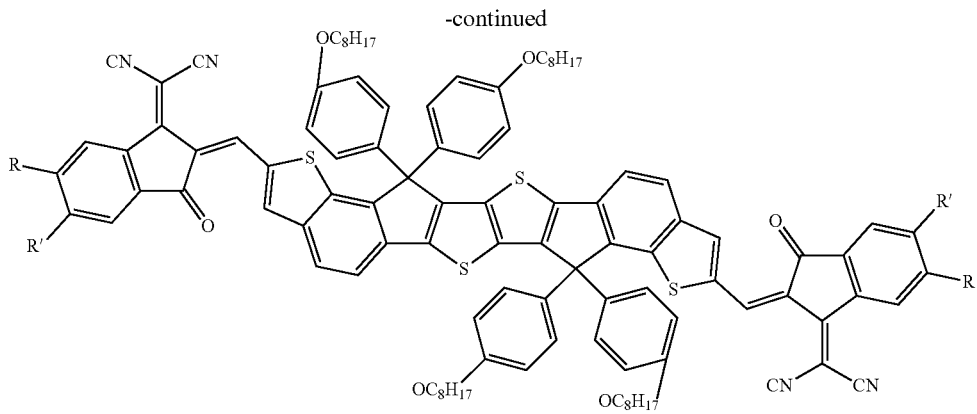

R = H or Me, R' = H or Me

To a degassed solution of intermediate 49 (215 mg; 0.17 mmol; 1.00 eq.) in a mixture of pyridine (1 cm³) and chloroform (10 cm³) is added an equimolar mixture of 2-(5-methyl-3-oxo-indan-1-ylidene)-malononitrile and 2-(6-methyl-3-oxo-indan-1-ylidene)-malononitrile (103 mg, 0.50 mmol) and the mixture stirred for 4 hours. The reaction is quenched by addition of aqueous hydrochloric acid solution (10 cm³, 2 M) and the aqueous layer extracted with dichloromethane (20 cm³). The combined organic layer is washed with brine (50 cm³), dried over anhydrous magnesium sulphate, filtered and the solvent removed in vacuo. The residue is purified column chromatography using a graded solvent system (cyclohexane:dichloromethane; 3:7 to 1:4). The solid is triturated in acetone (30 cm³) and filtered off to give compound 107 (73 mg, 23%) as a blue powder. $^1$H NMR (400 MHz, CDCl₃) 8.84 (2H, d, J 2.5), 8.59 (1H, d, J 8.1), 8.50 (1H, s), 8.29 (2H, s), 7.94 (2H, d, J 8.2), 7.86 (1H, d, J 7.8), 7.77 (1H, d, J 1.6), 7.55 (2H, d, J 8.2), 7.28 (8H, d, J 8.7), 6.87 (8H, d, J 8.7), 3.91 8H, (t, J 6.5), 1.67-1.80 (8H, m), 1.35-1.47 (8H, m), 1.18-1.35 (32H, m), 0.87 (12H, t, J 6.6).

Example 108

Intermediate 52

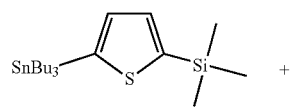

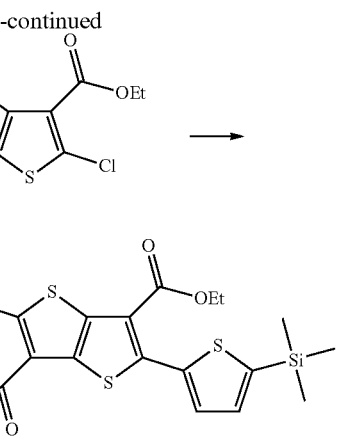

A mixture of intermediate 9 (7.1 g, 20 mmol), trimethyl-(5-tributylstannanyl-thiophen-2-yl)-silane (10 g, 23 mmol) and anhydrous toluene (300 cm³) is degassed by nitrogen for 25 minutes. To the mixture is added tetrakis(triphenylphosphine)palladium(0) (0.5 g, 0.4 mmol) and the mixture further degassed for 15 minutes. The mixture is stirred at 85° C. for 17 hours. The reaction mixture is filtered hot through a celite plug and washed through with hot toluene. The crude product is purified using silica gel column chromatography (40-60 petrol:dichloromethane: 4:1) to give intermediate 52 (2.3 g, 21%) as a pale yellow solid. $^1$H-NMR (400 MHz, CDCl₃) 7.40 (1H, d, J 3.7), 6.99-7.03 (1H, m), 4.13-4.29 (4H, m), 1.15-1.28 (6H, m), 0.10-0.37 (9H, s).

Intermediate 53

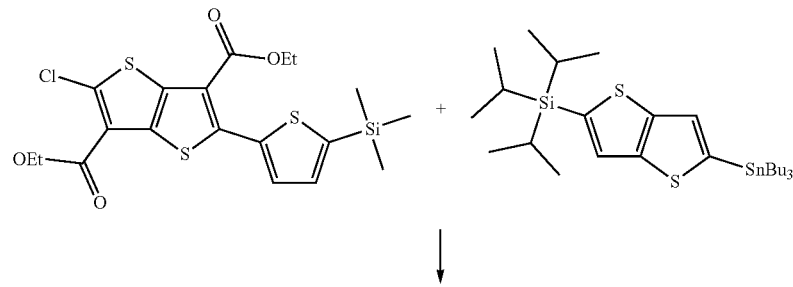

-continued

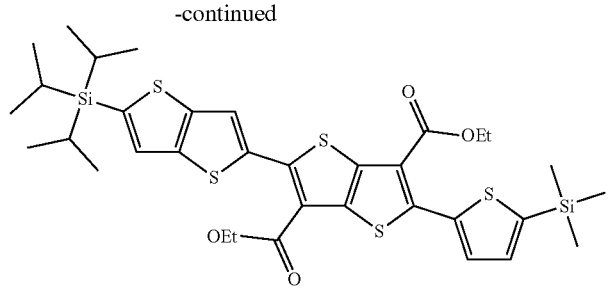

A mixture of intermediate 52 (2.2 g, 4.6 mmol), intermediate 23 (3.4 g, 5.8 mmol) and anhydrous toluene (300 cm$^3$) is degassed by nitrogen for 25 minutes. To the mixture is added tetrakis(triphenylphosphine)palladium(0) (0.5 g, 0.4 mmol) and the mixture further degassed for 15 minutes. The mixture is stirred at 85° C. for 17 hours. The reaction mixture is filtered hot through a celite plug and washed through with hot toluene. The crude product is stirred in acetone (100 cm$^3$) for 1 hour to form a heavy suspension. The solid is collected by filtration to give intermediate 53 (3.2 g, 75%) as a pale brown solid. $^1$H NMR (400 MHz, CDCl$_3$) 7.80-7.86 (1H, s), 7.65 (1H, d, J 3.4), 7.38 (1H, s), 7.24 (1H, d, J 3.4), 4.43 (4H, m), 1.31-1.51 (10H, m), 1.15 (18H, d, J 7.3), 0.38 (9H, s).

Intermediate 54

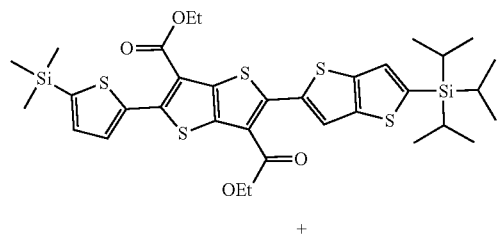

+

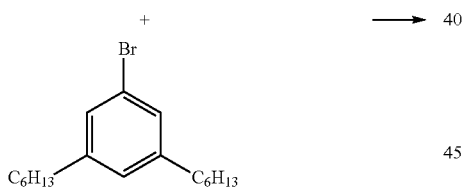

⟶

To a solution of 1-bromo-3,5-dihexyl-benzene (4.9 g, 15 mmol) in anhydrous tetrahydrofuran (100 cm$^3$) at −78° C. is added dropwise n-butyllithium (6.0 cm$^3$, 15.0 mmol, 2.5 M in hexane) over 30 minutes. After addition, the reaction mixture is stirred at −78° C. for 120 minutes. Intermediate 53 (2.2 g, 3.0 mmol) is added and the mixture allowed to warm to 23° C. over 17 hours. Diethyl ether (100 cm$^3$) and water (100 cm$^3$) are added and the mixture stirred at 23° C. for 30 minutes. The product is extracted with diethyl ether (3×100 cm$^3$). The organics are combined and dried over anhydrous magnesium sulfate, filtered and the solvent removed in vacuo to give intermediate 54 (2.30 g, 47%) as a brown oil. $^1$H NMR (400 MHz, CD$_2$Cl$_2$) 7.21 (1H, s), 7.06 (1H, s), 6.80-7.03 (12H, m), 6.42-6.55 (2H, m), 3.36 (2H, d, J 4.4), 2.44-2.62 (16H, m), 1.48-1.65 (16H, m), 1.24-1.35 (49H, m), 1.11-1.17 (18H, m), 0.83-0.94 (24H, m), 0.26 (9H, s).

Intermediate 55

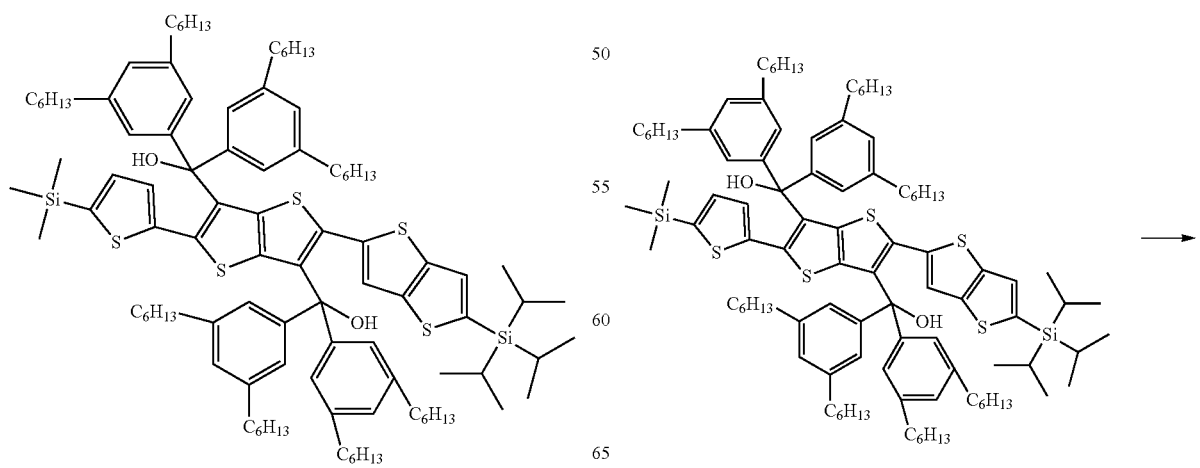

Intermediate 56

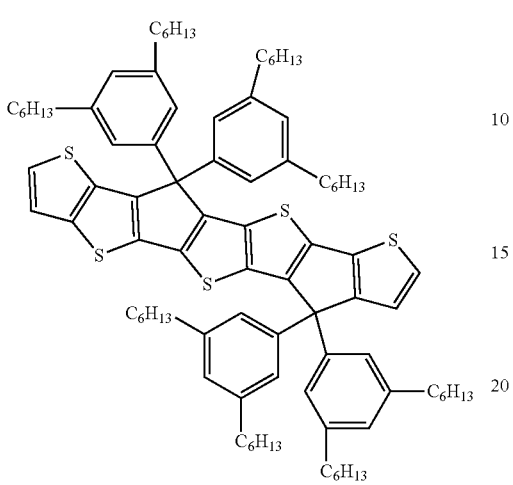

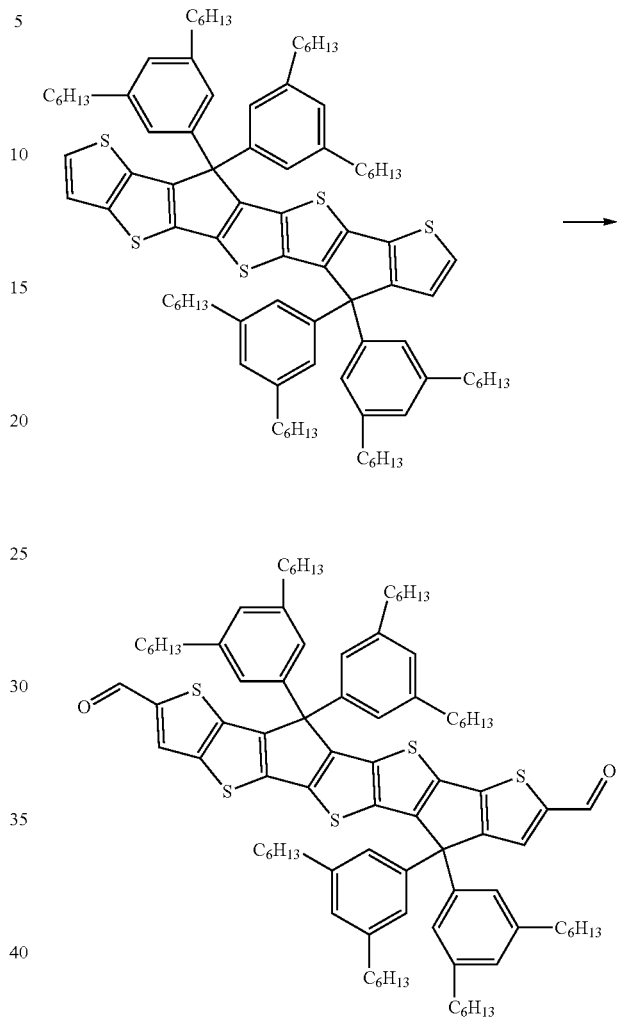

Nitrogen gas is bubbled through a suspension of amberlyst 15 strong acid (8.8 g) in anhydrous diethyl ether (100 cm³) at 0° C. for 60 minutes. Intermediate 54 (2.2 g, 1.4 mmol) is added whilst the mixture is degassed for a further 30 minutes. The resulting suspension is stirred at 23° C. for 2 hours. The reaction mixture is filtered and the solvent removed in vacuo. The crude is taken up in anhydrous tetrahydrofuran (50 cm³) and tetrabutylammonium fluoride (2.7 cm³, 2.7 mmol, 1 M in tetrahydrofuran) added. The mixture is stirred for 1 hour. Diethyl ether (100 cm³) and water (200 cm³) are added and the mixture stirred for 30 minutes. The product is extracted with diethyl ether (3×100 cm³). The organics are combined and dried over anhydrous magnesium sulfate, filtered and the solvent removed in vacuo. The crude is purified using silica gel column chromatography (40-60 petrol:dichloromethane; 9:1) to give intermediate 55 (1.0 g, 54%) as a dark orange solid. $^1$H NMR (400 MHz, CDCl$_3$) 7.25-7.31 (1H, m), 7.21-7.25 (1H, m), 7.17 (1H, d, J 4.9), 7.05 (1H, d, J 4.9), 6.81-6.91 (12H, m), 2.40-2.57 (16H, m), 1.54 (16H, d, J 6.8), 1.25 (48H, d, J 7.3), 0.85 (24H, q, J 6.2).

To a solution of intermediate 55 (500 mg, 0.37 mmol) in anhydrous tetrahydrofuran (22 cm³) at −78° C. is added dropwise n-butyllithium (0.6 cm³, 1.5 mmol, 2.5 M in hexane) over 10 minutes. After addition, the reaction mixture is stirred at −78° C. for 60 minutes. N,N-Dimethylformamide (0.15 cm³, 2.2 mmol) is added and the mixture allowed to warm to 23° C. over 17 hours. Diethyl ether (50 cm³) and water (50 cm³) are added and the mixture stirred at 23° C. for 30 minutes. The product is extracted with diethyl ether (3×100 cm³). The combined organics are dried over anhydrous magnesium sulfate, filtered and the solvent removed in vacuo. The crude is purified using silica gel column chromatography (40-60 petrol:dichloromethane; 8:2) to give intermediate 56 (95 mg, 18%) as a dark red oil. $^1$H NMR (400 MHz, CDCl$_3$) 9.70-9.85 (1H, s), 9.69-9.75 (1H, s), 7.83-7.87 (1H, s), 7.56 (1H, s), 6.83 (4H, s), 6.71 (8H, dd, J 12.8, 1.3), 2.29-2.53 (16H, m), 1.36-1.55 (16H, m), 1.05-1.27 (48H, m), 0.76 (24H, q, J 6.8).

Compound 108

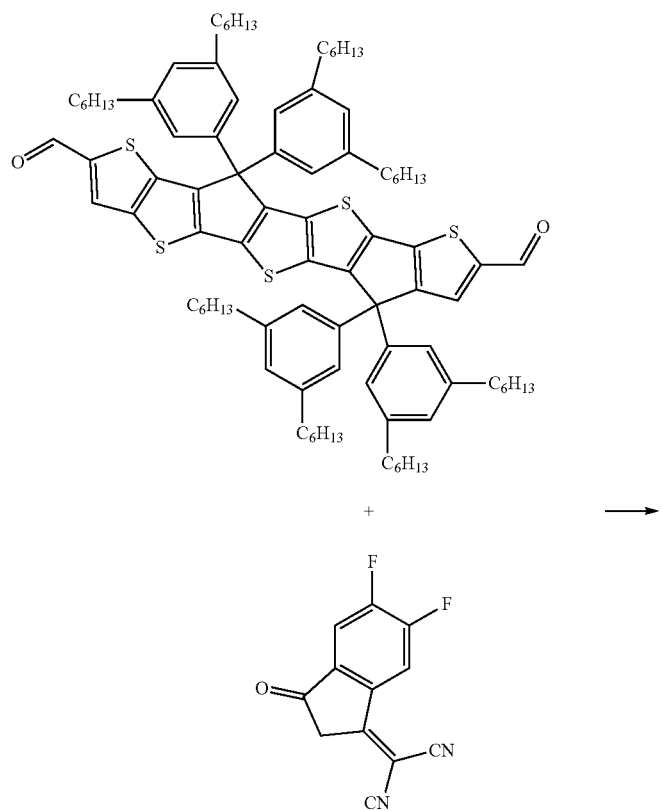

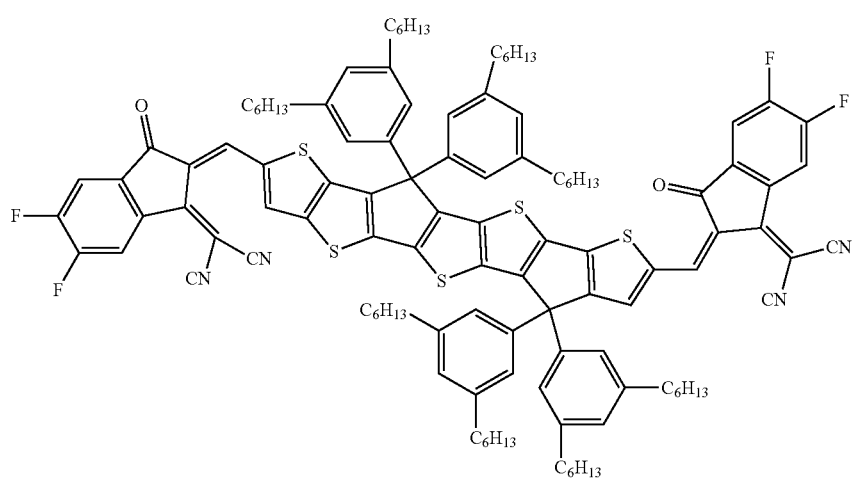

To a solution of intermediate 56 (100 mg, 0.07 mmol) in anhydrous chloroform (40 cm$^3$) at 0° C. is added pyridine (0.4 cm$^3$, 4.5 mmol). The mixture is then degassed with nitrogen before 2-(5,6-difluoro-3-oxo-indan-1-ylidene)-malononitrile (65 mg, 0.28 mmol) is added. The solution is further degassed and then stirred at 0° C. for 30 minutes. The ice bath is removed and the reaction is allowed to warm to 40° C. over 120 minutes. The mixture is diluted with 2-propanol (300 cm$^3$) to form a suspension and the solid collected by filtration. The crude is dissolved in dichloromethane (100 cm$^3$) then diluted with ethanol (300 cm$^3$) to produce a heavy suspension which is collected by filtration to give compound 108 (82 mg, 63%) as a blue/green solid. $^1$H NMR (400 MHz, CD$_2$Cl$_2$) 8.77 (2H, s), 8.42 (2H, dt, J 9.8, 6.1), 8.06 (1H, s), 7.67 (1H, s), 7.56 (2H, dt, J 11.4, 7.6), 6.66-6.96 (12H, m), 2.32-2.56 (16H, m), 1.35-1.57 (16H, m), 1.05-1.26 (48H, m), 0.63-0.80 (24H, m).

Example 109

Intermediate 57

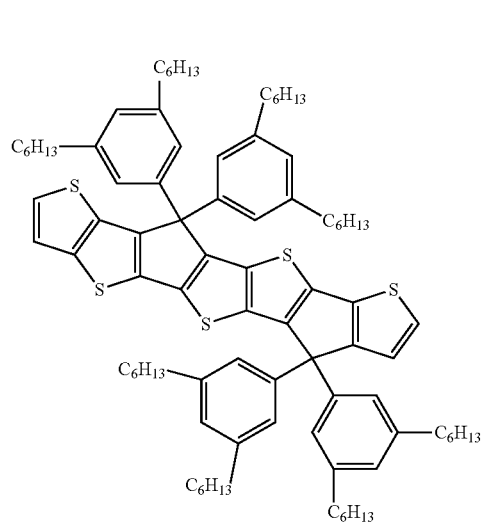

Intermediate 58

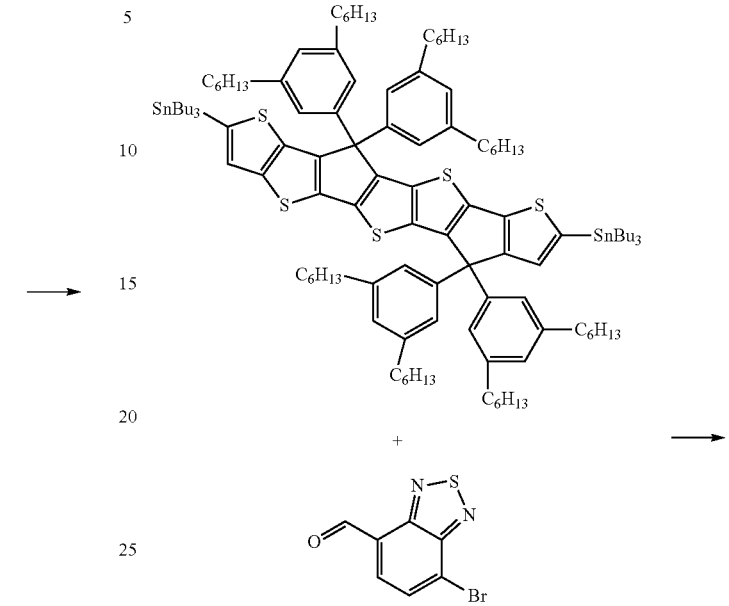

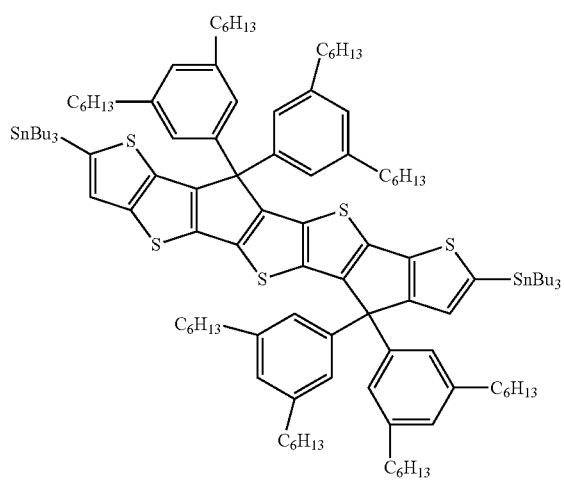

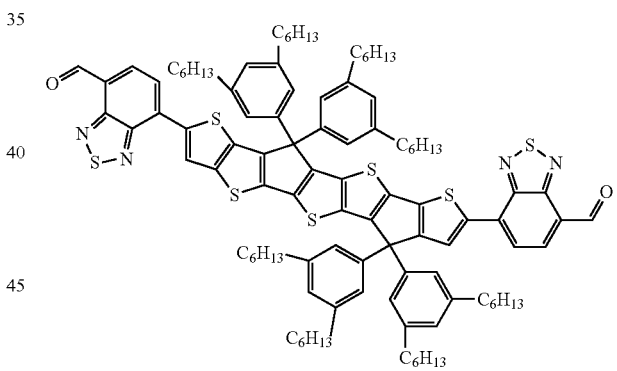

To a solution of intermediate 55 (500 mg, 0.37 mmol) in anhydrous tetrahydrofuran (22 cm$^3$) at −78° C. is added dropwise n-butyllithium (0.6 cm$^3$, 1.5 mmol, 2.5 M in hexane) over 10 minutes. After addition, the reaction mixture is stirred at −78° C. for 60 minutes before tributyltin chloride (0.4 cm$^3$, 1.6 mmol) is added. The mixture is then allowed to warm to 23° C. over 72 hours. The solvent removed in vacuo, and the residue passed through a zeolite plug (40-60 petrol). The crude is suspended in ethanol (100 cm$^3$) stirred for 30 minutes and the solvent decanted. This procedure is repeated twice to give partially purified intermediate 57 (860 mg) as a dark red oil. $^1$H NMR (400 MHz, CD$_2$Cl$_2$) 7.02-7.16 (1H, m), 6.82-6.93 (1H, m), 6.57-6.72 (12H, m), 2.20-2.32 (16H, m), 0.96-1.53 (48H, m), 0.54-0.78 (24H, m).

A mixture of intermediate 57 (712 mg, 0.37 mmol), 2-bromo-thiazole-5-carbaldehyde (178 mg, 0.73 mmol), tri-o-tolyl-phosphine (34 mg, 0.11 mmol) and anhydrous toluene (39 cm$^3$) is degassed by nitrogen for 10 minutes. To the mixture is added tris(dibenzylideneacetone) dipalladium(0) (27 mg, 0.03 mmol) and the mixture further degassed for 15 minutes. The mixture is stirred at 80° C. for 17 hours and, after cooling to 23° C., the solvent removed in vacuo. The crude is stirred in 2-propanol (100 cm$^3$) to form a suspension and the solid collected by filtration. The crude is purified using silica gel column chromatography (40-60 petrol:dichloromethane; 8:2) to give intermediate 58 (545 mg, 88%) as a dark blue solid. $^1$H NMR (400 MHz, CD$_2$Cl$_2$) 10.61 (2H, s), 8.67 (1H, s), 8.27 (1H, s), 8.10 (2H, d, J 7.6), 7.86 (2H, dd, J 11.9, 7.7), 6.84 (12H, d, J 12.0), 2.43 (16H, m), 1.43-1.57 (16H, m), 1.03-1.29 (48H, m), 0.63-0.80 (24H, m).

Compound 109

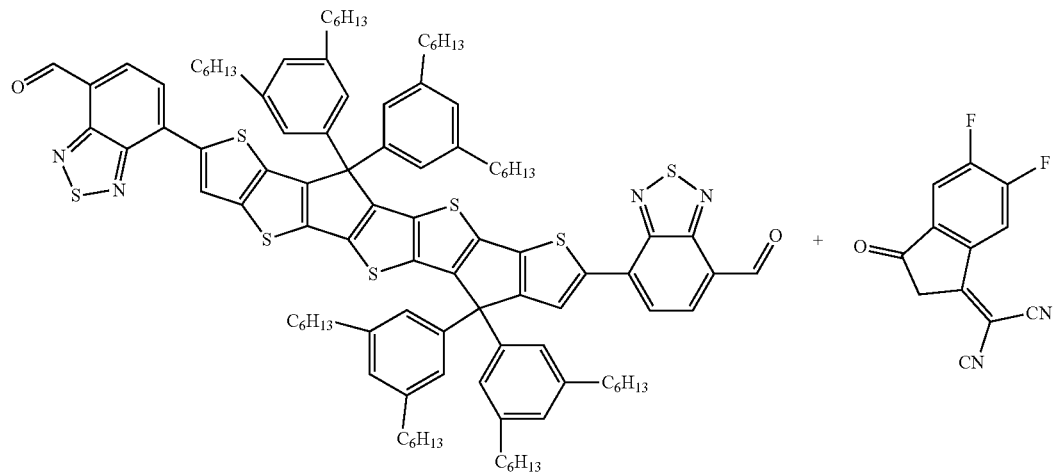

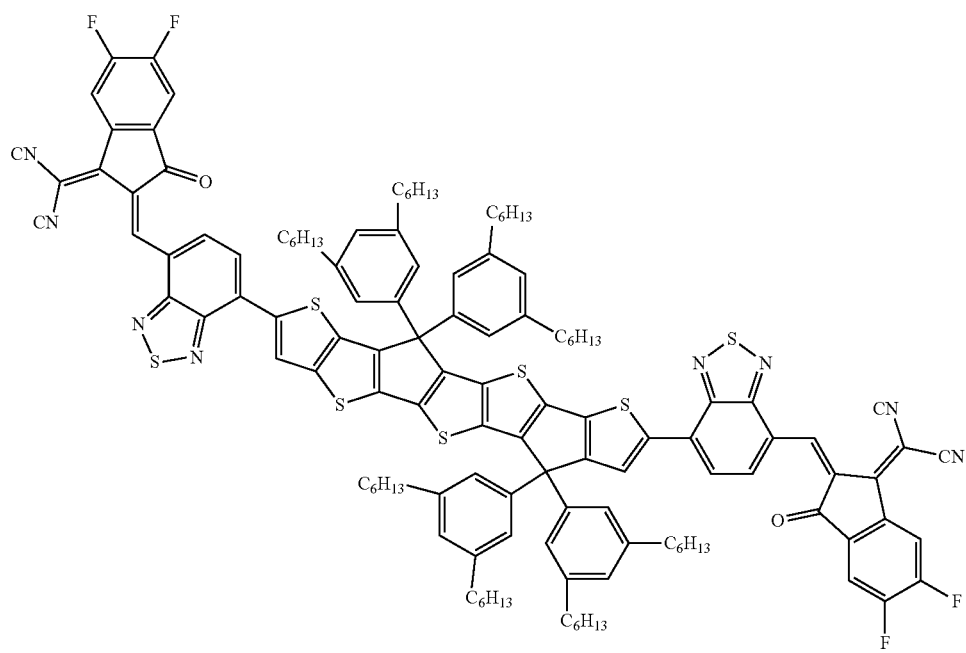

To a solution of intermediate 58 (120 mg, 0.07 mmol) in anhydrous chloroform (48 cm$^3$) at 0° C. is added pyridine (0.2 cm$^3$). The mixture is then degassed with nitrogen before 2-(5,6-difluoro-3-oxo-indan-1-ylidene)-malononitrile (66 mg, 0.29 mmol) is added. The solution is then further degassed and stirred at 0° C. for 20 minutes and at 23° C. for 3 hours. The mixture is diluted with ethanol (200 cm$^3$) to produce a heavy suspension. The solid is collected by filtration and washed with methanol (50 cm$^3$). The crude is suspended in a 1:1 mixture of acetone:diethyl ether (200 cm$^3$) to form a suspension and stirred for 30 minutes. The solid is collected by filtration to give compound 109 (110 mg, 73%) as a black solid. $^1$H NMR (400 MHz, CD$_2$Cl$_2$) 9.60 (2H, s), 9.31 (2H, t, J 8.4), 8.84 (1H, s), 8.57-8.65 (2H, m), 8.45 (1H, s), 8.04 (2H, dd, J 12.0, 8.1), 7.78 (2H, t, J 7.7), 6.93-7.03 (12H, m), 2.51-2.63 (16H, m), 1.57-1.66 (16H, m), 1.23-1.36 (48H, m), 0.79-0.90 (24H, m).

Example 110

Compound 110

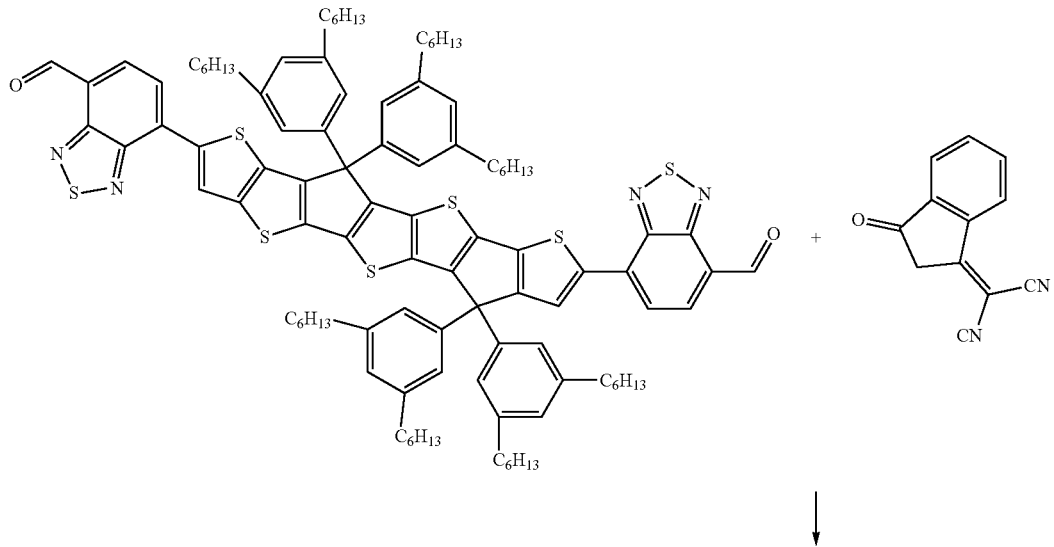

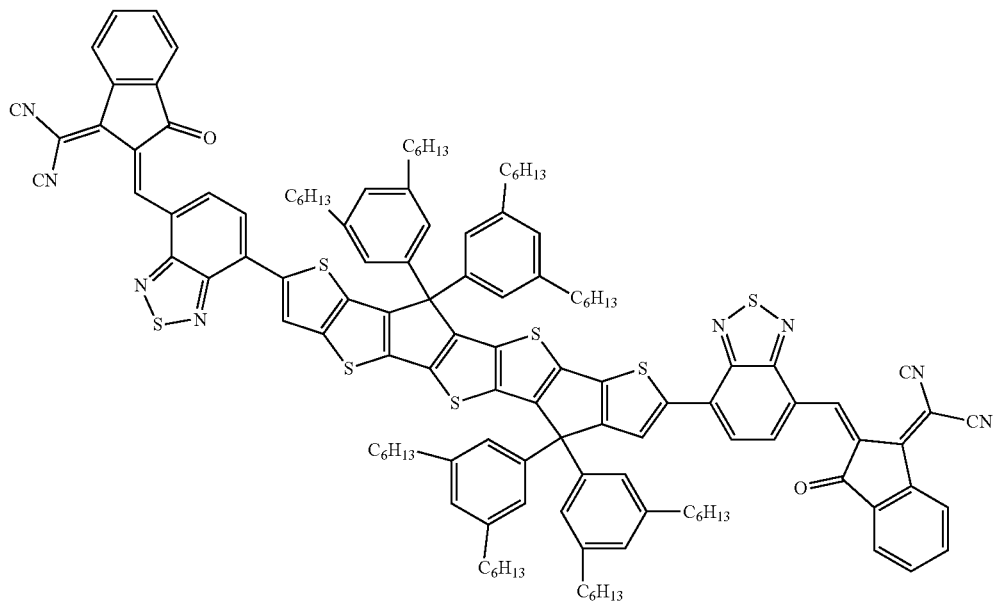

To a solution of intermediate 58 (150 mg, 0.09 mmol) in anhydrous chloroform (48 cm$^3$) at 0° C. is added pyridine (0.3 cm$^3$). The mixture is then degassed with nitrogen before a solution of 3-(dicyanomethylidene) indan-1-one (69 mg, 0.36 mmol) in chloroform (10 cm$^3$) is added. The solution is then further degassed and stirred at 23° C. for 4 hours. The mixture is diluted with ethanol (500 cm$^3$) to produce a heavy suspension. The solid is collected by filtration and washed with acetone (50 cm$^3$) to give compound 110 (98 mg, 54%) as a black solid. $^1$H NMR (400 MHz, CD$_2$Cl$_2$) 9.57 (2H, s), 9.33 (2H, t, J 7.9), 8.82 (1H, s), 8.76 (2H, d, J 7.3), 8.44 (1H, s), 8.01-8.07 (2H, m), 7.99 (2H, d, J 7.1), 7.78-7.90 (4H, m), 6.98 (12H, d, J 11.7), 2.48-2.62 (16H, m), 1.50-1.65 (24H, m), 1.20-1.41 (48H, m), 0.78-0.92 (24H, m).

Example 111

Intermediate 59

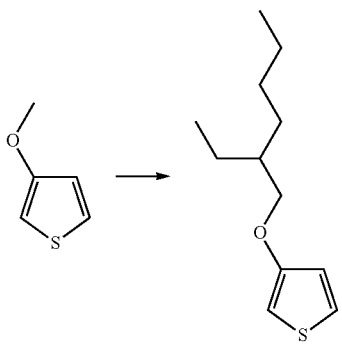

3-Methoxy-thiophene (25.0 g, 219 mmol) and 2-ethyl-hexan-1-ol (51.4 cm³, 329 mmol) are dissolved in anhydrous toluene (500 cm³). With stirring 4-methylbenzenesulfonic acid hydrate (4.17 g, 21.9 mmol) is added and after 35 minutes at 23° C. the reaction is heated at reflux for 20 hours. The reaction is then cooled to 23° C. before additional toluene (50 cm³) is added. The solution is washed with water (2×250 cm³) and brine (250 cm³) before drying over magnesium sulfate, filtered and concentrated in vacuo. The crude product is purified by silica plug (40-60 petrol) followed by column chromatography (40-60 petrol), to give intermediate 59 (23.4 g, 50% yield) as a yellow tinged oil. $^1$H NMR (400 MHz, CDCl$_3$) 7.18 (1H, dd, J 5.3, 3.1), 6.77 (1H, dd, J 5.3, 1.6), 6.24 (1H, dd, J 3.2, 1.5), 3.84 (2H, dd, J 5.8, 0.9), 1.72 (1H, spt, J 6.1), 1.26-1.56 (8H, m), 0.88-0.97 (6H, m).

Intermediate 60

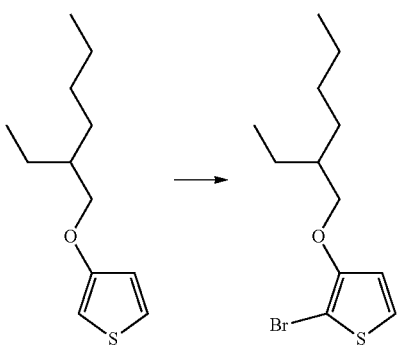

To a solution of intermediate 59 (23.1 g, 109 mmol) in anhydrous N,N-dimethylformamide (330 cm³) at 0° C. is added a solution of 1-bromo-pyrrolidine-2,5-dione (19.4 g, 109 mmol) in anhydrous N,N-dimethylformamide (110 cm³). The reaction mixture is then stirred at 23° C. for 41 hours before adding to ice (2000 cm³) with stirring. Once melted, half of the aqueous suspension is extracted with 40-60 petrol (300 cm³). The aqueous layer is removed and the second half of the aqueous suspension extracted. The aqueous layers are additionally extracted in this manner with a second washing of 40-60 petrol (200 cm³). The organic extracts are then combined and washed with brine (2×200 cm³), dried over magnesium sulfate and filtered. Due to stability concerns, the bulk sample is not concentrated in vacuo and is allowed to remain in solution until immediately prior to use. $^1$H NMR of sample suggests quantitative yield of intermediate 60 as a yellow oil. 1H NMR (400 MHz, CDCl$_3$) 7.19 (1H, d, J 5.9), 6.75 (1H, d, J 5.9), 3.93 (2H, d, J 5.9), 1.71 (1H, sept, J 6.1), 1.24-1.60 (8H, m), 0.88-0.98 (6H, m).

Intermediate 61

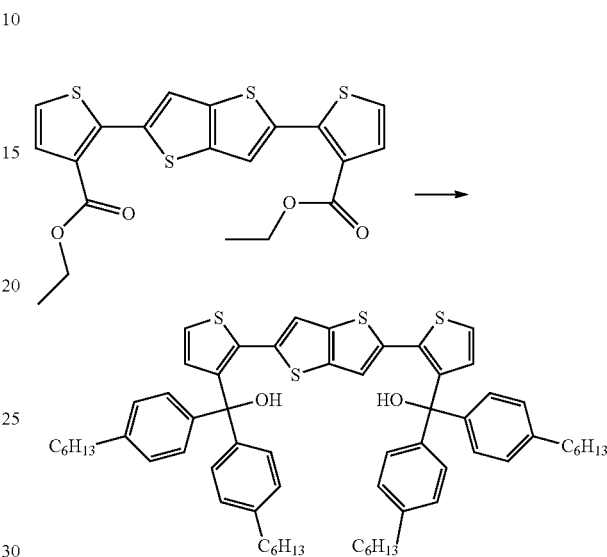

To a suspension of 1-bromo-4-hexylbenzene (10.3 g, 42.5 mmol) in anhydrous tetrahydrofuran (180 cm³) at −78° C. is added tert-butyllithium (50 cm³, 85 mmol, 1.7 M in pentane) over 30 minutes. The reaction is then allowed to warm to −30° C., before re-cooling to −78° C. Additional 1-bromo-4-hexylbenzene (1.00 g, 4.15 mmol) is then added to ensure consumption of any residual tert-butyllithium. Ethyl 2-[5-(3-ethoxycarbonyl-2-thienyl)thieno[3,2-b]thiophen-2-yl] thiophene-3-carboxylate (3.81 g, 8.50 mmol) is then added in one portion to the reaction mixture and the mixture allowed to stir at 23° C. for 17 hours. The reaction is diluted with diethyl ether (100 cm³) and washed with water (200 cm³). The organic layer is diluted with diethyl ether (100 cm³) then further washed with water (200 cm³) and brine (100 cm³). The organic layer is then dried over anhydrous magnesium sulfate, filtered and concentrated in vacuo. The crude product is then purified by column chromatography using a graded solvent system (40-60 petrol:dichloromethane; 1:0 to 2:3) to give intermediate 61 (5.61 g, 66% yield) as a light yellow oil. $^1$H NMR (400 MHz, CDCl$_3$) 7.07-7.18 (18H, m), 6.65 (2H, s), 6.45 (2H, d, J 5.4), 3.25 (2H, s), 2.60 (8H, t, J 7.7), 1.58-1.66 (8H, m), 1.24-1.39 (24H, m), 0.87-0.92 (12H, m).

Intermediate 62

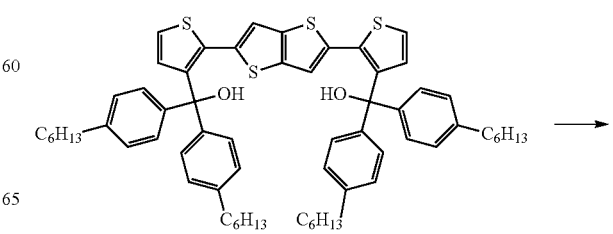

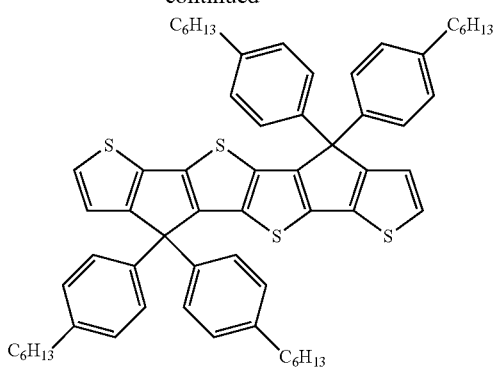

To a degassed suspension of amberlyst 15 strong acid (10.8 g) in anhydrous toluene (65 cm³) is added a degassed solution of intermediate 61 (2.69 g, 2.68 mmol) in anhydrous toluene (64 cm³) and the reaction mixture stirred at 23° C. for 15 minutes. The reaction mixture is then heated at 40° C. for 70 minutes and at 50° C. for a further 45 minutes. The reaction is then filtered through a layered bed of celite:magnesium sulfate:celite washing with toluene (3×40 cm³) and diethyl ether (5×50 cm³). The mixture is then concentrated in vacuo and purified by column chromatography, eluting with a graded solvent system (40-60 petrol: dichloromethane; 1:0 to 1:9) to give intermediate 62 (540 mg, 21%) as a yellow solid. ¹H NMR (400 MHz, CDCl₃) 7.12-7.18 (10H, m), 7.05-7.10 (10H, m), 2.55 (8H, t, J 7.8), 1.51-1.63 (8H, m), 1.23-1.37 (24H, m), 0.84-0.90 (12H, m).

Intermediate 63

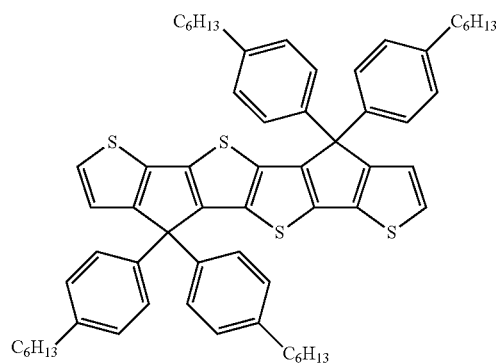

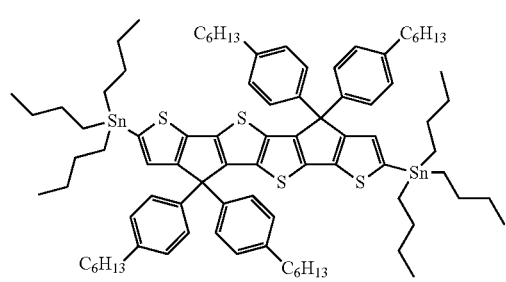

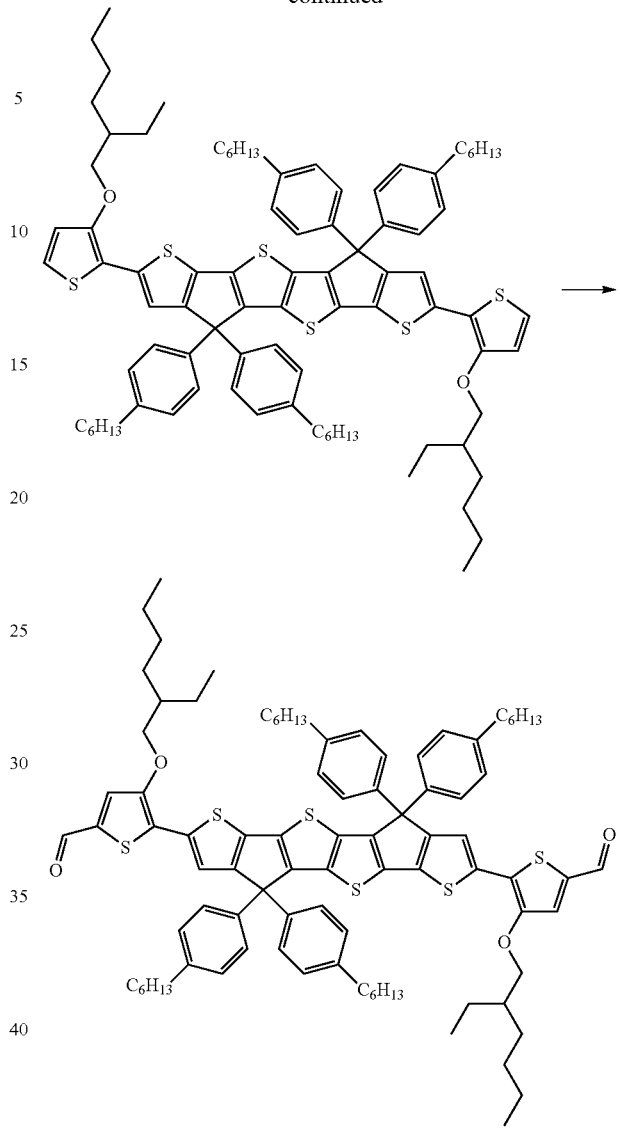

A solution of intermediate 62 (1.15 g, 1.19 mmol) in anhydrous tetrahydrofuran (70 cm³) is cooled to −78° C. before n-butyllithium (1.4 cm³, 3.6 mmol, 2.5 M in hexanes) is added via syringe. The mixture is then stirred at −78° C. for 1 hour before tributyltin chloride (1.1 cm³, 4.2 mmol) is added. The mixture is stirred at 23° C. for 17 hours, methanol (20 cm³) added and after stirring for 6 hours the reaction mixture is concentrated in vacuo. The crude is triturated with methanol (3×10 cm³) and then added to a solution of intermediate 61 (785 mg, 2.69 mmol) (freshly concentrated in vacuo) in anhydrous toluene (150 cm³). The solution is then degassed with nitrogen before tris(dibenzylideneacetone)dipalladium (90 mg, 0.10 mmol) and tris(o-tolyl)phosphine (112 mg, 0.368 mmol) are added. The reaction mixture is then further degassed before heating at 80° C. with continued degassing for 19 hours. The reaction is then stirred at 23° C. for 4 days after which it is concentrated in vacuo. The crude material is then partially purified by silica plug using a graded solvent system (petrol 40-60:dichloromethane; 1:0-2:3). The partially purified material is then triturated with methanol (6×10 cm³), taken up in anhydrous tetrahydrofuran (58 cm³) and cooled to −78° C. To this mixture is added dropwise n-butyllithium (1.4 cm³, 3.5 mmol, 2.5 M in hexanes) and the reaction mixture stirred for 1 hour. The reaction is then quenched by the addition of N,N-dimethylformamide (2.3 cm³, 30 mmol) and after 1 hour at −78° C. the reaction is allowed to stir at 23° C. for 15 hours. The reaction is diluted with diethyl ether (150 cm³) and washed with water (150 cm³) with added brine (20 cm³). The organic layer is then isolated and the aqueous layer additionally extracted with diethyl ether (50 cm³). The combined organic layers are then further washed with water (100 cm³) with added brine (20 cm³) and brine (100 cm³) before they are dried over magnesium sulfate, filtered and concentrated in vacuo. The crude product is purified by column chromatography using a graded solvent system (40-60 petrol:dichloromethane; 1:0 to 2:3) followed by further column chromatography using a graded solvent system (80-100 petrol:diethyl ether; 1:0 to 6:3) to give intermediate 63 (285 mg, 17% yield over 3 steps) as a black solid. ¹H NMR (400 MHz, CDCl₃) 9.73 (2H, s), 7.44 (2H, s), 7.41 (2H, s), 7.17 (8H, d, J 8.2), 7.11 (8H, d, J 8.2), 4.08 (4H, d, J 5.1), 2.57 (8H, t, J 7.8), 1.81 (2H, spt, J 6.0), 1.43-1.66 (16H, m), 1.22-1.40 (32H, m), 0.82-1.00 (24H, m).

Compound 111

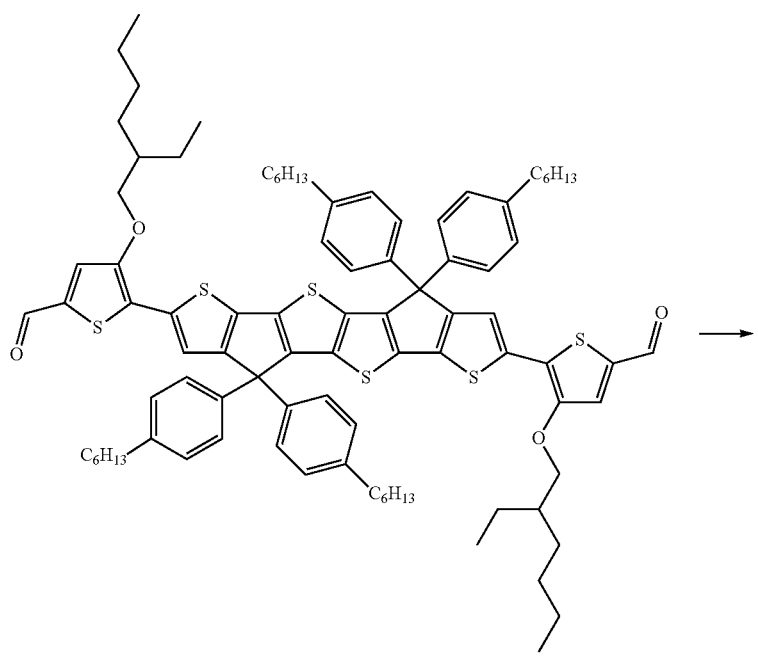

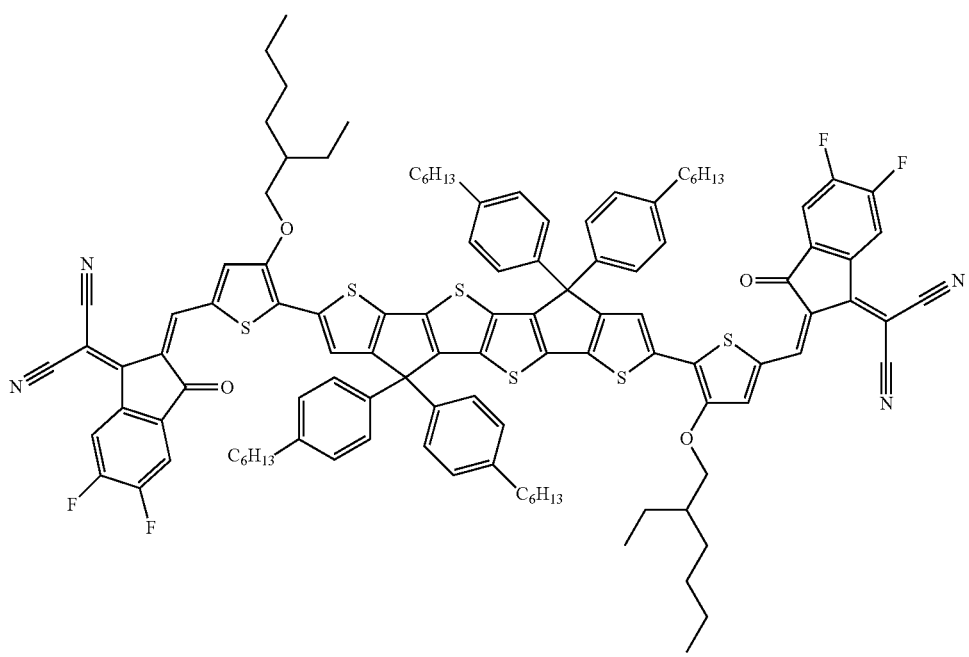

To a solution of intermediate 63 (150 mg, 0.104 mmol) in anhydrous chloroform (11 cm³) is added pyridine (0.59 cm³) and the solution degassed for 25 minutes. The reaction mixture is then cooled to −20° C. and 2-(5,6-difluoro-3-oxo-indan-1-ylidene)-malononitrile (95 mg, 0.41 mmol) is added. The reaction mixture is then degassed for a further 15 minutes and allowed to warm to 23° C. over 3 hours. The cooling bath is then removed and the reaction stirred at 23° C. for a further 2 hours before the reaction is added to stirring methanol (200 cm³) washing in with dichloromethane (10 cm³). After 30 minutes the precipitate is collected by filtration, washed with methanol (3×10 cm³) to give compound 45 (132 mg, 68% yield) as a black solid. ¹H NMR (400 MHz, CDCl₃) 8.67 (2H, s), 8.52 (2H, dd, J 10.2, 6.5), 7.67 (2H, s), 7.61-7.66 (2H, m), 7.51 (2H, s), 7.16-7.21 (8H, m), 7.11-7.16 (8H, m), 4.15 (4H, d, J 5.4), 2.60 (8H, t, J 7.7), 1.86 (2H, spt, J 6.1), 1.50-1.69 (16H, m), 1.25-1.43 (32H, m), 1.01 (6H, t, J 7.5), 0.92-0.97 (6H, m), 0.85-0.92 (12H, m).

Example 112

Compound 112

Intermediate 64

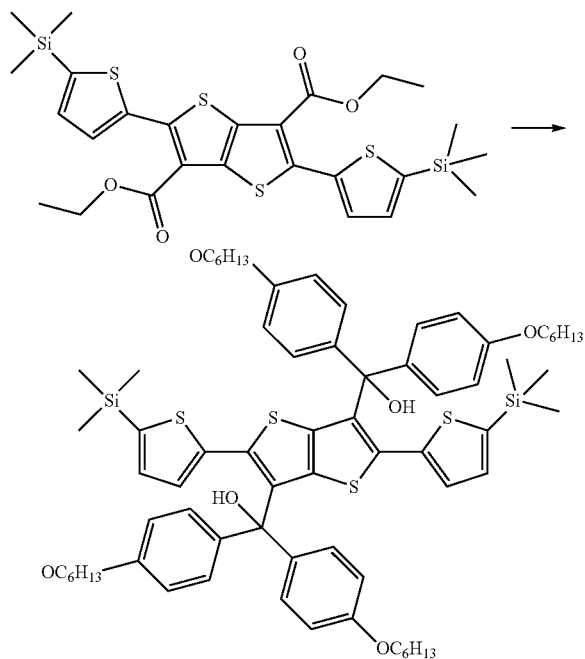

To a solution of 1-bromo-4-hexyloxy-benzene (1.43 g, 5.57 mmol) in anhydrous tetrahydrofuran (20 cm³) at −78° C. is added tert-butyllithium (6.55 cm³, 11.1 mmol, 1.7 M in pentane) over 5 minutes. The reaction mixture is then stirred for 45 minutes. Intermediate 10 (550 mg, 0.93 mmol) is added as a single portion, the cooling removed and the reaction mixture stirred at 23° C. for 17 hours. Water (50 cm³) and diethyl ether (50 cm³) are added. The organic phase is washed with water (2×30 cm³), dried over magnesium sulphate, filtered and concentrated in vacuo. The resulting solid is slurried in 40-60 petrol (10 cm³), filtered and washed with 40-60 petrol (2×10 cm³) to give intermediate 64 (1.13 g, 76%) as a pale green solid. ¹H NMR (400 MHz, CDCl₃) 7.11-7.22 (8H, m), 6.85 (2H, d, J 3.4), 6.75-6.82 (7H, m), 6.49 (2H, d, J 3.4), 3.94 (8H, t, J 6.6), 3.34 (2H, s), 1.67-1.84 (8H, m), 1.39-1.52 (8H, m), 1.25-1.38 (16H, m), 0.86-0.95 (12H, m), 0.22 (s, 18H).

Intermediate 65

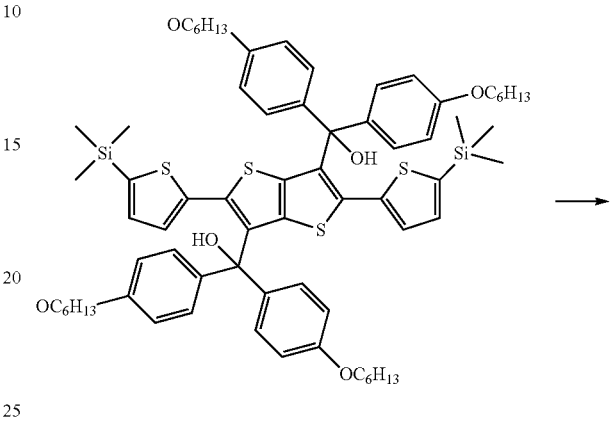

A solution of intermediate 64 (850 mg, 0.70 mmol) dissolved in toluene (34 cm³) at 75° C. is degassed with a flow of nitrogen for 20 minutes. Amberlyst 15 strong acid (4.0 g) is added and the reaction mixture degassed for a further 10 minutes and stirred for 17 hours. The reaction is allowed to cool to 23° C., filtered and the solid washed with toluene (50 cm³). The combined organic phases is concentrated in vacuo. The intermediate material is dissolved in chloroform (17 cm³), N,N-dimethylformamide (819 mg, 11.2 mmol) is added and the solution cooled to 0° C. Phosphoryl chloride (1.61 g, 10.5 mmol) is added over 10 minutes, the cooling removed and the reaction stirred at 65° C. for 17 hours. An aqueous solution of sodium acetate (100 cm³, 6 M) is added and the biphasic solution stirred at 65° C. for 2 hours. The mixture extracted with dichloromethane (15 cm³) and the combined organic phases washed with water (2×20 cm³), dried over anhydrous magnesium sulphate, filtered and concentrated in vacuo. The solid is triturated in 40-60 petrol (10 cm³) and collected by filtration to give intermediate 65 (763 mg, 63%) as an orange solid. ¹H NMR (400 MHz, CD₂Cl₂) 9.80 (2H, s), 7.69 (2H, s), 7.00-7.28 (8H, m), 6.60-6.91 (8H, m), 3.91 (8H, t, J 6.6), 1.61-1.85 (8H, m), 1.38-1.51 (8H, m), 1.32 (16H, m), 0.82-0.98 (12H, m).

Compound 112

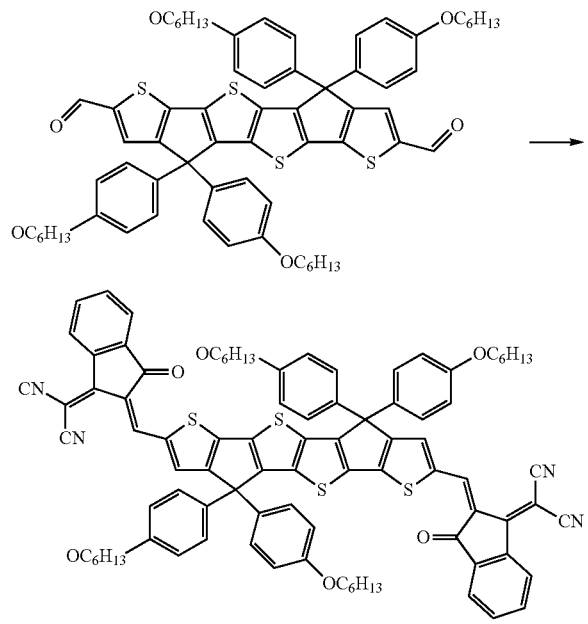

Intermediate 65 (200 mg, 0.18 mmol) and 2-(3-oxo-indan-1-ylidene)-malononitrile (250 mg, 1.28 mmol) are dissolved in chloroform (5 cm³) and nitrogen bubbled through the suspension for 20 minutes. Pyridine (30.6 cm³; 379 mmol) is added and nitrogen passed through the solution for a further 20 minutes. The solution is stirred for 17 hours. Methanol (35 cm³) is added and the solid collected by filtration and washed with methanol (3×10 cm³). The solid is triturated in acetone (5 cm³), filtered and washed with acetone (3×2 cm³). The material is purified on silica gel eluting with a graded solvent system (40-60 petrol:dichloromethane; 11:9 to 2:3) to give compound 66 (66 mg, 25%) as a blue solid. ¹H NMR (400 MHz, CDCl₃) 8.86 (2H, s), 8.68 (2H, d, J 7.4), 7.86-7.95 (2H, m), 7.70-7.78 (4H, m), 7.68 (2H, s), 7.14 (8H, d, J 8.7), 6.84 (8H, d, J 8.5), 3.92 (8H, t, J 6.5), 1.75 (8H, m), 1.39-1.47 (8H, m), 1.27-1.35 (16H, m), 0.88 (12H, m).

Example 113

Compound 113

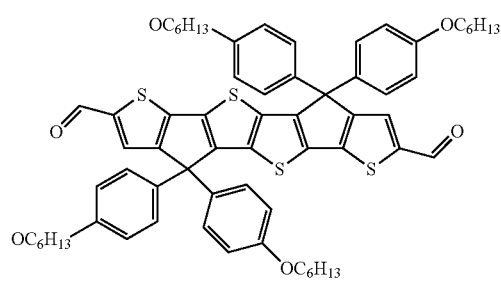

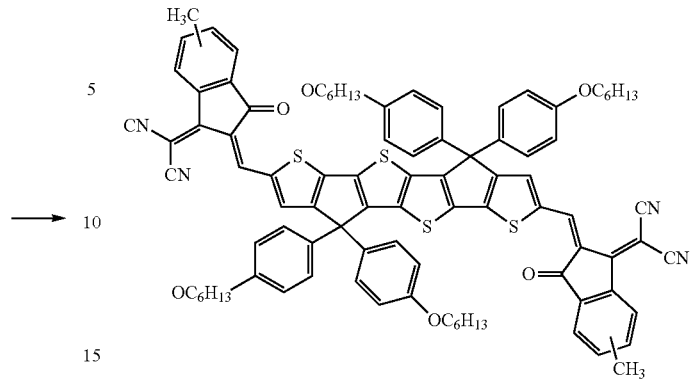

Intermediate 65 (200 mg, 0.18 mmol) and 2-(5-methyl-3-oxo-indan-1-ylidene)-malononitrile (268 mg, 1.28 mmol) are dissolved in chloroform (5 cm³) and nitrogen bubbled through the suspension for 20 minutes. Pyridine (1.04 cm³, 12.9 mmol) is added and nitrogen passed through the solution for a further 20 minutes. The solution is stirred for 17 hours. Methanol (35 cm³) added and the solid collected by filtration and washed with methanol (3×10 cm³). The solid is triturated in acetone (5 cm³), filtered and washed with acetone (3×2 cm³). The material is purified on silica gel eluting with a graded solvent system (40-60 petrol:dichloromethane; 11:9 to 2:3) to give compound 113 (69 mg, 26%) as a blue solid. ¹H NMR (400 MHz, CD₂Cl₂) 8.82-8.88 (2H, m), 8.48-8.59 (2H, m), 7.55-7.86 (6H, m), 7.16-7.25 (8H, m), 6.82-6.91 (8H, m), 3.95 (8H, t, J 6.6), 2.55-2.59 (6H, m), 1.71-1.83 (8H, m), 1.42-1.52 (8H, m), 1.31-1.40 (16H, m), 0.88-0.95 (12H, m).

Example 114

Intermediate 66

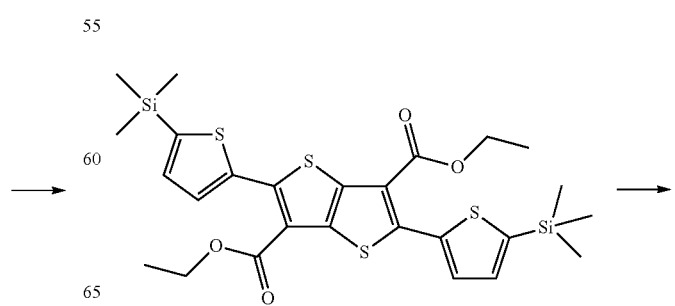

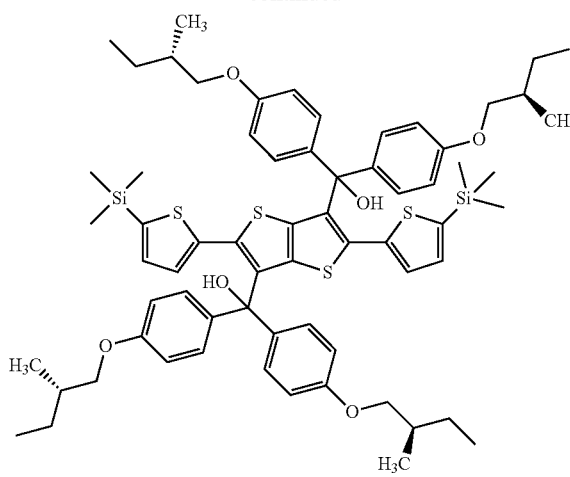

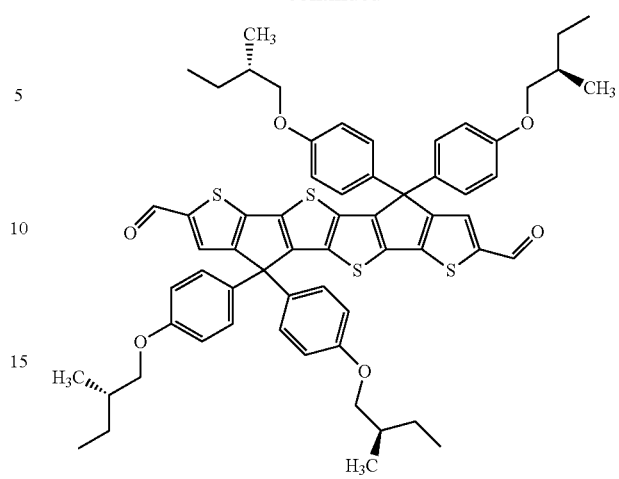

To a solution of 1-bromo-4-((S)-2-methyl-butoxy)-benzene (1.21 g, 4.98 mmol) in anhydrous tetrahydrofuran (20 cm³) at −78° C. is added tert-butyllithium (5.9 cm³, 10.0 mmol, 1.7 M in pentane) over 5 minutes and the reaction mixture stirred for 1 hour. Intermediate 10 (531 mg, 0.90 mmol) is added as a single portion, the cooling removed and the reaction mixture stirred for 65 hours. Water (25 cm³) is added, the mixture stirred for 20 minutes and extracted with ether (25 cm³). The organic portion is washed with water (2×15 cm³), dried over anhydrous magnesium sulphate, filtered, concentrated in vacuo and azeotroped with 40-60 petrol (10 cm³). The solid is collected by filtration and triturated in 40-60 petrol (10 cm³), filtered and washed with 40-60 petrol (2×10 cm³) to give intermediate 66 (785 mg, 68%) as a white solid. ¹H NMR (400 MHz, CD₂Cl₂) 7.15-7.23 (m, 8H), 6.92 (4H, dd, J 3.4, 1.94), 6.83 (8H, dd, J 8.8, 2.1), 6.56 (2H, dd, J 3.5, 1.9), 3.70-3.91 (8H, m), 3.33 (2H, d, J 2.0), 1.82-1.95 (4H, m), 1.48-1.67 (4H, m), 1.22-1.38 (4H, m), 1.00-1.07 (12H, m), 0.87-1.00 (12H, m), 0.24-0.30 (18H, m).

To a degassed mixture of intermediate 66 (785 mg, 0.68 mmol) and toluene (31 cm³) at 75° C. is added Amberlyst 15 strong acid (3.20 g) and the mixture further degassed for 10 minutes. The reaction mixture is then stirred for 17 hours. The suspension is filtered, washed with toluene (50 cm³) and the solvent removed in vacuo. The solid is dissolved in chloroform (15.7 cm³) and N,N-dimethylformamide (793 mg, 10.9 mmol) added. The solution is cooled to 0° C. and phosphorus oxychloride (1.56 g, 10.2 mmol) added over 10 minutes. The cooling is removed and the reaction heated at 65° C. for 17 hours. An aqueous sodium acetate solution (50 cm³, 10 M) is added and the mixture stirred for 3 hours. The solution is extracted with chloroform (15 cm³). The combined organic phases are washed with water (2×20 cm³), dried over anhydrous magnesium sulfate, filtered and the solvent removed in vacuo. The crude is purified by flash chromatography eluting with a graded solvent system (40-60 petrol:dichloromethane; 2:3 to 4:1) to give intermediate 67 (260 mg, 37%) as an orange solid. ¹H NMR (400 MHz, CD₂Cl₂) 9.83 (2H, d, J 0.9), 7.72 (2H, s), 7.17 (8H, d, J 8.6), 6.85 (8H, d, J 8.7), 3.68-3.85 (8H), 1.79-1.91 (4H, m), 1.49-1.61 (4H, m), 1.21-1.34 (4H, m), 1.01 (12H, d, J 6.7), 0.95 (12H, t, J 7.5).

Intermediate 67

Compound 114

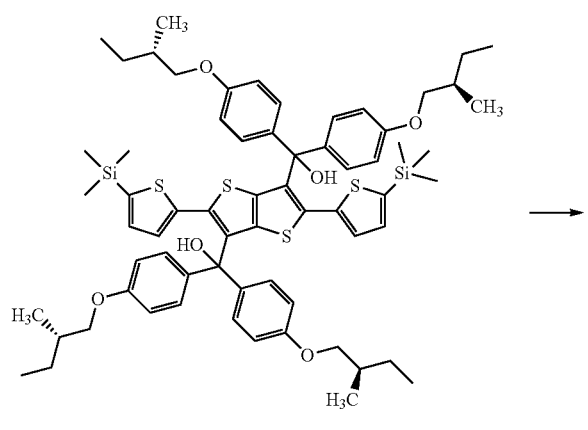

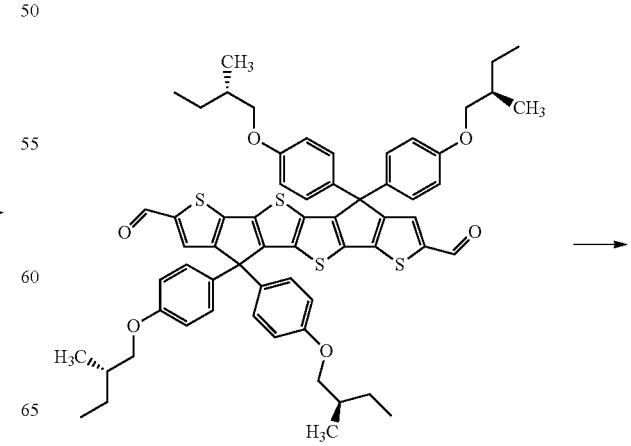

-continued

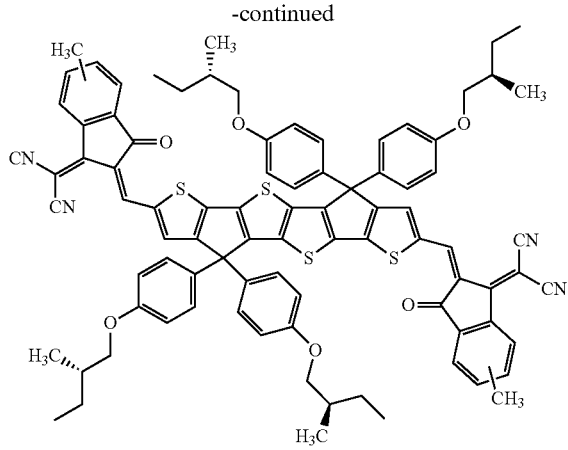

To a degassed mixture of intermediate 67 (108 mg, 0.10 mmol), 2-(5-methyl-3-oxo-indan-1-ylidene)-malononitrile (152 mg, 0.73 mmol) and chloroform (2.7 cm³) is added pyridine (0.59 cm³, 7.3 mmol) and the mixture degassed for a further 10 minutes. The reaction mixture stirred for 5 hours and methanol (30 cm³) added. The solid is collected by filtration and washed with methanol (2×10 cm³). The crude is purified by flash chromatography eluting with a graded solvent system (40-60 petrol:dichloromethane; 9:11 to 1:3) to give compound 114 (75 mg, 51%) as a blue solid. ¹H NMR (400 MHz, CDCl₃) 8.75 (2H, s), 8.37-8.51 (2H, s), 7.41-7.75 (6H, s), 7.04-7.12 (8H, s), 6.74-6.82 (8H, m), 3.58-3.77 (8H, m), 2.44-2.50 (6H, m), 1.70-1.82 (4H, m), 1.39-1.55 (4H, m), 1.09-1.23 (4H, m), 0.92 (12H, d, J 6.7), 0.85 (12H, t, J 7.5).

Example 115

Compound 115

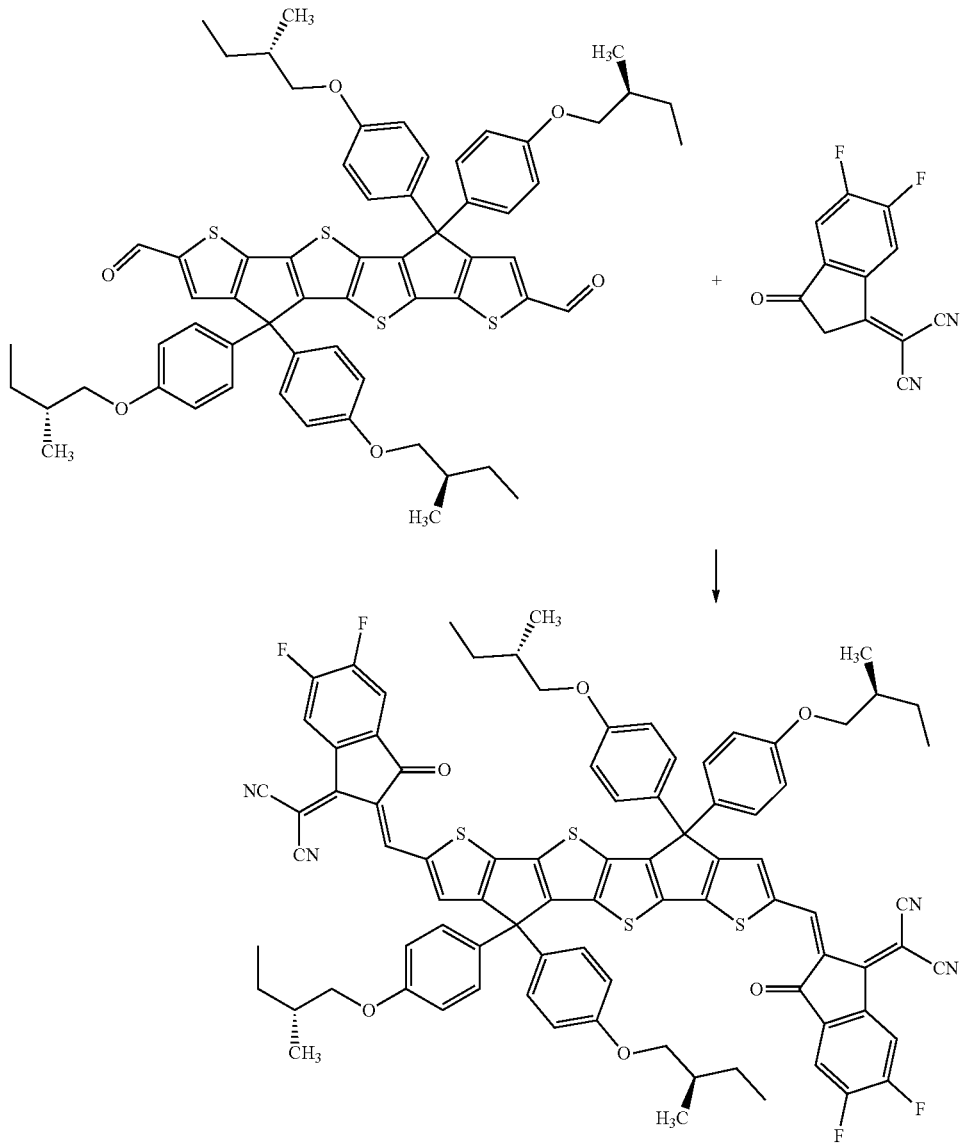

A solution of intermediate 67 (135 mg, 0.130 mmol) in chloroform (10 cm³) and pyridine (0.75 cm³) is degassed for 10 minutes with nitrogen. 2-(3-Oxo-indan-1-ylidene)-malononitrile (180 mg, 0.91 mmol) is added in one portion and the reaction mixture is stirred at 23° C. for 150 minutes. Methanol (15 cm³) is added and the obtained precipitate is collected by filtration and washed with methanol (3×10 cm³). The solid is filtered through a pad of silica (40-60 petrol:dichloromethane; 2:3). Concentration in vacuo followed by trituration in refluxing acetone (20 cm³) and then in a 3:1 mixture of acetone:chloroform (40 cm³) gives compound 115 (144 mg, 79%) as a dark blue powder. ¹H NMR (400 MHz, CDCl₃) 8.84 (2H, s), 8.61-8.67 (2H, m), 7.84-7.90 (2H, m), 7.63-7.72 (6H, m), 7.13-7.21 (8H, m), 6.83-6.90 (8H, m), 3.81 (4H, m), 3.72 (4H, m), 1.78-1.92 (4H, m, J 6.6), 1.56 (4H, m), 1.26 (4H, m), 1.00 (12H, d, J 6.7), 0.94 (12H, t, J 7.5).

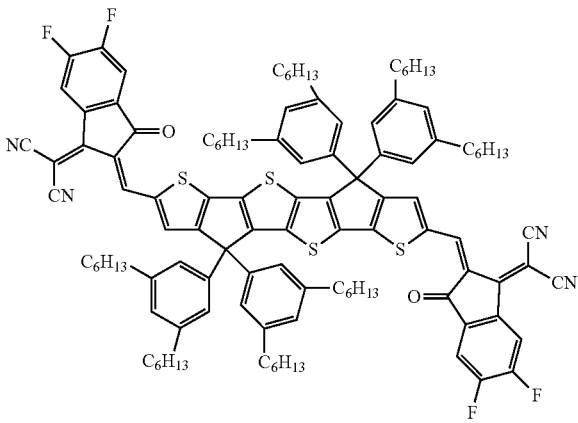

Example 116

Compound 116

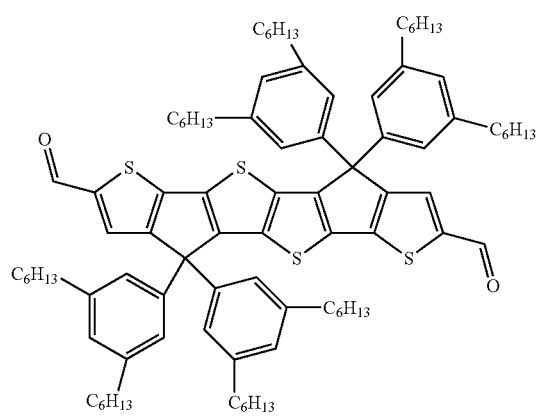

+

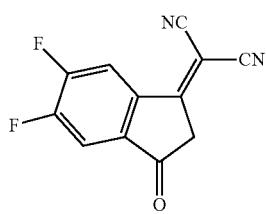

→

To a degassed solution of intermediate 22 (200 mg, 0.147 mmol) and pyridine (0.83 cm³, 10 mmol) in anhydrous chloroform (40 cm³) at −10° C. is added a degassed solution of 2-(5,6-difluoro-3-oxo-indan-1-ylidene)-malononitrile (135 mg, 0.587 mmol) in anhydrous chloroform (8 cm³) over 10 minutes. The resulting solution is then degassed for a further 30 minutes, warmed to 23° C. and stirred for 4 hours. The reaction mixture is diluted with 2-propanol (300 cm³) and stirred for 1 hour. The resulting solid is collected by filtration and washed with 2-propanol (100 cm³) and ethanol (100 cm³). The solid is then suspended in dichloromethane (50 cm³) and then poured into methanol (500 cm³). The solid is collected by filtration and washed with methanol (100 cm³) and ice-cold acetone (100 cm³) to give compound 116 (108 mg, 41%) as a dark blue solid. ¹H NMR (400 MHz, CDCl₃) 8.77 (2H, s), 8.45 (2H, dd, J 9.9, 6.5), 7.52-7.66 (4H, m), 6.88 (4H, s), 6.72 (8H, d, J 1.5), 2.34-2.52 (16H, m), 1.38-1.48 (16H, m), 1.19 (48H, d, J 2.0), 0.67-0.88 (24H, m).

Example 117

Intermediate 68

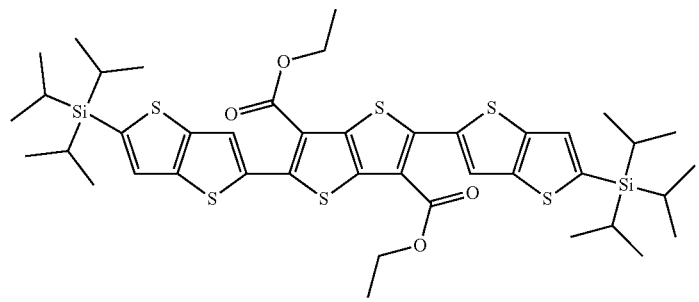

+

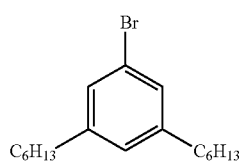

→

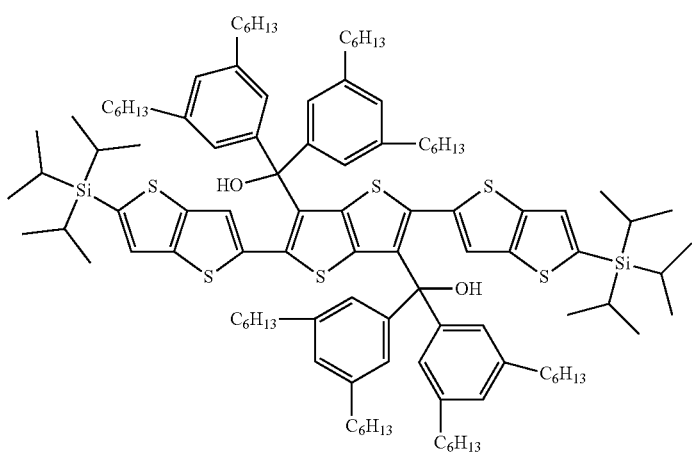

To a solution of 1-bromo-3,5-dihexyl-benzene (5.21 g, 16.0 mmol) in anhydrous tetrahydrofuran (100 cm$^3$) at −78° C. is added dropwise n-butyllithium (6.4 cm$^3$, 16 mmol, 2.5 M in haxane) over 30 minutes. The reaction mixture is then stirred for 2 hours. Intermediate 24 (2.80 g, 3.21 mmol) is then added and the reaction mixture allowed to warm to 23° C. and stirred for 17 hours. Water (100 cm$^3$) is added and the mixture stirred for a further 1 hour. Diethyl ether (100 cm$^3$) is added and the organic layer washed with water (2×50 cm$^3$), dried over anhydrous magnesium sulfate, filtered and the solvent removed in vacuo. The crude is purified by column chromatography using a graded solvent system (40-60 petrol:dichloromethane; 19:1 to 1:4) to give intermediate 68 (3.54 g, 63%) as a pale yellow oil. $^1$H NMR (400 MHz, CD$_2$Cl$_2$) 7.23 (2H, s), 6.86-7.01 (12H, m), 6.51 (2H, s), 3.41 (2H, s), 2.42-2.61 (16H, m), 1.49-1.61 (16H, m), 1.22-1.45 (54H, m), 1.15 (36H, d, J 7.3), 0.78-0.95 (24H, m).

Intermediate 69

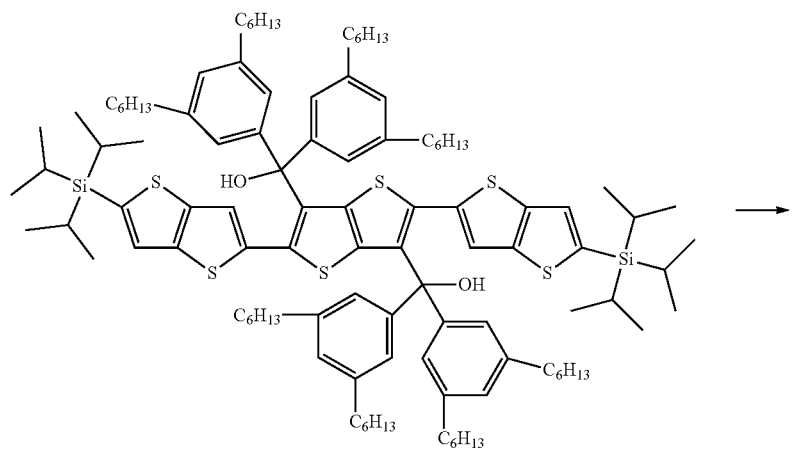

To a degased suspension of amberlyst 15 strong acid (12 g) in anhydrous diethyl ether (100 cm³) at 0° C. is added intermediate 68 (2.95 g, 1.67 mmol) followed by degassing for a further 30 minutes. The resulting suspension is allowed to warm to 23° C. and stirred for 1 hour. The reaction mixture is filtered through a thin celite plug and washed well with diethyl ether (200 cm³). The crude is then purified by column chromatography (40-60 petrol) and then taken up in anhydrous tetrahydrofuran (50 cm³) and cooled to 0° C. To the mixture is added a solution of tetrabutylammonium fluoride (3.34 cm³, 3.34 mmol, 1 M in tetrahydrofuran) and the resulting mixture stirred for 30 minutes at 23° C. The solvent is then removed in vacuo and the residue suspended in methanol (200 cm³) and stirred for 30 minutes. The solid collected by filtration to give intermediate 69 (2.02 g, 85%) as a dark orange solid. $^1$H NMR (400 MHz, CDCl$_3$) 7.13-7.21 (4H, m), 6.71-6.84 (12H, m), 2.33-2.49 (16H, m), 1.38-1.48 (16H, m), 1.08-1.22 (48H, m), 0.70-0.80 (24H, m).

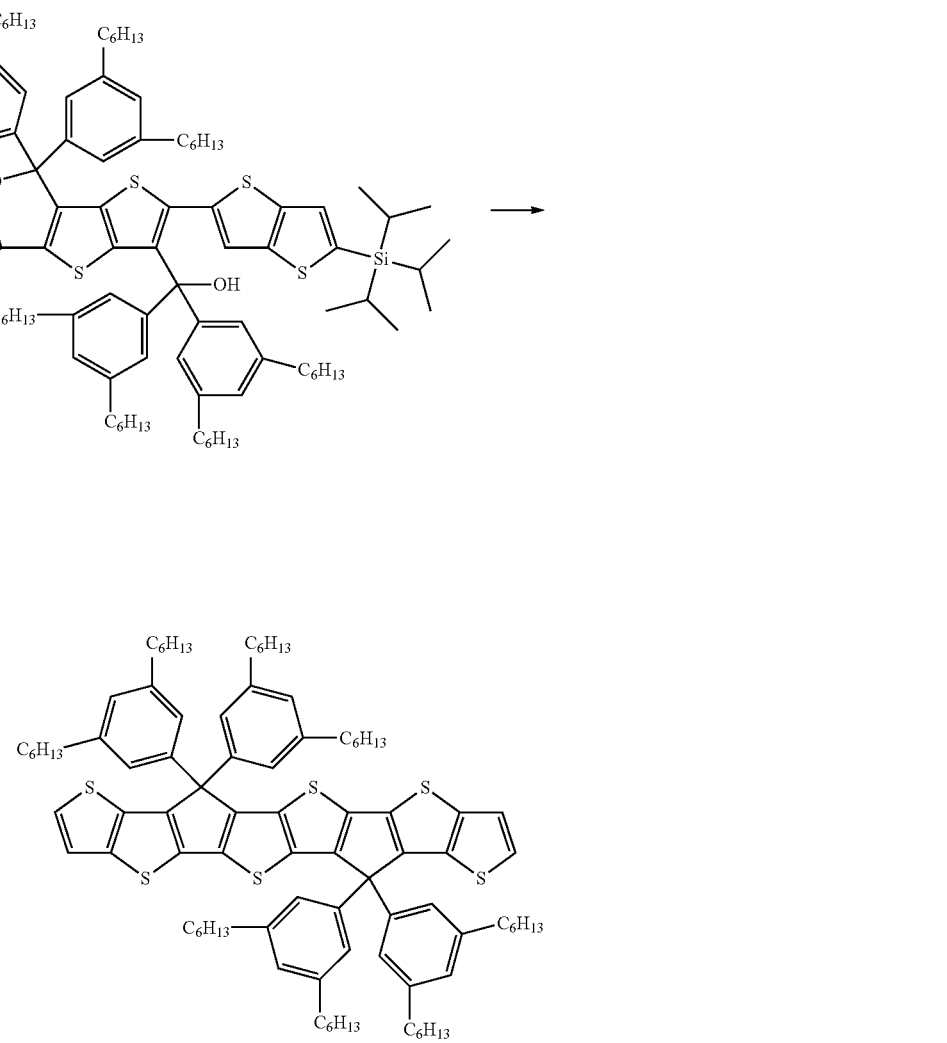

Intermediate 70

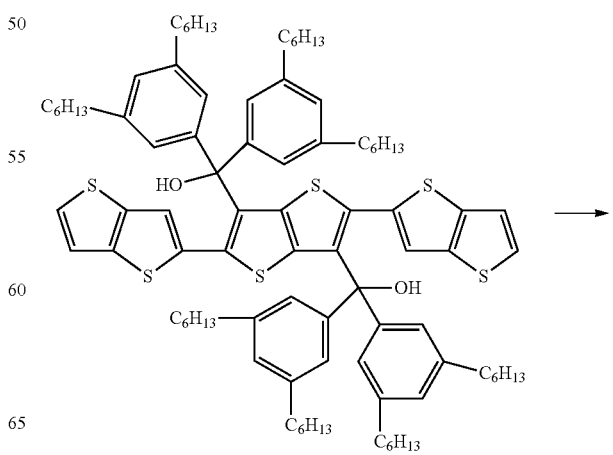

-continued

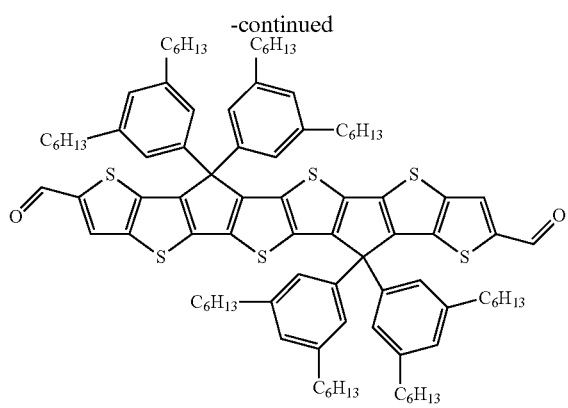

To a solution of intermediate 69 (600 mg, 0.42 mmol) in anhydrous tetrahydrofuran (25 cm³) at −78° C. is added dropwise n-butyllithium (0.68 cm³, 1.7 mmol, 2.5 M in haxane) over 10 minutes. The mixture is then stirred at −78° C. for 1 hour before anhydrous N,N-dimethylformamide (0.17 cm³, 2.5 mmol) is added. The cooling is then removed and the reaction mixture stirred at 23° C. for 2 hours. Water (50 cm³) is added and the mixture stirred for 30 minutes. The organics are extracted with diethyl ether (3×50 cm³), combined, dried over anhydrous magnesium sulfate, filtered and the solvent removed in vacuo. The crude product is purified by column chromatography using a graded solvent system (40-60 petrol:dichloromethane; 1:0 to 4:1) to give intermediate 70 (450 mg, 72%) as a dark red sticky solid. ¹H NMR (400 MHz, CDCl₃) 9.79 (2H, s), 7.85 (2H, s), 6.83 (4H, s), 6.71 (8H, d, J 1.0), 2.41 (16H, t, J 7.6), 1.39-1.50 (16H, m), 1.15 (48H, br. s), 0.70-0.80 (24H, m).

Compound 117

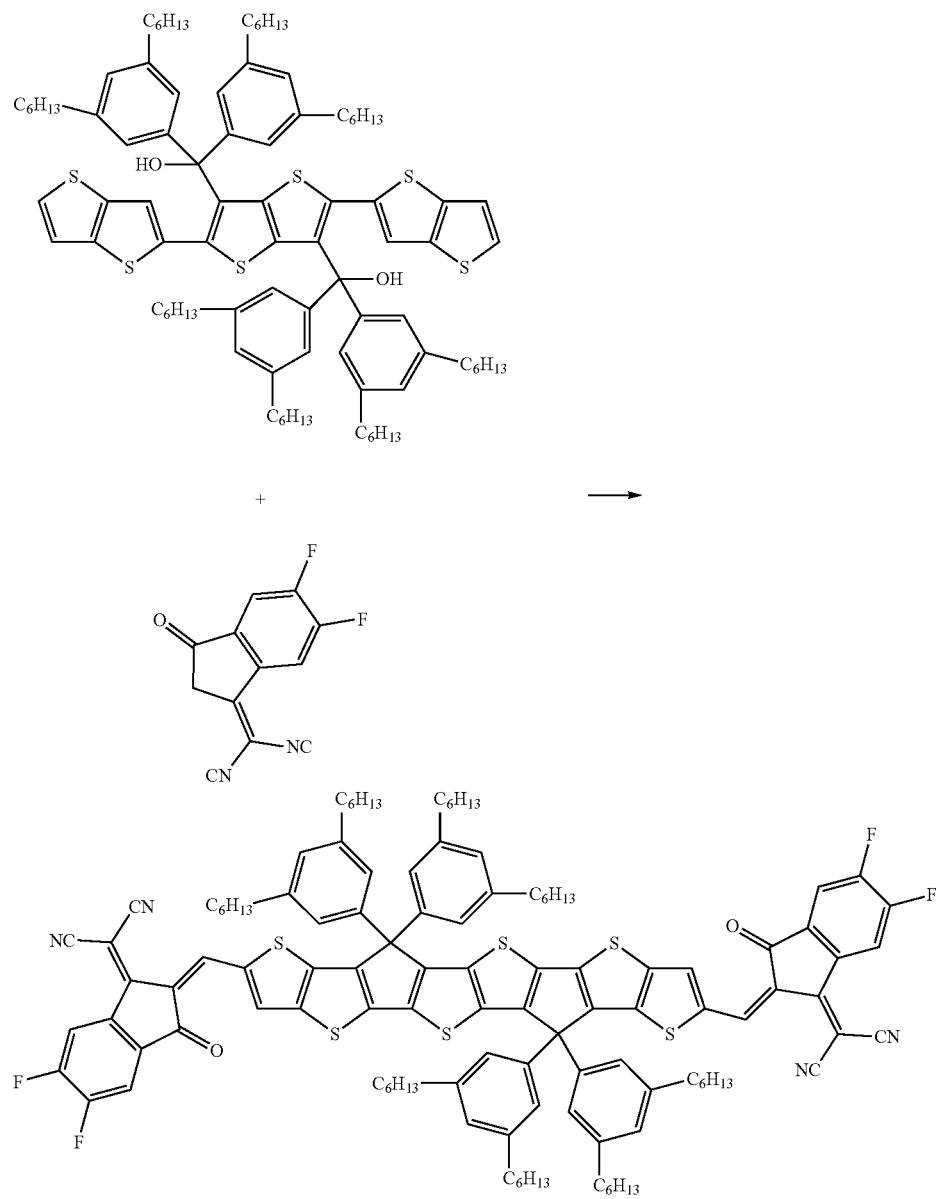

To a degassed solution of intermediate 70 (300 mg, 0.20 mmol) and pyridine (1.15 cm³) in anhydrous chloroform (40 cm³) at −10° C. is added a degassed solution of 2-(5,6-difluoro-3-oxo-indan-1-ylidene)-malononitrile (187 mg, 0.814 mmol) in anhydrous chloroform (8 cm³) over 10 minutes. The reaction mixture is then degassed for a further 30 minutes, warmed to 23° C. and stirred for 5 hours. The reaction mixture is diluted with methanol (300 cm³) and stirred for 65 hours. The solid collected by filtration, washed with ethanol (100 cm³) and methanol (100 cm³) to give compound 117 (62 mg, 16%) as a dark green solid. ¹H NMR (400 MHz, CD₂Cl₂) 8.90 (2H, s), 8.55 (2H, dd, J 10.1, 6.5), 8.19 (2H, s), 7.67 (2H, t, J 7.5), 6.85-7.10 (12H, m), 2.56 (16H, t, J 7.6), 1.46-1.67 (16H, m), 1.13-1.45 (48H, m), 0.70-0.93 (24H, m).

Use Example A

Current-voltage characteristics are measured using a Keithley 2400 SMU while the solar cells are illuminated by a Newport Solar Simulator at 100 mW·cm⁻² white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics are obtained for a composition, which contains Polymer 1 as shown below and an acceptor that is either a compound of formula I or a compound of prior art, and is coated from an organic solution. Details of the solution composition are shown in Table 1.

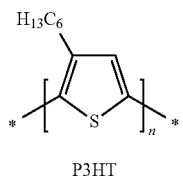

P3HT

P3HT is sourced from Merck KGaA.

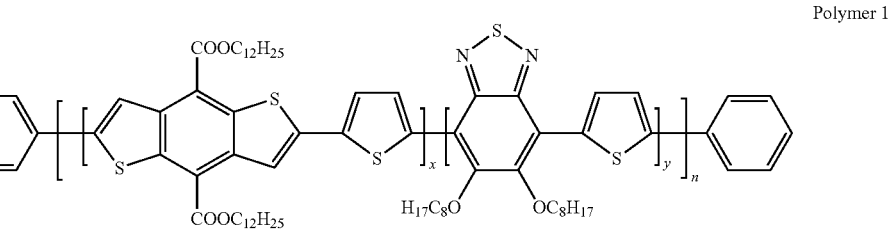

Polymer 1

Polymer 1 (x=y=1) and its preparation are disclosed in WO 2011/131280 A1.

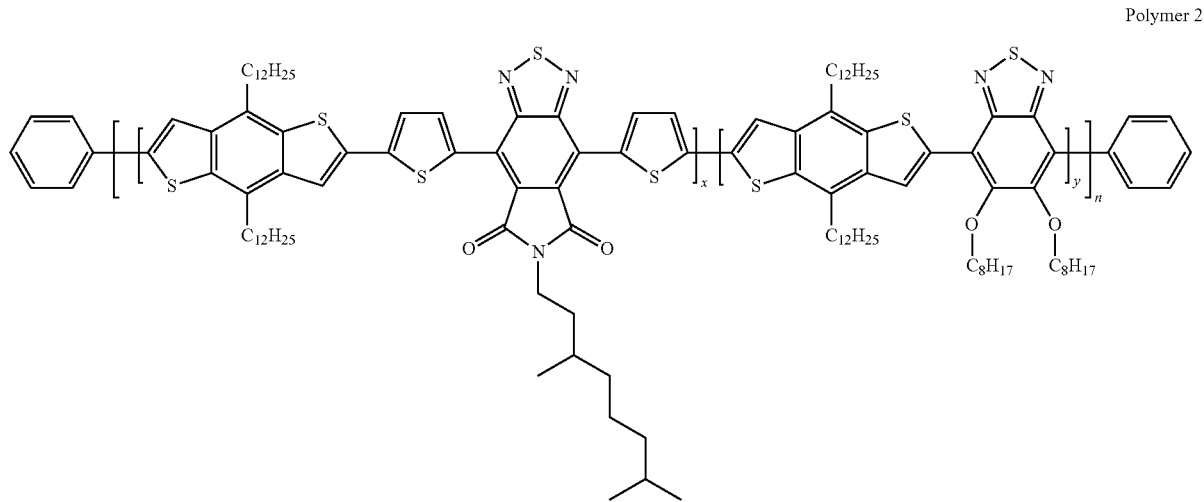

Polymer 2

Polymer 2 (x=y=1) and its preparation are disclosed in WO 2014/202184 A1.

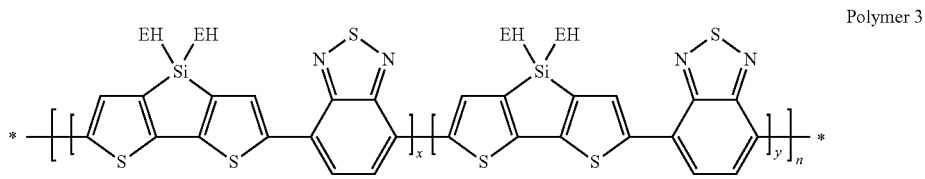

Polymer 3

Polymer 3 (x=5; y=1) and its preparation are disclosed in U.S. Pat. No. 8,455,606 B2.

PCBM-C60 and Lisicon® PV-A630 are fullerene derivatives sourced from Merck KGaA.

A1: Inverted Bulk Heterojunction Organic Photovoltaic Devices

Organic photovoltaic (OPV) devices are fabricated on pre-patterned ITO-glass substrates (13 Ω/sq.) purchased from LUMTEC Corporation.

Substrates are cleaned using common solvents (acetone, iso-propanol, deionized-water) in an ultrasonic bath. A layer of commercially available aluminium zinc oxide (AlZnO, Nanograde) was applied as a uniform coating by doctor blade at 40° C. The AlZnO Films are then annealed at 100° C. for 10 minutes in air. Active material solutions (i.e. polymer+acceptor) are prepared to fully dissolve the solutes at a 25 mg·cm$^{-3}$ solution concentration. Thin films are blade-coated in air atmosphere to achieve active layer thicknesses between 50 and 800 nm as measured using a profilometer. A short drying period follows to ensure removal of any residual solvent.

Typically, blade-coated films are dried at 70° C. for 2 minutes on a hotplate. Next the devices are transferred into an air atmosphere. On top of the active layer 0.1 mL of a conducting polymer poly(ethylene dioxythiophene) doped with poly(styrene sulfonic acid) [PEDOT:PSS Clevios HTL Solar SCA 434 (Heraeus)] was spread and uniformly coated by doctor blade at 70° C. Afterwards Ag (100 nm) cathodes are thermally evaporated through a shadow mask to define the cells.

Table 1 shows the characteristics of the individual photoactive formulations. The solvent is either o-dichlorobenzene (oDCB), o-xylene (oXyl), chlorobenzene (CB), toluene or mesitylene (mes).

TABLE 1

Formulation characteristics

| No. | Acceptor | Polymer | Ratio Polymer:Acceptor | Concentration g/L | Solvent |
|---|---|---|---|---|---|
| C1 | PCBM-C60 | 1 | 1.00:2.00 | 30 | oDCB |
| 1 | Compound 75 | 1 | 1.00:1.30 | 23 | oDCB |
| 2 | Compound 75 | 1 | 1.00:1.30 | 23 | oXyl |
| 3 | Compound 76 | 1 | 1.00:1.30 | 23 | oXyl |
| 4 | Compound 78 | 1 | 1.00:1.30 | 23 | oXyl |
| 5 | Compound 78 | P3HT | 1.00:1.30 | 23 | CB |
| 6 | Compound 79 | 1 | 1.00:1.30 | 23 | oXyl |
| 7 | Compound 80 | 1 | 1.00:1.30 | 23 | ODCB |
| 8 | Compound 80 | 1 | 1.00:1.30 | 23 | oXyl |
| 9 | Compound 80 | 1 | 1.00:1.30 | 23 | Toluene |
| 10 | Compound 81 | 1 | 1.00:1.30 | 23 | oXyl |
| 11 | Compound 81 | 1 | 1.00:1.30 | 23 | oDCB |
| 12 | Compound 81 | 2 | 1.00:1.30 | 23 | oDCB |
| 13 | Compound 81 | 2 | 1.00:1.30 | 23 | oXyl |

TABLE 1-continued

Formulation characteristics

| No. | Acceptor | Polymer | Ratio Polymer:Acceptor | Concentration g/L | Solvent |
|---|---|---|---|---|---|
| 14 | Compound 81 | 3 | 1.00:1.30 | 23 | oDCB |
| 15 | Compound 82 | 1 | 1.00:1.30 | 23 | oDCB |
| 16 | Compound 83 | 1 | 1.00:1.30 | 23 | oDCB |
| 17 | Compound 84 | 1 | 1.00:1.30 | 23 | oDCB |
| 18 | Compound 85 | 1 | 1.00:1.30 | 23 | oXyl |
| 19 | Compound 85 | P3HT | 1.00:1.30 | 23 | oDCB |
| 20 | Compound 86 | 1 | 1.00:1.30 | 23 | oXyl |
| 21 | Compound 87 | 1 | 1.00:1.30 | 23 | oXyl |
| 22 | Compound 88 | 1 | 1.00:1.30 | 23 | oXyl |
| 23 | Compound 89 | 1 | 1.00:1.30 | 23 | oXyl |
| 24 | Compound 77 | 1 | 1.00:1.30 | 23 | oXyl |
| 25 | Compound 90 | 1 | 1.00:1.30 | 23 | oXyl |
| 26 | Compound 91 | 1 | 1.00:1.30 | 23 | oXyl |
| 27 | Compound 92 | 1 | 1.00:1.30 | 23 | oXyl |
| 28 | Compound 93 | 1 | 1.00:1.30 | 23 | oXyl |
| 29 | Compound 94 | 1 | 1.00:1.30 | 23 | oXyl |
| 30 | Compound 95 | 1 | 1.00:1.30 | 23 | oXyl |
| 31 | Compound 95 | P3HT | 1.00:1.30 | 23 | oDCB |
| 32 | Compound 96 | 1 | 1.00:1.30 | 23 | oDCB |
| 33 | Compound 97 | 1 | 1.00:1.30 | 23 | oXyl |
| 34 | Compound 98 | 1 | 1.00:1.30 | 23 | oXyl |
| 35 | Compound 99 | 1 | 1.00:1.30 | 23 | oXyl |
| 36 | Compound 100 | 1 | 1.00:1.30 | 23 | oDCB |
| 37 | Compound 101 | 1 | 1.00:1.30 | 23 | oXyl |
| 38 | Compound 102 | 1 | 1.00:1.30 | 23 | oDCB |
| 39 | Compound 102 | 1 | 1.00:1.30 | 23 | oXyl |
| 40 | Compound 102 | 1 | 1.00:1.30 | 23 | Toluene |
| 41 | Compound 102 | 1 | 1.00:1.30 | 23 | CB |
| 42 | Compound 103 | 1 | 1.00:1.30 | 23 | oDCB |
| 43 | Compound 104 | 1 | 1.00:1.30 | 23 | oXyl |
| 44 | Compound 105 | 1 | 1.00:1.30 | 23 | CB |
| 45 | Compound 105 | P3HT | 1.00:1.30 | 23 | CB |
| 46 | Compound 106 | 1 | 1.00:1.30 | 23 | oXyl |
| 47 | Compound 108 | 1 | 1.00:1.30 | 20 | oXyl |
| 48 | Compound 109 | 1 | 1.00:1.30 | 20 | oXyl |
| 49 | Compound 110 | 1 | 1.00:1.30 | 23 | oXyl |
| 50 | Compound 112 | 1 | 1.00:1.30 | 23 | oXyl |
| 51 | Compound 115 | 1 | 1.00:1.30 | 23 | oXyl |
| 52 | Compound 116 | 1 | 1.00:1.30 | 23 | oDCB |
| 53 | Compound 117 | 1 | 1.00:1.30 | 23 | oDCB |

A2: Inverted Device Properties

Table 2 shows the device characteristics for the individual OPV devices comprising a photoactive layer with a BHJ formed from the photoactive acceptor/polymer formulations of Table 1.

TABLE 2

Photovoltaic cell characteristics under simulated solar irradiation at 1 sun (AM1.5G).

| | | | Average Performance | | |
|---|---|---|---|---|---|
| No. | Acceptor | Voc mV | Jsc mA·cm$^{-2}$ | FF % | PCE % |
| C1 | PCBM-C60 | 790 | 12.7 | 66 | 6.6 |
| 1 | Compound 75 | 751 | 14.5 | 50 | 5.4 |
| 2 | Compound 75 | 734 | 14.9 | 47 | 5.1 |
| 3 | Compound 76 | 747 | 0.4 | 32 | 0.1 |
| 4 | Compound 78 | 906 | 10.3 | 42 | 3.9 |
| 5 | Compound 78 | 609 | 4.3 | 29.9 | 0.78 |
| 6 | Compound 79 | 793 | 3.6 | 37 | 1.1 |
| 7 | Compound 80 | 789 | 6.4 | 41 | 2.0 |
| 8 | Compound 80 | 790 | 6.2 | 39 | 1.9 |
| 9 | Compound 80 | 761 | 9.7 | 55 | 4.1 |
| 10 | Compound 81 | 720 | 16.2 | 63 | 7.3 |
| 11 | Compound 81 | 746 | 15.8 | 47 | 5.6 |
| 12 | Compound 81 | 788 | 9 | 36 | 2.6 |
| 13 | Compound 81 | 760 | 9.9 | 35 | 2.7 |
| 14 | Compound 81 | 591 | 11.4 | 43 | 2.9 |
| 15 | Compound 82 | 970 | 8.5 | 39 | 3.3 |
| 16 | Compound 83 | 955 | 7.4 | 41 | 2.9 |
| 17 | Compound 84 | 605 | 1.9 | 36 | 0.4 |
| 18 | Compound 85 | 989 | 4.2 | 40 | 1.7 |
| 19 | Compound 85 | 742 | 5 | 43 | 1.6 |
| 20 | Compound 86 | 861 | 1.0 | 38 | 0.3 |
| 21 | Compound 87 | 1048 | 0.7 | 29 | 0.2 |
| 22 | Compound 88 | 1002 | 7.4 | 46 | 3.4 |
| 23 | Compound 89 | 751 | 12.5 | 41 | 3.9 |
| 24 | Compound 77 | 581 | 4.9 | 42 | 1.2 |
| 25 | Compound 90 | 866 | 3.6 | 37 | 1.2 |
| 26 | Compound 91 | 751 | 2.7 | 42 | 0.9 |
| 27 | Compound 92 | 607 | 1.5 | 37 | 0.3 |
| 28 | Compound 93 | 660 | 0.2 | 28 | 0.0 |
| 29 | Compound 94 | 988 | 0.6 | 23 | 0.1 |
| 30 | Compound 95 | 958 | 0.6 | 42 | 0.2 |
| 31 | Compound 95 | 824 | 1.7 | 30 | 0.4 |
| 32 | Compound 96 | 864 | 7.8 | 34 | 2.3 |
| 33 | Compound 97 | 776 | 3.1 | 39 | 0.9 |
| 34 | Compound 98 | 940 | 2.2 | 33 | 0.7 |
| 35 | Compound 99 | 881 | 5.2 | 48 | 2.2 |
| 36 | Compound 100 | 980 | 8.0 | 50 | 3.9 |
| 37 | Compound 101 | 596 | 16.0 | 49 | 4.6 |
| 38 | Compound 102 | 799 | 11.4 | 58 | 5.3 |
| 39 | Compound 102 | 792 | 12.7 | 48 | 4.8 |
| 40 | Compound 102 | 768 | 14 | 50 | 5.4 |
| 41 | Compound 102 | 799 | 13.9 | 51 | 5.7 |
| 42 | Compound 103 | 617 | 6.0 | 46 | 1.7 |
| 43 | Compound 104 | 854 | 6.6 | 38 | 2.1 |
| 44 | Compound 105 | 948 | 2.3 | 42 | 0.9 |
| 45 | Compound 105 | 935 | 1.8 | 42 | 0.7 |
| 46 | Compound 106 | 598 | 15.3 | 54 | 4.9 |
| 47 | Compound 108 | 713 | 11 | 34 | 2.7 |
| 48 | Compound 109 | 505 | 3.7 | 32 | 0.6 |
| 49 | Compound 110 | 642 | 2.9 | 36 | 0.7 |
| 50 | Compound 112 | 731 | 16.1 | 61 | 7.2 |
| 51 | Compound 115 | 725 | 16.2 | 65 | 7.6 |
| 52 | Compound 116 | 635 | 15.1 | 37 | 3.5 |
| 53 | Compound 117 | 652 | 10.5 | 41 | 2.8 |

Table 3 shows the characteristics of the individual photoactive formulation for an example ternary system.

TABLE 3

Formulation characteristics

| No. | Acceptor 1 | Acceptor 2 | Polymer | Ratio Polymer:Acceptor1:Acceptor2 | Conc. g/L | Solvent |
|---|---|---|---|---|---|---|
| 51 | Compound 81 | PV-A630 | 1 | 1.0:1.04:0.26 | 23 | mes |
| 52 | Compound 81 | PV-A630 | 1 | 1:1.3:0 | 23 | oXyl |
| 53 | Compound 81 | PV-A630 | 1 | 1:1.04:0.26 | 23 | oXyl |
| 54 | Compound 81 | PV-A630 | 1 | 1:0:1.3 | 23 | oXyl |

Table 4 shows the device characteristics for the individual OPV device comprising a photoactive layer with a BHJ formed from the photoactive acceptor/polymer formulations of Table 3 with the device annealed at the indicated temperature in table 4.

TABLE 4

Photovoltaic cell characteristics under simulated solar irradiation at 1 sun (AM1.5G).

| | | Annealing temperature °C | Average Performance | | |
|---|---|---|---|---|---|
| No. | Acceptor | | Voc mV | Jsc mA·cm$^{-2}$ | FF % | PCE % |
| 51 | Compound 81 | 140 | 735 | 16.6 | 62 | 7.5 |
| 52 | Compound 81 | 140 | 734 | 15.6 | 49 | 5.66 |
| 53 | Compound 81 | 140 | 761 | 15.5 | 50 | 5.89 |
| 54 | Compound 81 | 140 | 864 | 9.7 | 61 | 5.1 |

From Tables 2 and 4, it can be seen that OPV devices with a BHJ prepared from compounds according to the invention show high Voc and Jsc values and lead to functional OPV devices. From Table 4 example No 52-54, it can be seen that OPV devices from a ternary blend (No. 53) composed of two acceptors shows higher performance compared to individual example no. 52 and 54 using the same solvent system.

Use Example B

B1: Bulk Heterojunction Organic Photodetector Devices (OPDs)

Devices are fabricated onto glass substrates with six pre-patterned ITO dots of 5 mm diameter to provide the bottom electrode. The ITO substrates are cleaned using a standard process of ultrasonication in Decon90 solution (30 minutes) followed by washing with de-ionized water (×3) and ultrasonication in de-ionized water (30 minutes). The ZnO ETL layer was deposited by spin coating a ZnO nanoparticle dispersion onto the substrate and drying on a hotplate for 10 minutes at a temperature between 100 and 140° C. A formulation of Lisicon PV-D4650 (sourced from Merck KGaA) and compound as disclosed herein was prepared at a ratio of between 1:2 and 2:1 in o-dichlorobezene or o-xylene with 0-10% co-solvent at a concentration of between 18 and 40 mg/ml, and stirred for 17 hours at a temperature of between 23° C. and 60° C. The active layer was deposited using blade coating (K101 Control Coater System from RK). The stage temperature was set to 30° C., the blade gap set between 2-15 μm and the speed set between 2-8 m/min targeting a final dry film thickness of 500-1000 nm. Following coating the active layer was annealed at 100° C. for 10 minutes. The MoO$_3$ HTL layer was deposited by E-beam vacuum deposition from MoO$_3$ pellets at a rate of 1 Å/s, targeting 15 nm thickness. Finally, the top silver electrode was deposited by thermal evaporation through a shadow mask, to achieve Ag thickness between 30-80 nm.

The J-V curves are measured using a Keithley 4200 system under light and dark conditions at a bias from +5 to −5 V. The light source was a 580 nm LED with power 0.5 mW/cm².

The EQE of OPD devices were characterized between 400 and 1100 nm under −2V bias, using an External Quantum Efficiency (EQE) Measurement System from LOT-QuantumDesign Europe.

Table 5 shows the characteristics of the individual formulations. The polymer used is Lisicon PV-D4650. The solvent is either o-dichlorobenzene (oDCB) or o-xylene with 0-10% co-solvent (oXyl).

TABLE 5

Formulation characteristics

| No. | Acceptor | Ratio Polymer: Acceptor | Concentration g/L | Solvent |
|---|---|---|---|---|
| 55 | Compound 75 | 1.0:2.0 | 30 | oDCB |
| 56 | Compound 77 | 1.0:1.0 | 18 | oDCB |
| 57 | Compound 78 | 1.5:1.0 | 18 | oXyl |
| 58 | Compound 79 | 1.0:2.0 | 18 | oXyl |
| 59 | Compound 81 | 1.0:1.0 | 18 | oXyl |
| 60 | Compound 90 | 1.0:1.0 | 18 | oXyl |
| 61 | Compound 91 | 1.0:1.0 | 18 | oXyl |
| 62 | Compound 92 | 1.0:1.0 | 18 | oXyl |
| 63 | Compound 99 | 1.0:1.0 | 18 | oXyl |
| 64 | Compound 103 | 1.0:1.0 | 40 | oXyl |
| 65 | Compound 108 | 1.0:1.0 | 40 | oXyl |
| 66 | Compound 109 | 1.0:1.0 | 20 | oXyl |
| 67 | Compound 117 | 1.0:1.0 | 20 | oXyl |

Tables 6, 7 and 8 show the EQE values for the individual OPD devices comprising a photoactive layer with a BHJ formed from the photoactive acceptor/polymer formulations of Table 5.

TABLE 6

EQEs for the devices at 650 nm

| No. | EQE % |
|---|---|
| 55 | 32 |
| 56 | 4 |
| 57 | 33 |
| 58 | 7 |
| 59 | 42 |
| 60 | 4 |
| 61 | 4 |
| 62 | 2 |
| 63 | 8 |
| 64 | 3 |
| 65 | 60 |
| 66 | 17 |
| 67 | 40 |

TABLE 7

EQEs for the devices at 850 nm

| No. | EQE % |
|---|---|
| 55 | 28 |
| 56 | 3 |
| 58 | 5 |
| 59 | 33 |
| 60 | 1 |
| 61 | 1 |

TABLE 7-continued

EQEs for the devices at 850 nm

| No. | EQE % |
|---|---|
| 62 | 1 |
| 63 | 4 |
| 64 | 4 |
| 65 | 59 |
| 66 | 12 |
| 67 | 35 |

TABLE 8

EQEs for the devices at 940 nm

| No. | EQE % |
|---|---|
| 56 | 3 |
| 62 | 1 |
| 63 | 4 |
| 64 | 4 |
| 65 | 6 |
| 66 | 11 |
| 67 | 12 |

The invention claimed is:
1. A compound of formula I

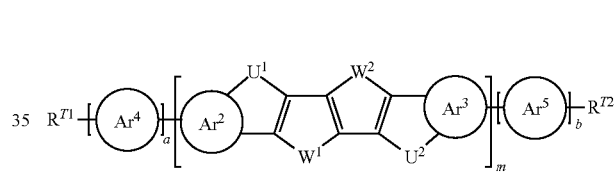

wherein individual radicals, independently of each other and on each occurrence identically or differently, have the following meanings $Ar^{2,3}$ arylene or heteroarylene that has from 5 to 20 ring atoms, is mono- or polycyclic, optionally contains fused rings, and is unsubstituted or substituted by one or more identical or different groups L, $Ar^{4,5}$ arylene or heteroarylene that has from 5 to 20 ring atoms, is mono- or polycyclic, optionally contains fused rings, and is unsubstituted or substituted by one or more identical or different groups L, or $CY^1{=}CY^2$ or —C≡C—, $Y^1, Y^2$ H, F, Cl or CN, $W^{1,2}$ S, O or Se, $U^1$ $CR^1R^2$, $SiR^1R^2$, $GeR^1R^2$, or C=O, $U^2$ $CR^3R^4$, $SiR^3R^4$, $GeR^3R^4$, or C=O, $R^{1-4}$ H, F, Cl or straight-chain, branched or cyclic alkyl with 1 to 30, C atoms, in which one or more $CH_2$ groups are optionally replaced by —O—, —S—, —C(=O)—, —C(=S)—, —C(=O)—O—, —O—C(=O)—, —NR⁰—, —SiR⁰R⁰⁰—, —CF₂—, —CR⁰=CR⁰⁰—, —CY¹=CY²— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and the pair of $R^1$ and $R^2$ and/or the pair of $R^3$ and $R^4$ together with the C, Si or Ge atom to which they are attached, may also form a spiro group with 5 to 20 ring atoms which is mono- or polycyclic, does optionally contain fused rings, and is unsubstituted or substituted by one or more identical or different groups L $R^{T1}$, $R^{T2}$ are selected from the group consisting of H, F, Cl, Br, —NO$_2$, —ON, —CF$_3$, R*, —CF$_2$—R*, —O—R*, —S—R*, —SO$_2$—R*, —SO$_3$—R*, —C(=O)—H, —C(=O)—R*, —C(=S)—R*, —C(=O)—CF$_2$—R*, —C(=O)—OR*, —C(=S)—OR*, —O—C(=O)—R*, —O—C(=S)—R*, —C(=O)—SR*, —S—C(=O)—R*, —C(=O)NR*R**, —NR*—C(=O)—R*, —NHR*, —NR*R**, —CR*=CR*R**, —C≡C—R*, —C≡C—SiR*RR*, —SiR*RR*, —CH=CH(CN), —CH=C(CN)$_2$, —C(CN)=C(CN)$_2$, —CH=C(CN)(R$^a$), CH=C(CN)—C(=O)—OR*, —CH=C(CO—OR*)$_2$, —CH=C(CO—NR*R**)$_2$, and the group consisting of the following formulae

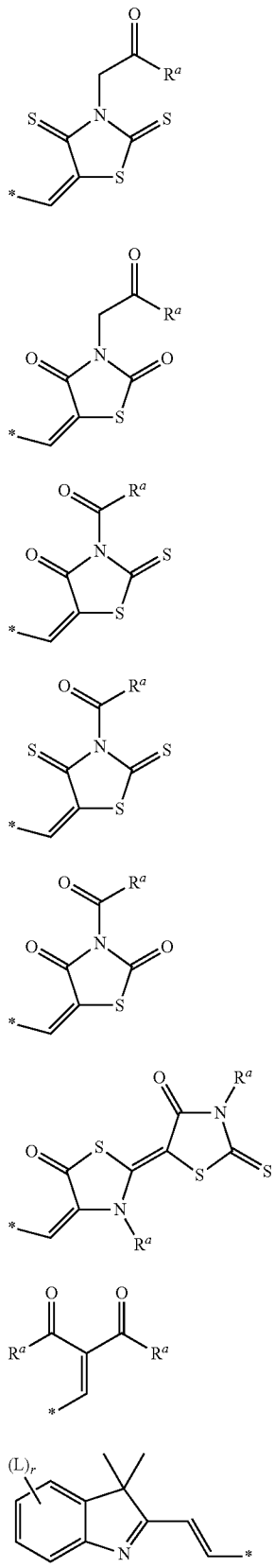
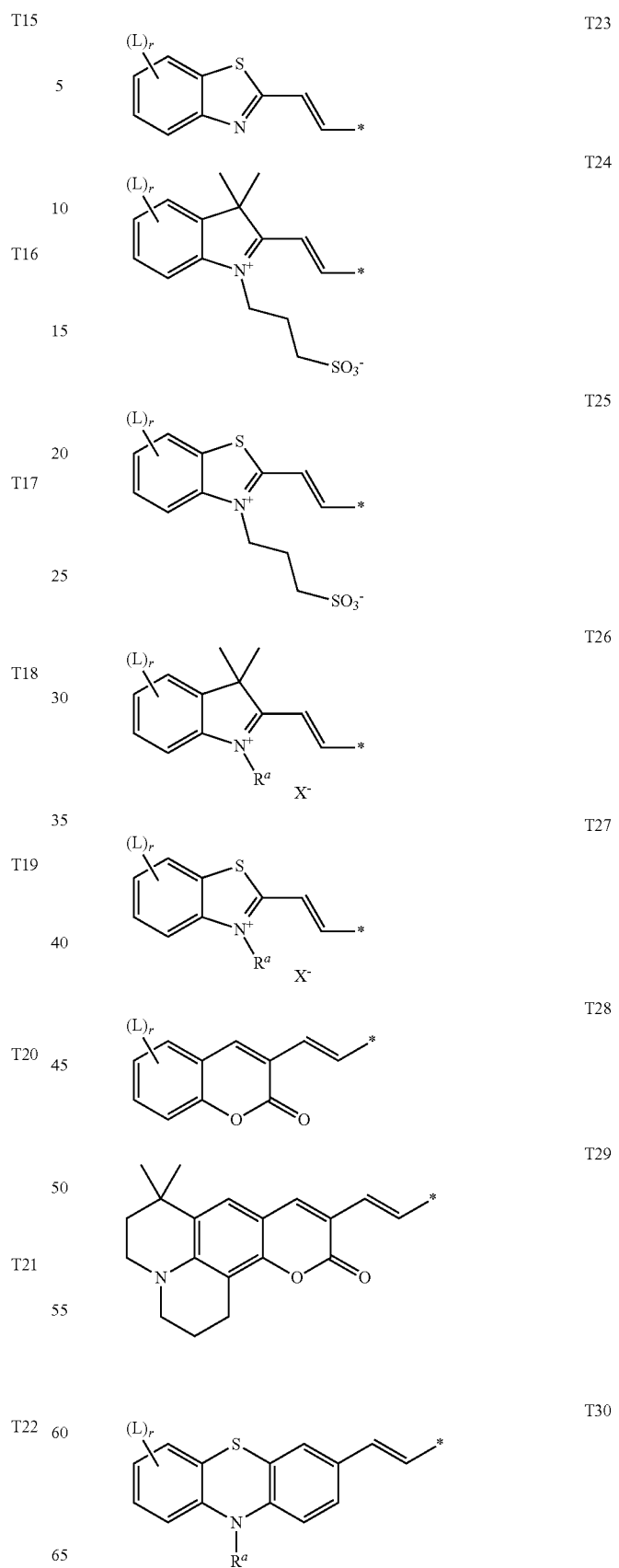

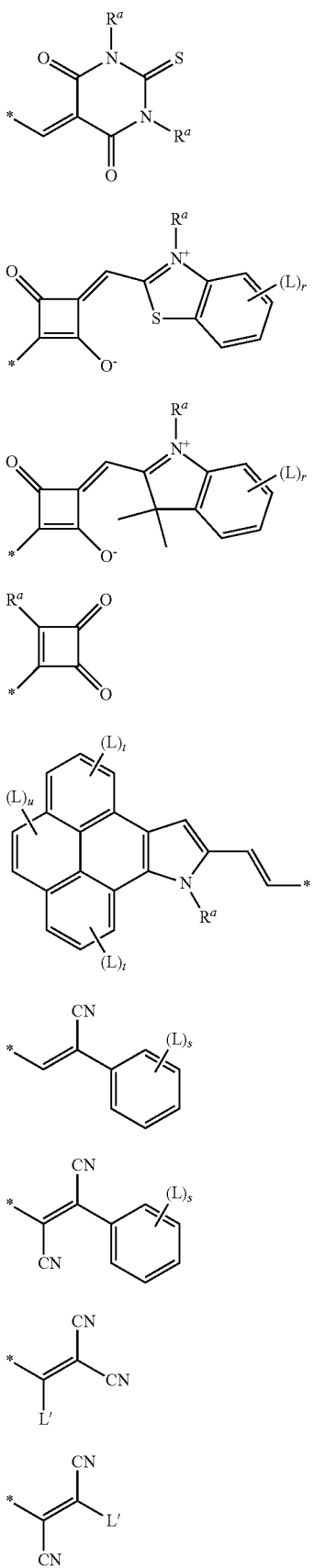
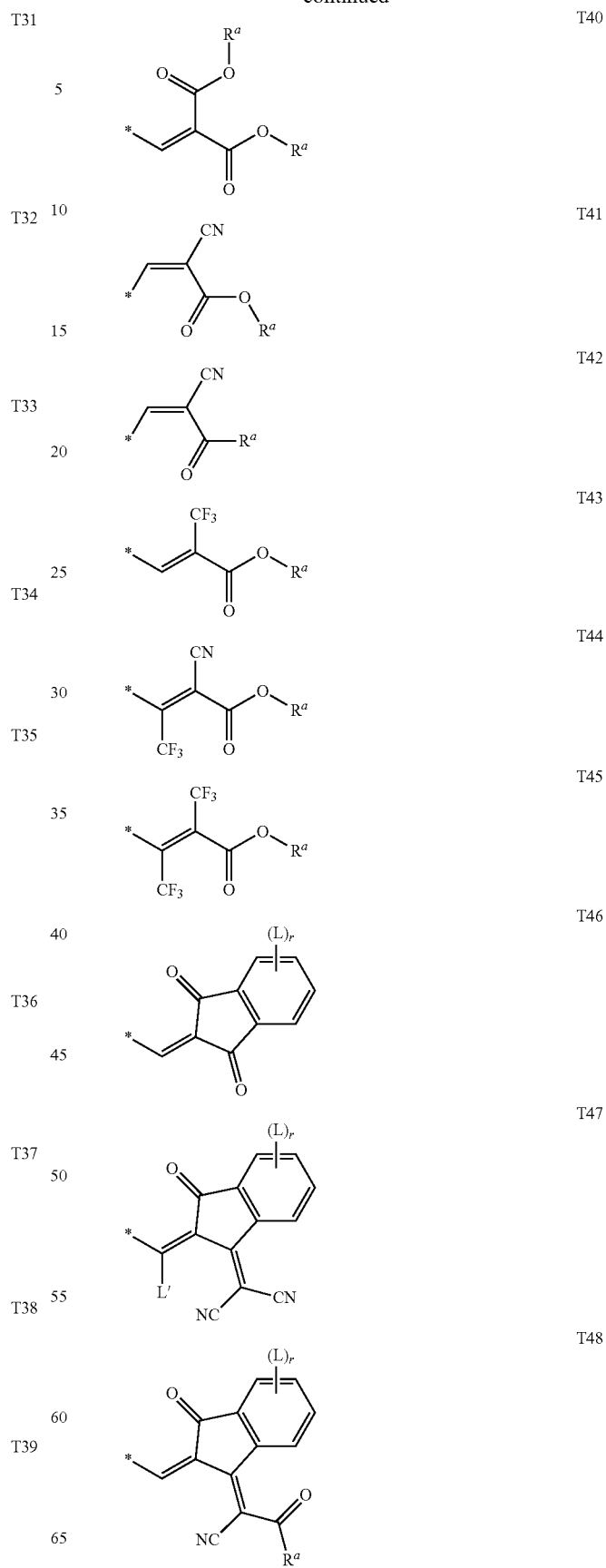

-continued

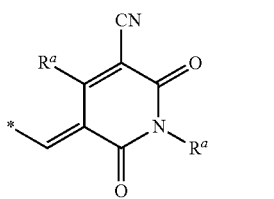

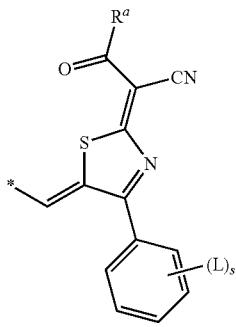

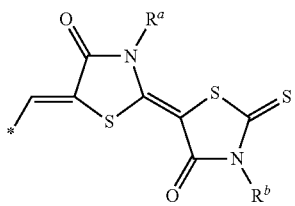

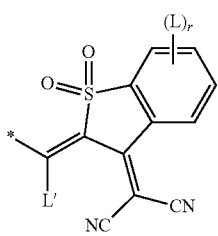

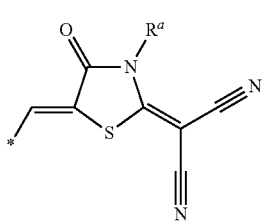

$R^a$, $R^b$ aryl or heteroaryl, each having from 4 to 30 ring atoms, optionally containing fused rings and being unsubstituted or substituted with one or more groups L, or one of the meanings given for L, R*, R, R* alkyl with 1 to 20 C atoms which is straight-chain, branched or cyclic, and is unsubstituted, or substituted with one or more F or $C_1$ atoms or CN groups, or perfluorinated, and in which one or more C atoms are optionally replaced by —O—, —S—, —C(=O)—, —C(=S)—, —$SiR^oR^{oo}$—, —$NR^oR^{oo}$—, —$CHR^o=CR^{oo}$— or —C≡C— such that O— and/or S-atoms are not directly linked to each other, L F, Cl, —$NO_2$, —CN, —NC, —NCO, —NCS, —OCN, —SCN, $R^o$, $OR^o$, $SR^o$, —C(=O)$X^o$, —C(=O)$R^o$, —C(=O)—$OR^o$, —O—C(=O)—$R^o$, —$NH_2$, —$NHR^o$, —$NR^oR^{oo}$, —C(=O)$NHR^o$, —C(=O)$NR^oR^{oo}$, —$SO_3R^o$, —$SO_2R^o$, —OH, —$NO_2$, —$CF_3$, —$SF_5$, or optionally substituted silyl, or carbyl or hydrocarbyl with 1 to 30, L' H or one of the meanings of L, $Y^1$, $Y^2$ H, F, Cl or CN, r 0, 1, 2, 3 or 4, s 0, 1, 2, 3, 4 or 5, t 0, 1, 2 or 3, u 0, 1 or 2, $R^o$, $R^{oo}$ H or straight-chain or branched alkyl with 1 to 20 C atoms that is optionally fluorinated, $X^o$ halogen, a, b 0, 1, 2 or 3, m 1, 2 or 3.

2. The compound according to claim 1, wherein $Ar^{2-5}$ in formula I are selected from the following formulae and their mirror images $Ar^2$

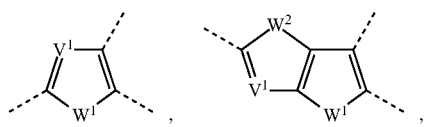

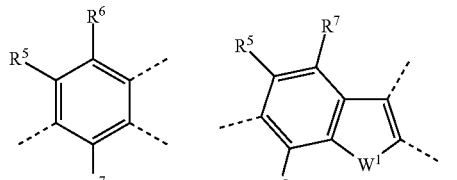

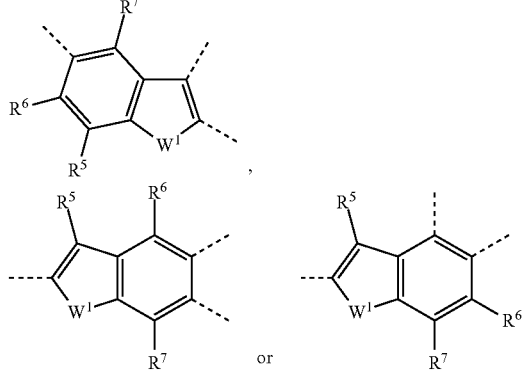

$Ar^3$

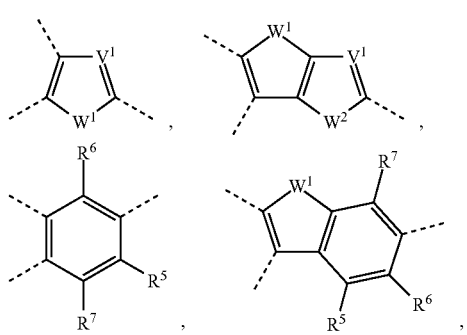

-continued

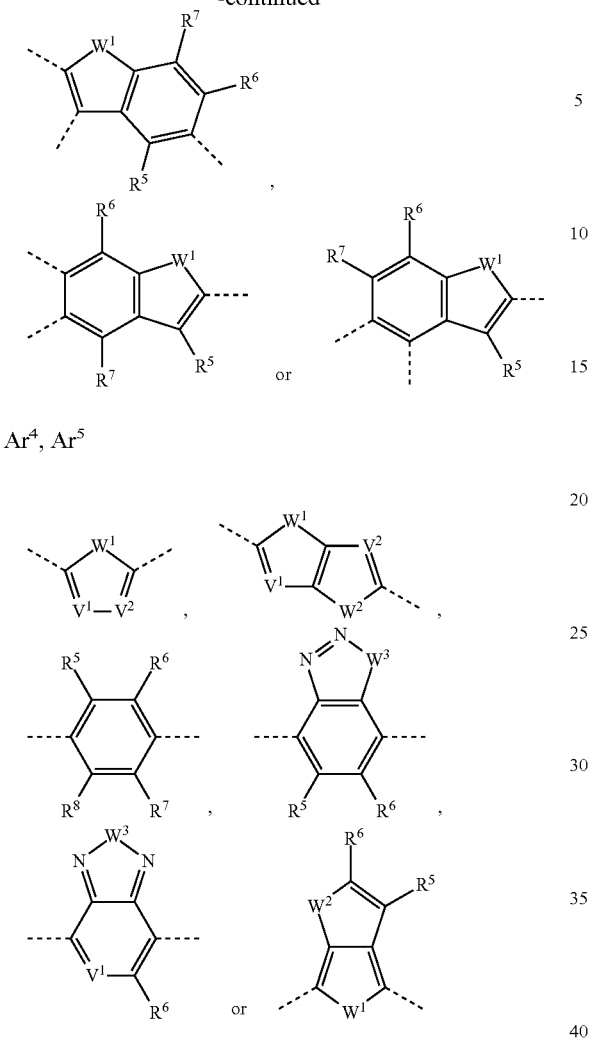

Ar⁴, Ar⁵ wherein the individual radicals, independently of each other and on each occurrence identically or differently, have the following meanings
$W^{1,2}$ S, O or Se,
$W^3$ $NR^0$, S, O or Se,
$V^1$ $CR^5$ or N,
$V^2$ $CR^6$ or N,
$R^{5-10}$ H, F, Cl, CN or straight-chain, branched or cyclic alkyl with 1 to 30, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L as defined in claim 1.

3. The compound according to claim 2, wherein Ar² and Ar³ in formula I are selected from the following formulae and their mirror images Ar²

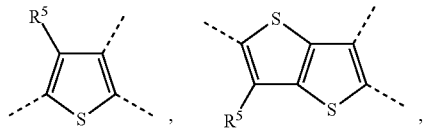
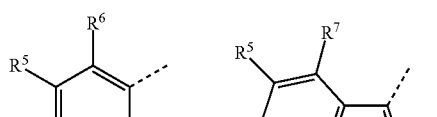
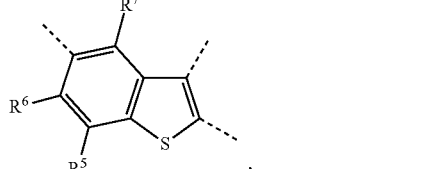
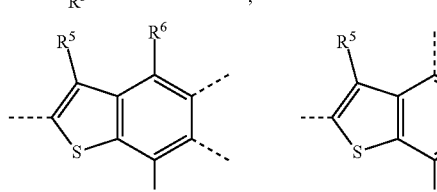

Ar³

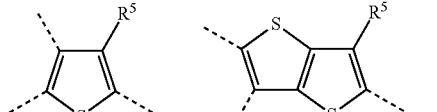
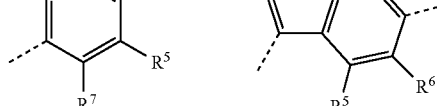
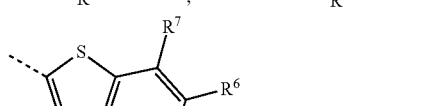
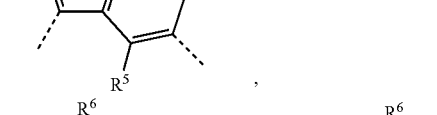
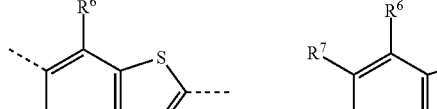
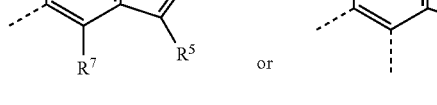

4. The compound according to claim 1, wherein Ar⁴ and Ar⁵ in formula I are selected from the following formulae and their mirror images

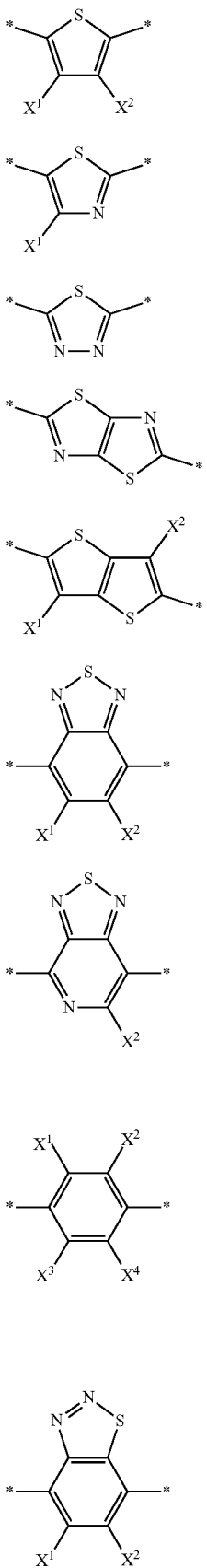
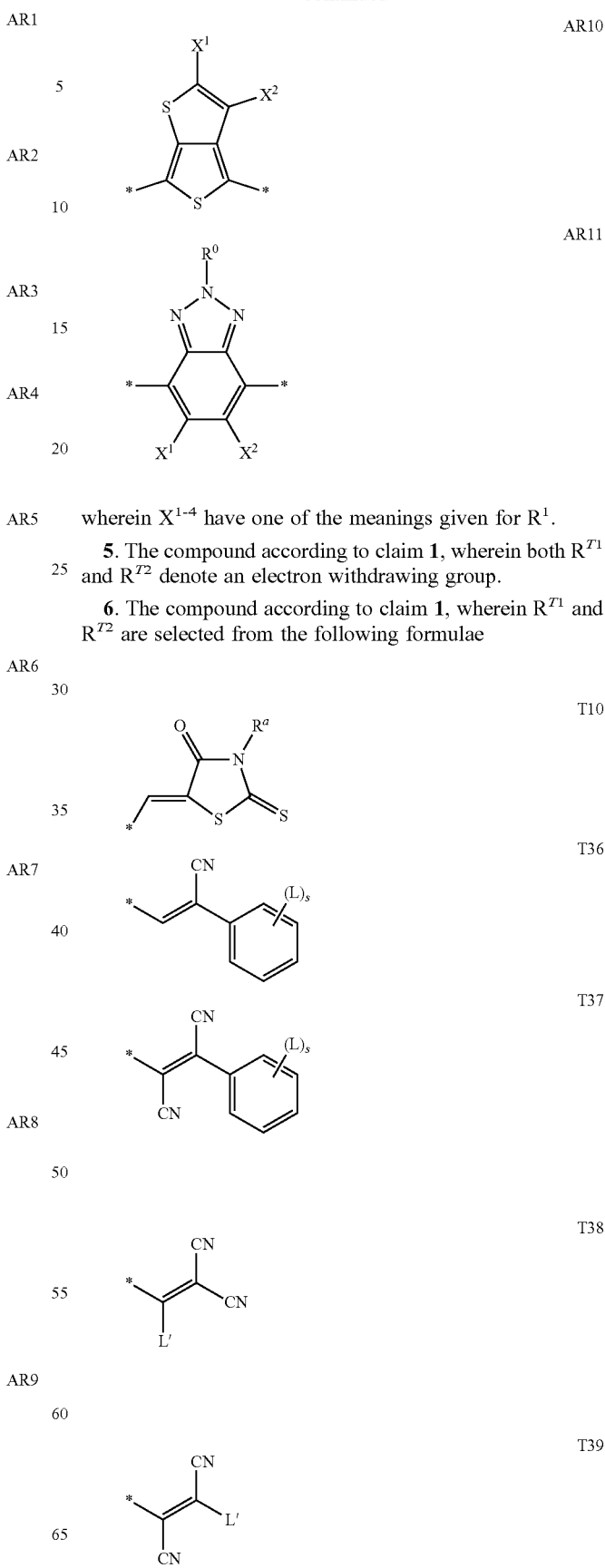
wherein $X^{1-4}$ have one of the meanings given for $R^1$.
5. The compound according to claim 1, wherein both $R^{T1}$ and $R^{T2}$ denote an electron withdrawing group.
6. The compound according to claim 1, wherein $R^{T1}$ and $R^{T2}$ are selected from the following formulae -continued
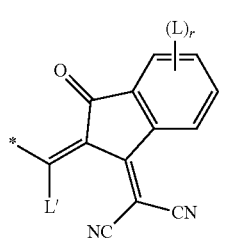
T47
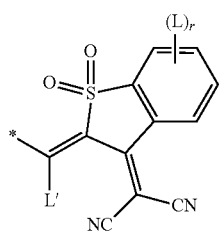
T52
7. The compound according to claim 1, which is selected from the following formulae
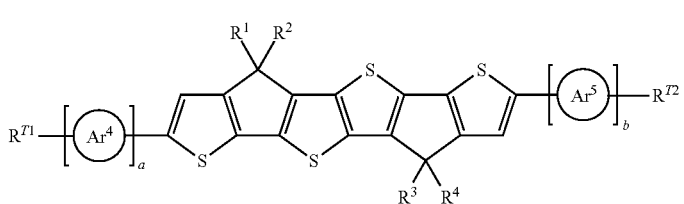
I1
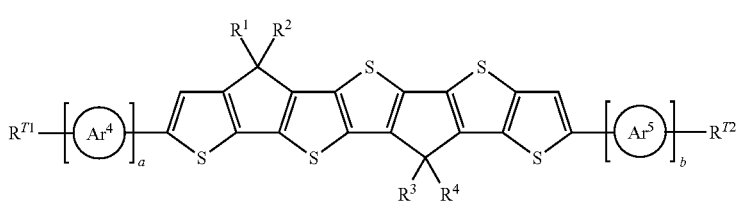
I2
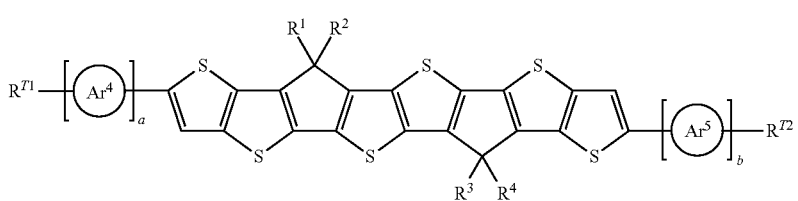
I3
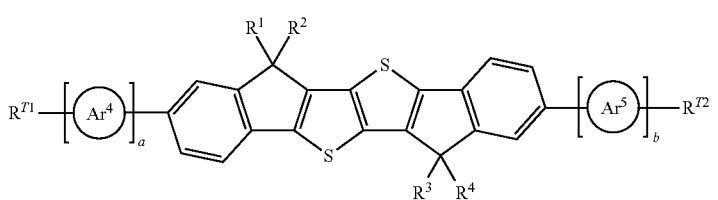
I4
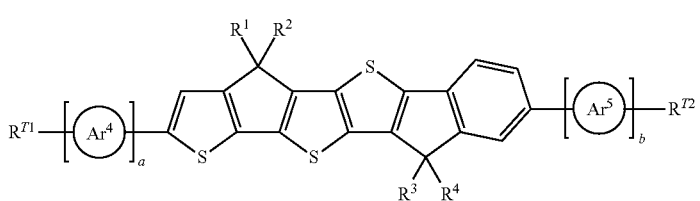
I5

-continued
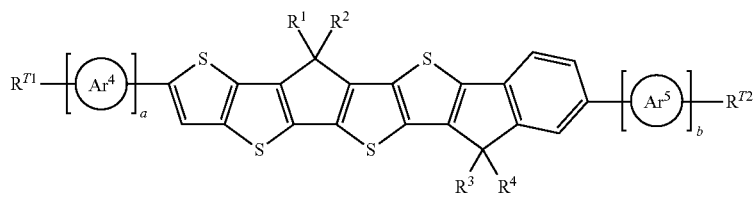
I6
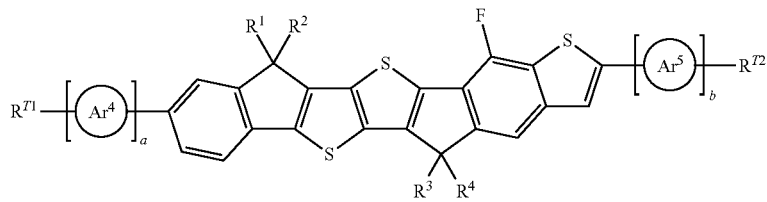
I7
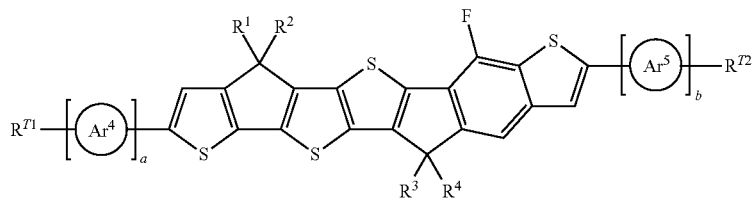
I8
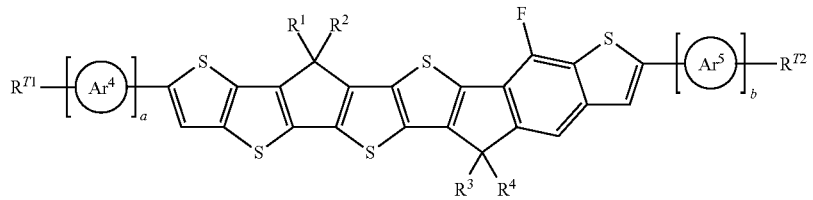
I9
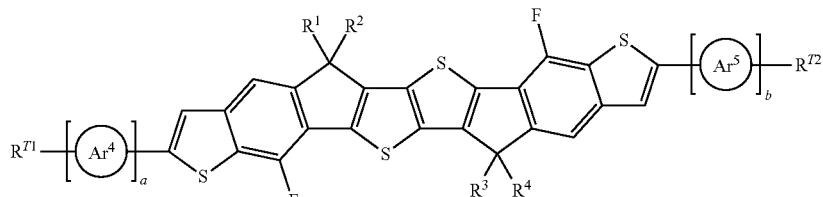
I10
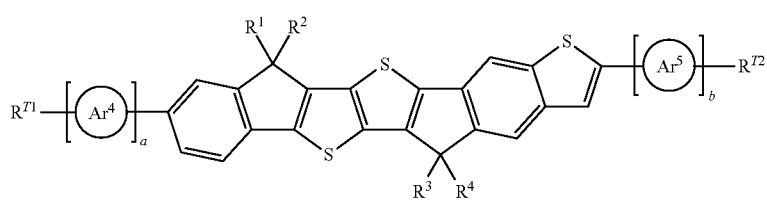
I11
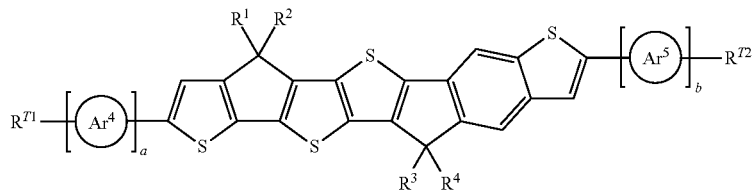
I12
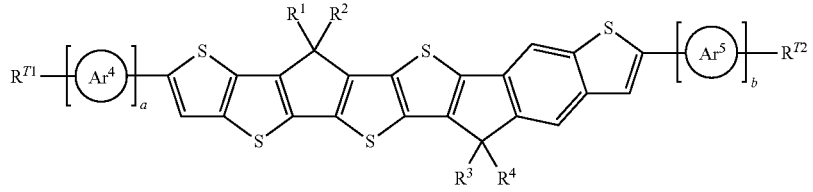
I13

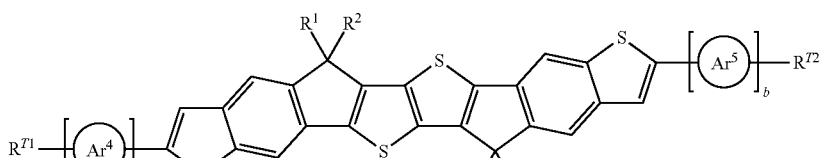

I14

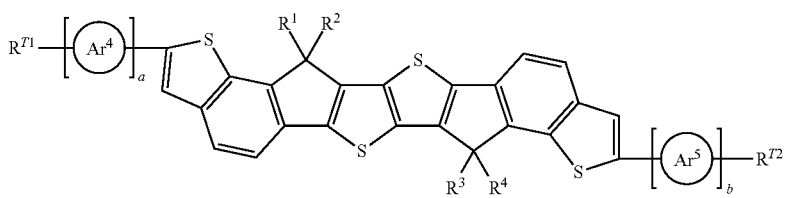

I15

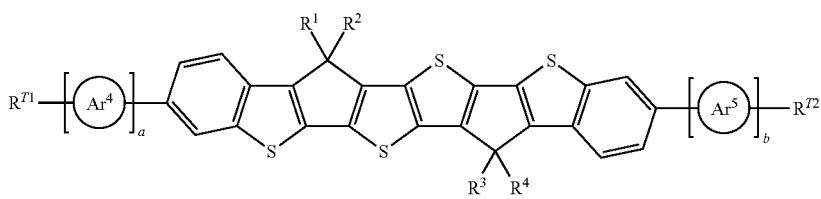

I16

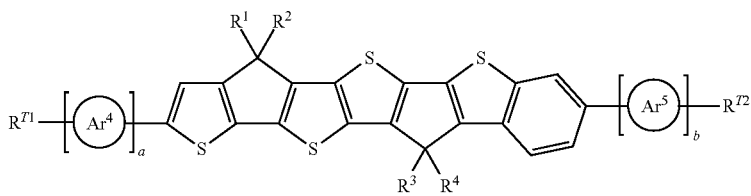

I17

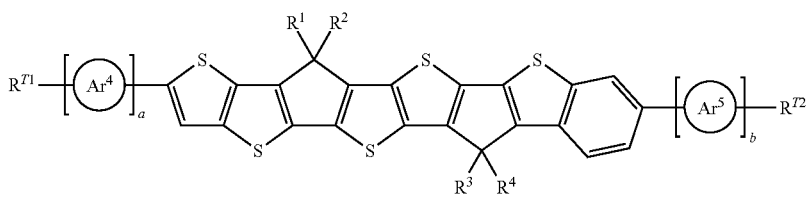

I18

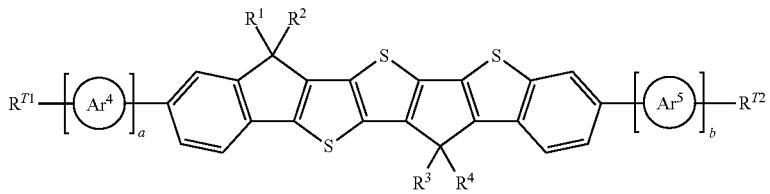

I19 wherein $R^1$, $R^2$, $R^3$, $R^4$, $R^{T1}$, $R^{T2}$, $Ar^4$, $Ar^5$, a and b have the meanings given in claim 1.

8. The compound according to claim 1, where $R^{1-4}$ are selected from alkyl or alkoxy with 1 to 16 C atoms which is optionally fluorinated or aryl or heteroaryl that is mono- or polycyclic, optionally contains fused rings, has 4 to 30 ring atoms, and is optionally substituted by one or more groups L as defined in claim 1.

9. A composition comprising one or more compounds of Formula I according to claim 1, and further comprising one or more compounds having one or more of a semiconducting, hole or electron transporting, hole or electron blocking, electrically conducting, photoconducting, photoactive or light emitting property, and/or a binder.

10. The composition of claim 9, comprising one or more n-type semiconductors, at least one of which is a compound of Formula I, and further comprising one or more p-type semiconductors.

11. The composition of claim 9, comprising one or more p-type semiconductors selected from conjugated polymers.

12. The composition of claim 11, wherein the conjugated polymers are selected from the following formulae P1
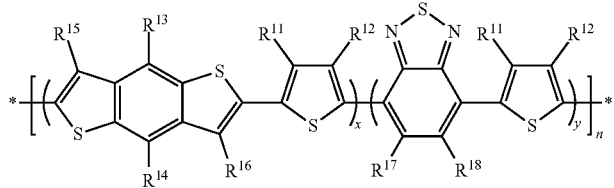
P2
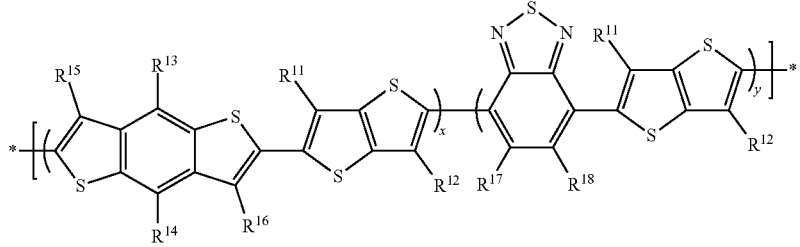
P3
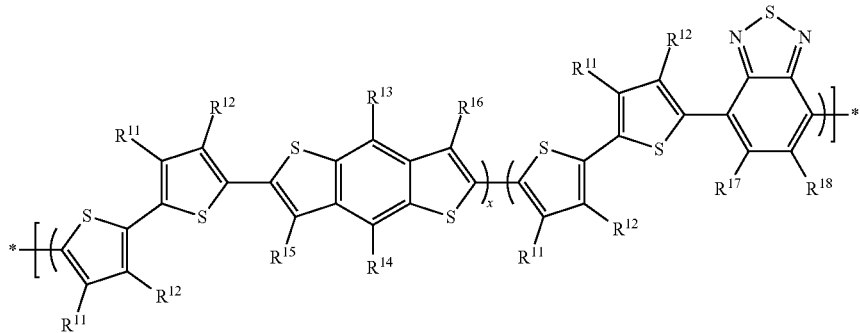
P4
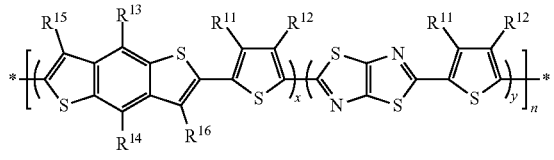
P5
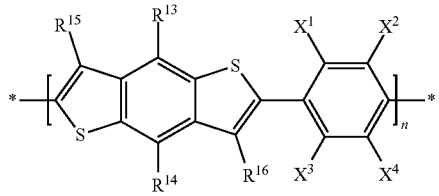
P6
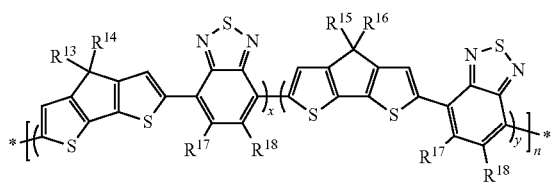
P7
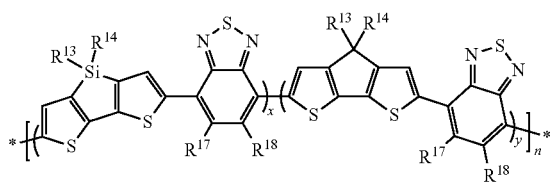
P8
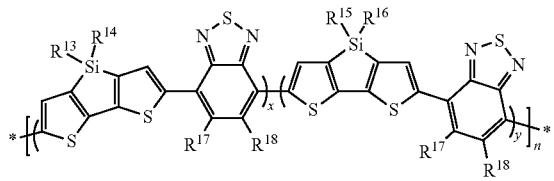
P9
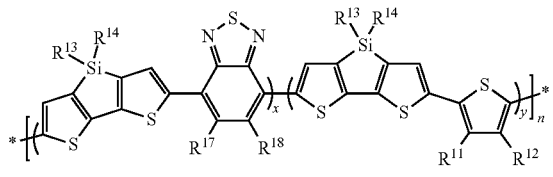
P10
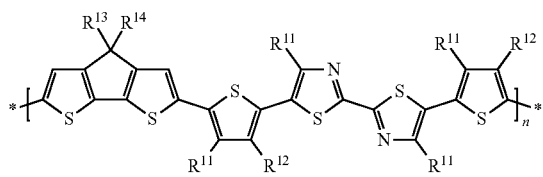
P11
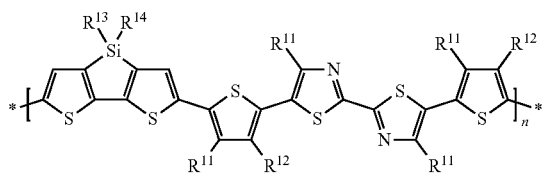

-continued
P12
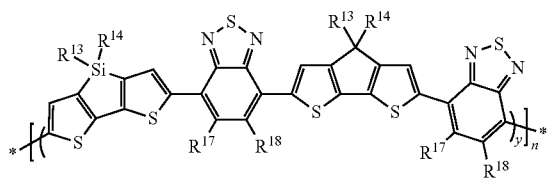
P13
P14
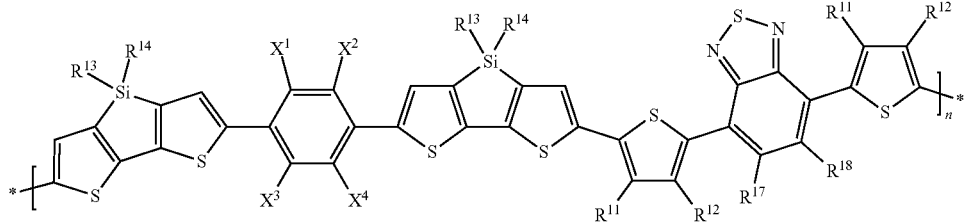
P15
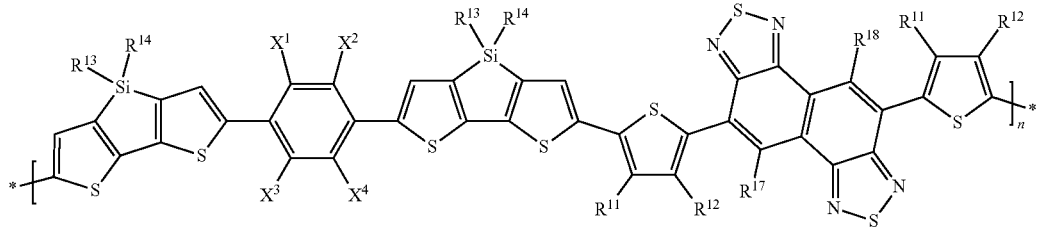
P16
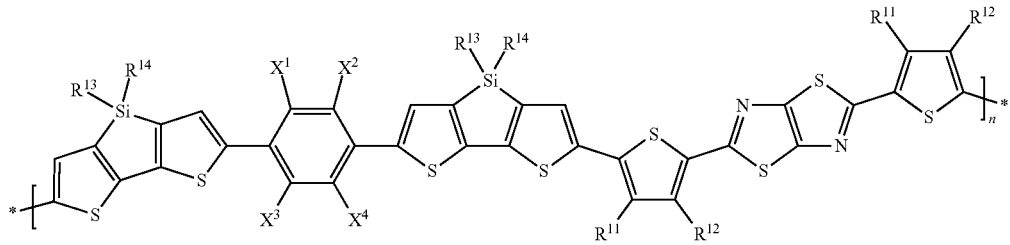
P17
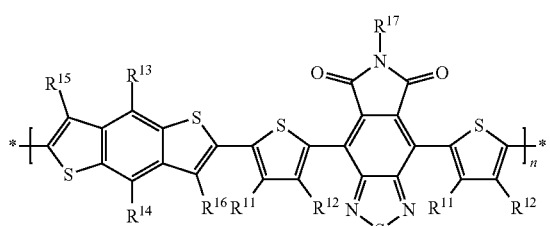
P18
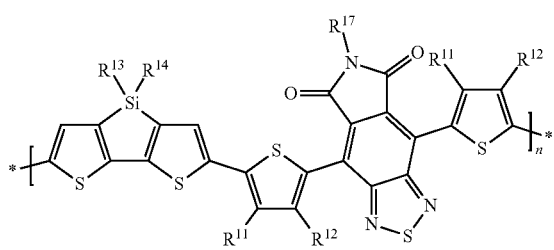
P19
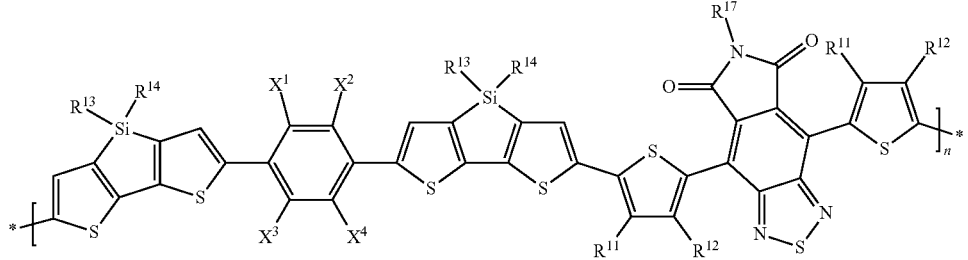

-continued
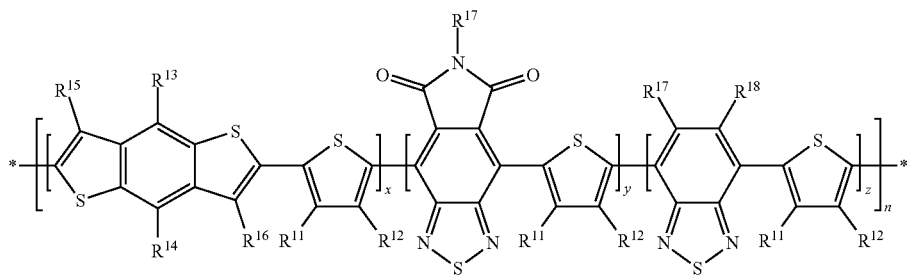
P20
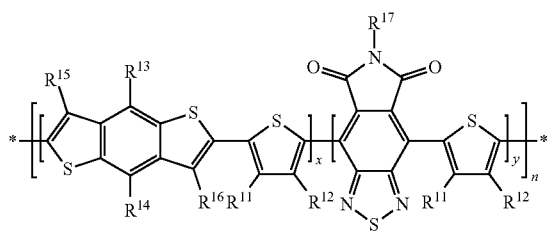
P21
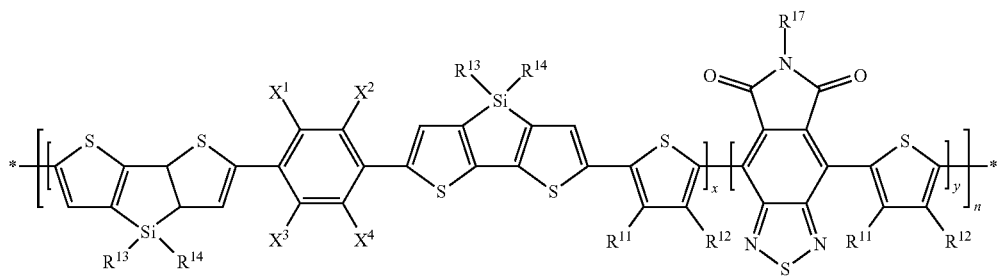
P22
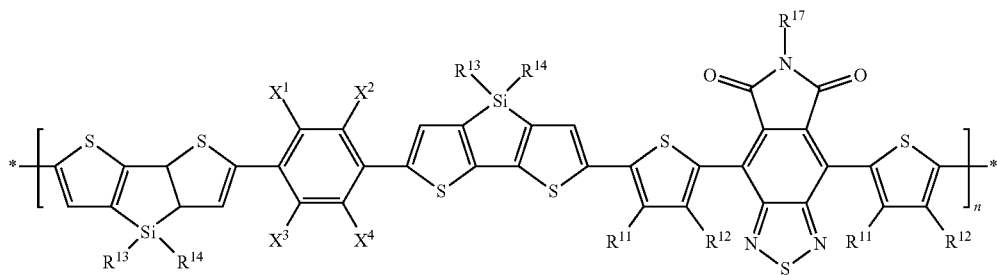
P23
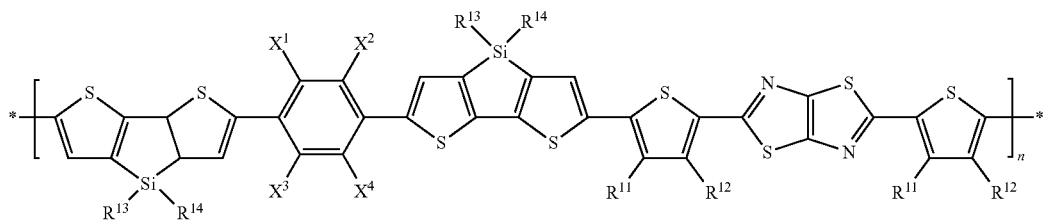
P24
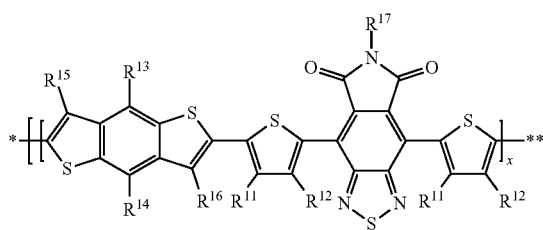 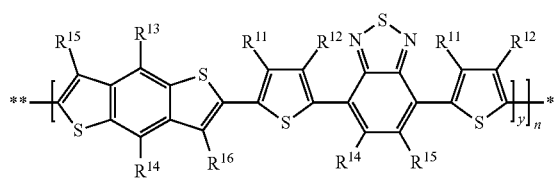
P25

P26
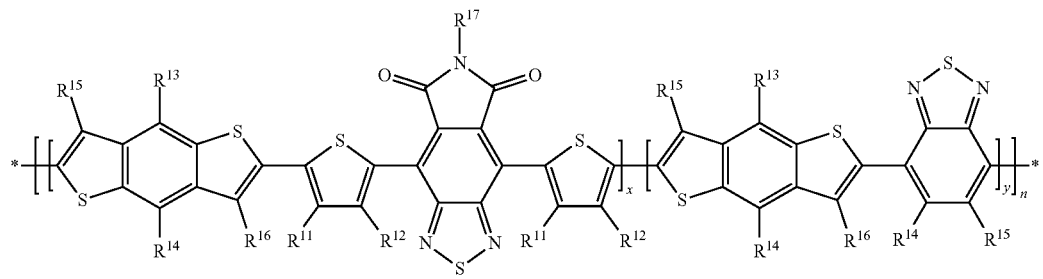
P27
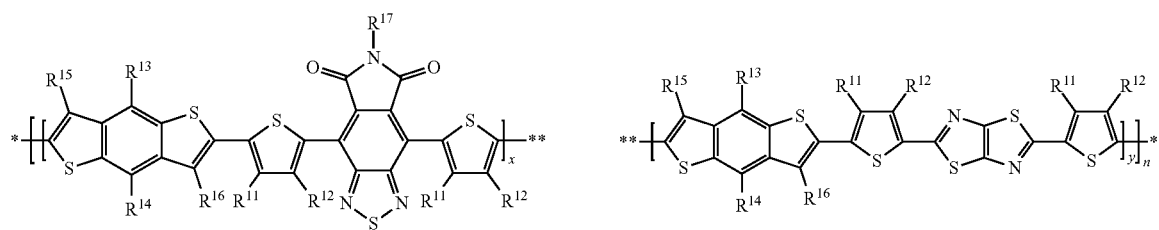
P28
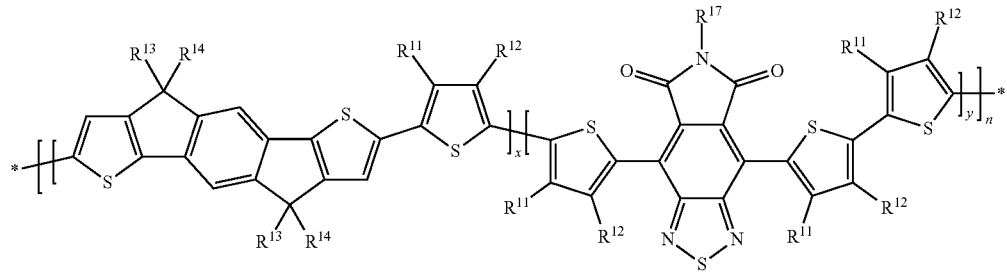
P29
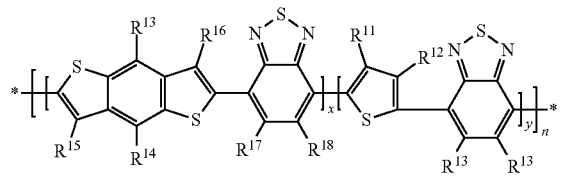
P30
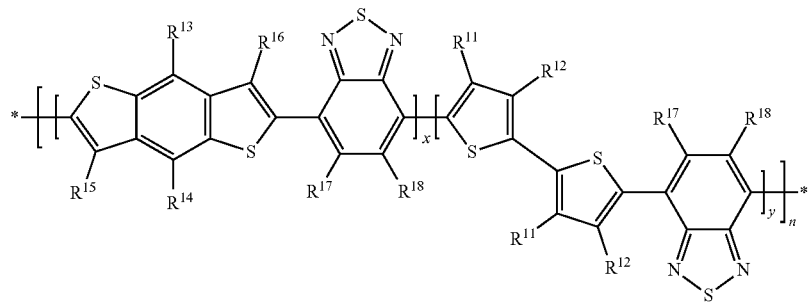
P31
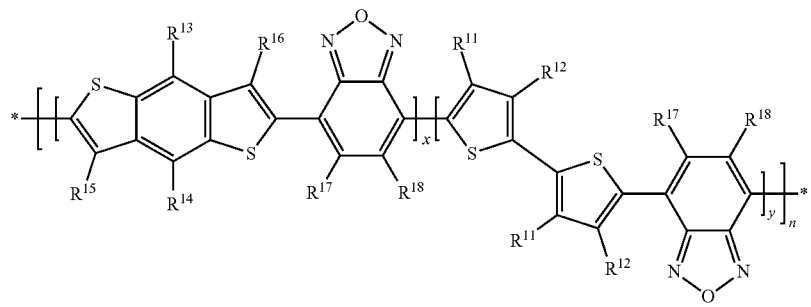

-continued
P32 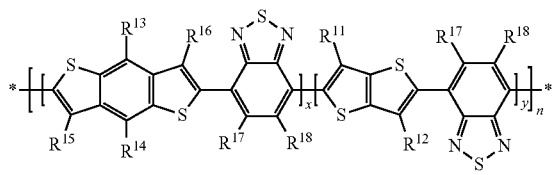
P33 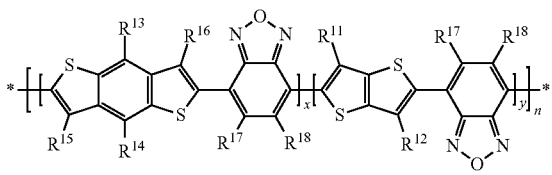
P34 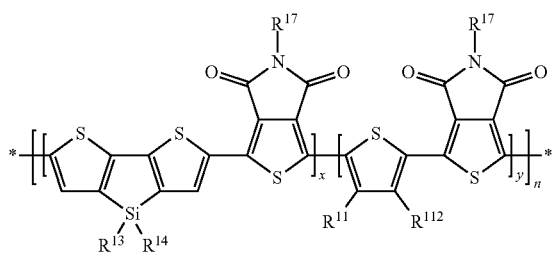
P35 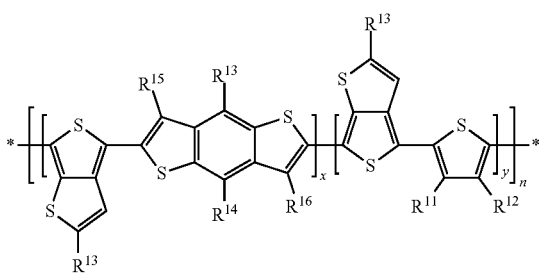
P36 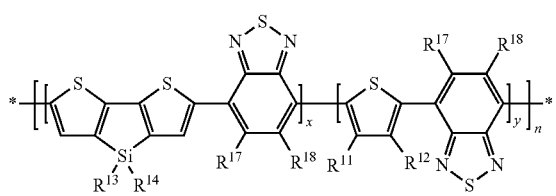
P37 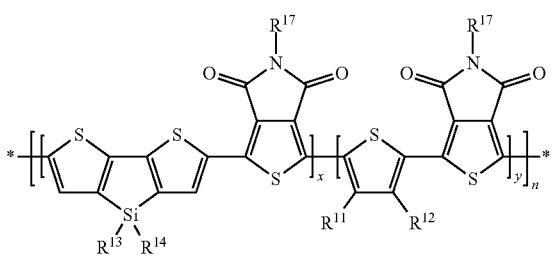
P38 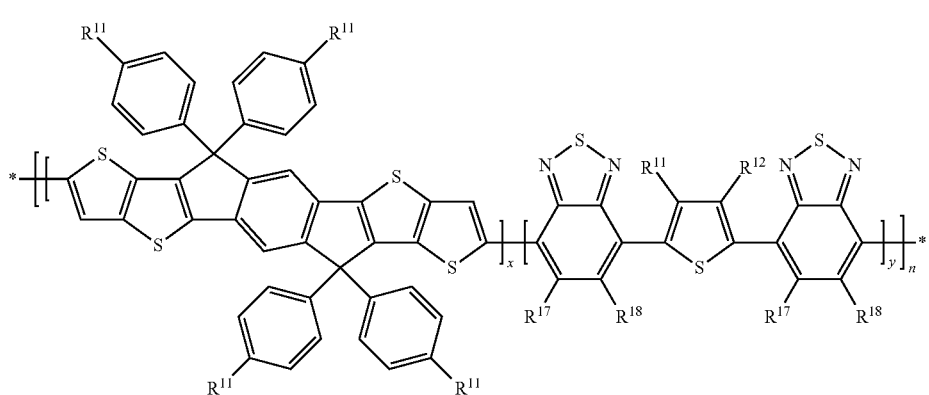
P39 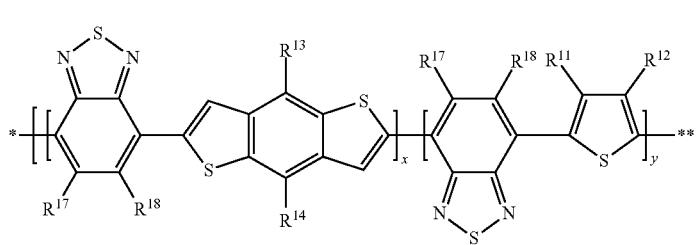

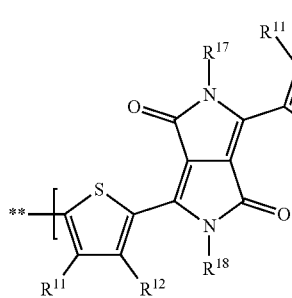
P40
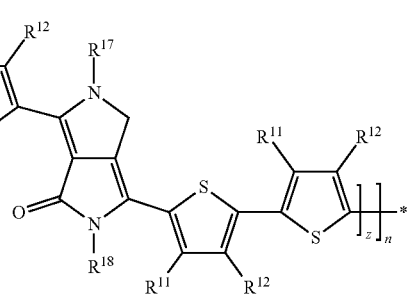
P41
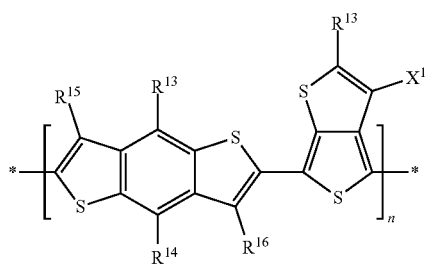
P42
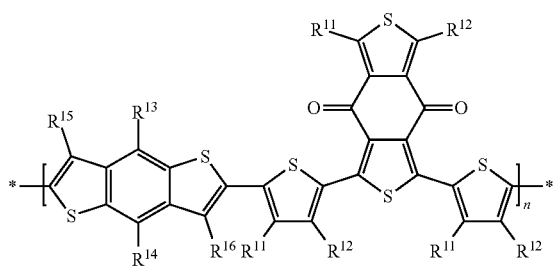
P43
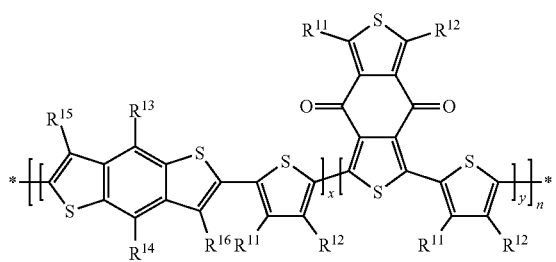
P44
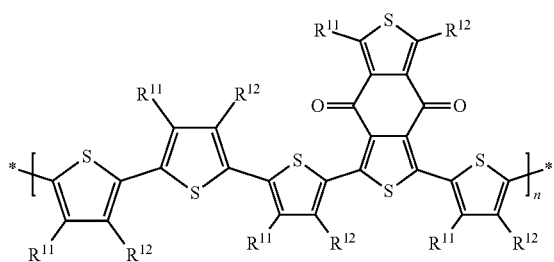
P45
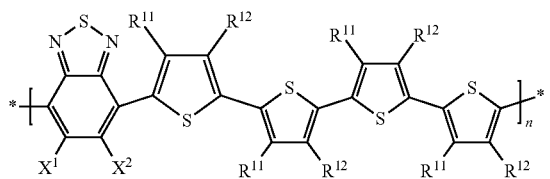
P46
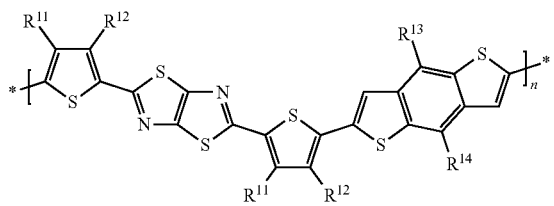
P47
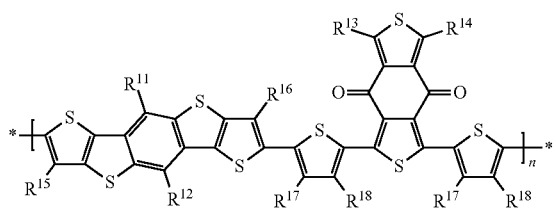
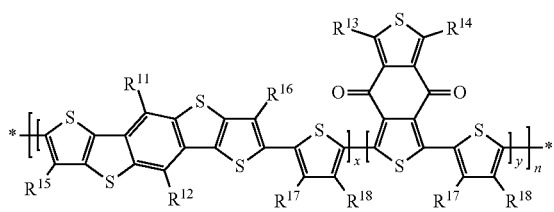

P48

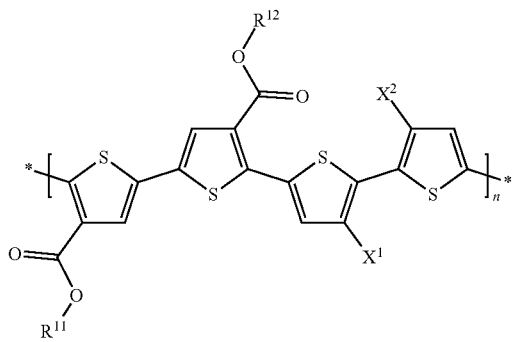

P49

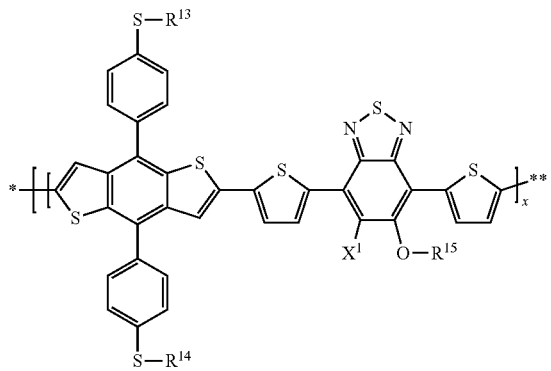

P50

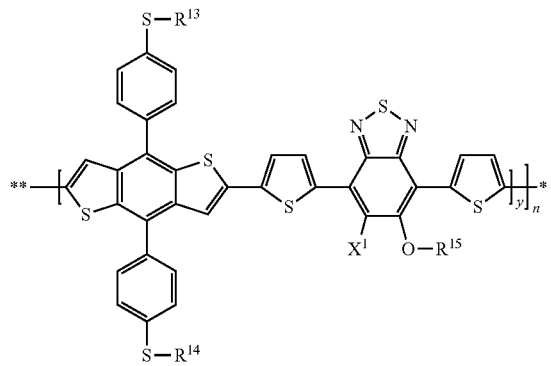

P51

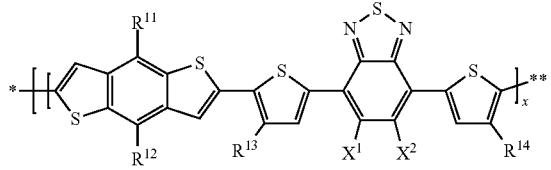

P52

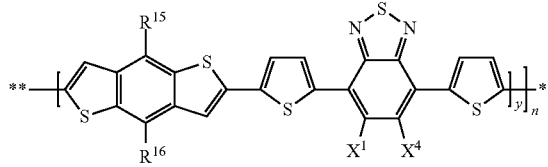

P53

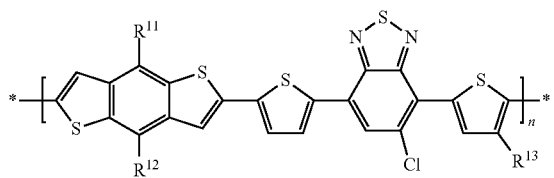

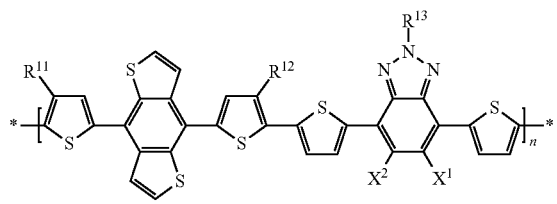

PT

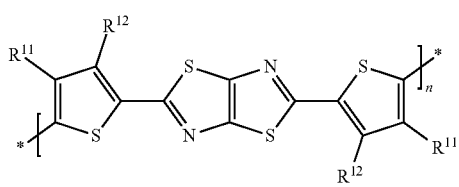

wherein $R^{11-19}$ independently of each other denote H or have one of the meanings of L, $X^1$, $X^2$, $X^3$ and $X^4$ denote H, F or Cl, x and y are each, independently of one another >0 and <1, with x+y=1, and n is an integer >1.

13. The composition of claim 11, wherein the conjugated polymers are selected from the following formula $R^{31}$-chain-$R^{32}$         PT wherein "chain" denotes a polymer chain selected from formulae P1-P53, and $R^{31}$ and $R^{32}$ denote an endcap groups selected from H, $C_{1-20}$ alkyl or optionally substituted $C_{6-12}$ aryl or $C_{2-10}$heteroaryl.

14. The composition according to claim 9, comprising one or more n-type semiconductors selected from fullerenes or fullerene derivatives.

15. A bulk heterojunction (BHJ) formed from a composition according to claim 9.

16. A formulation comprising a composition according to claim 9, and further comprising one or more solvents selected from organic solvents.

17. An electronic or optoelectronic device, or a component thereof, or an assembly comprising it, which comprises a composition according to claim 9.

18. A formulation comprising one or more compounds according to claim 1, and further comprising one or more solvents selected from organic solvents.

19. An electronic or optoelectronic device, or a component thereof, or an assembly comprising it, which comprises a compound according to claim 1.

20. The electronic or optoelectronic device according to claim 19, which is selected from organic field effect transistors (OFET), organic thin film transistors (OTFT), organic light emitting diodes (OLED), organic light emitting transistors (OLET), organic light emitting electro-chemical cells (OLEC), organic photovoltaic devices (OPV), organic photodetectors (OPD), organic solar cells, dye-sensitized solar cells (DSSC), perovskite-based solar cells (PSC), organic photoelectrochemical cells (OPEC), laser diodes, Schottky diodes, photoconductors, photodetectors, thermoelectric devices and LC windows.

21. The component according to claim 19, which is selected from charge injection layers, charge transport layers, interlayers, planarising layers, antistatic films, polymer electrolyte membranes (PEM), conducting substrates and conducting patterns.

22. The assembly according to claim 19, which is selected from integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

* * * * *